US007700340B2

(12) United States Patent
Brown et al.

(10) Patent No.: US 7,700,340 B2
(45) Date of Patent: Apr. 20, 2010

(54) CRYSTAL STRUCTURE OF POLO-LIKE KINASE 3 (PLK3) AND BINDING POCKETS THEREOF

(75) Inventors: Kieron Brown, Abingdon (GB); Graham M T Cheetham, Abingdon (GB); Suzanne B Renwick, Abingdon (GB); Joanna M Long, Abingdon (GB)

(73) Assignee: Vertex Pharmaceuticals incorporated, Cambridge, MA (US)

( * ) Notice: Subject to any disclaimer, the term of this patent is extended or adjusted under 35 U.S.C. 154(b) by 139 days.

(21) Appl. No.: 11/818,698

(22) Filed: Jun. 14, 2007

(65) Prior Publication Data

US 2008/0293579 A1 Nov. 27, 2008

Related U.S. Application Data

(60) Provisional application No. 60/813,427, filed on Jun. 14, 2006.

(51) Int. Cl.
*C12N 9/12* (2006.01)
(52) U.S. Cl. .................................................. 435/194
(58) Field of Classification Search ........................ None
See application file for complete search history.

(56) References Cited

U.S. PATENT DOCUMENTS

| | | | |
|---|---|---|---|
| 4,886,646 A | 12/1989 | Carter et al. | |
| 5,096,676 A | 3/1992 | McPherson et al. | |
| 5,130,105 A | 7/1992 | Carter et al. | |
| 5,221,410 A | 6/1993 | Kushner et al. | |
| 5,400,741 A | 3/1995 | DeTitta et al. | |
| 5,884,230 A | 3/1999 | Srinivasan et al. | |
| 7,432,260 B2* | 10/2008 | Wang et al. | 514/235.8 |
| 2003/0077681 A1 | 4/2003 | Cogswell | |
| 2005/0261836 A1 | 11/2005 | Meng et al. | |
| 2008/0201123 A1* | 8/2008 | Cosgrove | 703/11 |

FOREIGN PATENT DOCUMENTS

| | | |
|---|---|---|
| WO | WO 03/048340 | 6/2003 |
| WO | WO 2004/024759 | 3/2004 |
| WO | WO 2005/047526 | 5/2005 |
| WO | WO 2006/053125 | 5/2006 |

OTHER PUBLICATIONS

Ouyang et al., Oncogene 18:6029-6036, 1999.*
Amersham Protein Purification Handbook, Oct. 2001, p. 59.*
GenBank Accession No. Q9H4B4, May 2006, 8 pages.*
Abrieu et al., "The Polo-like kinase Plx1 is a component of the MPF amplification loop at the G2/M-phase transition of the cell cycle in Xenopus eggs," *Journal of Cell Sciences*, 111:1751-1757 (1998).
Bahassi et al., "Mammalian Polo-like kinase 3 (Plk3) is a multifunctional protein involved in stress response pathways," *Oncogene*, 21: 6633-6640 (2002).
Balbes et al., "A Perspective of Modern Methods in Computer-Aided Drug Design", *Reviews in Computational Chemistry*, vol. 5, K. B. Lipkowitz and D. B. Boyd, Eds., VCH, New York, pp. 337-379 (1994).
Bartlett et al., "CAVEAT: A Program to Facilitate the Structure-Derived Design of Biologically Active Molecules", *Molecular Recognition in Chemical and Biological Problems*, 78:182-196 (1989).
Blundell et al., "Knowledge-Based Prediction of Protein Structures and the Design of Novel Molecules," *Nature*, 326:347-352 (1987).
Blundell et al., "High-throughput crystallography for lead discovery in drug design," *Nature Reviews Drug Discovery*, 1(1):45-54 (2002).
Böhm, "The computer program LUDI: A new method for the *de novo* design of enzyme inhibits," *Journal of Computer-Aided Molecular Design*, 6:61-78 (1992).
Brown et al., "Crystal Structures of Interleukin-2 Tyrosine Kinase and Their Implications for the Design of Selective Inhibitors," *J. Biol. Chem.*, 279:18727-18732 (2004).
Brown et al., "Effects of Phosphorylation of Threonine 160 on Cyclin-dependent Kinase 2 Structure and Activity," *J. Biol. Chem.* 274:8746-8756 (1999).
Brünger et al., "Crystallography & NMR System: A New Softward Suite for Macromolecular Structure Determination," *Acta Crystallographica*, D54:905-921 (1998).
Carson, "Ribbons 2.0," *Journal of Applied Crystallography*, 24:958-961 (1991).
Chayen, "A Novel Technique to Control the Rate of Vapour Diffusion, Giving Larger Protein Crystals," *Journal of Applied Crystallography*, 30:198-202 (1997).
Cheng et al., "The crystal structure of the human polo-like kinase-1 polo box domain and its phospho-peptide complex," *EMBO Journal*, 22(21):5757-5768 (2003).
Cohen et al., "Molecular Modeling Software and Methods for Medicinal Chemistry," *Journal of Medicinal Chemistry*, 33(3):883-894 (1990).
Collaborative Computational Project, "The CCP4 Suite: Programs for Protein Crystallography," *Acta Crystallographica*, D50:760-763 (1994).

(Continued)

*Primary Examiner*—David J Steadman
(74) *Attorney, Agent, or Firm*—Ropes & Gray LLP

(57) ABSTRACT

The invention relates to molecules or molecular complexes, which comprise binding pockets of PLK3 or its structural homologues. The invention relates to crystallizable compositions and crystals comprising PLK3. The present invention also relates to a data storage medium encoded with the structural coordinates of molecules and molecular complexes which comprise the PLK3 or PLK3-like ATP-binding pockets. The present invention also relates to a computer comprising such data storage material. The computer may generate a three-dimensional structure or graphical three-dimensional representation of such molecules or molecular complexes. This invention also relates to methods of using the structure coordinates to solve the structure of homologous proteins or protein complexes. In addition, this invention relates to methods of using the structure coordinates to screen for, identify and design compounds, including inhibitory compounds that bind to PLK3 or homologues thereof.

2 Claims, 87 Drawing Sheets

OTHER PUBLICATIONS

Conn et al., "Incomplete Cytokinesis and Induction of Apoptosis by Overexpression of the Mammalian Polo-Like Kinase, Plk3l," *Cancer Research*, 60:6826-6831 (2000).

Dai et al., "*PRK*, a Cell Cycle Gene Localized in 8p21, Is Downregulated in Head and Neck Cancer," *Genes Chromosomes Cancer*, 27:332-336 (2000).

Dai et al., "Down-regulation of *PLK3* gene expression by types and amount of dietary fat in rat colon tumors," *Int. J. Oncol.*, 20:121-126 (2002).

D'Arcy et al., "A Novel Approach to Crystallising Proteins Under Oil," *Journal of Crystal Growth*, 168:175-180 (1996).

Dayhoff et al., "A Model of Evolutionary Change in Proteins," *Atlas of Protein Sequence and Structure*, 5:345-352 (1978).

Eisen et al., "HOOK: A Program for Finding Novel Molecular Architectures that Satisfy the Chemical and Steric Requirements of a Macromolecule Binding Site", *Proteins: Structure, Function, and Genetics*, 19:199-221 (1994).

Elia et al., "The Molecular Basis for Phosphodependent Substrate Targeting and Regulation of Plks by the Polo-Box Domain," *Cell*, 115:83-95 (2003).

Emsley et al., "*Coot*: Model-building tools for molecular graphics," *Acta Crysta.*, D60:2126-2132 (2004).

Fetrow et al., "New Programs for Protein Tertiary Structure Prediction," *Bio/Technology*, 11:479-484 (1993).

Fox et al., "A single amino acid substitution makes ERK2 susceptible to pyridinyl imidazole inhibitors of p38 MAP Kinase," *Protein Science*, 7, 2249-2255 (1998).

Garcia-Alvarez et al., "Crystallization and preliminary X-ray diffraction studies on the human Plk1 Polo-box domain in complex with an unphosphorylated and a phosphorylated target peptide from Cdc25C," *ACTA Crystallographica*, F62(4):372-375 (2006).

Garcia-Bustos et al., "PIK1, An Essential Phosphatidylinositol 4-Kinase Associated With The Yeast Nucleus," *EMBO Journal*, 13:2352-2361 (1994).

Gerstein et al., "Average Core Structures and Variability Measures for Protein Families: Application to the Immunoglobulins," *J. Mol. Biol.*, 251:161-175 (1995).

Giet et al, "Aurora/Ip11p-Related Kinases, A New Oncogenic Family Of Mitotic Serine-Threonine Kinases," *Journal of Cell Science*, 112:3591-3601 (1999).

Gillet et al., "SPROUT: A Program for Structure Generation", *Journal of Computer-Aided Molecular Design*, 7:127-153 (1993).

Golan et al, "The Cyclin-Ubiquitin Ligase Activity Of Cyclosome/APC Is Jointly Activated By Protein Kinases Cdk1-Cyclin B And Plk.," *Journal of Biological Chemistry*, 277(18):15552-15557 (2002).

Golsteyn et al, "Cell Cycle Regulation Of The Activity And Subcellular Localization Of Plk1, A Human Protein Kinase Implicated In Mitotic Spindle Function," *Journal of Cell Biology*, 129(6):1617-1628 (1995).

Goodford, "A Computational Procedure for Determining Energetically Favorable Binding Sites on Biologically Important Macromolecules," *Journal of Medicinal Chemistry*, 28: 849-857 (1985).

Goodsell et al., "Automated Docking of Substrates to Proteins by Simulated Annealing," *Proteins: Structure, Function, and Genetics*, 8:195-202 (1990).

Gray et al., "Identification of human polo-like kinase 1 as a potential therapeutic target in pancreatic cancer ," *Molecular Cancer Therapeutics*, 3:641-646 (2004).

Greer, "Comparative Modeling of Homologous Proteins," *Methods of Enzymology*, 202:239-252 (1991).

Guex et al., "Swiss-Model and the Swiss-Pdb Viewer: An Environment for Comparative Protein Modeling," *Electrophoresis*, 18:2714-2723 (1997).

Guida, "Software For Structure-Based Drug Design", *Current Opinion in Structural Biology*, 4:777-781 (1994).

Halgren et al., "Glide: A New Approach for Rapid, Accurate Docking and Scoring. 2. Enrichment Factors in Database Screening", *J. Med. Chem.*, 47:1750-1759 (2004).

Hanks et al. "Protein Kinase Catalytic Domain Sequence Database: Identification of Conserved Features of Primary Structure and Classification of Family Members," *Methods in Enzymology*, 200:38-62 (1991).

Hanks et al., "The Protein Kinase Family: Conserved Features and Deduced Phylogeny of the Catalytic Domains," *Science*, 241:42-52 (1988).

Hanks et al., "The Eukaryotic Protein Kinase Superfamily: Kinase (Catalytic) Domain Structure and Classification," *FASEB Journal*, 9:576-596 (1995).

Higgins et al., "Using CLUSTAL for Multiple Sequence Alignments," *Methods in Enzymology*, 266:383-402 (1996).

Hiles et al., "Phosphatidylinositol 3-Kinase: Structure And Expression Of The 110 kd Catalytic Subunit," *Cell*, 70:419-429 (1992).

Holtrich et al., "Adhesion induced expression of the serine/threonine kinase Fnk in human macrophages," *Oncogene*, 19(42):4832-4839 (2000).

Jackman et al., "Active Cyclin B1-Cdk1 First Appears On Centrosomes In Prophase," *Nature Cell Biology*, 5:143-148 (2003).

Johnson et al, "Knowledge-Based Protein Modeling," *Critical Reviews in Biochemistry and Molecular Biology*, 29(1):1-68 (1994).

Jones et al., "Improved Methods for Building Protein Models in Electron Density Maps and the Location of Errors in These Models," *Acta Crystallographica*, A47:110-119 (1991).

Knecht et al., "Prognostic Significance of *Polo-like Kinase (PLK)*. Expression in Squamous Cell Carcinomas of the Head and Neck," *Cancer Research*, 59:2794-2797 (1999).

Knighton et al., "Crystal Structure of the Catalytic Subunit of Cyclic Adenosine Monophosphate-Dependent Protein Kinase," *Science*, 253:407-414 (1991).

Komander et al., "Structural basis for UCN-01 (7-hydroxystaurosporine) specificity and PDK-1 (3-phosphoinositide-dependent protein kinase-1) inhibition," *Biochem J.*, 375: 255-261 (2003.

Kotani et al, "PKA And MPF-Activated Polo-Like Kinase Regulate Anaphase-Promoting Complex Activity And Mitosis Progression," *Mol. Cell*, 1:371-380 (1998).

Kuntz et al., "A Geometric Approach to Macromolecule-Ligand Interactions", *Journal of Molecular Biology*, 161:269-288 (1982).

Kunz et al., "Target Of Rapamycin In Yeast, TOR2, Is An Essential Phosphatidylinositol Kinase Homolog Required For G1 Progression," *Cell*, 73:585-596 (1993).

Lane et al, "Antibody Microinjection Reveals An Essential Role For Human Polo-Like Kinase 1 (Plk1) In The Functional Maturation Of Mitotic Centrosomes," *Journal of Cell Biology*, 135:1701-1713 (1996).

Lattman, "Use of the Rotation and Translation Functions", *Methods in Enzymology*, 115:55-77 (1985).

Lauri et al., "CAVEAT: a Program to Facilitate the Design of Organic Molecules", *Journal of Computer-Aided Molecular Design*, 8:51-66 (1994).

Lee et al., "Plk Is An M-Phase-Specific Protein Kinase And Interacts With A Kinesin-Like Protein, CHO1/MKLP-1," *Molecular and Cellular Biology*, 15(12)7143-7151 (1995).

Lee et al., "Mutation Of The Polo-Box Disrupts Localization And Mitotic Functions Of The Mammalian Polo Kinase Plk," *PNAS*, 95:9301-9306 (1998).

Leslie, "Integration of Macromolecular Diffraction Data," *Acta Crystallographica*, D55:1696-1702 (1999).

Li et al., "*prk*, A Cytokine-Inducible Human Protein Serine/Threonine Kinase Whose Expression Appears To Be Down-Regulated In Lung Carcinomas," *Journal of Biological Chemistry*, 271(32):19402-19408 (1996).

Li et al., "Function Of Polo-Like Kinase 3 In NF-Kappab-Mediated Proapoptotic Response," *Journal of Biological Chemistry*, 280(17):16843-16850 (2005).

Lowery et al., "Structure and function of polo-like kinases," *Oncogene*, 24(2):248-259 (2005).

Ma et al., "The Serum-Inducible Protein Kinase Snk Is A $G_1$ Phase Polo-Like Kinase that is Inhibited by the Calcium- and Integrin-Binding Protein CIB," *Mol. Cancer Res.*, 1:376-384 (2003).

Martin, "3D Database Searching in Drug Design", *Journal of Medicinal Chemistry*, 35(12):2145-2154 (1992).

May et al., "Polo Boxes And Cut23 (Apc8) Mediate An Interaction Between Polo Kinase And The Anaphase-Promoting Complex For Fission Yeast Mitosis," *Journal of Cell Biology*, 156(1):23-28 (2002).

Meng et al., "Automated Docking with Grid-Based Energy Evaluation," *Journal of Computational Chemistry*, 13(4):505-524 (1992).

Miranker et al., "Functionality Maps of Binding Sites: A Multiple Copy Simultaneous Search Method," *Proteins: Structure, Function and Genetics*, 11:29-34 (1991).

Myer et al., "The Plk3-Cdc25 circuit," *Oncogene*, 24(2):299-305 (2005).

Nakajima et al., "Identification Of A Consensus Motif For Plk (Polo-Like Kinase) Phosphorylation Reveals Myt1 As A Plk1 Substrate," *Journal of Biological Chemistry*, 278(28):25277-25280 (2003).

Navaza, "AMoRe: an Automated Package for Molecular Replacement," *Acta. Crystallographica*, A50:157-163 (1994).

Navia et al., "The Use of Structural Information in Drug Design," *Current Opinions in Structural Biology*, 2:202-210 (1992).

Nishibata et al., "Automatic Creation of Drug Candidate Structures Based on Receptor Structure. Starting Point for Artificial Lead Generation," *Tetrahedron*, 47(43):8985-8990 (1991).

Pav et al., "Microtube Batch Protein Crystallization: Applications to Human Immunodeficiency Virus Type 2 (HIV-2) Protease and Human Renin," *Proteins: Structure, Function, and Genetics*, 20:98-102 (1994).

Qian et al., "Activated Polo-Like Kinase Plx1 Is Required At Multiple Points During Mitosis In *Xenopus laevis*," *Molecular and Cellular Biology*, 18(7):4262-4271 (1998).

Reynolds et al., "Polo Boxes Form A Single Functional Domain That Mediates Interactions With Multiple Proteins In Fission Yeast Polo Kinase" *Journal of Cell Science*, 116:1377-1387 (2003).

Schnare et al., "Comprehensive Comparison of Structural Characteristics in Eukaryotic Cytoplasmic Large Subunit (23 S-Like) Ribinsomal RNA," *Journal of Molecular Biology*, 256: 701-719 (1996).

Smith et al., "Comparison of Biosequences" *Advances in Applied Mathematics*, 2:482-489 (1981).

Smith et al., "Malignant Transformation Of Mammalian Cells Initiated By Constitutive Expression Of The Polo-Like Kinase," *Biochem. Biophys. Res. Commun*, 234:379-405 (1997).

Smits et al., "Polo-Like Kinase-1 Is A Target Of The DNA Damage Checkpoint," *Nat. Cell Biol.*, 2(9):672-676 (2000).

Sonnhammer et al., "Pfam: Multiple Sequence Alignments And HMM-Profiles Of Protein Domains," *Nucleic Acids Research*, 26(1):320-322 (1998).

Squire et al., "Structure And Inhibition Of The Human Cell Cycle Checkpoint Kinase, Wee1A Kinase: An Atypical Tyrosine Kinase With A Key Role In CDK1 Regulation," *Structure* 13:541-550 (2005).

Sunkel et al., "Polo, A Mitotic Mutant Of *Drosophila* Displaying Abnormal Spindle Poles," *Journal of Cell Science*, 89:25-38 (1988).

Szklarz et al., "Use of Homology Modeling in Conjunction with Site-Directed Mutagenesis for Analysis of Structure-Function Relationships of Mammalian Cytocromes P450," *Life Sciences*, 61(26):2507-2520 (1997).

Tainer et al., "The Reactivity Of Anti-Peptide Antibodies Is A Function Of The Atomic Mobility Of Sites In A Protein," *Nature*, 312(5990):127-134 (1984).

Takahashi et al., "Polo-Like Kinase 1 (PLK1) Is Overexpressed In Primary Colorectal Cancers," *Cancer Sci.*, 94(2):148-152 (2003).

Takai et al., "Expression Of Polo-Like Kinase In Ovarian Cancer Is Associated With Histological Grade And Clinical Stage," *Cancer Letters*, 164:(1):41-49 (2001).

Takai et al., "Polo-Like Kinases (Plks) And Cancer," *Oncogene*, 24(2):287-291 (2005).

Toyoshima-Morimoto, et al., "Polo-like kinase 1 phophorylates cyclin B1 and targets it to the nucleus during prophase," *Nature*, 410:215-220 (2001).

Tschinke et al., "The NEWLEAD Program: A New Method For The Design Of Candidate Structures From Pharmacophoric Hypotheses", *J. Med. Chem.*, 36(24)3863-3870 (1993).

Wang et al., "The Structure Of Mitogen-Activated Protein Kinase P38 At 2.1-A Resolution," *PNAS*, 94(6):2327-2332 (1997).

Wang et al., "Cell Cycle Arrest And Apoptosis Induced By Human Polo-Like Kinase 3 Is Mediated Through Perturbation Of Microtubule Integrity," *Molecular and Cellular Biology*, 22(10)3450-3459 (2002).

Watanabe et al., "M-phase kinases induce phospho-dependent ubiquitination of somatic Wee1 by SCFbeta-TrCP," *PNAS*, 101(13):4419-4424 (2004).

Weichert et al., "Polo-Like Kinase 1 Is Overexpressed In Prostate Cancer And Linked To Higher Tumor Grades,"*Prostate*, 60(3):240-245 (2004).

Wilson et al., "Crystal Structure of p38 Mitogen-Activated Protein Kinase," *Journal of Biological Chemistry*, 271:27696-27700 (1996).

Wishart et al., "Constrained Multiple Sequence Alignment Using XALIGN," *CABIOS*, 10(6):687-888 (1994).

Wolf et al., "Prognostic significance of polo-like kinase (PLK) expression in non-small cell lunch cancer," *Oncogene*, 14:543-549 (1997).

Wolf et al., "Polo-like Kinase: A Novel Marker of Proliferation: Correlation with Estrogen-Receptor Expression in Human Breast Cancer," *Pathol. Res. Pract.*, 196:753-759 (2000).

Xie et al., "Plk3 Functionally Links DNA Damage To Cell Cycle Arrest And Apoptosis At Least In Part Via The P53 Pathway," *J. Biol. Chem.*, 276(46):43305-43312 (2001).

Xie et al., "Crystal structure of JNK3: a kinase implicated in neuronal apoptosis," *Structure*, 6:983-991 (1998).

\* cited by examiner

Figure 1-1

| | | Atom Type | Resid | # | X | Y | Z | OCC | B | | |
|---|---|---|---|---|---|---|---|---|---|---|---|
| ATOM | 1 | CB | LEU A | 52 | 51.078 | -20.617 | -16.657 | 1.00 | 54.72 | A | C |
| ATOM | 2 | CG | LEU A | 52 | 51.602 | -22.016 | -17.003 | 1.00 | 54.84 | A | C |
| ATOM | 3 | CD1 | LEU A | 52 | 51.164 | -23.012 | -15.931 | 1.00 | 54.93 | A | C |
| ATOM | 4 | CD2 | LEU A | 52 | 51.074 | -22.432 | -18.379 | 1.00 | 54.45 | A | C |
| ATOM | 5 | C | LEU A | 52 | 50.456 | -18.416 | -17.699 | 1.00 | 54.89 | A | C |
| ATOM | 6 | O | LEU A | 52 | 50.741 | -17.287 | -17.332 | 1.00 | 54.89 | A | O |
| ATOM | 7 | N | LEU A | 52 | 52.845 | -19.036 | -17.375 | 1.00 | 55.18 | A | N |
| ATOM | 8 | CA | LEU A | 52 | 51.481 | -19.540 | -17.673 | 1.00 | 55.17 | A | C |
| ATOM | 9 | N | ILE A | 53 | 49.254 | -18.756 | -18.139 | 1.00 | 54.68 | A | N |
| ATOM | 10 | CA | ILE A | 53 | 48.146 | -17.818 | -18.274 | 1.00 | 54.88 | A | C |
| ATOM | 11 | CB | ILE A | 53 | 47.321 | -18.194 | -19.539 | 1.00 | 54.67 | A | C |
| ATOM | 12 | CG2 | ILE A | 53 | 46.363 | -17.080 | -19.924 | 1.00 | 54.65 | A | C |
| ATOM | 13 | CG1 | ILE A | 53 | 48.275 | -18.487 | -20.684 | 1.00 | 54.80 | A | C |
| ATOM | 14 | CD1 | ILE A | 53 | 47.611 | -19.044 | -21.899 | 1.00 | 55.45 | A | C |
| ATOM | 15 | C | ILE A | 53 | 47.233 | -17.900 | -17.041 | 1.00 | 54.53 | A | C |
| ATOM | 16 | O | ILE A | 53 | 47.389 | -18..783 | -16.205 | 1.00 | 54.47 | A | O |
| ATOM | 17 | N | THR A | 54 | 46.288 | -16.974 | -16.930 | 1.00 | 54.05 | A | N |
| ATOM | 18 | CA | THR A | 54 | 45.329 | -16.988 | -15.835 | 1.00 | 55.08 | A | C |
| ATOM | 19 | CB | THR A | 54 | 45.733 | -16.008 | -14.710 | 1.00 | 54.66 | A | C |
| ATOM | 20 | OG1 | THR A | 54 | 45.655 | -14.673 | -15.190 | 1.00 | 55.50 | A | O |
| ATOM | 21 | CG2 | THR A | 54 | 47.165 | -16.263 | -14.251 | 1.00 | 54.40 | A | C |
| ATOM | 22 | C | THR A | 54 | 43.972 | -16.633 | -16.450 | 1.00 | 55.74 | A | C |
| ATOM | 23 | O | THR A | 54 | 43.886 | -15.750 | -17.298 | 1.00 | 54.23 | A | O |
| ATOM | 24 | N | ASP A | 55 | 42.911 | -17.326 | -16.036 | 1.00 | 58.19 | A | N |
| ATOM | 25 | CA | ASP A | 55 | 41.576 | -17.093 | -16.614 | 1.00 | 60.23 | A | C |
| ATOM | 26 | CB | ASP A | 55 | 41.268 | -18.188 | -17.599 | 1.00 | 60.62 | A | C |
| ATOM | 27 | CG | ASP A | 55 | 42.459 | -18.517 | -18.430 | 1.00 | 61.57 | A | C |
| ATOM | 28 | OD1 | ASP A | 55 | 43.027 | -17.571 | -19.010 | 1.00 | 62.36 | A | O |
| ATOM | 29 | OD2 | ASP A | 55 | 42.857 | -19.699 | -18.507 | 1.00 | 62.52 | A | O |
| ATOM | 30 | C | ASP A | 55 | 40.459 | -17.042 | -15.604 | 1.00 | 60.98 | A | C |
| ATOM | 31 | O | ASP A | 55 | 40.578 | -17.565 | -14.505 | 1.00 | 60.81 | A | O |
| ATOM | 32 | N | PRO A | 56 | 39.340 | -16.417 | -15.965 | 1.00 | 62.72 | A | N |
| ATOM | 33 | CD | PRO A | 56 | 39.143 | -15.417 | -17.029 | 1.00 | 62.59 | A | C |
| ATOM | 34 | CA | PRO A | 56 | 38.248 | -16.359 | -14.989 | 1.00 | 64.63 | A | C |
| ATOM | 35 | CB | PRO A | 56 | 37.470 | -15.128 | -15.457 | 1.00 | 63..60 | A | C |
| ATOM | 36 | CG | PRO A | 56 | 37.681 | -15.157 | -16.953 | 1.00 | 63.07 | A | C |
| ATOM | 37 | C | PRO A | 56 | 37.350 | -17.619 | -14.939 | 1.00 | 66.10 | A | C |
| ATOM | 38 | O | PRO A | 56 | 37.569 | -18.577 | -14.199 | 1.00 | 66.84 | A | O |
| ATOM | 39 | N | ARG A | 57 | 36.314 | -17.545 | -15.760 | 1.00 | 68.34 | A | N |
| ATOM | 40 | CA | ARG A | 57 | 35.260 | -18.527 | -15.980 | 1.00 | 69.15 | A | C |
| ATOM | 41 | CB | ARG A | 57 | 34.848 | -19.235 | -14.687 | 1.00 | 70.82 | A | C |
| ATOM | 42 | CG | ARG A | 57 | 34.603 | -18.354 | -13.494 | 1.00 | 73.07 | A | C |
| ATOM | 43 | CD | ARG A | 57 | 33.147 | -17.914 | -13.436 | 1.00 | 74.37 | A | C |
| ATOM | 44 | NE | ARG A | 57 | 32.752 | -17.521 | -12.080 | 1.00 | 75.46 | A | N |
| ATOM | 45 | CZ | ARG A | 57 | 33.119 | -16.385 | -11.491 | 1.00 | 75.61 | A | C |
| ATOM | 46 | NH1 | ARG A | 57 | 33.885 | -15.523 | -12.153 | 1.00 | 76.10 | A | N |
| ATOM | 47 | NH2 | ARG A | 57 | 32.752 | -16.118 | -10.236 | 1.00 | 75.56 | A | N |
| ATOM | 48 | C | ARG A | 57 | 34.196 | -17.598 | -16.552 | 1.00 | 69.05 | A | C |
| ATOM | 49 | O | ARG A | 57 | 33.081 | -17.439 | -16.041 | 1.00 | 68.97 | A | O |
| ATOM | 50 | N | SER A | 58 | 34.674 | -16.944 | -17.614 | 1.00 | 68.63 | A | N |
| ATOM | 51 | CA | SER A | 58 | 33.999 | -15.983 | -18.478 | 1.00 | 68.47 | A | C |
| ATOM | 52 | CB | SER A | 58 | 33.721 | -14.656 | -17.764 | 1.00 | 69.26 | A | C |
| ATOM | 53 | OG | SER A | 58 | 34.909 | -13.931 | -17.485 | 1.00 | 70.82 | A | O |
| ATOM | 54 | C | SER A | 58 | 35.072 | -15.801 | -19.580 | 1.00 | 67.57 | A | C |
| ATOM | 55 | O | SER A | 58 | 35.181 | -14.751 | -20.225 | 1.00 | 67.30 | A | O |
| ATOM | 56 | N | GLY A | 59 | 35.873 | -16.863 | -19.739 | 1.00 | 66.02 | A | N |
| ATOM | 57 | CA | GLY A | 59 | 36.933 | -16.944 | -20.735 | 1.00 | 64.64 | A | C |
| ATOM | 58 | C | GLY A | 59 | 38.196 | -16.135 | -20.478 | 1.00 | 63.30 | A | C |
| ATOM | 59 | O | GLY A | 59 | 39.141 | -16.630 | -19.874 | 1.00 | 64.96 | A | O |

Figure 1-2

| | Atom Type | Resid | # | X | Y | Z | OCC | B | | |
|---|---|---|---|---|---|---|---|---|---|---|
| ATOM | 60 | N | ARG A | 60 | 38.189 | -14.893 | -20.965 | 1.00 | 61.03 | A | N |
| ATOM | 61 | CA | ARG A | 60 | 39.276 | -13.904 | -20.889 | 1.00 | 58.26 | A | C |
| ATOM | 62 | CB | ARG A | 60 | 38.761 | -12.657 | -20.176 | 1.00 | 59.80 | A | C |
| ATOM | 63 | CG | ARG A | 60 | 39.564 | -11.385 | -20.380 | 1.00 | 61.83 | A | C |
| ATOM | 64 | CD | ARG A | 60 | 38.681 | -10.215 | -19.937 | 1.00 | 63.93 | A | C |
| ATOM | 65 | NE | ARG A | 60 | 39.317 | -8.902 | -20.091 | 1.00 | 66.48 | A | N |
| ATOM | 66 | CZ | ARG A | 60 | 38.769 | -7.731 | -19.737 | 1.00 | 67.74 | A | C |
| ATOM | 67 | NH1 | ARG A | 60 | 37.551 | -7.677 | -19.197 | 1.00 | 67.75 | A | N |
| ATOM | 68 | NH2 | ARG A | 60 | 39.448 | -6.598 | -19.914 | 1.00 | 68.32 | A | N |
| ATOM | 69 | C | ARG A | 60 | 40.599 | -14.329 | -20.261 | 1.00 | 55.31 | A | C |
| ATOM | 70 | O | ARG A | 60 | 40.749 | -14.343 | -19.030 | 1.00 | 54.95 | A | O |
| ATOM | 71 | N | THR A | 61 | 41.571 | -14.623 | -21.121 | 1.00 | 51.26 | A | N |
| ATOM | 72 | CA | THR A | 61 | 42.882 | -15.026 | -20.664 | 1.00 | 48.68 | A | C |
| ATOM | 73 | CB | THR A | 61 | 43.489 | -16.115 | -21.580 | 1.00 | 48.10 | A | C |
| ATOM | 74 | OG1 | THR A | 61 | 43.636 | -15.603 | -22.906 | 1.00 | 47.27 | A | O |
| ATOM | 75 | CG2 | THR A | 61 | 42.584 | -17.351 | -21.630 | 1.00 | 47.28 | A | C |
| ATOM | 76 | C | THR A | 61 | 43.827 | -13.828 | -20.597 | 1.00 | 47.38 | A | C |
| ATOM | 77 | O | THR A | 61 | 43.741 | -12.883 | -21.387 | 1.00 | 45.86 | A | O |
| ATOM | 78 | N | TYR A | 62 | 44.735 | -13.914 | -19.634 | 1.00 | 46.59 | A | N |
| ATOM | 79 | CA | TYR A | 62 | 45.730 | -12.896 | -19.343 | 1.00 | 46.11 | A | C |
| ATOM | 80 | CB | TYR A | 62 | 45.437 | -12.261 | -17.978 | 1.00 | 45.64 | A | C |
| ATOM | 81 | CG | TYR A | 62 | 44.062 | -11.637 | -17.808 | 1.00 | 44.43 | A | C |
| ATOM | 82 | CD1 | TYR A | 62 | 43.834 | -10.300 | -18.129 | 1.00 | 44.95 | A | C |
| ATOM | 83 | CE1 | TYR A | 62 | 42.580 | -9.705 | -17.916 | 1.00 | 45.88 | A | C |
| ATOM | 84 | CD2 | TYR A | 62 | 43.000 | -12.373 | -17.271 | 1.00 | 44.45 | A | C |
| ATOM | 85 | CE2 | TYR A | 62 | 41.746 | -11.786 | -17.053 | 1.00 | 45.01 | A | C |
| ATOM | 86 | CZ | TYR A | 62 | 41.540 | -10.448 | -17.378 | 1.00 | 45.10 | A | C |
| ATOM | 87 | OH | TYR A | 62 | 40.300 | -9.865 | -17.164 | 1.00 | 45.74 | A | O |
| ATOM | 88 | C | TYR A | 62 | 47.074 | -13.620 | -19.237 | 1.00 | 45.98 | A | C |
| ATOM | 89 | O | TYR A | 62 | 47.130 | -14.761 | -18.781 | 1.00 | 45.28 | A | O |
| ATOM | 90 | N | LEU A | 63 | 48.164 | -12.967 | -19.622 | 1.00 | 46.63 | A | N |
| ATOM | 91 | CA | LEU A | 63 | 49.466 | -13.619 | -19.517 | 1.00 | 47.05 | A | C |
| ATOM | 92 | CB | LEU A | 63 | 50.338 | -13.293 | -20.732 | 1.00 | 47.43 | A | C |
| ATOM | 93 | CG | LEU A | 63 | 51.781 | -13.813 | -20.594 | 1.00 | 47.55 | A | C |
| ATOM | 94 | CD1 | LEU A | 63 | 51.778 | -15.294 | -20.238 | 1.00 | 48.01 | A | C |
| ATOM | 95 | CD2 | LEU A | 63 | 52.548 | -13.568 | -21.876 | 1.00 | 47.60 | A | C |
| ATOM | 96 | C | LEU A | 63 | 50.224 | -13.263 | -18.241 | 1.00 | 47.19 | A | C |
| ATOM | 97 | O | LEU A | 63 | 50.982 | -12.302 | -18.212 | 1.00 | 45.92 | A | O |
| ATOM | 98 | N | LYS A | 64 | 50.020 | -14.062 | -17.198 | 1.00 | 49.83 | A | N |
| ATOM | 99 | CA | LYS A | 64 | 50.673 | -13.862 | -15.895 | 1.00 | 51.74 | A | C |
| ATOM | 100 | CB | LYS A | 64 | 50.130 | -14.860 | -14.868 | 1.00 | 52.67 | A | C |
| ATOM | 101 | CG | LYS A | 64 | 51.154 | -15.254 | -13.806 | 1.00 | 53.01 | A | C |
| ATOM | 102 | CD | LYS A | 64 | 50.864 | -16.634 | -13.257 | 1.00 | 53.42 | A | C |
| ATOM | 103 | CE | LYS A | 64 | 51.905 | -17.045 | -12.238 | 1.00 | 52.87 | A | C |
| ATOM | 104 | NZ | LYS A | 64 | 51.899 | -16.130 | -11.058 | 1.00 | 52.28 | A | N |
| ATOM | 105 | C | LYS A | 64 | 52.180 | -14.050 | -15.981 | 1.00 | 52.86 | A | C |
| ATOM | 106 | O | LYS A | 64 | 52.647 | -15.033 | -16.557 | 1.00 | 53.37 | A | O |
| ATOM | 107 | N | GLY A | 65 | 52.944 | -13.135 | -15.393 | 1.00 | 52.35 | A | N |
| ATOM | 108 | CA | GLY A | 65 | 54.380 | -13.299 | -15.456 | 1.00 | 52.97 | A | C |
| ATOM | 109 | C | GLY A | 65 | 55.180 | -12.025 | -15.528 | 1.00 | 53.10 | A | C |
| ATOM | 110 | O | GLY A | 65 | 54.922 | -11.158 | -16.370 | 1.00 | 53.73 | A | O |
| ATOM | 111 | N | ARG A | 66 | 56.171 | -11.970 | -14.634 | 1.00 | 53.00 | A | N |
| ATOM | 112 | CA | ARG A | 66 | 57.128 | -10.875 | -14.431 | 1.00 | 52.99 | A | C |
| ATOM | 113 | CB | ARG A | 66 | 56.929 | -9.752 | -15.443 | 1.00 | 54.39 | A | C |
| ATOM | 114 | CG | ARG A | 66 | 57.472 | -10.071 | -16.829 | 1.00 | 55.76 | A | C |
| ATOM | 115 | CD | ARG A | 66 | 57.229 | -8.912 | -17.765 | 1.00 | 57.91 | A | C |
| ATOM | 116 | NE | ARG A | 66 | 57.895 | -9.061 | -19.054 | 1.00 | 59.12 | A | N |
| ATOM | 117 | CZ | ARG A | 66 | 57.949 | -8.092 | -19.967 | 1.00 | 60.42 | A | C |
| ATOM | 118 | NH1 | ARG A | 66 | 57.376 | -6.914 | -19.719 | 1.00 | 59.71 | A | N |

Figure 1-3

| | | Atom Type | Resid | # | X | Y | Z | OCC | B | | |
|---|---|---|---|---|---|---|---|---|---|---|---|
| ATOM | 119 | NH2 | ARG A | 66 | 58.577 | -8.291 | -21.125 | 1.00 | 60.98 | A | N |
| ATOM | 120 | C | ARG A | 66 | 56.919 | -10.343 | -13.028 | 1.00 | 52.47 | A | C |
| ATOM | 121 | O | ARG A | 66 | 56.487 | -9.214 | -12.853 | 1.00 | 52.66 | A | O |
| ATOM | 122 | N | LEU A | 67 | 57.236 | -11.174 | -12.036 | 1.00 | 51.69 | A | N |
| ATOM | 123 | CA | LEU A | 67 | 57.060 | -10.854 | -10.618 | 1.00 | 51.88 | A | C |
| ATOM | 124 | CB | LEU A | 67 | 57.825 | -11.880 | -9.776 | 1.00 | 52.20 | A | C |
| ATOM | 125 | CG | LEU A | 67 | 57.595 | -11.918 | -8.265 | 1.00 | 52.52 | A | C |
| ATOM | 126 | CD1 | LEU A | 67 | 57.443 | -13.372 | -7.798 | 1.00 | 53.05 | A | C |
| ATOM | 127 | CD2 | LEU A | 67 | 58.761 | -11.208 | -7.564 | 1.00 | 52.98 | A | C |
| ATOM | 128 | C | LEU A | 67 | 57.425 | -9.423 | -10.203 | 1.00 | 51.30 | A | C |
| ATOM | 129 | O | LEU A | 67 | 58.591 | -9.036 | -10.169 | 1.00 | 51.79 | A | O |
| ATOM | 130 | N | LEU A | 68 | 56.391 | -8.651 | -9.876 | 1.00 | 51.05 | A | N |
| ATOM | 131 | CA | LEU A | 68 | 56.522 | -7.261 | -9.478 | 1.00 | 50.13 | A | C |
| ATOM | 132 | CB | LEU A | 68 | 55.299 | -6.476 | -9.962 | 1.00 | 49.06 | A | C |
| ATOM | 133 | CG | LEU A | 68 | 55.026 | -6.425 | -11.470 | 1.00 | 48.22 | A | C |
| ATOM | 134 | CD1 | LEU A | 68 | 53.659 | -5.825 | -11.677 | 1.00 | 48.05 | A | C |
| ATOM | 135 | CD2 | LEU A | 68 | 56.100 | -5.620 | -12.209 | 1.00 | 47.67 | A | C |
| ATOM | 136 | C | LEU A | 68 | 56.658 | -7.130 | -7.972 | 1.00 | 50.33 | A | C |
| ATOM | 137 | O | LEU A | 68 | 56.989 | -6.066 | -7.464 | 1.00 | 49.02 | A | O |
| ATOM | 138 | N | GLY A | 69 | 56.391 | -8.211 | -7.255 | 1.00 | 51.93 | A | N |
| ATOM | 139 | CA | GLY A | 69 | 56.503 | -8.160 | -5.811 | 1.00 | 54.23 | A | C |
| ATOM | 140 | C | GLY A | 69 | 55.965 | -9.376 | -5.087 | 1.00 | 55.86 | A | C |
| ATOM | 141 | O | GLY A | 69 | 55.356 | -10.249 | -5.705 | 1.00 | 55.51 | A | O |
| ATOM | 142 | N | LYS A | 70 | 56.215 | -9.434 | -3.778 | 1.00 | 57.75 | A | N |
| ATOM | 143 | CA | LYS A | 70 | 55.751 | -10.525 | -2.921 | 1.00 | 60.75 | A | C |
| ATOM | 144 | CB | LYS A | 70 | 56.791 | -11.653 | -2.859 | 1.00 | 61.10 | A | C |
| ATOM | 145 | CG | LYS A | 70 | 56.867 | -12.480 | -4.140 | 1.00 | 61.97 | A | C |
| ATOM | 146 | CD | LYS A | 70 | 57.527 | -13.841 | -3.925 | 1.00 | 62.43 | A | C |
| ATOM | 147 | CE | LYS A | 70 | 57.201 | -14.800 | -5.083 | 1.00 | 62.69 | A | C |
| ATOM | 148 | NZ | LYS A | 70 | 58.395 | -15.352 | -5.805 | 1.00 | 62.76 | A | N |
| ATOM | 149 | C | LYS A | 70 | 55.461 | -10.006 | -1.511 | 1.00 | 62.28 | A | C |
| ATOM | 150 | O | LYS A | 70 | 56.374 | -9.646 | -0.768 | 1.00 | 62.84 | A | O |
| ATOM | 151 | N | GLY A | 71 | 54.185 | -9.955 | -1.146 | 1.00 | 64.03 | A | N |
| ATOM | 152 | CA | GLY A | 71 | 53.820 | -9.462 | 0.170 | 1.00 | 65.72 | A | C |
| ATOM | 153 | C | GLY A | 71 | 53.035 | -10.460 | 0.996 | 1.00 | 66.67 | A | C |
| ATOM | 154 | O | GLY A | 71 | 51.807 | -10.521 | 0.918 | 1.00 | 66.97 | A | O |
| ATOM | 155 | N | GLY A | 72 | 53.751 | -11.240 | 1.800 | 1.00 | 67.89 | A | N |
| ATOM | 156 | CA | GLY A | 72 | 53.109 | -12.228 | 2.651 | 1.00 | 68.94 | A | C |
| ATOM | 157 | C | GLY A | 72 | 52.626 | -13.453 | 1.904 | 1.00 | 69.21 | A | C |
| ATOM | 158 | O | GLY A | 72 | 53.421 | -14.305 | 1.505 | 1.00 | 69.84 | A | O |
| ATOM | 159 | N | PHE A | 73 | 51.315 | -13.540 | 1.710 | 1.00 | 68.78 | A | N |
| ATOM | 160 | CA | PHE A | 73 | 50.726 | -14.674 | 1.005 | 1.00 | 68.66 | A | C |
| ATOM | 161 | CB | PHE A | 73 | 49.315 | -14.957 | 1.544 | 1.00 | 69.61 | A | C |
| ATOM | 162 | CG | PHE A | 73 | 49.310 | -15.590 | 2.915 | 1.00 | 70.61 | A | C |
| ATOM | 163 | CD1 | PHE A | 73 | 48.111 | -15.846 | 3.571 | 1.00 | 70.98 | A | C |
| ATOM | 164 | CD2 | PHE A | 73 | 50.508 | -15.941 | 3.546 | 1.00 | 71.10 | A | C |
| ATOM | 165 | CE1 | PHE A | 73 | 48.086 | -16.442 | 4.838 | 1.00 | 71.03 | A | C |
| ATOM | 166 | CE2 | PHE A | 73 | 50.497 | -16.537 | 4.810 | 1.00 | 71.67 | A | C |
| ATOM | 167 | CZ | PHE A | 73 | 49.285 | -16.788 | 5.456 | 1.00 | 71.35 | A | C |
| ATOM | 168 | C | PHE A | 73 | 50.686 | -14.425 | -0.492 | 1.00 | 67.28 | A | C |
| ATOM | 169 | O | PHE A | 73 | 50.873 | -15.339 | -1.293 | 1.00 | 67.29 | A | O |
| ATOM | 170 | N | ALA A | 74 | 50.459 | -13.174 | -0.867 | 1.00 | 64.80 | A | N |
| ATOM | 171 | CA | ALA A | 74 | 50.381 | -12.813 | -2.271 | 1.00 | 63.37 | A | C |
| ATOM | 172 | CB | ALA A | 74 | 50.000 | -11.348 | -2.406 | 1.00 | 63.66 | A | C |
| ATOM | 173 | C | ALA A | 74 | 51.671 | -13.080 | -3.045 | 1.00 | 62.48 | A | C |
| ATOM | 174 | O | ALA A | 74 | 52.725 | -13.374 | -2.481 | 1.00 | 62.17 | A | O |
| ATOM | 175 | N | ARG A | 75 | 51.537 | -12.987 | -4.363 | 1.00 | 61.61 | A | N |
| ATOM | 176 | CA | ARG A | 75 | 52.608 | -13.162 | -5.340 | 1.00 | 60.92 | A | C |
| ATOM | 177 | CB | ARG A | 75 | 52.706 | -14.619 | -5.805 | 1.00 | 62.59 | A | C |

Figure 1-4

| | | Atom Type | Resid | # | X | Y | Z | OCC | B | | |
|---|---|---|---|---|---|---|---|---|---|---|---|
| ATOM | 178 | CG | ARG A | 75 | 53.300 | -15.597 | -4.812 | 1.00 | 64.37 | A | C |
| ATOM | 179 | CD | ARG A | 75 | 53.302 | -17.027 | -5.369 | 1.00 | 66.36 | A | C |
| ATOM | 180 | NE | ARG A | 75 | 53.787 | -18.007 | -4.389 | 1.00 | 67.93 | A | N |
| ATOM | 181 | CZ | ARG A | 75 | 55.051 | -18.098 | -3.971 | 1.00 | 68.57 | A | C |
| ATOM | 182 | NH1 | ARG A | 75 | 55.971 | -17.272 | -4.452 | 1.00 | 69.05 | A | N |
| ATOM | 183 | NH2 | ARG A | 75 | 55.395 | -18.999 | -3.055 | 1.00 | 68.98 | A | N |
| ATOM | 184 | C | ARG A | 75 | 52.137 | -12.296 | -6.495 | 1.00 | 58.92 | A | C |
| ATOM | 185 | O | ARG A | 75 | 51.373 | -12.739 | -7.341 | 1.00 | 59.58 | A | O |
| ATOM | 186 | N | CYS A | 76 | 52.558 | -11.045 | -6.495 | 1.00 | 56.00 | A | N |
| ATOM | 187 | CA | CYS A | 76 | 52.148 | -10.114 | -7.526 | 1.00 | 53.78 | A | C |
| ATOM | 188 | CB | CYS A | 76 | 52.233 | -8.694 | -6.974 | 1.00 | 53.65 | A | C |
| ATOM | 189 | SG | CYS A | 76 | 51.566 | -7.416 | -8.035 | 1.00 | 55.84 | A | S |
| ATOM | 190 | C | CYS A | 76 | 52.974 | -10.240 | -8.805 | 1.00 | 52.30 | A | C |
| ATOM | 191 | O | CYS A | 76 | 54.204 | -10.199 | -8.778 | 1.00 | 50.76 | A | O |
| ATOM | 192 | N | TYR A | 77 | 52.286 | -10.408 | -9.926 | 1.00 | 50.55 | A | N |
| ATOM | 193 | CA | TYR A | 77 | 52.946 | -10.527 | -11.217 | 1.00 | 49.36 | A | C |
| ATOM | 194 | CB | TYR A | 77 | 52.711 | -11.909 | -11.835 | 1.00 | 49.71 | A | C |
| ATOM | 195 | CG | TYR A | 77 | 53.303 | -13.070 | -11.079 | 1.00 | 49.81 | A | C |
| ATOM | 196 | CD1 | TYR A | 77 | 52.896 | -13.357 | -9.784 | 1.00 | 50.73 | A | C |
| ATOM | 197 | CE1 | TYR A | 77 | 53.430 | -14.444 | -9.077 | 1.00 | 50.79 | A | C |
| ATOM | 198 | CD2 | TYR A | 77 | 54.262 | -13.896 | -11.667 | 1.00 | 50.24 | A | C |
| ATOM | 199 | CE2 | TYR A | 77 | 54.801 | -14.987 | -10.973 | 1.00 | 50.21 | A | C |
| ATOM | 200 | CZ | TYR A | 77 | 54.381 | -15.251 | -9.673 | 1.00 | 50.47 | A | C |
| ATOM | 201 | OH | TYR A | 77 | 54.918 | -16.293 | -8.945 | 1.00 | 51.45 | A | O |
| ATOM | 202 | C | TYR A | 77 | 52.397 | -9.489 | -12.181 | 1.00 | 47.97 | A | C |
| ATOM | 203 | O | TYR A | 77 | 51.258 | -9.042 | -12.070 | 1.00 | 46.83 | A | O |
| ATOM | 204 | N | GLU A | 78 | 53.232 | -9.101 | -13.127 | 1.00 | 47.75 | A | N |
| ATOM | 205 | CA | GLU A | 78 | 52.823 | -8.167 | -14.147 | 1.00 | 46.48 | A | C |
| ATOM | 206 | CB | GLU A | 78 | 54.056 | -7.797 | -14.987 | 1.00 | 47.57 | A | C |
| ATOM | 207 | CG | GLU A | 78 | 53.937 | -6.584 | -15.904 | 1.00 | 48.21 | A | C |
| ATOM | 208 | CD | GLU A | 78 | 55.254 | -6.267 | -16.609 | 1.00 | 48.95 | A | C |
| ATOM | 209 | OE1 | GLU A | 78 | 56.231 | -5.880 | -15.928 | 1.00 | 49.26 | A | O |
| ATOM | 210 | OE2 | GLU A | 78 | 55.310 | -6.406 | -17.847 | 1.00 | 49.56 | A | O |
| ATOM | 211 | C | GLU A | 78 | 51.863 | -9.091 | -14.902 | 1.00 | 45.38 | A | C |
| ATOM | 212 | O | GLU A | 78 | 51.952 | -10.306 | -14.743 | 1.00 | 43.41 | A | O |
| ATOM | 213 | N | ALA A | 79 | 50.936 | -8.541 | -15.683 | 1.00 | 44.78 | A | N |
| ATOM | 214 | CA | ALA A | 79 | 49.979 | -9.369 | -16.434 | 1.00 | 44.27 | A | C |
| ATOM | 215 | CB | ALA A | 79 | 49.008 | -10.075 | -15.461 | 1.00 | 43.12 | A | C |
| ATOM | 216 | C | ALA A | 79 | 49.185 | -8.570 | -17.474 | 1.00 | 43.98 | A | C |
| ATOM | 217 | O | ALA A | 79 | 48.699 | -7.472 | -17.189 | 1.00 | 43.24 | A | O |
| ATOM | 218 | N | THR A | 80 | 49.055 | -9.130 | -18.677 | 1.00 | 44.67 | A | N |
| ATOM | 219 | CA | THR A | 80 | 48.305 | -8.480 | -19.764 | 1.00 | 45.92 | A | C |
| ATOM | 220 | CB | THR A | 80 | 49.252 | -8.010 | -20.911 | 1.00 | 45.50 | A | C |
| ATOM | 221 | OG1 | THR A | 80 | 50.134 | -9.075 | -21.277 | 1.00 | 45.97 | A | O |
| ATOM | 222 | CG2 | THR A | 80 | 50.064 | -6.809 | -20.474 | 1.00 | 45.21 | A | C |
| ATOM | 223 | C | THR A | 80 | 47.227 | -9.390 | -20.366 | 1.00 | 46.39 | A | C |
| ATOM | 224 | O | THR A | 80 | 47.356 | -10.609 | -20.315 | 1.00 | 46.21 | A | O |
| ATOM | 225 | N | ASP A | 81 | 46.173 | -8.780 | -20.920 | 1.00 | 48.07 | A | N |
| ATOM | 226 | CA | ASP A | 81 | 45.058 | -9.494 | -21.554 | 1.00 | 49.49 | A | C |
| ATOM | 227 | CB | ASP A | 81 | 43.988 | -8.502 | -22.049 | 1.00 | 50.19 | A | C |
| ATOM | 228 | CG | ASP A | 81 | 42.631 | -8.683 | -21.369 | 1.00 | 50.84 | A | C |
| ATOM | 229 | OD1 | ASP A | 81 | 42.415 | -8.086 | -20.297 | 1.00 | 52.34 | A | O |
| ATOM | 230 | OD2 | ASP A | 81 | 41.773 | -9.416 | -21.903 | 1.00 | 50.33 | A | O |
| ATOM | 231 | C | ASP A | 81 | 45.549 | -10.314 | -22.756 | 1.00 | 50.48 | A | C |
| ATOM | 232 | O | ASP A | 81 | 46.586 | -10.967 | -22.704 | 1.00 | 51.47 | A | O |
| ATOM | 233 | N | THR A | 82 | 44.791 | -10.266 | -23.847 | 1.00 | 50.95 | A | N |
| ATOM | 234 | CA | THR A | 82 | 45.117 | -10.996 | -25.070 | 1.00 | 50.40 | A | C |
| ATOM | 235 | CB | THR A | 82 | 44.612 | -12.430 | -24.999 | 1.00 | 50.70 | A | C |
| ATOM | 236 | OG1 | THR A | 82 | 43.332 | -12.445 | -24.351 | 1.00 | 51.40 | A | O |

Figure 1-5

|  |  | Atom Type | Resid |  | # | X | Y | Z | OCC | B |  |  |
|---|---|---|---|---|---|---|---|---|---|---|---|---|
| ATOM | 237 | CG2 | THR | A | 82 | 45.598 | -13.297 | -24.240 | 1.00 | 50.71 | A | C |
| ATOM | 238 | C | THR | A | 82 | 44.438 | -10.293 | -26.233 | 1.00 | 50.68 | A | C |
| ATOM | 239 | O | THR | A | 82 | 45.008 | -10.174 | -27.319 | 1.00 | 51.78 | A | O |
| ATOM | 240 | N | GLU | A | 83 | 43.208 | -9.842 | -25.990 | 1.00 | 50.96 | A | N |
| ATOM | 241 | CA | GLU | A | 83 | 42.415 | -9.104 | -26.973 | 1.00 | 51.22 | A | C |
| ATOM | 242 | CB | GLU | A | 83 | 40.924 | -9.294 | -26.702 | 1.00 | 52.72 | A | C |
| ATOM | 243 | CG | GLU | A | 83 | 40.239 | -10.266 | -27.622 | 1.00 | 54.35 | A | C |
| ATOM | 244 | CD | GLU | A | 83 | 40.295 | -9.819 | -29.069 | 1.00 | 55.36 | A | C |
| ATOM | 245 | OE1 | GLU | A | 83 | 39.821 | -8.703 | -29.373 | 1.00 | 56.04 | A | O |
| ATOM | 246 | OE2 | GLU | A | 83 | 40.819 | -10.592 | -29.901 | 1.00 | 56.09 | A | O |
| ATOM | 247 | C | GLU | A | 83 | 42.754 | -7.620 | -26.835 | 1.00 | 50.35 | A | C |
| ATOM | 248 | O | GLU | A | 83 | 43.104 | -6.956 | -27.823 | 1.00 | 50.37 | A | O |
| ATOM | 249 | N | THR | A | 84 | 42.634 | -7.117 | -25.601 | 1.00 | 49.38 | A | N |
| ATOM | 250 | CA | THR | A | 84 | 42.929 | -5.724 | -25.274 | 1.00 | 49.34 | A | C |
| ATOM | 251 | CB | THR | A | 84 | 42.284 | -5.289 | -23.927 | 1.00 | 49.46 | A | C |
| ATOM | 252 | OG1 | THR | A | 84 | 42.395 | -6.353 | -22.970 | 1.00 | 49.15 | A | O |
| ATOM | 253 | CG2 | THR | A | 84 | 40.819 | -4.915 | -24.122 | 1.00 | 50.11 | A | C |
| ATOM | 254 | C | THR | A | 84 | 44.430 | -5.508 | -25.142 | 1.00 | 48.43 | A | C |
| ATOM | 255 | O | THR | A | 84 | 44.981 | -4.574 | -25.722 | 1.00 | 48.29 | A | O |
| ATOM | 256 | N | GLY | A | 85 | 45.083 | -6.381 | -24.376 | 1.00 | 48.56 | A | N |
| ATOM | 257 | CA | GLY | A | 85 | 46.512 | -6.262 | -24.154 | 1.00 | 46.86 | A | C |
| ATOM | 258 | C | GLY | A | 85 | 46.768 | -5.236 | -23.072 | 1.00 | 46.28 | A | C |
| ATOM | 259 | O | GLY | A | 85 | 47.845 | -4.649 | -23.007 | 1.00 | 45.26 | A | O |
| ATOM | 260 | N | SER | A | 86 | 45.765 | -5.024 | -22.221 | 1.00 | 47.33 | A | N |
| ATOM | 261 | CA | SER | A | 86 | 45.847 | -4.065 | -21.119 | 1.00 | 47.96 | A | C |
| ATOM | 262 | CB | SER | A | 86 | 44.451 | -3.773 | -20.572 | 1.00 | 48.49 | A | C |
| ATOM | 263 | OG | SER | A | 86 | 43.653 | -3.102 | -21.536 | 1.00 | 49.96 | A | O |
| ATOM | 264 | C | SER | A | 86 | 46.742 | -4.570 | -19.996 | 1.00 | 47.85 | A | C |
| ATOM | 265 | O | SER | A | 86 | 46.672 | -5.733 | -19.610 | 1.00 | 48.10 | A | O |
| ATOM | 266 | N | ALA | A | 87 | 47.579 | -3.684 | -19.468 | 1.00 | 47.70 | A | N |
| ATOM | 267 | CA | ALA | A | 87 | 48.500 | -4.051 | -18.404 | 1.00 | 47.59 | A | C |
| ATOM | 268 | CB | ALA | A | 87 | 49.796 | -3.274 | -18.561 | 1.00 | 47.10 | A | C |
| ATOM | 269 | C | ALA | A | 87 | 47.953 | -3.862 | -16.992 | 1.00 | 46.79 | A | C |
| ATOM | 270 | O | ALA | A | 87 | 47.413 | -2.813 | -16.642 | 1.00 | 47.39 | A | O |
| ATOM | 271 | N | TYR | A | 88 | 48.109 | -4.899 | -16.182 | 1.00 | 46.07 | A | N |
| ATOM | 272 | CA | TYR | A | 88 | 47.667 | -4.878 | -14.795 | 1.00 | 45.56 | A | C |
| ATOM | 273 | CB | TYR | A | 88 | 46.366 | -5.675 | -14.634 | 1.00 | 46.79 | A | C |
| ATOM | 274 | CG | TYR | A | 88 | 45.180 | -5.128 | -15.422 | 1.00 | 48.36 | A | C |
| ATOM | 275 | CD1 | TYR | A | 88 | 44.454 | -5.943 | -16.294 | 1.00 | 48.50 | A | C |
| ATOM | 276 | CE1 | TYR | A | 88 | 43.357 | -5.458 | -16.995 | 1.00 | 48.92 | A | C |
| ATOM | 277 | CD2 | TYR | A | 88 | 44.771 | -3.805 | -15.276 | 1.00 | 49.51 | A | C |
| ATOM | 278 | CE2 | TYR | A | 88 | 43.667 | -3.313 | -15.979 | 1.00 | 50.15 | A | C |
| ATOM | 279 | CZ | TYR | A | 88 | 42.970 | -4.146 | -16.831 | 1.00 | 49.10 | A | C |
| ATOM | 280 | OH | TYR | A | 88 | 41.886 | -3.645 | -17.513 | 1.00 | 49.70 | A | O |
| ATOM | 281 | C | TYR | A | 88 | 48.792 | -5.538 | -14.013 | 1.00 | 44.68 | A | C |
| ATOM | 282 | O | TYR | A | 88 | 49.827 | -5.865 | -14.585 | 1.00 | 43.82 | A | O |
| ATOM | 283 | N | ALA | A | 89 | 48.598 | -5.740 | -12.716 | 1.00 | 44.45 | A | N |
| ATOM | 284 | CA | ALA | A | 89 | 49.623 | -6.364 | -11.888 | 1.00 | 44.09 | A | C |
| ATOM | 285 | CB | ALA | A | 89 | 50.405 | -5.292 | -11.160 | 1.00 | 42.80 | A | C |
| ATOM | 286 | C | ALA | A | 89 | 48.945 | -7.276 | -10.883 | 1.00 | 44.48 | A | C |
| ATOM | 287 | O | ALA | A | 89 | 49.000 | -7.002 | -9.686 | 1.00 | 46.72 | A | O |
| ATOM | 288 | N | VAL | A | 90 | 48.320 | -8.358 | -11.355 | 1.00 | 44.07 | A | N |
| ATOM | 289 | CA | VAL | A | 90 | 47.590 | -9.272 | -10.471 | 1.00 | 43.45 | A | C |
| ATOM | 290 | CB | VAL | A | 90 | 47.063 | -10.519 | -11.239 | 1.00 | 44.21 | A | C |
| ATOM | 291 | CG1 | VAL | A | 90 | 47.670 | -11.800 | -10.649 | 1.00 | 44.40 | A | C |
| ATOM | 292 | CG2 | VAL | A | 90 | 45.516 | -10.568 | -11.179 | 1.00 | 44.04 | A | C |
| ATOM | 293 | C | VAL | A | 90 | 48.318 | -9.761 | -9.221 | 1.00 | 42.41 | A | C |
| ATOM | 294 | O | VAL | A | 90 | 49.482 | -10.157 | -9.268 | 1.00 | 42.12 | A | O |
| ATOM | 295 | N | LYS | A | 91 | 47.600 | -9.733 | -8.102 | 1.00 | 42.83 | A | N |

Figure 1-6

| | Atom Type | Resid | # | X | Y | Z | OCC | B | | |
|---|---|---|---|---|---|---|---|---|---|---|
| ATOM | 296 | CA | LYS A | 91 | 48.113 | -10.193 | -6.825 | 1.00 | 42.52 | A | C |
| ATOM | 297 | CB | LYS A | 91 | 47.525 | -9.310 | -5.718 | 1.00 | 43.45 | A | C |
| ATOM | 298 | CG | LYS A | 91 | 48.253 | -9.325 | -4.386 | 1.00 | 45.57 | A | C |
| ATOM | 299 | CD | LYS A | 91 | 47.688 | -8.229 | -3.471 | 1.00 | 47.80 | A | C |
| ATOM | 300 | CE | LYS A | 91 | 48.298 | -8.223 | -2.057 | 1.00 | 48.56 | A | C |
| ATOM | 301 | NZ | LYS A | 91 | 47.899 | -9.383 | -1.195 | 1.00 | 50.98 | A | N |
| ATOM | 302 | C | LYS A | 91 | 47.610 | -11.651 | -6.729 | 1.00 | 42.47 | A | C |
| ATOM | 303 | O | LYS A | 91 | 46.399 | -11.890 | -6.704 | 1.00 | 43.70 | A | O |
| ATOM | 304 | N | VAL A | 92 | 48.525 | -12.625 | -6.718 | 1.00 | 40.66 | A | N |
| ATOM | 305 | CA | VAL A | 92 | 48.138 | -14.039 | -6.639 | 1.00 | 38.59 | A | C |
| ATOM | 306 | CB | VAL A | 92 | 49.047 | -14.924 | -7.501 | 1.00 | 38.84 | A | C |
| ATOM | 307 | CG1 | VAL A | 92 | 48.477 | -16.338 | -7.589 | 1.00 | 37.81 | A | C |
| ATOM | 308 | CG2 | VAL A | 92 | 49.178 | -14.321 | -8.876 | 1.00 | 38.23 | A | C |
| ATOM | 309 | C | VAL A | 92 | 48.188 | -14.547 | -5.211 | 1.00 | 37.80 | A | C |
| ATOM | 310 | O | VAL A | 92 | 49.214 | -14.485 | -4.547 | 1.00 | 36.86 | A | O |
| ATOM | 311 | N | ILE A | 93 | 47.068 | -15.074 | -4.751 | 1.00 | 36.87 | A | N |
| ATOM | 312 | CA | ILE A | 93 | 46.963 | -15.563 | -3.392 | 1.00 | 36.52 | A | C |
| ATOM | 313 | CB | ILE A | 93 | 46.103 | -14.601 | -2.565 | 1.00 | 36.64 | A | C |
| ATOM | 314 | CG2 | ILE A | 93 | 46.141 | -14.981 | -1.080 | 1.00 | 35.96 | A | C |
| ATOM | 315 | CG1 | ILE A | 93 | 46.567 | -13.158 | -2.818 | 1.00 | 36.07 | A | C |
| ATOM | 316 | CD1 | ILE A | 93 | 45.533 | -12.105 | -2.462 | 1.00 | 37.93 | A | C |
| ATOM | 317 | C | ILE A | 93 | 46.290 | -16.918 | -3.401 | 1.00 | 38.31 | A | C |
| ATOM | 318 | O | ILE A | 93 | 45.160 | -17.054 | -3.862 | 1.00 | 38.43 | A | O |
| ATOM | 319 | N | PRO A | 94 | 46.976 | -17.955 | -2.913 | 1.00 | 39.15 | A | N |
| ATOM | 320 | CD | PRO A | 94 | 48.398 | -18.120 | -2.576 | 1.00 | 39.03 | A | C |
| ATOM | 321 | CA | PRO A | 94 | 46.277 | -19.241 | -2.935 | 1.00 | 40.13 | A | C |
| ATOM | 322 | CB | PRO A | 94 | 47.380 | -20.256 | -2.641 | 1.00 | 40.78 | A | C |
| ATOM | 323 | CG | PRO A | 94 | 48.413 | -19.464 | -1.922 | 1.00 | 39.26 | A | C |
| ATOM | 324 | C | PRO A | 94 | 45.128 | -19.290 | -1.929 | 1.00 | 41.73 | A | C |
| ATOM | 325 | O | PRO A | 94 | 45.126 | -18.586 | -0.919 | 1.00 | 41.83 | A | O |
| ATOM | 326 | N | GLN A | 95 | 44.140 | -20.118 | -2.238 | 1.00 | 43.51 | A | N |
| ATOM | 327 | CA | GLN A | 95 | 42.962 | -20.270 | -1.404 | 1.00 | 44.66 | A | C |
| ATOM | 328 | CB | GLN A | 95 | 41.870 | -20.999 | -2.188 | 1.00 | 43.55 | A | C |
| ATOM | 329 | CG | GLN A | 95 | 41.434 | -20.263 | -3.445 | 1.00 | 42.43 | A | C |
| ATOM | 330 | CD | GLN A | 95 | 40.172 | -19.438 | -3.254 | 1.00 | 42.57 | A | C |
| ATOM | 331 | OE1 | GLN A | 95 | 40.019 | -18.707 | -2.274 | 1.00 | 42.97 | A | O |
| ATOM | 332 | NE2 | GLN A | 95 | 39.268 | -19.539 | -4.213 | 1.00 | 41.54 | A | N |
| ATOM | 333 | C | GLN A | 95 | 43.322 | -21.047 | -0.154 | 1.00 | 46.79 | A | C |
| ATOM | 334 | O | GLN A | 95 | 42.675 | -20.906 | 0.887 | 1.00 | 45.25 | A | O |
| ATOM | 335 | N | SER A | 96 | 44.365 | -21.866 | -0.267 | 1.00 | 50.51 | A | N |
| ATOM | 336 | CA | SER A | 96 | 44.852 | -22.682 | 0.842 | 1.00 | 53.87 | A | C |
| ATOM | 337 | CB | SER A | 96 | 46.078 | -23.482 | 0.394 | 1.00 | 52.97 | A | C |
| ATOM | 338 | OG | SER A | 96 | 45.739 | -24.383 | -0.639 | 1.00 | 51.66 | A | O |
| ATOM | 339 | C | SER A | 96 | 45.220 | -21.822 | 2.051 | 1.00 | 56.53 | A | C |
| ATOM | 340 | O | SER A | 96 | 45.127 | -22.271 | 3.196 | 1.00 | 57.07 | A | O |
| ATOM | 341 | N | ARG A | 97 | 45.621 | -20.581 | 1.787 | 1.00 | 60.89 | A | N |
| ATOM | 342 | CA | ARG A | 97 | 46.035 | -19.658 | 2.834 | 1.00 | 64.49 | A | C |
| ATOM | 343 | CB | ARG A | 97 | 47.364 | -19.039 | 2.443 | 1.00 | 65.28 | A | C |
| ATOM | 344 | CG | ARG A | 97 | 47.969 | -19.657 | 1.211 | 1.00 | 65.79 | A | C |
| ATOM | 345 | CD | ARG A | 97 | 49.286 | -18.992 | 0.881 | 1.00 | 66.62 | A | C |
| ATOM | 346 | NE | ARG A | 97 | 50.240 | -19.066 | 1.983 | 1.00 | 67.13 | A | N |
| ATOM | 347 | CZ | ARG A | 97 | 51.515 | -18.697 | 1.890 | 1.00 | 67.01 | A | C |
| ATOM | 348 | NH1 | ARG A | 97 | 51.986 | -18.234 | 0.739 | 1.00 | 66.73 | A | N |
| ATOM | 349 | NH2 | ARG A | 97 | 52.319 | -18.781 | 2.948 | 1.00 | 67.38 | A | N |
| ATOM | 350 | C | ARG A | 97 | 45.055 | -18.535 | 3.134 | 1.00 | 67.02 | A | C |
| ATOM | 351 | O | ARG A | 97 | 45.418 | -17.551 | 3.769 | 1.00 | 68.07 | A | O |
| ATOM | 352 | N | VAL A | 98 | 43.819 | -18.661 | 2.679 | 1.00 | 69.49 | A | N |
| ATOM | 353 | CA | VAL A | 98 | 42.845 | -17.615 | 2.921 | 1.00 | 72.01 | A | C |
| ATOM | 354 | CB | VAL A | 98 | 42.343 | -17.013 | 1.609 | 1.00 | 71.98 | A | C |

Figure 1-7

| | | Atom Type | Resid | # | X | Y | Z | OCC | B | | |
|---|---|---|---|---|---|---|---|---|---|---|---|
| ATOM | 355 | CG1 | VAL A | 98 | 41.205 | -16.046 | 1.883 | 1.00 | 72.50 | A | C |
| ATOM | 356 | CG2 | VAL A | 98 | 43.479 | -16.316 | 0.900 | 1.00 | 72.60 | A | C |
| ATOM | 357 | C | VAL A | 98 | 41.665 | -18.193 | 3.654 | 1.00 | 73.96 | A | C |
| ATOM | 358 | O | VAL A | 98 | 41.151 | -17.597 | 4.596 | 1.00 | 74.10 | A | O |
| ATOM | 359 | N | ALA A | 99 | 41.234 | -19.363 | 3.207 | 1.00 | 76.78 | A | N |
| ATOM | 360 | CA | ALA A | 99 | 40.098 | -20.027 | 3.822 | 1.00 | 79.41 | A | C |
| ATOM | 361 | CB | ALA A | 99 | 39.598 | -21.151 | 2.925 | 1.00 | 79.53 | A | C |
| ATOM | 362 | C | ALA A | 99 | 40.508 | -20.578 | 5.177 | 1.00 | 80.96 | A | C |
| ATOM | 363 | O | ALA A | 99 | 39.667 | -20.772 | 6.060 | 1.00 | 81.10 | A | O |
| ATOM | 364 | N | LYS A | 100 | 41.808 | -20.809 | 5.338 | 1.00 | 82.91 | A | N |
| ATOM | 365 | CA | LYS A | 100 | 42.324 | -21.346 | 6.584 | 1.00 | 84.85 | A | C |
| ATOM | 366 | CB | LYS A | 100 | 43.643 | -22.085 | 6.332 | 1.00 | 84.95 | A | C |
| ATOM | 367 | CG | LYS A | 100 | 43.529 | -23.228 | 5.320 | 1.00 | 85.09 | A | C |
| ATOM | 368 | CD | LYS A | 100 | 42.617 | -24.361 | 5.801 | 1.00 | 84.99 | A | C |
| ATOM | 369 | CE | LYS A | 100 | 42.431 | -25.415 | 4.709 | 1.00 | 84.90 | A | C |
| ATOM | 370 | NZ | LYS A | 100 | 41.714 | -26.632 | 5.188 | 1.00 | 84.47 | A | N |
| ATOM | 371 | C | LYS A | 100 | 42.507 | -20.262 | 7.647 | 1.00 | 86.30 | A | C |
| ATOM | 372 | O | LYS A | 100 | 41.983 | -20.383 | 8.759 | 1.00 | 86.65 | A | O |
| ATOM | 373 | N | PRO A | 101 | 43.245 | -19.183 | 7.323 | 1.00 | 87.62 | A | N |
| ATOM | 374 | CD | PRO A | 101 | 44.022 | -18.926 | 6.094 | 1.00 | 88.00 | A | C |
| ATOM | 375 | CA | PRO A | 101 | 43.458 | -18.107 | 8.301 | 1.00 | 88.31 | A | C |
| ATOM | 376 | CB | PRO A | 101 | 44.734 | -17.438 | 7.797 | 1.00 | 88.37 | A | C |
| ATOM | 377 | CG | PRO A | 101 | 44.550 | -17.503 | 6.322 | 1.00 | 88.23 | A | C |
| ATOM | 378 | C | PRO A | 101 | 42.285 | -17.130 | 8.363 | 1.00 | 89.08 | A | C |
| ATOM | 379 | O | PRO A | 101 | 42.366 | -16.092 | 9.029 | 1.00 | 89.18 | A | O |
| ATOM | 380 | N | HIS A | 102 | 41.200 | -17.471 | 7.666 | 1.00 | 89.64 | A | N |
| ATOM | 381 | CA | HIS A | 102 | 40.003 | -16.632 | 7.619 | 1.00 | 89.82 | A | C |
| ATOM | 382 | CB | HIS A | 102 | 39.256 | -16.717 | 8.941 | 1.00 | 90.31 | A | C |
| ATOM | 383 | CG | HIS A | 102 | 39.037 | -18.124 | 9.385 | 1.00 | 90.76 | A | C |
| ATOM | 384 | CD2 | HIS A | 102 | 39.574 | -18.832 | 10.407 | 1.00 | 90.94 | A | C |
| ATOM | 385 | ND1 | HIS A | 102 | 38.257 | -19.010 | 8.672 | 1.00 | 90.71 | A | N |
| ATOM | 386 | CE1 | HIS A | 102 | 38.327 | -20.202 | 9.234 | 1.00 | 90.91 | A | C |
| ATOM | 387 | NE2 | HIS A | 102 | 39.121 | -20.122 | 10.289 | 1.00 | 91.04 | A | N |
| ATOM | 388 | C | HIS A | 102 | 40.426 | -15.212 | 7.321 | 1.00 | 89.25 | A | C |
| ATOM | 389 | O | HIS A | 102 | 39.834 | -14.246 | 7.809 | 1.00 | 89.33 | A | O |
| ATOM | 390 | N | GLN A | 103 | 41.483 | -15.112 | 6.519 | 1.00 | 88.45 | A | N |
| ATOM | 391 | CA | GLN A | 103 | 41.998 | -13.831 | 6.097 | 1.00 | 87.65 | A | C |
| ATOM | 392 | CB | GLN A | 103 | 43.403 | -13.956 | 5.495 | 1.00 | 88.19 | A | C |
| ATOM | 393 | CG | GLN A | 103 | 44.026 | -12.597 | 5.138 | 1.00 | 88.96 | A | C |
| ATOM | 394 | CD | GLN A | 103 | 45.384 | -12.705 | 4.461 | 1.00 | 89.41 | A | C |
| ATOM | 395 | OE1 | GLN A | 103 | 45.985 | -11.695 | 4.089 | 1.00 | 89.64 | A | O |
| ATOM | 396 | NE2 | GLN A | 103 | 45.872 | -13.930 | 4.297 | 1.00 | 89.79 | A | N |
| ATOM | 397 | C | GLN A | 103 | 41.013 | -13.361 | 5.041 | 1.00 | 86.57 | A | C |
| ATOM | 398 | O | GLN A | 103 | 41.289 | -12.428 | 4.293 | 1.00 | 87.38 | A | O |
| ATOM | 399 | N | ARG A | 104 | 39.871 | -14.041 | 4.962 | 1.00 | 84.45 | A | N |
| ATOM | 400 | CA | ARG A | 104 | 38.837 | -13.635 | 4.030 | 1.00 | 82.71 | A | C |
| ATOM | 401 | CB | ARG A | 104 | 37.587 | -14.511 | 4.170 | 1.00 | 84.01 | A | C |
| ATOM | 402 | CG | ARG A | 104 | 37.714 | -15.911 | 3.612 | 1.00 | 85.02 | A | C |
| ATOM | 403 | CD | ARG A | 104 | 36.487 | -16.775 | 3.916 | 1.00 | 85.64 | A | C |
| ATOM | 404 | NE | ARG A | 104 | 36.735 | -18.146 | 3.478 | 1.00 | 86.66 | A | N |
| ATOM | 405 | CZ | ARG A | 104 | 36.819 | -18.514 | 2.203 | 1.00 | 87.17 | A | C |
| ATOM | 406 | NH1 | ARG A | 104 | 36.657 | -17.613 | 1.241 | 1.00 | 87.64 | A | N |
| ATOM | 407 | NH2 | ARG A | 104 | 37.101 | -19.769 | 1.889 | 1.00 | 87.51 | A | N |
| ATOM | 408 | C | ARG A | 104 | 38.518 | -12.245 | 4.536 | 1.00 | 80.70 | A | C |
| ATOM | 409 | O | ARG A | 104 | 38.662 | -11.249 | 3.821 | 1.00 | 80.84 | A | O |
| ATOM | 410 | N | GLU A | 105 | 38.100 | -12.206 | 5.799 | 1.00 | 77.87 | A | N |
| ATOM | 411 | CA | GLU A | 105 | 37.755 | -10.972 | 6.480 | 1.00 | 74.97 | A | C |
| ATOM | 412 | CB | GLU A | 105 | 37.842 | -11.178 | 7.995 | 1.00 | 76.11 | A | C |
| ATOM | 413 | CG | GLU A | 105 | 36.900 | -12.251 | 8.567 | 1.00 | 77.47 | A | C |

Figure 1-8

| | | Atom Type | Resid | # | X | Y | Z | OCC | B | | |
|---|---|---|---|---|---|---|---|---|---|---|---|
| ATOM | 414 | CD | GLU A | 105 | 35.514 | -11.712 | 8.940 | 1.00 | 78.30 | A | C |
| ATOM | 415 | OE1 | GLU A | 105 | 35.431 | -10.789 | 9.786 | 1.00 | 78.79 | A | O |
| ATOM | 416 | OE2 | GLU A | 105 | 34.504 | -12.215 | 8.392 | 1.00 | 78.67 | A | O |
| ATOM | 417 | C | GLU A | 105 | 38.762 | -9.925 | 6.039 | 1.00 | 72.21 | A | C |
| ATOM | 418 | O | GLU A | 105 | 38.400 | -8.827 | 5.617 | 1.00 | 72.45 | A | O |
| ATOM | 419 | N | LYS A | 106 | 40.034 | -10.296 | 6.107 | 1.00 | 68.95 | A | N |
| ATOM | 420 | CA | LYS A | 106 | 41.118 | -9.400 | 5.732 | 1.00 | 65.62 | A | C |
| ATOM | 421 | CB | LYS A | 106 | 42.454 | -9.937 | 6.267 | 1.00 | 65.22 | A | C |
| ATOM | 422 | CG | LYS A | 106 | 43.594 | -8.957 | 6.093 | 1.00 | 65.21 | A | C |
| ATOM | 423 | CD | LYS A | 106 | 44.926 | -9.506 | 6.547 | 1.00 | 64.76 | A | C |
| ATOM | 424 | CE | LYS A | 106 | 46.018 | -8.477 | 6.272 | 1.00 | 64.33 | A | C |
| ATOM | 425 | NZ | LYS A | 106 | 47.394 | -9.005 | 6.477 | 1.00 | 64.51 | A | N |
| ATOM | 426 | C | LYS A | 106 | 41.221 | -9.158 | 4.222 | 1.00 | 63.40 | A | C |
| ATOM | 427 | O | LYS A | 106 | 41.363 | -8.016 | 3.780 | 1.00 | 62.06 | A | O |
| ATOM | 428 | N | ILE A | 107 | 41.140 | -10.227 | 3.437 | 1.00 | 60.81 | A | N |
| ATOM | 429 | CA | ILE A | 107 | 41.258 | -10.120 | 1.989 | 1.00 | 59.54 | A | C |
| ATOM | 430 | CB | ILE A | 107 | 41.665 | -11.492 | 1.361 | 1.00 | 59.24 | A | C |
| ATOM | 431 | CG2 | ILE A | 107 | 40.455 | -12.413 | 1.241 | 1.00 | 59.40 | A | C |
| ATOM | 432 | CG1 | ILE A | 107 | 42.319 | -11.263 | -0.006 | 1.00 | 59.59 | A | C |
| ATOM | 433 | CD1 | ILE A | 107 | 42.919 | -12.510 | -0.631 | 1.00 | 59.70 | A | C |
| ATOM | 434 | C | ILE A | 107 | 39.993 | -9.584 | 1.319 | 1.00 | 57.95 | A | C |
| ATOM | 435 | O | ILE A | 107 | 40.043 | -9.083 | 0.193 | 1.00 | 57.20 | A | O |
| ATOM | 436 | N | LEU A | 108 | 38.864 | -9.671 | 2.014 | 1.00 | 56.90 | A | N |
| ATOM | 437 | CA | LEU A | 108 | 37.603 | -9.176 | 1.469 | 1.00 | 55.99 | A | C |
| ATOM | 438 | CB | LEU A | 108 | 36.418 | -9.975 | 2.017 | 1.00 | 56.75 | A | C |
| ATOM | 439 | CG | LEU A | 108 | 36.268 | -11.410 | 1.507 | 1.00 | 57.70 | A | C |
| ATOM | 440 | CD1 | LEU A | 108 | 34.897 | -11.906 | 1.917 | 1.00 | 57.48 | A | C |
| ATOM | 441 | CD2 | LEU A | 108 | 36.412 | -11.485 | -0.019 | 1.00 | 57.01 | A | C |
| ATOM | 442 | C | LEU A | 108 | 37.394 | -7.702 | 1.777 | 1.00 | 54.56 | A | C |
| ATOM | 443 | O | LEU A | 108 | 36.888 | -6.960 | 0.939 | 1.00 | 53.68 | A | O |
| ATOM | 444 | N | ASN A | 109 | 37.769 | -7.278 | 2.981 | 1.00 | 52.59 | A | N |
| ATOM | 445 | CA | ASN A | 109 | 37.602 | -5.882 | 3.314 | 1.00 | 51.02 | A | C |
| ATOM | 446 | CB | ASN A | 109 | 37.760 | -5.648 | 4.839 | 1.00 | 52.25 | A | C |
| ATOM | 447 | CG | ASN A | 109 | 36.966 | -4.410 | 5.343 | 1.00 | 52.71 | A | C |
| ATOM | 448 | OD1 | ASN A | 109 | 35.775 | -4.230 | 5.022 | 1.00 | 53.36 | A | O |
| ATOM | 449 | ND2 | ASN A | 109 | 37.608 | -3.594 | 6.170 | 1.00 | 52.88 | A | N |
| ATOM | 450 | C | ASN A | 109 | 38.591 | -5.089 | 2.456 | 1.00 | 48.83 | A | C |
| ATOM | 451 | O | ASN A | 109 | 38.309 | -3.972 | 2.057 | 1.00 | 49.03 | A | O |
| ATOM | 452 | N | GLU A | 110 | 39.724 | -5.699 | 2.134 | 1.00 | 46.21 | A | N |
| ATOM | 453 | CA | GLU A | 110 | 40.755 | -5.078 | 1.300 | 1.00 | 44.55 | A | C |
| ATOM | 454 | CB | GLU A | 110 | 41.939 | -6.029 | 1.142 | 1.00 | 44.30 | A | C |
| ATOM | 455 | CG | GLU A | 110 | 43.025 | -5.522 | 0.204 | 1.00 | 45.19 | A | C |
| ATOM | 456 | CD | GLU A | 110 | 44.278 | -6.397 | 0.201 | 1.00 | 46.19 | A | C |
| ATOM | 457 | OE1 | GLU A | 110 | 44.625 | -6.924 | 1.277 | 1.00 | 47.29 | A | O |
| ATOM | 458 | OE2 | GLU A | 110 | 44.930 | -6.543 | -0.860 | 1.00 | 46.07 | A | O |
| ATOM | 459 | C | GLU A | 110 | 40.215 | -4.771 | -0.081 | 1.00 | 43.13 | A | C |
| ATOM | 460 | O | GLU A | 110 | 40.426 | -3.696 | -0.646 | 1.00 | 42.61 | A | O |
| ATOM | 461 | N | ILE A | 111 | 39.545 | -5.769 | -0.630 | 1.00 | 42.32 | A | N |
| ATOM | 462 | CA | ILE A | 111 | 38.939 | -5.681 | -1.947 | 1.00 | 41.04 | A | C |
| ATOM | 463 | CB | ILE A | 111 | 38.394 | -7.092 | -2.399 | 1.00 | 40.35 | A | C |
| ATOM | 464 | CG2 | ILE A | 111 | 37.537 | -6.949 | -3.648 | 1.00 | 39.91 | A | C |
| ATOM | 465 | CG1 | ILE A | 111 | 39.570 | -8.063 | -2.619 | 1.00 | 40.21 | A | C |
| ATOM | 466 | CD1 | ILE A | 111 | 39.157 | -9.519 | -2.709 | 1.00 | 39.31 | A | C |
| ATOM | 467 | C | ILE A | 111 | 37.790 | -4.686 | -1.798 | 1.00 | 40.31 | A | C |
| ATOM | 468 | O | ILE A | 111 | 37.605 | -3.794 | -2.648 | 1.00 | 37.59 | A | O |
| ATOM | 469 | N | GLU A | 112 | 37.038 | -4.833 | -0.703 | 1.00 | 39.55 | A | N |
| ATOM | 470 | CA | GLU A | 112 | 35.883 | -3.997 | -0.410 | 1.00 | 41.68 | A | C |
| ATOM | 471 | CB | GLU A | 112 | 34.977 | -4.711 | 0.613 | 1.00 | 45.41 | A | C |
| ATOM | 472 | CG | GLU A | 112 | 33.682 | -3.966 | 0.840 | 1.00 | 48.49 | A | C |

Figure 1-9

| | | Atom Type | Resid | # | X | Y | Z | OCC | B | | |
|---|---|---|---|---|---|---|---|---|---|---|---|
| ATOM | 473 | CD | GLU A | 112 | 33.191 | -4.122 | 2.241 | 1.00 | 51.18 | A | C |
| ATOM | 474 | OE1 | GLU A | 112 | 32.763 | -5.248 | 2.585 | 1.00 | 52.34 | A | O |
| ATOM | 475 | OE2 | GLU A | 112 | 33.248 | -3.124 | 2.996 | 1.00 | 52.55 | A | O |
| ATOM | 476 | C | GLU A | 112 | 36.240 | -2.598 | 0.091 | 1.00 | 40.43 | A | C |
| ATOM | 477 | O | GLU A | 112 | 35.341 | -1.822 | 0.408 | 1.00 | 40.88 | A | O |
| ATOM | 478 | N | LEU A | 113 | 37.522 | -2.265 | 0.166 | 1.00 | 40.83 | A | N |
| ATOM | 479 | CA | LEU A | 113 | 37.925 | -0.930 | 0.588 | 1.00 | 40.79 | A | C |
| ATOM | 480 | CB | LEU A | 113 | 38.837 | -0.972 | 1.847 | 1.00 | 40.49 | A | C |
| ATOM | 481 | CG | LEU A | 113 | 38.225 | -1.354 | 3.197 | 1.00 | 40.05 | A | C |
| ATOM | 482 | CD1 | LEU A | 113 | 39.259 | -1.241 | 4.249 | 1.00 | 40.11 | A | C |
| ATOM | 483 | CD2 | LEU A | 113 | 37.059 | -0.484 | 3.520 | 1.00 | 38.55 | A | C |
| ATOM | 484 | C | LEU A | 113 | 38.680 | -0.345 | -0.591 | 1.00 | 40.59 | A | C |
| ATOM | 485 | O | LEU A | 113 | 38.853 | 0.855 | -0.667 | 1.00 | 40.65 | A | O |
| ATOM | 486 | N | HIS A | 114 | 38.996 | -1.198 | -1.554 | 1.00 | 41.46 | A | N |
| ATOM | 487 | CA | HIS A | 114 | 39.651 | -0.799 | -2.780 | 1.00 | 42.37 | A | C |
| ATOM | 488 | CB | HIS A | 114 | 40.604 | -1.928 | -3.214 | 1.00 | 42.05 | A | C |
| ATOM | 489 | CG | HIS A | 114 | 42.011 | -1.473 | -3.501 | 1.00 | 42.31 | A | C |
| ATOM | 490 | CD2 | HIS A | 114 | 42.515 | -0.290 | -3.956 | 1.00 | 42.00 | A | C |
| ATOM | 491 | ND1 | HIS A | 114 | 43.095 | -2.304 | -3.298 | 1.00 | 41.11 | A | N |
| ATOM | 492 | CE1 | HIS A | 114 | 44.198 | -1.649 | -3.620 | 1.00 | 41.14 | A | C |
| ATOM | 493 | NE2 | HIS A | 114 | 43.875 | -0.431 | -4.024 | 1.00 | 42.56 | A | N |
| ATOM | 494 | C | HIS A | 114 | 38.634 | -0.490 | -3.864 | 1.00 | 44.53 | A | C |
| ATOM | 495 | O | HIS A | 114 | 38.990 | 0.190 | -4.782 | 1.00 | 44.77 | A | O |
| ATOM | 496 | N | ARG A | 115 | 37.409 | -1.016 | -3.709 | 1.00 | 46.57 | A | N |
| ATOM | 497 | CA | ARG A | 115 | 36.344 | -0.815 | -4.689 | 1.00 | 48.75 | A | C |
| ATOM | 498 | CB | ARG A | 115 | 35.051 | -1.444 | -4.212 | 1.00 | 51.13 | A | C |
| ATOM | 499 | CG | ARG A | 115 | 34.990 | -2.955 | -4.211 | 1.00 | 52.81 | A | C |
| ATOM | 500 | CD | ARG A | 115 | 34.647 | -3.510 | -5.559 | 1.00 | 53.75 | A | C |
| ATOM | 501 | NE | ARG A | 115 | 34.200 | -4.902 | -5.443 | 1.00 | 55.05 | A | N |
| ATOM | 502 | CZ | ARG A | 115 | 34.318 | -5.816 | -6.388 | 1.00 | 56.09 | A | C |
| ATOM | 503 | NH1 | ARG A | 115 | 34.877 | -5.495 | -7.548 | 1.00 | 56.70 | A | N |
| ATOM | 504 | NH2 | ARG A | 115 | 33.898 | -7.039 | -6.138 | 1.00 | 56.83 | A | N |
| ATOM | 505 | C | ARG A | 115 | 36.127 | 0.668 | -4.843 | 1.00 | 48.28 | A | C |
| ATOM | 506 | O | ARG A | 115 | 36.068 | 1.158 | -5.937 | 1.00 | 48.63 | A | O |
| ATOM | 507 | N | ASP A | 116 | 35.971 | 1.359 | -3.713 | 1.00 | 47.97 | A | N |
| ATOM | 508 | CA | ASP A | 116 | 35.767 | 2.827 | -3.676 | 1.00 | 46.98 | A | C |
| ATOM | 509 | CB | ASP A | 116 | 35.419 | 3.232 | -2.229 | 1.00 | 47.23 | A | C |
| ATOM | 510 | CG | ASP A | 116 | 34.959 | 4.676 | -2.102 | 1.00 | 47.60 | A | C |
| ATOM | 511 | OD1 | ASP A | 116 | 35.786 | 5.603 | -2.271 | 1.00 | 45.95 | A | O |
| ATOM | 512 | OD2 | ASP A | 116 | 33.757 | 4.884 | -1.839 | 1.00 | 47.72 | A | O |
| ATOM | 513 | C | ASP A | 116 | 36.973 | 3.688 | -4.177 | 1.00 | 45.82 | A | C |
| ATOM | 514 | O | ASP A | 116 | 36.908 | 4.324 | -5.235 | 1.00 | 45.30 | A | O |
| ATOM | 515 | N | LEU A | 117 | 38.047 | 3.701 | -3.382 | 1.00 | 45.28 | A | N |
| ATOM | 516 | CA | LEU A | 117 | 39.280 | 4.453 | -3.642 | 1.00 | 43.81 | A | C |
| ATOM | 517 | CB | LEU A | 117 | 40.458 | 3.710 | -3.022 | 1.00 | 42.36 | A | C |
| ATOM | 518 | CG | LEU A | 117 | 40.187 | 3.319 | -1.574 | 1.00 | 41.72 | A | C |
| ATOM | 519 | CD1 | LEU A | 117 | 41.401 | 2.627 | -1.025 | 1.00 | 41.60 | A | C |
| ATOM | 520 | CD2 | LEU A | 117 | 39.851 | 4.555 | -0.751 | 1.00 | 41.88 | A | C |
| ATOM | 521 | C | LEU A | 117 | 39.593 | 4.794 | -5.097 | 1.00 | 43.78 | A | C |
| ATOM | 522 | O | LEU A | 117 | 40.146 | 3.982 | -5.840 | 1.00 | 43.49 | A | O |
| ATOM | 523 | N | GLN A | 118 | 39.225 | 6.010 | -5.487 | 1.00 | 42.80 | A | N |
| ATOM | 524 | CA | GLN A | 118 | 39.447 | 6.512 | -6.836 | 1.00 | 43.05 | A | C |
| ATOM | 525 | CB | GLN A | 118 | 38.100 | 6.783 | -7.532 | 1.00 | 44.57 | A | C |
| ATOM | 526 | CG | GLN A | 118 | 37.348 | 5.534 | -8.008 | 1.00 | 45.86 | A | C |
| ATOM | 527 | CD | GLN A | 118 | 37.467 | 5.331 | -9.514 | 1.00 | 47.11 | A | C |
| ATOM | 528 | OE1 | GLN A | 118 | 37.029 | 6.182 | -10.299 | 1.00 | 46.56 | A | O |
| ATOM | 529 | NE2 | GLN A | 118 | 38.066 | 4.205 | -9.926 | 1.00 | 47.78 | A | N |
| ATOM | 530 | C | GLN A | 118 | 40.260 | 7.806 | -6.766 | 1.00 | 41.97 | A | C |
| ATOM | 531 | O | GLN A | 118 | 39.754 | 8.890 | -7.033 | 1.00 | 40.40 | A | O |

Figure 1-10

| | | Atom Type | Resid | # | X | Y | Z | OCC | B | | |
|---|---|---|---|---|---|---|---|---|---|---|---|
| ATOM | 532 | N | HIS A | 119 | 41.519 | 7.687 | -6.373 | 1.00 | 41.47 | A | N |
| ATOM | 533 | CA | HIS A | 119 | 42.389 | 8.842 | -6.310 | 1.00 | 41.05 | A | C |
| ATOM | 534 | CB | HIS A | 119 | 42.729 | 9.197 | -4.852 | 1.00 | 40.85 | A | C |
| ATOM | 535 | CG | HIS A | 119 | 43.623 | 10.398 | -4.702 | 1.00 | 41.88 | A | C |
| ATOM | 536 | CD2 | HIS A | 119 | 43.333 | 11.686 | -4.394 | 1.00 | 41.44 | A | C |
| ATOM | 537 | ND1 | HIS A | 119 | 44.996 | 10.343 | -4.849 | 1.00 | 41.59 | A | N |
| ATOM | 538 | CE1 | HIS A | 119 | 45.508 | 11.542 | -4.634 | 1.00 | 42.01 | A | C |
| ATOM | 539 | NE2 | HIS A | 119 | 44.521 | 12.375 | -4.356 | 1.00 | 41.50 | A | N |
| ATOM | 540 | C | HIS A | 119 | 43.650 | 8.592 | -7.120 | 1.00 | 39.68 | A | C |
| ATOM | 541 | O | HIS A | 119 | 44.178 | 7.472 | -7.182 | 1.00 | 36.68 | A | O |
| ATOM | 542 | N | ARG A | 120 | 44.115 | 9.694 | -7.700 | 1.00 | 38.97 | A | N |
| ATOM | 543 | CA | ARG A | 120 | 45.298 | 9.779 | -8.540 | 1.00 | 37.79 | A | C |
| ATOM | 544 | CB | ARG A | 120 | 45.524 | 11.260 | -8.869 | 1.00 | 39.69 | A | C |
| ATOM | 545 | CG | ARG A | 120 | 46.912 | 11.750 | -9.086 | 1.00 | 42.00 | A | C |
| ATOM | 546 | CD | ARG A | 120 | 46.915 | 13.254 | -8.779 | 1.00 | 44.02 | A | C |
| ATOM | 547 | NE | ARG A | 120 | 48.240 | 13.870 | -8.892 | 1.00 | 46.61 | A | N |
| ATOM | 548 | CZ | ARG A | 120 | 48.567 | 15.061 | -8.391 | 1.00 | 48.03 | A | C |
| ATOM | 549 | NH1 | ARG A | 120 | 47.660 | 15.773 | -7.726 | 1.00 | 49.55 | A | N |
| ATOM | 550 | NH2 | ARG A | 120 | 49.797 | 15.544 | -8.567 | 1.00 | 48.78 | A | N |
| ATOM | 551 | C | ARG A | 120 | 46.528 | 9.131 | -7.941 | 1.00 | 36.14 | A | C |
| ATOM | 552 | O | ARG A | 120 | 47.371 | 8.628 | -8.675 | 1.00 | 35.10 | A | O |
| ATOM | 553 | N | HIS A | 121 | 46.610 | 9.125 | -6.612 | 1.00 | 32.59 | A | N |
| ATOM | 554 | CA | HIS A | 121 | 47.742 | 8.528 | -5.903 | 1.00 | 30.25 | A | C |
| ATOM | 555 | CB | HIS A | 121 | 48.455 | 9.594 | -5.080 | 1.00 | 27.30 | A | C |
| ATOM | 556 | CG | HIS A | 121 | 49.069 | 10.666 | -5.913 | 1.00 | 27.79 | A | C |
| ATOM | 557 | CD2 | HIS A | 121 | 48.864 | 12.003 | -5.941 | 1.00 | 28.32 | A | C |
| ATOM | 558 | ND1 | HIS A | 121 | 50.007 | 10.403 | -6.888 | 1.00 | 29.24 | A | N |
| ATOM | 559 | CE1 | HIS A | 121 | 50.349 | 11.532 | -7.481 | 1.00 | 28.07 | A | C |
| ATOM | 560 | NE2 | HIS A | 121 | 49.670 | 12.517 | -6.924 | 1.00 | 27.80 | A | N |
| ATOM | 561 | C | HIS A | 121 | 47.347 | 7.362 | -4.999 | 1.00 | 28.96 | A | C |
| ATOM | 562 | O | HIS A | 121 | 47.842 | 7.243 | -3.887 | 1.00 | 27.21 | A | O |
| ATOM | 563 | N | ILE A | 122 | 46.459 | 6.511 | -5.502 | 1.00 | 28.90 | A | N |
| ATOM | 564 | CA | ILE A | 122 | 45.955 | 5.346 | -4.779 | 1.00 | 27.29 | A | C |
| ATOM | 565 | CB | ILE A | 122 | 44.517 | 5.587 | -4.319 | 1.00 | 25.37 | A | C |
| ATOM | 566 | CG2 | ILE A | 122 | 43.937 | 4.318 | -3.769 | 1.00 | 23.15 | A | C |
| ATOM | 567 | CG1 | ILE A | 122 | 44.467 | 6.756 | -3.336 | 1.00 | 23.61 | A | C |
| ATOM | 568 | CD1 | ILE A | 122 | 45.056 | 6.466 | -1.986 | 1.00 | 25.29 | A | C |
| ATOM | 569 | C | ILE A | 122 | 45.915 | 4.248 | -5.820 | 1.00 | 28.23 | A | C |
| ATOM | 570 | O | ILE A | 122 | 45.198 | 4.395 | -6.797 | 1.00 | 29.12 | A | O |
| ATOM | 571 | N | VAL A | 123 | 46.647 | 3.150 | -5.640 | 1.00 | 30.26 | A | N |
| ATOM | 572 | CA | VAL A | 123 | 46.634 | 2.107 | -6.678 | 1.00 | 31.12 | A | C |
| ATOM | 573 | CB | VAL A | 123 | 47.401 | 0.813 | -6.257 | 1.00 | 32.06 | A | C |
| ATOM | 574 | CG1 | VAL A | 123 | 47.455 | -0.152 | -7.414 | 1.00 | 31.84 | A | C |
| ATOM | 575 | CG2 | VAL A | 123 | 48.833 | 1.150 | -5.870 | 1.00 | 30.57 | A | C |
| ATOM | 576 | C | VAL A | 123 | 45.201 | 1.740 | -7.055 | 1.00 | 32.50 | A | C |
| ATOM | 577 | O | VAL A | 123 | 44.394 | 1.386 | -6.193 | 1.00 | 32.51 | A | O |
| ATOM | 578 | N | ARG A | 124 | 44.897 | 1.833 | -8.350 | 1.00 | 34.42 | A | N |
| ATOM | 579 | CA | ARG A | 124 | 43.562 | 1.518 | -8.854 | 1.00 | 36.21 | A | C |
| ATOM | 580 | CB | ARG A | 124 | 43.355 | 2.112 | -10.266 | 1.00 | 38.46 | A | C |
| ATOM | 581 | CG | ARG A | 124 | 43.790 | 1.184 | -11.408 | 1.00 | 42.42 | A | C |
| ATOM | 582 | CD | ARG A | 124 | 43.516 | 1.775 | -12.783 | 1.00 | 43.89 | A | C |
| ATOM | 583 | NE | ARG A | 124 | 43.513 | 0.757 | -13.833 | 1.00 | 46.27 | A | N |
| ATOM | 584 | CZ | ARG A | 124 | 43.112 | 0.987 | -15.081 | 1.00 | 47.65 | A | C |
| ATOM | 585 | NH1 | ARG A | 124 | 42.689 | 2.199 | -15.424 | 1.00 | 47.23 | A | N |
| ATOM | 586 | NH2 | ARG A | 124 | 43.114 | 0.009 | -15.985 | 1.00 | 48.11 | A | N |
| ATOM | 587 | C | ARG A | 124 | 43.228 | 0.016 | -8.866 | 1.00 | 34.57 | A | C |
| ATOM | 588 | O | ARG A | 124 | 43.941 | -0.811 | -9.451 | 1.00 | 35.60 | A | O |
| ATOM | 589 | N | PHE A | 125 | 42.134 | -0.312 | -8.191 | 1.00 | 32.08 | A | N |
| ATOM | 590 | CA | PHE A | 125 | 41.643 | -1.665 | -8.121 | 1.00 | 31.68 | A | C |

Figure 1-11

| | | Atom Type | Resid | # | X | Y | Z | OCC | B | | |
|---|---|---|---|---|---|---|---|---|---|---|---|
| ATOM | 591 | CB | PHE A | 125 | 40.688 | -1.808 | -6.939 | 1.00 | 29.07 | A | C |
| ATOM | 592 | CG | PHE A | 125 | 40.185 | -3.193 | -6.738 | 1.00 | 29.14 | A | C |
| ATOM | 593 | CD1 | PHE A | 125 | 40.744 | -4.010 | -5.765 | 1.00 | 28.19 | A | C |
| ATOM | 594 | CD2 | PHE A | 125 | 39.154 | -3.692 | -7.526 | 1.00 | 27.34 | A | C |
| ATOM | 595 | CE1 | PHE A | 125 | 40.276 | -5.309 | -5.583 | 1.00 | 28.06 | A | C |
| ATOM | 596 | CE2 | PHE A | 125 | 38.682 | -4.980 | -7.355 | 1.00 | 28.26 | A | C |
| ATOM | 597 | CZ | PHE A | 125 | 39.241 | -5.794 | -6.381 | 1.00 | 28.32 | A | C |
| ATOM | 598 | C | PHE A | 125 | 40.890 | -1.779 | -9.431 | 1.00 | 33.21 | A | C |
| ATOM | 599 | O | PHE A | 125 | 40.000 | -0.965 | -9.697 | 1.00 | 32.91 | A | O |
| ATOM | 600 | N | SER A | 126 | 41.275 | -2.744 | -10.268 | 1.00 | 35.74 | A | N |
| ATOM | 601 | CA | SER A | 126 | 40.631 | -2.955 | -11.567 | 1.00 | 37.77 | A | C |
| ATOM | 602 | CB | SER A | 126 | 41.559 | -2.529 | -12.714 | 1.00 | 38.70 | A | C |
| ATOM | 603 | OG | SER A | 126 | 41.041 | -2.965 | -13.977 | 1.00 | 40.02 | A | O |
| ATOM | 604 | C | SER A | 126 | 40.310 | -4.437 | -11.717 | 1.00 | 39.09 | A | C |
| ATOM | 605 | O | SER A | 126 | 41.134 | -5.200 | -12.218 | 1.00 | 42.09 | A | O |
| ATOM | 606 | N | HIS A | 127 | 39.121 | -4.830 | -11.260 | 1.00 | 38.18 | A | N |
| ATOM | 607 | CA | HIS A | 127 | 38.573 | -6.202 | -11.287 | 1.00 | 36.80 | A | C |
| ATOM | 608 | CB | HIS A | 127 | 38.239 | -6.652 | -12.723 | 1.00 | 35.65 | A | C |
| ATOM | 609 | CG | HIS A | 127 | 39.409 | -7.186 | -13.500 | 1.00 | 35.38 | A | C |
| ATOM | 610 | CD2 | HIS A | 127 | 39.736 | -8.450 | -13.868 | 1.00 | 35.04 | A | C |
| ATOM | 611 | ND1 | HIS A | 127 | 40.378 | -6.369 | -14.046 | 1.00 | 35.21 | A | N |
| ATOM | 612 | CE1 | HIS A | 127 | 41.246 | -7.103 | -14.717 | 1.00 | 34.79 | A | C |
| ATOM | 613 | NE2 | HIS A | 127 | 40.879 | -8.370 | -14.626 | 1.00 | 35.40 | A | N |
| ATOM | 614 | C | HIS A | 127 | 39.349 | -7.298 | -10.569 | 1.00 | 35.60 | A | C |
| ATOM | 615 | O | HIS A | 127 | 40.551 | -7.215 | -10.357 | 1.00 | 37.68 | A | O |
| ATOM | 616 | N | HIS A | 128 | 38.608 | -8.314 | -10.159 | 1.00 | 34.34 | A | N |
| ATOM | 617 | CA | HIS A | 128 | 39.168 | -9.427 | -9.431 | 1.00 | 31.91 | A | C |
| ATOM | 618 | CB | HIS A | 128 | 39.324 | -9.057 | -7.934 | 1.00 | 31.66 | A | C |
| ATOM | 619 | CG | HIS A | 128 | 38.170 | -9.485 | -7.070 | 1.00 | 30.41 | A | C |
| ATOM | 620 | CD2 | HIS A | 128 | 37.946 | -10.638 | -6.394 | 1.00 | 30.10 | A | C |
| ATOM | 621 | ND1 | HIS A | 128 | 37.041 | -8.712 | -6.881 | 1.00 | 29.46 | A | N |
| ATOM | 622 | CE1 | HIS A | 128 | 36.174 | -9.369 | -6.132 | 1.00 | 29.45 | A | C |
| ATOM | 623 | NE2 | HIS A | 128 | 36.699 | -10.542 | -5.824 | 1.00 | 30.83 | A | N |
| ATOM | 624 | C | HIS A | 128 | 38.246 | -10.638 | -9.579 | 1.00 | 32.34 | A | C |
| ATOM | 625 | O | HIS A | 128 | 37.034 | -10.485 | -9.699 | 1.00 | 33.58 | A | O |
| ATOM | 626 | N | PHE A | 129 | 38.814 | -11.840 | -9.575 | 1.00 | 32.34 | A | N |
| ATOM | 627 | CA | PHE A | 129 | 38.031 | -13.075 | -9.675 | 1.00 | 30.07 | A | C |
| ATOM | 628 | CB | PHE A | 129 | 37.719 | -13.413 | -11.143 | 1.00 | 31.49 | A | C |
| ATOM | 629 | CG | PHE A | 129 | 38.949 | -13.580 | -12.031 | 1.00 | 30.25 | A | C |
| ATOM | 630 | CD1 | PHE A | 129 | 39.871 | -14.602 | -11.797 | 1.00 | 30.10 | A | C |
| ATOM | 631 | CD2 | PHE A | 129 | 39.138 | -12.750 | -13.151 | 1.00 | 29.95 | A | C |
| ATOM | 632 | CE1 | PHE A | 129 | 40.950 | -14.800 | -12.663 | 1.00 | 29.95 | A | C |
| ATOM | 633 | CE2 | PHE A | 129 | 40.207 | -12.940 | -14.017 | 1.00 | 29.27 | A | C |
| ATOM | 634 | CZ | PHE A | 129 | 41.116 | -13.965 | -13.778 | 1.00 | 30.40 | A | C |
| ATOM | 635 | C | PHE A | 129 | 38.869 | -14.168 | -9.013 | 1.00 | 30.49 | A | C |
| ATOM | 636 | O | PHE A | 129 | 40.009 | -13.919 | -8.623 | 1.00 | 28.75 | A | O |
| ATOM | 637 | N | GLU A | 130 | 38.319 | -15.369 | -8.870 | 1.00 | 31.34 | A | N |
| ATOM | 638 | CA | GLU A | 130 | 39.064 | -16.448 | -8.224 | 1.00 | 32.69 | A | C |
| ATOM | 639 | CB | GLU A | 130 | 38.878 | -16.376 | -6.694 | 1.00 | 33.68 | A | C |
| ATOM | 640 | CG | GLU A | 130 | 37.433 | -16.247 | -6.195 | 1.00 | 34.27 | A | C |
| ATOM | 641 | CD | GLU A | 130 | 36.948 | -14.811 | -6.175 | 1.00 | 35.89 | A | C |
| ATOM | 642 | OE1 | GLU A | 130 | 35.721 | -14.573 | -6.113 | 1.00 | 38.12 | A | O |
| ATOM | 643 | OE2 | GLU A | 130 | 37.803 | -13.909 | -6.219 | 1.00 | 36.07 | A | O |
| ATOM | 644 | C | GLU A | 130 | 38.793 | -17.885 | -8.689 | 1.00 | 34.81 | A | C |
| ATOM | 645 | O | GLU A | 130 | 37.647 | -18.326 | -8.783 | 1.00 | 34.68 | A | O |
| ATOM | 646 | N | ASP A | 131 | 39.880 | -18.600 | -8.980 | 1.00 | 36.38 | A | N |
| ATOM | 647 | CA | ASP A | 131 | 39.840 | -20.003 | -9.389 | 1.00 | 38.68 | A | C |
| ATOM | 648 | CB | ASP A | 131 | 41.205 | -20.509 | -9.896 | 1.00 | 40.60 | A | C |
| ATOM | 649 | CG | ASP A | 131 | 41.589 | -19.972 | -11.270 | 1.00 | 43.42 | A | C |

Figure 1-12

| Atom Type | # | Resid |   |   | X | Y | Z | OCC | B |   |   |
|---|---|---|---|---|---|---|---|---|---|---|---|
| ATOM | 650 | OD1 | ASP | A 131 | 40.711 | -19.826 | -12.148 | 1.00 | 44.60 | A | O |
| ATOM | 651 | OD2 | ASP | A 131 | 42.796 | -19.720 | -11.483 | 1.00 | 44.76 | A | O |
| ATOM | 652 | C | ASP | A 131 | 39.562 | -20.774 | -8.117 | 1.00 | 38.45 | A | C |
| ATOM | 653 | O | ASP | A 131 | 39.402 | -20.198 | -7.042 | 1.00 | 36.91 | A | O |
| ATOM | 654 | N | ALA | A 132 | 39.556 | -22.093 | -8.245 | 1.00 | 40.18 | A | N |
| ATOM | 655 | CA | ALA | A 132 | 39.325 | -22.974 | -7.117 | 1.00 | 40.53 | A | C |
| ATOM | 656 | CB | ALA | A 132 | 38.781 | -24.302 | -7.609 | 1.00 | 41.17 | A | C |
| ATOM | 657 | C | ALA | A 132 | 40.623 | -23.202 | -6.348 | 1.00 | 41.79 | A | C |
| ATOM | 658 | O | ALA | A 132 | 40.737 | -24.165 | -5.598 | 1.00 | 41.35 | A | O |
| ATOM | 659 | N | ASP | A 133 | 41.612 | -22.332 | -6.529 | 1.00 | 42.35 | A | N |
| ATOM | 660 | CA | ASP | A 133 | 42.876 | -22.521 | -5.818 | 1.00 | 42.95 | A | C |
| ATOM | 661 | CB | ASP | A 133 | 43.730 | -23.580 | -6.523 | 1.00 | 44.65 | A | C |
| ATOM | 662 | CG | ASP | A 133 | 43.777 | -23.389 | -8.035 | 1.00 | 46.66 | A | C |
| ATOM | 663 | OD1 | ASP | A 133 | 43.739 | -22.222 | -8.492 | 1.00 | 46.56 | A | O |
| ATOM | 664 | OD2 | ASP | A 133 | 43.865 | -24.414 | -8.759 | 1.00 | 47.46 | A | O |
| ATOM | 665 | C | ASP | A 133 | 43.711 | -21.267 | -5.606 | 1.00 | 41.22 | A | C |
| ATOM | 666 | O | ASP | A 133 | 44.646 | -21.280 | -4.799 | 1.00 | 42.04 | A | O |
| ATOM | 667 | N | ASN | A 134 | 43.375 | -20.200 | -6.332 | 1.00 | 39.00 | A | N |
| ATOM | 668 | CA | ASN | A 134 | 44.075 | -18.920 | -6.232 | 1.00 | 36.55 | A | C |
| ATOM | 669 | CB | ASN | A 134 | 45.174 | -18.794 | -7.295 | 1.00 | 36.53 | A | C |
| ATOM | 670 | CG | ASN | A 134 | 46.395 | -19.644 | -6.993 | 1.00 | 36.96 | A | C |
| ATOM | 671 | OD1 | ASN | A 134 | 46.881 | -19.679 | -5.864 | 1.00 | 40.06 | A | O |
| ATOM | 672 | ND2 | ASN | A 134 | 46.911 | -20.317 | -8.010 | 1.00 | 36.32 | A | N |
| ATOM | 673 | C | ASN | A 134 | 43.132 | -17.742 | -6.411 | 1.00 | 35.38 | A | C |
| ATOM | 674 | O | ASN | A 134 | 42.240 | -17.769 | -7.247 | 1.00 | 33.11 | A | O |
| ATOM | 675 | N | ILE | A 135 | 43.338 | -16.699 | -5.618 | 1.00 | 33.98 | A | N |
| ATOM | 676 | CA | ILE | A 135 | 42.534 | -15.501 | -5.748 | 1.00 | 31.08 | A | C |
| ATOM | 677 | CB | ILE | A 135 | 42.276 | -14.855 | -4.376 | 1.00 | 31.48 | A | C |
| ATOM | 678 | CG2 | ILE | A 135 | 41.469 | -13.565 | -4.536 | 1.00 | 29.64 | A | C |
| ATOM | 679 | CG1 | ILE | A 135 | 41.553 | -15.861 | -3.480 | 1.00 | 30.78 | A | C |
| ATOM | 680 | CD1 | ILE | A 135 | 41.192 | -15.337 | -2.125 | 1.00 | 32.19 | A | C |
| ATOM | 681 | C | ILE | A 135 | 43.325 | -14.540 | -6.635 | 1.00 | 30.64 | A | C |
| ATOM | 682 | O | ILE | A 135 | 44.514 | -14.314 | -6.412 | 1.00 | 32.14 | A | O |
| ATOM | 683 | N | TYR | A 136 | 42.676 | -13.995 | -7.659 | 1.00 | 29.38 | A | N |
| ATOM | 684 | CA | TYR | A 136 | 43.349 | -13.066 | -8.562 | 1.00 | 27.91 | A | C |
| ATOM | 685 | CB | TYR | A 136 | 43.187 | -13.504 | -10.016 | 1.00 | 27.05 | A | C |
| ATOM | 686 | CG | TYR | A 136 | 43.688 | -14.899 | -10.244 | 1.00 | 27.97 | A | C |
| ATOM | 687 | CD1 | TYR | A 136 | 42.864 | -16.004 | -9.992 | 1.00 | 28.97 | A | C |
| ATOM | 688 | CE1 | TYR | A 136 | 43.338 | -17.291 | -10.116 | 1.00 | 28.35 | A | C |
| ATOM | 689 | CD2 | TYR | A 136 | 45.011 | -15.129 | -10.630 | 1.00 | 28.43 | A | C |
| ATOM | 690 | CE2 | TYR | A 136 | 45.498 | -16.417 | -10.757 | 1.00 | 29.44 | A | C |
| ATOM | 691 | CZ | TYR | A 136 | 44.650 | -17.493 | -10.497 | 1.00 | 28.81 | A | C |
| ATOM | 692 | OH | TYR | A 136 | 45.091 | -18.782 | -10.616 | 1.00 | 30.93 | A | O |
| ATOM | 693 | C | TYR | A 136 | 42.835 | -11.656 | -8.438 | 1.00 | 26.66 | A | C |
| ATOM | 694 | O | TYR | A 136 | 41.685 | -11.389 | -8.758 | 1.00 | 25.62 | A | O |
| ATOM | 695 | N | ILE | A 137 | 43.695 | -10.756 | -7.975 | 1.00 | 27.32 | A | N |
| ATOM | 696 | CA | ILE | A 137 | 43.333 | -9.345 | -7.850 | 1.00 | 29.57 | A | C |
| ATOM | 697 | CB | ILE | A 137 | 43.715 | -8.757 | -6.487 | 1.00 | 27.71 | A | C |
| ATOM | 698 | CG2 | ILE | A 137 | 43.007 | -7.447 | -6.300 | 1.00 | 27.09 | A | C |
| ATOM | 699 | CG1 | ILE | A 137 | 43.399 | -9.746 | -5.352 | 1.00 | 27.62 | A | C |
| ATOM | 700 | CD1 | ILE | A 137 | 41.977 | -9.791 | -4.894 | 1.00 | 26.28 | A | C |
| ATOM | 701 | C | ILE | A 137 | 44.100 | -8.542 | -8.890 | 1.00 | 28.10 | A | C |
| ATOM | 702 | O | ILE | A 137 | 45.314 | -8.359 | -8.784 | 1.00 | 29.41 | A | O |
| ATOM | 703 | N | PHE | A 138 | 43.389 | -8.031 | -9.880 | 1.00 | 28.00 | A | N |
| ATOM | 704 | CA | PHE | A 138 | 44.039 | -7.243 | -10.917 | 1.00 | 28.68 | A | C |
| ATOM | 705 | CB | PHE | A 138 | 43.336 | -7.402 | -12.250 | 1.00 | 28.93 | A | C |
| ATOM | 706 | CG | PHE | A 138 | 43.301 | -8.802 | -12.747 | 1.00 | 28.99 | A | C |
| ATOM | 707 | CD1 | PHE | A 138 | 42.421 | -9.725 | -12.201 | 1.00 | 29.77 | A | C |
| ATOM | 708 | CD2 | PHE | A 138 | 44.200 | -9.221 | -13.721 | 1.00 | 29.33 | A | C |

Figure 1-13

|  |  | Atom Type | Resid | # | X | Y | Z | OCC | B |  |  |
|---|---|---|---|---|---|---|---|---|---|---|---|
| ATOM | 709 | CE1 | PHE A | 138 | 42.414 | -11.029 | -12.631 | 1.00 | 30.52 | A | C |
| ATOM | 710 | CE2 | PHE A | 138 | 44.199 | -10.523 | -14.152 | 1.00 | 29.17 | A | C |
| ATOM | 711 | CZ | PHE A | 138 | 43.310 | -11.434 | -13.595 | 1.00 | 30.49 | A | C |
| ATOM | 712 | C | PHE A | 138 | 44.020 | -5.794 | -10.532 | 1.00 | 27.37 | A | C |
| ATOM | 713 | O | PHE A | 138 | 42.951 | -5.227 | -10.297 | 1.00 | 27.81 | A | O |
| ATOM | 714 | N | LEU A | 139 | 45.204 | -5.200 | -10.453 | 1.00 | 28.58 | A | N |
| ATOM | 715 | CA | LEU A | 139 | 45.297 | -3.810 | -10.058 | 1.00 | 29.93 | A | C |
| ATOM | 716 | CB | LEU A | 139 | 46.093 | -3.683 | -8.759 | 1.00 | 29.16 | A | C |
| ATOM | 717 | CG | LEU A | 139 | 45.526 | -4.223 | -7.444 | 1.00 | 29.47 | A | C |
| ATOM | 718 | CD1 | LEU A | 139 | 46.308 | -3.585 | -6.307 | 1.00 | 29.97 | A | C |
| ATOM | 719 | CD2 | LEU A | 139 | 44.071 | -3.904 | -7.299 | 1.00 | 29.94 | A | C |
| ATOM | 720 | C | LEU A | 139 | 46.001 | -3.085 | -11.173 | 1.00 | 31.78 | A | C |
| ATOM | 721 | O | LEU A | 139 | 46.297 | -3.693 | -12.205 | 1.00 | 31.44 | A | O |
| ATOM | 722 | N | GLU A | 140 | 46.245 | -1.787 | -10.995 | 1.00 | 34.04 | A | N |
| ATOM | 723 | CA | GLU A | 140 | 46.961 | -1.050 | -12.034 | 1.00 | 35.50 | A | C |
| ATOM | 724 | CB | GLU A | 140 | 46.722 | 0.453 | -11.942 | 1.00 | 36.77 | A | C |
| ATOM | 725 | CG | GLU A | 140 | 47.237 | 1.120 | -10.713 | 1.00 | 37.95 | A | C |
| ATOM | 726 | CD | GLU A | 140 | 47.408 | 2.607 | -10.943 | 1.00 | 39.18 | A | C |
| ATOM | 727 | OE1 | GLU A | 140 | 48.306 | 2.959 | -11.738 | 1.00 | 38.50 | A | O |
| ATOM | 728 | OE2 | GLU A | 140 | 46.650 | 3.415 | -10.349 | 1.00 | 39.85 | A | O |
| ATOM | 729 | C | GLU A | 140 | 48.457 | -1.339 | -11.920 | 1.00 | 35.97 | A | C |
| ATOM | 730 | O | GLU A | 140 | 48.937 | -1.755 | -10.870 | 1.00 | 34.83 | A | O |
| ATOM | 731 | N | LEU A | 141 | 49.191 | -1.118 | -13.004 | 1.00 | 37.27 | A | N |
| ATOM | 732 | CA | LEU A | 141 | 50.617 | -1.394 | -13.007 | 1.00 | 38.26 | A | C |
| ATOM | 733 | CB | LEU A | 141 | 51.012 | -2.078 | -14.313 | 1.00 | 39.95 | A | C |
| ATOM | 734 | CG | LEU A | 141 | 52.492 | -2.405 | -14.483 | 1.00 | 39.80 | A | C |
| ATOM | 735 | CD1 | LEU A | 141 | 52.943 | -3.433 | -13.462 | 1.00 | 40.20 | A | C |
| ATOM | 736 | CD2 | LEU A | 141 | 52.685 | -2.928 | -15.883 | 1.00 | 39.32 | A | C |
| ATOM | 737 | C | LEU A | 141 | 51.548 | -0.213 | -12.775 | 1.00 | 38.21 | A | C |
| ATOM | 738 | O | LEU A | 141 | 51.604 | 0.751 | -13.550 | 1.00 | 37.62 | A | O |
| ATOM | 739 | N | CYS A | 142 | 52.285 | -0.325 | -11.682 | 1.00 | 37.84 | A | N |
| ATOM | 740 | CA | CYS A | 142 | 53.272 | 0.656 | -11.296 | 1.00 | 38.52 | A | C |
| ATOM | 741 | CB | CYS A | 142 | 53.124 | 0.968 | -9.808 | 1.00 | 39.22 | A | C |
| ATOM | 742 | SG | CYS A | 142 | 51.524 | 1.701 | -9.360 | 1.00 | 40.97 | A | S |
| ATOM | 743 | C | CYS A | 142 | 54.550 | -0.118 | -11.610 | 1.00 | 38.03 | A | C |
| ATOM | 744 | O | CYS A | 142 | 55.186 | -0.713 | -10.734 | 1.00 | 36.92 | A | O |
| ATOM | 745 | N | SER A | 143 | 54.891 | -0.119 | -12.896 | 1.00 | 38.05 | A | N |
| ATOM | 746 | CA | SER A | 143 | 56.037 | -0.844 | -13.422 | 1.00 | 39.78 | A | C |
| ATOM | 747 | CB | SER A | 143 | 56.201 | -0.506 | -14.888 | 1.00 | 39.75 | A | C |
| ATOM | 748 | OG | SER A | 143 | 57.088 | -1.420 | -15.483 | 1.00 | 41.10 | A | O |
| ATOM | 749 | C | SER A | 143 | 57.396 | -0.709 | -12.743 | 1.00 | 41.16 | A | C |
| ATOM | 750 | O | SER A | 143 | 58.336 | -1.439 | -13.083 | 1.00 | 41.96 | A | O |
| ATOM | 751 | N | ARG A | 144 | 57.500 | 0.205 | -11.786 | 1.00 | 43.22 | A | N |
| ATOM | 752 | CA | ARG A | 144 | 58.753 | 0.442 | -11.077 | 1.00 | 45.21 | A | C |
| ATOM | 753 | CB | ARG A | 144 | 58.981 | 1.944 | -10.954 | 1.00 | 46.15 | A | C |
| ATOM | 754 | CG | ARG A | 144 | 59.204 | 2.615 | -12.283 | 1.00 | 46.31 | A | C |
| ATOM | 755 | CD | ARG A | 144 | 60.628 | 2.396 | -12.727 | 1.00 | 48.30 | A | C |
| ATOM | 756 | NE | ARG A | 144 | 60.728 | 2.232 | -14.167 | 1.00 | 49.18 | A | N |
| ATOM | 757 | CZ | ARG A | 144 | 60.377 | 3.154 | -15.053 | 1.00 | 50.13 | A | C |
| ATOM | 758 | NH1 | ARG A | 144 | 59.904 | 4.329 | -14.656 | 1.00 | 50.23 | A | N |
| ATOM | 759 | NH2 | ARG A | 144 | 60.480 | 2.889 | -16.346 | 1.00 | 50.89 | A | N |
| ATOM | 760 | C | ARG A | 144 | 58.845 | -0.210 | -9.698 | 1.00 | 46.12 | A | C |
| ATOM | 761 | O | ARG A | 144 | 59.780 | 0.070 | -8.937 | 1.00 | 46.71 | A | O |
| ATOM | 762 | N | LYS A | 145 | 57.886 | -1.084 | -9.389 | 1.00 | 47.14 | A | N |
| ATOM | 763 | CA | LYS A | 145 | 57.839 | -1.793 | -8.104 | 1.00 | 47.29 | A | C |
| ATOM | 764 | CB | LYS A | 145 | 59.103 | -2.660 | -7.939 | 1.00 | 48.89 | A | C |
| ATOM | 765 | CG | LYS A | 145 | 59.029 | -3.963 | -8.750 | 1.00 | 49.00 | A | C |
| ATOM | 766 | CD | LYS A | 145 | 60.331 | -4.752 | -8.806 | 1.00 | 49.69 | A | C |
| ATOM | 767 | CE | LYS A | 145 | 61.261 | -4.180 | -9.849 | 1.00 | 50.43 | A | C |

Figure 1-14

| | | Atom Type | Resid | # | X | Y | Z | OCC | B | | |
|---|---|---|---|---|---|---|---|---|---|---|---|
| ATOM | 768 | NZ | LYS A | 145 | 62.349 | -5.126 | -10.212 | 1.00 | 50.32 | A | N |
| ATOM | 769 | C | LYS A | 145 | 57.630 | -0.849 | -6.905 | 1.00 | 47.08 | A | C |
| ATOM | 770 | O | LYS A | 145 | 57.171 | 0.287 | -7.080 | 1.00 | 46.31 | A | O |
| ATOM | 771 | N | SER A | 146 | 57.955 | -1.318 | -5.699 | 1.00 | 47.57 | A | N |
| ATOM | 772 | CA | SER A | 146 | 57.766 | -0.525 | -4.479 | 1.00 | 47.75 | A | C |
| ATOM | 773 | CB | SER A | 146 | 57.646 | -1.449 | -3.277 | 1.00 | 47.91 | A | C |
| ATOM | 774 | OG | SER A | 146 | 58.803 | -2.250 | -3.166 | 1.00 | 49.50 | A | O |
| ATOM | 775 | C | SER A | 146 | 58.881 | 0.475 | -4.221 | 1.00 | 47.69 | A | C |
| ATOM | 776 | O | SER A | 146 | 59.991 | 0.305 | -4.713 | 1.00 | 48.71 | A | O |
| ATOM | 777 | N | LEU A | 147 | 58.591 | 1.525 | -3.455 | 1.00 | 45.91 | A | N |
| ATOM | 778 | CA | LEU A | 147 | 59.615 | 2.518 | -3.148 | 1.00 | 44.52 | A | C |
| ATOM | 779 | CB | LEU A | 147 | 58.984 | 3.791 | -2.569 | 1.00 | 44.46 | A | C |
| ATOM | 780 | CG | LEU A | 147 | 59.790 | 5.095 | -2.640 | 1.00 | 44.29 | A | C |
| ATOM | 781 | CD1 | LEU A | 147 | 58.862 | 6.251 | -2.339 | 1.00 | 45.12 | A | C |
| ATOM | 782 | CD2 | LEU A | 147 | 60.945 | 5.091 | -1.668 | 1.00 | 43.96 | A | C |
| ATOM | 783 | C | LEU A | 147 | 60.601 | 1.888 | -2.154 | 1.00 | 44.45 | A | C |
| ATOM | 784 | O | LEU A | 147 | 61.447 | 2.563 | -1.566 | 1.00 | 42.67 | A | O |
| ATOM | 785 | N | ALA A | 148 | 60.476 | 0.574 | -1.981 | 1.00 | 44.69 | A | N |
| ATOM | 786 | CA | ALA A | 148 | 61.363 | -0.182 | -1.107 | 1.00 | 44.14 | A | C |
| ATOM | 787 | CB | ALA A | 148 | 60.632 | -1.370 | -0.521 | 1.00 | 44.04 | A | C |
| ATOM | 788 | C | ALA A | 148 | 62.539 | -0.644 | -1.969 | 1.00 | 43.31 | A | C |
| ATOM | 789 | O | ALA A | 148 | 63.655 | -0.822 | -1.478 | 1.00 | 42.63 | A | O |
| ATOM | 790 | N | HIS A | 149 | 62.283 | -0.847 | -3.260 | 1.00 | 44.05 | A | N |
| ATOM | 791 | CA | HIS A | 149 | 63.344 | -1.246 | -4.190 | 1.00 | 46.01 | A | C |
| ATOM | 792 | CB | HIS A | 149 | 62.771 | -1.882 | -5.465 | 1.00 | 46.24 | A | C |
| ATOM | 793 | CG | HIS A | 149 | 62.466 | -3.342 | -5.323 | 1.00 | 48.26 | A | C |
| ATOM | 794 | CD2 | HIS A | 149 | 61.304 | -4.029 | -5.445 | 1.00 | 49.22 | A | C |
| ATOM | 795 | ND1 | HIS A | 149 | 63.426 | -4.273 | -4.977 | 1.00 | 49.11 | A | N |
| ATOM | 796 | CE1 | HIS A | 149 | 62.867 | -5.469 | -4.888 | 1.00 | 49.99 | A | C |
| ATOM | 797 | NE2 | HIS A | 149 | 61.580 | -5.349 | -5.168 | 1.00 | 49.84 | A | N |
| ATOM | 798 | C | HIS A | 149 | 64.137 | -0.002 | -4.533 | 1.00 | 45.35 | A | C |
| ATOM | 799 | O | HIS A | 149 | 65.348 | -0.067 | -4.754 | 1.00 | 45.70 | A | O |
| ATOM | 800 | N | ILE A | 150 | 63.441 | 1.131 | -4.564 | 1.00 | 45.23 | A | N |
| ATOM | 801 | CA | ILE A | 150 | 64.062 | 2.416 | -4.844 | 1.00 | 46.62 | A | C |
| ATOM | 802 | CB | ILE A | 150 | 63.026 | 3.555 | -4.983 | 1.00 | 46.71 | A | C |
| ATOM | 803 | CG2 | ILE A | 150 | 63.728 | 4.903 | -5.015 | 1.00 | 46.07 | A | C |
| ATOM | 804 | CG1 | ILE A | 150 | 62.196 | 3.376 | -6.240 | 1.00 | 46.22 | A | C |
| ATOM | 805 | CD1 | ILE A | 150 | 61.176 | 4.473 | -6.414 | 1.00 | 47.74 | A | C |
| ATOM | 806 | C | ILE A | 150 | 64.985 | 2.823 | -3.707 | 1.00 | 47.50 | A | C |
| ATOM | 807 | O | ILE A | 150 | 66.094 | 3.294 | -3.945 | 1.00 | 47.55 | A | O |
| ATOM | 808 | N | TRP A | 151 | 64.535 | 2.646 | -2.468 | 1.00 | 48.57 | A | N |
| ATOM | 809 | CA | TRP A | 151 | 65.357 | 3.064 | -1.354 | 1.00 | 50.58 | A | C |
| ATOM | 810 | CB | TRP A | 151 | 64.537 | 3.116 | -0.050 | 1.00 | 50.83 | A | C |
| ATOM | 811 | CG | TRP A | 151 | 64.721 | 1.999 | 0.892 | 1.00 | 51.14 | A | C |
| ATOM | 812 | CD2 | TRP A | 151 | 65.348 | 2.057 | 2.184 | 1.00 | 50.75 | A | C |
| ATOM | 813 | CE2 | TRP A | 151 | 65.228 | 0.767 | 2.756 | 1.00 | 51.04 | A | C |
| ATOM | 814 | CE3 | TRP A | 151 | 65.991 | 3.066 | 2.910 | 1.00 | 49.83 | A | C |
| ATOM | 815 | CD1 | TRP A | 151 | 64.274 | 0.721 | 0.738 | 1.00 | 51.40 | A | C |
| ATOM | 816 | NE1 | TRP A | 151 | 64.572 | -0.026 | 1.856 | 1.00 | 51.39 | A | N |
| ATOM | 817 | CZ2 | TRP A | 151 | 65.734 | 0.469 | 4.031 | 1.00 | 50.95 | A | C |
| ATOM | 818 | CZ3 | TRP A | 151 | 66.486 | 2.764 | 4.165 | 1.00 | 49.87 | A | C |
| ATOM | 819 | CH2 | TRP A | 151 | 66.355 | 1.480 | 4.716 | 1.00 | 50.37 | A | C |
| ATOM | 820 | C | TRP A | 151 | 66.623 | 2.245 | -1.226 | 1.00 | 52.25 | A | C |
| ATOM | 821 | O | TRP A | 151 | 67.489 | 2.566 | -0.426 | 1.00 | 51.60 | A | O |
| ATOM | 822 | N | LYS A | 152 | 66.747 | 1.178 | -2.002 | 1.00 | 54.88 | A | N |
| ATOM | 823 | CA | LYS A | 152 | 68.004 | 0.452 | -1.955 | 1.00 | 57.22 | A | C |
| ATOM | 824 | CB | LYS A | 152 | 67.890 | -1.004 | -2.365 | 1.00 | 58.06 | A | C |
| ATOM | 825 | CG | LYS A | 152 | 69.279 | -1.643 | -2.429 | 1.00 | 59.58 | A | C |
| ATOM | 826 | CD | LYS A | 152 | 69.269 | -3.156 | -2.584 | 1.00 | 60.73 | A | C |

Figure 1-15

| | | Atom Type | Resid | # | X | Y | Z | OCC | B | | |
|---|---|---|---|---|---|---|---|---|---|---|---|
| ATOM | 827 | CE | LYS A | 152 | 68.845 | -3.867 | -1.304 | 1.00 | 61.82 | A | C |
| ATOM | 828 | NZ | LYS A | 152 | 68.902 | -5.367 | -1.413 | 1.00 | 62.43 | A | N |
| ATOM | 829 | C | LYS A | 152 | 68.817 | 1.170 | -3.023 | 1.00 | 58.27 | A | C |
| ATOM | 830 | O | LYS A | 152 | 69.863 | 1.765 | -2.738 | 1.00 | 58.94 | A | O |
| ATOM | 831 | N | ALA A | 153 | 68.307 | 1.120 | -4.252 | 1.00 | 58.97 | A | N |
| ATOM | 832 | CA | ALA A | 153 | 68.936 | 1.758 | -5.385 | 1.00 | 58.62 | A | C |
| ATOM | 833 | CB | ALA A | 153 | 67.867 | 2.088 | -6.448 | 1.00 | 59.12 | A | C |
| ATOM | 834 | C | ALA A | 153 | 69.685 | 3.013 | -4.955 | 1.00 | 58.45 | A | C |
| ATOM | 835 | O | ALA A | 153 | 70.919 | 3.053 | -5.018 | 1.00 | 58.58 | A | O |
| ATOM | 836 | N | ARG A | 154 | 68.961 | 4.025 | -4.480 | 1.00 | 57.39 | A | N |
| ATOM | 837 | CA | ARG A | 154 | 69.602 | 5.282 | -4.071 | 1.00 | 56.44 | A | C |
| ATOM | 838 | CB | ARG A | 154 | 68.691 | 6.466 | -4.456 | 1.00 | 56.86 | A | C |
| ATOM | 839 | CG | ARG A | 154 | 68.526 | 6.598 | -5.968 | 1.00 | 57.55 | A | C |
| ATOM | 840 | CD | ARG A | 154 | 67.384 | 7.517 | -6.353 | 1.00 | 58.73 | A | C |
| ATOM | 841 | NE | ARG A | 154 | 67.024 | 7.414 | -7.770 | 1.00 | 59.14 | A | N |
| ATOM | 842 | CZ | ARG A | 154 | 66.012 | 8.074 | -8.338 | 1.00 | 60.15 | A | C |
| ATOM | 843 | NH1 | ARG A | 154 | 65.259 | 8.882 | -7.614 | 1.00 | 61.50 | A | N |
| ATOM | 844 | NH2 | ARG A | 154 | 65.749 | 7.946 | -9.631 | 1.00 | 59.39 | A | N |
| ATOM | 845 | C | ARG A | 154 | 69.933 | 5.321 | -2.550 | 1.00 | 55.23 | A | C |
| ATOM | 846 | O | ARG A | 154 | 70.448 | 6.340 | -2.091 | 1.00 | 56.84 | A | O |
| ATOM | 847 | N | HIS A | 155 | 69.760 | 4.189 | -1.835 | 1.00 | 52.65 | A | N |
| ATOM | 848 | CA | HIS A | 155 | 69.926 | 4.000 | -0.368 | 1.00 | 50.62 | A | C |
| ATOM | 849 | CB | HIS A | 155 | 71.398 | 3.933 | 0.097 | 1.00 | 49.62 | A | C |
| ATOM | 850 | CG | HIS A | 155 | 71.556 | 3.708 | 1.573 | 1.00 | 49.17 | A | C |
| ATOM | 851 | CD2 | HIS A | 155 | 72.668 | 3.678 | 2.344 | 1.00 | 49.10 | A | C |
| ATOM | 852 | ND1 | HIS A | 155 | 70.492 | 3.524 | 2.437 | 1.00 | 49.56 | A | N |
| ATOM | 853 | CE1 | HIS A | 155 | 70.947 | 3.393 | 3.671 | 1.00 | 49.19 | A | C |
| ATOM | 854 | NE2 | HIS A | 155 | 72.264 | 3.484 | 3.640 | 1.00 | 49.43 | A | N |
| ATOM | 855 | C | HIS A | 155 | 69.152 | 5.042 | 0.437 | 1.00 | 49.30 | A | C |
| ATOM | 856 | O | HIS A | 155 | 68.266 | 4.710 | 1.225 | 1.00 | 49.96 | A | O |
| ATOM | 857 | N | THR A | 156 | 69.507 | 6.304 | 0.257 | 1.00 | 46.69 | A | N |
| ATOM | 858 | CA | THR A | 156 | 68.863 | 7.416 | 0.955 | 1.00 | 44.62 | A | C |
| ATOM | 859 | CB | THR A | 156 | 69.866 | 8.156 | 1.904 | 1.00 | 44.69 | A | C |
| ATOM | 860 | OG1 | THR A | 156 | 71.022 | 8.557 | 1.156 | 1.00 | 45.48 | A | O |
| ATOM | 861 | CG2 | THR A | 156 | 70.315 | 7.241 | 3.059 | 1.00 | 44.45 | A | C |
| ATOM | 862 | C | THR A | 156 | 68.416 | 8.383 | -0.158 | 1.00 | 42.90 | A | C |
| ATOM | 863 | O | THR A | 156 | 68.971 | 8.354 | -1.264 | 1.00 | 40.76 | A | O |
| ATOM | 864 | N | LEU A | 157 | 67.410 | 9.220 | 0.109 | 1.00 | 40.05 | A | N |
| ATOM | 865 | CA | LEU A | 157 | 66.923 | 10.180 | -0.892 | 1.00 | 38.61 | A | C |
| ATOM | 866 | CB | LEU A | 157 | 65.405 | 10.061 | -1.010 | 1.00 | 39.13 | A | C |
| ATOM | 867 | CG | LEU A | 157 | 64.868 | 8.716 | -1.495 | 1.00 | 38.58 | A | C |
| ATOM | 868 | CD1 | LEU A | 157 | 63.348 | 8.747 | -1.503 | 1.00 | 38.63 | A | C |
| ATOM | 869 | CD2 | LEU A | 157 | 65.408 | 8.442 | -2.905 | 1.00 | 39.09 | A | C |
| ATOM | 870 | C | LEU A | 157 | 67.278 | 11.642 | -0.599 | 1.00 | 38.24 | A | C |
| ATOM | 871 | O | LEU A | 157 | 67.430 | 12.039 | 0.561 | 1.00 | 36.73 | A | O |
| ATOM | 872 | N | LEU A | 158 | 67.412 | 12.433 | -1.663 | 1.00 | 38.23 | A | N |
| ATOM | 873 | CA | LEU A | 158 | 67.696 | 13.867 | -1.525 | 1.00 | 37.65 | A | C |
| ATOM | 874 | CB | LEU A | 158 | 68.058 | 14.509 | -2.866 | 1.00 | 36.60 | A | C |
| ATOM | 875 | CG | LEU A | 158 | 69.406 | 14.184 | -3.493 | 1.00 | 36.06 | A | C |
| ATOM | 876 | CD1 | LEU A | 158 | 69.545 | 14.978 | -4.788 | 1.00 | 36.27 | A | C |
| ATOM | 877 | CD2 | LEU A | 158 | 70.538 | 14.520 | -2.527 | 1.00 | 36.92 | A | C |
| ATOM | 878 | C | LEU A | 158 | 66.453 | 14.579 | -1.009 | 1.00 | 36.39 | A | C |
| ATOM | 879 | O | LEU A | 158 | 65.338 | 14.131 | -1.258 | 1.00 | 36.03 | A | O |
| ATOM | 880 | N | GLU A | 159 | 66.649 | 15.696 | -0.315 | 1.00 | 35.31 | A | N |
| ATOM | 881 | CA | GLU A | 159 | 65.532 | 16.472 | 0.206 | 1.00 | 36.65 | A | C |
| ATOM | 882 | CB | GLU A | 159 | 65.968 | 17.895 | 0.597 | 1.00 | 38.20 | A | C |
| ATOM | 883 | CG | GLU A | 159 | 67.084 | 17.976 | 1.622 | 1.00 | 40.29 | A | C |
| ATOM | 884 | CD | GLU A | 159 | 66.600 | 17.903 | 3.054 | 1.00 | 41.46 | A | C |
| ATOM | 885 | OE1 | GLU A | 159 | 65.748 | 18.735 | 3.427 | 1.00 | 41.25 | A | O |

Figure 1-16

| | | Atom Type | Resid | # | X | Y | Z | OCC | B | | |
|---|---|---|---|---|---|---|---|---|---|---|---|
| ATOM | 886 | OE2 | GLU A | 159 | 67.087 | 17.028 | 3.806 | 1.00 | 42.10 | A | O |
| ATOM | 887 | C | GLU A | 159 | 64.431 | 16.581 | -0.845 | 1.00 | 35.02 | A | C |
| ATOM | 888 | O | GLU A | 159 | 63.277 | 16.282 | -0.565 | 1.00 | 35.88 | A | O |
| ATOM | 889 | N | PRO A | 160 | 64.778 | 16.997 | -2.076 | 1.00 | 35.11 | A | N |
| ATOM | 890 | CD | PRO A | 160 | 66.127 | 17.306 | -2.589 | 1.00 | 35.45 | A | C |
| ATOM | 891 | CA | PRO A | 160 | 63.776 | 17.138 | -3.139 | 1.00 | 35.38 | A | C |
| ATOM | 892 | CB | PRO A | 160 | 64.567 | 17.782 | -4.283 | 1.00 | 35.33 | A | C |
| ATOM | 893 | CG | PRO A | 160 | 65.939 | 17.204 | -4.091 | 1.00 | 35.53 | A | C |
| ATOM | 894 | C | PRO A | 160 | 63.076 | 15.846 | -3.561 | 1.00 | 33.55 | A | C |
| ATOM | 895 | O | PRO A | 160 | 61.891 | 15.856 | -3.882 | 1.00 | 35.31 | A | O |
| ATOM | 896 | N | GLU A | 161 | 63.800 | 14.735 | -3.581 | 1.00 | 33.63 | A | N |
| ATOM | 897 | CA | GLU A | 161 | 63.196 | 13.462 | -3.953 | 1.00 | 33.05 | A | C |
| ATOM | 898 | CB | GLU A | 161 | 64.291 | 12.420 | -4.139 | 1.00 | 33.92 | A | C |
| ATOM | 899 | CG | GLU A | 161 | 65.332 | 12.757 | -5.190 | 1.00 | 36.10 | A | C |
| ATOM | 900 | CD | GLU A | 161 | 66.421 | 11.699 | -5.249 | 1.00 | 37.61 | A | C |
| ATOM | 901 | OE1 | GLU A | 161 | 67.160 | 11.530 | -4.242 | 1.00 | 38.51 | A | O |
| ATOM | 902 | OE2 | GLU A | 161 | 66.534 | 11.024 | -6.292 | 1.00 | 38.20 | A | O |
| ATOM | 903 | C | GLU A | 161 | 62.242 | 13.057 | -2.814 | 1.00 | 32.43 | A | C |
| ATOM | 904 | O | GLU A | 161 | 61.262 | 12.339 | -3.006 | 1.00 | 30.40 | A | O |
| ATOM | 905 | N | VAL A | 162 | 62.554 | 13.533 | -1.618 | 1.00 | 31.58 | A | N |
| ATOM | 906 | CA | VAL A | 162 | 61.733 | 13.273 | -0.450 | 1.00 | 32.09 | A | C |
| ATOM | 907 | CB | VAL A | 162 | 62.520 | 13.614 | 0.831 | 1.00 | 32.19 | A | C |
| ATOM | 908 | CG1 | VAL A | 162 | 61.683 | 13.345 | 2.063 | 1.00 | 30.56 | A | C |
| ATOM | 909 | CG2 | VAL A | 162 | 63.795 | 12.791 | 0.863 | 1.00 | 33.01 | A | C |
| ATOM | 910 | C | VAL A | 162 | 60.472 | 14.146 | -0.554 | 1.00 | 31.99 | A | C |
| ATOM | 911 | O | VAL A | 162 | 59.349 | 13.646 | -0.510 | 1.00 | 31.90 | A | O |
| ATOM | 912 | N | ARG A | 163 | 60.670 | 15.452 | -0.695 | 1.00 | 31.45 | A | N |
| ATOM | 913 | CA | ARG A | 163 | 59.564 | 16.384 | -0.828 | 1.00 | 33.21 | A | C |
| ATOM | 914 | CB | ARG A | 163 | 60.082 | 17.785 | -1.146 | 1.00 | 32.29 | A | C |
| ATOM | 915 | CG | ARG A | 163 | 60.022 | 18.746 | 0.022 | 1.00 | 34.98 | A | C |
| ATOM | 916 | CD | ARG A | 163 | 60.540 | 20.110 | -0.390 | 1.00 | 33.83 | A | C |
| ATOM | 917 | NE | ARG A | 163 | 61.957 | 20.060 | -0.748 | 1.00 | 34.92 | A | N |
| ATOM | 918 | CZ | ARG A | 163 | 62.961 | 20.236 | 0.112 | 1.00 | 35.49 | A | C |
| ATOM | 919 | NH1 | ARG A | 163 | 62.698 | 20.479 | 1.393 | 1.00 | 32.73 | A | N |
| ATOM | 920 | NH2 | ARG A | 163 | 64.227 | 20.175 | -0.311 | 1.00 | 35.97 | A | N |
| ATOM | 921 | C | ARG A | 163 | 58.705 | 15.895 | -1.973 | 1.00 | 32.36 | A | C |
| ATOM | 922 | O | ARG A | 163 | 57.470 | 15.910 | -1.904 | 1.00 | 32.29 | A | O |
| ATOM | 923 | N | TYR A | 164 | 59.364 | 15.448 | -3.031 | 1.00 | 30.32 | A | N |
| ATOM | 924 | CA | TYR A | 164 | 58.641 | 14.949 | -4.185 | 1.00 | 29.21 | A | C |
| ATOM | 925 | CB | TYR A | 164 | 59.607 | 14.414 | -5.261 | 1.00 | 29.76 | A | C |
| ATOM | 926 | CG | TYR A | 164 | 58.903 | 14.056 | -6.547 | 1.00 | 31.56 | A | C |
| ATOM | 927 | CD1 | TYR A | 164 | 58.293 | 15.044 | -7.327 | 1.00 | 33.14 | A | C |
| ATOM | 928 | CE1 | TYR A | 164 | 57.575 | 14.721 | -8.480 | 1.00 | 34.25 | A | C |
| ATOM | 929 | CD2 | TYR A | 164 | 58.783 | 12.722 | -6.962 | 1.00 | 33.57 | A | C |
| ATOM | 930 | CE2 | TYR A | 164 | 58.068 | 12.387 | -8.124 | 1.00 | 34.12 | A | C |
| ATOM | 931 | CZ | TYR A | 164 | 57.462 | 13.394 | -8.875 | 1.00 | 34.62 | A | C |
| ATOM | 932 | OH | TYR A | 164 | 56.721 | 13.073 | -10.003 | 1.00 | 36.80 | A | O |
| ATOM | 933 | C | TYR A | 164 | 57.640 | 13.857 | -3.798 | 1.00 | 27.21 | A | C |
| ATOM | 934 | O | TYR A | 164 | 56.445 | 14.022 | -3.993 | 1.00 | 25.96 | A | O |
| ATOM | 935 | N | TYR A | 165 | 58.124 | 12.757 | -3.226 | 1.00 | 26.15 | A | N |
| ATOM | 936 | CA | TYR A | 165 | 57.272 | 11.629 | -2.864 | 1.00 | 25.64 | A | C |
| ATOM | 937 | CB | TYR A | 165 | 58.131 | 10.390 | -2.581 | 1.00 | 28.72 | A | C |
| ATOM | 938 | CG | TYR A | 165 | 58.863 | 9.878 | -3.800 | 1.00 | 31.52 | A | C |
| ATOM | 939 | CD1 | TYR A | 165 | 58.249 | 9.887 | -5.051 | 1.00 | 32.01 | A | C |
| ATOM | 940 | CE1 | TYR A | 165 | 58.901 | 9.406 | -6.184 | 1.00 | 33.17 | A | C |
| ATOM | 941 | CD2 | TYR A | 165 | 60.158 | 9.372 | -3.708 | 1.00 | 32.16 | A | C |
| ATOM | 942 | CE2 | TYR A | 165 | 60.824 | 8.882 | -4.846 | 1.00 | 32.77 | A | C |
| ATOM | 943 | CZ | TYR A | 165 | 60.185 | 8.903 | -6.076 | 1.00 | 33.38 | A | C |
| ATOM | 944 | OH | TYR A | 165 | 60.820 | 8.410 | -7.192 | 1.00 | 33.00 | A | O |

Figure 1-17

|  | Atom Type | Resid |  | # | X | Y | Z | OCC | B |  |  |
|---|---|---|---|---|---|---|---|---|---|---|---|
| ATOM | 945 | C | TYR A | 165 | 56.284 | 11.847 | -1.734 | 1.00 | 24.58 | A | C |
| ATOM | 946 | O | TYR A | 165 | 55.169 | 11.333 | -1.787 | 1.00 | 23.98 | A | O |
| ATOM | 947 | N | LEU A | 166 | 56.680 | 12.593 | -0.710 | 1.00 | 23.89 | A | N |
| ATOM | 948 | CA | LEU A | 166 | 55.785 | 12.869 | 0.411 | 1.00 | 23.39 | A | C |
| ATOM | 949 | CB | LEU A | 166 | 56.527 | 13.594 | 1.530 | 1.00 | 20.67 | A | C |
| ATOM | 950 | CG | LEU A | 166 | 57.470 | 12.770 | 2.393 | 1.00 | 23.56 | A | C |
| ATOM | 951 | CD1 | LEU A | 166 | 58.305 | 13.732 | 3.222 | 1.00 | 22.76 | A | C |
| ATOM | 952 | CD2 | LEU A | 166 | 56.677 | 11.814 | 3.285 | 1.00 | 22.12 | A | C |
| ATOM | 953 | C | LEU A | 166 | 54.597 | 13.719 | -0.041 | 1.00 | 23.84 | A | C |
| ATOM | 954 | O | LEU A | 166 | 53.451 | 13.449 | 0.346 | 1.00 | 20.85 | A | O |
| ATOM | 955 | N | ARG A | 167 | 54.867 | 14.751 | -0.844 | 1.00 | 24.55 | A | N |
| ATOM | 956 | CA | ARG A | 167 | 53.786 | 15.595 | -1.348 | 1.00 | 27.74 | A | C |
| ATOM | 957 | CB | ARG A | 167 | 54.257 | 16.488 | -2.501 | 1.00 | 30.21 | A | C |
| ATOM | 958 | CG | ARG A | 167 | 53.092 | 17.194 | -3.193 | 1.00 | 32.21 | A | C |
| ATOM | 959 | CD | ARG A | 167 | 53.422 | 17.870 | -4.545 | 1.00 | 36.29 | A | C |
| ATOM | 960 | NE | ARG A | 167 | 52.238 | 18.600 | -5.032 | 1.00 | 38.95 | A | N |
| ATOM | 961 | CZ | ARG A | 167 | 52.254 | 19.652 | -5.853 | 1.00 | 40.52 | A | C |
| ATOM | 962 | NH1 | ARG A | 167 | 53.410 | 20.126 | -6.314 | 1.00 | 40.32 | A | N |
| ATOM | 963 | NH2 | ARG A | 167 | 51.107 | 20.253 | -6.183 | 1.00 | 42.09 | A | N |
| ATOM | 964 | C | ARG A | 167 | 52.726 | 14.647 | -1.876 | 1.00 | 27.00 | A | C |
| ATOM | 965 | O | ARG A | 167 | 51.546 | 14.781 | -1.581 | 1.00 | 26.86 | A | O |
| ATOM | 966 | N | GLN A | 168 | 53.186 | 13.671 | -2.655 | 1.00 | 27.67 | A | N |
| ATOM | 967 | CA | GLN A | 168 | 52.332 | 12.651 | -3.276 | 1.00 | 28.92 | A | C |
| ATOM | 968 | CB | GLN A | 168 | 53.161 | 11.834 | -4.269 | 1.00 | 30.29 | A | C |
| ATOM | 969 | CG | GLN A | 168 | 53.709 | 12.652 | -5.427 | 1.00 | 32.47 | A | C |
| ATOM | 970 | CD | GLN A | 168 | 54.242 | 11.772 | -6.522 | 1.00 | 34.72 | A | C |
| ATOM | 971 | OE1 | GLN A | 168 | 53.529 | 10.898 | -7.030 | 1.00 | 35.59 | A | O |
| ATOM | 972 | NE2 | GLN A | 168 | 55.495 | 11.987 | -6.900 | 1.00 | 36.38 | A | N |
| ATOM | 973 | C | GLN A | 168 | 51.660 | 11.708 | -2.262 | 1.00 | 28.68 | A | C |
| ATOM | 974 | O | GLN A | 168 | 50.440 | 11.498 | -2.281 | 1.00 | 25.85 | A | O |
| ATOM | 975 | N | ILE A | 169 | 52.489 | 11.129 | -1.397 | 1.00 | 29.53 | A | N |
| ATOM | 976 | CA | ILE A | 169 | 52.051 | 10.229 | -0.328 | 1.00 | 29.03 | A | C |
| ATOM | 977 | CB | ILE A | 169 | 53.252 | 9.858 | 0.592 | 1.00 | 28.73 | A | C |
| ATOM | 978 | CG2 | ILE A | 169 | 52.766 | 9.144 | 1.845 | 1.00 | 26.73 | A | C |
| ATOM | 979 | CG1 | ILE A | 169 | 54.260 | 9.017 | -0.201 | 1.00 | 27.23 | A | C |
| ATOM | 980 | CD1 | ILE A | 169 | 55.479 | 8.619 | 0.566 | 1.00 | 25.37 | A | C |
| ATOM | 981 | C | ILE A | 169 | 50.980 | 10.921 | 0.512 | 1.00 | 28.70 | A | C |
| ATOM | 982 | O | ILE A | 169 | 49.921 | 10.348 | 0.766 | 1.00 | 28.55 | A | O |
| ATOM | 983 | N | LEU A | 170 | 51.270 | 12.146 | 0.948 | 1.00 | 28.81 | A | N |
| ATOM | 984 | CA | LEU A | 170 | 50.344 | 12.928 | 1.767 | 1.00 | 29.23 | A | C |
| ATOM | 985 | CB | LEU A | 170 | 51.052 | 14.201 | 2.255 | 1.00 | 28.47 | A | C |
| ATOM | 986 | CG | LEU A | 170 | 52.290 | 13.962 | 3.153 | 1.00 | 29.83 | A | C |
| ATOM | 987 | CD1 | LEU A | 170 | 53.303 | 15.065 | 2.957 | 1.00 | 30.83 | A | C |
| ATOM | 988 | CD2 | LEU A | 170 | 51.878 | 13.887 | 4.619 | 1.00 | 30.74 | A | C |
| ATOM | 989 | C | LEU A | 170 | 49.087 | 13.261 | 0.966 | 1.00 | 30.30 | A | C |
| ATOM | 990 | O | LEU A | 170 | 47.982 | 13.266 | 1.505 | 1.00 | 31.17 | A | O |
| ATOM | 991 | N | SER A | 171 | 49.247 | 13.519 | -0.327 | 1.00 | 30.26 | A | N |
| ATOM | 992 | CA | SER A | 171 | 48.095 | 13.821 | -1.164 | 1.00 | 29.93 | A | C |
| ATOM | 993 | CB | SER A | 171 | 48.494 | 13.950 | -2.641 | 1.00 | 32.38 | A | C |
| ATOM | 994 | OG | SER A | 171 | 47.356 | 14.157 | -3.474 | 1.00 | 31.88 | A | O |
| ATOM | 995 | C | SER A | 171 | 47.100 | 12.684 | -1.041 | 1.00 | 29.95 | A | C |
| ATOM | 996 | O | SER A | 171 | 45.959 | 12.883 | -0.630 | 1.00 | 30.90 | A | O |
| ATOM | 997 | N | GLY A | 172 | 47.564 | 11.486 | -1.387 | 1.00 | 28.18 | A | N |
| ATOM | 998 | CA | GLY A | 172 | 46.739 | 10.291 | -1.358 | 1.00 | 26.61 | A | C |
| ATOM | 999 | C | GLY A | 172 | 46.099 | 9.924 | -0.042 | 1.00 | 25.84 | A | C |
| ATOM | 1000 | O | GLY A | 172 | 45.014 | 9.364 | -0.045 | 1.00 | 23.99 | A | O |
| ATOM | 1001 | N | LEU A | 173 | 46.768 | 10.219 | 1.072 | 1.00 | 28.53 | A | N |
| ATOM | 1002 | CA | LEU A | 173 | 46.243 | 9.912 | 2.405 | 1.00 | 28.81 | A | C |
| ATOM | 1003 | CB | LEU A | 173 | 47.320 | 10.071 | 3.496 | 1.00 | 27.88 | A | C |

Figure 1-18

| | | Atom Type | Resid | # | X | Y | Z | OCC | B | | |
|---|---|---|---|---|---|---|---|---|---|---|---|
| ATOM | 1004 | CG | LEU A | 173 | 47.612 | 8.957 | 4.535 | 1.00 | 27.53 | A | C |
| ATOM | 1005 | CD1 | LEU A | 173 | 48.143 | 9.606 | 5.812 | 1.00 | 25.21 | A | C |
| ATOM | 1006 | CD2 | LEU A | 173 | 46.379 | 8.118 | 4.856 | 1.00 | 24.08 | A | C |
| ATOM | 1007 | C | LEU A | 173 | 45.107 | 10.880 | 2.695 | 1.00 | 29.58 | A | C |
| ATOM | 1008 | O | LEU A | 173 | 44.050 | 10.473 | 3.190 | 1.00 | 32.03 | A | O |
| ATOM | 1009 | N | LYS A | 174 | 45.337 | 12.159 | 2.384 | 1.00 | 30.45 | A | N |
| ATOM | 1010 | CA | LYS A | 174 | 44.339 | 13.215 | 2.587 | 1.00 | 32.08 | A | C |
| ATOM | 1011 | CB | LYS A | 174 | 44.750 | 14.511 | 1.871 | 1.00 | 33.03 | A | C |
| ATOM | 1012 | CG | LYS A | 174 | 43.848 | 15.731 | 2.166 | 1.00 | 34.56 | A | C |
| ATOM | 1013 | CD | LYS A | 174 | 43.668 | 16.683 | 0.939 | 1.00 | 35.92 | A | C |
| ATOM | 1014 | CE | LYS A | 174 | 44.960 | 17.389 | 0.486 | 1.00 | 35.81 | A | C |
| ATOM | 1015 | NZ | LYS A | 174 | 44.868 | 18.048 | -0.869 | 1.00 | 36.20 | A | N |
| ATOM | 1016 | C | LYS A | 174 | 43.041 | 12.717 | 1.984 | 1.00 | 33.57 | A | C |
| ATOM | 1017 | O | LYS A | 174 | 41.964 | 12.981 | 2.508 | 1.00 | 34.67 | A | O |
| ATOM | 1018 | N | TYR A | 175 | 43.161 | 11.996 | 0.871 | 1.00 | 31.10 | A | N |
| ATOM | 1019 | CA | TYR A | 175 | 42.020 | 11.440 | 0.166 | 1.00 | 31.66 | A | C |
| ATOM | 1020 | CB | TYR A | 175 | 42.467 | 10.895 | -1.185 | 1.00 | 31.86 | A | C |
| ATOM | 1021 | CG | TYR A | 175 | 41.368 | 10.164 | -1.924 | 1.00 | 34.06 | A | C |
| ATOM | 1022 | CD1 | TYR A | 175 | 40.360 | 10.865 | -2.571 | 1.00 | 33.56 | A | C |
| ATOM | 1023 | CE1 | TYR A | 175 | 39.313 | 10.203 | -3.193 | 1.00 | 33.23 | A | C |
| ATOM | 1024 | CD2 | TYR A | 175 | 41.301 | 8.766 | -1.923 | 1.00 | 33.31 | A | C |
| ATOM | 1025 | CE2 | TYR A | 175 | 40.259 | 8.094 | -2.540 | 1.00 | 33.06 | A | C |
| ATOM | 1026 | CZ | TYR A | 175 | 39.267 | 8.819 | -3.171 | 1.00 | 33.99 | A | C |
| ATOM | 1027 | OH | TYR A | 175 | 38.215 | 8.157 | -3.768 | 1.00 | 35.87 | A | O |
| ATOM | 1028 | C | TYR A | 175 | 41.412 | 10.316 | 0.993 | 1.00 | 30.77 | A | C |
| ATOM | 1029 | O | TYR A | 175 | 40.223 | 10.334 | 1.317 | 1.00 | 30.38 | A | O |
| ATOM | 1030 | N | LEU A | 176 | 42.245 | 9.338 | 1.330 | 1.00 | 29.34 | A | N |
| ATOM | 1031 | CA | LEU A | 176 | 41.823 | 8.191 | 2.130 | 1.00 | 28.29 | A | C |
| ATOM | 1032 | CB | LEU A | 176 | 43.044 | 7.419 | 2.606 | 1.00 | 29.17 | A | C |
| ATOM | 1033 | CG | LEU A | 176 | 43.989 | 6.936 | 1.520 | 1.00 | 29.94 | A | C |
| ATOM | 1034 | CD1 | LEU A | 176 | 45.188 | 6.318 | 2.189 | 1.00 | 29.94 | A | C |
| ATOM | 1035 | CD2 | LEU A | 176 | 43.275 | 5.941 | 0.608 | 1.00 | 30.26 | A | C |
| ATOM | 1036 | C | LEU A | 176 | 41.031 | 8.645 | 3.344 | 1.00 | 26.96 | A | C |
| ATOM | 1037 | O | LEU A | 176 | 39.867 | 8.285 | 3.516 | 1.00 | 23.14 | A | O |
| ATOM | 1038 | N | HIS A | 177 | 41.703 | 9.427 | 4.184 | 1.00 | 24.66 | A | N |
| ATOM | 1039 | CA | HIS A | 177 | 41.122 | 9.984 | 5.395 | 1.00 | 25.40 | A | C |
| ATOM | 1040 | CB | HIS A | 177 | 42.134 | 10.946 | 6.034 | 1.00 | 24.92 | A | C |
| ATOM | 1041 | CG | HIS A | 177 | 43.197 | 10.259 | 6.831 | 1.00 | 26.47 | A | C |
| ATOM | 1042 | CD2 | HIS A | 177 | 43.934 | 10.681 | 7.883 | 1.00 | 27.06 | A | C |
| ATOM | 1043 | ND1 | HIS A | 177 | 43.617 | 8.974 | 6.565 | 1.00 | 27.60 | A | N |
| ATOM | 1044 | CE1 | HIS A | 177 | 44.566 | 8.636 | 7.417 | 1.00 | 26.27 | A | C |
| ATOM | 1045 | NE2 | HIS A | 177 | 44.779 | 9.655 | 8.228 | 1.00 | 27.67 | A | N |
| ATOM | 1046 | C | HIS A | 177 | 39.796 | 10.691 | 5.106 | 1.00 | 22.39 | A | C |
| ATOM | 1047 | O | HIS A | 177 | 38.842 | 10.558 | 5.868 | 1.00 | 20.56 | A | O |
| ATOM | 1048 | N | GLN A | 178 | 39.748 | 11.439 | 4.006 | 1.00 | 24.66 | A | N |
| ATOM | 1049 | CA | GLN A | 178 | 38.544 | 12.159 | 3.605 | 1.00 | 26.69 | A | C |
| ATOM | 1050 | CB | GLN A | 178 | 38.815 | 13.085 | 2.420 | 1.00 | 28.29 | A | C |
| ATOM | 1051 | CG | GLN A | 178 | 39.316 | 14.445 | 2.859 | 1.00 | 31.11 | A | C |
| ATOM | 1052 | CD | GLN A | 178 | 39.510 | 15.410 | 1.711 | 1.00 | 32.95 | A | C |
| ATOM | 1053 | OE1 | GLN A | 178 | 39.745 | 16.598 | 1.935 | 1.00 | 34.79 | A | O |
| ATOM | 1054 | NE2 | GLN A | 178 | 39.417 | 14.911 | 0.476 | 1.00 | 34.05 | A | N |
| ATOM | 1055 | C | GLN A | 178 | 37.420 | 11.211 | 3.252 | 1.00 | 27.63 | A | C |
| ATOM | 1056 | O | GLN A | 178 | 36.308 | 11.648 | 2.985 | 1.00 | 31.08 | A | O |
| ATOM | 1057 | N | ARG A | 179 | 37.718 | 9.914 | 3.238 | 1.00 | 28.17 | A | N |
| ATOM | 1058 | CA | ARG A | 179 | 36.713 | 8.889 | 2.969 | 1.00 | 28.25 | A | C |
| ATOM | 1059 | CB | ARG A | 179 | 37.180 | 7.985 | 1.830 | 1.00 | 30.98 | A | C |
| ATOM | 1060 | CG | ARG A | 179 | 37.372 | 8.709 | 0.520 | 1.00 | 34.54 | A | C |
| ATOM | 1061 | CD | ARG A | 179 | 37.075 | 7.769 | -0.639 | 1.00 | 37.80 | A | C |
| ATOM | 1062 | NE | ARG A | 179 | 35.855 | 6.999 | -0.393 | 1.00 | 39.78 | A | N |

Figure 1-19

| | | Atom Type | Resid | # | X | Y | Z | OCC | B | | |
|---|---|---|---|---|---|---|---|---|---|---|---|
| ATOM | 1063 | CZ | ARG A | 179 | 34.660 | 7.514 | -0.120 | 1.00 | 40.96 | A | C |
| ATOM | 1064 | NH1 | ARG A | 179 | 34.484 | 8.827 | -0.061 | 1.00 | 41.94 | A | N |
| ATOM | 1065 | NH2 | ARG A | 179 | 33.639 | 6.698 | 0.127 | 1.00 | 41.33 | A | N |
| ATOM | 1066 | C | ARG A | 179 | 36.438 | 8.045 | 4.234 | 1.00 | 25.06 | A | C |
| ATOM | 1067 | O | ARG A | 179 | 35.680 | 7.072 | 4.185 | 1.00 | 26.34 | A | O |
| ATOM | 1068 | N | GLY A | 180 | 37.052 | 8.433 | 5.357 | 1.00 | 23.87 | A | N |
| ATOM | 1069 | CA | GLY A | 180 | 36.880 | 7.712 | 6.609 | 1.00 | 20.19 | A | C |
| ATOM | 1070 | C | GLY A | 180 | 37.783 | 6.504 | 6.813 | 1.00 | 19.82 | A | C |
| ATOM | 1071 | O | GLY A | 180 | 37.624 | 5.759 | 7.774 | 1.00 | 21.23 | A | O |
| ATOM | 1072 | N | ILE A | 181 | 38.751 | 6.324 | 5.925 | 1.00 | 21.28 | A | N |
| ATOM | 1073 | CA | ILE A | 181 | 39.666 | 5.190 | 5.981 | 1.00 | 22.90 | A | C |
| ATOM | 1074 | CB | ILE A | 181 | 39.697 | 4.506 | 4.598 | 1.00 | 23.03 | A | C |
| ATOM | 1075 | CG2 | ILE A | 181 | 40.426 | 3.174 | 4.671 | 1.00 | 25.81 | A | C |
| ATOM | 1076 | CG1 | ILE A | 181 | 38.260 | 4.284 | 4.107 | 1.00 | 24.97 | A | C |
| ATOM | 1077 | CD1 | ILE A | 181 | 37.419 | 3.410 | 5.052 | 1.00 | 26.12 | A | C |
| ATOM | 1078 | C | ILE A | 181 | 41.112 | 5.483 | 6.432 | 1.00 | 20.99 | A | C |
| ATOM | 1079 | O | ILE A | 181 | 41.716 | 6.500 | 6.070 | 1.00 | 22.76 | A | O |
| ATOM | 1080 | N | LEU A | 182 | 41.635 | 4.554 | 7.231 | 1.00 | 23.10 | A | N |
| ATOM | 1081 | CA | LEU A | 182 | 42.992 | 4.568 | 7.773 | 1.00 | 22.94 | A | C |
| ATOM | 1082 | CB | LEU A | 182 | 42.970 | 4.268 | 9.270 | 1.00 | 23.26 | A | C |
| ATOM | 1083 | CG | LEU A | 182 | 42.224 | 5.286 | 10.130 | 1.00 | 22.32 | A | C |
| ATOM | 1084 | CD1 | LEU A | 182 | 42.132 | 4.818 | 11.559 | 1.00 | 22.32 | A | C |
| ATOM | 1085 | CD2 | LEU A | 182 | 42.954 | 6.608 | 10.058 | 1.00 | 22.65 | A | C |
| ATOM | 1086 | C | LEU A | 182 | 43.714 | 3.431 | 7.052 | 1.00 | 24.96 | A | C |
| ATOM | 1087 | O | LEU A | 182 | 43.170 | 2.337 | 6.928 | 1.00 | 25.58 | A | O |
| ATOM | 1088 | N | HIS A | 183 | 44.927 | 3.692 | 6.570 | 1.00 | 26.53 | A | N |
| ATOM | 1089 | CA | HIS A | 183 | 45.711 | 2.689 | 5.863 | 1.00 | 25.64 | A | C |
| ATOM | 1090 | CB | HIS A | 183 | 46.731 | 3.375 | 4.971 | 1.00 | 24.28 | A | C |
| ATOM | 1091 | CG | HIS A | 183 | 47.458 | 2.443 | 4.048 | 1.00 | 24.04 | A | C |
| ATOM | 1092 | CD2 | HIS A | 183 | 47.365 | 2.261 | 2.706 | 1.00 | 24.51 | A | C |
| ATOM | 1093 | ND1 | HIS A | 183 | 48.454 | 1.590 | 4.475 | 1.00 | 24.68 | A | N |
| ATOM | 1094 | CE1 | HIS A | 183 | 48.945 | 0.929 | 3.441 | 1.00 | 23.89 | A | C |
| ATOM | 1095 | NE2 | HIS A | 183 | 48.302 | 1.317 | 2.353 | 1.00 | 24.86 | A | N |
| ATOM | 1096 | C | HIS A | 183 | 46.428 | 1.853 | 6.893 | 1.00 | 25.47 | A | C |
| ATOM | 1097 | O | HIS A | 183 | 46.617 | 0.649 | 6.719 | 1.00 | 24.96 | A | O |
| ATOM | 1098 | N | ARG A | 184 | 46.805 | 2.543 | 7.968 | 1.00 | 26.92 | A | N |
| ATOM | 1099 | CA | ARG A | 184 | 47.517 | 2.025 | 9.138 | 1.00 | 29.26 | A | C |
| ATOM | 1100 | CB | ARG A | 184 | 46.514 | 1.428 | 10.140 | 1.00 | 28.42 | A | C |
| ATOM | 1101 | CG | ARG A | 184 | 45.694 | 0.305 | 9.611 | 1.00 | 29.29 | A | C |
| ATOM | 1102 | CD | ARG A | 184 | 44.245 | 0.511 | 9.936 | 1.00 | 29.40 | A | C |
| ATOM | 1103 | NE | ARG A | 184 | 43.879 | 0.104 | 11.284 | 1.00 | 30.96 | A | N |
| ATOM | 1104 | CZ | ARG A | 184 | 43.477 | -1.116 | 11.635 | 1.00 | 30.96 | A | C |
| ATOM | 1105 | NH1 | ARG A | 184 | 43.383 | -2.097 | 10.743 | 1.00 | 30.97 | A | N |
| ATOM | 1106 | NH2 | ARG A | 184 | 43.138 | -1.348 | 12.893 | 1.00 | 30.02 | A | N |
| ATOM | 1107 | C | ARG A | 184 | 48.691 | 1.068 | 8.895 | 1.00 | 29.76 | A | C |
| ATOM | 1108 | O | ARG A | 184 | 48.871 | 0.081 | 9.607 | 1.00 | 29.89 | A | O |
| ATOM | 1109 | N | ASP A | 185 | 49.510 | 1.402 | 7.902 | 1.00 | 33.37 | A | N |
| ATOM | 1110 | CA | ASP A | 185 | 50.681 | 0.609 | 7.560 | 1.00 | 33.25 | A | C |
| ATOM | 1111 | CB | ASP A | 185 | 50.250 | -0.804 | 7.191 | 1.00 | 35.28 | A | C |
| ATOM | 1112 | CG | ASP A | 185 | 51.415 | -1.735 | 7.021 | 1.00 | 36.91 | A | C |
| ATOM | 1113 | OD1 | ASP A | 185 | 52.291 | -1.757 | 7.907 | 1.00 | 36.19 | A | O |
| ATOM | 1114 | OD2 | ASP A | 185 | 51.456 | -2.445 | 6.000 | 1.00 | 39.04 | A | O |
| ATOM | 1115 | C | ASP A | 185 | 51.401 | 1.263 | 6.394 | 1.00 | 33.01 | A | C |
| ATOM | 1116 | O | ASP A | 185 | 51.679 | 0.629 | 5.372 | 1.00 | 33.18 | A | O |
| ATOM | 1117 | N | LEU A | 186 | 51.695 | 2.547 | 6.554 | 1.00 | 31.86 | A | N |
| ATOM | 1118 | CA | LEU A | 186 | 52.392 | 3.302 | 5.520 | 1.00 | 32.46 | A | C |
| ATOM | 1119 | CB | LEU A | 186 | 52.119 | 4.790 | 5.673 | 1.00 | 30.37 | A | C |
| ATOM | 1120 | CG | LEU A | 186 | 50.646 | 5.147 | 5.752 | 1.00 | 30.36 | A | C |
| ATOM | 1121 | CD1 | LEU A | 186 | 50.489 | 6.637 | 5.987 | 1.00 | 30.41 | A | C |

Figure 1-20

|  |  | Atom Type | Resid |  | # | X | Y | Z | OCC | B |  |  |
|---|---|---|---|---|---|---|---|---|---|---|---|---|
| ATOM | 1122 | CD2 | LEU | A | 186 | 49.965 | 4.717 | 4.467 | 1.00 | 28.58 | A | C |
| ATOM | 1123 | C | LEU | A | 186 | 53.885 | 3.042 | 5.629 | 1.00 | 32.60 | A | C |
| ATOM | 1124 | O | LEU | A | 186 | 54.596 | 3.691 | 6.402 | 1.00 | 33.67 | A | O |
| ATOM | 1125 | N | LYS | A | 187 | 54.344 | 2.071 | 4.849 | 1.00 | 33.41 | A | N |
| ATOM | 1126 | CA | LYS | A | 187 | 55.741 | 1.669 | 4.819 | 1.00 | 33.47 | A | C |
| ATOM | 1127 | CB | LYS | A | 187 | 55.804 | 0.156 | 5.050 | 1.00 | 36.48 | A | C |
| ATOM | 1128 | CG | LYS | A | 187 | 57.139 | -0.380 | 5.514 | 1.00 | 39.67 | A | C |
| ATOM | 1129 | CD | LYS | A | 187 | 58.040 | -0.766 | 4.355 | 1.00 | 41.57 | A | C |
| ATOM | 1130 | CE | LYS | A | 187 | 59.266 | -1.518 | 4.846 | 1.00 | 43.17 | A | C |
| ATOM | 1131 | NZ | LYS | A | 187 | 60.034 | -2.027 | 3.674 | 1.00 | 44.67 | A | N |
| ATOM | 1132 | C | LYS | A | 187 | 56.200 | 2.046 | 3.418 | 1.00 | 32.15 | A | C |
| ATOM | 1133 | O | LYS | A | 187 | 55.423 | 2.598 | 2.667 | 1.00 | 32.20 | A | O |
| ATOM | 1134 | N | LEU | A | 188 | 57.447 | 1.775 | 3.058 | 1.00 | 30.59 | A | N |
| ATOM | 1135 | CA | LEU | A | 188 | 57.913 | 2.103 | 1.709 | 1.00 | 29.61 | A | C |
| ATOM | 1136 | CB | LEU | A | 188 | 59.431 | 2.246 | 1.662 | 1.00 | 27.69 | A | C |
| ATOM | 1137 | CG | LEU | A | 188 | 60.037 | 3.423 | 2.432 | 1.00 | 27.85 | A | C |
| ATOM | 1138 | CD1 | LEU | A | 188 | 61.529 | 3.272 | 2.410 | 1.00 | 26.76 | A | C |
| ATOM | 1139 | CD2 | LEU | A | 188 | 59.620 | 4.767 | 1.836 | 1.00 | 28.20 | A | C |
| ATOM | 1140 | C | LEU | A | 188 | 57.483 | 1.015 | 0.737 | 1.00 | 28.86 | A | C |
| ATOM | 1141 | O | LEU | A | 188 | 57.120 | 1.297 | -0.406 | 1.00 | 30.30 | A | O |
| ATOM | 1142 | N | GLY | A | 189 | 57.518 | -0.230 | 1.191 | 1.00 | 28.29 | A | N |
| ATOM | 1143 | CA | GLY | A | 189 | 57.107 | -1.332 | 0.343 | 1.00 | 28.00 | A | C |
| ATOM | 1144 | C | GLY | A | 189 | 55.639 | -1.242 | -0.020 | 1.00 | 29.68 | A | C |
| ATOM | 1145 | O | GLY | A | 189 | 55.112 | -2.120 | -0.710 | 1.00 | 28.89 | A | O |
| ATOM | 1146 | N | ASN | A | 190 | 54.983 | -0.175 | 0.443 | 1.00 | 30.41 | A | N |
| ATOM | 1147 | CA | ASN | A | 190 | 53.557 | 0.054 | 0.187 | 1.00 | 30.16 | A | C |
| ATOM | 1148 | CB | ASN | A | 190 | 52.780 | 0.058 | 1.509 | 1.00 | 33.27 | A | C |
| ATOM | 1149 | CG | ASN | A | 190 | 52.493 | -1.352 | 2.025 | 1.00 | 34.62 | A | C |
| ATOM | 1150 | OD1 | ASN | A | 190 | 53.343 | -2.240 | 1.975 | 1.00 | 35.97 | A | O |
| ATOM | 1151 | ND2 | ASN | A | 190 | 51.296 | -1.552 | 2.531 | 1.00 | 36.24 | A | N |
| ATOM | 1152 | C | ASN | A | 190 | 53.250 | 1.324 | -0.597 | 1.00 | 29.43 | A | C |
| ATOM | 1153 | O | ASN | A | 190 | 52.119 | 1.790 | -0.589 | 1.00 | 29.51 | A | O |
| ATOM | 1154 | N | PHE | A | 191 | 54.265 | 1.869 | -1.266 | 1.00 | 28.29 | A | N |
| ATOM | 1155 | CA | PHE | A | 191 | 54.141 | 3.068 | -2.100 | 1.00 | 27.04 | A | C |
| ATOM | 1156 | CB | PHE | A | 191 | 54.916 | 4.240 | -1.500 | 1.00 | 26.33 | A | C |
| ATOM | 1157 | CG | PHE | A | 191 | 54.411 | 4.678 | -0.155 | 1.00 | 25.06 | A | C |
| ATOM | 1158 | CD1 | PHE | A | 191 | 55.304 | 5.033 | 0.855 | 1.00 | 23.38 | A | C |
| ATOM | 1159 | CD2 | PHE | A | 191 | 53.044 | 4.728 | 0.109 | 1.00 | 22.57 | A | C |
| ATOM | 1160 | CE1 | PHE | A | 191 | 54.838 | 5.428 | 2.112 | 1.00 | 21.69 | A | C |
| ATOM | 1161 | CE2 | PHE | A | 191 | 52.575 | 5.119 | 1.359 | 1.00 | 23.15 | A | C |
| ATOM | 1162 | CZ | PHE | A | 191 | 53.471 | 5.468 | 2.363 | 1.00 | 21.69 | A | C |
| ATOM | 1163 | C | PHE | A | 191 | 54.801 | 2.682 | -3.402 | 1.00 | 28.40 | A | C |
| ATOM | 1164 | O | PHE | A | 191 | 56.029 | 2.720 | -3.501 | 1.00 | 29.98 | A | O |
| ATOM | 1165 | N | PHE | A | 192 | 53.986 | 2.326 | -4.397 | 1.00 | 29.54 | A | N |
| ATOM | 1166 | CA | PHE | A | 192 | 54.484 | 1.882 | -5.701 | 1.00 | 29.29 | A | C |
| ATOM | 1167 | CB | PHE | A | 192 | 53.558 | 0.783 | -6.231 | 1.00 | 29.47 | A | C |
| ATOM | 1168 | CG | PHE | A | 192 | 53.033 | -0.095 | -5.152 | 1.00 | 30.03 | A | C |
| ATOM | 1169 | CD1 | PHE | A | 192 | 51.793 | 0.152 | -4.589 | 1.00 | 30.58 | A | C |
| ATOM | 1170 | CD2 | PHE | A | 192 | 53.831 | -1.087 | -4.597 | 1.00 | 29.92 | A | C |
| ATOM | 1171 | CE1 | PHE | A | 192 | 51.350 | -0.565 | -3.478 | 1.00 | 31.20 | A | C |
| ATOM | 1172 | CE2 | PHE | A | 192 | 53.399 | -1.813 | -3.480 | 1.00 | 30.93 | A | C |
| ATOM | 1173 | CZ | PHE | A | 192 | 52.153 | -1.547 | -2.918 | 1.00 | 30.38 | A | C |
| ATOM | 1174 | C | PHE | A | 192 | 54.648 | 3.009 | -6.711 | 1.00 | 29.84 | A | C |
| ATOM | 1175 | O | PHE | A | 192 | 53.795 | 3.902 | -6.810 | 1.00 | 31.67 | A | O |
| ATOM | 1176 | N | ILE | A | 193 | 55.758 | 2.956 | -7.450 | 1.00 | 28.56 | A | N |
| ATOM | 1177 | CA | ILE | A | 193 | 56.089 | 3.973 | -8.436 | 1.00 | 27.86 | A | C |
| ATOM | 1178 | CB | ILE | A | 193 | 57.593 | 4.294 | -8.403 | 1.00 | 26.30 | A | C |
| ATOM | 1179 | CG2 | ILE | A | 193 | 57.962 | 5.185 | -9.565 | 1.00 | 27.03 | A | C |
| ATOM | 1180 | CG1 | ILE | A | 193 | 57.958 | 4.957 | -7.077 | 1.00 | 25.97 | A | C |

Figure 1-21

| | | Atom Type | Resid | # | X | Y | Z | OCC | B | | |
|---|---|---|---|---|---|---|---|---|---|---|---|
| ATOM | 1181 | CD1 | ILE A | 193 | 56.923 | 5.957 | -6.585 | 1.00 | 25.29 | A | C |
| ATOM | 1182 | C | ILE A | 193 | 55.710 | 3.571 | -9.838 | 1.00 | 27.81 | A | C |
| ATOM | 1183 | O | ILE A | 193 | 55.836 | 2.421 | -10.209 | 1.00 | 27.29 | A | O |
| ATOM | 1184 | N | THR A | 194 | 55.242 | 4.531 | -10.620 | 1.00 | 28.38 | A | N |
| ATOM | 1185 | CA | THR A | 194 | 54.853 | 4.243 | -11.993 | 1.00 | 29.30 | A | C |
| ATOM | 1186 | CB | THR A | 194 | 53.616 | 5.074 | -12.449 | 1.00 | 28.68 | A | C |
| ATOM | 1187 | OG1 | THR A | 194 | 53.918 | 6.477 | -12.414 | 1.00 | 29.87 | A | O |
| ATOM | 1188 | CG2 | THR A | 194 | 52.439 | 4.797 | -11.562 | 1.00 | 28.34 | A | C |
| ATOM | 1189 | C | THR A | 194 | 55.944 | 4.482 | -13.025 | 1.00 | 30.15 | A | C |
| ATOM | 1190 | O | THR A | 194 | 57.049 | 4.971 | -12.738 | 1.00 | 26.67 | A | O |
| ATOM | 1191 | N | GLU A | 195 | 55.597 | 4.096 | -14.242 | 1.00 | 32.66 | A | N |
| ATOM | 1192 | CA | GLU A | 195 | 56.463 | 4.250 | -15.388 | 1.00 | 36.32 | A | C |
| ATOM | 1193 | CB | GLU A | 195 | 55.760 | 3.709 | -16.636 | 1.00 | 37.45 | A | C |
| ATOM | 1194 | CG | GLU A | 195 | 55.587 | 2.195 | -16.627 | 1.00 | 39.66 | A | C |
| ATOM | 1195 | CD | GLU A | 195 | 54.144 | 1.738 | -16.425 | 1.00 | 41.31 | A | C |
| ATOM | 1196 | OE1 | GLU A | 195 | 53.552 | 2.024 | -15.348 | 1.00 | 42.31 | A | O |
| ATOM | 1197 | OE2 | GLU A | 195 | 53.614 | 1.083 | -17.356 | 1.00 | 40.34 | A | O |
| ATOM | 1198 | C | GLU A | 195 | 56.786 | 5.730 | -15.545 | 1.00 | 37.92 | A | C |
| ATOM | 1199 | O | GLU A | 195 | 57.744 | 6.090 | -16.217 | 1.00 | 38.89 | A | O |
| ATOM | 1200 | N | ASN A | 196 | 55.980 | 6.584 | -14.916 | 1.00 | 40.39 | A | N |
| ATOM | 1201 | CA | ASN A | 196 | 56.192 | 8.031 | -14.982 | 1.00 | 43.28 | A | C |
| ATOM | 1202 | CB | ASN A | 196 | 54.869 | 8.798 | -15.080 | 1.00 | 46.26 | A | C |
| ATOM | 1203 | CG | ASN A | 196 | 53.806 | 8.040 | -15.846 | 1.00 | 48.72 | A | C |
| ATOM | 1204 | OD1 | ASN A | 196 | 53.034 | 7.253 | -15.262 | 1.00 | 49.77 | A | O |
| ATOM | 1205 | ND2 | ASN A | 196 | 53.758 | 8.259 | -17.164 | 1.00 | 49.24 | A | N |
| ATOM | 1206 | C | ASN A | 196 | 56.924 | 8.507 | -13.736 | 1.00 | 43.11 | A | C |
| ATOM | 1207 | O | ASN A | 196 | 57.413 | 9.628 | -13.703 | 1.00 | 44.24 | A | O |
| ATOM | 1208 | N | MET A | 197 | 56.983 | 7.658 | -12.714 | 1.00 | 43.61 | A | N |
| ATOM | 1209 | CA | MET A | 197 | 57.669 | 8.001 | -11.482 | 1.00 | 43.25 | A | C |
| ATOM | 1210 | CB | MET A | 197 | 58.878 | 8.878 | -11.785 | 1.00 | 44.22 | A | C |
| ATOM | 1211 | CG | MET A | 197 | 59.974 | 8.127 | -12.497 | 1.00 | 44.49 | A | C |
| ATOM | 1212 | SD | MET A | 197 | 60.584 | 6.862 | -11.398 | 1.00 | 45.75 | A | S |
| ATOM | 1213 | CE | MET A | 197 | 61.537 | 7.872 | -10.268 | 1.00 | 44.84 | A | C |
| ATOM | 1214 | C | MET A | 197 | 56.769 | 8.680 | -10.471 | 1.00 | 42.24 | A | C |
| ATOM | 1215 | O | MET A | 197 | 57.172 | 9.588 | -9.753 | 1.00 | 43.34 | A | O |
| ATOM | 1216 | N | GLU A | 198 | 55.533 | 8.228 | -10.426 | 1.00 | 41.82 | A | N |
| ATOM | 1217 | CA | GLU A | 198 | 54.579 | 8.752 | -9.476 | 1.00 | 41.04 | A | C |
| ATOM | 1218 | CB | GLU A | 198 | 53.404 | 9.383 | -10.196 | 1.00 | 43.16 | A | C |
| ATOM | 1219 | CG | GLU A | 198 | 53.506 | 9.239 | -11.682 | 1.00 | 45.48 | A | C |
| ATOM | 1220 | CD | GLU A | 198 | 52.159 | 9.096 | -12.310 | 1.00 | 46.50 | A | C |
| ATOM | 1221 | OE1 | GLU A | 198 | 52.099 | 8.878 | -13.545 | 1.00 | 48.18 | A | O |
| ATOM | 1222 | OE2 | GLU A | 198 | 51.164 | 9.202 | -11.559 | 1.00 | 45.72 | A | O |
| ATOM | 1223 | C | GLU A | 198 | 54.131 | 7.534 | -8.693 | 1.00 | 38.95 | A | C |
| ATOM | 1224 | O | GLU A | 198 | 54.028 | 6.438 | -9.252 | 1.00 | 36.67 | A | O |
| ATOM | 1225 | N | LEU A | 199 | 53.872 | 7.731 | -7.402 | 1.00 | 36.83 | A | N |
| ATOM | 1226 | CA | LEU A | 199 | 53.475 | 6.639 | -6.528 | 1.00 | 36.00 | A | C |
| ATOM | 1227 | CB | LEU A | 199 | 54.199 | 6.758 | -5.179 | 1.00 | 35.67 | A | C |
| ATOM | 1228 | CG | LEU A | 199 | 54.046 | 7.994 | -4.303 | 1.00 | 35.25 | A | C |
| ATOM | 1229 | CD1 | LEU A | 199 | 52.605 | 8.146 | -3.776 | 1.00 | 34.97 | A | C |
| ATOM | 1230 | CD2 | LEU A | 199 | 55.024 | 7.847 | -3.157 | 1.00 | 34.24 | A | C |
| ATOM | 1231 | C | LEU A | 199 | 51.981 | 6.525 | -6.305 | 1.00 | 34.48 | A | C |
| ATOM | 1232 | O | LEU A | 199 | 51.230 | 7.454 | -6.594 | 1.00 | 31.82 | A | O |
| ATOM | 1233 | N | LYS A | 200 | 51.568 | 5.377 | -5.779 | 1.00 | 34.69 | A | N |
| ATOM | 1234 | CA | LYS A | 200 | 50.162 | 5.124 | -5.515 | 1.00 | 35.03 | A | C |
| ATOM | 1235 | CB | LYS A | 200 | 49.567 | 4.343 | -6.681 | 1.00 | 34.76 | A | C |
| ATOM | 1236 | CG | LYS A | 200 | 50.003 | 4.835 | -8.036 | 1.00 | 32.58 | A | C |
| ATOM | 1237 | CD | LYS A | 200 | 49.347 | 6.146 | -8.393 | 1.00 | 34.47 | A | C |
| ATOM | 1238 | CE | LYS A | 200 | 49.809 | 6.596 | -9.763 | 1.00 | 32.40 | A | C |
| ATOM | 1239 | NZ | LYS A | 200 | 49.675 | 5.478 | -10.731 | 1.00 | 31.53 | A | N |

Figure 1-22

| | Atom Type | Resid | # | X | Y | Z | OCC | B | | |
|---|---|---|---|---|---|---|---|---|---|---|
| ATOM | 1240 | C | LYS A | 200 | 50.050 | 4.293 | -4.249 | 1.00 | 35.52 | A | C |
| ATOM | 1241 | O | LYS A | 200 | 50.153 | 3.067 | -4.316 | 1.00 | 38.51 | A | O |
| ATOM | 1242 | N | VAL A | 201 | 49.841 | 4.929 | -3.098 | 1.00 | 35.48 | A | N |
| ATOM | 1243 | CA | VAL A | 201 | 49.753 | 4.144 | -1.873 | 1.00 | 34.78 | A | C |
| ATOM | 1244 | CB | VAL A | 201 | 49.208 | 4.969 | -0.673 | 1.00 | 34.69 | A | C |
| ATOM | 1245 | CG1 | VAL A | 201 | 50.009 | 6.238 | -0.521 | 1.00 | 34.06 | A | C |
| ATOM | 1246 | CG2 | VAL A | 201 | 47.748 | 5.268 | -0.850 | 1.00 | 35.94 | A | C |
| ATOM | 1247 | C | VAL A | 201 | 48.855 | 2.946 | -2.157 | 1.00 | 34.13 | A | C |
| ATOM | 1248 | O | VAL A | 201 | 47.810 | 3.073 | -2.797 | 1.00 | 35.69 | A | O |
| ATOM | 1249 | N | GLY A | 202 | 49.279 | 1.768 | -1.723 | 1.00 | 33.92 | A | N |
| ATOM | 1250 | CA | GLY A | 202 | 48.472 | 0.595 | -1.982 | 1.00 | 33.80 | A | C |
| ATOM | 1251 | C | GLY A | 202 | 48.543 | -0.482 | -0.924 | 1.00 | 33.68 | A | C |
| ATOM | 1252 | O | GLY A | 202 | 48.767 | -0.185 | 0.249 | 1.00 | 33.71 | A | O |
| ATOM | 1253 | N | ASP A | 203 | 48.358 | -1.727 | -1.359 | 1.00 | 32.92 | A | N |
| ATOM | 1254 | CA | ASP A | 203 | 48.371 | -2.889 | -0.487 | 1.00 | 34.11 | A | C |
| ATOM | 1255 | CB | ASP A | 203 | 49.800 | -3.293 | -0.103 | 1.00 | 35.50 | A | C |
| ATOM | 1256 | CG | ASP A | 203 | 50.532 | -4.031 | -1.226 | 1.00 | 36.36 | A | C |
| ATOM | 1257 | OD1 | ASP A | 203 | 49.887 | -4.775 | -1.988 | 1.00 | 36.83 | A | O |
| ATOM | 1258 | OD2 | ASP A | 203 | 51.765 | -3.889 | -1.335 | 1.00 | 37.84 | A | O |
| ATOM | 1259 | C | ASP A | 203 | 47.567 | -2.624 | 0.763 | 1.00 | 34.27 | A | C |
| ATOM | 1260 | O | ASP A | 203 | 48.068 | -2.776 | 1.877 | 1.00 | 34.05 | A | O |
| ATOM | 1261 | N | PHE A | 204 | 46.313 | -2.221 | 0.580 | 1.00 | 34.74 | A | N |
| ATOM | 1262 | CA | PHE A | 204 | 45.446 | -1.949 | 1.710 | 1.00 | 33.37 | A | C |
| ATOM | 1263 | CB | PHE A | 204 | 44.169 | -1.296 | 1.215 | 1.00 | 33.42 | A | C |
| ATOM | 1264 | CG | PHE A | 204 | 44.415 | 0.007 | 0.512 | 1.00 | 32.27 | A | C |
| ATOM | 1265 | CD1 | PHE A | 204 | 44.620 | 0.045 | -0.861 | 1.00 | 30.57 | A | C |
| ATOM | 1266 | CD2 | PHE A | 204 | 44.466 | 1.202 | 1.232 | 1.00 | 30.42 | A | C |
| ATOM | 1267 | CE1 | PHE A | 204 | 44.871 | 1.250 | -1.512 | 1.00 | 31.27 | A | C |
| ATOM | 1268 | CE2 | PHE A | 204 | 44.715 | 2.411 | 0.591 | 1.00 | 30.66 | A | C |
| ATOM | 1269 | CZ | PHE A | 204 | 44.917 | 2.438 | -0.787 | 1.00 | 31.62 | A | C |
| ATOM | 1270 | C | PHE A | 204 | 45.194 | -3.257 | 2.436 | 1.00 | 34.28 | A | C |
| ATOM | 1271 | O | PHE A | 204 | 46.027 | -4.160 | 2.356 | 1.00 | 34.38 | A | O |
| ATOM | 1272 | N | GLY A | 205 | 44.077 | -3.401 | 3.132 | 1.00 | 35.29 | A | N |
| ATOM | 1273 | CA | GLY A | 205 | 43.878 | -4.658 | 3.842 | 1.00 | 38.59 | A | C |
| ATOM | 1274 | C | GLY A | 205 | 44.841 | -4.729 | 5.025 | 1.00 | 38.19 | A | C |
| ATOM | 1275 | O | GLY A | 205 | 45.907 | -5.344 | 4.989 | 1.00 | 39.07 | A | O |
| ATOM | 1276 | N | LEU A | 206 | 44.415 | -4.066 | 6.084 | 1.00 | 38.86 | A | N |
| ATOM | 1277 | CA | LEU A | 206 | 45.099 | -3.902 | 7.356 | 1.00 | 36.45 | A | C |
| ATOM | 1278 | CB | LEU A | 206 | 46.635 | -3.910 | 7.210 | 1.00 | 38.23 | A | C |
| ATOM | 1279 | CG | LEU A | 206 | 47.484 | -3.585 | 8.466 | 1.00 | 39.24 | A | C |
| ATOM | 1280 | CD1 | LEU A | 206 | 46.772 | -3.969 | 9.763 | 1.00 | 40.01 | A | C |
| ATOM | 1281 | CD2 | LEU A | 206 | 48.809 | -4.320 | 8.381 | 1.00 | 39.00 | A | C |
| ATOM | 1282 | C | LEU A | 206 | 44.552 | -2.511 | 7.551 | 1.00 | 34.79 | A | C |
| ATOM | 1283 | O | LEU A | 206 | 44.633 | -1.928 | 8.616 | 1.00 | 35.02 | A | O |
| ATOM | 1284 | N | ALA A | 207 | 43.955 | -2.029 | 6.455 | 1.00 | 32.53 | A | N |
| ATOM | 1285 | CA | ALA A | 207 | 43.286 | -0.735 | 6.361 | 1.00 | 30.93 | A | C |
| ATOM | 1286 | CB | ALA A | 207 | 43.106 | -0.331 | 4.893 | 1.00 | 29.27 | A | C |
| ATOM | 1287 | C | ALA A | 207 | 41.921 | -0.934 | 7.012 | 1.00 | 30.32 | A | C |
| ATOM | 1288 | O | ALA A | 207 | 41.368 | -2.034 | 6.969 | 1.00 | 27.20 | A | O |
| ATOM | 1289 | N | ALA A | 208 | 41.370 | 0.119 | 7.610 | 1.00 | 29.48 | A | N |
| ATOM | 1290 | CA | ALA A | 208 | 40.068 | 0.010 | 8.271 | 1.00 | 30.07 | A | C |
| ATOM | 1291 | CB | ALA A | 208 | 40.258 | -0.507 | 9.705 | 1.00 | 30.18 | A | C |
| ATOM | 1292 | C | ALA A | 208 | 39.320 | 1.333 | 8.295 | 1.00 | 29.80 | A | C |
| ATOM | 1293 | O | ALA A | 208 | 39.915 | 2.399 | 8.230 | 1.00 | 29.17 | A | O |
| ATOM | 1294 | N | ARG A | 209 | 38.001 | 1.253 | 8.381 | 1.00 | 30.89 | A | N |
| ATOM | 1295 | CA | ARG A | 209 | 37.202 | 2.458 | 8.446 | 1.00 | 32.43 | A | C |
| ATOM | 1296 | CB | ARG A | 209 | 35.726 | 2.147 | 8.210 | 1.00 | 33.01 | A | C |
| ATOM | 1297 | CG | ARG A | 209 | 35.140 | 1.045 | 9.067 | 1.00 | 36.80 | A | C |
| ATOM | 1298 | CD | ARG A | 209 | 33.988 | 0.390 | 8.309 | 1.00 | 38.74 | A | C |

Figure 1-23

| | | Atom Type | Resid | # | X | Y | Z | OCC | B | | |
|---|---|---|---|---|---|---|---|---|---|---|---|
| ATOM | 1299 | NE | ARG A | 209 | 34.370 | 0.127 | 6.924 | 1.00 | 40.71 | A | N |
| ATOM | 1300 | CZ | ARG A | 209 | 33.672 | -0.627 | 6.081 | 1.00 | 42.78 | A | C |
| ATOM | 1301 | NH1 | ARG A | 209 | 32.546 | -1.206 | 6.474 | 1.00 | 43.19 | A | N |
| ATOM | 1302 | NH2 | ARG A | 209 | 34.100 | -0.805 | 4.837 | 1.00 | 43.97 | A | N |
| ATOM | 1303 | C | ARG A | 209 | 37.387 | 3.101 | 9.802 | 1.00 | 31.93 | A | C |
| ATOM | 1304 | O | ARG A | 209 | 36.986 | 2.549 | 10.816 | 1.00 | 32.59 | A | O |
| ATOM | 1305 | N | LEU A | 210 | 38.016 | 4.270 | 9.805 | 1.00 | 33.16 | A | N |
| ATOM | 1306 | CA | LEU A | 210 | 38.270 | 5.005 | 11.028 | 1.00 | 35.85 | A | C |
| ATOM | 1307 | CB | LEU A | 210 | 38.687 | 6.449 | 10.706 | 1.00 | 35.80 | A | C |
| ATOM | 1308 | CG | LEU A | 210 | 38.415 | 7.551 | 11.751 | 1.00 | 34.93 | A | C |
| ATOM | 1309 | CD1 | LEU A | 210 | 38.918 | 7.170 | 13.129 | 1.00 | 35.44 | A | C |
| ATOM | 1310 | CD2 | LEU A | 210 | 39.105 | 8.819 | 11.292 | 1.00 | 35.77 | A | C |
| ATOM | 1311 | C | LEU A | 210 | 37.056 | 5.018 | 11.939 | 1.00 | 37.16 | A | C |
| ATOM | 1312 | O | LEU A | 210 | 35.930 | 5.138 | 11.474 | 1.00 | 36.66 | A | O |
| ATOM | 1313 | N | GLU A | 211 | 37.298 | 4.897 | 13.240 | 1.00 | 40.07 | A | N |
| ATOM | 1314 | CA | GLU A | 211 | 36.228 | 4.898 | 14.215 | 1.00 | 41.55 | A | C |
| ATOM | 1315 | CB | GLU A | 211 | 35.940 | 3.487 | 14.685 | 1.00 | 42.81 | A | C |
| ATOM | 1316 | CG | GLU A | 211 | 35.565 | 2.567 | 13.570 | 1.00 | 45.65 | A | C |
| ATOM | 1317 | CD | GLU A | 211 | 34.290 | 1.850 | 13.873 | 1.00 | 47.42 | A | C |
| ATOM | 1318 | OE1 | GLU A | 211 | 34.247 | 1.187 | 14.934 | 1.00 | 48.53 | A | O |
| ATOM | 1319 | OE2 | GLU A | 211 | 33.337 | 1.958 | 13.065 | 1.00 | 49.23 | A | O |
| ATOM | 1320 | C | GLU A | 211 | 36.660 | 5.720 | 15.386 | 1.00 | 41.46 | A | C |
| ATOM | 1321 | O | GLU A | 211 | 37.854 | 5.905 | 15.600 | 1.00 | 40.40 | A | O |
| ATOM | 1322 | N | PRO A | 212 | 35.689 | 6.219 | 16.171 | 1.00 | 42.46 | A | N |
| ATOM | 1323 | CD | PRO A | 212 | 34.255 | 5.920 | 16.018 | 1.00 | 42.44 | A | C |
| ATOM | 1324 | CA | PRO A | 212 | 35.900 | 7.044 | 17.361 | 1.00 | 43.79 | A | C |
| ATOM | 1325 | CB | PRO A | 212 | 34.524 | 7.051 | 18.026 | 1.00 | 43.59 | A | C |
| ATOM | 1326 | CG | PRO A | 212 | 33.609 | 6.984 | 16.886 | 1.00 | 43.34 | A | C |
| ATOM | 1327 | C | PRO A | 212 | 36.969 | 6.479 | 18.287 | 1.00 | 44.42 | A | C |
| ATOM | 1328 | O | PRO A | 212 | 37.109 | 5.269 | 18.449 | 1.00 | 42.85 | A | O |
| ATOM | 1329 | N | PRO A | 213 | 37.746 | 7.368 | 18.898 | 1.00 | 47.34 | A | N |
| ATOM | 1330 | CD | PRO A | 213 | 37.639 | 8.817 | 18.686 | 1.00 | 48.25 | A | C |
| ATOM | 1331 | CA | PRO A | 213 | 38.832 | 7.070 | 19.829 | 1.00 | 49.55 | A | C |
| ATOM | 1332 | CB | PRO A | 213 | 39.298 | 8.464 | 20.269 | 1.00 | 48.39 | A | C |
| ATOM | 1333 | CG | PRO A | 213 | 38.106 | 9.336 | 19.997 | 1.00 | 49.00 | A | C |
| ATOM | 1334 | C | PRO A | 213 | 38.434 | 6.186 | 21.010 | 1.00 | 51.20 | A | C |
| ATOM | 1335 | O | PRO A | 213 | 39.147 | 6.130 | 22.012 | 1.00 | 52.55 | A | O |
| ATOM | 1336 | N | GLU A | 214 | 37.303 | 5.500 | 20.906 | 1.00 | 53.51 | A | N |
| ATOM | 1337 | CA | GLU A | 214 | 36.883 | 4.636 | 21.998 | 1.00 | 55.34 | A | C |
| ATOM | 1338 | CB | GLU A | 214 | 36.212 | 5.449 | 23.095 | 1.00 | 57.90 | A | C |
| ATOM | 1339 | CG | GLU A | 214 | 36.217 | 4.724 | 24.427 | 1.00 | 60.85 | A | C |
| ATOM | 1340 | CD | GLU A | 214 | 36.501 | 5.650 | 25.592 | 1.00 | 62.71 | A | C |
| ATOM | 1341 | OE1 | GLU A | 214 | 37.475 | 6.434 | 25.506 | 1.00 | 64.23 | A | O |
| ATOM | 1342 | OE2 | GLU A | 214 | 35.760 | 5.581 | 26.599 | 1.00 | 63.63 | A | O |
| ATOM | 1343 | C | GLU A | 214 | 35.956 | 3.523 | 21.555 | 1.00 | 55.39 | A | C |
| ATOM | 1344 | O | GLU A | 214 | 35.554 | 2.691 | 22.361 | 1.00 | 54.90 | A | O |
| ATOM | 1345 | N | GLN A | 215 | 35.602 | 3.526 | 20.275 | 1.00 | 56.12 | A | N |
| ATOM | 1346 | CA | GLN A | 215 | 34.747 | 2.495 | 19.686 | 1.00 | 57.24 | A | C |
| ATOM | 1347 | CB | GLN A | 215 | 33.583 | 3.138 | 18.901 | 1.00 | 58.30 | A | C |
| ATOM | 1348 | CG | GLN A | 215 | 32.688 | 2.118 | 18.186 | 1.00 | 59.88 | A | C |
| ATOM | 1349 | CD | GLN A | 215 | 31.675 | 1.458 | 19.122 | 1.00 | 60.52 | A | C |
| ATOM | 1350 | OE1 | GLN A | 215 | 31.052 | 0.443 | 18.772 | 1.00 | 60.79 | A | O |
| ATOM | 1351 | NE2 | GLN A | 215 | 31.505 | 2.036 | 20.319 | 1.00 | 60.72 | A | N |
| ATOM | 1352 | C | GLN A | 215 | 35.681 | 1.783 | 18.723 | 1.00 | 57.28 | A | C |
| ATOM | 1353 | O | GLN A | 215 | 35.383 | 0.744 | 18.167 | 1.00 | 58.17 | A | O |
| ATOM | 1354 | N | ARG A | 216 | 36.849 | 2.380 | 18.586 | 1.00 | 56.80 | A | N |
| ATOM | 1355 | CA | ARG A | 216 | 37.904 | 1.957 | 17.681 | 1.00 | 56.77 | A | C |
| ATOM | 1356 | CB | ARG A | 216 | 39.167 | 2.726 | 18.068 | 1.00 | 55.33 | A | C |
| ATOM | 1357 | CG | ARG A | 216 | 40.292 | 2.711 | 17.055 | 1.00 | 54.00 | A | C |

Figure 1-24

| | | Atom Type | Resid | # | X | Y | Z | OCC | B | | |
|---|---|---|---|---|---|---|---|---|---|---|---|
| ATOM | 1358 | CD | ARG A | 216 | 41.148 | 3.935 | 17.312 | 1.00 | 53.35 | A | C |
| ATOM | 1359 | NE | ARG A | 216 | 40.365 | 5.134 | 17.041 | 1.00 | 51.91 | A | N |
| ATOM | 1360 | CZ | ARG A | 216 | 40.739 | 6.405 | 17.193 | 1.00 | 50.37 | A | C |
| ATOM | 1361 | NH1 | ARG A | 216 | 41.918 | 6.774 | 17.685 | 1.00 | 50.29 | A | N |
| ATOM | 1362 | NH2 | ARG A | 216 | 39.993 | 7.335 | 16.615 | 1.00 | 48.94 | A | N |
| ATOM | 1363 | C | ARG A | 216 | 38.266 | 0.455 | 17.458 | 1.00 | 56.73 | A | C |
| ATOM | 1364 | O | ARG A | 216 | 37.989 | -0.089 | 16.386 | 1.00 | 57.82 | A | O |
| ATOM | 1365 | N | LYS A | 217 | 38.885 | -0.204 | 18.440 | 1.00 | 55.85 | A | N |
| ATOM | 1366 | CA | LYS A | 217 | 39.368 | -1.594 | 18.311 | 1.00 | 55.21 | A | C |
| ATOM | 1367 | CB | LYS A | 217 | 39.143 | -2.191 | 16.901 | 1.00 | 55.45 | A | C |
| ATOM | 1368 | CG | LYS A | 217 | 39.962 | -3.460 | 16.607 | 1.00 | 55.52 | A | C |
| ATOM | 1369 | CD | LYS A | 217 | 39.185 | -4.510 | 15.810 | 1.00 | 56.22 | A | C |
| ATOM | 1370 | CE | LYS A | 217 | 38.118 | -5.183 | 16.681 | 1.00 | 55.85 | A | C |
| ATOM | 1371 | NZ | LYS A | 217 | 37.099 | -5.928 | 15.877 | 1.00 | 56.93 | A | N |
| ATOM | 1372 | C | LYS A | 217 | 40.844 | -1.372 | 18.541 | 1.00 | 54.48 | A | C |
| ATOM | 1373 | O | LYS A | 217 | 41.571 | -0.953 | 17.646 | 1.00 | 53.60 | A | O |
| ATOM | 1374 | N | LYS A | 218 | 41.260 | -1.625 | 19.776 | 1.00 | 54.39 | A | N |
| ATOM | 1375 | CA | LYS A | 218 | 42.632 | -1.426 | 20.229 | 1.00 | 53.38 | A | C |
| ATOM | 1376 | CB | LYS A | 218 | 42.627 | -1.086 | 21.728 | 1.00 | 53.71 | A | C |
| ATOM | 1377 | CG | LYS A | 218 | 42.135 | 0.331 | 22.102 | 1.00 | 53.76 | A | C |
| ATOM | 1378 | CD | LYS A | 218 | 40.615 | 0.496 | 22.002 | 1.00 | 54.19 | A | C |
| ATOM | 1379 | CE | LYS A | 218 | 40.133 | 1.867 | 22.471 | 1.00 | 54.07 | A | C |
| ATOM | 1380 | NZ | LYS A | 218 | 40.633 | 2.947 | 21.591 | 1.00 | 54.37 | A | N |
| ATOM | 1381 | C | LYS A | 218 | 43.576 | -2.593 | 19.988 | 1.00 | 52.77 | A | C |
| ATOM | 1382 | O | LYS A | 218 | 44.172 | -3.116 | 20.923 | 1.00 | 53.48 | A | O |
| ATOM | 1383 | N | THR A | 219 | 43.685 | -3.030 | 18.743 | 1.00 | 51.59 | A | N |
| ATOM | 1384 | CA | THR A | 219 | 44.585 | -4.125 | 18.433 | 1.00 | 50.14 | A | C |
| ATOM | 1385 | CB | THR A | 219 | 43.979 | -5.093 | 17.377 | 1.00 | 50.18 | A | C |
| ATOM | 1386 | OG1 | THR A | 219 | 43.764 | -4.408 | 16.129 | 1.00 | 51.38 | A | O |
| ATOM | 1387 | CG2 | THR A | 219 | 42.674 | -5.674 | 17.887 | 1.00 | 50.41 | A | C |
| ATOM | 1388 | C | THR A | 219 | 45.906 | -3.555 | 17.912 | 1.00 | 49.18 | A | C |
| ATOM | 1389 | O | THR A | 219 | 45.920 | -2.597 | 17.127 | 1.00 | 50.39 | A | O |
| ATOM | 1390 | N | ILE A | 220 | 47.013 | -4.133 | 18.378 | 1.00 | 47.69 | A | N |
| ATOM | 1391 | CA | ILE A | 220 | 48.362 | -3.718 | 17.976 | 1.00 | 45.65 | A | C |
| ATOM | 1392 | CB | ILE A | 220 | 49.444 | -4.210 | 18.977 | 1.00 | 45.76 | A | C |
| ATOM | 1393 | CG2 | ILE A | 220 | 50.821 | -3.771 | 18.513 | 1.00 | 45.07 | A | C |
| ATOM | 1394 | CG1 | ILE A | 220 | 49.160 | -3.669 | 20.379 | 1.00 | 46.11 | A | C |
| ATOM | 1395 | CD1 | ILE A | 220 | 50.196 | -4.057 | 21.404 | 1.00 | 45.75 | A | C |
| ATOM | 1396 | C | ILE A | 220 | 48.733 | -4.307 | 16.620 | 1.00 | 44.01 | A | C |
| ATOM | 1397 | O | ILE A | 220 | 49.159 | -5.454 | 16.547 | 1.00 | 45.06 | A | O |
| ATOM | 1398 | N | CYS A | 221 | 48.567 | -3.539 | 15.548 | 1.00 | 40.99 | A | N |
| ATOM | 1399 | CA | CYS A | 221 | 48.932 | -4.035 | 14.224 | 1.00 | 37.90 | A | C |
| ATOM | 1400 | CB | CYS A | 221 | 47.691 | -4.504 | 13.445 | 1.00 | 37.99 | A | C |
| ATOM | 1401 | SG | CYS A | 221 | 46.474 | -3.244 | 13.013 | 1.00 | 42.03 | A | S |
| ATOM | 1402 | C | CYS A | 221 | 49.701 | -2.985 | 13.414 | 1.00 | 35.23 | A | C |
| ATOM | 1403 | O | CYS A | 221 | 49.764 | -1.810 | 13.794 | 1.00 | 34.20 | A | O |
| ATOM | 1404 | N | GLY A | 222 | 50.292 | -3.418 | 12.304 | 1.00 | 32.59 | A | N |
| ATOM | 1405 | CA | GLY A | 222 | 51.041 | -2.507 | 11.463 | 1.00 | 30.65 | A | C |
| ATOM | 1406 | C | GLY A | 222 | 52.532 | -2.795 | 11.495 | 1.00 | 31.16 | A | C |
| ATOM | 1407 | O | GLY A | 222 | 53.056 | -3.282 | 12.506 | 1.00 | 29.91 | A | O |
| ATOM | 1408 | N | THR A | 223 | 53.211 | -2.506 | 10.384 | 1.00 | 29.51 | A | N |
| ATOM | 1409 | CA | THR A | 223 | 54.649 | -2.711 | 10.265 | 1.00 | 27.64 | A | C |
| ATOM | 1410 | CB | THR A | 223 | 55.179 | -2.190 | 8.914 | 1.00 | 28.48 | A | C |
| ATOM | 1411 | OG1 | THR A | 223 | 54.640 | -0.885 | 8.646 | 1.00 | 29.55 | A | O |
| ATOM | 1412 | CG2 | THR A | 223 | 54.772 | -3.138 | 7.807 | 1.00 | 28.41 | A | C |
| ATOM | 1413 | C | THR A | 223 | 55.373 | -1.997 | 11.393 | 1.00 | 27.95 | A | C |
| ATOM | 1414 | O | THR A | 223 | 55.330 | -0.775 | 11.484 | 1.00 | 27.72 | A | O |
| ATOM | 1415 | N | PRO A | 224 | 56.056 | -2.763 | 12.263 | 1.00 | 28.66 | A | N |
| ATOM | 1416 | CD | PRO A | 224 | 56.162 | -4.216 | 12.048 | 1.00 | 29.69 | A | C |

Figure 1-25

| | | Atom Type | Resid | # | X | Y | Z | OCC | B | | |
|---|---|---|---|---|---|---|---|---|---|---|---|
| ATOM | 1417 | CA | PRO A | 224 | 56.842 | -2.382 | 13.443 | 1.00 | 29.63 | A | C |
| ATOM | 1418 | CB | PRO A | 224 | 57.804 | -3.553 | 13.575 | 1.00 | 30.29 | A | C |
| ATOM | 1419 | CG | PRO A | 224 | 56.880 | -4.688 | 13.302 | 1.00 | 30.73 | A | C |
| ATOM | 1420 | C | PRO A | 224 | 57.533 | -0.998 | 13.513 | 1.00 | 30.33 | A | C |
| ATOM | 1421 | O | PRO A | 224 | 57.153 | -0.161 | 14.340 | 1.00 | 28.88 | A | O |
| ATOM | 1422 | N | ASN A | 225 | 58.535 | -0.757 | 12.670 | 1.00 | 31.05 | A | N |
| ATOM | 1423 | CA | ASN A | 225 | 59.230 | 0.523 | 12.664 | 1.00 | 31.11 | A | C |
| ATOM | 1424 | CB | ASN A | 225 | 60.303 | 0.525 | 11.590 | 1.00 | 29.46 | A | C |
| ATOM | 1425 | CG | ASN A | 225 | 61.507 | -0.299 | 11.969 | 1.00 | 30.11 | A | C |
| ATOM | 1426 | OD1 | ASN A | 225 | 62.126 | -0.937 | 11.111 | 1.00 | 29.75 | A | O |
| ATOM | 1427 | ND2 | ASN A | 225 | 61.860 | -0.287 | 13.250 | 1.00 | 29.64 | A | N |
| ATOM | 1428 | C | ASN A | 225 | 58.276 | 1.665 | 12.389 | 1.00 | 32.44 | A | C |
| ATOM | 1429 | O | ASN A | 225 | 58.435 | 2.764 | 12.918 | 1.00 | 33.08 | A | O |
| ATOM | 1430 | N | TYR A | 226 | 57.288 | 1.400 | 11.547 | 1.00 | 33.86 | A | N |
| ATOM | 1431 | CA | TYR A | 226 | 56.309 | 2.403 | 11.180 | 1.00 | 35.84 | A | C |
| ATOM | 1432 | CB | TYR A | 226 | 55.982 | 2.288 | 9.685 | 1.00 | 36.11 | A | C |
| ATOM | 1433 | CG | TYR A | 226 | 57.207 | 2.135 | 8.796 | 1.00 | 37.65 | A | C |
| ATOM | 1434 | CD1 | TYR A | 226 | 58.066 | 1.031 | 8.923 | 1.00 | 38.08 | A | C |
| ATOM | 1435 | CE1 | TYR A | 226 | 59.197 | 0.888 | 8.104 | 1.00 | 38.11 | A | C |
| ATOM | 1436 | CD2 | TYR A | 226 | 57.511 | 3.090 | 7.828 | 1.00 | 38.37 | A | C |
| ATOM | 1437 | CE2 | TYR A | 226 | 58.642 | 2.956 | 6.999 | 1.00 | 38.80 | A | C |
| ATOM | 1438 | CZ | TYR A | 226 | 59.478 | 1.855 | 7.141 | 1.00 | 38.42 | A | C |
| ATOM | 1439 | OH | TYR A | 226 | 60.579 | 1.736 | 6.309 | 1.00 | 39.49 | A | O |
| ATOM | 1440 | C | TYR A | 226 | 55.049 | 2.206 | 12.011 | 1.00 | 37.08 | A | C |
| ATOM | 1441 | O | TYR A | 226 | 53.946 | 2.134 | 11.467 | 1.00 | 39.67 | A | O |
| ATOM | 1442 | N | VAL A | 227 | 55.213 | 2.097 | 13.328 | 1.00 | 35.78 | A | N |
| ATOM | 1443 | CA | VAL A | 227 | 54.072 | 1.911 | 14.228 | 1.00 | 36.09 | A | C |
| ATOM | 1444 | CB | VAL A | 227 | 54.083 | 0.514 | 14.881 | 1.00 | 37.18 | A | C |
| ATOM | 1445 | CG1 | VAL A | 227 | 52.812 | 0.305 | 15.690 | 1.00 | 36.60 | A | C |
| ATOM | 1446 | CG2 | VAL A | 227 | 54.167 | -0.550 | 13.824 | 1.00 | 36.97 | A | C |
| ATOM | 1447 | C | VAL A | 227 | 54.104 | 2.975 | 15.320 | 1.00 | 35.32 | A | C |
| ATOM | 1448 | O | VAL A | 227 | 55.097 | 3.113 | 16.034 | 1.00 | 36.13 | A | O |
| ATOM | 1449 | N | ALA A | 228 | 53.010 | 3.725 | 15.437 | 1.00 | 32.54 | A | N |
| ATOM | 1450 | CA | ALA A | 228 | 52.899 | 4.812 | 16.407 | 1.00 | 32.00 | A | C |
| ATOM | 1451 | CB | ALA A | 228 | 51.659 | 5.663 | 16.082 | 1.00 | 30.43 | A | C |
| ATOM | 1452 | C | ALA A | 228 | 52.865 | 4.378 | 17.872 | 1.00 | 31.29 | A | C |
| ATOM | 1453 | O | ALA A | 228 | 52.399 | 3.284 | 18.210 | 1.00 | 30.70 | A | O |
| ATOM | 1454 | N | PRO A | 229 | 53.357 | 5.243 | 18.767 | 1.00 | 30.49 | A | N |
| ATOM | 1455 | CD | PRO A | 229 | 53.985 | 6.541 | 18.466 | 1.00 | 31.30 | A | C |
| ATOM | 1456 | CA | PRO A | 229 | 53.391 | 4.984 | 20.206 | 1.00 | 31.90 | A | C |
| ATOM | 1457 | CB | PRO A | 229 | 53.717 | 6.358 | 20.778 | 1.00 | 31.53 | A | C |
| ATOM | 1458 | CG | PRO A | 229 | 54.669 | 6.894 | 19.772 | 1.00 | 30.81 | A | C |
| ATOM | 1459 | C | PRO A | 229 | 52.089 | 4.402 | 20.793 | 1.00 | 31.86 | A | C |
| ATOM | 1460 | O | PRO A | 229 | 52.132 | 3.391 | 21.498 | 1.00 | 31.11 | A | O |
| ATOM | 1461 | N | GLU A | 230 | 50.954 | 5.041 | 20.489 | 1.00 | 33.89 | A | N |
| ATOM | 1462 | CA | GLU A | 230 | 49.628 | 4.657 | 20.989 | 1.00 | 34.53 | A | C |
| ATOM | 1463 | CB | GLU A | 230 | 48.562 | 5.601 | 20.450 | 1.00 | 35.64 | A | C |
| ATOM | 1464 | CG | GLU A | 230 | 48.957 | 7.036 | 20.321 | 1.00 | 37.22 | A | C |
| ATOM | 1465 | CD | GLU A | 230 | 49.571 | 7.363 | 18.976 | 1.00 | 37.26 | A | C |
| ATOM | 1466 | OE1 | GLU A | 230 | 48.973 | 7.030 | 17.930 | 1.00 | 36.45 | A | O |
| ATOM | 1467 | OE2 | GLU A | 230 | 50.656 | 7.971 | 18.974 | 1.00 | 37.21 | A | O |
| ATOM | 1468 | C | GLU A | 230 | 49.151 | 3.255 | 20.657 | 1.00 | 34.01 | A | C |
| ATOM | 1469 | O | GLU A | 230 | 48.506 | 2.589 | 21.472 | 1.00 | 33.96 | A | O |
| ATOM | 1470 | N | VAL A | 231 | 49.418 | 2.826 | 19.433 | 1.00 | 33.50 | A | N |
| ATOM | 1471 | CA | VAL A | 231 | 48.977 | 1.513 | 19.042 | 1.00 | 33.66 | A | C |
| ATOM | 1472 | CB | VAL A | 231 | 49.193 | 1.256 | 17.530 | 1.00 | 34.87 | A | C |
| ATOM | 1473 | CG1 | VAL A | 231 | 49.767 | 2.493 | 16.873 | 1.00 | 35.51 | A | C |
| ATOM | 1474 | CG2 | VAL A | 231 | 50.061 | 0.031 | 17.323 | 1.00 | 35.95 | A | C |
| ATOM | 1475 | C | VAL A | 231 | 49.674 | 0.458 | 19.873 | 1.00 | 34.05 | A | C |

Figure 1-26

| | | Atom Type | Resid | # | X | Y | Z | OCC | B | | |
|---|---|---|---|---|---|---|---|---|---|---|---|
| ATOM | 1476 | O | VAL A | 231 | 49.075 | -0.568 | 20.167 | 1.00 | 33.40 | A | O |
| ATOM | 1477 | N | LEU A | 232 | 50.929 | 0.719 | 20.248 | 1.00 | 33.86 | A | N |
| ATOM | 1478 | CA | LEU A | 232 | 51.732 | -0.192 | 21.071 | 1.00 | 33.14 | A | C |
| ATOM | 1479 | CB | LEU A | 232 | 53.193 | 0.257 | 21.111 | 1.00 | 31.01 | A | C |
| ATOM | 1480 | CG | LEU A | 232 | 53.951 | 0.265 | 19.777 | 1.00 | 30.64 | A | C |
| ATOM | 1481 | CD1 | LEU A | 232 | 55.289 | 0.861 | 20.023 | 1.00 | 28.96 | A | C |
| ATOM | 1482 | CD2 | LEU A | 232 | 54.106 | -1.130 | 19.191 | 1.00 | 28.75 | A | C |
| ATOM | 1483 | C | LEU A | 232 | 51.176 | -0.218 | 22.478 | 1.00 | 34.70 | A | C |
| ATOM | 1484 | O | LEU A | 232 | 51.089 | -1.284 | 23.092 | 1.00 | 35.82 | A | O |
| ATOM | 1485 | N | LEU A | 233 | 50.829 | 0.964 | 22.987 | 1.00 | 36.20 | A | N |
| ATOM | 1486 | CA | LEU A | 233 | 50.215 | 1.095 | 24.307 | 1.00 | 38.34 | A | C |
| ATOM | 1487 | CB | LEU A | 233 | 50.624 | 2.399 | 24.994 | 1.00 | 39.36 | A | C |
| ATOM | 1488 | CG | LEU A | 233 | 51.292 | 3.530 | 24.218 | 1.00 | 40.34 | A | C |
| ATOM | 1489 | CD1 | LEU A | 233 | 50.856 | 4.888 | 24.778 | 1.00 | 40.00 | A | C |
| ATOM | 1490 | CD2 | LEU A | 233 | 52.808 | 3.378 | 24.298 | 1.00 | 40.21 | A | C |
| ATOM | 1491 | C | LEU A | 233 | 48.695 | 1.048 | 24.061 | 1.00 | 39.78 | A | C |
| ATOM | 1492 | O | LEU A | 233 | 47.932 | 1.963 | 24.358 | 1.00 | 39.03 | A | O |
| ATOM | 1493 | N | ARG A | 234 | 48.324 | -0.080 | 23.472 | 1.00 | 39.74 | A | N |
| ATOM | 1494 | CA | ARG A | 234 | 46.992 | -0.507 | 23.054 | 1.00 | 40.44 | A | C |
| ATOM | 1495 | CB | ARG A | 234 | 46.662 | -1.795 | 23.819 | 1.00 | 42.60 | A | C |
| ATOM | 1496 | CG | ARG A | 234 | 47.933 | -2.620 | 24.026 | 1.00 | 44.73 | A | C |
| ATOM | 1497 | CD | ARG A | 234 | 47.703 | -4.075 | 24.329 | 1.00 | 46.05 | A | C |
| ATOM | 1498 | NE | ARG A | 234 | 48.980 | -4.801 | 24.386 | 1.00 | 48.08 | A | N |
| ATOM | 1499 | CZ | ARG A | 234 | 49.092 | -6.126 | 24.477 | 1.00 | 48.70 | A | C |
| ATOM | 1500 | NH1 | ARG A | 234 | 48.002 | -6.875 | 24.513 | 1.00 | 49.80 | A | N |
| ATOM | 1501 | NH2 | ARG A | 234 | 50.286 | -6.706 | 24.565 | 1.00 | 48.70 | A | N |
| ATOM | 1502 | C | ARG A | 234 | 45.787 | 0.442 | 23.026 | 1.00 | 39.83 | A | C |
| ATOM | 1503 | O | ARG A | 234 | 44.706 | 0.114 | 23.532 | 1.00 | 37.77 | A | O |
| ATOM | 1504 | N | GLN A | 235 | 45.971 | 1.602 | 22.394 | 1.00 | 39.68 | A | N |
| ATOM | 1505 | CA | GLN A | 235 | 44.899 | 2.595 | 22.236 | 1.00 | 38.53 | A | C |
| ATOM | 1506 | CB | GLN A | 235 | 45.440 | 4.020 | 22.306 | 1.00 | 40.55 | A | C |
| ATOM | 1507 | CG | GLN A | 235 | 45.958 | 4.484 | 23.669 | 1.00 | 43.56 | A | C |
| ATOM | 1508 | CD | GLN A | 235 | 46.298 | 5.992 | 23.687 | 1.00 | 46.44 | A | C |
| ATOM | 1509 | OE1 | GLN A | 235 | 47.273 | 6.418 | 24.317 | 1.00 | 46.67 | A | O |
| ATOM | 1510 | NE2 | GLN A | 235 | 45.485 | 6.797 | 22.999 | 1.00 | 48.34 | A | N |
| ATOM | 1511 | C | GLN A | 235 | 44.330 | 2.398 | 20.834 | 1.00 | 36.60 | A | C |
| ATOM | 1512 | O | GLN A | 235 | 43.491 | 3.162 | 20.383 | 1.00 | 35.80 | A | O |
| ATOM | 1513 | N | GLY A | 236 | 44.798 | 1.375 | 20.132 | 1.00 | 35.74 | A | N |
| ATOM | 1514 | CA | GLY A | 236 | 44.317 | 1.167 | 18.783 | 1.00 | 34.96 | A | C |
| ATOM | 1515 | C | GLY A | 236 | 44.847 | 2.325 | 17.954 | 1.00 | 34.07 | A | C |
| ATOM | 1516 | O | GLY A | 236 | 45.562 | 3.175 | 18.483 | 1.00 | 33.90 | A | O |
| ATOM | 1517 | N | HIS A | 237 | 44.490 | 2.378 | 16.668 | 1.00 | 33.27 | A | N |
| ATOM | 1518 | CA | HIS A | 237 | 44.950 | 3.435 | 15.753 | 1.00 | 31.82 | A | C |
| ATOM | 1519 | CB | HIS A | 237 | 44.940 | 2.917 | 14.317 | 1.00 | 31.07 | A | C |
| ATOM | 1520 | CG | HIS A | 237 | 46.023 | 1.925 | 14.052 | 1.00 | 30.55 | A | C |
| ATOM | 1521 | CD2 | HIS A | 237 | 47.180 | 2.029 | 13.357 | 1.00 | 30.77 | A | C |
| ATOM | 1522 | ND1 | HIS A | 237 | 46.007 | 0.659 | 14.590 | 1.00 | 31.23 | A | N |
| ATOM | 1523 | CE1 | HIS A | 237 | 47.108 | 0.019 | 14.235 | 1.00 | 32.02 | A | C |
| ATOM | 1524 | NE2 | HIS A | 237 | 47.835 | 0.827 | 13.488 | 1.00 | 31.26 | A | N |
| ATOM | 1525 | C | HIS A | 237 | 44.328 | 4.827 | 15.792 | 1.00 | 31.03 | A | C |
| ATOM | 1526 | O | HIS A | 237 | 44.073 | 5.391 | 16.869 | 1.00 | 33.83 | A | O |
| ATOM | 1527 | N | GLY A | 238 | 44.162 | 5.399 | 14.607 | 1.00 | 26.67 | A | N |
| ATOM | 1528 | CA | GLY A | 238 | 43.644 | 6.751 | 14.493 | 1.00 | 22.94 | A | C |
| ATOM | 1529 | C | GLY A | 238 | 44.447 | 7.481 | 13.420 | 1.00 | 19.58 | A | C |
| ATOM | 1530 | O | GLY A | 238 | 45.603 | 7.139 | 13.155 | 1.00 | 17.96 | A | O |
| ATOM | 1531 | N | PRO A | 239 | 43.887 | 8.527 | 12.815 | 1.00 | 20.00 | A | N |
| ATOM | 1532 | CD | PRO A | 239 | 42.665 | 9.195 | 13.276 | 1.00 | 20.92 | A | C |
| ATOM | 1533 | CA | PRO A | 239 | 44.529 | 9.312 | 11.749 | 1.00 | 19.43 | A | C |
| ATOM | 1534 | CB | PRO A | 239 | 43.526 | 10.441 | 11.508 | 1.00 | 19.50 | A | C |

Figure 1-27

| | | Atom Type | Resid | # | X | Y | Z | OCC | B | | |
|---|---|---|---|---|---|---|---|---|---|---|---|
| ATOM | 1535 | CG | PRO A | 239 | 42.243 | 9.892 | 12.026 | 1.00 | 20.69 | A | C |
| ATOM | 1536 | C | PRO A | 239 | 45.938 | 9.857 | 12.011 | 1.00 | 21.73 | A | C |
| ATOM | 1537 | O | PRO A | 239 | 46.697 | 10.111 | 11.064 | 1.00 | 22.76 | A | O |
| ATOM | 1538 | N | GLU A | 240 | 46.267 | 10.084 | 13.281 | 1.00 | 20.69 | A | N |
| ATOM | 1539 | CA | GLU A | 240 | 47.583 | 10.608 | 13.624 | 1.00 | 24.16 | A | C |
| ATOM | 1540 | CB | GLU A | 240 | 47.588 | 11.278 | 15.011 | 1.00 | 26.76 | A | C |
| ATOM | 1541 | CG | GLU A | 240 | 46.851 | 10.532 | 16.103 | 1.00 | 31.11 | A | C |
| ATOM | 1542 | CD | GLU A | 240 | 45.371 | 10.845 | 16.104 | 1.00 | 33.54 | A | C |
| ATOM | 1543 | OE1 | GLU A | 240 | 45.004 | 11.985 | 16.479 | 1.00 | 34.75 | A | O |
| ATOM | 1544 | OE2 | GLU A | 240 | 44.576 | 9.957 | 15.713 | 1.00 | 33.62 | A | O |
| ATOM | 1545 | C | GLU A | 240 | 48.570 | 9.469 | 13.590 | 1.00 | 23.76 | A | C |
| ATOM | 1546 | O | GLU A | 240 | 49.782 | 9.692 | 13.486 | 1.00 | 24.62 | A | O |
| ATOM | 1547 | N | ALA A | 241 | 48.028 | 8.251 | 13.677 | 1.00 | 21.74 | A | N |
| ATOM | 1548 | CA | ALA A | 241 | 48.812 | 7.034 | 13.650 | 1.00 | 18.33 | A | C |
| ATOM | 1549 | CB | ALA A | 241 | 47.931 | 5.830 | 13.983 | 1.00 | 17.19 | A | C |
| ATOM | 1550 | C | ALA A | 241 | 49.418 | 6.888 | 12.266 | 1.00 | 19.07 | A | C |
| ATOM | 1551 | O | ALA A | 241 | 50.509 | 6.361 | 12.123 | 1.00 | 18.23 | A | O |
| ATOM | 1552 | N | ASP A | 242 | 48.699 | 7.356 | 11.250 | 1.00 | 18.83 | A | N |
| ATOM | 1553 | CA | ASP A | 242 | 49.174 | 7.307 | 9.869 | 1.00 | 21.58 | A | C |
| ATOM | 1554 | CB | ASP A | 242 | 48.021 | 7.553 | 8.895 | 1.00 | 22.88 | A | C |
| ATOM | 1555 | CG | ASP A | 242 | 47.009 | 6.418 | 8.880 | 1.00 | 25.45 | A | C |
| ATOM | 1556 | OD1 | ASP A | 242 | 47.342 | 5.305 | 8.414 | 1.00 | 23.37 | A | O |
| ATOM | 1557 | OD2 | ASP A | 242 | 45.871 | 6.649 | 9.339 | 1.00 | 29.85 | A | O |
| ATOM | 1558 | C | ASP A | 242 | 50.208 | 8.403 | 9.706 | 1.00 | 20.56 | A | C |
| ATOM | 1559 | O | ASP A | 242 | 51.206 | 8.250 | 8.991 | 1.00 | 22.77 | A | O |
| ATOM | 1560 | N | VAL A | 243 | 49.939 | 9.520 | 10.378 | 1.00 | 20.35 | A | N |
| ATOM | 1561 | CA | VAL A | 243 | 50.806 | 10.699 | 10.376 | 1.00 | 18.70 | A | C |
| ATOM | 1562 | CB | VAL A | 243 | 50.130 | 11.844 | 11.145 | 1.00 | 18.01 | A | C |
| ATOM | 1563 | CG1 | VAL A | 243 | 51.129 | 12.927 | 11.506 | 1.00 | 13.57 | A | C |
| ATOM | 1564 | CG2 | VAL A | 243 | 49.028 | 12.409 | 10.295 | 1.00 | 15.47 | A | C |
| ATOM | 1565 | C | VAL A | 243 | 52.152 | 10.324 | 11.003 | 1.00 | 19.00 | A | C |
| ATOM | 1566 | O | VAL A | 243 | 53.209 | 10.743 | 10.551 | 1.00 | 17.45 | A | O |
| ATOM | 1567 | N | TRP A | 244 | 52.102 | 9.511 | 12.041 | 1.00 | 22.36 | A | N |
| ATOM | 1568 | CA | TRP A | 244 | 53.313 | 9.051 | 12.665 | 1.00 | 21.65 | A | C |
| ATOM | 1569 | CB | TRP A | 244 | 52.993 | 8.159 | 13.843 | 1.00 | 21.21 | A | C |
| ATOM | 1570 | CG | TRP A | 244 | 54.200 | 7.445 | 14.356 | 1.00 | 23.54 | A | C |
| ATOM | 1571 | CD2 | TRP A | 244 | 55.004 | 7.850 | 15.463 | 1.00 | 23.51 | A | C |
| ATOM | 1572 | CE2 | TRP A | 244 | 55.992 | 6.863 | 15.639 | 1.00 | 25.06 | A | C |
| ATOM | 1573 | CE3 | TRP A | 244 | 55.003 | 8.968 | 16.303 | 1.00 | 25.09 | A | C |
| ATOM | 1574 | CD1 | TRP A | 244 | 54.709 | 6.251 | 13.917 | 1.00 | 21.71 | A | C |
| ATOM | 1575 | NE1 | TRP A | 244 | 55.778 | 5.892 | 14.693 | 1.00 | 23.02 | A | N |
| ATOM | 1576 | CZ2 | TRP A | 244 | 56.946 | 6.939 | 16.660 | 1.00 | 25.52 | A | C |
| ATOM | 1577 | CZ3 | TRP A | 244 | 55.941 | 9.049 | 17.307 | 1.00 | 25.42 | A | C |
| ATOM | 1578 | CH2 | TRP A | 244 | 56.917 | 8.046 | 17.471 | 1.00 | 27.37 | A | C |
| ATOM | 1579 | C | TRP A | 244 | 54.175 | 8.258 | 11.698 | 1.00 | 21.55 | A | C |
| ATOM | 1580 | O | TRP A | 244 | 55.315 | 8.625 | 11.437 | 1.00 | 20.53 | A | O |
| ATOM | 1581 | N | SER A | 245 | 53.645 | 7.150 | 11.185 | 1.00 | 22.89 | A | N |
| ATOM | 1582 | CA | SER A | 245 | 54.425 | 6.307 | 10.278 | 1.00 | 24.34 | A | C |
| ATOM | 1583 | CB | SER A | 245 | 53.586 | 5.134 | 9.736 | 1.00 | 25.99 | A | C |
| ATOM | 1584 | OG | SER A | 245 | 52.439 | 5.602 | 9.057 | 1.00 | 29.93 | A | O |
| ATOM | 1585 | C | SER A | 245 | 55.018 | 7.134 | 9.156 | 1.00 | 24.55 | A | C |
| ATOM | 1586 | O | SER A | 245 | 56.164 | 6.907 | 8.774 | 1.00 | 25.46 | A | O |
| ATOM | 1587 | N | LEU A | 246 | 54.260 | 8.110 | 8.652 | 1.00 | 22.77 | A | N |
| ATOM | 1588 | CA | LEU A | 246 | 54.776 | 8.976 | 7.598 | 1.00 | 20.68 | A | C |
| ATOM | 1589 | CB | LEU A | 246 | 53.739 | 10.003 | 7.163 | 1.00 | 20.96 | A | C |
| ATOM | 1590 | CG | LEU A | 246 | 52.672 | 9.548 | 6.163 | 1.00 | 23.96 | A | C |
| ATOM | 1591 | CD1 | LEU A | 246 | 52.068 | 10.784 | 5.488 | 1.00 | 23.84 | A | C |
| ATOM | 1592 | CD2 | LEU A | 246 | 53.280 | 8.618 | 5.099 | 1.00 | 22.43 | A | C |
| ATOM | 1593 | C | LEU A | 246 | 56.020 | 9.719 | 8.080 | 1.00 | 20.82 | A | C |

Figure 1-28

| | | Atom Type | Resid | | # | X | Y | Z | OCC | B | | |
|---|---|---|---|---|---|---|---|---|---|---|---|---|
| ATOM | 1594 | O | LEU | A | 246 | 56.887 | 10.077 | 7.286 | 1.00 | 19.44 | A | O |
| ATOM | 1595 | N | GLY | A | 247 | 56.078 | 9.976 | 9.387 | 1.00 | 19.46 | A | N |
| ATOM | 1596 | CA | GLY | A | 247 | 57.211 | 10.661 | 9.999 | 1.00 | 20.76 | A | C |
| ATOM | 1597 | C | GLY | A | 247 | 58.375 | 9.686 | 10.045 | 1.00 | 24.05 | A | C |
| ATOM | 1598 | O | GLY | A | 247 | 59.552 | 10.075 | 10.098 | 1.00 | 25.47 | A | O |
| ATOM | 1599 | N | CYS | A | 248 | 58.023 | 8.402 | 10.054 | 1.00 | 23.88 | A | N |
| ATOM | 1600 | CA | CYS | A | 248 | 58.999 | 7.325 | 10.037 | 1.00 | 25.58 | A | C |
| ATOM | 1601 | CB | CYS | A | 248 | 58.378 | 6.025 | 10.568 | 1.00 | 27.05 | A | C |
| ATOM | 1602 | SG | CYS | A | 248 | 58.141 | 5.960 | 12.401 | 1.00 | 26.23 | A | S |
| ATOM | 1603 | C | CYS | A | 248 | 59.391 | 7.166 | 8.567 | 1.00 | 24.20 | A | C |
| ATOM | 1604 | O | CYS | A | 248 | 60.552 | 7.002 | 8.247 | 1.00 | 21.88 | A | O |
| ATOM | 1605 | N | VAL | A | 249 | 58.416 | 7.232 | 7.669 | 1.00 | 25.27 | A | N |
| ATOM | 1606 | CA | VAL | A | 249 | 58.702 | 7.119 | 6.236 | 1.00 | 24.70 | A | C |
| ATOM | 1607 | CB | VAL | A | 249 | 57.378 | 7.224 | 5.372 | 1.00 | 23.54 | A | C |
| ATOM | 1608 | CG1 | VAL | A | 249 | 57.694 | 7.649 | 3.961 | 1.00 | 23.89 | A | C |
| ATOM | 1609 | CG2 | VAL | A | 249 | 56.657 | 5.889 | 5.334 | 1.00 | 23.92 | A | C |
| ATOM | 1610 | C | VAL | A | 249 | 59.688 | 8.226 | 5.847 | 1.00 | 25.03 | A | C |
| ATOM | 1611 | O | VAL | A | 249 | 60.760 | 7.935 | 5.361 | 1.00 | 26.16 | A | O |
| ATOM | 1612 | N | MET | A | 250 | 59.340 | 9.485 | 6.091 | 1.00 | 25.56 | A | N |
| ATOM | 1613 | CA | MET | A | 250 | 60.208 | 10.601 | 5.743 | 1.00 | 26.17 | A | C |
| ATOM | 1614 | CB | MET | A | 250 | 59.627 | 11.910 | 6.274 | 1.00 | 27.21 | A | C |
| ATOM | 1615 | CG | MET | A | 250 | 60.454 | 13.155 | 5.909 | 1.00 | 27.93 | A | C |
| ATOM | 1616 | SD | MET | A | 250 | 60.237 | 14.594 | 7.024 | 1.00 | 32.14 | A | S |
| ATOM | 1617 | CE | MET | A | 250 | 59.939 | 15.946 | 5.872 | 1.00 | 30.91 | A | C |
| ATOM | 1618 | C | MET | A | 250 | 61.607 | 10.437 | 6.302 | 1.00 | 26.61 | A | C |
| ATOM | 1619 | O | MET | A | 250 | 62.591 | 10.636 | 5.599 | 1.00 | 23.53 | A | O |
| ATOM | 1620 | N | TYR | A | 251 | 61.693 | 10.099 | 7.583 | 1.00 | 27.12 | A | N |
| ATOM | 1621 | CA | TYR | A | 251 | 62.983 | 9.933 | 8.238 | 1.00 | 29.49 | A | C |
| ATOM | 1622 | CB | TYR | A | 251 | 62.797 | 9.419 | 9.661 | 1.00 | 29.66 | A | C |
| ATOM | 1623 | CG | TYR | A | 251 | 64.094 | 9.264 | 10.439 | 1.00 | 31.47 | A | C |
| ATOM | 1624 | CD1 | TYR | A | 251 | 64.526 | 10.250 | 11.337 | 1.00 | 32.34 | A | C |
| ATOM | 1625 | CE1 | TYR | A | 251 | 65.700 | 10.093 | 12.073 | 1.00 | 33.17 | A | C |
| ATOM | 1626 | CD2 | TYR | A | 251 | 64.886 | 8.120 | 10.298 | 1.00 | 32.69 | A | C |
| ATOM | 1627 | CE2 | TYR | A | 251 | 66.070 | 7.962 | 11.031 | 1.00 | 33.62 | A | C |
| ATOM | 1628 | CZ | TYR | A | 251 | 66.464 | 8.952 | 11.913 | 1.00 | 32.79 | A | C |
| ATOM | 1629 | OH | TYR | A | 251 | 67.621 | 8.797 | 12.636 | 1.00 | 35.11 | A | O |
| ATOM | 1630 | C | TYR | A | 251 | 63.901 | 8.981 | 7.479 | 1.00 | 30.53 | A | C |
| ATOM | 1631 | O | TYR | A | 251 | 64.863 | 9.420 | 6.843 | 1.00 | 30.96 | A | O |
| ATOM | 1632 | N | THR | A | 252 | 63.599 | 7.682 | 7.542 | 1.00 | 30.71 | A | N |
| ATOM | 1633 | CA | THR | A | 252 | 64.412 | 6.664 | 6.889 | 1.00 | 30.48 | A | C |
| ATOM | 1634 | CB | THR | A | 252 | 63.716 | 5.268 | 6.926 | 1.00 | 31.58 | A | C |
| ATOM | 1635 | OG1 | THR | A | 252 | 63.226 | 4.935 | 5.627 | 1.00 | 29.77 | A | O |
| ATOM | 1636 | CG2 | THR | A | 252 | 62.567 | 5.253 | 7.919 | 1.00 | 30.05 | A | C |
| ATOM | 1637 | C | THR | A | 252 | 64.823 | 7.010 | 5.454 | 1.00 | 30.48 | A | C |
| ATOM | 1638 | O | THR | A | 252 | 65.793 | 6.465 | 4.937 | 1.00 | 29.03 | A | O |
| ATOM | 1639 | N | LEU | A | 253 | 64.101 | 7.924 | 4.821 | 1.00 | 28.93 | A | N |
| ATOM | 1640 | CA | LEU | A | 253 | 64.428 | 8.348 | 3.467 | 1.00 | 29.40 | A | C |
| ATOM | 1641 | CB | LEU | A | 253 | 63.224 | 9.025 | 2.822 | 1.00 | 27.52 | A | C |
| ATOM | 1642 | CG | LEU | A | 253 | 62.089 | 8.082 | 2.500 | 1.00 | 28.53 | A | C |
| ATOM | 1643 | CD1 | LEU | A | 253 | 61.021 | 8.817 | 1.684 | 1.00 | 28.92 | A | C |
| ATOM | 1644 | CD2 | LEU | A | 253 | 62.654 | 6.904 | 1.735 | 1.00 | 27.11 | A | C |
| ATOM | 1645 | C | LEU | A | 253 | 65.592 | 9.326 | 3.462 | 1.00 | 29.09 | A | C |
| ATOM | 1646 | O | LEU | A | 253 | 66.373 | 9.415 | 2.504 | 1.00 | 29.35 | A | O |
| ATOM | 1647 | N | LEU | A | 254 | 65.680 | 10.064 | 4.553 | 1.00 | 28.01 | A | N |
| ATOM | 1648 | CA | LEU | A | 254 | 66.685 | 11.085 | 4.724 | 1.00 | 30.72 | A | C |
| ATOM | 1649 | CB | LEU | A | 254 | 66.117 | 12.159 | 5.661 | 1.00 | 29.65 | A | C |
| ATOM | 1650 | CG | LEU | A | 254 | 64.849 | 12.839 | 5.128 | 1.00 | 30.68 | A | C |
| ATOM | 1651 | CD1 | LEU | A | 254 | 64.250 | 13.783 | 6.184 | 1.00 | 29.68 | A | C |
| ATOM | 1652 | CD2 | LEU | A | 254 | 65.215 | 13.594 | 3.857 | 1.00 | 31.73 | A | C |

Figure 1-29

| | | Atom Type | Resid | # | X | Y | Z | OCC | B | | |
|---|---|---|---|---|---|---|---|---|---|---|---|
| ATOM | 1653 | C | LEU A | 254 | 68.007 | 10.526 | 5.261 | 1.00 | 31.74 | A | C |
| ATOM | 1654 | O | LEU A | 254 | 69.096 | 10.996 | 4.880 | 1.00 | 33.21 | A | O |
| ATOM | 1655 | N | CYS A | 255 | 67.903 | 9.518 | 6.128 | 1.00 | 32.31 | A | N |
| ATOM | 1656 | CA | CYS A | 255 | 69.071 | 8.886 | 6.732 | 1.00 | 34.07 | A | C |
| ATOM | 1657 | CB | CYS A | 255 | 68.890 | 8.803 | 8.230 | 1.00 | 33.68 | A | C |
| ATOM | 1658 | SG | CYS A | 255 | 67.800 | 10.086 | 8.820 | 1.00 | 36.29 | A | S |
| ATOM | 1659 | C | CYS A | 255 | 69.301 | 7.489 | 6.200 | 1.00 | 34.80 | A | C |
| ATOM | 1660 | O | CYS A | 255 | 70.372 | 6.917 | 6.405 | 1.00 | 35.85 | A | O |
| ATOM | 1661 | N | GLY A | 256 | 68.286 | 6.932 | 5.543 | 1.00 | 35.53 | A | N |
| ATOM | 1662 | CA | GLY A | 256 | 68.401 | 5.599 | 4.978 | 1.00 | 37.00 | A | C |
| ATOM | 1663 | C | GLY A | 256 | 68.242 | 4.453 | 5.961 | 1.00 | 38.13 | A | C |
| ATOM | 1664 | O | GLY A | 256 | 68.717 | 3.341 | 5.711 | 1.00 | 36.88 | A | O |
| ATOM | 1665 | N | SER A | 257 | 67.574 | 4.717 | 7.078 | 1.00 | 39.15 | A | N |
| ATOM | 1666 | CA | SER A | 257 | 67.349 | 3.689 | 8.081 | 1.00 | 39.76 | A | C |
| ATOM | 1667 | CB | SER A | 257 | 68.634 | 3.438 | 8.878 | 1.00 | 39.21 | A | C |
| ATOM | 1668 | OG | SER A | 257 | 69.080 | 4.622 | 9.513 | 1.00 | 40.42 | A | O |
| ATOM | 1669 | C | SER A | 257 | 66.222 | 4.116 | 9.009 | 1.00 | 40.79 | A | C |
| ATOM | 1670 | O | SER A | 257 | 66.183 | 5.259 | 9.459 | 1.00 | 42.11 | A | O |
| ATOM | 1671 | N | PRO A | 258 | 65.284 | 3.200 | 9.307 | 1.00 | 41.16 | A | N |
| ATOM | 1672 | CD | PRO A | 258 | 65.157 | 1.817 | 8.810 | 1.00 | 41.65 | A | C |
| ATOM | 1673 | CA | PRO A | 258 | 64.167 | 3.539 | 10.195 | 1.00 | 42.23 | A | C |
| ATOM | 1674 | CB | PRO A | 258 | 63.591 | 2.173 | 10.545 | 1.00 | 42.25 | A | C |
| ATOM | 1675 | CG | PRO A | 258 | 63.748 | 1.436 | 9.249 | 1.00 | 42.22 | A | C |
| ATOM | 1676 | C | PRO A | 258 | 64.526 | 4.387 | 11.428 | 1.00 | 42.65 | A | C |
| ATOM | 1677 | O | PRO A | 258 | 65.550 | 4.180 | 12.072 | 1.00 | 42.45 | A | O |
| ATOM | 1678 | N | PRO A | 259 | 63.657 | 5.348 | 11.773 | 1.00 | 43.97 | A | N |
| ATOM | 1679 | CD | PRO A | 259 | 62.248 | 5.321 | 11.344 | 1.00 | 44.79 | A | C |
| ATOM | 1680 | CA | PRO A | 259 | 63.824 | 6.263 | 12.907 | 1.00 | 45.56 | A | C |
| ATOM | 1681 | CB | PRO A | 259 | 62.465 | 6.951 | 12.987 | 1.00 | 45.75 | A | C |
| ATOM | 1682 | CG | PRO A | 259 | 61.531 | 5.857 | 12.570 | 1.00 | 45.43 | A | C |
| ATOM | 1683 | C | PRO A | 259 | 64.174 | 5.523 | 14.188 | 1.00 | 46.57 | A | C |
| ATOM | 1684 | O | PRO A | 259 | 65.135 | 5.850 | 14.879 | 1.00 | 46.33 | A | O |
| ATOM | 1685 | N | PHE A | 260 | 63.348 | 4.538 | 14.509 | 1.00 | 48.61 | A | N |
| ATOM | 1686 | CA | PHE A | 260 | 63.558 | 3.715 | 15.679 | 1.00 | 49.07 | A | C |
| ATOM | 1687 | CB | PHE A | 260 | 62.329 | 3.702 | 16.592 | 1.00 | 48.45 | A | C |
| ATOM | 1688 | CG | PHE A | 260 | 61.641 | 5.027 | 16.707 | 1.00 | 46.97 | A | C |
| ATOM | 1689 | CD1 | PHE A | 260 | 60.617 | 5.361 | 15.836 | 1.00 | 45.98 | A | C |
| ATOM | 1690 | CD2 | PHE A | 260 | 62.012 | 5.936 | 17.690 | 1.00 | 46.84 | A | C |
| ATOM | 1691 | CE1 | PHE A | 260 | 59.973 | 6.569 | 15.944 | 1.00 | 45.18 | A | C |
| ATOM | 1692 | CE2 | PHE A | 260 | 61.366 | 7.156 | 17.803 | 1.00 | 45.90 | A | C |
| ATOM | 1693 | CZ | PHE A | 260 | 60.344 | 7.471 | 16.926 | 1.00 | 46.01 | A | C |
| ATOM | 1694 | C | PHE A | 260 | 63.760 | 2.335 | 15.095 | 1.00 | 51.13 | A | C |
| ATOM | 1695 | O | PHE A | 260 | 62.943 | 1.860 | 14.304 | 1.00 | 52.79 | A | O |
| ATOM | 1696 | N | GLU A | 261 | 64.867 | 1.712 | 15.463 | 1.00 | 53.66 | A | N |
| ATOM | 1697 | CA | GLU A | 261 | 65.193 | 0.382 | 14.996 | 1.00 | 55.70 | A | C |
| ATOM | 1698 | CB | GLU A | 261 | 65.723 | 0.428 | 13.571 | 1.00 | 55.96 | A | C |
| ATOM | 1699 | CG | GLU A | 261 | 65.797 | -0.930 | 12.925 | 1.00 | 57.12 | A | C |
| ATOM | 1700 | CD | GLU A | 261 | 66.374 | -0.857 | 11.540 | 1.00 | 57.13 | A | C |
| ATOM | 1701 | OE1 | GLU A | 261 | 65.805 | -1.487 | 10.620 | 1.00 | 57.17 | A | O |
| ATOM | 1702 | OE2 | GLU A | 261 | 67.398 | -0.165 | 11.371 | 1.00 | 56.80 | A | O |
| ATOM | 1703 | C | GLU A | 261 | 66.277 | -0.096 | 15.935 | 1.00 | 57.02 | A | C |
| ATOM | 1704 | O | GLU A | 261 | 67.130 | 0.690 | 16.345 | 1.00 | 55.96 | A | O |
| ATOM | 1705 | N | THR A | 262 | 66.230 | -1.373 | 16.297 | 1.00 | 59.32 | A | N |
| ATOM | 1706 | CA | THR A | 262 | 67.218 | -1.943 | 17.206 | 1.00 | 61.29 | A | C |
| ATOM | 1707 | CB | THR A | 262 | 66.885 | -1.617 | 18.694 | 1.00 | 61.68 | A | C |
| ATOM | 1708 | OG1 | THR A | 262 | 65.463 | -1.550 | 18.873 | 1.00 | 61.16 | A | O |
| ATOM | 1709 | CG2 | THR A | 262 | 67.523 | -0.298 | 19.118 | 1.00 | 62.14 | A | C |
| ATOM | 1710 | C | THR A | 262 | 67.267 | -3.450 | 17.029 | 1.00 | 62.33 | A | C |
| ATOM | 1711 | O | THR A | 262 | 66.752 | -3.968 | 16.032 | 1.00 | 63.31 | A | O |

Figure 1-30

| | | Atom Type | Resid | # | X | Y | Z | OCC | B | | |
|---|---|---|---|---|---|---|---|---|---|---|---|
| ATOM | 1712 | N | ALA A | 263 | 67.883 | -4.143 | 17.990 | 1.00 | 63.38 | A | N |
| ATOM | 1713 | CA | ALA A | 263 | 67.991 | -5.601 | 17.947 | 1.00 | 64.47 | A | C |
| ATOM | 1714 | CB | ALA A | 263 | 68.065 | -6.173 | 19.369 | 1.00 | 64.16 | A | C |
| ATOM | 1715 | C | ALA A | 263 | 66.754 | -6.122 | 17.229 | 1.00 | 65.26 | A | C |
| ATOM | 1716 | O | ALA A | 263 | 66.809 | -6.497 | 16.050 | 1.00 | 65.81 | A | O |
| ATOM | 1717 | N | ASP A | 264 | 65.633 | -6.104 | 17.942 | 1.00 | 65.84 | A | N |
| ATOM | 1718 | CA | ASP A | 264 | 64.352 | -6.530 | 17.398 | 1.00 | 66.09 | A | C |
| ATOM | 1719 | CB | ASP A | 264 | 64.279 | -8.067 | 17.362 | 1.00 | 66.61 | A | C |
| ATOM | 1720 | CG | ASP A | 264 | 65.105 | -8.673 | 16.211 | 1.00 | 67.71 | A | C |
| ATOM | 1721 | OD1 | ASP A | 264 | 64.759 | -8.430 | 15.033 | 1.00 | 67.38 | A | O |
| ATOM | 1722 | OD2 | ASP A | 264 | 66.100 | -9.389 | 16.479 | 1.00 | 68.59 | A | O |
| ATOM | 1723 | C | ASP A | 264 | 63.217 | -5.924 | 18.233 | 1.00 | 65.39 | A | C |
| ATOM | 1724 | O | ASP A | 264 | 63.459 | -5.106 | 19.119 | 1.00 | 65.28 | A | O |
| ATOM | 1725 | N | LEU A | 265 | 61.985 | -6.309 | 17.919 | 1.00 | 64.49 | A | N |
| ATOM | 1726 | CA | LEU A | 265 | 60.787 | -5.832 | 18.610 | 1.00 | 63.63 | A | C |
| ATOM | 1727 | CB | LEU A | 265 | 59.929 | -7.041 | 18.981 | 1.00 | 64.21 | A | C |
| ATOM | 1728 | CG | LEU A | 265 | 59.641 | -7.961 | 17.795 | 1.00 | 64.70 | A | C |
| ATOM | 1729 | CD1 | LEU A | 265 | 59.073 | -9.310 | 18.267 | 1.00 | 64.41 | A | C |
| ATOM | 1730 | CD2 | LEU A | 265 | 58.686 | -7.231 | 16.848 | 1.00 | 64.85 | A | C |
| ATOM | 1731 | C | LEU A | 265 | 61.010 | -4.957 | 19.855 | 1.00 | 62.73 | A | C |
| ATOM | 1732 | O | LEU A | 265 | 61.416 | -3.800 | 19.750 | 1.00 | 62.08 | A | O |
| ATOM | 1733 | N | LYS A | 266 | 60.727 | -5.530 | 21.024 | 1.00 | 61.60 | A | N |
| ATOM | 1734 | CA | LYS A | 266 | 60.849 | -4.865 | 22.322 | 1.00 | 60.33 | A | C |
| ATOM | 1735 | CB | LYS A | 266 | 61.476 | -5.834 | 23.332 | 1.00 | 60.95 | A | C |
| ATOM | 1736 | CG | LYS A | 266 | 60.805 | -7.210 | 23.398 | 1.00 | 61.49 | A | C |
| ATOM | 1737 | CD | LYS A | 266 | 59.367 | -7.131 | 23.935 | 1.00 | 61.98 | A | C |
| ATOM | 1738 | CE | LYS A | 266 | 58.626 | -8.468 | 23.806 | 1.00 | 62.10 | A | C |
| ATOM | 1739 | NZ | LYS A | 266 | 59.301 | -9.566 | 24.553 | 1.00 | 62.43 | A | N |
| ATOM | 1740 | C | LYS A | 266 | 61.632 | -3.546 | 22.320 | 1.00 | 59.12 | A | C |
| ATOM | 1741 | O | LYS A | 266 | 61.088 | -2.488 | 22.635 | 1.00 | 58.75 | A | O |
| ATOM | 1742 | N | GLU A | 267 | 62.912 | -3.624 | 21.969 | 1.00 | 57.81 | A | N |
| ATOM | 1743 | CA | GLU A | 267 | 63.791 | -2.457 | 21.928 | 1.00 | 56.77 | A | C |
| ATOM | 1744 | CB | GLU A | 267 | 65.094 | -2.796 | 21.208 | 1.00 | 57.73 | A | C |
| ATOM | 1745 | CG | GLU A | 267 | 65.925 | -3.889 | 21.855 | 1.00 | 58.80 | A | C |
| ATOM | 1746 | CD | GLU A | 267 | 65.477 | -5.301 | 21.481 | 1.00 | 59.58 | A | C |
| ATOM | 1747 | OE1 | GLU A | 267 | 65.506 | -5.641 | 20.278 | 1.00 | 58.81 | A | O |
| ATOM | 1748 | OE2 | GLU A | 267 | 65.105 | -6.077 | 22.394 | 1.00 | 60.09 | A | O |
| ATOM | 1749 | C | GLU A | 267 | 63.137 | -1.292 | 21.216 | 1.00 | 55.40 | A | C |
| ATOM | 1750 | O | GLU A | 267 | 62.705 | -0.326 | 21.843 | 1.00 | 55.65 | A | O |
| ATOM | 1751 | N | THR A | 268 | 63.083 | -1.389 | 19.894 | 1.00 | 53.63 | A | N |
| ATOM | 1752 | CA | THR A | 268 | 62.473 | -0.353 | 19.082 | 1.00 | 50.95 | A | C |
| ATOM | 1753 | CB | THR A | 268 | 62.523 | -0.751 | 17.592 | 1.00 | 51.13 | A | C |
| ATOM | 1754 | OG1 | THR A | 268 | 61.415 | -0.170 | 16.895 | 1.00 | 50.72 | A | O |
| ATOM | 1755 | CG2 | THR A | 268 | 62.506 | -2.265 | 17.445 | 1.00 | 50.66 | A | C |
| ATOM | 1756 | C | THR A | 268 | 61.029 | -0.035 | 19.509 | 1.00 | 49.05 | A | C |
| ATOM | 1757 | O | THR A | 268 | 60.460 | 0.971 | 19.070 | 1.00 | 48.55 | A | O |
| ATOM | 1758 | N | TYR A | 269 | 60.443 | -0.892 | 20.355 | 1.00 | 47.24 | A | N |
| ATOM | 1759 | CA | TYR A | 269 | 59.082 | -0.691 | 20.872 | 1.00 | 46.34 | A | C |
| ATOM | 1760 | CB | TYR A | 269 | 58.501 | -1.982 | 21.468 | 1.00 | 47.32 | A | C |
| ATOM | 1761 | CG | TYR A | 269 | 57.830 | -2.881 | 20.466 | 1.00 | 47.62 | A | C |
| ATOM | 1762 | CD1 | TYR A | 269 | 58.490 | -3.270 | 19.307 | 1.00 | 48.42 | A | C |
| ATOM | 1763 | CE1 | TYR A | 269 | 57.865 | -4.068 | 18.348 | 1.00 | 48.40 | A | C |
| ATOM | 1764 | CD2 | TYR A | 269 | 56.522 | -3.315 | 20.655 | 1.00 | 47.72 | A | C |
| ATOM | 1765 | CE2 | TYR A | 269 | 55.882 | -4.113 | 19.704 | 1.00 | 48.46 | A | C |
| ATOM | 1766 | CZ | TYR A | 269 | 56.560 | -4.484 | 18.545 | 1.00 | 48.26 | A | C |
| ATOM | 1767 | OH | TYR A | 269 | 55.933 | -5.233 | 17.560 | 1.00 | 48.00 | A | O |
| ATOM | 1768 | C | TYR A | 269 | 59.205 | 0.339 | 21.966 | 1.00 | 45.46 | A | C |
| ATOM | 1769 | O | TYR A | 269 | 58.335 | 1.186 | 22.121 | 1.00 | 43.27 | A | O |
| ATOM | 1770 | N | ARG A | 270 | 60.312 | 0.245 | 22.708 | 1.00 | 45.03 | A | N |

Figure 1-31

| | | Atom Type | Resid | # | X | Y | Z | OCC | B | | |
|---|---|---|---|---|---|---|---|---|---|---|---|
| ATOM | 1771 | CA | ARG A 270 | | 60.640 | 1.151 | 23.806 | 1.00 | 44.38 | A | C |
| ATOM | 1772 | CB | ARG A 270 | | 61.770 | 0.570 | 24.653 | 1.00 | 45.83 | A | C |
| ATOM | 1773 | CG | ARG A 270 | | 61.466 | -0.744 | 25.308 | 1.00 | 48.07 | A | C |
| ATOM | 1774 | CD | ARG A 270 | | 62.773 | -1.397 | 25.734 | 1.00 | 49.62 | A | C |
| ATOM | 1775 | NE | ARG A 270 | | 62.580 | -2.735 | 26.291 | 1.00 | 51.45 | A | N |
| ATOM | 1776 | CZ | ARG A 270 | | 63.331 | -3.787 | 25.972 | 1.00 | 51.10 | A | C |
| ATOM | 1777 | NH1 | ARG A 270 | | 64.326 | -3.647 | 25.095 | 1.00 | 50.27 | A | N |
| ATOM | 1778 | NH2 | ARG A 270 | | 63.082 | -4.972 | 26.530 | 1.00 | 50.87 | A | N |
| ATOM | 1779 | C | ARG A 270 | | 61.106 | 2.493 | 23.251 | 1.00 | 42.29 | A | C |
| ATOM | 1780 | O | ARG A 270 | | 60.735 | 3.561 | 23.735 | 1.00 | 41.85 | A | O |
| ATOM | 1781 | N | CYS A 271 | | 61.943 | 2.425 | 22.234 | 1.00 | 40.10 | A | N |
| ATOM | 1782 | CA | CYS A 271 | | 62.456 | 3.620 | 21.611 | 1.00 | 39.22 | A | C |
| ATOM | 1783 | CB | CYS A 271 | | 63.540 | 3.232 | 20.626 | 1.00 | 37.83 | A | C |
| ATOM | 1784 | SG | CYS A 271 | | 64.844 | 2.362 | 21.483 | 1.00 | 35.51 | A | S |
| ATOM | 1785 | C | CYS A 271 | | 61.347 | 4.386 | 20.920 | 1.00 | 39.44 | A | C |
| ATOM | 1786 | O | CYS A 271 | | 61.435 | 5.601 | 20.770 | 1.00 | 40.57 | A | O |
| ATOM | 1787 | N | ILE A 272 | | 60.306 | 3.681 | 20.482 | 1.00 | 39.80 | A | N |
| ATOM | 1788 | CA | ILE A 272 | | 59.175 | 4.339 | 19.840 | 1.00 | 38.79 | A | C |
| ATOM | 1789 | CB | ILE A 272 | | 58.483 | 3.402 | 18.818 | 1.00 | 39.35 | A | C |
| ATOM | 1790 | CG2 | ILE A 272 | | 57.131 | 2.980 | 19.344 | 1.00 | 38.85 | A | C |
| ATOM | 1791 | CG1 | ILE A 272 | | 58.287 | 4.125 | 17.475 | 1.00 | 40.47 | A | C |
| ATOM | 1792 | CD1 | ILE A 272 | | 57.739 | 3.251 | 16.338 | 1.00 | 39.99 | A | C |
| ATOM | 1793 | C | ILE A 272 | | 58.183 | 4.757 | 20.942 | 1.00 | 37.76 | A | C |
| ATOM | 1794 | O | ILE A 272 | | 57.651 | 5.867 | 20.919 | 1.00 | 33.06 | A | O |
| ATOM | 1795 | N | LYS A 273 | | 57.951 | 3.875 | 21.912 | 1.00 | 38.93 | A | N |
| ATOM | 1796 | CA | LYS A 273 | | 57.037 | 4.200 | 23.016 | 1.00 | 41.90 | A | C |
| ATOM | 1797 | CB | LYS A 273 | | 56.893 | 3.029 | 24.003 | 1.00 | 42.37 | A | C |
| ATOM | 1798 | CG | LYS A 273 | | 55.983 | 1.911 | 23.513 | 1.00 | 44.13 | A | C |
| ATOM | 1799 | CD | LYS A 273 | | 55.843 | 0.799 | 24.547 | 1.00 | 44.89 | A | C |
| ATOM | 1800 | CE | LYS A 273 | | 54.960 | -0.329 | 24.012 | 1.00 | 46.07 | A | C |
| ATOM | 1801 | NZ | LYS A 273 | | 54.689 | -1.394 | 25.021 | 1.00 | 46.46 | A | N |
| ATOM | 1802 | C | LYS A 273 | | 57.546 | 5.421 | 23.773 | 1.00 | 43.06 | A | C |
| ATOM | 1803 | O | LYS A 273 | | 56.764 | 6.182 | 24.347 | 1.00 | 42.01 | A | O |
| ATOM | 1804 | N | GLN A 274 | | 58.864 | 5.592 | 23.760 | 1.00 | 44.37 | A | N |
| ATOM | 1805 | CA | GLN A 274 | | 59.509 | 6.709 | 24.422 | 1.00 | 45.67 | A | C |
| ATOM | 1806 | CB | GLN A 274 | | 60.690 | 6.217 | 25.258 | 1.00 | 47.45 | A | C |
| ATOM | 1807 | CG | GLN A 274 | | 60.317 | 5.416 | 26.480 | 1.00 | 49.11 | A | C |
| ATOM | 1808 | CD | GLN A 274 | | 61.538 | 5.004 | 27.273 | 1.00 | 50.08 | A | C |
| ATOM | 1809 | OE1 | GLN A 274 | | 61.423 | 4.435 | 28.355 | 1.00 | 51.28 | A | O |
| ATOM | 1810 | NE2 | GLN A 274 | | 62.721 | 5.285 | 26.734 | 1.00 | 50.92 | A | N |
| ATOM | 1811 | C | GLN A 274 | | 60.014 | 7.741 | 23.421 | 1.00 | 44.96 | A | C |
| ATOM | 1812 | O | GLN A 274 | | 60.871 | 8.553 | 23.770 | 1.00 | 45.63 | A | O |
| ATOM | 1813 | N | VAL A 275 | | 59.498 | 7.723 | 22.193 | 1.00 | 45.35 | A | N |
| ATOM | 1814 | CA | VAL A 275 | | 59.948 | 8.685 | 21.192 | 1.00 | 45.40 | A | C |
| ATOM | 1815 | CB | VAL A 275 | | 59.167 | 9.979 | 21.304 | 1.00 | 44.91 | A | C |
| ATOM | 1816 | CG1 | VAL A 275 | | 59.635 | 10.950 | 20.239 | 1.00 | 44.00 | A | C |
| ATOM | 1817 | CG2 | VAL A 275 | | 57.690 | 9.706 | 21.179 | 1.00 | 45.85 | A | C |
| ATOM | 1818 | C | VAL A 275 | | 61.412 | 8.983 | 21.409 | 1.00 | 45.86 | A | C |
| ATOM | 1819 | O | VAL A 275 | | 61.814 | 10.089 | 21.769 | 1.00 | 43.80 | A | O |
| ATOM | 1820 | N | HIS A 276 | | 62.192 | 7.937 | 21.219 | 1.00 | 47.50 | A | N |
| ATOM | 1821 | CA | HIS A 276 | | 63.630 | 7.967 | 21.412 | 1.00 | 49.79 | A | C |
| ATOM | 1822 | CB | HIS A 276 | | 63.976 | 6.791 | 22.348 | 1.00 | 49.70 | A | C |
| ATOM | 1823 | CG | HIS A 276 | | 65.367 | 6.800 | 22.873 | 1.00 | 49.66 | A | C |
| ATOM | 1824 | CD2 | HIS A 276 | | 66.165 | 5.784 | 23.280 | 1.00 | 50.63 | A | C |
| ATOM | 1825 | ND1 | HIS A 276 | | 66.060 | 7.962 | 23.114 | 1.00 | 50.22 | A | N |
| ATOM | 1826 | CE1 | HIS A 276 | | 67.232 | 7.663 | 23.647 | 1.00 | 50.10 | A | C |
| ATOM | 1827 | NE2 | HIS A 276 | | 67.318 | 6.350 | 23.757 | 1.00 | 50.41 | A | N |
| ATOM | 1828 | C | HIS A 276 | | 64.333 | 7.845 | 20.033 | 1.00 | 51.00 | A | C |
| ATOM | 1829 | O | HIS A 276 | | 64.662 | 6.754 | 19.570 | 1.00 | 52.70 | A | O |

Figure 1-32

| | | Atom Type | Resid | # | X | Y | Z | OCC | B | | |
|---|---|---|---|---|---|---|---|---|---|---|---|
| ATOM | 1830 | N | TYR A | 277 | 64.589 | 8.964 | 19.370 | 1.00 | 52.37 | A | N |
| ATOM | 1831 | CA | TYR A | 277 | 65.229 | 8.892 | 18.059 | 1.00 | 52.40 | A | C |
| ATOM | 1832 | CB | TYR A | 277 | 64.185 | 9.103 | 16.929 | 1.00 | 53.04 | A | C |
| ATOM | 1833 | CG | TYR A | 277 | 63.384 | 10.395 | 16.986 | 1.00 | 53.99 | A | C |
| ATOM | 1834 | CD1 | TYR A | 277 | 63.731 | 11.501 | 16.199 | 1.00 | 53.80 | A | C |
| ATOM | 1835 | CE1 | TYR A | 277 | 62.974 | 12.690 | 16.240 | 1.00 | 54.07 | A | C |
| ATOM | 1836 | CD2 | TYR A | 277 | 62.266 | 10.504 | 17.816 | 1.00 | 54.08 | A | C |
| ATOM | 1837 | CE2 | TYR A | 277 | 61.501 | 11.682 | 17.870 | 1.00 | 54.67 | A | C |
| ATOM | 1838 | CZ | TYR A | 277 | 61.854 | 12.773 | 17.084 | 1.00 | 54.36 | A | C |
| ATOM | 1839 | OH | TYR A | 277 | 61.091 | 13.929 | 17.163 | 1.00 | 54.03 | A | O |
| ATOM | 1840 | C | TYR A | 277 | 66.373 | 9.880 | 17.948 | 1.00 | 52.41 | A | C |
| ATOM | 1841 | O | TYR A | 277 | 66.398 | 10.899 | 18.632 | 1.00 | 52.77 | A | O |
| ATOM | 1842 | N | THR A | 278 | 67.334 | 9.557 | 17.093 | 1.00 | 51.49 | A | N |
| ATOM | 1843 | CA | THR A | 278 | 68.509 | 10.407 | 16.906 | 1.00 | 50.91 | A | C |
| ATOM | 1844 | CB | THR A | 278 | 69.802 | 9.547 | 16.981 | 1.00 | 51.45 | A | C |
| ATOM | 1845 | OG1 | THR A | 278 | 69.460 | 8.193 | 17.310 | 1.00 | 52.22 | A | O |
| ATOM | 1846 | CG2 | THR A | 278 | 70.766 | 10.082 | 18.019 | 1.00 | 51.48 | A | C |
| ATOM | 1847 | C | THR A | 278 | 68.490 | 11.141 | 15.558 | 1.00 | 49.11 | A | C |
| ATOM | 1848 | O | THR A | 278 | 68.621 | 10.509 | 14.515 | 1.00 | 49.59 | A | O |
| ATOM | 1849 | N | LEU A | 279 | 68.344 | 12.463 | 15.562 | 1.00 | 47.24 | A | N |
| ATOM | 1850 | CA | LEU A | 279 | 68.330 | 13.194 | 14.294 | 1.00 | 45.71 | A | C |
| ATOM | 1851 | CB | LEU A | 279 | 67.552 | 14.503 | 14.425 | 1.00 | 43.78 | A | C |
| ATOM | 1852 | CG | LEU A | 279 | 66.024 | 14.384 | 14.524 | 1.00 | 43.37 | A | C |
| ATOM | 1853 | CD1 | LEU A | 279 | 65.398 | 15.756 | 14.708 | 1.00 | 42.95 | A | C |
| ATOM | 1854 | CD2 | LEU A | 279 | 65.476 | 13.734 | 13.268 | 1.00 | 41.44 | A | C |
| ATOM | 1855 | C | LEU A | 279 | 69.739 | 13.478 | 13.781 | 1.00 | 45.13 | A | C |
| ATOM | 1856 | O | LEU A | 279 | 70.612 | 13.932 | 14.540 | 1.00 | 45.34 | A | O |
| ATOM | 1857 | N | PRO A | 280 | 69.978 | 13.213 | 12.477 | 1.00 | 44.12 | A | N |
| ATOM | 1858 | CD | PRO A | 280 | 69.061 | 12.545 | 11.534 | 1.00 | 43.92 | A | C |
| ATOM | 1859 | CA | PRO A | 280 | 71.276 | 13.425 | 11.826 | 1.00 | 44.13 | A | C |
| ATOM | 1860 | CB | PRO A | 280 | 71.046 | 12.857 | 10.428 | 1.00 | 44.27 | A | C |
| ATOM | 1861 | CG | PRO A | 280 | 70.029 | 11.776 | 10.685 | 1.00 | 43.74 | A | C |
| ATOM | 1862 | C | PRO A | 280 | 71.726 | 14.886 | 11.784 | 1.00 | 43.37 | A | C |
| ATOM | 1863 | O | PRO A | 280 | 70.917 | 15.794 | 11.548 | 1.00 | 41.99 | A | O |
| ATOM | 1864 | N | ALA A | 281 | 73.019 | 15.092 | 12.022 | 1.00 | 42.38 | A | N |
| ATOM | 1865 | CA | ALA A | 281 | 73.633 | 16.412 | 12.000 | 1.00 | 42.74 | A | C |
| ATOM | 1866 | CB | ALA A | 281 | 75.147 | 16.266 | 12.074 | 1.00 | 43.29 | A | C |
| ATOM | 1867 | C | ALA A | 281 | 73.244 | 17.160 | 10.726 | 1.00 | 42.16 | A | C |
| ATOM | 1868 | O | ALA A | 281 | 72.996 | 18.367 | 10.747 | 1.00 | 41.97 | A | O |
| ATOM | 1869 | N | SER A | 282 | 73.236 | 16.432 | 9.613 | 1.00 | 42.09 | A | N |
| ATOM | 1870 | CA | SER A | 282 | 72.853 | 16.983 | 8.321 | 1.00 | 43.92 | A | C |
| ATOM | 1871 | CB | SER A | 282 | 73.547 | 16.231 | 7.179 | 1.00 | 45.14 | A | C |
| ATOM | 1872 | OG | SER A | 282 | 72.924 | 16.514 | 5.929 | 1.00 | 48.54 | A | O |
| ATOM | 1873 | C | SER A | 282 | 71.342 | 16.823 | 8.192 | 1.00 | 43.13 | A | C |
| ATOM | 1874 | O | SER A | 282 | 70.772 | 15.851 | 8.695 | 1.00 | 44.18 | A | O |
| ATOM | 1875 | N | LEU A | 283 | 70.713 | 17.793 | 7.530 | 1.00 | 43.00 | A | N |
| ATOM | 1876 | CA | LEU A | 283 | 69.267 | 17.843 | 7.292 | 1.00 | 41.08 | A | C |
| ATOM | 1877 | CB | LEU A | 283 | 68.484 | 16.882 | 8.200 | 1.00 | 39.94 | A | C |
| ATOM | 1878 | CG | LEU A | 283 | 68.286 | 15.420 | 7.788 | 1.00 | 39.37 | A | C |
| ATOM | 1879 | CD1 | LEU A | 283 | 67.155 | 14.777 | 8.623 | 1.00 | 38.15 | A | C |
| ATOM | 1880 | CD2 | LEU A | 283 | 67.966 | 15.368 | 6.294 | 1.00 | 37.94 | A | C |
| ATOM | 1881 | C | LEU A | 283 | 68.720 | 19.244 | 7.514 | 1.00 | 42.02 | A | C |
| ATOM | 1882 | O | LEU A | 283 | 68.759 | 19.767 | 8.627 | 1.00 | 42.71 | A | O |
| ATOM | 1883 | N | SER A | 284 | 68.208 | 19.839 | 6.441 | 1.00 | 42.59 | A | N |
| ATOM | 1884 | CA | SER A | 284 | 67.621 | 21.170 | 6.483 | 1.00 | 42.78 | A | C |
| ATOM | 1885 | CB | SER A | 284 | 66.641 | 21.341 | 5.321 | 1.00 | 43.96 | A | C |
| ATOM | 1886 | OG | SER A | 284 | 65.501 | 20.507 | 5.493 | 1.00 | 42.34 | A | O |
| ATOM | 1887 | C | SER A | 284 | 66.854 | 21.305 | 7.779 | 1.00 | 44.51 | A | C |
| ATOM | 1888 | O | SER A | 284 | 66.130 | 20.390 | 8.145 | 1.00 | 45.90 | A | O |

Figure 1-33

| | Atom Type | Resid | # | X | Y | Z | OCC | B | | |
|---|---|---|---|---|---|---|---|---|---|---|
| ATOM | 1889 | N | LEU A 285 | 66.998 | 22.430 | 8.474 | 1.00 | 44.79 | A | N |
| ATOM | 1890 | CA | LEU A 285 | 66.263 | 22.603 | 9.719 | 1.00 | 44.96 | A | C |
| ATOM | 1891 | CB | LEU A 285 | 66.310 | 24.056 | 10.193 | 1.00 | 45.41 | A | C |
| ATOM | 1892 | CG | LEU A 285 | 67.383 | 24.515 | 11.178 | 1.00 | 45.95 | A | C |
| ATOM | 1893 | CD1 | LEU A 285 | 66.698 | 25.368 | 12.210 | 1.00 | 46.48 | A | C |
| ATOM | 1894 | CD2 | LEU A 285 | 68.076 | 23.353 | 11.871 | 1.00 | 47.22 | A | C |
| ATOM | 1895 | C | LEU A 285 | 64.804 | 22.182 | 9.560 | 1.00 | 44.49 | A | C |
| ATOM | 1896 | O | LEU A 285 | 64.280 | 21.417 | 10.367 | 1.00 | 43.82 | A | O |
| ATOM | 1897 | N | PRO A 286 | 64.133 | 22.662 | 8.505 | 1.00 | 44.99 | A | N |
| ATOM | 1898 | CD | PRO A 286 | 64.585 | 23.526 | 7.398 | 1.00 | 45.12 | A | C |
| ATOM | 1899 | CA | PRO A 286 | 62.732 | 22.276 | 8.331 | 1.00 | 45.13 | A | C |
| ATOM | 1900 | CB | PRO A 286 | 62.360 | 22.941 | 7.008 | 1.00 | 45.47 | A | C |
| ATOM | 1901 | CG | PRO A 286 | 63.298 | 24.128 | 6.931 | 1.00 | 46.28 | A | C |
| ATOM | 1902 | C | PRO A 286 | 62.517 | 20.753 | 8.312 | 1.00 | 45.08 | A | C |
| ATOM | 1903 | O | PRO A 286 | 61.565 | 20.254 | 8.913 | 1.00 | 46.06 | A | O |
| ATOM | 1904 | N | ALA A 287 | 63.391 | 20.023 | 7.614 | 1.00 | 44.24 | A | N |
| ATOM | 1905 | CA | ALA A 287 | 63.275 | 18.567 | 7.538 | 1.00 | 44.45 | A | C |
| ATOM | 1906 | CB | ALA A 287 | 64.420 | 17.984 | 6.714 | 1.00 | 44.19 | A | C |
| ATOM | 1907 | C | ALA A 287 | 63.297 | 17.989 | 8.944 | 1.00 | 43.72 | A | C |
| ATOM | 1908 | O | ALA A 287 | 62.408 | 17.243 | 9.338 | 1.00 | 42.37 | A | O |
| ATOM | 1909 | N | ARG A 288 | 64.324 | 18.350 | 9.701 | 1.00 | 44.60 | A | N |
| ATOM | 1910 | CA | ARG A 288 | 64.467 | 17.875 | 11.068 | 1.00 | 45.65 | A | C |
| ATOM | 1911 | CB | ARG A 288 | 65.891 | 18.132 | 11.542 | 1.00 | 47.90 | A | C |
| ATOM | 1912 | CG | ARG A 288 | 66.447 | 19.428 | 11.026 | 1.00 | 50.89 | A | C |
| ATOM | 1913 | CD | ARG A 288 | 67.547 | 19.935 | 11.924 | 1.00 | 53.31 | A | C |
| ATOM | 1914 | NE | ARG A 288 | 67.079 | 20.017 | 13.301 | 1.00 | 55.78 | A | N |
| ATOM | 1915 | CZ | ARG A 288 | 67.413 | 19.150 | 14.254 | 1.00 | 56.52 | A | C |
| ATOM | 1916 | NH1 | ARG A 288 | 68.229 | 18.133 | 13.972 | 1.00 | 56.66 | A | N |
| ATOM | 1917 | NH2 | ARG A 288 | 66.927 | 19.299 | 15.487 | 1.00 | 56.67 | A | N |
| ATOM | 1918 | C | ARG A 288 | 63.446 | 18.533 | 12.013 | 1.00 | 44.43 | A | C |
| ATOM | 1919 | O | ARG A 288 | 63.321 | 18.142 | 13.180 | 1.00 | 44.59 | A | O |
| ATOM | 1920 | N | GLN A 289 | 62.724 | 19.532 | 11.500 | 1.00 | 42.84 | A | N |
| ATOM | 1921 | CA | GLN A 289 | 61.691 | 20.217 | 12.278 | 1.00 | 40.62 | A | C |
| ATOM | 1922 | CB | GLN A 289 | 61.535 | 21.681 | 11.850 | 1.00 | 41.19 | A | C |
| ATOM | 1923 | CG | GLN A 289 | 62.686 | 22.572 | 12.250 | 1.00 | 42.74 | A | C |
| ATOM | 1924 | CD | GLN A 289 | 62.479 | 24.018 | 11.856 | 1.00 | 42.65 | A | C |
| ATOM | 1925 | OE1 | GLN A 289 | 63.411 | 24.814 | 11.883 | 1.00 | 44.91 | A | O |
| ATOM | 1926 | NE2 | GLN A 289 | 61.254 | 24.366 | 11.497 | 1.00 | 43.37 | A | N |
| ATOM | 1927 | C | GLN A 289 | 60.362 | 19.509 | 12.069 | 1.00 | 37.60 | A | C |
| ATOM | 1928 | O | GLN A 289 | 59.525 | 19.479 | 12.968 | 1.00 | 36.89 | A | O |
| ATOM | 1929 | N | LEU A 290 | 60.171 | 18.953 | 10.874 | 1.00 | 33.95 | A | N |
| ATOM | 1930 | CA | LEU A 290 | 58.939 | 18.248 | 10.561 | 1.00 | 33.40 | A | C |
| ATOM | 1931 | CB | LEU A 290 | 58.813 | 18.008 | 9.057 | 1.00 | 31.93 | A | C |
| ATOM | 1932 | CG | LEU A 290 | 57.440 | 18.345 | 8.473 | 1.00 | 31.13 | A | C |
| ATOM | 1933 | CD1 | LEU A 290 | 57.340 | 17.751 | 7.099 | 1.00 | 27.76 | A | C |
| ATOM | 1934 | CD2 | LEU A 290 | 56.329 | 17.828 | 9.361 | 1.00 | 30.48 | A | C |
| ATOM | 1935 | C | LEU A 290 | 58.966 | 16.922 | 11.288 | 1.00 | 32.64 | A | C |
| ATOM | 1936 | O | LEU A 290 | 57.965 | 16.482 | 11.847 | 1.00 | 32.99 | A | O |
| ATOM | 1937 | N | LEU A 291 | 60.133 | 16.290 | 11.279 | 1.00 | 33.63 | A | N |
| ATOM | 1938 | CA | LEU A 291 | 60.310 | 15.004 | 11.925 | 1.00 | 33.07 | A | C |
| ATOM | 1939 | CB | LEU A 291 | 61.693 | 14.439 | 11.602 | 1.00 | 33.90 | A | C |
| ATOM | 1940 | CG | LEU A 291 | 61.854 | 13.996 | 10.151 | 1.00 | 34.81 | A | C |
| ATOM | 1941 | CD1 | LEU A 291 | 63.285 | 13.609 | 9.925 | 1.00 | 34.90 | A | C |
| ATOM | 1942 | CD2 | LEU A 291 | 60.912 | 12.833 | 9.837 | 1.00 | 34.64 | A | C |
| ATOM | 1943 | C | LEU A 291 | 60.129 | 15.149 | 13.421 | 1.00 | 32.72 | A | C |
| ATOM | 1944 | O | LEU A 291 | 59.713 | 14.208 | 14.090 | 1.00 | 31.49 | A | O |
| ATOM | 1945 | N | ALA A 292 | 60.437 | 16.327 | 13.951 | 1.00 | 32.81 | A | N |
| ATOM | 1946 | CA | ALA A 292 | 60.276 | 16.565 | 15.379 | 1.00 | 32.95 | A | C |
| ATOM | 1947 | CB | ALA A 292 | 61.222 | 17.669 | 15.818 | 1.00 | 33.54 | A | C |

Figure 1-34

|  |  | Atom Type | Resid | # | X | Y | Z | OCC | B |  |  |
|---|---|---|---|---|---|---|---|---|---|---|---|
| ATOM | 1948 | C | ALA A 292 | | 58.811 | 16.923 | 15.712 | 1.00 | 32.35 | A | C |
| ATOM | 1949 | O | ALA A 292 | | 58.306 | 16.555 | 16.776 | 1.00 | 32.00 | A | O |
| ATOM | 1950 | N | ALA A 293 | | 58.146 | 17.623 | 14.781 | 1.00 | 31.98 | A | N |
| ATOM | 1951 | CA | ALA A 293 | | 56.735 | 18.042 | 14.903 | 1.00 | 32.02 | A | C |
| ATOM | 1952 | CB | ALA A 293 | | 56.401 | 19.116 | 13.857 | 1.00 | 31.84 | A | C |
| ATOM | 1953 | C | ALA A 293 | | 55.803 | 16.854 | 14.717 | 1.00 | 33.24 | A | C |
| ATOM | 1954 | O | ALA A 293 | | 54.799 | 16.734 | 15.404 | 1.00 | 32.65 | A | O |
| ATOM | 1955 | N | ILE A 294 | | 56.152 | 15.979 | 13.775 | 1.00 | 34.19 | A | N |
| ATOM | 1956 | CA | ILE A 294 | | 55.368 | 14.786 | 13.472 | 1.00 | 34.36 | A | C |
| ATOM | 1957 | CB | ILE A 294 | | 55.801 | 14.175 | 12.103 | 1.00 | 33.54 | A | C |
| ATOM | 1958 | CG2 | ILE A 294 | | 55.179 | 12.789 | 11.899 | 1.00 | 32.98 | A | C |
| ATOM | 1959 | CG1 | ILE A 294 | | 55.393 | 15.105 | 10.968 | 1.00 | 33.47 | A | C |
| ATOM | 1960 | CD1 | ILE A 294 | | 55.814 | 14.595 | 9.604 | 1.00 | 33.37 | A | C |
| ATOM | 1961 | C | ILE A 294 | | 55.515 | 13.714 | 14.545 | 1.00 | 34.66 | A | C |
| ATOM | 1962 | O | ILE A 294 | | 54.544 | 13.270 | 15.136 | 1.00 | 34.32 | A | O |
| ATOM | 1963 | N | LEU A 295 | | 56.750 | 13.315 | 14.800 | 1.00 | 37.82 | A | N |
| ATOM | 1964 | CA | LEU A 295 | | 57.014 | 12.259 | 15.758 | 1.00 | 39.55 | A | C |
| ATOM | 1965 | CB | LEU A 295 | | 58.333 | 11.553 | 15.396 | 1.00 | 39.52 | A | C |
| ATOM | 1966 | CG | LEU A 295 | | 58.412 | 10.949 | 13.976 | 1.00 | 40.43 | A | C |
| ATOM | 1967 | CD1 | LEU A 295 | | 59.730 | 10.183 | 13.808 | 1.00 | 39.69 | A | C |
| ATOM | 1968 | CD2 | LEU A 295 | | 57.214 | 10.026 | 13.721 | 1.00 | 39.90 | A | C |
| ATOM | 1969 | C | LEU A 295 | | 57.012 | 12.673 | 17.221 | 1.00 | 40.04 | A | C |
| ATOM | 1970 | O | LEU A 295 | | 58.066 | 12.742 | 17.857 | 1.00 | 41.78 | A | O |
| ATOM | 1971 | N | ARG A 296 | | 55.804 | 12.920 | 17.738 | 1.00 | 41.11 | A | N |
| ATOM | 1972 | CA | ARG A 296 | | 55.552 | 13.303 | 19.132 | 1.00 | 40.96 | A | C |
| ATOM | 1973 | CB | ARG A 296 | | 54.703 | 14.585 | 19.198 | 1.00 | 42.12 | A | C |
| ATOM | 1974 | CG | ARG A 296 | | 55.400 | 15.845 | 18.707 | 1.00 | 43.68 | A | C |
| ATOM | 1975 | CD | ARG A 296 | | 55.669 | 16.832 | 19.833 | 1.00 | 44.51 | A | C |
| ATOM | 1976 | NE | ARG A 296 | | 54.664 | 17.893 | 19.905 | 1.00 | 46.43 | A | N |
| ATOM | 1977 | CZ | ARG A 296 | | 54.310 | 18.678 | 18.881 | 1.00 | 47.78 | A | C |
| ATOM | 1978 | NH1 | ARG A 296 | | 54.868 | 18.528 | 17.680 | 1.00 | 47.42 | A | N |
| ATOM | 1979 | NH2 | ARG A 296 | | 53.413 | 19.643 | 19.061 | 1.00 | 48.53 | A | N |
| ATOM | 1980 | C | ARG A 296 | | 54.772 | 12.158 | 19.765 | 1.00 | 40.31 | A | C |
| ATOM | 1981 | O | ARG A 296 | | 53.872 | 11.627 | 19.136 | 1.00 | 39.97 | A | O |
| ATOM | 1982 | N | ALA A 297 | | 55.118 | 11.785 | 20.997 | 1.00 | 40.40 | A | N |
| ATOM | 1983 | CA | ALA A 297 | | 54.446 | 10.691 | 21.722 | 1.00 | 39.90 | A | C |
| ATOM | 1984 | CB | ALA A 297 | | 54.995 | 10.565 | 23.152 | 1.00 | 39.47 | A | C |
| ATOM | 1985 | C | ALA A 297 | | 52.950 | 10.894 | 21.792 | 1.00 | 39.39 | A | C |
| ATOM | 1986 | O | ALA A 297 | | 52.184 | 9.930 | 21.774 | 1.00 | 36.78 | A | O |
| ATOM | 1987 | N | SER A 298 | | 52.550 | 12.158 | 21.890 | 1.00 | 39.71 | A | N |
| ATOM | 1988 | CA | SER A 298 | | 51.149 | 12.528 | 21.976 | 1.00 | 41.33 | A | C |
| ATOM | 1989 | CB | SER A 298 | | 51.016 | 13.829 | 22.773 | 1.00 | 42.59 | A | C |
| ATOM | 1990 | OG | SER A 298 | | 49.772 | 13.882 | 23.445 | 1.00 | 44.31 | A | O |
| ATOM | 1991 | C | SER A 298 | | 50.550 | 12.677 | 20.569 | 1.00 | 40.41 | A | C |
| ATOM | 1992 | O | SER A 298 | | 50.899 | 13.588 | 19.808 | 1.00 | 40.00 | A | O |
| ATOM | 1993 | N | PRO A 299 | | 49.625 | 11.772 | 20.214 | 1.00 | 40.48 | A | N |
| ATOM | 1994 | CD | PRO A 299 | | 48.894 | 10.907 | 21.156 | 1.00 | 39.34 | A | C |
| ATOM | 1995 | CA | PRO A 299 | | 48.964 | 11.769 | 18.910 | 1.00 | 40.71 | A | C |
| ATOM | 1996 | CB | PRO A 299 | | 47.959 | 10.635 | 19.054 | 1.00 | 41.10 | A | C |
| ATOM | 1997 | CG | PRO A 299 | | 47.567 | 10.745 | 20.469 | 1.00 | 40.12 | A | C |
| ATOM | 1998 | C | PRO A 299 | | 48.305 | 13.111 | 18.645 | 1.00 | 40.59 | A | C |
| ATOM | 1999 | O | PRO A 299 | | 48.350 | 13.637 | 17.522 | 1.00 | 41.77 | A | O |
| ATOM | 2000 | N | ARG A 300 | | 47.702 | 13.641 | 19.705 | 1.00 | 39.68 | A | N |
| ATOM | 2001 | CA | ARG A 300 | | 47.023 | 14.928 | 19.725 | 1.00 | 39.50 | A | C |
| ATOM | 2002 | CB | ARG A 300 | | 46.508 | 15.171 | 21.140 | 1.00 | 41.98 | A | C |
| ATOM | 2003 | CG | ARG A 300 | | 47.420 | 14.570 | 22.216 | 1.00 | 44.37 | A | C |
| ATOM | 2004 | CD | ARG A 300 | | 47.004 | 15.007 | 23.620 | 1.00 | 47.54 | A | C |
| ATOM | 2005 | NE | ARG A 300 | | 45.552 | 14.992 | 23.797 | 1.00 | 49.49 | A | N |
| ATOM | 2006 | CZ | ARG A 300 | | 44.915 | 15.327 | 24.916 | 1.00 | 50.46 | A | C |

Figure 1-35

| | Atom Type | Resid | # | X | Y | Z | OCC | B | | |
|---|---|---|---|---|---|---|---|---|---|---|
| ATOM | 2007 | NH1 | ARG A 300 | 45.598 | 15.710 | 25.991 | 1.00 | 51.18 | A | N |
| ATOM | 2008 | NH2 | ARG A 300 | 43.586 | 15.284 | 24.946 | 1.00 | 51.15 | A | N |
| ATOM | 2009 | C | ARG A 300 | 47.927 | 16.091 | 19.307 | 1.00 | 38.42 | A | C |
| ATOM | 2010 | O | ARG A 300 | 47.460 | 17.081 | 18.759 | 1.00 | 37.41 | A | O |
| ATOM | 2011 | N | ASP A 301 | 49.221 | 15.961 | 19.574 | 1.00 | 36.98 | A | N |
| ATOM | 2012 | CA | ASP A 301 | 50.193 | 16.990 | 19.244 | 1.00 | 35.48 | A | C |
| ATOM | 2013 | CB | ASP A 301 | 51.300 | 17.018 | 20.306 | 1.00 | 36.20 | A | C |
| ATOM | 2014 | CG | ASP A 301 | 50.954 | 17.894 | 21.520 | 1.00 | 36.06 | A | C |
| ATOM | 2015 | OD1 | ASP A 301 | 50.006 | 17.550 | 22.268 | 1.00 | 35.35 | A | O |
| ATOM | 2016 | OD2 | ASP A 301 | 51.651 | 18.925 | 21.722 | 1.00 | 36.14 | A | O |
| ATOM | 2017 | C | ASP A 301 | 50.826 | 16.838 | 17.856 | 1.00 | 34.70 | A | C |
| ATOM | 2018 | O | ASP A 301 | 51.572 | 17.713 | 17.412 | 1.00 | 34.68 | A | O |
| ATOM | 2019 | N | ARG A 302 | 50.558 | 15.731 | 17.170 | 1.00 | 33.34 | A | N |
| ATOM | 2020 | CA | ARG A 302 | 51.117 | 15.549 | 15.828 | 1.00 | 30.41 | A | C |
| ATOM | 2021 | CB | ARG A 302 | 50.925 | 14.110 | 15.348 | 1.00 | 30.05 | A | C |
| ATOM | 2022 | CG | ARG A 302 | 51.764 | 13.122 | 16.088 | 1.00 | 29.05 | A | C |
| ATOM | 2023 | CD | ARG A 302 | 51.298 | 11.715 | 15.831 | 1.00 | 29.64 | A | C |
| ATOM | 2024 | NE | ARG A 302 | 51.989 | 10.746 | 16.671 | 1.00 | 27.58 | A | N |
| ATOM | 2025 | CZ | ARG A 302 | 51.546 | 9.522 | 16.942 | 1.00 | 28.92 | A | C |
| ATOM | 2026 | NH1 | ARG A 302 | 50.389 | 9.102 | 16.445 | 1.00 | 28.52 | A | N |
| ATOM | 2027 | NH2 | ARG A 302 | 52.283 | 8.709 | 17.692 | 1.00 | 27.68 | A | N |
| ATOM | 2028 | C | ARG A 302 | 50.377 | 16.508 | 14.912 | 1.00 | 29.73 | A | C |
| ATOM | 2029 | O | ARG A 302 | 49.176 | 16.745 | 15.094 | 1.00 | 28.29 | A | O |
| ATOM | 2030 | N | PRO A 303 | 51.072 | 17.074 | 13.912 | 1.00 | 29.83 | A | N |
| ATOM | 2031 | CD | PRO A 303 | 52.398 | 16.731 | 13.384 | 1.00 | 27.65 | A | C |
| ATOM | 2032 | CA | PRO A 303 | 50.407 | 18.002 | 13.009 | 1.00 | 27.78 | A | C |
| ATOM | 2033 | CB | PRO A 303 | 51.562 | 18.594 | 12.222 | 1.00 | 28.08 | A | C |
| ATOM | 2034 | CG | PRO A 303 | 52.399 | 17.418 | 12.009 | 1.00 | 27.56 | A | C |
| ATOM | 2035 | C | PRO A 303 | 49.459 | 17.216 | 12.136 | 1.00 | 28.83 | A | C |
| ATOM | 2036 | O | PRO A 303 | 49.634 | 16.014 | 11.952 | 1.00 | 29.17 | A | O |
| ATOM | 2037 | N | SER A 304 | 48.438 | 17.887 | 11.620 | 1.00 | 30.58 | A | N |
| ATOM | 2038 | CA | SER A 304 | 47.477 | 17.238 | 10.750 | 1.00 | 30.86 | A | C |
| ATOM | 2039 | CB | SER A 304 | 46.092 | 17.874 | 10.925 | 1.00 | 32.57 | A | C |
| ATOM | 2040 | OG | SER A 304 | 45.916 | 18.978 | 10.049 | 1.00 | 32.42 | A | O |
| ATOM | 2041 | C | SER A 304 | 47.942 | 17.434 | 9.306 | 1.00 | 31.55 | A | C |
| ATOM | 2042 | O | SER A 304 | 48.748 | 18.326 | 9.008 | 1.00 | 30.72 | A | O |
| ATOM | 2043 | N | ILE A 305 | 47.453 | 16.578 | 8.416 | 1.00 | 32.17 | A | N |
| ATOM | 2044 | CA | ILE A 305 | 47.771 | 16.719 | 6.999 | 1.00 | 34.24 | A | C |
| ATOM | 2045 | CB | ILE A 305 | 47.331 | 15.482 | 6.176 | 1.00 | 35.06 | A | C |
| ATOM | 2046 | CG2 | ILE A 305 | 47.815 | 15.620 | 4.727 | 1.00 | 34.47 | A | C |
| ATOM | 2047 | CG1 | ILE A 305 | 47.897 | 14.210 | 6.811 | 1.00 | 35.17 | A | C |
| ATOM | 2048 | CD1 | ILE A 305 | 47.605 | 12.962 | 6.037 | 1.00 | 36.00 | A | C |
| ATOM | 2049 | C | ILE A 305 | 46.945 | 17.953 | 6.587 | 1.00 | 36.36 | A | C |
| ATOM | 2050 | O | ILE A 305 | 45.705 | 17.981 | 6.728 | 1.00 | 36.85 | A | O |
| ATOM | 2051 | N | ASP A 306 | 47.666 | 18.959 | 6.103 | 1.00 | 36.61 | A | N |
| ATOM | 2052 | CA | ASP A 306 | 47.162 | 20.269 | 5.693 | 1.00 | 37.59 | A | C |
| ATOM | 2053 | CB | ASP A 306 | 45.780 | 20.609 | 6.306 | 1.00 | 40.39 | A | C |
| ATOM | 2054 | CG | ASP A 306 | 44.589 | 20.333 | 5.351 | 1.00 | 41.94 | A | C |
| ATOM | 2055 | OD1 | ASP A 306 | 44.721 | 20.586 | 4.126 | 1.00 | 43.38 | A | O |
| ATOM | 2056 | OD2 | ASP A 306 | 43.503 | 19.901 | 5.835 | 1.00 | 41.85 | A | O |
| ATOM | 2057 | C | ASP A 306 | 48.233 | 21.120 | 6.379 | 1.00 | 36.13 | A | C |
| ATOM | 2058 | O | ASP A 306 | 48.817 | 22.023 | 5.775 | 1.00 | 33.17 | A | O |
| ATOM | 2059 | N | GLN A 307 | 48.490 | 20.787 | 7.649 | 1.00 | 35.65 | A | N |
| ATOM | 2060 | CA | GLN A 307 | 49.496 | 21.455 | 8.482 | 1.00 | 36.50 | A | C |
| ATOM | 2061 | CB | GLN A 307 | 49.334 | 21.076 | 9.951 | 1.00 | 36.49 | A | C |
| ATOM | 2062 | CG | GLN A 307 | 48.199 | 21.766 | 10.658 | 1.00 | 38.38 | A | C |
| ATOM | 2063 | CD | GLN A 307 | 48.444 | 21.915 | 12.148 | 1.00 | 39.41 | A | C |
| ATOM | 2064 | OE1 | GLN A 307 | 47.518 | 22.110 | 12.921 | 1.00 | 41.70 | A | O |
| ATOM | 2065 | NE2 | GLN A 307 | 49.702 | 21.848 | 12.551 | 1.00 | 41.03 | A | N |

Figure 1-36

| | Atom Type | Resid | # | X | Y | Z | OCC | B | | |
|---|---|---|---|---|---|---|---|---|---|---|
| ATOM | 2066 | C | GLN A 307 | 50.904 | 21.075 | 8.054 | 1.00 | 36.36 | A | C |
| ATOM | 2067 | O | GLN A 307 | 51.803 | 21.912 | 8.054 | 1.00 | 36.14 | A | O |
| ATOM | 2068 | N | ILE A 308 | 51.088 | 19.799 | 7.724 | 1.00 | 35.90 | A | N |
| ATOM | 2069 | CA | ILE A 308 | 52.378 | 19.291 | 7.272 | 1.00 | 35.48 | A | C |
| ATOM | 2070 | CB | ILE A 308 | 52.398 | 17.719 | 7.136 | 1.00 | 36.06 | A | C |
| ATOM | 2071 | CG2 | ILE A 308 | 53.643 | 17.271 | 6.378 | 1.00 | 35.45 | A | C |
| ATOM | 2072 | CG1 | ILE A 308 | 52.341 | 17.041 | 8.503 | 1.00 | 36.02 | A | C |
| ATOM | 2073 | CD1 | ILE A 308 | 50.990 | 16.456 | 8.822 | 1.00 | 37.69 | A | C |
| ATOM | 2074 | C | ILE A 308 | 52.710 | 19.876 | 5.893 | 1.00 | 35.24 | A | C |
| ATOM | 2075 | O | ILE A 308 | 53.804 | 20.403 | 5.680 | 1.00 | 33.56 | A | O |
| ATOM | 2076 | N | LEU A 309 | 51.773 | 19.776 | 4.953 | 1.00 | 35.35 | A | N |
| ATOM | 2077 | CA | LEU A 309 | 52.020 | 20.280 | 3.609 | 1.00 | 37.30 | A | C |
| ATOM | 2078 | CB | LEU A 309 | 50.830 | 19.987 | 2.695 | 1.00 | 36.45 | A | C |
| ATOM | 2079 | CG | LEU A 309 | 50.731 | 18.566 | 2.147 | 1.00 | 35.31 | A | C |
| ATOM | 2080 | CD1 | LEU A 309 | 49.355 | 18.325 | 1.562 | 1.00 | 35.75 | A | C |
| ATOM | 2081 | CD2 | LEU A 309 | 51.794 | 18.370 | 1.097 | 1.00 | 35.98 | A | C |
| ATOM | 2082 | C | LEU A 309 | 52.311 | 21.769 | 3.622 | 1.00 | 40.09 | A | C |
| ATOM | 2083 | O | LEU A 309 | 52.880 | 22.319 | 2.673 | 1.00 | 40.28 | A | O |
| ATOM | 2084 | N | ARG A 310 | 51.925 | 22.431 | 4.701 | 1.00 | 43.21 | A | N |
| ATOM | 2085 | CA | ARG A 310 | 52.161 | 23.856 | 4.777 | 1.00 | 46.41 | A | C |
| ATOM | 2086 | CB | ARG A 310 | 50.883 | 24.584 | 5.217 | 1.00 | 49.09 | A | C |
| ATOM | 2087 | CG | ARG A 310 | 49.682 | 24.344 | 4.264 | 1.00 | 51.41 | A | C |
| ATOM | 2088 | CD | ARG A 310 | 49.977 | 24.727 | 2.787 | 1.00 | 53.18 | A | C |
| ATOM | 2089 | NE | ARG A 310 | 48.832 | 24.519 | 1.886 | 1.00 | 54.37 | A | N |
| ATOM | 2090 | CZ | ARG A 310 | 48.794 | 24.864 | 0.594 | 1.00 | 55.02 | A | C |
| ATOM | 2091 | NH1 | ARG A 310 | 49.839 | 25.443 | 0.015 | 1.00 | 55.21 | A | N |
| ATOM | 2092 | NH2 | ARG A 310 | 47.697 | 24.639 | -0.124 | 1.00 | 55.74 | A | N |
| ATOM | 2093 | C | ARG A 310 | 53.329 | 24.164 | 5.696 | 1.00 | 47.40 | A | C |
| ATOM | 2094 | O | ARG A 310 | 53.606 | 25.321 | 5.986 | 1.00 | 47.71 | A | O |
| ATOM | 2095 | N | HIS A 311 | 54.015 | 23.119 | 6.143 | 1.00 | 48.00 | A | N |
| ATOM | 2096 | CA | HIS A 311 | 55.182 | 23.282 | 6.995 | 1.00 | 49.96 | A | C |
| ATOM | 2097 | CB | HIS A 311 | 55.595 | 21.922 | 7.564 | 1.00 | 49.56 | A | C |
| ATOM | 2098 | CG | HIS A 311 | 56.844 | 21.949 | 8.397 | 1.00 | 48.95 | A | C |
| ATOM | 2099 | CD2 | HIS A 311 | 57.021 | 21.986 | 9.740 | 1.00 | 48.30 | A | C |
| ATOM | 2100 | ND1 | HIS A 311 | 58.108 | 21.899 | 7.848 | 1.00 | 49.22 | A | N |
| ATOM | 2101 | CE1 | HIS A 311 | 59.008 | 21.901 | 8.814 | 1.00 | 48.27 | A | C |
| ATOM | 2102 | NE2 | HIS A 311 | 58.374 | 21.953 | 9.971 | 1.00 | 47.79 | A | N |
| ATOM | 2103 | C | HIS A 311 | 56.244 | 23.842 | 6.050 | 1.00 | 52.79 | A | C |
| ATOM | 2104 | O | HIS A 311 | 55.924 | 24.223 | 4.930 | 1.00 | 53.13 | A | O |
| ATOM | 2105 | N | ASP A 312 | 57.497 | 23.908 | 6.483 | 1.00 | 55.75 | A | N |
| ATOM | 2106 | CA | ASP A 312 | 58.534 | 24.439 | 5.625 | 1.00 | 58.39 | A | C |
| ATOM | 2107 | CB | ASP A 312 | 59.794 | 24.723 | 6.430 | 1.00 | 59.75 | A | C |
| ATOM | 2108 | CG | ASP A 312 | 59.660 | 25.975 | 7.279 | 1.00 | 60.60 | A | C |
| ATOM | 2109 | OD1 | ASP A 312 | 58.747 | 26.033 | 8.133 | 1.00 | 62.10 | A | O |
| ATOM | 2110 | OD2 | ASP A 312 | 60.459 | 26.915 | 7.092 | 1.00 | 61.30 | A | O |
| ATOM | 2111 | C | ASP A 312 | 58.803 | 23.512 | 4.452 | 1.00 | 60.06 | A | C |
| ATOM | 2112 | O | ASP A 312 | 59.893 | 22.983 | 4.260 | 1.00 | 59.87 | A | O |
| ATOM | 2113 | N | PHE A 313 | 57.739 | 23.311 | 3.687 | 1.00 | 62.35 | A | N |
| ATOM | 2114 | CA | PHE A 313 | 57.724 | 22.529 | 2.459 | 1.00 | 64.18 | A | C |
| ATOM | 2115 | CB | PHE A 313 | 56.363 | 21.846 | 2.264 | 1.00 | 63.36 | A | C |
| ATOM | 2116 | CG | PHE A 313 | 56.380 | 20.345 | 2.376 | 1.00 | 63.02 | A | C |
| ATOM | 2117 | CD1 | PHE A 313 | 56.461 | 19.722 | 3.616 | 1.00 | 62.75 | A | C |
| ATOM | 2118 | CD2 | PHE A 313 | 56.270 | 19.552 | 1.238 | 1.00 | 62.38 | A | C |
| ATOM | 2119 | CE1 | PHE A 313 | 56.429 | 18.329 | 3.720 | 1.00 | 62.16 | A | C |
| ATOM | 2120 | CE2 | PHE A 313 | 56.239 | 18.164 | 1.334 | 1.00 | 62.08 | A | C |
| ATOM | 2121 | CZ | PHE A 313 | 56.319 | 17.552 | 2.580 | 1.00 | 62.21 | A | C |
| ATOM | 2122 | C | PHE A 313 | 57.811 | 23.656 | 1.447 | 1.00 | 66.37 | A | C |
| ATOM | 2123 | O | PHE A 313 | 58.029 | 23.408 | 0.263 | 1.00 | 66.37 | A | O |
| ATOM | 2124 | N | PHE A 314 | 57.624 | 24.885 | 1.952 | 1.00 | 69.07 | A | N |

Figure 1-37

| | | Atom Type | Resid | # | X | Y | Z | OCC | B | | |
|---|---|---|---|---|---|---|---|---|---|---|---|
| ATOM | 2125 | CA | PHE A | 314 | 57.645 | 26.087 | 1.130 | 1.00 | 71.89 | A | C |
| ATOM | 2126 | CB | PHE A | 314 | 57.194 | 27.323 | 1.920 | 1.00 | 72.66 | A | C |
| ATOM | 2127 | CG | PHE A | 314 | 58.215 | 27.868 | 2.894 | 1.00 | 73.14 | A | C |
| ATOM | 2128 | CD1 | PHE A | 314 | 59.425 | 28.420 | 2.448 | 1.00 | 72.96 | A | C |
| ATOM | 2129 | CD2 | PHE A | 314 | 57.929 | 27.898 | 4.260 | 1.00 | 73.36 | A | C |
| ATOM | 2130 | CE1 | PHE A | 314 | 60.330 | 28.996 | 3.344 | 1.00 | 73.34 | A | C |
| ATOM | 2131 | CE2 | PHE A | 314 | 58.830 | 28.474 | 5.162 | 1.00 | 73.78 | A | C |
| ATOM | 2132 | CZ | PHE A | 314 | 60.031 | 29.024 | 4.702 | 1.00 | 73.68 | A | C |
| ATOM | 2133 | C | PHE A | 314 | 59.005 | 26.343 | 0.502 | 1.00 | 73.32 | A | C |
| ATOM | 2134 | O | PHE A | 314 | 59.305 | 27.452 | 0.042 | 1.00 | 73.79 | A | O |
| ATOM | 2135 | N | THR A | 315 | 59.827 | 25.303 | 0.464 | 1.00 | 74.81 | A | N |
| ATOM | 2136 | CA | THR A | 315 | 61.143 | 25.427 | -0.127 | 1.00 | 75.76 | A | C |
| ATOM | 2137 | CB | THR A | 315 | 62.170 | 25.796 | 1.013 | 1.00 | 76.07 | A | C |
| ATOM | 2138 | OG1 | THR A | 315 | 63.501 | 25.820 | 0.491 | 1.00 | 76.60 | A | O |
| ATOM | 2139 | CG2 | THR A | 315 | 62.095 | 24.794 | 2.134 | 1.00 | 76.41 | A | C |
| ATOM | 2140 | C | THR A | 315 | 61.562 | 24.179 | -0.956 | 1.00 | 76.44 | A | C |
| ATOM | 2141 | O | THR A | 315 | 61.090 | 23.078 | -0.740 | 1.00 | 76.62 | A | O |
| ATOM | 2142 | N | LYS A | 316 | 62.433 | 24.434 | -1.926 | 1.00 | 77.31 | A | N |
| ATOM | 2143 | CA | LYS A | 316 | 63.050 | 23.477 | -2.845 | 1.00 | 77.57 | A | C |
| ATOM | 2144 | CB | LYS A | 316 | 64.508 | 23.299 | -2.436 | 1.00 | 77.88 | A | C |
| ATOM | 2145 | CG | LYS A | 316 | 65.527 | 24.057 | -3.313 | 1.00 | 78.61 | A | C |
| ATOM | 2146 | CD | LYS A | 316 | 66.954 | 23.913 | -2.759 | 1.00 | 78.97 | A | C |
| ATOM | 2147 | CE | LYS A | 316 | 67.919 | 23.353 | -3.816 | 1.00 | 79.51 | A | C |
| ATOM | 2148 | NZ | LYS A | 316 | 69.365 | 23.463 | -3.459 | 1.00 | 79.90 | A | N |
| ATOM | 2149 | C | LYS A | 316 | 62.510 | 22.043 | -3.099 | 1.00 | 77.49 | A | C |
| ATOM | 2150 | O | LYS A | 316 | 63.206 | 21.085 | -2.762 | 1.00 | 77.48 | A | O |
| ATOM | 2151 | N | GLY A | 317 | 61.366 | 21.862 | -3.769 | 1.00 | 77.65 | A | N |
| ATOM | 2152 | CA | GLY A | 317 | 60.814 | 20.517 | -4.038 | 1.00 | 78.07 | A | C |
| ATOM | 2153 | C | GLY A | 317 | 60.324 | 20.354 | -5.465 | 1.00 | 78.32 | A | C |
| ATOM | 2154 | O | GLY A | 317 | 59.378 | 20.985 | -5.903 | 1.00 | 78.25 | A | O |
| ATOM | 2155 | N | TYR A | 318 | 60.957 | 19.419 | -6.145 | 1.00 | 78.45 | A | N |
| ATOM | 2156 | CA | TYR A | 318 | 60.794 | 19.140 | -7.576 | 1.00 | 78.86 | A | C |
| ATOM | 2157 | CB | TYR A | 318 | 61.883 | 18.173 | -7.914 | 1.00 | 80.03 | A | C |
| ATOM | 2158 | CG | TYR A | 318 | 63.169 | 18.908 | -8.077 | 1.00 | 81.60 | A | C |
| ATOM | 2159 | CD1 | TYR A | 318 | 63.413 | 20.123 | -7.390 | 1.00 | 82.03 | A | C |
| ATOM | 2160 | CE1 | TYR A | 318 | 64.579 | 20.823 | -7.613 | 1.00 | 82.63 | A | C |
| ATOM | 2161 | CD2 | TYR A | 318 | 64.139 | 18.438 | -8.961 | 1.00 | 82.12 | A | C |
| ATOM | 2162 | CE2 | TYR A | 318 | 65.301 | 19.142 | -9.178 | 1.00 | 82.87 | A | C |
| ATOM | 2163 | CZ | TYR A | 318 | 65.513 | 20.328 | -8.509 | 1.00 | 83.22 | A | C |
| ATOM | 2164 | OH | TYR A | 318 | 66.661 | 21.032 | -8.807 | 1.00 | 84.44 | A | O |
| ATOM | 2165 | C | TYR A | 318 | 59.538 | 18.772 | -8.399 | 1.00 | 78.26 | A | C |
| ATOM | 2166 | O | TYR A | 318 | 58.459 | 18.569 | -7.846 | 1.00 | 78.43 | A | O |
| ATOM | 2167 | N | THR A | 319 | 59.700 | 18.693 | -9.733 | 1.00 | 77.48 | A | N |
| ATOM | 2168 | CA | THR A | 319 | 58.587 | 18.438 | -10.676 | 1.00 | 77.30 | A | C |
| ATOM | 2169 | CB | THR A | 319 | 58.435 | 19.599 | -11.693 | 1.00 | 77.11 | A | C |
| ATOM | 2170 | OG1 | THR A | 319 | 59.715 | 20.187 | -11.966 | 1.00 | 77.29 | A | O |
| ATOM | 2171 | CG2 | THR A | 319 | 57.461 | 20.663 | -11.194 | 1.00 | 77.15 | A | C |
| ATOM | 2172 | C | THR A | 319 | 58.526 | 17.130 | -11.488 | 1.00 | 77.00 | A | C |
| ATOM | 2173 | O | THR A | 319 | 57.481 | 16.496 | -11.517 | 1.00 | 77.07 | A | O |
| ATOM | 2174 | N | PRO A | 320 | 59.605 | 16.751 | -12.210 | 1.00 | 77.04 | A | N |
| ATOM | 2175 | CD | PRO A | 320 | 60.629 | 17.642 | -12.780 | 1.00 | 77.17 | A | C |
| ATOM | 2176 | CA | PRO A | 320 | 59.556 | 15.487 | -12.973 | 1.00 | 76.85 | A | C |
| ATOM | 2177 | CB | PRO A | 320 | 60.225 | 15.837 | -14.300 | 1.00 | 76.91 | A | C |
| ATOM | 2178 | CG | PRO A | 320 | 60.424 | 17.382 | -14.255 | 1.00 | 77.19 | A | C |
| ATOM | 2179 | C | PRO A | 320 | 60.309 | 14.311 | -12.276 | 1.00 | 76.50 | A | C |
| ATOM | 2180 | O | PRO A | 320 | 59.697 | 13.279 | -11.955 | 1.00 | 76.58 | A | O |
| ATOM | 2181 | N | ASP A | 321 | 61.634 | 14.470 | -12.106 | 1.00 | 76.31 | A | N |
| ATOM | 2182 | CA | ASP A | 321 | 62.561 | 13.479 | -11.489 | 1.00 | 76.19 | A | C |
| ATOM | 2183 | CB | ASP A | 321 | 61.799 | 12.527 | -10.559 | 1.00 | 75.20 | A | C |

Figure 1-38

| | | Atom Type | Resid | | # | X | Y | Z | OCC | B | | |
|---|---|---|---|---|---|---|---|---|---|---|---|---|
| ATOM | 2184 | CG | ASP | A | 321 | 62.154 | 12.722 | -9.110 | 1.00 | 74.64 | A | C |
| ATOM | 2185 | OD1 | ASP | A | 321 | 63.351 | 12.846 | -8.798 | 1.00 | 74.61 | A | O |
| ATOM | 2186 | OD2 | ASP | A | 321 | 61.239 | 12.694 | -8.283 | 1.00 | 74.29 | A | O |
| ATOM | 2187 | C | ASP | A | 321 | 63.355 | 12.649 | -12.520 | 1.00 | 76.47 | A | C |
| ATOM | 2188 | O | ASP | A | 321 | 64.569 | 12.761 | -12.683 | 1.00 | 76.24 | A | O |
| ATOM | 2189 | N | ARG | A | 322 | 62.615 | 11.796 | -13.209 | 1.00 | 77.43 | A | N |
| ATOM | 2190 | CA | ARG | A | 322 | 63.121 | 10.909 | -14.277 | 1.00 | 78.81 | A | C |
| ATOM | 2191 | CB | ARG | A | 322 | 64.355 | 11.507 | -14.958 | 1.00 | 79.26 | A | C |
| ATOM | 2192 | CG | ARG | A | 322 | 63.895 | 12.411 | -16.079 | 1.00 | 80.20 | A | C |
| ATOM | 2193 | CD | ARG | A | 322 | 64.969 | 13.221 | -16.781 | 1.00 | 80.70 | A | C |
| ATOM | 2194 | NE | ARG | A | 322 | 64.352 | 13.955 | -17.895 | 1.00 | 80.84 | A | N |
| ATOM | 2195 | CZ | ARG | A | 322 | 63.321 | 14.804 | -17.779 | 1.00 | 80.76 | A | C |
| ATOM | 2196 | NH1 | ARG | A | 322 | 62.771 | 15.057 | -16.593 | 1.00 | 80.89 | A | N |
| ATOM | 2197 | NH2 | ARG | A | 322 | 62.807 | 15.388 | -18.857 | 1.00 | 80.83 | A | N |
| ATOM | 2198 | C | ARG | A | 322 | 63.347 | 9.430 | -14.022 | 1.00 | 78.88 | A | C |
| ATOM | 2199 | O | ARG | A | 322 | 62.483 | 8.647 | -14.314 | 1.00 | 79.62 | A | O |
| ATOM | 2200 | N | LEU | A | 323 | 64.510 | 9.034 | -13.539 | 1.00 | 78.77 | A | N |
| ATOM | 2201 | CA | LEU | A | 323 | 64.769 | 7.627 | -13.243 | 1.00 | 79.02 | A | C |
| ATOM | 2202 | CB | LEU | A | 323 | 64.646 | 6.727 | -14.527 | 1.00 | 78.59 | A | C |
| ATOM | 2203 | CG | LEU | A | 323 | 63.413 | 6.600 | -15.458 | 1.00 | 78.52 | A | C |
| ATOM | 2204 | CD1 | LEU | A | 323 | 63.827 | 5.878 | -16.726 | 1.00 | 78.44 | A | C |
| ATOM | 2205 | CD2 | LEU | A | 323 | 62.234 | 5.901 | -14.783 | 1.00 | 78.49 | A | C |
| ATOM | 2206 | C | LEU | A | 323 | 66.171 | 7.313 | -12.624 | 1.00 | 79.09 | A | C |
| ATOM | 2207 | O | LEU | A | 323 | 66.317 | 6.291 | -11.966 | 1.00 | 78.99 | A | O |
| ATOM | 2208 | N | PRO | A | 324 | 67.183 | 8.202 | -12.749 | 1.00 | 79.50 | A | N |
| ATOM | 2209 | CD | PRO | A | 324 | 67.046 | 9.621 | -13.119 | 1.00 | 79.80 | A | C |
| ATOM | 2210 | CA | PRO | A | 324 | 68.539 | 7.957 | -12.229 | 1.00 | 79.68 | A | C |
| ATOM | 2211 | CB | PRO | A | 324 | 69.241 | 9.280 | -12.509 | 1.00 | 79.42 | A | C |
| ATOM | 2212 | CG | PRO | A | 324 | 68.142 | 10.268 | -12.314 | 1.00 | 79.81 | A | C |
| ATOM | 2213 | C | PRO | A | 324 | 68.686 | 7.502 | -10.774 | 1.00 | 79.88 | A | C |
| ATOM | 2214 | O | PRO | A | 324 | 68.097 | 8.079 | -9.848 | 1.00 | 80.29 | A | O |
| ATOM | 2215 | N | ILE | A | 325 | 69.512 | 6.478 | -10.574 | 1.00 | 80.28 | A | N |
| ATOM | 2216 | CA | ILE | A | 325 | 69.785 | 5.954 | -9.236 | 1.00 | 80.45 | A | C |
| ATOM | 2217 | CB | ILE | A | 325 | 70.062 | 4.429 | -9.300 | 1.00 | 80.14 | A | C |
| ATOM | 2218 | CG2 | ILE | A | 325 | 70.348 | 3.888 | -7.914 | 1.00 | 79.89 | A | C |
| ATOM | 2219 | CG1 | ILE | A | 325 | 68.850 | 3.699 | -9.898 | 1.00 | 79.82 | A | C |
| ATOM | 2220 | CD1 | ILE | A | 325 | 69.069 | 2.213 | -10.083 | 1.00 | 79.71 | A | C |
| ATOM | 2221 | C | ILE | A | 325 | 70.998 | 6.705 | -8.640 | 1.00 | 80.81 | A | C |
| ATOM | 2222 | O | ILE | A | 325 | 72.067 | 6.126 | -8.405 | 1.00 | 80.63 | A | O |
| ATOM | 2223 | N | SER | A | 326 | 70.804 | 8.006 | -8.419 | 1.00 | 81.18 | A | N |
| ATOM | 2224 | CA | SER | A | 326 | 71.812 | 8.914 | -7.858 | 1.00 | 81.78 | A | C |
| ATOM | 2225 | CB | SER | A | 326 | 73.172 | 8.778 | -8.562 | 1.00 | 82.13 | A | C |
| ATOM | 2226 | OG | SER | A | 326 | 73.275 | 9.693 | -9.646 | 1.00 | 82.64 | A | O |
| ATOM | 2227 | C | SER | A | 326 | 71.299 | 10.334 | -8.080 | 1.00 | 81.99 | A | C |
| ATOM | 2228 | O | SER | A | 326 | 71.906 | 11.302 | -7.620 | 1.00 | 82.33 | A | O |
| ATOM | 2229 | N | SER | A | 327 | 70.183 | 10.428 | -8.808 | 1.00 | 81.89 | A | N |
| ATOM | 2230 | CA | SER | A | 327 | 69.517 | 11.685 | -9.150 | 1.00 | 81.82 | A | C |
| ATOM | 2231 | CB | SER | A | 327 | 69.025 | 12.404 | -7.888 | 1.00 | 81.81 | A | C |
| ATOM | 2232 | OG | SER | A | 327 | 70.080 | 13.045 | -7.200 | 1.00 | 81.68 | A | O |
| ATOM | 2233 | C | SER | A | 327 | 70.429 | 12.601 | -9.953 | 1.00 | 82.06 | A | C |
| ATOM | 2234 | OT1 | SER | A | 327 | 69.960 | 13.154 | -10.967 | 1.00 | 82.01 | A | O |
| ATOM | 2235 | OT2 | SER | A | 327 | 71.604 | 12.755 | -9.560 | 1.00 | 82.85 | A | O |
| TER | 2236 | | SER | A | 327 | | | | | | A | |
| ATOM | 2237 | O5* | ADN | B | 1 | 51.917 | -8.086 | -2.515 | 1.00 | 71.37 | B | O |
| ATOM | 2238 | C5* | ADN | B | 1 | 52.822 | -7.028 | -2.165 | 1.00 | 72.26 | B | C |
| ATOM | 2239 | C4* | ADN | B | 1 | 53.762 | -6.847 | -3.392 | 1.00 | 72.08 | B | C |
| ATOM | 2240 | O4* | ADN | B | 1 | 52.816 | -6.093 | -4.192 | 1.00 | 71.75 | B | O |
| ATOM | 2241 | C3* | ADN | B | 1 | 54.812 | -5.776 | -3.097 | 1.00 | 72.06 | B | C |
| ATOM | 2242 | O3* | ADN | B | 1 | 56.071 | -6.490 | -2.991 | 1.00 | 72.24 | B | O |

Figure 1-39

| | | Atom Type | Resid | # | X | Y | Z | OCC | B | | |
|---|---|---|---|---|---|---|---|---|---|---|---|
| ATOM | 2243 | C2* | ADN B | 1 | 54.760 | -4.774 | -4.297 | 1.00 | 71.95 | B | C |
| ATOM | 2244 | O2* | ADN B | 1 | 56.005 | -4.479 | -4.957 | 1.00 | 71.48 | B | O |
| ATOM | 2245 | C1* | ADN B | 1 | 53.623 | -5.433 | -5.131 | 1.00 | 71.63 | B | C |
| ATOM | 2246 | N9 | ADN B | 1 | 52.731 | -4.553 | -5.957 | 1.00 | 71.49 | B | N |
| ATOM | 2247 | C8 | ADN B | 1 | 51.360 | -4.222 | -5.681 | 1.00 | 71.49 | B | C |
| ATOM | 2248 | N7 | ADN B | 1 | 50.788 | -3.421 | -6.542 | 1.00 | 71.36 | B | N |
| ATOM | 2249 | C5 | ADN B | 1 | 51.810 | -3.168 | -7.459 | 1.00 | 71.23 | B | C |
| ATOM | 2250 | C6 | ADN B | 1 | 51.892 | -2.357 | -8.687 | 1.00 | 71.03 | B | C |
| ATOM | 2251 | N6 | ADN B | 1 | 50.857 | -1.650 | -9.140 | 1.00 | 70.47 | B | N |
| ATOM | 2252 | N1 | ADN B | 1 | 53.125 | -2.325 | -9.400 | 1.00 | 71.15 | B | N |
| ATOM | 2253 | C2 | ADN B | 1 | 54.233 | -3.043 | -8.959 | 1.00 | 71.00 | B | C |
| ATOM | 2254 | N3 | ADN B | 1 | 54.260 | -3.844 | -7.815 | 1.00 | 71.32 | B | N |
| ATOM | 2255 | C4 | ADN B | 1 | 53.028 | -3.854 | -7.115 | 1.00 | 71.18 | B | C |
| TER | 2256 | | ADN B | 1 | | | | | | B | |
| ATOM | 2257 | O | HOH W | 1 | 57.845 | -4.588 | -22.146 | 1.00 | 36.05 | W | O |
| ATOM | 2258 | O | HOH W | 2 | 39.705 | -0.442 | -17.277 | 1.00 | 69.98 | W | O |
| ATOM | 2259 | O | HOH W | 3 | 34.715 | 0.188 | -1.520 | 1.00 | 51.74 | W | O |
| ATOM | 2260 | O | HOH W | 4 | 40.848 | 4.056 | -10.745 | 1.00 | 75.81 | W | O |
| ATOM | 2261 | O | HOH W | 5 | 48.371 | -22.797 | -7.087 | 1.00 | 69.26 | W | O |
| ATOM | 2262 | O | HOH W | 6 | 66.855 | -2.523 | -5.043 | 1.00 | 59.57 | W | O |
| ATOM | 2263 | O | HOH W | 7 | 67.842 | -2.328 | -8.466 | 1.00 | 33.09 | W | O |
| ATOM | 2264 | O | HOH W | 8 | 43.976 | 13.279 | 8.750 | 1.00 | 23.83 | W | O |
| ATOM | 2265 | O | HOH W | 9 | 40.964 | 20.077 | 4.596 | 1.00 | 32.95 | W | O |
| ATOM | 2266 | O | HOH W | 10 | 55.696 | -2.745 | 5.154 | 1.00 | 41.33 | W | O |
| ATOM | 2267 | O | HOH W | 11 | 62.785 | 0.006 | 5.791 | 1.00 | 56.62 | W | O |
| ATOM | 2268 | O | HOH W | 12 | 57.364 | 4.176 | -18.784 | 1.00 | 37.05 | W | O |
| ATOM | 2269 | O | HOH W | 13 | 55.106 | 12.097 | -13.026 | 1.00 | 49.73 | W | O |
| ATOM | 2270 | O | HOH W | 14 | 47.420 | 13.897 | 12.694 | 1.00 | 39.43 | W | O |
| ATOM | 2271 | O | HOH W | 15 | 69.827 | 1.356 | 17.731 | 1.00 | 45.49 | W | O |
| ATOM | 2272 | O | HOH W | 16 | 71.612 | 1.128 | 20.138 | 1.00 | 69.38 | W | O |
| ATOM | 2273 | O | HOH W | 17 | 67.573 | -5.390 | 10.735 | 1.00 | 36.51 | W | O |
| ATOM | 2274 | O | HOH W | 18 | 63.714 | 3.226 | 25.084 | 1.00 | 65.47 | W | O |
| ATOM | 2275 | O | HOH W | 19 | 66.007 | 2.440 | 25.267 | 1.00 | 70.29 | W | O |
| ATOM | 2276 | O | HOH W | 20 | 61.329 | 0.359 | 29.688 | 1.00 | 57.25 | W | O |
| ATOM | 2277 | O | HOH W | 21 | 61.451 | 17.636 | 22.355 | 1.00 | 33.55 | W | O |
| ATOM | 2278 | O | HOH W | 22 | 28.648 | -21.551 | -26.332 | 1.00 | 68.01 | W | O |
| ATOM | 2279 | O | HOH W | 23 | 47.470 | -23.875 | 5.276 | 1.00 | 71.23 | W | O |
| ATOM | 2280 | O | HOH W | 24 | 33.466 | -11.998 | 13.107 | 1.00 | 107.49 | W | O |
| ATOM | 2281 | O | HOH W | 25 | 48.242 | -11.150 | 0.943 | 1.00 | 36.08 | W | O |
| ATOM | 2282 | O | HOH W | 26 | 39.627 | -4.659 | 5.979 | 1.00 | 14.75 | W | O |
| ATOM | 2283 | O | HOH W | 27 | 28.923 | -1.890 | 6.893 | 1.00 | 25.76 | W | O |
| ATOM | 2284 | O | HOH W | 28 | 39.929 | 4.254 | -13.271 | 1.00 | 60.09 | W | O |
| ATOM | 2285 | O | HOH W | 29 | 61.626 | -1.209 | -12.669 | 1.00 | 55.80 | W | O |
| ATOM | 2286 | O | HOH W | 30 | 63.400 | 4.550 | -10.363 | 1.00 | 25.46 | W | O |
| ATOM | 2287 | O | HOH W | 31 | 64.706 | 0.399 | -8.140 | 1.00 | 40.54 | W | O |
| ATOM | 2288 | O | HOH W | 32 | 65.558 | -3.356 | -1.015 | 1.00 | 40.66 | W | O |
| ATOM | 2289 | O | HOH W | 33 | 64.297 | -7.883 | -0.279 | 1.00 | 52.81 | W | O |
| ATOM | 2290 | O | HOH W | 34 | 72.346 | -1.189 | -4.032 | 1.00 | 63.27 | W | O |
| ATOM | 2291 | O | HOH W | 35 | 69.700 | 16.821 | -0.358 | 1.00 | 31.27 | W | O |
| ATOM | 2292 | O | HOH W | 36 | 39.541 | -3.024 | 12.404 | 1.00 | 39.60 | W | O |
| ATOM | 2293 | O | HOH W | 37 | 43.763 | -5.541 | 12.469 | 1.00 | 36.30 | W | O |
| ATOM | 2294 | O | HOH W | 38 | 60.203 | -5.053 | 4.674 | 1.00 | 40.19 | W | O |
| ATOM | 2295 | O | HOH W | 39 | 54.394 | 6.703 | -19.006 | 1.00 | 51.52 | W | O |
| ATOM | 2296 | O | HOH W | 40 | 55.024 | 11.404 | -21.325 | 1.00 | 66.49 | W | O |
| ATOM | 2297 | O | HOH W | 41 | 49.798 | -9.865 | 10.291 | 1.00 | 33.96 | W | O |
| ATOM | 2298 | O | HOH W | 42 | 53.982 | 6.727 | 23.753 | 1.00 | 37.18 | W | O |
| ATOM | 2299 | O | HOH W | 43 | 48.768 | 11.591 | 27.467 | 1.00 | 74.49 | W | O |
| ATOM | 2300 | O | HOH W | 44 | 49.829 | 16.250 | 25.919 | 1.00 | 35.86 | W | O |
| ATOM | 2301 | O | HOH W | 45 | 46.484 | 19.971 | 14.172 | 1.00 | 45.25 | W | O |

Figure 1-40

|  |  | Atom Type | Resid |  | # | X | Y | Z | OCC | B |  |  |
|---|---|---|---|---|---|---|---|---|---|---|---|---|
| ATOM | 2302 | O | HOH | W | 46 | 49.670 | 17.987 | 5.563 | 1.00 | 36.24 | W | O |
| ATOM | 2303 | O | HOH | W | 47 | 32.789 | -5.211 | 8.008 | 1.00 | 56.60 | W | O |
| ATOM | 2304 | O | HOH | W | 48 | 47.506 | -11.938 | 13.618 | 1.00 | 54.07 | W | O |
| ATOM | 2305 | O | HOH | W | 49 | 43.590 | 12.699 | -7.759 | 1.00 | 30.03 | W | O |
| ATOM | 2306 | O | HOH | W | 50 | 51.776 | 14.529 | -10.083 | 1.00 | 62.35 | W | O |
| ATOM | 2307 | O | HOH | W | 51 | 35.431 | -3.518 | -9.683 | 1.00 | 62.90 | W | O |
| ATOM | 2308 | O | HOH | W | 52 | 33.171 | -1.613 | -17.087 | 1.00 | 46.96 | W | O |
| ATOM | 2309 | O | HOH | W | 53 | 49.409 | -22.602 | -4.492 | 1.00 | 56.05 | W | O |
| ATOM | 2310 | O | HOH | W | 54 | 51.213 | -19.088 | -8.232 | 1.00 | 32.73 | W | O |
| ATOM | 2311 | O | HOH | W | 55 | 55.813 | 13.768 | -15.492 | 1.00 | 23.09 | W | O |
| ATOM | 2312 | O | HOH | W | 56 | 51.652 | -12.514 | 13.544 | 1.00 | 33.15 | W | O |
| ATOM | 2313 | O | HOH | W | 57 | 53.716 | -11.715 | 17.497 | 1.00 | 68.21 | W | O |
| ATOM | 2314 | O | HOH | W | 58 | 72.645 | 11.016 | 1.257 | 1.00 | 21.15 | W | O |
| ATOM | 2315 | O | HOH | W | 59 | 63.953 | -3.338 | 14.998 | 1.00 | 47.79 | W | O |
| ATOM | 2316 | O | HOH | W | 60 | 42.984 | 16.069 | 17.338 | 1.00 | 40.85 | W | O |
| ATOM | 2317 | O | HOH | W | 61 | 47.125 | 20.200 | 24.431 | 1.00 | 58.35 | W | O |
| ATOM | 2318 | O | HOH | W | 62 | 45.232 | 22.627 | 25.086 | 1.00 | 57.31 | W | O |
| ATOM | 2319 | O | HOH | W | 63 | 44.563 | 19.073 | 22.305 | 1.00 | 83.23 | W | O |
| ATOM | 2320 | O | HOH | W | 64 | 37.792 | 9.762 | -13.756 | 1.00 | 78.68 | W | O |
| ATOM | 2321 | O | HOH | W | 65 | 62.478 | -5.835 | -12.628 | 1.00 | 88.91 | W | O |
| ATOM | 2322 | O | HOH | W | 66 | 58.222 | -5.019 | -14.673 | 1.00 | 41.52 | W | O |
| ATOM | 2323 | O | HOH | W | 67 | 69.783 | 18.107 | 2.784 | 1.00 | 37.38 | W | O |
| ATOM | 2324 | O | HOH | W | 68 | 45.024 | 17.357 | -3.688 | 1.00 | 35.86 | W | O |
| ATOM | 2325 | O | HOH | W | 69 | 41.798 | 16.892 | 10.767 | 1.00 | 49.66 | W | O |
| ATOM | 2326 | O | HOH | W | 70 | 44.917 | 14.626 | 9.966 | 1.00 | 65.03 | W | O |
| ATOM | 2327 | O | HOH | W | 71 | 58.934 | -2.905 | 10.041 | 1.00 | 58.78 | W | O |
| ATOM | 2328 | O | HOH | W | 72 | 48.674 | -2.679 | 27.327 | 1.00 | 27.05 | W | O |
| ATOM | 2329 | O | HOH | W | 73 | 69.528 | 1.317 | 12.917 | 1.00 | 48.94 | W | O |
| ATOM | 2330 | O | HOH | W | 74 | 65.354 | -12.119 | 14.880 | 1.00 | 66.25 | W | O |
| ATOM | 2331 | O | HOH | W | 75 | 57.585 | -5.210 | 27.800 | 1.00 | 38.72 | W | O |
| ATOM | 2332 | O | HOH | W | 76 | 56.230 | -3.789 | 24.050 | 1.00 | 59.44 | W | O |
| ATOM | 2333 | O | HOH | W | 77 | 62.901 | 27.722 | 8.979 | 1.00 | 48.10 | W | O |
| ATOM | 2334 | O | HOH | W | 78 | 42.869 | 20.773 | 8.533 | 1.00 | 42.07 | W | O |
| ATOM | 2335 | O | HOH | W | 79 | 47.457 | 21.838 | 2.391 | 1.00 | 33.16 | W | O |
| ATOM | 2336 | O | HOH | W | 80 | 64.894 | -1.936 | -16.848 | 1.00 | 68.39 | W | O |
| ATOM | 2337 | O | HOH | W | 81 | 58.666 | -9.682 | 1.446 | 1.00 | 75.17 | W | O |
| ATOM | 2338 | O | HOH | W | 82 | 48.842 | -8.496 | -25.168 | 1.00 | 21.64 | W | O |
| ATOM | 2339 | O | HOH | W | 83 | 51.172 | -5.918 | -24.695 | 1.00 | 44.62 | W | O |
| ATOM | 2340 | O | HOH | W | 84 | 44.045 | -15.434 | -26.097 | 1.00 | 83.15 | W | O |
| ATOM | 2341 | O | HOH | W | 85 | 43.588 | -9.423 | -31.085 | 1.00 | 52.47 | W | O |
| ATOM | 2342 | O | HOH | W | 86 | 52.963 | -10.807 | -25.237 | 1.00 | 24.57 | W | O |
| ATOM | 2343 | O | HOH | W | 87 | 38.916 | -4.313 | -20.259 | 1.00 | 36.19 | W | O |
| ATOM | 2344 | O | HOH | W | 88 | 50.347 | -17.152 | -5.611 | 1.00 | 37.29 | W | O |
| ATOM | 2345 | O | HOH | W | 89 | 41.780 | -23.285 | 10.234 | 1.00 | 29.56 | W | O |
| ATOM | 2346 | O | HOH | W | 90 | 43.579 | -15.555 | 12.503 | 1.00 | 27.96 | W | O |
| ATOM | 2347 | O | HOH | W | 91 | 30.168 | -0.731 | 2.418 | 1.00 | 54.96 | W | O |
| ATOM | 2348 | O | HOH | W | 92 | 30.409 | -1.603 | -0.131 | 1.00 | 48.84 | W | O |
| ATOM | 2349 | O | HOH | W | 93 | 30.481 | -2.457 | 8.846 | 1.00 | 61.84 | W | O |
| ATOM | 2350 | O | HOH | W | 94 | 40.608 | 9.786 | -10.349 | 1.00 | 51.98 | W | O |
| ATOM | 2351 | O | HOH | W | 95 | 49.294 | 11.067 | -11.187 | 1.00 | 32.56 | W | O |
| ATOM | 2352 | O | HOH | W | 96 | 44.746 | 16.115 | -11.480 | 1.00 | 112.25 | W | O |
| ATOM | 2353 | O | HOH | W | 97 | 36.851 | 3.465 | -17.296 | 1.00 | 50.90 | W | O |
| ATOM | 2354 | O | HOH | W | 98 | 50.372 | 6.293 | -14.421 | 1.00 | 53.22 | W | O |
| ATOM | 2355 | O | HOH | W | 99 | 66.785 | -4.339 | 1.967 | 1.00 | 53.62 | W | O |
| ATOM | 2356 | O | HOH | W | 100 | 66.398 | 3.687 | -8.921 | 1.00 | 43.08 | W | O |
| ATOM | 2357 | O | HOH | W | 101 | 71.344 | 9.020 | -1.846 | 1.00 | 41.62 | W | O |
| ATOM | 2358 | O | HOH | W | 102 | 71.602 | 19.414 | 4.067 | 1.00 | 40.26 | W | O |
| ATOM | 2359 | O | HOH | W | 103 | 48.877 | 17.126 | -5.370 | 1.00 | 45.52 | W | O |
| ATOM | 2360 | O | HOH | W | 104 | 52.306 | 12.213 | -10.989 | 1.00 | 45.79 | W | O |

Figure 1-41

| | | Atom Type | Resid | # | X | Y | Z | OCC | B | | |
|---|---|---|---|---|---|---|---|---|---|---|---|
| ATOM | 2361 | O | HOH W | 105 | 41.875 | -4.429 | 8.592 | 1.00 | 30.81 | W | O |
| ATOM | 2362 | O | HOH W | 106 | 69.039 | 13.422 | 2.568 | 1.00 | 66.37 | W | O |
| ATOM | 2363 | O | HOH W | 107 | 71.834 | -4.574 | 11.928 | 1.00 | 62.32 | W | O |
| ATOM | 2364 | O | HOH W | 108 | 68.499 | 3.918 | 13.014 | 1.00 | 64.33 | W | O |
| ATOM | 2365 | O | HOH W | 109 | 65.915 | -0.775 | 24.095 | 1.00 | 59.28 | W | O |
| ATOM | 2366 | O | HOH W | 110 | 62.680 | -12.687 | 13.954 | 1.00 | 78.12 | W | O |
| ATOM | 2367 | O | HOH W | 111 | 59.599 | -13.887 | 25.263 | 1.00 | 74.56 | W | O |
| ATOM | 2368 | O | HOH W | 112 | 64.570 | 7.998 | 25.380 | 1.00 | 58.24 | W | O |
| ATOM | 2369 | O | HOH W | 113 | 63.070 | 8.824 | 26.974 | 1.00 | 43.57 | W | O |
| ATOM | 2370 | O | HOH W | 114 | 69.571 | 16.585 | 17.115 | 1.00 | 34.92 | W | O |
| ATOM | 2371 | O | HOH W | 115 | 73.411 | 15.955 | 15.797 | 1.00 | 74.39 | W | O |
| ATOM | 2372 | O | HOH W | 116 | 76.291 | 21.206 | 10.317 | 1.00 | 39.07 | W | O |
| ATOM | 2373 | O | HOH W | 117 | 51.732 | 20.725 | 26.300 | 1.00 | 45.96 | W | O |
| ATOM | 2374 | O | HOH W | 118 | 51.003 | 24.918 | 24.674 | 1.00 | 61.24 | W | O |
| ATOM | 2375 | O | HOH W | 119 | 55.349 | 24.170 | 20.042 | 1.00 | 34.26 | W | O |
| ATOM | 2376 | O | HOH W | 120 | 52.052 | 22.782 | 21.474 | 1.00 | 25.27 | W | O |
| ATOM | 2377 | O | HOH W | 121 | 50.961 | 20.981 | 17.934 | 1.00 | 49.17 | W | O |
| ATOM | 2378 | O | HOH W | 122 | 41.444 | 20.487 | 12.237 | 1.00 | 25.98 | W | O |
| ATOM | 2379 | O | HOH W | 123 | 55.212 | 25.804 | 3.225 | 1.00 | 46.08 | W | O |
| ATOM | 2380 | O | HOH W | 124 | 62.279 | 30.291 | 0.228 | 1.00 | 24.03 | W | O |
| ATOM | 2381 | O | HOH W | 125 | 39.262 | -13.531 | -29.969 | 1.00 | 54.30 | W | O |
| ATOM | 2382 | O | HOH W | 126 | 37.461 | -16.110 | -30.375 | 1.00 | 85.26 | W | O |
| ATOM | 2383 | O | HOH W | 127 | 58.451 | -3.286 | -18.249 | 1.00 | 36.31 | W | O |
| ATOM | 2384 | O | HOH W | 128 | 65.186 | 5.412 | -9.339 | 1.00 | 49.47 | W | O |
| ATOM | 2385 | O | HOH W | 129 | 37.740 | 1.601 | -9.319 | 1.00 | 41.79 | W | O |
| ATOM | 2386 | O | HOH W | 130 | 61.966 | 0.423 | 3.079 | 1.00 | 63.48 | W | O |
| ATOM | 2387 | O | HOH W | 131 | 44.185 | -19.522 | -14.082 | 1.00 | 37.31 | W | O |
| ATOM | 2388 | O | HOH W | 132 | 60.424 | -10.873 | -20.408 | 1.00 | 50.51 | W | O |
| ATOM | 2389 | O | HOH W | 133 | 60.453 | -7.137 | -0.550 | 1.00 | 44.78 | W | O |
| ATOM | 2390 | O | HOH W | 134 | 59.853 | -4.841 | -1.556 | 1.00 | 62.21 | W | O |
| ATOM | 2391 | O | HOH W | 135 | 41.279 | -5.106 | -20.983 | 1.00 | 24.80 | W | O |
| ATOM | 2392 | O | HOH W | 136 | 39.114 | -8.880 | -31.761 | 1.00 | 36.25 | W | O |
| ATOM | 2393 | O | HOH W | 137 | 42.876 | -0.007 | -22.495 | 1.00 | 24.98 | W | O |
| ATOM | 2394 | O | HOH W | 138 | 49.933 | -19.445 | -5.167 | 1.00 | 59.38 | W | O |
| ATOM | 2395 | O | HOH W | 139 | 46.845 | -25.913 | -3.714 | 1.00 | 37.91 | W | O |
| ATOM | 2396 | O | HOH W | 140 | 37.567 | -7.310 | 9.635 | 1.00 | 63.58 | W | O |
| ATOM | 2397 | O | HOH W | 141 | 40.870 | -6.562 | 11.905 | 1.00 | 45.82 | W | O |
| ATOM | 2398 | O | HOH W | 142 | 36.504 | -7.384 | 13.264 | 1.00 | 28.16 | W | O |
| ATOM | 2399 | O | HOH W | 143 | 47.248 | -6.485 | 1.013 | 1.00 | 30.58 | W | O |
| ATOM | 2400 | O | HOH W | 144 | 32.519 | -8.817 | 0.294 | 1.00 | 51.45 | W | O |
| ATOM | 2401 | O | HOH W | 145 | 31.571 | -11.879 | 1.022 | 1.00 | 25.21 | W | O |
| ATOM | 2402 | O | HOH W | 146 | 35.970 | -8.151 | 6.444 | 1.00 | 59.45 | W | O |
| ATOM | 2403 | O | HOH W | 147 | 41.898 | 15.995 | -12.736 | 1.00 | 32.09 | W | O |
| ATOM | 2404 | O | HOH W | 148 | 35.441 | -7.707 | -9.579 | 1.00 | 30.79 | W | O |
| ATOM | 2405 | O | HOH W | 149 | 35.737 | -5.403 | -10.889 | 1.00 | 56.35 | W | O |
| ATOM | 2406 | O | HOH W | 150 | 42.915 | -25.030 | -3.373 | 1.00 | 44.44 | W | O |
| ATOM | 2407 | O | HOH W | 151 | 40.739 | -24.951 | -11.212 | 1.00 | 52.15 | W | O |
| ATOM | 2408 | O | HOH W | 152 | 39.009 | -14.046 | -0.469 | 1.00 | 60.16 | W | O |
| ATOM | 2409 | O | HOH W | 153 | 58.318 | 2.331 | -18.125 | 1.00 | 40.62 | W | O |
| ATOM | 2410 | O | HOH W | 154 | 62.951 | -3.795 | 3.196 | 1.00 | 53.85 | W | O |
| ATOM | 2411 | O | HOH W | 156 | 66.797 | 16.345 | -6.986 | 1.00 | 20.77 | W | O |
| ATOM | 2412 | O | HOH W | 157 | 69.039 | 17.583 | -5.852 | 1.00 | 39.81 | W | O |
| ATOM | 2413 | O | HOH W | 158 | 66.355 | 12.160 | -8.569 | 1.00 | 40.64 | W | O |
| ATOM | 2414 | O | HOH W | 159 | 68.587 | 20.221 | -1.296 | 1.00 | 21.53 | W | O |
| ATOM | 2415 | O | HOH W | 160 | 61.165 | 18.317 | 3.674 | 1.00 | 36.21 | W | O |
| ATOM | 2416 | O | HOH W | 161 | 63.186 | 8.316 | -7.118 | 1.00 | 23.10 | W | O |
| ATOM | 2417 | O | HOH W | 164 | 38.493 | 10.148 | 8.306 | 1.00 | 36.91 | W | O |
| ATOM | 2418 | O | HOH W | 165 | 46.454 | 4.172 | 11.275 | 1.00 | 32.92 | W | O |
| ATOM | 2419 | O | HOH W | 166 | 46.947 | -1.310 | 4.851 | 1.00 | 22.75 | W | O |

Figure 1-42

| | | Atom Type | Resid | # | X | Y | Z | OCC | B | | |
|---|---|---|---|---|---|---|---|---|---|---|---|
| ATOM | 2420 | O | HOH W | 167 | 51.061 | 1.305 | 11.527 | 1.00 | 41.61 | W | O |
| ATOM | 2421 | O | HOH W | 168 | 49.740 | 4.103 | 9.115 | 1.00 | 26.78 | W | O |
| ATOM | 2422 | O | HOH W | 169 | 55.567 | -4.337 | 3.093 | 1.00 | 34.98 | W | O |
| ATOM | 2423 | O | HOH W | 170 | 37.790 | -1.740 | 9.307 | 1.00 | 37.67 | W | O |
| ATOM | 2424 | O | HOH W | 171 | 38.507 | 0.267 | 13.668 | 1.00 | 24.73 | W | O |
| ATOM | 2425 | O | HOH W | 172 | 39.911 | 2.794 | 13.310 | 1.00 | 21.08 | W | O |
| ATOM | 2426 | O | HOH W | 173 | 32.473 | -1.964 | 9.805 | 1.00 | 34.56 | W | O |
| ATOM | 2427 | O | HOH W | 174 | 30.284 | 5.431 | 17.454 | 1.00 | 38.26 | W | O |
| ATOM | 2428 | O | HOH W | 176 | 34.865 | 0.299 | 24.255 | 1.00 | 32.81 | W | O |
| ATOM | 2429 | O | HOH W | 178 | 44.620 | 7.757 | 20.941 | 1.00 | 30.59 | W | O |
| ATOM | 2430 | O | HOH W | 179 | 37.821 | 13.999 | 9.357 | 1.00 | 34.55 | W | O |
| ATOM | 2431 | O | HOH W | 180 | 46.726 | 16.385 | 15.267 | 1.00 | 41.58 | W | O |
| ATOM | 2432 | O | HOH W | 182 | 67.665 | -11.506 | 19.232 | 1.00 | 43.24 | W | O |
| ATOM | 2433 | O | HOH W | 183 | 65.259 | -8.239 | 26.217 | 1.00 | 75.80 | W | O |
| ATOM | 2434 | O | HOH W | 184 | 55.843 | 4.528 | 27.058 | 1.00 | 50.97 | W | O |
| ATOM | 2435 | O | HOH W | 185 | 48.990 | 14.241 | 27.533 | 1.00 | 71.37 | W | O |
| ATOM | 2436 | O | HOH W | 186 | 53.744 | 23.018 | 10.934 | 1.00 | 39.84 | W | O |
| ATOM | 2437 | O | HOH W | 187 | 53.455 | 22.287 | 0.212 | 1.00 | 26.79 | W | O |
| ATOM | 2438 | O | HOH W | 188 | 53.493 | 20.219 | -1.724 | 1.00 | 47.56 | W | O |
| ATOM | 2439 | O | HOH W | 189 | 63.729 | 27.490 | 4.306 | 1.00 | 33.08 | W | O |
| ATOM | 2440 | O | HOH W | 190 | 68.134 | 18.184 | -8.756 | 1.00 | 45.73 | W | O |
| ATOM | 2441 | O | HOH W | 191 | 58.938 | 14.020 | -17.825 | 1.00 | 24.59 | W | O |
| ATOM | 2442 | O | HOH W | 192 | 44.658 | -3.975 | -2.152 | 1.00 | 36.58 | W | O |
| TER | 2443 | | HOH W | 192 | | | | | | W | |
| END | | | | | | | | | | | |

Figure 6-1

|  | Atom Type | Resid | # | X | Y | Z | OCC | B | |
|---|---|---|---|---|---|---|---|---|---|
| ATOM | 1 | CB | LEU A | 52 | 51.294 | -20.116 | -16.879 | 1.00 | 58.12 | C |
| ATOM | 2 | CG | LEU A | 52 | 51.680 | -21.490 | -17.463 | 1.00 | 64.41 | C |
| ATOM | 3 | CD1 | LEU A | 52 | 51.490 | -22.600 | -16.437 | 1.00 | 65.37 | C |
| ATOM | 4 | CD2 | LEU A | 52 | 50.933 | -21.825 | -18.761 | 1.00 | 66.43 | C |
| ATOM | 5 | C | LEU A | 52 | 50.629 | -18.050 | -18.184 | 1.00 | 58.33 | C |
| ATOM | 6 | O | LEU A | 52 | 50.794 | -16.959 | -18.746 | 1.00 | 56.39 | O |
| ATOM | 7 | N | LEU A | 52 | 52.623 | -18.069 | -16.692 | 1.00 | 58.54 | N |
| ATOM | 8 | CA | LEU A | 52 | 51.805 | -18.859 | -17.604 | 1.00 | 57.61 | C |
| ATOM | 9 | N | ILE A | 53 | 49.443 | -18.638 | -18.117 | 1.00 | 52.06 | N |
| ATOM | 10 | CA | ILE A | 53 | 48.259 | -17.982 | -18.604 | 1.00 | 51.64 | C |
| ATOM | 11 | CB | ILE A | 53 | 47.655 | -18.751 | -19.812 | 1.00 | 54.34 | C |
| ATOM | 12 | CG2 | ILE A | 53 | 46.185 | -18.478 | -19.912 | 1.00 | 54.95 | C |
| ATOM | 13 | CG1 | ILE A | 53 | 48.299 | -18.315 | -21.128 | 1.00 | 54.07 | C |
| ATOM | 14 | CD1 | ILE A | 53 | 47.502 | -17.248 | -21.861 | 1.00 | 56.23 | C |
| ATOM | 15 | C | ILE A | 53 | 47.317 | -18.023 | -17.409 | 1.00 | 53.73 | C |
| ATOM | 16 | O | ILE A | 53 | 47.369 | -18.972 | -16.627 | 1.00 | 54.10 | O |
| ATOM | 17 | N | THR A | 54 | 46.501 | -16.987 | -17.246 | 1.00 | 48.09 | N |
| ATOM | 18 | CA | THR A | 54 | 45.465 | -16.978 | -16.212 | 1.00 | 46.44 | C |
| ATOM | 19 | CB | THR A | 54 | 45.816 | -16.169 | -14.917 | 1.00 | 54.01 | C |
| ATOM | 20 | OG1 | THR A | 54 | 44.842 | -15.147 | -14.685 | 1.00 | 52.98 | O |
| ATOM | 21 | CG2 | THR A | 54 | 47.229 | -15.593 | -14.924 | 1.00 | 51.75 | C |
| ATOM | 22 | C | THR A | 54 | 44.075 | -16.681 | -16.815 | 1.00 | 48.66 | C |
| ATOM | 23 | O | THR A | 54 | 43.930 | -15.747 | -17.602 | 1.00 | 48.36 | O |
| ATOM | 24 | N | ASP A | 55 | 43.068 | -17.502 | -16.474 | 1.00 | 44.66 | N |
| ATOM | 25 | CA | ASP A | 55 | 41.696 | -17.371 | -17.018 | 1.00 | 44.40 | C |
| ATOM | 26 | CB | ASP A | 55 | 41.438 | -18.586 | -17.921 | 1.00 | 45.47 | C |
| ATOM | 27 | CG | ASP A | 55 | 42.720 | -19.212 | -18.408 | 1.00 | 58.31 | C |
| ATOM | 28 | OD1 | ASP A | 55 | 42.979 | -19.163 | -19.624 | 1.00 | 61.89 | O |
| ATOM | 29 | OD2 | ASP A | 55 | 43.508 | -19.715 | -17.580 | 1.00 | 71.42 | O |
| ATOM | 30 | C | ASP A | 55 | 40.631 | -17.315 | -15.908 | 1.00 | 48.61 | C |
| ATOM | 31 | O | ASP A | 55 | 40.843 | -17.906 | -14.852 | 1.00 | 49.43 | O |
| ATOM | 32 | N | PRO A | 56 | 39.456 | -16.665 | -16.155 | 1.00 | 47.77 | N |
| ATOM | 33 | CD | PRO A | 56 | 39.811 | -15.420 | -16.819 | 1.00 | 46.56 | C |
| ATOM | 34 | CA | PRO A | 56 | 38.249 | -16.472 | -15.303 | 1.00 | 50.58 | C |
| ATOM | 35 | CB | PRO A | 56 | 37.741 | -15.059 | -15.704 | 1.00 | 50.95 | C |
| ATOM | 36 | CG | PRO A | 56 | 38.507 | -14.682 | -16.864 | 1.00 | 51.64 | C |
| ATOM | 37 | C | PRO A | 56 | 37.091 | -17.521 | -15.321 | 1.00 | 60.24 | C |
| ATOM | 38 | O | PRO A | 56 | 37.243 | -18.669 | -14.873 | 1.00 | 60.17 | O |
| ATOM | 39 | N | ARG A | 57 | 35.899 | -17.066 | -15.730 | 1.00 | 59.28 | N |
| ATOM | 40 | CA | ARG A | 57 | 34.690 | -17.901 | -15.863 | 1.00 | 57.19 | C |
| ATOM | 41 | CB | ARG A | 57 | 33.796 | -17.741 | -14.645 | 1.00 | 62.86 | C |
| ATOM | 42 | CG | ARG A | 57 | 33.689 | -16.310 | -14.137 | 1.00 | 76.71 | C |
| ATOM | 43 | CD | ARG A | 57 | 32.234 | -15.849 | -14.015 | 1.00 | 84.39 | C |
| ATOM | 44 | NE | ARG A | 57 | 31.665 | -16.001 | -12.667 | 1.00 | 88.37 | N |
| ATOM | 45 | CZ | ARG A | 57 | 32.313 | -15.770 | -11.521 | 1.00 | 92.41 | C |
| ATOM | 46 | NH1 | ARG A | 57 | 33.580 | -15.378 | -11.536 | 1.00 | 87.16 | N |
| ATOM | 47 | NH2 | ARG A | 57 | 31.695 | -15.940 | -10.349 | 1.00 | 54.82 | N |
| ATOM | 48 | C | ARG A | 57 | 33.952 | -17.378 | -17.119 | 1.00 | 57.09 | C |
| ATOM | 49 | O | ARG A | 57 | 32.883 | -17.873 | -17.502 | 1.00 | 54.81 | O |
| ATOM | 50 | N | SER A | 58 | 34.574 | -16.374 | -17.746 | 1.00 | 51.61 | N |
| ATOM | 51 | CA | SER A | 58 | 34.154 | -15.751 | -19.014 | 1.00 | 49.50 | C |
| ATOM | 52 | CB | SER A | 58 | 34.448 | -14.258 | -18.958 | 1.00 | 51.39 | C |
| ATOM | 53 | OG | SER A | 58 | 35.860 | -14.051 | -18.925 | 1.00 | 45.56 | O |
| ATOM | 54 | C | SER A | 58 | 35.104 | -16.317 | -20.077 | 1.00 | 50.60 | C |
| ATOM | 55 | O | SER A | 58 | 34.897 | -16.130 | -21.284 | 1.00 | 49.24 | O |
| ATOM | 56 | N | GLY A | 59 | 36.188 | -16.933 | -19.590 | 1.00 | 46.08 | N |
| ATOM | 57 | CA | GLY A | 59 | 37.243 | -17.525 | -20.390 | 1.00 | 45.98 | C |
| ATOM | 58 | C | GLY A | 59 | 38.338 | -16.543 | -20.841 | 1.00 | 50.81 | C |
| ATOM | 59 | O | GLY A | 59 | 39.295 | -16.956 | -21.495 | 1.00 | 49.73 | O |

Figure 6-2

|  |  | Atom Type | Resid | # | X | Y | Z | OCC | B |  |
|---|---|---|---|---|---|---|---|---|---|---|
| ATOM | 60 | N | ARG A | 60 | 38.213 | -15.254 | -20.519 | 1.00 | 48.21 | N |
| ATOM | 61 | CA | ARG A | 60 | 39.242 | -14.273 | -20.923 | 1.00 | 46.66 | C |
| ATOM | 62 | CB | ARG A | 60 | 38.907 | -12.839 | -20.485 | 1.00 | 49.06 | C |
| ATOM | 63 | CG | ARG A | 60 | 39.806 | -11.767 | -21.148 | 1.00 | 62.31 | C |
| ATOM | 64 | CD | ARG A | 60 | 39.009 | -10.562 | -21.648 | 1.00 | 77.81 | C |
| ATOM | 65 | NE | ARG A | 60 | 38.783 | -9.590 | -20.581 | 1.00 | 91.18 | N |
| ATOM | 66 | CZ | ARG A | 60 | 37.799 | -9.664 | -19.683 | 1.00 | 115.86 | C |
| ATOM | 67 | NH1 | ARG A | 60 | 36.917 | -10.657 | -19.729 | 1.00 | 104.62 | N |
| ATOM | 68 | NH2 | ARG A | 60 | 37.692 | -8.737 | -18.735 | 1.00 | 106.80 | N |
| ATOM | 69 | C | ARG A | 60 | 40.607 | -14.681 | -20.395 | 1.00 | 46.47 | C |
| ATOM | 70 | O | ARG A | 60 | 40.753 | -15.072 | -19.261 | 1.00 | 42.02 | O |
| ATOM | 71 | N | THR A | 61 | 41.614 | -14.628 | -21.252 | 1.00 | 43.39 | N |
| ATOM | 72 | CA | THR A | 61 | 42.942 | -15.048 | -20.854 | 1.00 | 42.02 | C |
| ATOM | 73 | CB | THR A | 61 | 43.443 | -16.173 | -21.777 | 1.00 | 53.89 | C |
| ATOM | 74 | OG1 | THR A | 61 | 44.737 | -16.626 | -21.355 | 1.00 | 55.30 | O |
| ATOM | 75 | CG2 | THR A | 61 | 43.523 | -15.655 | -23.199 | 1.00 | 44.78 | C |
| ATOM | 76 | C | THR A | 61 | 43.919 | -13.852 | -20.773 | 1.00 | 42.72 | C |
| ATOM | 77 | O | THR A | 61 | 43.767 | -12.831 | -21.489 | 1.00 | 40.35 | O |
| ATOM | 78 | N | TYR A | 62 | 44.846 | -13.986 | -19.822 | 1.00 | 38.31 | N |
| ATOM | 79 | CA | TYR A | 62 | 45.906 | -13.020 | -19.507 | 1.00 | 38.15 | C |
| ATOM | 80 | CB | TYR A | 62 | 45.760 | -12.459 | -18.058 | 1.00 | 37.28 | C |
| ATOM | 81 | CG | TYR A | 62 | 44.443 | -11.767 | -17.787 | 1.00 | 37.32 | C |
| ATOM | 82 | CD1 | TYR A | 62 | 44.334 | -10.406 | -17.928 | 1.00 | 38.14 | C |
| ATOM | 83 | CE1 | TYR A | 62 | 43.130 | -9.783 | -17.783 | 1.00 | 41.44 | C |
| ATOM | 84 | CD2 | TYR A | 62 | 43.267 | -12.507 | -17.570 | 1.00 | 37.14 | C |
| ATOM | 85 | CE2 | TYR A | 62 | 42.075 | -11.884 | -17.347 | 1.00 | 36.93 | C |
| ATOM | 86 | CZ | TYR A | 62 | 42.000 | -10.525 | -17.498 | 1.00 | 42.08 | C |
| ATOM | 87 | OH | TYR A | 62 | 40.808 | -9.876 | -17.362 | 1.00 | 37.92 | O |
| ATOM | 88 | C | TYR A | 62 | 47.215 | -13.752 | -19.510 | 1.00 | 42.48 | C |
| ATOM | 89 | O | TYR A | 62 | 47.355 | -14.788 | -18.840 | 1.00 | 41.27 | O |
| ATOM | 90 | N | LEU A | 63 | 48.208 | -13.146 | -20.147 | 1.00 | 39.67 | N |
| ATOM | 91 | CA | LEU A | 63 | 49.552 | -13.685 | -20.087 | 1.00 | 41.64 | C |
| ATOM | 92 | CB | LEU A | 63 | 50.359 | -13.269 | -21.329 | 1.00 | 42.93 | C |
| ATOM | 93 | CG | LEU A | 63 | 51.865 | -13.240 | -21.090 | 1.00 | 49.25 | C |
| ATOM | 94 | CD1 | LEU A | 63 | 52.358 | -14.619 | -20.651 | 1.00 | 50.36 | C |
| ATOM | 95 | CD2 | LEU A | 63 | 52.617 | -12.747 | -22.345 | 1.00 | 51.40 | C |
| ATOM | 96 | C | LEU A | 63 | 50.227 | -13.136 | -18.832 | 1.00 | 43.78 | C |
| ATOM | 97 | O | LEU A | 63 | 50.286 | -11.929 | -18.612 | 1.00 | 42.63 | O |
| ATOM | 98 | N | LYS A | 64 | 50.760 | -14.017 | -18.014 | 1.00 | 42.00 | N |
| ATOM | 99 | CA | LYS A | 64 | 51.402 | -13.556 | -16.815 | 1.00 | 44.05 | C |
| ATOM | 100 | CB | LYS A | 64 | 50.900 | -14.318 | -15.570 | 1.00 | 46.81 | C |
| ATOM | 101 | CG | LYS A | 64 | 51.966 | -15.100 | -14.822 | 1.00 | 55.19 | C |
| ATOM | 102 | CD | LYS A | 64 | 51.401 | -15.827 | -13.611 | 1.00 | 69.73 | C |
| ATOM | 103 | CE | LYS A | 64 | 51.659 | -17.339 | -13.697 | 1.00 | 79.73 | C |
| ATOM | 104 | NZ | LYS A | 64 | 52.893 | -17.767 | -12.970 | 1.00 | 86.79 | N |
| ATOM | 105 | C | LYS A | 64 | 52.900 | -13.629 | -16.907 | 1.00 | 54.25 | C |
| ATOM | 106 | O | LYS A | 64 | 53.472 | -14.027 | -17.925 | 1.00 | 53.60 | O |
| ATOM | 107 | N | GLY A | 65 | 53.540 | -13.196 | -15.834 | 1.00 | 54.94 | N |
| ATOM | 108 | CA | GLY A | 65 | 54.966 | -13.307 | -15.746 | 1.00 | 55.47 | C |
| ATOM | 109 | C | GLY A | 65 | 55.609 | -11.976 | -15.806 | 1.00 | 59.67 | C |
| ATOM | 110 | O | GLY A | 65 | 55.322 | -11.186 | -16.702 | 1.00 | 61.58 | O |
| ATOM | 111 | N | ARG A | 66 | 56.545 | -11.820 | -14.876 | 1.00 | 54.21 | N |
| ATOM | 112 | CA | ARG A | 66 | 57.351 | -10.645 | -14.629 | 1.00 | 51.62 | C |
| ATOM | 113 | CB | ARG A | 66 | 56.953 | -9.481 | -15.524 | 1.00 | 53.74 | C |
| ATOM | 114 | CG | ARG A | 66 | 57.583 | -9.527 | -16.898 | 1.00 | 71.81 | C |
| ATOM | 115 | CD | ARG A | 66 | 56.618 | -9.093 | -18.001 | 1.00 | 88.03 | C |
| ATOM | 116 | NE | ARG A | 66 | 57.336 | -8.701 | -19.214 | 1.00 | 107.36 | N |
| ATOM | 117 | CZ | ARG A | 66 | 56.766 | -8.153 | -20.286 | 1.00 | 125.30 | C |
| ATOM | 118 | NH1 | ARG A | 66 | 55.455 | -7.935 | -20.314 | 1.00 | 109.64 | N |

Figure 6-3

| | | Atom Type | Resid | # | X | Y | Z | OCC | B | |
|---|---|---|---|---|---|---|---|---|---|---|
| ATOM | 119 | NH2 | ARG A | 66 | 57.512 | -7.822 | -21.336 | 1.00 | 113.08 | N |
| ATOM | 120 | C | ARG A | 66 | 56.932 | -10.388 | -13.204 | 1.00 | 51.03 | C |
| ATOM | 121 | O | ARG A | 66 | 55.879 | -9.801 | -12.968 | 1.00 | 47.71 | O |
| ATOM | 122 | N | LEU A | 67 | 57.640 | -11.014 | -12.268 | 1.00 | 47.20 | N |
| ATOM | 123 | CA | LEU A | 67 | 57.319 | -10.871 | -10.864 | 1.00 | 46.03 | C |
| ATOM | 124 | CB | LEU A | 67 | 58.152 | -11.807 | -10.007 | 1.00 | 45.76 | C |
| ATOM | 125 | CG | LEU A | 67 | 57.766 | -11.715 | -8.534 | 1.00 | 51.07 | C |
| ATOM | 126 | CD1 | LEU A | 67 | 56.380 | -12.278 | -8.314 | 1.00 | 49.99 | C |
| ATOM | 127 | CD2 | LEU A | 67 | 58.794 | -12.418 | -7.645 | 1.00 | 54.10 | C |
| ATOM | 128 | C | LEU A | 67 | 57.598 | -9.437 | -10.493 | 1.00 | 51.30 | C |
| ATOM | 129 | O | LEU A | 67 | 58.693 | -8.939 | -10.716 | 1.00 | 52.50 | O |
| ATOM | 130 | N | LEU A | 68 | 56.575 | -8.758 | -9.998 | 1.00 | 47.14 | N |
| ATOM | 131 | CA | LEU A | 68 | 56.666 | -7.358 | -9.630 | 1.00 | 45.59 | C |
| ATOM | 132 | CB | LEU A | 68 | 55.354 | -6.632 | -9.965 | 1.00 | 44.69 | C |
| ATOM | 133 | CG | LEU A | 68 | 54.900 | -6.483 | -11.420 | 1.00 | 47.86 | C |
| ATOM | 134 | CD1 | LEU A | 68 | 53.524 | -5.796 | -11.434 | 1.00 | 47.62 | C |
| ATOM | 135 | CD2 | LEU A | 68 | 55.928 | -5.684 | -12.274 | 1.00 | 47.41 | C |
| ATOM | 136 | C | LEU A | 68 | 56.905 | -7.227 | -8.147 | 1.00 | 49.39 | C |
| ATOM | 137 | O | LEU A | 68 | 57.405 | -6.208 | -7.684 | 1.00 | 50.19 | O |
| ATOM | 138 | N | GLY A | 69 | 56.459 | -8.214 | -7.389 | 1.00 | 47.20 | N |
| ATOM | 139 | CA | GLY A | 69 | 56.580 | -8.171 | -5.943 | 1.00 | 48.03 | C |
| ATOM | 140 | C | GLY A | 69 | 56.125 | -9.409 | -5.191 | 1.00 | 53.42 | C |
| ATOM | 141 | O | GLY A | 69 | 55.429 | -10.262 | -5.725 | 1.00 | 53.45 | O |
| ATOM | 142 | N | LYS A | 70 | 56.490 | -9.457 | -3.913 | 1.00 | 52.39 | N |
| ATOM | 143 | CA | LYS A | 70 | 56.207 | -10.562 | -2.995 | 1.00 | 52.74 | C |
| ATOM | 144 | CB | LYS A | 70 | 57.528 | -11.302 | -2.713 | 1.00 | 55.35 | C |
| ATOM | 145 | CG | LYS A | 70 | 57.413 | -12.725 | -2.208 | 1.00 | 62.90 | C |
| ATOM | 146 | CD | LYS A | 70 | 58.266 | -13.652 | -3.059 | 1.00 | 72.59 | C |
| ATOM | 147 | CE | LYS A | 70 | 59.629 | -13.919 | -2.430 | 1.00 | 84.41 | C |
| ATOM | 148 | NZ | LYS A | 70 | 60.370 | -15.023 | -3.123 | 1.00 | 89.59 | N |
| ATOM | 149 | C | LYS A | 70 | 55.698 | -9.921 | -1.699 | 1.00 | 57.51 | C |
| ATOM | 150 | O | LYS A | 70 | 56.120 | -8.823 | -1.357 | 1.00 | 58.29 | O |
| ATOM | 151 | N | GLY A | 71 | 54.815 | -10.583 | -0.964 | 1.00 | 54.65 | N |
| ATOM | 152 | CA | GLY A | 71 | 54.312 | -9.978 | 0.258 | 1.00 | 55.84 | C |
| ATOM | 153 | C | GLY A | 71 | 52.976 | -10.488 | 0.772 | 1.00 | 63.55 | C |
| ATOM | 154 | O | GLY A | 71 | 51.998 | -10.565 | 0.031 | 1.00 | 63.05 | O |
| ATOM | 155 | N | GLY A | 72 | 52.927 | -10.800 | 2.062 | 1.00 | 63.33 | N |
| ATOM | 156 | CA | GLY A | 72 | 51.737 | -11.339 | 2.685 | 1.00 | 64.33 | C |
| ATOM | 157 | C | GLY A | 72 | 51.552 | -12.746 | 2.159 | 1.00 | 71.47 | C |
| ATOM | 158 | O | GLY A | 72 | 52.499 | -13.540 | 2.117 | 1.00 | 72.97 | O |
| ATOM | 159 | N | PHE A | 73 | 50.344 | -13.044 | 1.700 | 1.00 | 68.24 | N |
| ATOM | 160 | CA | PHE A | 73 | 50.063 | -14.360 | 1.146 | 1.00 | 67.70 | C |
| ATOM | 161 | CB | PHE A | 73 | 48.701 | -14.858 | 1.623 | 1.00 | 70.60 | C |
| ATOM | 162 | CG | PHE A | 73 | 48.730 | -15.478 | 2.991 | 1.00 | 73.52 | C |
| ATOM | 163 | CD1 | PHE A | 73 | 47.668 | -15.313 | 3.864 | 1.00 | 77.27 | C |
| ATOM | 164 | CD2 | PHE A | 73 | 49.822 | -16.224 | 3.403 | 1.00 | 76.71 | C |
| ATOM | 165 | CE1 | PHE A | 73 | 47.686 | -15.892 | 5.109 | 1.00 | 78.50 | C |
| ATOM | 166 | CE2 | PHE A | 73 | 49.847 | -16.805 | 4.654 | 1.00 | 79.89 | C |
| ATOM | 167 | CZ | PHE A | 73 | 48.776 | -16.643 | 5.504 | 1.00 | 77.89 | C |
| ATOM | 168 | C | PHE A | 73 | 50.109 | -14.342 | -0.372 | 1.00 | 66.01 | C |
| ATOM | 169 | O | PHE A | 73 | 49.793 | -15.341 | -1.019 | 1.00 | 66.84 | O |
| ATOM | 170 | N | ALA A | 74 | 50.537 | -13.222 | -0.944 | 1.00 | 55.78 | N |
| ATOM | 171 | CA | ALA A | 74 | 50.546 | -13.099 | -2.392 | 1.00 | 53.87 | C |
| ATOM | 172 | CB | ALA A | 74 | 49.680 | -11.919 | -2.796 | 1.00 | 54.29 | C |
| ATOM | 173 | C | ALA A | 74 | 51.885 | -13.024 | -3.115 | 1.00 | 55.44 | C |
| ATOM | 174 | O | ALA A | 74 | 52.939 | -12.790 | -2.518 | 1.00 | 54.98 | O |
| ATOM | 175 | N | ARG A | 75 | 51.798 | -13.152 | -4.431 | 1.00 | 50.58 | N |
| ATOM | 176 | CA | ARG A | 75 | 52.918 | -12.962 | -5.343 | 1.00 | 51.17 | C |
| ATOM | 177 | CB | ARG A | 75 | 53.416 | -14.288 | -5.924 | 1.00 | 53.50 | C |

Figure 6-4

| | | Atom Type | Resid | # | X | Y | Z | OCC | B | |
|---|---|---|---|---|---|---|---|---|---|---|
| ATOM | 178 | CG | ARG A | 75 | 54.559 | -14.909 | -5.126 | 1.00 | 63.67 | C |
| ATOM | 179 | CD | ARG A | 75 | 55.104 | -16.164 | -5.793 | 1.00 | 75.26 | C |
| ATOM | 180 | NE | ARG A | 75 | 56.091 | -15.859 | -6.828 | 1.00 | 91.07 | N |
| ATOM | 181 | CZ | ARG A | 75 | 57.314 | -15.382 | -6.599 | 1.00 | 102.14 | C |
| ATOM | 182 | NH1 | ARG A | 75 | 57.725 | -15.149 | -5.358 | 1.00 | 87.90 | N |
| ATOM | 183 | NH2 | ARG A | 75 | 58.126 | -15.129 | -7.619 | 1.00 | 82.01 | N |
| ATOM | 184 | C | ARG A | 75 | 52.275 | -12.129 | -6.431 | 1.00 | 54.30 | C |
| ATOM | 185 | O | ARG A | 75 | 51.199 | -12.478 | -6.915 | 1.00 | 55.43 | O |
| ATOM | 186 | N | CYS A | 76 | 52.858 | -10.979 | -6.732 | 1.00 | 46.44 | N |
| ATOM | 187 | CA | CYS A | 76 | 52.280 | -10.095 | -7.719 | 1.00 | 46.11 | C |
| ATOM | 188 | CB | CYS A | 76 | 52.141 | -8.694 | -7.131 | 1.00 | 47.29 | C |
| ATOM | 189 | SG | CYS A | 76 | 51.583 | -7.402 | -8.241 | 1.00 | 52.23 | S |
| ATOM | 190 | C | CYS A | 76 | 53.080 | -10.097 | -9.026 | 1.00 | 48.73 | C |
| ATOM | 191 | O | CYS A | 76 | 54.307 | -9.983 | -9.022 | 1.00 | 49.95 | O |
| ATOM | 192 | N | TYR A | 77 | 52.381 | -10.238 | -10.144 | 1.00 | 42.09 | N |
| ATOM | 193 | CA | TYR A | 77 | 53.018 | -10.267 | -11.456 | 1.00 | 41.16 | C |
| ATOM | 194 | CB | TYR A | 77 | 52.803 | -11.635 | -12.126 | 1.00 | 42.25 | C |
| ATOM | 195 | CG | TYR A | 77 | 53.242 | -12.816 | -11.306 | 1.00 | 43.60 | C |
| ATOM | 196 | CD1 | TYR A | 77 | 52.484 | -13.258 | -10.224 | 1.00 | 46.08 | C |
| ATOM | 197 | CE1 | TYR A | 77 | 52.870 | -14.337 | -9.487 | 1.00 | 46.75 | C |
| ATOM | 198 | CD2 | TYR A | 77 | 54.378 | -13.536 | -11.648 | 1.00 | 43.86 | C |
| ATOM | 199 | CE2 | TYR A | 77 | 54.761 | -14.630 | -10.928 | 1.00 | 44.11 | C |
| ATOM | 200 | CZ | TYR A | 77 | 54.026 | -15.014 | -9.830 | 1.00 | 53.50 | C |
| ATOM | 201 | OH | TYR A | 77 | 54.405 | -16.113 | -9.099 | 1.00 | 51.40 | O |
| ATOM | 202 | C | TYR A | 77 | 52.459 | -9.218 | -12.405 | 1.00 | 41.25 | C |
| ATOM | 203 | O | TYR A | 77 | 51.309 | -8.825 | -12.294 | 1.00 | 38.68 | O |
| ATOM | 204 | N | GLU A | 78 | 53.262 | -8.791 | -13.373 | 1.00 | 37.92 | N |
| ATOM | 205 | CA | GLU A | 78 | 52.723 | -7.971 | -14.431 | 1.00 | 39.43 | C |
| ATOM | 206 | CB | GLU A | 78 | 53.824 | -7.544 | -15.420 | 1.00 | 41.69 | C |
| ATOM | 207 | CG | GLU A | 78 | 53.767 | -6.090 | -15.823 | 1.00 | 54.26 | C |
| ATOM | 208 | CD | GLU A | 78 | 54.862 | -5.708 | -16.812 | 1.00 | 87.08 | C |
| ATOM | 209 | OE1 | GLU A | 78 | 55.987 | -5.339 | -16.381 | 1.00 | 93.42 | O |
| ATOM | 210 | OE2 | GLU A | 78 | 54.572 | -5.737 | -18.024 | 1.00 | 66.90 | O |
| ATOM | 211 | C | GLU A | 78 | 51.795 | -8.973 | -15.132 | 1.00 | 44.01 | C |
| ATOM | 212 | O | GLU A | 78 | 52.042 | -10.176 | -15.075 | 1.00 | 42.58 | O |
| ATOM | 213 | N | ALA A | 79 | 50.728 | -8.491 | -15.768 | 1.00 | 44.20 | N |
| ATOM | 214 | CA | ALA A | 79 | 49.779 | -9.384 | -16.443 | 1.00 | 45.20 | C |
| ATOM | 215 | CB | ALA A | 79 | 48.665 | -9.826 | -15.464 | 1.00 | 45.88 | C |
| ATOM | 216 | C | ALA A | 79 | 49.179 | -8.685 | -17.645 | 1.00 | 48.99 | C |
| ATOM | 217 | O | ALA A | 79 | 48.817 | -7.520 | -17.570 | 1.00 | 49.26 | O |
| ATOM | 218 | N | THR A | 80 | 49.072 | -9.395 | -18.760 | 1.00 | 45.48 | N |
| ATOM | 219 | CA | THR A | 80 | 48.497 | -8.806 | -19.977 | 1.00 | 44.18 | C |
| ATOM | 220 | CB | THR A | 80 | 49.579 | -8.568 | -21.073 | 1.00 | 49.45 | C |
| ATOM | 221 | OG1 | THR A | 80 | 50.863 | -8.989 | -20.586 | 1.00 | 56.68 | O |
| ATOM | 222 | CG2 | THR A | 80 | 49.650 | -7.097 | -21.422 | 1.00 | 48.52 | C |
| ATOM | 223 | C | THR A | 80 | 47.284 | -9.542 | -20.567 | 1.00 | 47.76 | C |
| ATOM | 224 | O | THR A | 80 | 47.328 | -10.748 | -20.834 | 1.00 | 49.34 | O |
| ATOM | 225 | N | ASP A | 81 | 46.245 | -8.775 | -20.867 | 1.00 | 43.41 | N |
| ATOM | 226 | CA | ASP A | 81 | 45.050 | -9.282 | -21.520 | 1.00 | 42.99 | C |
| ATOM | 227 | CB | ASP A | 81 | 44.000 | -8.195 | -21.581 | 1.00 | 44.32 | C |
| ATOM | 228 | CG | ASP A | 81 | 42.632 | -8.739 | -21.907 | 1.00 | 60.65 | C |
| ATOM | 229 | OD1 | ASP A | 81 | 41.731 | -8.603 | -21.052 | 1.00 | 61.83 | O |
| ATOM | 230 | OD2 | ASP A | 81 | 42.468 | -9.310 | -23.006 | 1.00 | 68.58 | O |
| ATOM | 231 | C | ASP A | 81 | 45.440 | -9.651 | -22.947 | 1.00 | 49.23 | C |
| ATOM | 232 | O | ASP A | 81 | 45.945 | -8.811 | -23.709 | 1.00 | 48.28 | O |
| ATOM | 233 | N | THR A | 82 | 45.175 | -10.893 | -23.322 | 1.00 | 46.54 | N |
| ATOM | 234 | CA | THR A | 82 | 45.549 | -11.346 | -24.651 | 1.00 | 47.01 | C |
| ATOM | 235 | CB | THR A | 82 | 45.701 | -12.839 | -24.690 | 1.00 | 48.39 | C |
| ATOM | 236 | OG1 | THR A | 82 | 44.430 | -13.407 | -24.417 | 1.00 | 41.44 | O |

Figure 6-5

| | Atom Type | Resid | # | X | Y | Z | OCC | B | |
|---|---|---|---|---|---|---|---|---|---|
| ATOM | 237 | CG2 | THR A | 82 | 46.690 | -13.285 | -23.605 | 1.00 | 44.36 | C |
| ATOM | 238 | C | THR A | 82 | 44.741 | -10.772 | -25.816 | 1.00 | 54.50 | C |
| ATOM | 239 | O | THR A | 82 | 45.291 | -10.610 | -26.900 | 1.00 | 57.39 | O |
| ATOM | 240 | N | GLU A | 83 | 43.481 | -10.402 | -25.586 | 1.00 | 50.06 | N |
| ATOM | 241 | CA | GLU A | 83 | 42.666 | -9.798 | -26.645 | 1.00 | 51.14 | C |
| ATOM | 242 | CB | GLU A | 83 | 41.165 | -9.920 | -26.325 | 1.00 | 53.09 | C |
| ATOM | 243 | CG | GLU A | 83 | 40.295 | -10.582 | -27.429 | 1.00 | 67.90 | C |
| ATOM | 244 | CD | GLU A | 83 | 40.361 | -9.876 | -28.790 | 1.00 | 97.46 | C |
| ATOM | 245 | OE1 | GLU A | 83 | 39.736 | -8.798 | -28.939 | 1.00 | 92.52 | O |
| ATOM | 246 | OE2 | GLU A | 83 | 40.978 | -10.438 | -29.732 | 1.00 | 92.41 | O |
| ATOM | 247 | C | GLU A | 83 | 42.980 | -8.318 | -26.822 | 1.00 | 55.20 | C |
| ATOM | 248 | O | GLU A | 83 | 43.320 | -7.853 | -27.930 | 1.00 | 54.68 | O |
| ATOM | 249 | N | THR A | 84 | 42.835 | -7.590 | -25.710 | 1.00 | 50.64 | N |
| ATOM | 250 | CA | THR A | 84 | 42.990 | -6.146 | -25.659 | 1.00 | 48.82 | C |
| ATOM | 251 | CB | THR A | 84 | 42.190 | -5.557 | -24.476 | 1.00 | 51.70 | C |
| ATOM | 252 | OG1 | THR A | 84 | 42.635 | -6.163 | -23.264 | 1.00 | 53.52 | O |
| ATOM | 253 | CG2 | THR A | 84 | 40.750 | -5.839 | -24.641 | 1.00 | 49.34 | C |
| ATOM | 254 | C | THR A | 84 | 44.398 | -5.587 | -25.634 | 1.00 | 49.65 | C |
| ATOM | 255 | O | THR A | 84 | 44.616 | -4.489 | -26.146 | 1.00 | 48.77 | O |
| ATOM | 256 | N | GLY A | 85 | 45.309 | -6.282 | -24.959 | 1.00 | 43.88 | N |
| ATOM | 257 | CA | GLY A | 85 | 46.685 | -5.836 | -24.724 | 1.00 | 43.74 | C |
| ATOM | 258 | C | GLY A | 85 | 46.829 | -5.111 | -23.383 | 1.00 | 44.63 | C |
| ATOM | 259 | O | GLY A | 85 | 47.930 | -4.835 | -22.907 | 1.00 | 42.43 | O |
| ATOM | 260 | N | SER A | 86 | 45.685 | -4.806 | -22.777 | 1.00 | 41.72 | N |
| ATOM | 261 | CA | SER A | 86 | 45.620 | -4.131 | -21.474 | 1.00 | 41.02 | C |
| ATOM | 262 | CB | SER A | 86 | 44.164 | -4.023 | -21.006 | 1.00 | 45.65 | C |
| ATOM | 263 | OG | SER A | 86 | 43.448 | -3.077 | -21.791 | 1.00 | 56.91 | O |
| ATOM | 264 | C | SER A | 86 | 46.492 | -4.771 | -20.386 | 1.00 | 41.06 | C |
| ATOM | 265 | O | SER A | 86 | 46.441 | -5.994 | -20.147 | 1.00 | 38.14 | O |
| ATOM | 266 | N | ALA A | 87 | 47.324 | -3.934 | -19.761 | 1.00 | 37.16 | N |
| ATOM | 267 | CA | ALA A | 87 | 48.259 | -4.343 | -18.704 | 1.00 | 37.87 | C |
| ATOM | 268 | CB | ALA A | 87 | 49.623 | -3.634 | -18.902 | 1.00 | 38.86 | C |
| ATOM | 269 | C | ALA A | 87 | 47.751 | -4.054 | -17.287 | 1.00 | 41.92 | C |
| ATOM | 270 | O | ALA A | 87 | 47.042 | -3.070 | -17.049 | 1.00 | 43.85 | O |
| ATOM | 271 | N | TYR A | 88 | 48.155 | -4.897 | -16.347 | 1.00 | 37.84 | N |
| ATOM | 272 | CA | TYR A | 88 | 47.789 | -4.742 | -14.946 | 1.00 | 37.40 | C |
| ATOM | 273 | CB | TYR A | 88 | 46.572 | -5.613 | -14.588 | 1.00 | 39.45 | C |
| ATOM | 274 | CG | TYR A | 88 | 45.327 | -5.333 | -15.344 | 1.00 | 43.56 | C |
| ATOM | 275 | CD1 | TYR A | 88 | 45.074 | -5.990 | -16.535 | 1.00 | 45.93 | C |
| ATOM | 276 | CE1 | TYR A | 88 | 43.930 | -5.762 | -17.231 | 1.00 | 48.06 | C |
| ATOM | 277 | CD2 | TYR A | 88 | 44.350 | -4.494 | -14.819 | 1.00 | 45.21 | C |
| ATOM | 278 | CE2 | TYR A | 88 | 43.178 | -4.269 | -15.513 | 1.00 | 47.49 | C |
| ATOM | 279 | CZ | TYR A | 88 | 42.982 | -4.918 | -16.724 | 1.00 | 54.41 | C |
| ATOM | 280 | OH | TYR A | 88 | 41.844 | -4.727 | -17.456 | 1.00 | 60.65 | O |
| ATOM | 281 | C | TYR A | 88 | 48.904 | -5.375 | -14.162 | 1.00 | 40.72 | C |
| ATOM | 282 | O | TYR A | 88 | 49.788 | -6.007 | -14.713 | 1.00 | 38.81 | O |
| ATOM | 283 | N | ALA A | 89 | 48.766 | -5.284 | -12.849 | 1.00 | 37.57 | N |
| ATOM | 284 | CA | ALA A | 89 | 49.616 | -5.963 | -11.904 | 1.00 | 37.30 | C |
| ATOM | 285 | CB | ALA A | 89 | 50.121 | -4.992 | -10.837 | 1.00 | 37.22 | C |
| ATOM | 286 | C | ALA A | 89 | 48.575 | -6.886 | -11.302 | 1.00 | 42.76 | C |
| ATOM | 287 | O | ALA A | 89 | 47.457 | -6.426 | -10.978 | 1.00 | 42.65 | O |
| ATOM | 288 | N | VAL A | 90 | 48.883 | -8.179 | -11.216 | 1.00 | 37.88 | N |
| ATOM | 289 | CA | VAL A | 90 | 47.939 | -9.113 | -10.627 | 1.00 | 36.45 | C |
| ATOM | 290 | CB | VAL A | 90 | 47.327 | -10.121 | -11.673 | 1.00 | 40.44 | C |
| ATOM | 291 | CG1 | VAL A | 90 | 48.426 | -11.010 | -12.287 | 1.00 | 41.68 | C |
| ATOM | 292 | CG2 | VAL A | 90 | 46.212 | -10.993 | -11.047 | 1.00 | 38.97 | C |
| ATOM | 293 | C | VAL A | 90 | 48.508 | -9.763 | -9.372 | 1.00 | 38.73 | C |
| ATOM | 294 | O | VAL A | 90 | 49.579 | -10.332 | -9.377 | 1.00 | 40.60 | O |
| ATOM | 295 | N | LYS A | 91 | 47.794 | -9.609 | -8.276 | 1.00 | 35.27 | N |

Figure 6-6

| | Atom Type | Resid | # | X | Y | Z | OCC | B | |
|---|---|---|---|---|---|---|---|---|---|
| ATOM | 296 | CA | LYS A | 91 | 48.126 | -10.247 | -7.028 | 1.00 | 34.48 | C |
| ATOM | 297 | CB | LYS A | 91 | 47.421 | -9.501 | -5.903 | 1.00 | 36.93 | C |
| ATOM | 298 | CG | LYS A | 91 | 48.163 | -8.374 | -5.266 | 1.00 | 56.09 | C |
| ATOM | 299 | CD | LYS A | 91 | 47.348 | -7.873 | -4.064 | 1.00 | 59.34 | C |
| ATOM | 300 | CE | LYS A | 91 | 48.171 | -6.989 | -3.151 | 1.00 | 67.87 | C |
| ATOM | 301 | NZ | LYS A | 91 | 47.535 | -6.824 | -1.810 | 1.00 | 82.51 | N |
| ATOM | 302 | C | LYS A | 91 | 47.535 | -11.672 | -7.099 | 1.00 | 41.10 | C |
| ATOM | 303 | O | LYS A | 91 | 46.352 | -11.856 | -7.458 | 1.00 | 41.34 | O |
| ATOM | 304 | N | VAL A | 92 | 48.323 | -12.668 | -6.698 | 1.00 | 36.32 | N |
| ATOM | 305 | CA | VAL A | 92 | 47.871 | -14.057 | -6.716 | 1.00 | 36.48 | C |
| ATOM | 306 | CB | VAL A | 92 | 48.699 | -14.890 | -7.745 | 1.00 | 40.17 | C |
| ATOM | 307 | CG1 | VAL A | 92 | 48.155 | -16.335 | -7.885 | 1.00 | 41.01 | C |
| ATOM | 308 | CG2 | VAL A | 92 | 48.813 | -14.170 | -9.075 | 1.00 | 38.83 | C |
| ATOM | 309 | C | VAL A | 92 | 47.973 | -14.652 | -5.308 | 1.00 | 40.88 | C |
| ATOM | 310 | O | VAL A | 92 | 49.054 | -14.735 | -4.731 | 1.00 | 42.26 | O |
| ATOM | 311 | N | ILE A | 93 | 46.837 | -15.022 | -4.731 | 1.00 | 33.34 | N |
| ATOM | 312 | CA | ILE A | 93 | 46.823 | -15.576 | -3.394 | 1.00 | 33.28 | C |
| ATOM | 313 | CB | ILE A | 93 | 46.011 | -14.658 | -2.466 | 1.00 | 37.17 | C |
| ATOM | 314 | CG2 | ILE A | 93 | 46.043 | -15.167 | -1.026 | 1.00 | 35.81 | C |
| ATOM | 315 | CG1 | ILE A | 93 | 46.420 | -13.184 | -2.659 | 1.00 | 37.36 | C |
| ATOM | 316 | CD1 | ILE A | 93 | 45.325 | -12.168 | -2.294 | 1.00 | 43.31 | C |
| ATOM | 317 | C | ILE A | 93 | 46.218 | -16.978 | -3.430 | 1.00 | 42.07 | C |
| ATOM | 318 | O | ILE A | 93 | 45.133 | -17.174 | -4.000 | 1.00 | 40.66 | O |
| ATOM | 319 | N | PRO A | 94 | 46.922 | -17.977 | -2.842 | 1.00 | 43.42 | N |
| ATOM | 320 | CD | PRO A | 94 | 48.369 | -17.851 | -2.540 | 1.00 | 43.84 | C |
| ATOM | 321 | CA | PRO A | 94 | 46.473 | -19.375 | -2.731 | 1.00 | 42.66 | C |
| ATOM | 322 | CB | PRO A | 94 | 47.661 | -20.060 | -2.027 | 1.00 | 44.30 | C |
| ATOM | 323 | CG | PRO A | 94 | 48.846 | -19.274 | -2.473 | 1.00 | 47.71 | C |
| ATOM | 324 | C | PRO A | 94 | 45.265 | -19.503 | -1.838 | 1.00 | 43.76 | C |
| ATOM | 325 | O | PRO A | 94 | 45.282 | -19.037 | -0.709 | 1.00 | 44.82 | O |
| ATOM | 326 | N | GLN A | 95 | 44.223 | -20.160 | -2.332 | 1.00 | 39.95 | N |
| ATOM | 327 | CA | GLN A | 95 | 42.998 | -20.354 | -1.556 | 1.00 | 39.14 | C |
| ATOM | 328 | CB | GLN A | 95 | 42.014 | -21.197 | -2.388 | 1.00 | 39.26 | C |
| ATOM | 329 | CG | GLN A | 95 | 41.308 | -20.399 | -3.528 | 1.00 | 32.55 | C |
| ATOM | 330 | CD | GLN A | 95 | 40.163 | -19.514 | -3.004 | 1.00 | 40.69 | C |
| ATOM | 331 | OE1 | GLN A | 95 | 39.956 | -19.416 | -1.800 | 1.00 | 41.19 | O |
| ATOM | 332 | NE2 | GLN A | 95 | 39.339 | -19.002 | -3.910 | 1.00 | 27.08 | N |
| ATOM | 333 | C | GLN A | 95 | 43.299 | -21.023 | -0.198 | 1.00 | 47.15 | C |
| ATOM | 334 | O | GLN A | 95 | 42.643 | -20.750 | 0.821 | 1.00 | 44.33 | O |
| ATOM | 335 | N | SER A | 96 | 44.336 | -21.860 | -0.193 | 1.00 | 49.01 | N |
| ATOM | 336 | CA | SER A | 96 | 44.776 | -22.619 | 0.986 | 1.00 | 50.39 | C |
| ATOM | 337 | CB | SER A | 96 | 45.864 | -23.620 | 0.589 | 1.00 | 54.04 | C |
| ATOM | 338 | OG | SER A | 96 | 45.657 | -24.064 | -0.746 | 1.00 | 65.73 | O |
| ATOM | 339 | C | SER A | 96 | 45.254 | -21.772 | 2.156 | 1.00 | 57.24 | C |
| ATOM | 340 | O | SER A | 96 | 45.007 | -22.113 | 3.311 | 1.00 | 56.51 | O |
| ATOM | 341 | N | ARG A | 97 | 45.907 | -20.654 | 1.860 | 1.00 | 57.50 | N |
| ATOM | 342 | CA | ARG A | 97 | 46.418 | -19.772 | 2.914 | 1.00 | 58.07 | C |
| ATOM | 343 | CB | ARG A | 97 | 47.556 | -18.908 | 2.367 | 1.00 | 59.45 | C |
| ATOM | 344 | CG | ARG A | 97 | 47.986 | -19.307 | 0.977 | 1.00 | 70.72 | C |
| ATOM | 345 | CD | ARG A | 97 | 49.494 | -19.328 | 0.832 | 1.00 | 88.07 | C |
| ATOM | 346 | NE | ARG A | 97 | 50.171 | -18.917 | 2.058 | 1.00 | 101.26 | N |
| ATOM | 347 | CZ | ARG A | 97 | 51.395 | -18.396 | 2.098 | 1.00 | 113.39 | C |
| ATOM | 348 | NH1 | ARG A | 97 | 52.083 | -18.215 | 0.977 | 1.00 | 100.05 | N |
| ATOM | 349 | NH2 | ARG A | 97 | 51.926 | -18.053 | 3.265 | 1.00 | 97.06 | N |
| ATOM | 350 | C | ARG A | 97 | 45.313 | -18.899 | 3.506 | 1.00 | 62.36 | C |
| ATOM | 351 | O | ARG A | 97 | 45.386 | -18.458 | 4.671 | 1.00 | 63.31 | O |
| ATOM | 352 | N | VAL A | 98 | 44.278 | -18.667 | 2.704 | 1.00 | 55.10 | N |
| ATOM | 353 | CA | VAL A | 98 | 43.147 | -17.859 | 3.132 | 1.00 | 53.89 | C |
| ATOM | 354 | CB | VAL A | 98 | 42.693 | -16.896 | 2.036 | 1.00 | 58.09 | C |

Figure 6-7

| | Atom Type | Resid | # | X | Y | Z | OCC | B | |
|---|---|---|---|---|---|---|---|---|---|
| ATOM | 355 | CG1 | VAL A | 98 | 41.676 | -15.929 | 2.593 | 1.00 | 57.94 | C |
| ATOM | 356 | CG2 | VAL A | 98 | 43.911 | -16.149 | 1.504 | 1.00 | 58.02 | C |
| ATOM | 357 | C | VAL A | 98 | 42.031 | -18.693 | 3.768 | 1.00 | 54.40 | C |
| ATOM | 358 | O | VAL A | 98 | 40.864 | -18.300 | 3.806 | 1.00 | 48.74 | O |
| ATOM | 359 | N | ALA A | 99 | 42.477 | -19.812 | 4.339 | 1.00 | 54.71 | N |
| ATOM | 360 | CA | ALA A | 99 | 41.720 | -20.759 | 5.157 | 1.00 | 56.73 | C |
| ATOM | 361 | CB | ALA A | 99 | 42.642 | -21.259 | 6.308 | 1.00 | 57.94 | C |
| ATOM | 362 | C | ALA A | 99 | 40.396 | -20.263 | 5.741 | 1.00 | 62.11 | C |
| ATOM | 363 | O | ALA A | 99 | 39.329 | -20.581 | 5.200 | 1.00 | 60.42 | O |
| ATOM | 364 | N | LYS A | 100 | 40.465 | -19.568 | 6.888 | 1.00 | 61.21 | N |
| ATOM | 365 | CA | LYS A | 100 | 39.272 | -18.981 | 7.541 | 1.00 | 62.87 | C |
| ATOM | 366 | CB | LYS A | 100 | 38.926 | -19.686 | 8.853 | 1.00 | 65.52 | C |
| ATOM | 367 | CG | LYS A | 100 | 37.502 | -20.282 | 8.870 | 1.00 | 78.87 | C |
| ATOM | 368 | CD | LYS A | 100 | 36.613 | -19.816 | 7.668 | 1.00 | 85.96 | C |
| ATOM | 369 | CE | LYS A | 100 | 36.788 | -20.663 | 6.390 | 1.00 | 80.46 | C |
| ATOM | 370 | NZ | LYS A | 100 | 36.817 | -19.850 | 5.136 | 1.00 | 62.74 | N |
| ATOM | 371 | C | LYS A | 100 | 39.418 | -17.468 | 7.727 | 1.00 | 71.72 | C |
| ATOM | 372 | O | LYS A | 100 | 40.441 | -16.924 | 7.328 | 1.00 | 72.91 | O |
| ATOM | 373 | N | PRO A | 101 | 38.391 | -16.763 | 8.290 | 1.00 | 70.96 | N |
| ATOM | 374 | CD | PRO A | 101 | 37.195 | -17.319 | 8.948 | 1.00 | 72.29 | C |
| ATOM | 375 | CA | PRO A | 101 | 38.448 | -15.302 | 8.482 | 1.00 | 71.07 | C |
| ATOM | 376 | CB | PRO A | 101 | 37.372 | -15.053 | 9.527 | 1.00 | 72.87 | C |
| ATOM | 377 | CG | PRO A | 101 | 36.384 | -16.104 | 9.257 | 1.00 | 76.97 | C |
| ATOM | 378 | C | PRO A | 101 | 39.802 | -14.849 | 8.999 | 1.00 | 78.01 | C |
| ATOM | 379 | O | PRO A | 101 | 40.054 | -14.811 | 10.206 | 1.00 | 77.50 | O |
| ATOM | 380 | N | HIS A | 102 | 40.638 | -14.511 | 8.022 | 1.00 | 76.96 | N |
| ATOM | 381 | CA | HIS A | 102 | 42.043 | -14.190 | 8.134 | 1.00 | 77.97 | C |
| ATOM | 382 | CB | HIS A | 102 | 42.480 | -13.823 | 9.558 | 1.00 | 81.14 | C |
| ATOM | 383 | CG | HIS A | 102 | 42.924 | -12.393 | 9.712 | 1.00 | 86.13 | C |
| ATOM | 384 | CD2 | HIS A | 102 | 42.220 | -11.232 | 9.684 | 1.00 | 88.68 | C |
| ATOM | 385 | ND1 | HIS A | 102 | 44.234 | -12.039 | 9.969 | 1.00 | 88.38 | N |
| ATOM | 386 | CE1 | HIS A | 102 | 44.319 | -10.726 | 10.085 | 1.00 | 88.17 | C |
| ATOM | 387 | NE2 | HIS A | 102 | 43.113 | -10.212 | 9.919 | 1.00 | 88.57 | N |
| ATOM | 388 | C | HIS A | 102 | 42.749 | -15.441 | 7.613 | 1.00 | 77.43 | C |
| ATOM | 389 | O | HIS A | 102 | 42.809 | -16.474 | 8.269 | 1.00 | 77.00 | O |
| ATOM | 390 | N | GLN A | 103 | 43.161 | -15.362 | 6.362 | 1.00 | 71.96 | N |
| ATOM | 391 | CA | GLN A | 103 | 43.013 | -14.104 | 5.651 | 1.00 | 70.99 | C |
| ATOM | 392 | CB | GLN A | 103 | 43.940 | -14.044 | 4.430 | 1.00 | 72.85 | C |
| ATOM | 393 | CG | GLN A | 103 | 44.567 | -12.678 | 4.169 | 1.00 | 91.68 | C |
| ATOM | 394 | CD | GLN A | 103 | 46.085 | -12.743 | 4.053 | 1.00 | 106.76 | C |
| ATOM | 395 | OE1 | GLN A | 103 | 46.653 | -12.545 | 2.972 | 1.00 | 95.52 | O |
| ATOM | 396 | NE2 | GLN A | 103 | 46.749 | -13.027 | 5.172 | 1.00 | 100.76 | N |
| ATOM | 397 | C | GLN A | 103 | 41.583 | -13.841 | 5.223 | 1.00 | 69.63 | C |
| ATOM | 398 | O | GLN A | 103 | 41.205 | -12.688 | 5.064 | 1.00 | 70.42 | O |
| ATOM | 399 | N | ARG A | 104 | 40.805 | -14.904 | 5.027 | 1.00 | 61.35 | N |
| ATOM | 400 | CA | ARG A | 104 | 39.445 | -14.781 | 4.509 | 1.00 | 58.58 | C |
| ATOM | 401 | CB | ARG A | 104 | 38.535 | -15.926 | 4.951 | 1.00 | 54.62 | C |
| ATOM | 402 | CG | ARG A | 104 | 37.076 | -15.514 | 5.058 | 1.00 | 55.27 | C |
| ATOM | 403 | CD | ARG A | 104 | 36.138 | -16.608 | 4.591 | 1.00 | 69.20 | C |
| ATOM | 404 | NE | ARG A | 104 | 35.792 | -16.447 | 3.182 | 1.00 | 80.85 | N |
| ATOM | 405 | CZ | ARG A | 104 | 34.678 | -15.860 | 2.749 | 1.00 | 90.96 | C |
| ATOM | 406 | NH1 | ARG A | 104 | 33.799 | -15.386 | 3.633 | 1.00 | 77.92 | N |
| ATOM | 407 | NH2 | ARG A | 104 | 34.440 | -15.751 | 1.437 | 1.00 | 64.16 | N |
| ATOM | 408 | C | ARG A | 104 | 38.783 | -13.453 | 4.793 | 1.00 | 59.66 | C |
| ATOM | 409 | O | ARG A | 104 | 38.505 | -12.675 | 3.878 | 1.00 | 59.03 | O |
| ATOM | 410 | N | GLU A | 105 | 38.583 | -13.169 | 6.070 | 1.00 | 54.06 | N |
| ATOM | 411 | CA | GLU A | 105 | 37.951 | -11.919 | 6.446 | 1.00 | 53.05 | C |
| ATOM | 412 | CB | GLU A | 105 | 37.560 | -11.940 | 7.916 | 1.00 | 54.88 | C |
| ATOM | 413 | CG | GLU A | 105 | 36.098 | -11.617 | 8.100 | 1.00 | 71.20 | C |

Figure 6-8

| | | Atom Type | Resid | # | X | Y | Z | OCC | B | |
|---|---|---|---|---|---|---|---|---|---|---|
| ATOM | 414 | CD | GLU A | 105 | 35.418 | -11.322 | 6.772 | 1.00 | 95.36 | C |
| ATOM | 415 | OE1 | GLU A | 105 | 35.362 | -10.137 | 6.379 | 1.00 | 106.62 | O |
| ATOM | 416 | OE2 | GLU A | 105 | 34.984 | -12.280 | 6.098 | 1.00 | 83.71 | O |
| ATOM | 417 | C | GLU A | 105 | 38.863 | -10.736 | 6.124 | 1.00 | 51.36 | C |
| ATOM | 418 | O | GLU A | 105 | 38.405 | -9.663 | 5.756 | 1.00 | 49.57 | O |
| ATOM | 419 | N | LYS A | 106 | 40.162 | -10.984 | 6.194 | 1.00 | 45.09 | N |
| ATOM | 420 | CA | LYS A | 106 | 41.158 | -9.972 | 5.894 | 1.00 | 43.83 | C |
| ATOM | 421 | CB | LYS A | 106 | 42.544 | -10.473 | 6.317 | 1.00 | 44.40 | C |
| ATOM | 422 | CG | LYS A | 106 | 43.630 | -9.441 | 6.284 | 1.00 | 61.17 | C |
| ATOM | 423 | CD | LYS A | 106 | 45.003 | -10.097 | 6.256 | 1.00 | 69.28 | C |
| ATOM | 424 | CE | LYS A | 106 | 46.107 | -9.051 | 6.186 | 1.00 | 75.56 | C |
| ATOM | 425 | NZ | LYS A | 106 | 46.385 | -8.454 | 7.525 | 1.00 | 84.35 | N |
| ATOM | 426 | C | LYS A | 106 | 41.153 | -9.584 | 4.409 | 1.00 | 46.06 | C |
| ATOM | 427 | O | LYS A | 106 | 41.233 | -8.402 | 4.059 | 1.00 | 44.55 | O |
| ATOM | 428 | N | ILE A | 107 | 41.128 | -10.583 | 3.537 | 1.00 | 40.94 | N |
| ATOM | 429 | CA | ILE A | 107 | 41.156 | -10.299 | 2.123 | 1.00 | 41.14 | C |
| ATOM | 430 | CB | ILE A | 107 | 41.859 | -11.383 | 1.274 | 1.00 | 43.36 | C |
| ATOM | 431 | CG2 | ILE A | 107 | 41.939 | -12.697 | 1.992 | 1.00 | 43.90 | C |
| ATOM | 432 | CG1 | ILE A | 107 | 41.181 | -11.521 | -0.066 | 1.00 | 44.02 | C |
| ATOM | 433 | CD1 | ILE A | 107 | 42.045 | -11.055 | -1.175 | 1.00 | 55.16 | C |
| ATOM | 434 | C | ILE A | 107 | 39.836 | -9.756 | 1.582 | 1.00 | 43.79 | C |
| ATOM | 435 | O | ILE A | 107 | 39.837 | -8.920 | 0.683 | 1.00 | 42.54 | O |
| ATOM | 436 | N | LEU A | 108 | 38.722 | -10.139 | 2.200 | 1.00 | 39.97 | N |
| ATOM | 437 | CA | LEU A | 108 | 37.428 | -9.588 | 1.770 | 1.00 | 40.94 | C |
| ATOM | 438 | CB | LEU A | 108 | 36.267 | -10.228 | 2.545 | 1.00 | 40.28 | C |
| ATOM | 439 | CG | LEU A | 108 | 35.884 | -11.607 | 2.000 | 1.00 | 44.74 | C |
| ATOM | 440 | CD1 | LEU A | 108 | 34.746 | -12.200 | 2.822 | 1.00 | 45.55 | C |
| ATOM | 441 | CD2 | LEU A | 108 | 35.547 | -11.550 | 0.485 | 1.00 | 40.84 | C |
| ATOM | 442 | C | LEU A | 108 | 37.432 | -8.081 | 2.046 | 1.00 | 46.47 | C |
| ATOM | 443 | O | LEU A | 108 | 36.901 | -7.290 | 1.270 | 1.00 | 45.41 | O |
| ATOM | 444 | N | ASN A | 109 | 38.017 | -7.723 | 3.190 | 1.00 | 44.83 | N |
| ATOM | 445 | CA | ASN A | 109 | 38.135 | -6.342 | 3.655 | 1.00 | 44.28 | C |
| ATOM | 446 | CB | ASN A | 109 | 38.753 | -6.312 | 5.074 | 1.00 | 47.61 | C |
| ATOM | 447 | CG | ASN A | 109 | 38.924 | -4.890 | 5.614 | 1.00 | 53.64 | C |
| ATOM | 448 | OD1 | ASN A | 109 | 37.950 | -4.196 | 5.901 | 1.00 | 51.51 | O |
| ATOM | 449 | ND2 | ASN A | 109 | 40.167 | -4.445 | 5.711 | 1.00 | 49.09 | N |
| ATOM | 450 | C | ASN A | 109 | 38.989 | -5.546 | 2.695 | 1.00 | 43.08 | C |
| ATOM | 451 | O | ASN A | 109 | 38.637 | -4.453 | 2.316 | 1.00 | 44.33 | O |
| ATOM | 452 | N | GLU A | 110 | 40.134 | -6.080 | 2.325 | 1.00 | 37.29 | N |
| ATOM | 453 | CA | GLU A | 110 | 40.983 | -5.393 | 1.372 | 1.00 | 36.53 | C |
| ATOM | 454 | CB | GLU A | 110 | 42.212 | -6.234 | 1.018 | 1.00 | 37.77 | C |
| ATOM | 455 | CG | GLU A | 110 | 43.026 | -5.638 | -0.135 | 1.00 | 50.59 | C |
| ATOM | 456 | CD | GLU A | 110 | 44.339 | -6.370 | -0.400 | 1.00 | 67.27 | C |
| ATOM | 457 | OE1 | GLU A | 110 | 44.678 | -7.264 | 0.400 | 1.00 | 64.39 | O |
| ATOM | 458 | OE2 | GLU A | 110 | 45.031 | -6.047 | -1.403 | 1.00 | 54.89 | O |
| ATOM | 459 | C | GLU A | 110 | 40.189 | -5.071 | 0.105 | 1.00 | 38.19 | C |
| ATOM | 460 | O | GLU A | 110 | 40.219 | -3.956 | -0.380 | 1.00 | 36.76 | O |
| ATOM | 461 | N | ILE A | 111 | 39.483 | -6.059 | -0.446 | 1.00 | 35.90 | N |
| ATOM | 462 | CA | ILE A | 111 | 38.735 | -5.820 | -1.676 | 1.00 | 34.70 | C |
| ATOM | 463 | CB | ILE A | 111 | 38.214 | -7.141 | -2.334 | 1.00 | 35.45 | C |
| ATOM | 464 | CG2 | ILE A | 111 | 37.232 | -6.784 | -3.481 | 1.00 | 33.55 | C |
| ATOM | 465 | CG1 | ILE A | 111 | 39.390 | -8.018 | -2.816 | 1.00 | 33.09 | C |
| ATOM | 466 | CD1 | ILE A | 111 | 38.967 | -9.485 | -3.132 | 1.00 | 31.23 | C |
| ATOM | 467 | C | ILE A | 111 | 37.629 | -4.767 | -1.502 | 1.00 | 38.00 | C |
| ATOM | 468 | O | ILE A | 111 | 37.468 | -3.835 | -2.310 | 1.00 | 36.29 | O |
| ATOM | 469 | N | GLU A | 112 | 36.920 | -4.897 | -0.392 | 1.00 | 35.45 | N |
| ATOM | 470 | CA | GLU A | 112 | 35.830 | -4.022 | -0.039 | 1.00 | 34.60 | C |
| ATOM | 471 | CB | GLU A | 112 | 35.261 | -4.467 | 1.318 | 1.00 | 36.49 | C |
| ATOM | 472 | CG | GLU A | 112 | 34.219 | -3.558 | 1.897 | 1.00 | 52.29 | C |

Figure 6-9

|  |  | Atom Type | Resid | # | X | Y | Z | OCC | B |  |
|---|---|---|---|---|---|---|---|---|---|---|
| ATOM | 473 | CD | GLU A | 112 | 33.605 | -4.152 | 3.158 | 1.00 | 96.73 | C |
| ATOM | 474 | OE1 | GLU A | 112 | 34.322 | -4.899 | 3.871 | 1.00 | 95.62 | O |
| ATOM | 475 | OE2 | GLU A | 112 | 32.408 | -3.887 | 3.427 | 1.00 | 100.78 | O |
| ATOM | 476 | C | GLU A | 112 | 36.247 | -2.582 | 0.037 | 1.00 | 36.52 | C |
| ATOM | 477 | O | GLU A | 112 | 35.594 | -1.721 | -0.516 | 1.00 | 36.99 | O |
| ATOM | 478 | N | LEU A | 113 | 37.306 | -2.315 | 0.789 | 1.00 | 35.40 | N |
| ATOM | 479 | CA | LEU A | 113 | 37.817 | -0.952 | 0.974 | 1.00 | 35.54 | C |
| ATOM | 480 | CB | LEU A | 113 | 38.750 | -0.889 | 2.209 | 1.00 | 35.10 | C |
| ATOM | 481 | CG | LEU A | 113 | 38.095 | -1.224 | 3.557 | 1.00 | 37.99 | C |
| ATOM | 482 | CD1 | LEU A | 113 | 39.016 | -1.082 | 4.765 | 1.00 | 36.97 | C |
| ATOM | 483 | CD2 | LEU A | 113 | 36.750 | -0.572 | 3.803 | 1.00 | 36.14 | C |
| ATOM | 484 | C | LEU A | 113 | 38.554 | -0.399 | -0.268 | 1.00 | 37.55 | C |
| ATOM | 485 | O | LEU A | 113 | 38.494 | 0.786 | -0.545 | 1.00 | 36.26 | O |
| ATOM | 486 | N | HIS A | 114 | 39.268 | -1.256 | -0.992 | 1.00 | 33.47 | N |
| ATOM | 487 | CA | HIS A | 114 | 40.065 | -0.809 | -2.133 | 1.00 | 31.38 | C |
| ATOM | 488 | CB | HIS A | 114 | 41.219 | -1.786 | -2.393 | 1.00 | 30.52 | C |
| ATOM | 489 | CG | HIS A | 114 | 42.326 | -1.223 | -3.243 | 1.00 | 32.29 | C |
| ATOM | 490 | CD2 | HIS A | 114 | 42.418 | -0.066 | -3.955 | 1.00 | 32.18 | C |
| ATOM | 491 | ND1 | HIS A | 114 | 43.466 | -1.943 | -3.537 | 1.00 | 32.53 | N |
| ATOM | 492 | CE1 | HIS A | 114 | 44.237 | -1.231 | -4.344 | 1.00 | 30.88 | C |
| ATOM | 493 | NE2 | HIS A | 114 | 43.607 | -0.104 | -4.638 | 1.00 | 31.12 | N |
| ATOM | 494 | C | HIS A | 114 | 39.245 | -0.597 | -3.378 | 1.00 | 37.31 | C |
| ATOM | 495 | O | HIS A | 114 | 39.550 | 0.273 | -4.198 | 1.00 | 35.25 | O |
| ATOM | 496 | N | ARG A | 115 | 38.175 | -1.382 | -3.490 | 1.00 | 35.47 | N |
| ATOM | 497 | CA | ARG A | 115 | 37.299 | -1.420 | -4.669 | 1.00 | 34.58 | C |
| ATOM | 498 | CB | ARG A | 115 | 36.023 | -2.215 | -4.322 | 1.00 | 36.53 | C |
| ATOM | 499 | CG | ARG A | 115 | 35.054 | -2.445 | -5.489 | 1.00 | 52.85 | C |
| ATOM | 500 | CD | ARG A | 115 | 33.705 | -2.937 | -4.990 | 1.00 | 63.29 | C |
| ATOM | 501 | NE | ARG A | 115 | 33.739 | -4.319 | -4.512 | 1.00 | 72.72 | N |
| ATOM | 502 | CZ | ARG A | 115 | 33.708 | -5.388 | -5.306 | 1.00 | 82.45 | C |
| ATOM | 503 | NH1 | ARG A | 115 | 33.669 | -5.241 | -6.625 | 1.00 | 70.34 | N |
| ATOM | 504 | NH2 | ARG A | 115 | 33.730 | -6.608 | -4.783 | 1.00 | 59.31 | N |
| ATOM | 505 | C | ARG A | 115 | 36.922 | -0.094 | -5.330 | 1.00 | 39.14 | C |
| ATOM | 506 | O | ARG A | 115 | 37.005 | 0.061 | -6.574 | 1.00 | 34.11 | O |
| ATOM | 507 | N | ASP A | 116 | 36.433 | 0.826 | -4.503 | 1.00 | 41.30 | N |
| ATOM | 508 | CA | ASP A | 116 | 35.944 | 2.135 | -4.955 | 1.00 | 42.51 | C |
| ATOM | 509 | CB | ASP A | 116 | 34.617 | 2.463 | -4.251 | 1.00 | 47.37 | C |
| ATOM | 510 | CG | ASP A | 116 | 34.801 | 2.836 | -2.768 | 1.00 | 74.25 | C |
| ATOM | 511 | OD1 | ASP A | 116 | 35.912 | 2.629 | -2.217 | 1.00 | 79.10 | O |
| ATOM | 512 | OD2 | ASP A | 116 | 33.810 | 3.307 | -2.151 | 1.00 | 78.20 | O |
| ATOM | 513 | C | ASP A | 116 | 36.914 | 3.335 | -4.877 | 1.00 | 41.94 | C |
| ATOM | 514 | O | ASP A | 116 | 36.548 | 4.462 | -5.223 | 1.00 | 38.39 | O |
| ATOM | 515 | N | LEU A | 117 | 38.159 | 3.095 | -4.478 | 1.00 | 35.91 | N |
| ATOM | 516 | CA | LEU A | 117 | 39.133 | 4.188 | -4.392 | 1.00 | 34.10 | C |
| ATOM | 517 | CB | LEU A | 117 | 40.310 | 3.840 | -3.477 | 1.00 | 31.93 | C |
| ATOM | 518 | CG | LEU A | 117 | 39.955 | 3.268 | -2.090 | 1.00 | 31.41 | C |
| ATOM | 519 | CD1 | LEU A | 117 | 41.229 | 2.751 | -1.471 | 1.00 | 30.18 | C |
| ATOM | 520 | CD2 | LEU A | 117 | 39.215 | 4.211 | -1.149 | 1.00 | 35.82 | C |
| ATOM | 521 | C | LEU A | 117 | 39.607 | 4.778 | -5.719 | 1.00 | 38.07 | C |
| ATOM | 522 | O | LEU A | 117 | 40.354 | 4.160 | -6.463 | 1.00 | 40.49 | O |
| ATOM | 523 | N | GLN A | 118 | 39.211 | 6.017 | -5.969 | 1.00 | 35.23 | N |
| ATOM | 524 | CA | GLN A | 118 | 39.573 | 6.706 | -7.200 | 1.00 | 36.19 | C |
| ATOM | 525 | CB | GLN A | 118 | 38.294 | 7.050 | -7.975 | 1.00 | 38.95 | C |
| ATOM | 526 | CG | GLN A | 118 | 37.753 | 5.890 | -8.758 | 1.00 | 50.04 | C |
| ATOM | 527 | CD | GLN A | 118 | 36.643 | 6.309 | -9.692 | 1.00 | 58.80 | C |
| ATOM | 528 | OE1 | GLN A | 118 | 36.887 | 6.714 | -10.834 | 1.00 | 51.80 | O |
| ATOM | 529 | NE2 | GLN A | 118 | 35.409 | 6.197 | -9.216 | 1.00 | 35.97 | N |
| ATOM | 530 | C | GLN A | 118 | 40.352 | 7.995 | -6.953 | 1.00 | 35.97 | C |
| ATOM | 531 | O | GLN A | 118 | 39.770 | 9.034 | -6.691 | 1.00 | 33.15 | O |

Figure 6-10

| | | Atom Type | Resid | # | X | Y | Z | OCC | B | |
|---|---|---|---|---|---|---|---|---|---|---|
| ATOM | 532 | N | HIS A | 119 | 41.667 | 7.925 | -7.099 | 1.00 | 35.17 | N |
| ATOM | 533 | CA | HIS A | 119 | 42.545 | 9.066 | -6.850 | 1.00 | 34.29 | C |
| ATOM | 534 | CB | HIS A | 119 | 42.736 | 9.260 | -5.328 | 1.00 | 34.07 | C |
| ATOM | 535 | CG | HIS A | 119 | 43.421 | 10.545 | -4.968 | 1.00 | 38.02 | C |
| ATOM | 536 | CD2 | HIS A | 119 | 42.926 | 11.772 | -4.680 | 1.00 | 38.12 | C |
| ATOM | 537 | ND1 | HIS A | 119 | 44.798 | 10.665 | -4.890 | 1.00 | 39.85 | N |
| ATOM | 538 | CE1 | HIS A | 119 | 45.114 | 11.903 | -4.543 | 1.00 | 37.09 | C |
| ATOM | 539 | NE2 | HIS A | 119 | 43.995 | 12.591 | -4.406 | 1.00 | 37.23 | N |
| ATOM | 540 | C | HIS A | 119 | 43.897 | 8.859 | -7.542 | 1.00 | 36.95 | C |
| ATOM | 541 | O | HIS A | 119 | 44.401 | 7.734 | -7.654 | 1.00 | 34.43 | O |
| ATOM | 542 | N | ARG A | 120 | 44.472 | 9.942 | -8.042 | 1.00 | 34.82 | N |
| ATOM | 543 | CA | ARG A | 120 | 45.731 | 9.835 | -8.753 | 1.00 | 33.69 | C |
| ATOM | 544 | CB | ARG A | 120 | 46.080 | 11.130 | -9.510 | 1.00 | 35.23 | C |
| ATOM | 545 | CG | ARG A | 120 | 46.378 | 12.326 | -8.630 | 1.00 | 40.33 | C |
| ATOM | 546 | CD | ARG A | 120 | 46.416 | 13.626 | -9.431 | 1.00 | 48.22 | C |
| ATOM | 547 | NE | ARG A | 120 | 47.208 | 14.629 | -8.736 | 1.00 | 56.07 | N |
| ATOM | 548 | CZ | ARG A | 120 | 46.817 | 15.241 | -7.624 | 1.00 | 70.89 | C |
| ATOM | 549 | NH1 | ARG A | 120 | 45.610 | 15.003 | -7.135 | 1.00 | 50.01 | N |
| ATOM | 550 | NH2 | ARG A | 120 | 47.627 | 16.104 | -7.017 | 1.00 | 66.79 | N |
| ATOM | 551 | C | ARG A | 120 | 46.873 | 9.256 | -7.925 | 1.00 | 35.61 | C |
| ATOM | 552 | O | ARG A | 120 | 47.787 | 8.628 | -8.463 | 1.00 | 34.35 | O |
| ATOM | 553 | N | HIS A | 121 | 46.734 | 9.300 | -6.604 | 1.00 | 30.78 | N |
| ATOM | 554 | CA | HIS A | 121 | 47.787 | 8.779 | -5.733 | 1.00 | 28.99 | C |
| ATOM | 555 | CB | HIS A | 121 | 48.429 | 9.904 | -4.929 | 1.00 | 27.85 | C |
| ATOM | 556 | CG | HIS A | 121 | 49.085 | 10.926 | -5.803 | 1.00 | 30.65 | C |
| ATOM | 557 | CD2 | HIS A | 121 | 48.730 | 12.190 | -6.114 | 1.00 | 32.97 | C |
| ATOM | 558 | ND1 | HIS A | 121 | 50.185 | 10.637 | -6.581 | 1.00 | 32.32 | N |
| ATOM | 559 | CE1 | HIS A | 121 | 50.504 | 11.692 | -7.301 | 1.00 | 31.54 | C |
| ATOM | 560 | NE2 | HIS A | 121 | 49.637 | 12.649 | -7.039 | 1.00 | 32.14 | N |
| ATOM | 561 | C | HIS A | 121 | 47.448 | 7.557 | -4.883 | 1.00 | 32.72 | C |
| ATOM | 562 | O | HIS A | 121 | 48.066 | 7.304 | -3.837 | 1.00 | 30.52 | O |
| ATOM | 563 | N | ILE A | 122 | 46.472 | 6.807 | -5.381 | 1.00 | 30.45 | N |
| ATOM | 564 | CA | ILE A | 122 | 45.966 | 5.560 | -4.799 | 1.00 | 29.13 | C |
| ATOM | 565 | CB | ILE A | 122 | 44.531 | 5.744 | -4.275 | 1.00 | 30.57 | C |
| ATOM | 566 | CG2 | ILE A | 122 | 43.972 | 4.441 | -3.849 | 1.00 | 28.16 | C |
| ATOM | 567 | CG1 | ILE A | 122 | 44.452 | 6.831 | -3.159 | 1.00 | 31.59 | C |
| ATOM | 568 | CD1 | ILE A | 122 | 45.329 | 6.489 | -1.934 | 1.00 | 32.41 | C |
| ATOM | 569 | C | ILE A | 122 | 45.955 | 4.521 | -5.953 | 1.00 | 36.23 | C |
| ATOM | 570 | O | ILE A | 122 | 45.390 | 4.775 | -7.018 | 1.00 | 36.25 | O |
| ATOM | 571 | N | VAL A | 123 | 46.585 | 3.374 | -5.743 | 1.00 | 34.73 | N |
| ATOM | 572 | CA | VAL A | 123 | 46.610 | 2.301 | -6.740 | 1.00 | 34.97 | C |
| ATOM | 573 | CB | VAL A | 123 | 47.349 | 1.036 | -6.193 | 1.00 | 40.06 | C |
| ATOM | 574 | CG1 | VAL A | 123 | 47.267 | -0.138 | -7.187 | 1.00 | 39.95 | C |
| ATOM | 575 | CG2 | VAL A | 123 | 48.824 | 1.335 | -5.830 | 1.00 | 39.83 | C |
| ATOM | 576 | C | VAL A | 123 | 45.158 | 1.984 | -7.138 | 1.00 | 37.32 | C |
| ATOM | 577 | O | VAL A | 123 | 44.312 | 1.762 | -6.262 | 1.00 | 34.79 | O |
| ATOM | 578 | N | ARG A | 124 | 44.862 | 2.040 | -8.445 | 1.00 | 34.08 | N |
| ATOM | 579 | CA | ARG A | 124 | 43.514 | 1.764 | -8.961 | 1.00 | 34.39 | C |
| ATOM | 580 | CB | ARG A | 124 | 43.313 | 2.356 | -10.375 | 1.00 | 31.04 | C |
| ATOM | 581 | CG | ARG A | 124 | 41.846 | 2.407 | -10.896 | 1.00 | 25.36 | C |
| ATOM | 582 | CD | ARG A | 124 | 40.778 | 2.370 | -9.786 | 1.00 | 46.41 | C |
| ATOM | 583 | NE | ARG A | 124 | 39.455 | 2.842 | -10.231 | 1.00 | 48.34 | N |
| ATOM | 584 | CZ | ARG A | 124 | 38.292 | 2.473 | -9.686 | 1.00 | 64.06 | C |
| ATOM | 585 | NH1 | ARG A | 124 | 38.256 | 1.615 | -8.667 | 1.00 | 56.25 | N |
| ATOM | 586 | NH2 | ARG A | 124 | 37.151 | 2.951 | -10.167 | 1.00 | 56.82 | N |
| ATOM | 587 | C | ARG A | 124 | 43.241 | 0.261 | -8.960 | 1.00 | 36.68 | C |
| ATOM | 588 | O | ARG A | 124 | 44.032 | -0.510 | -9.480 | 1.00 | 35.96 | O |
| ATOM | 589 | N | PHE A | 125 | 42.192 | -0.136 | -8.235 | 1.00 | 31.93 | N |
| ATOM | 590 | CA | PHE A | 125 | 41.730 | -1.512 | -8.173 | 1.00 | 30.31 | C |

Figure 6-11

| | | Atom Type | Resid | # | X | Y | Z | OCC | B | |
|---|---|---|---|---|---|---|---|---|---|---|
| ATOM | 591 | CB | PHE A | 125 | 40.876 | -1.728 | -6.904 | 1.00 | 31.36 | C |
| ATOM | 592 | CG | PHE A | 125 | 40.341 | -3.129 | -6.748 | 1.00 | 32.65 | C |
| ATOM | 593 | CD1 | PHE A | 125 | 40.921 | -4.011 | -5.845 | 1.00 | 33.31 | C |
| ATOM | 594 | CD2 | PHE A | 125 | 39.219 | -3.540 | -7.448 | 1.00 | 34.97 | C |
| ATOM | 595 | CE1 | PHE A | 125 | 40.437 | -5.275 | -5.679 | 1.00 | 34.31 | C |
| ATOM | 596 | CE2 | PHE A | 125 | 38.745 | -4.831 | -7.310 | 1.00 | 38.59 | C |
| ATOM | 597 | CZ | PHE A | 125 | 39.364 | -5.704 | -6.441 | 1.00 | 35.80 | C |
| ATOM | 598 | C | PHE A | 125 | 40.855 | -1.703 | -9.427 | 1.00 | 34.98 | C |
| ATOM | 599 | O | PHE A | 125 | 40.002 | -0.861 | -9.763 | 1.00 | 36.02 | O |
| ATOM | 600 | N | SER A | 126 | 41.097 | -2.795 | -10.128 | 1.00 | 33.92 | N |
| ATOM | 601 | CA | SER A | 126 | 40.385 | -3.145 | -11.343 | 1.00 | 33.61 | C |
| ATOM | 602 | CB | SER A | 126 | 41.366 | -3.647 | -12.418 | 1.00 | 38.01 | C |
| ATOM | 603 | OG | SER A | 126 | 40.668 | -3.817 | -13.649 | 1.00 | 43.97 | O |
| ATOM | 604 | C | SER A | 126 | 39.280 | -4.183 | -11.184 | 1.00 | 36.39 | C |
| ATOM | 605 | O | SER A | 126 | 38.122 | -3.899 | -11.493 | 1.00 | 37.29 | O |
| ATOM | 606 | N | HIS A | 127 | 39.656 | -5.401 | -10.794 | 1.00 | 33.45 | N |
| ATOM | 607 | CA | HIS A | 127 | 38.730 | -6.540 | -10.737 | 1.00 | 34.31 | C |
| ATOM | 608 | CB | HIS A | 127 | 38.132 | -6.866 | -12.153 | 1.00 | 35.36 | C |
| ATOM | 609 | CG | HIS A | 127 | 39.118 | -7.446 | -13.147 | 1.00 | 37.85 | C |
| ATOM | 610 | CD2 | HIS A | 127 | 39.406 | -8.731 | -13.468 | 1.00 | 38.58 | C |
| ATOM | 611 | ND1 | HIS A | 127 | 39.849 | -6.666 | -14.025 | 1.00 | 39.08 | N |
| ATOM | 612 | CE1 | HIS A | 127 | 40.573 | -7.441 | -14.809 | 1.00 | 38.19 | C |
| ATOM | 613 | NE2 | HIS A | 127 | 40.310 | -8.701 | -14.503 | 1.00 | 38.53 | N |
| ATOM | 614 | C | HIS A | 127 | 39.402 | -7.758 | -10.128 | 1.00 | 39.48 | C |
| ATOM | 615 | O | HIS A | 127 | 40.605 | -7.758 | -9.884 | 1.00 | 42.17 | O |
| ATOM | 616 | N | HIS A | 128 | 38.612 | -8.760 | -9.778 | 1.00 | 34.72 | N |
| ATOM | 617 | CA | HIS A | 128 | 39.156 | -9.969 | -9.173 | 1.00 | 33.83 | C |
| ATOM | 618 | CB | HIS A | 128 | 39.193 | -9.851 | -7.646 | 1.00 | 33.48 | C |
| ATOM | 619 | CG | HIS A | 128 | 37.837 | -9.793 | -7.020 | 1.00 | 35.99 | C |
| ATOM | 620 | CD2 | HIS A | 128 | 37.054 | -10.766 | -6.508 | 1.00 | 36.32 | C |
| ATOM | 621 | ND1 | HIS A | 128 | 37.096 | -8.630 | -6.960 | 1.00 | 37.59 | N |
| ATOM | 622 | CE1 | HIS A | 128 | 35.928 | -8.890 | -6.405 | 1.00 | 36.83 | C |
| ATOM | 623 | NE2 | HIS A | 128 | 35.879 | -10.178 | -6.123 | 1.00 | 36.67 | N |
| ATOM | 624 | C | HIS A | 128 | 38.308 | -11.150 | -9.589 | 1.00 | 36.13 | C |
| ATOM | 625 | O | HIS A | 128 | 37.208 | -10.991 | -10.080 | 1.00 | 35.12 | O |
| ATOM | 626 | N | PHE A | 129 | 38.856 | -12.346 | -9.477 | 1.00 | 31.62 | N |
| ATOM | 627 | CA | PHE A | 129 | 38.071 | -13.535 | -9.744 | 1.00 | 29.62 | C |
| ATOM | 628 | CB | PHE A | 129 | 37.754 | -13.788 | -11.248 | 1.00 | 30.58 | C |
| ATOM | 629 | CG | PHE A | 129 | 38.951 | -13.840 | -12.140 | 1.00 | 31.09 | C |
| ATOM | 630 | CD1 | PHE A | 129 | 39.863 | -14.862 | -12.029 | 1.00 | 34.24 | C |
| ATOM | 631 | CD2 | PHE A | 129 | 39.143 | -12.864 | -13.120 | 1.00 | 32.71 | C |
| ATOM | 632 | CE1 | PHE A | 129 | 41.007 | -14.878 | -12.859 | 1.00 | 35.04 | C |
| ATOM | 633 | CE2 | PHE A | 129 | 40.223 | -12.912 | -13.987 | 1.00 | 33.89 | C |
| ATOM | 634 | CZ | PHE A | 129 | 41.138 | -13.957 | -13.862 | 1.00 | 33.24 | C |
| ATOM | 635 | C | PHE A | 129 | 38.822 | -14.639 | -9.074 | 1.00 | 34.79 | C |
| ATOM | 636 | O | PHE A | 129 | 39.972 | -14.455 | -8.675 | 1.00 | 34.84 | O |
| ATOM | 637 | N | GLU A | 130 | 38.149 | -15.748 | -8.840 | 1.00 | 32.55 | N |
| ATOM | 638 | CA | GLU A | 130 | 38.777 | -16.821 | -8.125 | 1.00 | 32.89 | C |
| ATOM | 639 | CB | GLU A | 130 | 38.447 | -16.721 | -6.619 | 1.00 | 34.86 | C |
| ATOM | 640 | CG | GLU A | 130 | 37.136 | -16.078 | -6.265 | 1.00 | 36.92 | C |
| ATOM | 641 | CD | GLU A | 130 | 37.117 | -14.537 | -6.250 | 1.00 | 50.24 | C |
| ATOM | 642 | OE1 | GLU A | 130 | 36.018 | -13.994 | -6.438 | 1.00 | 51.09 | O |
| ATOM | 643 | OE2 | GLU A | 130 | 38.149 | -13.851 | -6.107 | 1.00 | 42.96 | O |
| ATOM | 644 | C | GLU A | 130 | 38.554 | -18.204 | -8.739 | 1.00 | 36.66 | C |
| ATOM | 645 | O | GLU A | 130 | 37.591 | -18.394 | -9.478 | 1.00 | 32.74 | O |
| ATOM | 646 | N | ASP A | 131 | 39.497 | -19.122 | -8.454 | 1.00 | 36.53 | N |
| ATOM | 647 | CA | ASP A | 131 | 39.586 | -20.529 | -8.916 | 1.00 | 35.46 | C |
| ATOM | 648 | CB | ASP A | 131 | 41.094 | -20.882 | -9.228 | 1.00 | 38.30 | C |
| ATOM | 649 | CG | ASP A | 131 | 41.517 | -20.515 | -10.585 | 1.00 | 54.06 | C |

Figure 6-12

| | | Atom Type | Resid | # | X | Y | Z | OCC | B | |
|---|---|---|---|---|---|---|---|---|---|---|
| ATOM | 650 | OD1 | ASP A | 131 | 40.677 | -19.983 | -11.331 | 1.00 | 61.96 | O |
| ATOM | 651 | OD2 | ASP A | 131 | 42.700 | -20.738 | -10.902 | 1.00 | 57.37 | O |
| ATOM | 652 | C | ASP A | 131 | 39.457 | -21.252 | -7.628 | 1.00 | 32.62 | C |
| ATOM | 653 | O | ASP A | 131 | 39.727 | -20.655 | -6.613 | 1.00 | 30.93 | O |
| ATOM | 654 | N | ALA A | 132 | 39.422 | -22.583 | -7.681 | 1.00 | 31.85 | N |
| ATOM | 655 | CA | ALA A | 132 | 39.525 | -23.348 | -6.435 | 1.00 | 33.19 | C |
| ATOM | 656 | CB | ALA A | 132 | 39.079 | -24.812 | -6.585 | 1.00 | 33.17 | C |
| ATOM | 657 | C | ALA A | 132 | 40.941 | -23.291 | -5.907 | 1.00 | 42.14 | C |
| ATOM | 658 | O | ALA A | 132 | 41.181 | -23.688 | -4.764 | 1.00 | 42.34 | O |
| ATOM | 659 | N | ASP A | 133 | 41.904 | -22.867 | -6.727 | 1.00 | 42.58 | N |
| ATOM | 660 | CA | ASP A | 133 | 43.269 | -22.765 | -6.174 | 1.00 | 43.43 | C |
| ATOM | 661 | CB | ASP A | 133 | 44.315 | -23.641 | -6.863 | 1.00 | 46.97 | C |
| ATOM | 662 | CG | ASP A | 133 | 44.028 | -23.859 | -8.306 | 1.00 | 60.37 | C |
| ATOM | 663 | OD1 | ASP A | 133 | 43.861 | -22.844 | -9.014 | 1.00 | 64.61 | O |
| ATOM | 664 | OD2 | ASP A | 133 | 44.059 | -25.038 | -8.728 | 1.00 | 55.22 | O |
| ATOM | 665 | C | ASP A | 133 | 43.793 | -21.377 | -5.825 | 1.00 | 43.49 | C |
| ATOM | 666 | O | ASP A | 133 | 44.448 | -21.218 | -4.812 | 1.00 | 42.85 | O |
| ATOM | 667 | N | ASN A | 134 | 43.421 | -20.370 | -6.607 | 1.00 | 39.87 | N |
| ATOM | 668 | CA | ASN A | 134 | 43.857 | -18.993 | -6.355 | 1.00 | 38.65 | C |
| ATOM | 669 | CB | ASN A | 134 | 44.989 | -18.623 | -7.314 | 1.00 | 36.25 | C |
| ATOM | 670 | CG | ASN A | 134 | 46.237 | -19.426 | -7.082 | 1.00 | 36.93 | C |
| ATOM | 671 | OD1 | ASN A | 134 | 46.746 | -19.475 | -5.978 | 1.00 | 46.82 | O |
| ATOM | 672 | ND2 | ASN A | 134 | 46.793 | -19.979 | -8.146 | 1.00 | 33.13 | N |
| ATOM | 673 | C | ASN A | 134 | 42.808 | -17.899 | -6.486 | 1.00 | 39.24 | C |
| ATOM | 674 | O | ASN A | 134 | 41.877 | -17.981 | -7.302 | 1.00 | 36.11 | O |
| ATOM | 675 | N | ILE A | 135 | 43.060 | -16.816 | -5.748 | 1.00 | 35.42 | N |
| ATOM | 676 | CA | ILE A | 135 | 42.309 | -15.562 | -5.828 | 1.00 | 32.28 | C |
| ATOM | 677 | CB | ILE A | 135 | 42.118 | -14.933 | -4.419 | 1.00 | 34.08 | C |
| ATOM | 678 | CG2 | ILE A | 135 | 41.617 | -13.485 | -4.542 | 1.00 | 32.14 | C |
| ATOM | 679 | CG1 | ILE A | 135 | 41.136 | -15.777 | -3.582 | 1.00 | 34.23 | C |
| ATOM | 680 | CD1 | ILE A | 135 | 41.567 | -16.039 | -2.138 | 1.00 | 38.94 | C |
| ATOM | 681 | C | ILE A | 135 | 43.213 | -14.663 | -6.687 | 1.00 | 36.87 | C |
| ATOM | 682 | O | ILE A | 135 | 44.446 | -14.614 | -6.474 | 1.00 | 36.52 | O |
| ATOM | 683 | N | TYR A | 136 | 42.630 | -14.039 | -7.709 | 1.00 | 32.29 | N |
| ATOM | 684 | CA | TYR A | 136 | 43.347 | -13.099 | -8.579 | 1.00 | 32.27 | C |
| ATOM | 685 | CB | TYR A | 136 | 43.256 | -13.542 | -10.046 | 1.00 | 34.24 | C |
| ATOM | 686 | CG | TYR A | 136 | 43.796 | -14.915 | -10.274 | 1.00 | 39.11 | C |
| ATOM | 687 | CD1 | TYR A | 136 | 42.968 | -16.028 | -10.173 | 1.00 | 41.63 | C |
| ATOM | 688 | CE1 | TYR A | 136 | 43.461 | -17.313 | -10.365 | 1.00 | 44.25 | C |
| ATOM | 689 | CD2 | TYR A | 136 | 45.156 | -15.121 | -10.492 | 1.00 | 41.54 | C |
| ATOM | 690 | CE2 | TYR A | 136 | 45.669 | -16.413 | -10.652 | 1.00 | 43.27 | C |
| ATOM | 691 | CZ | TYR A | 136 | 44.807 | -17.495 | -10.614 | 1.00 | 54.73 | C |
| ATOM | 692 | OH | TYR A | 136 | 45.291 | -18.772 | -10.744 | 1.00 | 63.29 | O |
| ATOM | 693 | C | TYR A | 136 | 42.763 | -11.701 | -8.439 | 1.00 | 34.02 | C |
| ATOM | 694 | O | TYR A | 136 | 41.612 | -11.502 | -8.761 | 1.00 | 32.31 | O |
| ATOM | 695 | N | ILE A | 137 | 43.568 | -10.744 | -7.958 | 1.00 | 30.58 | N |
| ATOM | 696 | CA | ILE A | 137 | 43.160 | -9.341 | -7.808 | 1.00 | 29.77 | C |
| ATOM | 697 | CB | ILE A | 137 | 43.352 | -8.810 | -6.351 | 1.00 | 31.36 | C |
| ATOM | 698 | CG2 | ILE A | 137 | 43.179 | -7.295 | -6.289 | 1.00 | 29.68 | C |
| ATOM | 699 | CG1 | ILE A | 137 | 42.386 | -9.470 | -5.355 | 1.00 | 30.35 | C |
| ATOM | 700 | CD1 | ILE A | 137 | 42.924 | -9.526 | -3.947 | 1.00 | 40.14 | C |
| ATOM | 701 | C | ILE A | 137 | 43.957 | -8.509 | -8.818 | 1.00 | 36.83 | C |
| ATOM | 702 | O | ILE A | 137 | 45.186 | -8.443 | -8.746 | 1.00 | 38.42 | O |
| ATOM | 703 | N | PHE A | 138 | 43.248 | -7.865 | -9.743 | 1.00 | 34.58 | N |
| ATOM | 704 | CA | PHE A | 138 | 43.868 | -7.053 | -10.783 | 1.00 | 33.34 | C |
| ATOM | 705 | CB | PHE A | 138 | 43.157 | -7.225 | -12.136 | 1.00 | 34.25 | C |
| ATOM | 706 | CG | PHE A | 138 | 43.317 | -8.608 | -12.738 | 1.00 | 34.45 | C |
| ATOM | 707 | CD1 | PHE A | 138 | 42.649 | -9.706 | -12.197 | 1.00 | 36.32 | C |
| ATOM | 708 | CD2 | PHE A | 138 | 44.193 | -8.816 | -13.798 | 1.00 | 35.38 | C |

Figure 6-13

| | | Atom Type | Resid | # | X | Y | Z | OCC | B | |
|---|---|---|---|---|---|---|---|---|---|---|
| ATOM | 709 | CE1 | PHE A | 138 | 42.816 | -10.983 | -12.735 | 1.00 | 37.51 | C |
| ATOM | 710 | CE2 | PHE A | 138 | 44.407 | -10.087 | -14.304 | 1.00 | 38.18 | C |
| ATOM | 711 | CZ | PHE A | 138 | 43.705 | -11.177 | -13.799 | 1.00 | 36.10 | C |
| ATOM | 712 | C | PHE A | 138 | 43.872 | -5.590 | -10.398 | 1.00 | 35.19 | C |
| ATOM | 713 | O | PHE A | 138 | 42.847 | -5.012 | -10.059 | 1.00 | 32.10 | O |
| ATOM | 714 | N | LEU A | 139 | 45.053 | -4.997 | -10.493 | 1.00 | 34.29 | N |
| ATOM | 715 | CA | LEU A | 139 | 45.274 | -3.606 | -10.142 | 1.00 | 35.04 | C |
| ATOM | 716 | CB | LEU A | 139 | 46.134 | -3.533 | -8.863 | 1.00 | 34.41 | C |
| ATOM | 717 | CG | LEU A | 139 | 45.693 | -4.333 | -7.631 | 1.00 | 37.18 | C |
| ATOM | 718 | CD1 | LEU A | 139 | 46.755 | -4.360 | -6.570 | 1.00 | 38.57 | C |
| ATOM | 719 | CD2 | LEU A | 139 | 44.406 | -3.841 | -7.062 | 1.00 | 31.27 | C |
| ATOM | 720 | C | LEU A | 139 | 46.013 | -2.835 | -11.236 | 1.00 | 40.98 | C |
| ATOM | 721 | O | LEU A | 139 | 46.621 | -3.407 | -12.159 | 1.00 | 40.03 | O |
| ATOM | 722 | N | GLU A | 140 | 45.957 | -1.522 | -11.096 | 1.00 | 38.33 | N |
| ATOM | 723 | CA | GLU A | 140 | 46.747 | -0.590 | -11.886 | 1.00 | 38.01 | C |
| ATOM | 724 | CB | GLU A | 140 | 46.600 | 0.794 | -11.281 | 1.00 | 39.79 | C |
| ATOM | 725 | CG | GLU A | 140 | 47.720 | 1.747 | -11.554 | 1.00 | 43.87 | C |
| ATOM | 726 | CD | GLU A | 140 | 47.349 | 3.180 | -11.216 | 1.00 | 54.34 | C |
| ATOM | 727 | OE1 | GLU A | 140 | 48.007 | 4.091 | -11.759 | 1.00 | 62.72 | O |
| ATOM | 728 | OE2 | GLU A | 140 | 46.415 | 3.409 | -10.405 | 1.00 | 48.18 | O |
| ATOM | 729 | C | GLU A | 140 | 48.217 | -1.014 | -11.813 | 1.00 | 39.34 | C |
| ATOM | 730 | O | GLU A | 140 | 48.765 | -1.333 | -10.748 | 1.00 | 37.61 | O |
| ATOM | 731 | N | LEU A | 141 | 48.844 | -1.100 | -12.974 | 1.00 | 35.99 | N |
| ATOM | 732 | CA | LEU A | 141 | 50.224 | -1.508 | -13.009 | 1.00 | 35.43 | C |
| ATOM | 733 | CB | LEU A | 141 | 50.525 | -2.241 | -14.335 | 1.00 | 35.65 | C |
| ATOM | 734 | CG | LEU A | 141 | 52.020 | -2.434 | -14.632 | 1.00 | 40.47 | C |
| ATOM | 735 | CD1 | LEU A | 141 | 52.648 | -3.485 | -13.686 | 1.00 | 40.97 | C |
| ATOM | 736 | CD2 | LEU A | 141 | 52.290 | -2.732 | -16.107 | 1.00 | 38.89 | C |
| ATOM | 737 | C | LEU A | 141 | 51.206 | -0.328 | -12.746 | 1.00 | 38.89 | C |
| ATOM | 738 | O | LEU A | 141 | 51.190 | 0.696 | -13.442 | 1.00 | 38.68 | O |
| ATOM | 739 | N | CYS A | 142 | 52.054 | -0.492 | -11.731 | 1.00 | 33.87 | N |
| ATOM | 740 | CA | CYS A | 142 | 53.109 | 0.473 | -11.408 | 1.00 | 33.78 | C |
| ATOM | 741 | CB | CYS A | 142 | 53.063 | 0.890 | -9.921 | 1.00 | 34.52 | C |
| ATOM | 742 | SG | CYS A | 142 | 51.444 | 1.597 | -9.390 | 1.00 | 37.59 | S |
| ATOM | 743 | C | CYS A | 142 | 54.429 | -0.212 | -11.750 | 1.00 | 37.58 | C |
| ATOM | 744 | O | CYS A | 142 | 54.995 | -0.957 | -10.962 | 1.00 | 36.50 | O |
| ATOM | 745 | N | SER A | 143 | 54.862 | 0.009 | -12.983 | 1.00 | 37.82 | N |
| ATOM | 746 | CA | SER A | 143 | 56.058 | -0.585 | -13.547 | 1.00 | 37.84 | C |
| ATOM | 747 | CB | SER A | 143 | 56.273 | -0.064 | -14.957 | 1.00 | 42.56 | C |
| ATOM | 748 | OG | SER A | 143 | 56.577 | -1.148 | -15.803 | 1.00 | 61.13 | O |
| ATOM | 749 | C | SER A | 143 | 57.367 | -0.454 | -12.776 | 1.00 | 43.01 | C |
| ATOM | 750 | O | SER A | 143 | 58.222 | -1.342 | -12.879 | 1.00 | 41.33 | O |
| ATOM | 751 | N | ARG A | 144 | 57.579 | 0.660 | -12.069 | 1.00 | 39.56 | N |
| ATOM | 752 | CA | ARG A | 144 | 58.849 | 0.824 | -11.327 | 1.00 | 39.81 | C |
| ATOM | 753 | CB | ARG A | 144 | 59.304 | 2.289 | -11.329 | 1.00 | 41.59 | C |
| ATOM | 754 | CG | ARG A | 144 | 59.470 | 2.866 | -12.730 | 1.00 | 48.03 | C |
| ATOM | 755 | CD | ARG A | 144 | 60.946 | 2.971 | -13.042 | 1.00 | 63.43 | C |
| ATOM | 756 | NE | ARG A | 144 | 61.234 | 3.267 | -14.442 | 1.00 | 69.71 | N |
| ATOM | 757 | CZ | ARG A | 144 | 60.579 | 4.167 | -15.164 | 1.00 | 81.91 | C |
| ATOM | 758 | NH1 | ARG A | 144 | 59.581 | 4.864 | -14.624 | 1.00 | 62.93 | N |
| ATOM | 759 | NH2 | ARG A | 144 | 60.930 | 4.375 | -16.426 | 1.00 | 72.48 | N |
| ATOM | 760 | C | ARG A | 144 | 58.860 | 0.235 | -9.902 | 1.00 | 42.50 | C |
| ATOM | 761 | O | ARG A | 144 | 59.806 | 0.461 | -9.112 | 1.00 | 41.56 | O |
| ATOM | 762 | N | LYS A | 145 | 57.825 | -0.535 | -9.571 | 1.00 | 37.16 | N |
| ATOM | 763 | CA | LYS A | 145 | 57.787 | -1.190 | -8.257 | 1.00 | 36.57 | C |
| ATOM | 764 | CB | LYS A | 145 | 58.990 | -2.103 | -8.112 | 1.00 | 40.56 | C |
| ATOM | 765 | CG | LYS A | 145 | 59.069 | -3.216 | -9.161 | 1.00 | 51.09 | C |
| ATOM | 766 | CD | LYS A | 145 | 60.069 | -4.268 | -8.729 | 1.00 | 53.91 | C |
| ATOM | 767 | CE | LYS A | 145 | 60.790 | -4.881 | -9.934 | 1.00 | 66.24 | C |

Figure 6-14

| | | Atom Type | Resid | # | X | Y | Z | OCC | B | |
|---|---|---|---|---|---|---|---|---|---|---|
| ATOM | 768 | NZ | LYS A | 145 | 61.733 | -5.968 | -9.519 | 1.00 | 70.41 | N |
| ATOM | 769 | C | LYS A | 145 | 57.715 | -0.215 | -7.081 | 1.00 | 38.61 | C |
| ATOM | 770 | O | LYS A | 145 | 57.399 | 0.944 | -7.274 | 1.00 | 40.20 | O |
| ATOM | 771 | N | SER A | 146 | 58.056 | -0.665 | -5.876 | 1.00 | 35.96 | N |
| ATOM | 772 | CA | SER A | 146 | 57.942 | 0.182 | -4.659 | 1.00 | 36.63 | C |
| ATOM | 773 | CB | SER A | 146 | 57.471 | -0.674 | -3.494 | 1.00 | 36.10 | C |
| ATOM | 774 | OG | SER A | 146 | 58.570 | -1.247 | -2.868 | 1.00 | 39.54 | O |
| ATOM | 775 | C | SER A | 146 | 59.128 | 1.103 | -4.210 | 1.00 | 39.42 | C |
| ATOM | 776 | O | SER A | 146 | 60.285 | 0.948 | -4.661 | 1.00 | 35.25 | O |
| ATOM | 777 | N | LEU A | 147 | 58.832 | 2.037 | -3.300 | 1.00 | 35.08 | N |
| ATOM | 778 | CA | LEU A | 147 | 59.849 | 2.950 | -2.770 | 1.00 | 33.61 | C |
| ATOM | 779 | CB | LEU A | 147 | 59.252 | 4.077 | -1.909 | 1.00 | 33.63 | C |
| ATOM | 780 | CG | LEU A | 147 | 58.938 | 5.362 | -2.649 | 1.00 | 41.73 | C |
| ATOM | 781 | CD1 | LEU A | 147 | 58.765 | 6.528 | -1.634 | 1.00 | 42.48 | C |
| ATOM | 782 | CD2 | LEU A | 147 | 60.012 | 5.679 | -3.737 | 1.00 | 42.31 | C |
| ATOM | 783 | C | LEU A | 147 | 60.799 | 2.154 | -1.919 | 1.00 | 36.08 | C |
| ATOM | 784 | O | LEU A | 147 | 61.919 | 2.598 | -1.618 | 1.00 | 35.76 | O |
| ATOM | 785 | N | ALA A | 148 | 60.332 | 0.991 | -1.493 | 1.00 | 32.48 | N |
| ATOM | 786 | CA | ALA A | 148 | 61.176 | 0.091 | -0.704 | 1.00 | 32.10 | C |
| ATOM | 787 | CB | ALA A | 148 | 60.348 | -1.019 | -0.093 | 1.00 | 32.37 | C |
| ATOM | 788 | C | ALA A | 148 | 62.239 | -0.469 | -1.669 | 1.00 | 36.94 | C |
| ATOM | 789 | O | ALA A | 148 | 63.423 | -0.528 | -1.336 | 1.00 | 38.14 | O |
| ATOM | 790 | N | HIS A | 149 | 61.816 | -0.783 | -2.885 | 1.00 | 36.05 | N |
| ATOM | 791 | CA | HIS A | 149 | 62.716 | -1.268 | -3.925 | 1.00 | 40.69 | C |
| ATOM | 792 | CB | HIS A | 149 | 61.931 | -1.742 | -5.137 | 1.00 | 43.50 | C |
| ATOM | 793 | CG | HIS A | 149 | 62.729 | -2.619 | -6.038 | 1.00 | 49.27 | C |
| ATOM | 794 | CD2 | HIS A | 149 | 63.281 | -3.840 | -5.820 | 1.00 | 52.79 | C |
| ATOM | 795 | ND1 | HIS A | 149 | 63.159 | -2.214 | -7.285 | 1.00 | 52.51 | N |
| ATOM | 796 | CE1 | HIS A | 149 | 63.894 | -3.177 | -7.824 | 1.00 | 53.02 | C |
| ATOM | 797 | NE2 | HIS A | 149 | 63.997 | -4.165 | -6.950 | 1.00 | 53.33 | N |
| ATOM | 798 | C | HIS A | 149 | 63.723 | -0.193 | -4.370 | 1.00 | 44.47 | C |
| ATOM | 799 | O | HIS A | 149 | 64.923 | -0.459 | -4.546 | 1.00 | 43.53 | O |
| ATOM | 800 | N | ILE A | 150 | 63.232 | 1.021 | -4.575 | 1.00 | 39.49 | N |
| ATOM | 801 | CA | ILE A | 150 | 64.111 | 2.116 | -4.960 | 1.00 | 39.54 | C |
| ATOM | 802 | CB | ILE A | 150 | 63.289 | 3.370 | -5.324 | 1.00 | 41.97 | C |
| ATOM | 803 | CG2 | ILE A | 150 | 64.159 | 4.625 | -5.255 | 1.00 | 41.80 | C |
| ATOM | 804 | CG1 | ILE A | 150 | 62.573 | 3.171 | -6.654 | 1.00 | 41.87 | C |
| ATOM | 805 | CD1 | ILE A | 150 | 61.711 | 4.322 | -7.069 | 1.00 | 50.01 | C |
| ATOM | 806 | C | ILE A | 150 | 65.056 | 2.412 | -3.805 | 1.00 | 42.35 | C |
| ATOM | 807 | O | ILE A | 150 | 66.241 | 2.688 | -3.960 | 1.00 | 41.18 | O |
| ATOM | 808 | N | TRP A | 151 | 64.515 | 2.338 | -2.613 | 1.00 | 40.77 | N |
| ATOM | 809 | CA | TRP A | 151 | 65.274 | 2.709 | -1.458 | 1.00 | 41.28 | C |
| ATOM | 810 | CB | TRP A | 151 | 64.304 | 2.980 | -0.326 | 1.00 | 42.96 | C |
| ATOM | 811 | CG | TRP A | 151 | 64.549 | 2.144 | 0.791 | 1.00 | 46.46 | C |
| ATOM | 812 | CD2 | TRP A | 151 | 65.399 | 2.443 | 1.877 | 1.00 | 46.61 | C |
| ATOM | 813 | CE2 | TRP A | 151 | 65.422 | 1.302 | 2.708 | 1.00 | 52.39 | C |
| ATOM | 814 | CE3 | TRP A | 151 | 66.012 | 3.607 | 2.318 | 1.00 | 48.41 | C |
| ATOM | 815 | CD1 | TRP A | 151 | 64.172 | 0.831 | 0.933 | 1.00 | 50.47 | C |
| ATOM | 816 | NE1 | TRP A | 151 | 64.666 | 0.329 | 2.111 | 1.00 | 50.91 | N |
| ATOM | 817 | CZ2 | TRP A | 151 | 66.060 | 1.291 | 3.920 | 1.00 | 52.38 | C |
| ATOM | 818 | CZ3 | TRP A | 151 | 66.661 | 3.581 | 3.500 | 1.00 | 50.11 | C |
| ATOM | 819 | CH2 | TRP A | 151 | 66.700 | 2.425 | 4.278 | 1.00 | 51.40 | C |
| ATOM | 820 | C | TRP A | 151 | 66.413 | 1.758 | -1.100 | 1.00 | 44.44 | C |
| ATOM | 821 | O | TRP A | 151 | 67.465 | 2.169 | -0.584 | 1.00 | 42.67 | O |
| ATOM | 822 | N | LYS A | 152 | 66.235 | 0.496 | -1.450 | 1.00 | 42.87 | N |
| ATOM | 823 | CA | LYS A | 152 | 67.253 | -0.521 | -1.223 | 1.00 | 43.65 | C |
| ATOM | 824 | CB | LYS A | 152 | 66.645 | -1.922 | -1.413 | 1.00 | 45.88 | C |
| ATOM | 825 | CG | LYS A | 152 | 67.461 | -3.047 | -0.757 | 1.00 | 79.23 | C |
| ATOM | 826 | CD | LYS A | 152 | 68.848 | -3.227 | -1.425 | 1.00 | 93.23 | C |

Figure 6-15

| | | Atom Type | Resid | # | X | Y | Z | OCC | B | |
|---|---|---|---|---|---|---|---|---|---|---|
| ATOM | 827 | CE | LYS A | 152 | 69.377 | -4.664 | -1.332 | 1.00 | 97.26 | C |
| ATOM | 828 | NZ | LYS A | 152 | 70.129 | -5.079 | -2.560 | 1.00 | 99.15 | N |
| ATOM | 829 | C | LYS A | 152 | 68.415 | -0.299 | -2.206 | 1.00 | 47.39 | C |
| ATOM | 830 | O | LYS A | 152 | 69.569 | -0.581 | -1.906 | 1.00 | 44.16 | O |
| ATOM | 831 | N | ALA A | 153 | 68.095 | 0.227 | -3.379 | 1.00 | 45.45 | N |
| ATOM | 832 | CA | ALA A | 153 | 69.125 | 0.536 | -4.360 | 1.00 | 46.29 | C |
| ATOM | 833 | CB | ALA A | 153 | 68.507 | 0.655 | -5.744 | 1.00 | 46.91 | C |
| ATOM | 834 | C | ALA A | 153 | 69.869 | 1.833 | -3.997 | 1.00 | 51.73 | C |
| ATOM | 835 | O | ALA A | 153 | 71.092 | 1.931 | -4.147 | 1.00 | 50.34 | O |
| ATOM | 836 | N | ARG A | 154 | 69.126 | 2.829 | -3.516 | 1.00 | 48.90 | N |
| ATOM | 837 | CA | ARG A | 154 | 69.687 | 4.157 | -3.237 | 1.00 | 46.51 | C |
| ATOM | 838 | CB | ARG A | 154 | 68.720 | 5.269 | -3.725 | 1.00 | 42.12 | C |
| ATOM | 839 | CG | ARG A | 154 | 69.357 | 6.350 | -4.663 | 1.00 | 52.21 | C |
| ATOM | 840 | CD | ARG A | 154 | 68.274 | 7.072 | -5.467 | 1.00 | 60.10 | C |
| ATOM | 841 | NE | ARG A | 154 | 68.439 | 8.521 | -5.666 | 1.00 | 39.79 | N |
| ATOM | 842 | CZ | ARG A | 154 | 69.143 | 9.335 | -4.890 | 1.00 | 68.37 | C |
| ATOM | 843 | NH1 | ARG A | 154 | 69.755 | 8.894 | -3.800 | 1.00 | 70.57 | N |
| ATOM | 844 | NH2 | ARG A | 154 | 69.225 | 10.618 | -5.201 | 1.00 | 69.38 | N |
| ATOM | 845 | C | ARG A | 154 | 70.180 | 4.418 | -1.819 | 1.00 | 47.68 | C |
| ATOM | 846 | O | ARG A | 154 | 71.079 | 5.227 | -1.640 | 1.00 | 47.21 | O |
| ATOM | 847 | N | HIS A | 155 | 69.632 | 3.689 | -0.837 | 1.00 | 43.71 | N |
| ATOM | 848 | CA | HIS A | 155 | 69.869 | 3.863 | 0.615 | 1.00 | 41.88 | C |
| ATOM | 849 | CB | HIS A | 155 | 71.312 | 3.568 | 1.047 | 1.00 | 44.30 | C |
| ATOM | 850 | CG | HIS A | 155 | 71.472 | 3.436 | 2.534 | 1.00 | 48.36 | C |
| ATOM | 851 | CD2 | HIS A | 155 | 72.197 | 4.156 | 3.424 | 1.00 | 51.49 | C |
| ATOM | 852 | ND1 | HIS A | 155 | 70.778 | 2.499 | 3.280 | 1.00 | 50.59 | N |
| ATOM | 853 | CE1 | HIS A | 155 | 71.103 | 2.618 | 4.555 | 1.00 | 50.46 | C |
| ATOM | 854 | NE2 | HIS A | 155 | 71.961 | 3.619 | 4.673 | 1.00 | 51.41 | N |
| ATOM | 855 | C | HIS A | 155 | 69.330 | 5.160 | 1.265 | 1.00 | 41.97 | C |
| ATOM | 856 | O | HIS A | 155 | 68.891 | 5.161 | 2.418 | 1.00 | 39.43 | O |
| ATOM | 857 | N | THR A | 156 | 69.436 | 6.275 | 0.536 | 1.00 | 38.90 | N |
| ATOM | 858 | CA | THR A | 156 | 68.918 | 7.583 | 0.953 | 1.00 | 39.30 | C |
| ATOM | 859 | CB | THR A | 156 | 69.930 | 8.446 | 1.808 | 1.00 | 43.14 | C |
| ATOM | 860 | OG1 | THR A | 156 | 71.066 | 8.803 | 1.017 | 1.00 | 44.00 | O |
| ATOM | 861 | CG2 | THR A | 156 | 70.366 | 7.770 | 3.065 | 1.00 | 38.98 | C |
| ATOM | 862 | C | THR A | 156 | 68.565 | 8.342 | -0.332 | 1.00 | 42.44 | C |
| ATOM | 863 | O | THR A | 156 | 69.055 | 8.013 | -1.432 | 1.00 | 38.81 | O |
| ATOM | 864 | N | LEU A | 157 | 67.676 | 9.322 | -0.192 | 1.00 | 38.43 | N |
| ATOM | 865 | CA | LEU A | 157 | 67.280 | 10.179 | -1.311 | 1.00 | 38.10 | C |
| ATOM | 866 | CB | LEU A | 157 | 65.755 | 10.138 | -1.545 | 1.00 | 38.36 | C |
| ATOM | 867 | CG | LEU A | 157 | 65.035 | 8.941 | -2.151 | 1.00 | 42.62 | C |
| ATOM | 868 | CD1 | LEU A | 157 | 63.538 | 9.285 | -2.307 | 1.00 | 41.78 | C |
| ATOM | 869 | CD2 | LEU A | 157 | 65.639 | 8.621 | -3.527 | 1.00 | 47.51 | C |
| ATOM | 870 | C | LEU A | 157 | 67.656 | 11.586 | -0.884 | 1.00 | 39.83 | C |
| ATOM | 871 | O | LEU A | 157 | 67.792 | 11.862 | 0.332 | 1.00 | 36.06 | O |
| ATOM | 872 | N | LEU A | 158 | 67.831 | 12.470 | -1.867 | 1.00 | 37.95 | N |
| ATOM | 873 | CA | LEU A | 158 | 68.153 | 13.879 | -1.566 | 1.00 | 38.02 | C |
| ATOM | 874 | CB | LEU A | 158 | 68.633 | 14.577 | -2.842 | 1.00 | 37.46 | C |
| ATOM | 875 | CG | LEU A | 158 | 69.685 | 13.719 | -3.548 | 1.00 | 41.58 | C |
| ATOM | 876 | CD1 | LEU A | 158 | 70.007 | 14.253 | -4.934 | 1.00 | 40.48 | C |
| ATOM | 877 | CD2 | LEU A | 158 | 70.905 | 13.678 | -2.678 | 1.00 | 43.23 | C |
| ATOM | 878 | C | LEU A | 158 | 66.874 | 14.575 | -1.069 | 1.00 | 41.08 | C |
| ATOM | 879 | O | LEU A | 158 | 65.777 | 14.185 | -1.486 | 1.00 | 41.85 | O |
| ATOM | 880 | N | GLU A | 159 | 66.998 | 15.585 | -0.201 | 1.00 | 34.75 | N |
| ATOM | 881 | CA | GLU A | 159 | 65.807 | 16.323 | 0.260 | 1.00 | 34.65 | C |
| ATOM | 882 | CB | GLU A | 159 | 66.140 | 17.598 | 1.073 | 1.00 | 36.03 | C |
| ATOM | 883 | CG | GLU A | 159 | 67.085 | 17.319 | 2.233 | 1.00 | 49.13 | C |
| ATOM | 884 | CD | GLU A | 159 | 66.790 | 18.116 | 3.504 | 1.00 | 67.63 | C |
| ATOM | 885 | OE1 | GLU A | 159 | 65.915 | 19.021 | 3.478 | 1.00 | 38.91 | O |

Figure 6-16

| | | Atom Type | Resid | # | X | Y | Z | OCC | B | |
|---|---|---|---|---|---|---|---|---|---|---|
| ATOM | 886 | OE2 | GLU A | 159 | 67.435 | 17.790 | 4.539 | 1.00 | 40.12 | O |
| ATOM | 887 | C | GLU A | 159 | 64.755 | 16.599 | -0.810 | 1.00 | 37.27 | C |
| ATOM | 888 | O | GLU A | 159 | 63.587 | 16.287 | -0.607 | 1.00 | 36.90 | O |
| ATOM | 889 | N | PRO A | 160 | 65.155 | 17.135 | -1.980 | 1.00 | 35.79 | N |
| ATOM | 890 | CD | PRO A | 160 | 66.462 | 17.704 | -2.395 | 1.00 | 37.07 | C |
| ATOM | 891 | CA | PRO A | 160 | 64.104 | 17.399 | -2.980 | 1.00 | 34.77 | C |
| ATOM | 892 | CB | PRO A | 160 | 64.871 | 18.033 | -4.163 | 1.00 | 36.01 | C |
| ATOM | 893 | CG | PRO A | 160 | 66.121 | 18.581 | -3.564 | 1.00 | 40.25 | C |
| ATOM | 894 | C | PRO A | 160 | 63.367 | 16.147 | -3.456 | 1.00 | 39.25 | C |
| ATOM | 895 | O | PRO A | 160 | 62.234 | 16.242 | -3.971 | 1.00 | 39.53 | O |
| ATOM | 896 | N | GLU A | 161 | 64.031 | 14.987 | -3.335 | 1.00 | 35.18 | N |
| ATOM | 897 | CA | GLU A | 161 | 63.427 | 13.706 | -3.719 | 1.00 | 32.52 | C |
| ATOM | 898 | CB | GLU A | 161 | 64.476 | 12.606 | -3.892 | 1.00 | 33.75 | C |
| ATOM | 899 | CG | GLU A | 161 | 65.254 | 12.670 | -5.186 | 1.00 | 40.21 | C |
| ATOM | 900 | CD | GLU A | 161 | 66.253 | 11.533 | -5.309 | 1.00 | 38.38 | C |
| ATOM | 901 | OE1 | GLU A | 161 | 67.162 | 11.420 | -4.437 | 1.00 | 39.95 | O |
| ATOM | 902 | OE2 | GLU A | 161 | 66.070 | 10.699 | -6.218 | 1.00 | 50.29 | O |
| ATOM | 903 | C | GLU A | 161 | 62.456 | 13.309 | -2.631 | 1.00 | 32.69 | C |
| ATOM | 904 | O | GLU A | 161 | 61.366 | 12.867 | -2.921 | 1.00 | 32.07 | O |
| ATOM | 905 | N | VAL A | 162 | 62.874 | 13.465 | -1.378 | 1.00 | 30.87 | N |
| ATOM | 906 | CA | VAL A | 162 | 62.002 | 13.203 | -0.240 | 1.00 | 33.35 | C |
| ATOM | 907 | CB | VAL A | 162 | 62.756 | 13.261 | 1.108 | 1.00 | 37.48 | C |
| ATOM | 908 | CG1 | VAL A | 162 | 61.798 | 12.953 | 2.273 | 1.00 | 36.14 | C |
| ATOM | 909 | CG2 | VAL A | 162 | 63.955 | 12.221 | 1.080 | 1.00 | 37.73 | C |
| ATOM | 910 | C | VAL A | 162 | 60.726 | 14.083 | -0.317 | 1.00 | 39.59 | C |
| ATOM | 911 | O | VAL A | 162 | 59.621 | 13.566 | -0.190 | 1.00 | 41.28 | O |
| ATOM | 912 | N | ARG A | 163 | 60.877 | 15.370 | -0.655 | 1.00 | 33.55 | N |
| ATOM | 913 | CA | ARG A | 163 | 59.736 | 16.282 | -0.828 | 1.00 | 33.61 | C |
| ATOM | 914 | CB | ARG A | 163 | 60.244 | 17.710 | -1.118 | 1.00 | 34.45 | C |
| ATOM | 915 | CG | ARG A | 163 | 59.348 | 18.833 | -0.645 | 1.00 | 46.32 | C |
| ATOM | 916 | CD | ARG A | 163 | 60.154 | 20.039 | -0.140 | 1.00 | 49.96 | C |
| ATOM | 917 | NE | ARG A | 163 | 61.408 | 20.135 | -0.854 | 1.00 | 45.31 | N |
| ATOM | 918 | CZ | ARG A | 163 | 62.579 | 20.326 | -0.279 | 1.00 | 55.22 | C |
| ATOM | 919 | NH1 | ARG A | 163 | 62.637 | 20.474 | 1.030 | 1.00 | 35.38 | N |
| ATOM | 920 | NH2 | ARG A | 163 | 63.682 | 20.387 | -1.019 | 1.00 | 54.55 | N |
| ATOM | 921 | C | ARG A | 163 | 58.759 | 15.850 | -1.951 | 1.00 | 37.05 | C |
| ATOM | 922 | O | ARG A | 163 | 57.529 | 15.849 | -1.773 | 1.00 | 36.20 | O |
| ATOM | 923 | N | TYR A | 164 | 59.317 | 15.590 | -3.126 | 1.00 | 30.92 | N |
| ATOM | 924 | CA | TYR A | 164 | 58.563 | 15.101 | -4.281 | 1.00 | 29.90 | C |
| ATOM | 925 | CB | TYR A | 164 | 59.558 | 14.744 | -5.385 | 1.00 | 30.19 | C |
| ATOM | 926 | CG | TYR A | 164 | 58.967 | 14.133 | -6.645 | 1.00 | 32.85 | C |
| ATOM | 927 | CD1 | TYR A | 164 | 58.565 | 14.930 | -7.698 | 1.00 | 36.57 | C |
| ATOM | 928 | CE1 | TYR A | 164 | 58.034 | 14.386 | -8.881 | 1.00 | 38.65 | C |
| ATOM | 929 | CD2 | TYR A | 164 | 58.894 | 12.751 | -6.811 | 1.00 | 34.06 | C |
| ATOM | 930 | CE2 | TYR A | 164 | 58.411 | 12.193 | -7.996 | 1.00 | 34.67 | C |
| ATOM | 931 | CZ | TYR A | 164 | 57.979 | 13.024 | -9.032 | 1.00 | 41.98 | C |
| ATOM | 932 | OH | TYR A | 164 | 57.531 | 12.490 | -10.232 | 1.00 | 41.44 | O |
| ATOM | 933 | C | TYR A | 164 | 57.683 | 13.874 | -3.924 | 1.00 | 34.68 | C |
| ATOM | 934 | O | TYR A | 164 | 56.536 | 13.810 | -4.308 | 1.00 | 35.00 | O |
| ATOM | 935 | N | TYR A | 165 | 58.240 | 12.881 | -3.232 | 1.00 | 32.88 | N |
| ATOM | 936 | CA | TYR A | 165 | 57.484 | 11.699 | -2.869 | 1.00 | 33.70 | C |
| ATOM | 937 | CB | TYR A | 165 | 58.382 | 10.522 | -2.500 | 1.00 | 35.32 | C |
| ATOM | 938 | CG | TYR A | 165 | 59.029 | 9.880 | -3.703 | 1.00 | 35.57 | C |
| ATOM | 939 | CD1 | TYR A | 165 | 58.297 | 9.578 | -4.851 | 1.00 | 34.44 | C |
| ATOM | 940 | CE1 | TYR A | 165 | 58.908 | 8.969 | -5.935 | 1.00 | 35.01 | C |
| ATOM | 941 | CD2 | TYR A | 165 | 60.394 | 9.665 | -3.720 | 1.00 | 35.99 | C |
| ATOM | 942 | CE2 | TYR A | 165 | 61.011 | 9.073 | -4.798 | 1.00 | 36.67 | C |
| ATOM | 943 | CZ | TYR A | 165 | 60.278 | 8.728 | -5.895 | 1.00 | 43.80 | C |
| ATOM | 944 | OH | TYR A | 165 | 60.952 | 8.144 | -6.942 | 1.00 | 50.09 | O |

Figure 6-17

| | | Atom Type | Resid | # | X | Y | Z | OCC | B | |
|---|---|---|---|---|---|---|---|---|---|---|
| ATOM | 945 | C | TYR A | 165 | 56.456 | 11.956 | -1.779 | 1.00 | 34.90 | C |
| ATOM | 946 | O | TYR A | 165 | 55.321 | 11.515 | -1.888 | 1.00 | 33.15 | O |
| ATOM | 947 | N | LEU A | 166 | 56.858 | 12.668 | -0.739 | 1.00 | 32.61 | N |
| ATOM | 948 | CA | LEU A | 166 | 55.934 | 12.974 | 0.352 | 1.00 | 32.50 | C |
| ATOM | 949 | CB | LEU A | 166 | 56.622 | 13.727 | 1.475 | 1.00 | 32.47 | C |
| ATOM | 950 | CG | LEU A | 166 | 57.477 | 12.948 | 2.457 | 1.00 | 38.53 | C |
| ATOM | 951 | CD1 | LEU A | 166 | 57.969 | 14.005 | 3.508 | 1.00 | 39.02 | C |
| ATOM | 952 | CD2 | LEU A | 166 | 56.626 | 11.808 | 3.141 | 1.00 | 36.94 | C |
| ATOM | 953 | C | LEU A | 166 | 54.691 | 13.714 | -0.109 | 1.00 | 34.71 | C |
| ATOM | 954 | O | LEU A | 166 | 53.595 | 13.379 | 0.335 | 1.00 | 34.43 | O |
| ATOM | 955 | N | ARG A | 167 | 54.830 | 14.712 | -0.985 | 1.00 | 29.63 | N |
| ATOM | 956 | CA | ARG A | 167 | 53.625 | 15.429 | -1.482 | 1.00 | 30.22 | C |
| ATOM | 957 | CB | ARG A | 167 | 53.948 | 16.430 | -2.618 | 1.00 | 34.49 | C |
| ATOM | 958 | CG | ARG A | 167 | 54.633 | 17.669 | -2.119 | 1.00 | 44.70 | C |
| ATOM | 959 | CD | ARG A | 167 | 54.671 | 18.747 | -3.196 | 1.00 | 54.54 | C |
| ATOM | 960 | NE | ARG A | 167 | 55.502 | 19.857 | -2.748 | 1.00 | 64.45 | N |
| ATOM | 961 | CZ | ARG A | 167 | 55.076 | 20.855 | -1.981 | 1.00 | 68.77 | C |
| ATOM | 962 | NH1 | ARG A | 167 | 53.794 | 20.919 | -1.589 | 1.00 | 44.15 | N |
| ATOM | 963 | NH2 | ARG A | 167 | 55.944 | 21.781 | -1.596 | 1.00 | 47.18 | N |
| ATOM | 964 | C | ARG A | 167 | 52.554 | 14.479 | -2.015 | 1.00 | 29.09 | C |
| ATOM | 965 | O | ARG A | 167 | 51.353 | 14.697 | -1.793 | 1.00 | 25.82 | O |
| ATOM | 966 | N | GLN A | 168 | 52.996 | 13.514 | -2.830 | 1.00 | 25.39 | N |
| ATOM | 967 | CA | GLN A | 168 | 52.125 | 12.485 | -3.393 | 1.00 | 26.08 | C |
| ATOM | 968 | CB | GLN A | 168 | 52.921 | 11.649 | -4.434 | 1.00 | 25.96 | C |
| ATOM | 969 | CG | GLN A | 168 | 53.640 | 12.558 | -5.420 | 1.00 | 28.99 | C |
| ATOM | 970 | CD | GLN A | 168 | 54.197 | 11.825 | -6.615 | 1.00 | 46.14 | C |
| ATOM | 971 | OE1 | GLN A | 168 | 53.484 | 11.095 | -7.316 | 1.00 | 40.45 | O |
| ATOM | 972 | NE2 | GLN A | 168 | 55.456 | 12.071 | -6.904 | 1.00 | 44.48 | N |
| ATOM | 973 | C | GLN A | 168 | 51.530 | 11.565 | -2.301 | 1.00 | 29.55 | C |
| ATOM | 974 | O | GLN A | 168 | 50.382 | 11.185 | -2.390 | 1.00 | 29.08 | O |
| ATOM | 975 | N | ILE A | 169 | 52.350 | 11.122 | -1.343 | 1.00 | 26.34 | N |
| ATOM | 976 | CA | ILE A | 169 | 51.847 | 10.258 | -0.272 | 1.00 | 26.68 | C |
| ATOM | 977 | CB | ILE A | 169 | 52.988 | 9.747 | 0.659 | 1.00 | 27.98 | C |
| ATOM | 978 | CG2 | ILE A | 169 | 52.416 | 8.949 | 1.826 | 1.00 | 28.27 | C |
| ATOM | 979 | CG1 | ILE A | 169 | 53.971 | 8.870 | -0.119 | 1.00 | 23.95 | C |
| ATOM | 980 | CD1 | ILE A | 169 | 55.318 | 8.749 | 0.614 | 1.00 | 22.29 | C |
| ATOM | 981 | C | ILE A | 169 | 50.826 | 11.038 | 0.543 | 1.00 | 31.64 | C |
| ATOM | 982 | O | ILE A | 169 | 49.741 | 10.554 | 0.849 | 1.00 | 33.42 | O |
| ATOM | 983 | N | LEU A | 170 | 51.185 | 12.247 | 0.913 | 1.00 | 30.90 | N |
| ATOM | 984 | CA | LEU A | 170 | 50.289 | 13.090 | 1.698 | 1.00 | 30.18 | C |
| ATOM | 985 | CB | LEU A | 170 | 50.985 | 14.391 | 2.133 | 1.00 | 29.26 | C |
| ATOM | 986 | CG | LEU A | 170 | 52.055 | 14.230 | 3.223 | 1.00 | 31.32 | C |
| ATOM | 987 | CD1 | LEU A | 170 | 52.987 | 15.439 | 3.233 | 1.00 | 31.76 | C |
| ATOM | 988 | CD2 | LEU A | 170 | 51.459 | 13.921 | 4.652 | 1.00 | 30.40 | C |
| ATOM | 989 | C | LEU A | 170 | 48.985 | 13.336 | 0.966 | 1.00 | 33.36 | C |
| ATOM | 990 | O | LEU A | 170 | 47.929 | 13.312 | 1.586 | 1.00 | 32.43 | O |
| ATOM | 991 | N | SER A | 171 | 49.062 | 13.531 | -0.351 | 1.00 | 29.42 | N |
| ATOM | 992 | CA | SER A | 171 | 47.886 | 13.740 | -1.231 | 1.00 | 28.69 | C |
| ATOM | 993 | CB | SER A | 171 | 48.335 | 14.084 | -2.679 | 1.00 | 33.02 | C |
| ATOM | 994 | OG | SER A | 171 | 47.213 | 14.265 | -3.550 | 1.00 | 35.78 | O |
| ATOM | 995 | C | SER A | 171 | 46.957 | 12.505 | -1.278 | 1.00 | 35.17 | C |
| ATOM | 996 | O | SER A | 171 | 45.716 | 12.637 | -1.170 | 1.00 | 32.63 | O |
| ATOM | 997 | N | GLY A | 172 | 47.561 | 11.325 | -1.511 | 1.00 | 31.50 | N |
| ATOM | 998 | CA | GLY A | 172 | 46.873 | 10.038 | -1.492 | 1.00 | 28.93 | C |
| ATOM | 999 | C | GLY A | 172 | 46.269 | 9.800 | -0.098 | 1.00 | 31.18 | C |
| ATOM | 1000 | O | GLY A | 172 | 45.096 | 9.481 | 0.012 | 1.00 | 29.38 | O |
| ATOM | 1001 | N | LEU A | 173 | 47.050 | 10.026 | 0.963 | 1.00 | 28.04 | N |
| ATOM | 1002 | CA | LEU A | 173 | 46.561 | 9.843 | 2.355 | 1.00 | 28.18 | C |
| ATOM | 1003 | CB | LEU A | 173 | 47.677 | 9.914 | 3.410 | 1.00 | 27.93 | C |

Figure 6-18

| | | Atom Type | Resid | # | X | Y | Z | OCC | B | |
|---|---|---|---|---|---|---|---|---|---|---|
| ATOM | 1004 | CG | LEU A | 173 | 47.304 | 9.509 | 4.848 | 1.00 | 31.59 | C |
| ATOM | 1005 | CD1 | LEU A | 173 | 48.504 | 9.823 | 5.792 | 1.00 | 32.52 | C |
| ATOM | 1006 | CD2 | LEU A | 173 | 46.903 | 8.005 | 4.933 | 1.00 | 32.31 | C |
| ATOM | 1007 | C | LEU A | 173 | 45.418 | 10.749 | 2.739 | 1.00 | 30.78 | C |
| ATOM | 1008 | O | LEU A | 173 | 44.560 | 10.357 | 3.502 | 1.00 | 30.00 | O |
| ATOM | 1009 | N | LYS A | 174 | 45.436 | 11.978 | 2.244 | 1.00 | 27.99 | N |
| ATOM | 1010 | CA | LYS A | 174 | 44.370 | 12.929 | 2.521 | 1.00 | 28.97 | C |
| ATOM | 1011 | CB | LYS A | 174 | 44.679 | 14.305 | 1.879 | 1.00 | 31.50 | C |
| ATOM | 1012 | CG | LYS A | 174 | 43.853 | 15.450 | 2.440 | 1.00 | 43.84 | C |
| ATOM | 1013 | CD | LYS A | 174 | 43.773 | 16.612 | 1.469 | 1.00 | 60.50 | C |
| ATOM | 1014 | CE | LYS A | 174 | 45.134 | 16.916 | 0.822 | 1.00 | 89.44 | C |
| ATOM | 1015 | NZ | LYS A | 174 | 45.170 | 16.702 | -0.667 | 1.00 | 97.65 | N |
| ATOM | 1016 | C | LYS A | 174 | 43.037 | 12.413 | 1.972 | 1.00 | 32.17 | C |
| ATOM | 1017 | O | LYS A | 174 | 41.984 | 12.567 | 2.617 | 1.00 | 33.77 | O |
| ATOM | 1018 | N | TYR A | 175 | 43.086 | 11.834 | 0.772 | 1.00 | 24.08 | N |
| ATOM | 1019 | CA | TYR A | 175 | 41.895 | 11.307 | 0.130 | 1.00 | 24.66 | C |
| ATOM | 1020 | CB | TYR A | 175 | 42.216 | 10.914 | -1.308 | 1.00 | 26.81 | C |
| ATOM | 1021 | CG | TYR A | 175 | 41.182 | 10.007 | -1.956 | 1.00 | 29.78 | C |
| ATOM | 1022 | CD1 | TYR A | 175 | 40.088 | 10.552 | -2.647 | 1.00 | 32.49 | C |
| ATOM | 1023 | CE1 | TYR A | 175 | 39.134 | 9.740 | -3.242 | 1.00 | 34.69 | C |
| ATOM | 1024 | CD2 | TYR A | 175 | 41.243 | 8.629 | -1.802 | 1.00 | 29.66 | C |
| ATOM | 1025 | CE2 | TYR A | 175 | 40.299 | 7.791 | -2.413 | 1.00 | 29.03 | C |
| ATOM | 1026 | CZ | TYR A | 175 | 39.232 | 8.364 | -3.097 | 1.00 | 38.56 | C |
| ATOM | 1027 | OH | TYR A | 175 | 38.305 | 7.581 | -3.713 | 1.00 | 42.50 | O |
| ATOM | 1028 | C | TYR A | 175 | 41.364 | 10.138 | 0.932 | 1.00 | 29.04 | C |
| ATOM | 1029 | O | TYR A | 175 | 40.201 | 10.095 | 1.259 | 1.00 | 32.21 | O |
| ATOM | 1030 | N | LEU A | 176 | 42.265 | 9.278 | 1.396 | 1.00 | 26.22 | N |
| ATOM | 1031 | CA | LEU A | 176 | 41.882 | 8.139 | 2.205 | 1.00 | 25.78 | C |
| ATOM | 1032 | CB | LEU A | 176 | 43.094 | 7.307 | 2.612 | 1.00 | 24.76 | C |
| ATOM | 1033 | CG | LEU A | 176 | 43.666 | 6.535 | 1.402 | 1.00 | 29.57 | C |
| ATOM | 1034 | CD1 | LEU A | 176 | 44.896 | 5.790 | 1.854 | 1.00 | 27.48 | C |
| ATOM | 1035 | CD2 | LEU A | 176 | 42.637 | 5.558 | 0.829 | 1.00 | 32.84 | C |
| ATOM | 1036 | C | LEU A | 176 | 41.146 | 8.601 | 3.435 | 1.00 | 27.98 | C |
| ATOM | 1037 | O | LEU A | 176 | 40.057 | 8.137 | 3.726 | 1.00 | 27.76 | O |
| ATOM | 1038 | N | HIS A | 177 | 41.755 | 9.551 | 4.134 | 1.00 | 23.54 | N |
| ATOM | 1039 | CA | HIS A | 177 | 41.190 | 10.061 | 5.379 | 1.00 | 24.29 | C |
| ATOM | 1040 | CB | HIS A | 177 | 42.171 | 11.001 | 6.104 | 1.00 | 24.01 | C |
| ATOM | 1041 | CG | HIS A | 177 | 43.307 | 10.311 | 6.801 | 1.00 | 25.85 | C |
| ATOM | 1042 | CD2 | HIS A | 177 | 44.262 | 10.803 | 7.623 | 1.00 | 26.38 | C |
| ATOM | 1043 | ND1 | HIS A | 177 | 43.540 | 8.959 | 6.717 | 1.00 | 27.20 | N |
| ATOM | 1044 | CE1 | HIS A | 177 | 44.606 | 8.650 | 7.432 | 1.00 | 25.49 | C |
| ATOM | 1045 | NE2 | HIS A | 177 | 45.075 | 9.762 | 7.968 | 1.00 | 26.91 | N |
| ATOM | 1046 | C | HIS A | 177 | 39.855 | 10.768 | 5.141 | 1.00 | 31.00 | C |
| ATOM | 1047 | O | HIS A | 177 | 38.944 | 10.669 | 5.964 | 1.00 | 32.16 | O |
| ATOM | 1048 | N | GLN A | 178 | 39.747 | 11.472 | 4.017 | 1.00 | 29.66 | N |
| ATOM | 1049 | CA | GLN A | 178 | 38.520 | 12.160 | 3.647 | 1.00 | 30.17 | C |
| ATOM | 1050 | CB | GLN A | 178 | 38.719 | 13.014 | 2.400 | 1.00 | 31.02 | C |
| ATOM | 1051 | CG | GLN A | 178 | 39.410 | 14.343 | 2.694 | 1.00 | 44.39 | C |
| ATOM | 1052 | CD | GLN A | 178 | 39.766 | 15.098 | 1.439 | 1.00 | 45.23 | C |
| ATOM | 1053 | OE1 | GLN A | 178 | 39.942 | 16.307 | 1.479 | 1.00 | 57.59 | O |
| ATOM | 1054 | NE2 | GLN A | 178 | 39.865 | 14.389 | 0.310 | 1.00 | 37.04 | N |
| ATOM | 1055 | C | GLN A | 178 | 37.393 | 11.159 | 3.420 | 1.00 | 33.49 | C |
| ATOM | 1056 | O | GLN A | 178 | 36.218 | 11.483 | 3.639 | 1.00 | 33.76 | O |
| ATOM | 1057 | N | ARG A | 179 | 37.769 | 9.955 | 2.988 | 1.00 | 29.34 | N |
| ATOM | 1058 | CA | ARG A | 179 | 36.852 | 8.835 | 2.786 | 1.00 | 29.44 | C |
| ATOM | 1059 | CB | ARG A | 179 | 37.420 | 7.857 | 1.733 | 1.00 | 29.73 | C |
| ATOM | 1060 | CG | ARG A | 179 | 37.361 | 8.350 | 0.285 | 1.00 | 38.10 | C |
| ATOM | 1061 | CD | ARG A | 179 | 35.921 | 8.565 | -0.157 | 1.00 | 49.66 | C |
| ATOM | 1062 | NE | ARG A | 179 | 35.235 | 7.335 | -0.569 | 1.00 | 52.51 | N |

Figure 6-19

| | | Atom Type | Resid | # | X | Y | Z | OCC | B | |
|---|---|---|---|---|---|---|---|---|---|---|
| ATOM | 1063 | CZ | ARG A | 179 | 35.511 | 6.672 | -1.694 | 1.00 | 72.71 | C |
| ATOM | 1064 | NH1 | ARG A | 179 | 36.450 | 7.104 | -2.516 | 1.00 | 75.37 | N |
| ATOM | 1065 | NH2 | ARG A | 179 | 34.838 | 5.589 | -2.023 | 1.00 | 50.58 | N |
| ATOM | 1066 | C | ARG A | 179 | 36.545 | 8.063 | 4.077 | 1.00 | 30.34 | C |
| ATOM | 1067 | O | ARG A | 179 | 35.757 | 7.137 | 4.055 | 1.00 | 32.28 | O |
| ATOM | 1068 | N | GLY A | 180 | 37.127 | 8.453 | 5.212 | 1.00 | 26.22 | N |
| ATOM | 1069 | CA | GLY A | 180 | 36.887 | 7.768 | 6.463 | 1.00 | 24.05 | C |
| ATOM | 1070 | C | GLY A | 180 | 37.721 | 6.487 | 6.637 | 1.00 | 29.90 | C |
| ATOM | 1071 | O | GLY A | 180 | 37.439 | 5.654 | 7.501 | 1.00 | 30.29 | O |
| ATOM | 1072 | N | ILE A | 181 | 38.784 | 6.355 | 5.856 | 1.00 | 27.98 | N |
| ATOM | 1073 | CA | ILE A | 181 | 39.638 | 5.139 | 5.837 | 1.00 | 28.08 | C |
| ATOM | 1074 | CB | ILE A | 181 | 39.740 | 4.594 | 4.336 | 1.00 | 32.90 | C |
| ATOM | 1075 | CG2 | ILE A | 181 | 40.630 | 3.338 | 4.215 | 1.00 | 30.65 | C |
| ATOM | 1076 | CG1 | ILE A | 181 | 38.371 | 4.246 | 3.750 | 1.00 | 35.41 | C |
| ATOM | 1077 | CD1 | ILE A | 181 | 37.609 | 3.236 | 4.591 | 1.00 | 33.07 | C |
| ATOM | 1078 | C | ILE A | 181 | 41.081 | 5.417 | 6.364 | 1.00 | 25.96 | C |
| ATOM | 1079 | O | ILE A | 181 | 41.748 | 6.342 | 5.907 | 1.00 | 27.75 | O |
| ATOM | 1080 | N | LEU A | 182 | 41.564 | 4.566 | 7.272 | 1.00 | 24.43 | N |
| ATOM | 1081 | CA | LEU A | 182 | 42.942 | 4.596 | 7.775 | 1.00 | 24.39 | C |
| ATOM | 1082 | CB | LEU A | 182 | 43.017 | 4.208 | 9.269 | 1.00 | 24.24 | C |
| ATOM | 1083 | CG | LEU A | 182 | 42.097 | 5.079 | 10.121 | 1.00 | 27.69 | C |
| ATOM | 1084 | CD1 | LEU A | 182 | 42.292 | 4.661 | 11.591 | 1.00 | 29.26 | C |
| ATOM | 1085 | CD2 | LEU A | 182 | 42.426 | 6.531 | 9.938 | 1.00 | 26.57 | C |
| ATOM | 1086 | C | LEU A | 182 | 43.662 | 3.522 | 7.011 | 1.00 | 27.27 | C |
| ATOM | 1087 | O | LEU A | 182 | 43.098 | 2.455 | 6.768 | 1.00 | 28.29 | O |
| ATOM | 1088 | N | HIS A | 183 | 44.892 | 3.807 | 6.603 | 1.00 | 25.13 | N |
| ATOM | 1089 | CA | HIS A | 183 | 45.645 | 2.824 | 5.851 | 1.00 | 26.30 | C |
| ATOM | 1090 | CB | HIS A | 183 | 46.737 | 3.550 | 5.083 | 1.00 | 25.53 | C |
| ATOM | 1091 | CG | HIS A | 183 | 47.555 | 2.641 | 4.241 | 1.00 | 27.02 | C |
| ATOM | 1092 | CD2 | HIS A | 183 | 47.524 | 2.390 | 2.911 | 1.00 | 26.97 | C |
| ATOM | 1093 | ND1 | HIS A | 183 | 48.534 | 1.831 | 4.770 | 1.00 | 26.88 | N |
| ATOM | 1094 | CE1 | HIS A | 183 | 49.044 | 1.085 | 3.802 | 1.00 | 26.33 | C |
| ATOM | 1095 | NE2 | HIS A | 183 | 48.489 | 1.445 | 2.661 | 1.00 | 26.68 | N |
| ATOM | 1096 | C | HIS A | 183 | 46.265 | 1.845 | 6.856 | 1.00 | 28.39 | C |
| ATOM | 1097 | O | HIS A | 183 | 46.250 | 0.635 | 6.677 | 1.00 | 24.52 | O |
| ATOM | 1098 | N | ARG A | 184 | 46.844 | 2.430 | 7.894 | 1.00 | 30.22 | N |
| ATOM | 1099 | CA | ARG A | 184 | 47.498 | 1.723 | 8.997 | 1.00 | 31.86 | C |
| ATOM | 1100 | CB | ARG A | 184 | 46.513 | 1.153 | 10.003 | 1.00 | 36.89 | C |
| ATOM | 1101 | CG | ARG A | 184 | 45.536 | 0.263 | 9.446 | 1.00 | 42.32 | C |
| ATOM | 1102 | CD | ARG A | 184 | 44.228 | 0.567 | 10.112 | 1.00 | 38.80 | C |
| ATOM | 1103 | NE | ARG A | 184 | 44.114 | -0.002 | 11.436 | 1.00 | 42.46 | N |
| ATOM | 1104 | CZ | ARG A | 184 | 43.806 | -1.269 | 11.749 | 1.00 | 57.31 | C |
| ATOM | 1105 | NH1 | ARG A | 184 | 43.647 | -2.208 | 10.831 | 1.00 | 40.68 | N |
| ATOM | 1106 | NH2 | ARG A | 184 | 43.647 | -1.598 | 13.033 | 1.00 | 35.24 | N |
| ATOM | 1107 | C | ARG A | 184 | 48.687 | 0.807 | 8.746 | 1.00 | 32.92 | C |
| ATOM | 1108 | O | ARG A | 184 | 49.167 | 0.096 | 9.640 | 1.00 | 34.69 | O |
| ATOM | 1109 | N | ASP A | 185 | 49.255 | 0.915 | 7.561 | 1.00 | 28.97 | N |
| ATOM | 1110 | CA | ASP A | 185 | 50.460 | 0.169 | 7.282 | 1.00 | 31.00 | C |
| ATOM | 1111 | CB | ASP A | 185 | 50.176 | -1.241 | 6.765 | 1.00 | 33.38 | C |
| ATOM | 1112 | CG | ASP A | 185 | 51.383 | -2.168 | 6.921 | 1.00 | 43.37 | C |
| ATOM | 1113 | OD1 | ASP A | 185 | 52.277 | -1.834 | 7.727 | 1.00 | 42.20 | O |
| ATOM | 1114 | OD2 | ASP A | 185 | 51.425 | -3.222 | 6.243 | 1.00 | 42.89 | O |
| ATOM | 1115 | C | ASP A | 185 | 51.320 | 0.919 | 6.297 | 1.00 | 34.54 | C |
| ATOM | 1116 | O | ASP A | 185 | 51.860 | 0.324 | 5.379 | 1.00 | 32.88 | O |
| ATOM | 1117 | N | LEU A | 186 | 51.428 | 2.227 | 6.472 | 1.00 | 31.92 | N |
| ATOM | 1118 | CA | LEU A | 186 | 52.253 | 3.010 | 5.562 | 1.00 | 31.52 | C |
| ATOM | 1119 | CB | LEU A | 186 | 51.868 | 4.489 | 5.623 | 1.00 | 30.80 | C |
| ATOM | 1120 | CG | LEU A | 186 | 50.416 | 4.905 | 5.505 | 1.00 | 32.19 | C |
| ATOM | 1121 | CD1 | LEU A | 186 | 50.240 | 6.198 | 6.291 | 1.00 | 31.03 | C |

Figure 6-20

| | Atom Type | Resid | # | X | Y | Z | OCC | B | |
|---|---|---|---|---|---|---|---|---|---|
| ATOM | 1122 | CD2 | LEU A 186 | 50.041 | 5.081 | 4.032 | 1.00 | 30.87 | C |
| ATOM | 1123 | C | LEU A 186 | 53.753 | 2.824 | 5.817 | 1.00 | 34.08 | C |
| ATOM | 1124 | O | LEU A 186 | 54.257 | 3.108 | 6.900 | 1.00 | 35.85 | O |
| ATOM | 1125 | N | LYS A 187 | 54.452 | 2.357 | 4.788 | 1.00 | 29.17 | N |
| ATOM | 1126 | CA | LYS A 187 | 55.869 | 2.106 | 4.854 | 1.00 | 27.74 | C |
| ATOM | 1127 | CB | LYS A 187 | 56.125 | 0.782 | 5.574 | 1.00 | 31.34 | C |
| ATOM | 1128 | CG | LYS A 187 | 55.455 | -0.403 | 4.940 | 1.00 | 33.41 | C |
| ATOM | 1129 | CD | LYS A 187 | 55.842 | -1.658 | 5.694 | 1.00 | 39.90 | C |
| ATOM | 1130 | CE | LYS A 187 | 55.113 | -2.849 | 5.144 | 1.00 | 47.94 | C |
| ATOM | 1131 | NZ | LYS A 187 | 55.966 | -4.070 | 5.200 | 1.00 | 45.14 | N |
| ATOM | 1132 | C | LYS A 187 | 56.297 | 2.068 | 3.397 | 1.00 | 32.54 | C |
| ATOM | 1133 | O | LYS A 187 | 55.460 | 2.010 | 2.500 | 1.00 | 29.91 | O |
| ATOM | 1134 | N | LEU A 188 | 57.590 | 2.155 | 3.153 | 1.00 | 30.94 | N |
| ATOM | 1135 | CA | LEU A 188 | 58.104 | 2.190 | 1.802 | 1.00 | 31.49 | C |
| ATOM | 1136 | CB | LEU A 188 | 59.633 | 2.140 | 1.833 | 1.00 | 31.16 | C |
| ATOM | 1137 | CG | LEU A 188 | 60.359 | 3.191 | 2.678 | 1.00 | 33.98 | C |
| ATOM | 1138 | CD1 | LEU A 188 | 61.825 | 3.133 | 2.324 | 1.00 | 34.15 | C |
| ATOM | 1139 | CD2 | LEU A 188 | 59.795 | 4.612 | 2.447 | 1.00 | 33.48 | C |
| ATOM | 1140 | C | LEU A 188 | 57.549 | 1.127 | 0.860 | 1.00 | 37.30 | C |
| ATOM | 1141 | O | LEU A 188 | 57.332 | 1.378 | -0.328 | 1.00 | 38.51 | O |
| ATOM | 1142 | N | GLY A 189 | 57.345 | -0.068 | 1.392 | 1.00 | 35.10 | N |
| ATOM | 1143 | CA | GLY A 189 | 56.867 | -1.207 | 0.633 | 1.00 | 35.02 | C |
| ATOM | 1144 | C | GLY A 189 | 55.456 | -1.104 | 0.101 | 1.00 | 36.55 | C |
| ATOM | 1145 | O | GLY A 189 | 55.092 | -1.863 | -0.810 | 1.00 | 36.94 | O |
| ATOM | 1146 | N | ASN A 190 | 54.689 | -0.132 | 0.606 | 1.00 | 27.20 | N |
| ATOM | 1147 | CA | ASN A 190 | 53.309 | 0.063 | 0.173 | 1.00 | 25.16 | C |
| ATOM | 1148 | CB | ASN A 190 | 52.361 | 0.081 | 1.390 | 1.00 | 28.48 | C |
| ATOM | 1149 | CG | ASN A 190 | 52.426 | -1.204 | 2.204 | 1.00 | 41.42 | C |
| ATOM | 1150 | OD1 | ASN A 190 | 52.719 | -2.264 | 1.682 | 1.00 | 36.00 | O |
| ATOM | 1151 | ND2 | ASN A 190 | 52.133 | -1.110 | 3.485 | 1.00 | 36.15 | N |
| ATOM | 1152 | C | ASN A 190 | 53.094 | 1.279 | -0.715 | 1.00 | 29.88 | C |
| ATOM | 1153 | O | ASN A 190 | 51.962 | 1.693 | -0.923 | 1.00 | 31.03 | O |
| ATOM | 1154 | N | PHE A 191 | 54.180 | 1.861 | -1.237 | 1.00 | 28.01 | N |
| ATOM | 1155 | CA | PHE A 191 | 54.105 | 3.036 | -2.134 | 1.00 | 26.87 | C |
| ATOM | 1156 | CB | PHE A 191 | 54.983 | 4.194 | -1.566 | 1.00 | 27.69 | C |
| ATOM | 1157 | CG | PHE A 191 | 54.571 | 4.669 | -0.188 | 1.00 | 29.12 | C |
| ATOM | 1158 | CD1 | PHE A 191 | 55.519 | 4.908 | 0.797 | 1.00 | 30.64 | C |
| ATOM | 1159 | CD2 | PHE A 191 | 53.220 | 4.820 | 0.142 | 1.00 | 31.12 | C |
| ATOM | 1160 | CE1 | PHE A 191 | 55.127 | 5.300 | 2.096 | 1.00 | 30.13 | C |
| ATOM | 1161 | CE2 | PHE A 191 | 52.836 | 5.173 | 1.437 | 1.00 | 32.99 | C |
| ATOM | 1162 | CZ | PHE A 191 | 53.794 | 5.422 | 2.403 | 1.00 | 30.12 | C |
| ATOM | 1163 | C | PHE A 191 | 54.696 | 2.537 | -3.462 | 1.00 | 35.43 | C |
| ATOM | 1164 | O | PHE A 191 | 55.812 | 2.080 | -3.478 | 1.00 | 38.67 | O |
| ATOM | 1165 | N | PHE A 192 | 53.944 | 2.589 | -4.557 | 1.00 | 34.19 | N |
| ATOM | 1166 | CA | PHE A 192 | 54.398 | 2.034 | -5.851 | 1.00 | 33.52 | C |
| ATOM | 1167 | CB | PHE A 192 | 53.471 | 0.888 | -6.302 | 1.00 | 34.62 | C |
| ATOM | 1168 | CG | PHE A 192 | 53.131 | -0.078 | -5.186 | 1.00 | 35.66 | C |
| ATOM | 1169 | CD1 | PHE A 192 | 51.895 | -0.070 | -4.583 | 1.00 | 37.22 | C |
| ATOM | 1170 | CD2 | PHE A 192 | 54.075 | -0.954 | -4.700 | 1.00 | 38.81 | C |
| ATOM | 1171 | CE1 | PHE A 192 | 51.605 | -0.934 | -3.553 | 1.00 | 37.52 | C |
| ATOM | 1172 | CE2 | PHE A 192 | 53.763 | -1.841 | -3.635 | 1.00 | 40.25 | C |
| ATOM | 1173 | CZ | PHE A 192 | 52.571 | -1.779 | -3.040 | 1.00 | 36.23 | C |
| ATOM | 1174 | C | PHE A 192 | 54.580 | 3.106 | -6.912 | 1.00 | 37.40 | C |
| ATOM | 1175 | O | PHE A 192 | 53.833 | 4.096 | -6.945 | 1.00 | 34.06 | O |
| ATOM | 1176 | N | ILE A 193 | 55.651 | 2.970 | -7.689 | 1.00 | 34.63 | N |
| ATOM | 1177 | CA | ILE A 193 | 56.021 | 3.992 | -8.654 | 1.00 | 34.14 | C |
| ATOM | 1178 | CB | ILE A 193 | 57.545 | 4.293 | -8.544 | 1.00 | 36.96 | C |
| ATOM | 1179 | CG2 | ILE A 193 | 57.927 | 5.478 | -9.429 | 1.00 | 39.92 | C |
| ATOM | 1180 | CG1 | ILE A 193 | 58.003 | 4.461 | -7.072 | 1.00 | 35.98 | C |

Figure 6-21

| | | Atom Type | Resid | # | X | Y | Z | OCC | B | |
|---|---|---|---|---|---|---|---|---|---|---|
| ATOM | 1181 | CD1 | ILE A | 193 | 57.162 | 5.502 | -6.255 | 1.00 | 31.81 | C |
| ATOM | 1182 | C | ILE A | 193 | 55.659 | 3.607 | -10.088 | 1.00 | 35.73 | C |
| ATOM | 1183 | O | ILE A | 193 | 56.071 | 2.584 | -10.572 | 1.00 | 33.83 | O |
| ATOM | 1184 | N | THR A | 194 | 54.946 | 4.464 | -10.788 | 1.00 | 35.47 | N |
| ATOM | 1185 | CA | THR A | 194 | 54.602 | 4.170 | -12.167 | 1.00 | 36.11 | C |
| ATOM | 1186 | CB | THR A | 194 | 53.354 | 4.955 | -12.634 | 1.00 | 44.56 | C |
| ATOM | 1187 | OG1 | THR A | 194 | 53.680 | 6.349 | -12.692 | 1.00 | 48.90 | O |
| ATOM | 1188 | CG2 | THR A | 194 | 52.164 | 4.744 | -11.669 | 1.00 | 39.89 | C |
| ATOM | 1189 | C | THR A | 194 | 55.788 | 4.425 | -13.110 | 1.00 | 42.75 | C |
| ATOM | 1190 | O | THR A | 194 | 56.890 | 4.825 | -12.688 | 1.00 | 40.44 | O |
| ATOM | 1191 | N | GLU A | 195 | 55.535 | 4.199 | -14.399 | 1.00 | 42.13 | N |
| ATOM | 1192 | CA | GLU A | 195 | 56.521 | 4.431 | -15.465 | 1.00 | 41.37 | C |
| ATOM | 1193 | CB | GLU A | 195 | 55.907 | 4.007 | -16.813 | 1.00 | 42.38 | C |
| ATOM | 1194 | CG | GLU A | 195 | 56.729 | 4.410 | -18.047 | 1.00 | 51.92 | C |
| ATOM | 1195 | CD | GLU A | 195 | 57.892 | 3.473 | -18.301 | 1.00 | 63.62 | C |
| ATOM | 1196 | OE1 | GLU A | 195 | 57.860 | 2.344 | -17.761 | 1.00 | 59.86 | O |
| ATOM | 1197 | OE2 | GLU A | 195 | 58.825 | 3.858 | -19.045 | 1.00 | 63.11 | O |
| ATOM | 1198 | C | GLU A | 195 | 56.861 | 5.928 | -15.480 | 1.00 | 46.09 | C |
| ATOM | 1199 | O | GLU A | 195 | 58.032 | 6.303 | -15.504 | 1.00 | 46.36 | O |
| ATOM | 1200 | N | ASN A | 196 | 55.817 | 6.763 | -15.446 | 1.00 | 43.34 | N |
| ATOM | 1201 | CA | ASN A | 196 | 55.920 | 8.233 | -15.453 | 1.00 | 43.07 | C |
| ATOM | 1202 | CB | ASN A | 196 | 54.603 | 8.863 | -15.937 | 1.00 | 45.61 | C |
| ATOM | 1203 | CG | ASN A | 196 | 54.203 | 8.384 | -17.341 | 1.00 | 93.07 | C |
| ATOM | 1204 | OD1 | ASN A | 196 | 53.723 | 7.258 | -17.514 | 1.00 | 96.34 | O |
| ATOM | 1205 | ND2 | ASN A | 196 | 54.421 | 9.230 | -18.349 | 1.00 | 83.02 | N |
| ATOM | 1206 | C | ASN A | 196 | 56.345 | 8.858 | -14.111 | 1.00 | 43.63 | C |
| ATOM | 1207 | O | ASN A | 196 | 56.178 | 10.064 | -13.899 | 1.00 | 45.56 | O |
| ATOM | 1208 | N | MET A | 197 | 56.909 | 8.043 | -13.231 | 1.00 | 38.29 | N |
| ATOM | 1209 | CA | MET A | 197 | 57.430 | 8.497 | -11.930 | 1.00 | 39.36 | C |
| ATOM | 1210 | CB | MET A | 197 | 58.553 | 9.525 | -12.130 | 1.00 | 41.79 | C |
| ATOM | 1211 | CG | MET A | 197 | 59.861 | 8.928 | -12.730 | 1.00 | 45.24 | C |
| ATOM | 1212 | SD | MET A | 197 | 60.301 | 7.225 | -12.183 | 1.00 | 47.43 | S |
| ATOM | 1213 | CE | MET A | 197 | 61.521 | 7.507 | -10.916 | 1.00 | 41.68 | C |
| ATOM | 1214 | C | MET A | 197 | 56.381 | 9.015 | -10.933 | 1.00 | 42.96 | C |
| ATOM | 1215 | O | MET A | 197 | 56.689 | 9.832 | -10.047 | 1.00 | 43.36 | O |
| ATOM | 1216 | N | GLU A | 198 | 55.140 | 8.574 | -11.105 | 1.00 | 36.94 | N |
| ATOM | 1217 | CA | GLU A | 198 | 54.067 | 8.962 | -10.206 | 1.00 | 36.08 | C |
| ATOM | 1218 | CB | GLU A | 198 | 52.754 | 9.125 | -10.966 | 1.00 | 37.09 | C |
| ATOM | 1219 | CG | GLU A | 198 | 51.609 | 9.709 | -10.133 | 1.00 | 53.45 | C |
| ATOM | 1220 | CD | GLU A | 198 | 50.332 | 9.900 | -10.940 | 1.00 | 73.02 | C |
| ATOM | 1221 | OE1 | GLU A | 198 | 50.182 | 9.260 | -12.009 | 1.00 | 88.00 | O |
| ATOM | 1222 | OE2 | GLU A | 198 | 49.476 | 10.691 | -10.506 | 1.00 | 60.90 | O |
| ATOM | 1223 | C | GLU A | 198 | 53.965 | 7.918 | -9.084 | 1.00 | 40.14 | C |
| ATOM | 1224 | O | GLU A | 198 | 54.218 | 6.744 | -9.303 | 1.00 | 39.83 | O |
| ATOM | 1225 | N | LEU A | 199 | 53.673 | 8.358 | -7.858 | 1.00 | 35.06 | N |
| ATOM | 1226 | CA | LEU A | 199 | 53.580 | 7.419 | -6.744 | 1.00 | 32.90 | C |
| ATOM | 1227 | CB | LEU A | 199 | 54.236 | 8.023 | -5.483 | 1.00 | 31.22 | C |
| ATOM | 1228 | CG | LEU A | 199 | 54.224 | 7.288 | -4.138 | 1.00 | 31.50 | C |
| ATOM | 1229 | CD1 | LEU A | 199 | 52.863 | 7.528 | -3.391 | 1.00 | 30.52 | C |
| ATOM | 1230 | CD2 | LEU A | 199 | 55.426 | 7.764 | -3.278 | 1.00 | 28.06 | C |
| ATOM | 1231 | C | LEU A | 199 | 52.109 | 7.093 | -6.491 | 1.00 | 37.14 | C |
| ATOM | 1232 | O | LEU A | 199 | 51.253 | 7.977 | -6.558 | 1.00 | 36.14 | O |
| ATOM | 1233 | N | LYS A | 200 | 51.820 | 5.822 | -6.224 | 1.00 | 34.62 | N |
| ATOM | 1234 | CA | LYS A | 200 | 50.458 | 5.386 | -5.881 | 1.00 | 33.37 | C |
| ATOM | 1235 | CB | LYS A | 200 | 49.839 | 4.517 | -6.981 | 1.00 | 36.96 | C |
| ATOM | 1236 | CG | LYS A | 200 | 50.074 | 5.030 | -8.406 | 1.00 | 37.45 | C |
| ATOM | 1237 | CD | LYS A | 200 | 48.860 | 5.662 | -8.955 | 1.00 | 44.70 | C |
| ATOM | 1238 | CE | LYS A | 200 | 49.196 | 6.415 | -10.238 | 1.00 | 38.66 | C |
| ATOM | 1239 | NZ | LYS A | 200 | 47.954 | 6.903 | -10.870 | 1.00 | 38.23 | N |

Figure 6-22

| | | Atom Type | Resid | # | X | Y | Z | OCC | B | |
|---|---|---|---|---|---|---|---|---|---|---|
| ATOM | 1240 | C | LYS A | 200 | 50.501 | 4.606 | -4.583 | 1.00 | 32.87 | C |
| ATOM | 1241 | O | LYS A | 200 | 51.337 | 3.726 | -4.406 | 1.00 | 31.53 | O |
| ATOM | 1242 | N | VAL A | 201 | 49.679 | 4.986 | -3.618 | 1.00 | 31.78 | N |
| ATOM | 1243 | CA | VAL A | 201 | 49.677 | 4.208 | -2.377 | 1.00 | 30.80 | C |
| ATOM | 1244 | CB | VAL A | 201 | 49.564 | 5.033 | -1.020 | 1.00 | 34.42 | C |
| ATOM | 1245 | CG1 | VAL A | 201 | 49.405 | 6.504 | -1.186 | 1.00 | 35.44 | C |
| ATOM | 1246 | CG2 | VAL A | 201 | 48.706 | 4.406 | 0.054 | 1.00 | 32.59 | C |
| ATOM | 1247 | C | VAL A | 201 | 48.819 | 2.957 | -2.548 | 1.00 | 31.73 | C |
| ATOM | 1248 | O | VAL A | 201 | 47.811 | 2.981 | -3.234 | 1.00 | 29.68 | O |
| ATOM | 1249 | N | GLY A | 202 | 49.309 | 1.814 | -2.086 | 1.00 | 31.76 | N |
| ATOM | 1250 | CA | GLY A | 202 | 48.541 | 0.602 | -2.232 | 1.00 | 31.47 | C |
| ATOM | 1251 | C | GLY A | 202 | 48.622 | -0.222 | -0.968 | 1.00 | 33.81 | C |
| ATOM | 1252 | O | GLY A | 202 | 49.093 | 0.253 | 0.097 | 1.00 | 28.03 | O |
| ATOM | 1253 | N | ASP A | 203 | 48.268 | -1.486 | -1.159 | 1.00 | 32.26 | N |
| ATOM | 1254 | CA | ASP A | 203 | 48.284 | -2.504 | -0.136 | 1.00 | 32.90 | C |
| ATOM | 1255 | CB | ASP A | 203 | 49.705 | -2.920 | 0.287 | 1.00 | 36.06 | C |
| ATOM | 1256 | CG | ASP A | 203 | 50.419 | -3.823 | -0.770 | 1.00 | 54.81 | C |
| ATOM | 1257 | OD1 | ASP A | 203 | 49.755 | -4.504 | -1.595 | 1.00 | 55.05 | O |
| ATOM | 1258 | OD2 | ASP A | 203 | 51.669 | -3.882 | -0.756 | 1.00 | 65.07 | O |
| ATOM | 1259 | C | ASP A | 203 | 47.307 | -2.211 | 0.989 | 1.00 | 32.98 | C |
| ATOM | 1260 | O | ASP A | 203 | 47.647 | -1.736 | 2.083 | 1.00 | 30.18 | O |
| ATOM | 1261 | N | PHE A | 204 | 46.039 | -2.372 | 0.653 | 1.00 | 30.01 | N |
| ATOM | 1262 | CA | PHE A | 204 | 44.964 | -2.107 | 1.624 | 1.00 | 30.03 | C |
| ATOM | 1263 | CB | PHE A | 204 | 43.757 | -1.511 | 0.895 | 1.00 | 30.91 | C |
| ATOM | 1264 | CG | PHE A | 204 | 44.049 | -0.138 | 0.353 | 1.00 | 30.94 | C |
| ATOM | 1265 | CD1 | PHE A | 204 | 44.669 | 0.009 | -0.884 | 1.00 | 30.89 | C |
| ATOM | 1266 | CD2 | PHE A | 204 | 43.970 | 0.978 | 1.185 | 1.00 | 32.13 | C |
| ATOM | 1267 | CE1 | PHE A | 204 | 44.978 | 1.265 | -1.379 | 1.00 | 29.96 | C |
| ATOM | 1268 | CE2 | PHE A | 204 | 44.339 | 2.240 | 0.709 | 1.00 | 32.04 | C |
| ATOM | 1269 | CZ | PHE A | 204 | 44.844 | 2.365 | -0.589 | 1.00 | 28.88 | C |
| ATOM | 1270 | C | PHE A | 204 | 44.605 | -3.258 | 2.598 | 1.00 | 34.57 | C |
| ATOM | 1271 | O | PHE A | 204 | 43.557 | -3.251 | 3.220 | 1.00 | 35.48 | O |
| ATOM | 1272 | N | GLY A | 205 | 45.493 | -4.232 | 2.736 | 1.00 | 31.53 | N |
| ATOM | 1273 | CA | GLY A | 205 | 45.217 | -5.392 | 3.580 | 1.00 | 32.59 | C |
| ATOM | 1274 | C | GLY A | 205 | 44.956 | -5.134 | 5.054 | 1.00 | 36.55 | C |
| ATOM | 1275 | O | GLY A | 205 | 44.319 | -5.920 | 5.740 | 1.00 | 37.53 | O |
| ATOM | 1276 | N | LEU A | 206 | 45.490 | -4.041 | 5.545 | 1.00 | 35.78 | N |
| ATOM | 1277 | CA | LEU A | 206 | 45.357 | -3.617 | 6.955 | 1.00 | 35.64 | C |
| ATOM | 1278 | CB | LEU A | 206 | 46.765 | -3.234 | 7.414 | 1.00 | 37.76 | C |
| ATOM | 1279 | CG | LEU A | 206 | 47.499 | -3.722 | 8.652 | 1.00 | 45.37 | C |
| ATOM | 1280 | CD1 | LEU A | 206 | 46.649 | -3.611 | 9.886 | 1.00 | 48.25 | C |
| ATOM | 1281 | CD2 | LEU A | 206 | 48.255 | -5.052 | 8.518 | 1.00 | 46.57 | C |
| ATOM | 1282 | C | LEU A | 206 | 44.449 | -2.373 | 7.052 | 1.00 | 31.43 | C |
| ATOM | 1283 | O | LEU A | 206 | 44.263 | -1.802 | 8.135 | 1.00 | 28.41 | O |
| ATOM | 1284 | N | ALA A | 207 | 43.934 | -1.887 | 5.918 | 1.00 | 26.48 | N |
| ATOM | 1285 | CA | ALA A | 207 | 43.076 | -0.692 | 5.975 | 1.00 | 25.54 | C |
| ATOM | 1286 | CB | ALA A | 207 | 42.611 | -0.242 | 4.573 | 1.00 | 25.05 | C |
| ATOM | 1287 | C | ALA A | 207 | 41.862 | -0.917 | 6.911 | 1.00 | 32.42 | C |
| ATOM | 1288 | O | ALA A | 207 | 41.400 | -2.052 | 7.093 | 1.00 | 31.25 | O |
| ATOM | 1289 | N | ALA A | 208 | 41.355 | 0.182 | 7.479 | 1.00 | 30.12 | N |
| ATOM | 1290 | CA | ALA A | 208 | 40.151 | 0.175 | 8.307 | 1.00 | 30.66 | C |
| ATOM | 1291 | CB | ALA A | 208 | 40.429 | -0.197 | 9.764 | 1.00 | 30.99 | C |
| ATOM | 1292 | C | ALA A | 208 | 39.363 | 1.460 | 8.259 | 1.00 | 34.19 | C |
| ATOM | 1293 | O | ALA A | 208 | 39.902 | 2.550 | 8.122 | 1.00 | 33.05 | O |
| ATOM | 1294 | N | ARG A | 209 | 38.065 | 1.298 | 8.487 | 1.00 | 32.62 | N |
| ATOM | 1295 | CA | ARG A | 209 | 37.159 | 2.403 | 8.619 | 1.00 | 32.22 | C |
| ATOM | 1296 | CB | ARG A | 209 | 35.733 | 1.883 | 8.691 | 1.00 | 29.00 | C |
| ATOM | 1297 | CG | ARG A | 209 | 35.336 | 1.228 | 7.343 | 1.00 | 44.87 | C |
| ATOM | 1298 | CD | ARG A | 209 | 33.894 | 0.703 | 7.395 | 1.00 | 53.87 | C |

Figure 6-23

| | | Atom Type | Resid | # | X | Y | Z | OCC | B | |
|---|---|---|---|---|---|---|---|---|---|---|
| ATOM | 1299 | NE  | ARG A | 209 | 33.568 | -0.142 | 6.246  | 1.00 | 68.41  | N |
| ATOM | 1300 | CZ  | ARG A | 209 | 34.211 | -1.259 | 5.906  | 1.00 | 80.82  | C |
| ATOM | 1301 | NH1 | ARG A | 209 | 35.265 | -1.689 | 6.597  | 1.00 | 64.72  | N |
| ATOM | 1302 | NH2 | ARG A | 209 | 33.809 | -1.935 | 4.843  | 1.00 | 64.93  | N |
| ATOM | 1303 | C   | ARG A | 209 | 37.534 | 3.082  | 9.904  | 1.00 | 35.04  | C |
| ATOM | 1304 | O   | ARG A | 209 | 37.748 | 2.437  | 10.911 | 1.00 | 36.10  | O |
| ATOM | 1305 | N   | LEU A | 210 | 37.663 | 4.393  | 9.832  | 1.00 | 33.21  | N |
| ATOM | 1306 | CA  | LEU A | 210 | 38.036 | 5.203  | 10.968 | 1.00 | 33.87  | C |
| ATOM | 1307 | CB  | LEU A | 210 | 38.363 | 6.624  | 10.501 | 1.00 | 33.58  | C |
| ATOM | 1308 | CG  | LEU A | 210 | 38.408 | 7.637  | 11.665 | 1.00 | 37.57  | C |
| ATOM | 1309 | CD1 | LEU A | 210 | 39.660 | 7.429  | 12.478 | 1.00 | 36.76  | C |
| ATOM | 1310 | CD2 | LEU A | 210 | 38.370 | 9.028  | 11.109 | 1.00 | 40.97  | C |
| ATOM | 1311 | C   | LEU A | 210 | 36.925 | 5.224  | 12.024 | 1.00 | 38.60  | C |
| ATOM | 1312 | O   | LEU A | 210 | 35.776 | 5.422  | 11.691 | 1.00 | 37.15  | O |
| ATOM | 1313 | N   | GLU A | 211 | 37.279 | 5.006  | 13.290 | 1.00 | 37.66  | N |
| ATOM | 1314 | CA  | GLU A | 211 | 36.292 | 4.960  | 14.372 | 1.00 | 38.01  | C |
| ATOM | 1315 | CB  | GLU A | 211 | 36.161 | 3.534  | 14.916 | 1.00 | 39.29  | C |
| ATOM | 1316 | CG  | GLU A | 211 | 35.468 | 2.615  | 13.961 | 1.00 | 49.65  | C |
| ATOM | 1317 | CD  | GLU A | 211 | 34.609 | 1.622  | 14.669 | 1.00 | 85.63  | C |
| ATOM | 1318 | OE1 | GLU A | 211 | 35.005 | 0.439  | 14.704 | 1.00 | 94.33  | O |
| ATOM | 1319 | OE2 | GLU A | 211 | 33.568 | 2.034  | 15.233 | 1.00 | 85.13  | O |
| ATOM | 1320 | C   | GLU A | 211 | 36.705 | 5.896  | 15.478 | 1.00 | 41.49  | C |
| ATOM | 1321 | O   | GLU A | 211 | 37.874 | 6.223  | 15.586 | 1.00 | 40.11  | O |
| ATOM | 1322 | N   | PRO A | 212 | 35.736 | 6.380  | 16.292 | 1.00 | 37.43  | N |
| ATOM | 1323 | CD  | PRO A | 212 | 34.272 | 6.230  | 16.147 | 1.00 | 37.23  | C |
| ATOM | 1324 | CA  | PRO A | 212 | 36.102 | 7.315  | 17.376 | 1.00 | 34.87  | C |
| ATOM | 1325 | CB  | PRO A | 212 | 34.754 | 7.647  | 18.038 | 1.00 | 37.05  | C |
| ATOM | 1326 | CG  | PRO A | 212 | 33.725 | 7.300  | 17.041 | 1.00 | 42.38  | C |
| ATOM | 1327 | C   | PRO A | 212 | 37.020 | 6.604  | 18.375 | 1.00 | 35.08  | C |
| ATOM | 1328 | O   | PRO A | 212 | 37.074 | 5.381  | 18.416 | 1.00 | 32.76  | O |
| ATOM | 1329 | N   | PRO A | 213 | 37.730 | 7.364  | 19.210 | 1.00 | 33.73  | N |
| ATOM | 1330 | CD  | PRO A | 213 | 37.966 | 8.816  | 19.181 | 1.00 | 34.69  | C |
| ATOM | 1331 | CA  | PRO A | 213 | 38.662 | 6.667  | 20.121 | 1.00 | 35.45  | C |
| ATOM | 1332 | CB  | PRO A | 213 | 39.233 | 7.811  | 20.992 | 1.00 | 36.27  | C |
| ATOM | 1333 | CG  | PRO A | 213 | 39.143 | 9.014  | 20.142 | 1.00 | 39.20  | C |
| ATOM | 1334 | C   | PRO A | 213 | 38.059 | 5.571  | 21.013 | 1.00 | 40.23  | C |
| ATOM | 1335 | O   | PRO A | 213 | 38.630 | 4.487  | 21.179 | 1.00 | 38.34  | O |
| ATOM | 1336 | N   | GLU A | 214 | 36.942 | 5.861  | 21.648 | 1.00 | 41.86  | N |
| ATOM | 1337 | CA  | GLU A | 214 | 36.374 | 4.861  | 22.545 | 1.00 | 43.83  | C |
| ATOM | 1338 | CB  | GLU A | 214 | 35.393 | 5.486  | 23.550 | 1.00 | 46.20  | C |
| ATOM | 1339 | CG  | GLU A | 214 | 36.068 | 5.889  | 24.888 | 1.00 | 63.64  | C |
| ATOM | 1340 | CD  | GLU A | 214 | 37.316 | 6.800  | 24.725 | 1.00 | 101.03 | C |
| ATOM | 1341 | OE1 | GLU A | 214 | 37.160 | 8.023  | 24.493 | 1.00 | 101.87 | O |
| ATOM | 1342 | OE2 | GLU A | 214 | 38.459 | 6.312  | 24.898 | 1.00 | 95.69  | O |
| ATOM | 1343 | C   | GLU A | 214 | 35.802 | 3.638  | 21.834 | 1.00 | 46.77  | C |
| ATOM | 1344 | O   | GLU A | 214 | 35.645 | 2.591  | 22.432 | 1.00 | 48.11  | O |
| ATOM | 1345 | N   | GLN A | 215 | 35.569 | 3.760  | 20.536 | 1.00 | 43.22  | N |
| ATOM | 1346 | CA  | GLN A | 215 | 35.019 | 2.666  | 19.734 | 1.00 | 42.97  | C |
| ATOM | 1347 | CB  | GLN A | 215 | 34.014 | 3.246  | 18.727 | 1.00 | 44.06  | C |
| ATOM | 1348 | CG  | GLN A | 215 | 32.650 | 2.568  | 18.687 | 1.00 | 77.12  | C |
| ATOM | 1349 | CD  | GLN A | 215 | 31.986 | 2.490  | 20.050 | 1.00 | 111.06 | C |
| ATOM | 1350 | OE1 | GLN A | 215 | 31.638 | 1.402  | 20.527 | 1.00 | 108.18 | O |
| ATOM | 1351 | NE2 | GLN A | 215 | 31.798 | 3.646  | 20.684 | 1.00 | 105.55 | N |
| ATOM | 1352 | C   | GLN A | 215 | 36.110 | 1.857  | 18.985 | 1.00 | 46.33  | C |
| ATOM | 1353 | O   | GLN A | 215 | 35.937 | 0.673  | 18.710 | 1.00 | 44.77  | O |
| ATOM | 1354 | N   | ARG A | 216 | 37.173 | 2.544  | 18.580 | 1.00 | 41.17  | N |
| ATOM | 1355 | CA  | ARG A | 216 | 38.325 | 1.956  | 17.860 | 1.00 | 41.20  | C |
| ATOM | 1356 | CB  | ARG A | 216 | 39.540 | 2.795  | 18.287 | 1.00 | 41.51  | C |
| ATOM | 1357 | CG  | ARG A | 216 | 40.495 | 3.194  | 17.260 | 1.00 | 52.86  | C |

Figure 6-24

| | Atom Type | Resid | # | X | Y | Z | OCC | B | |
|---|---|---|---|---|---|---|---|---|---|
| ATOM | 1358 | CD | ARG A 216 | 41.110 | 4.472 | 17.734 | 1.00 | 56.84 | C |
| ATOM | 1359 | NE | ARG A 216 | 40.446 | 5.536 | 17.030 | 1.00 | 38.05 | N |
| ATOM | 1360 | CZ | ARG A 216 | 40.860 | 6.786 | 16.975 | 1.00 | 46.15 | C |
| ATOM | 1361 | NH1 | ARG A 216 | 41.927 | 7.172 | 17.648 | 1.00 | 35.61 | N |
| ATOM | 1362 | NH2 | ARG A 216 | 40.181 | 7.647 | 16.244 | 1.00 | 34.37 | N |
| ATOM | 1363 | C | ARG A 216 | 38.679 | 0.521 | 18.316 | 1.00 | 43.59 | C |
| ATOM | 1364 | O | ARG A 216 | 38.810 | 0.271 | 19.515 | 1.00 | 42.57 | O |
| ATOM | 1365 | N | LYS A 217 | 38.958 | -0.391 | 17.386 | 1.00 | 40.43 | N |
| ATOM | 1366 | CA | LYS A 217 | 39.492 | -1.703 | 17.781 | 1.00 | 40.59 | C |
| ATOM | 1367 | CB | LYS A 217 | 39.663 | -2.610 | 16.556 | 1.00 | 44.55 | C |
| ATOM | 1368 | CG | LYS A 217 | 39.922 | -4.070 | 16.902 | 1.00 | 64.54 | C |
| ATOM | 1369 | CD | LYS A 217 | 38.939 | -4.983 | 16.171 | 1.00 | 76.85 | C |
| ATOM | 1370 | CE | LYS A 217 | 37.578 | -5.015 | 16.859 | 1.00 | 81.55 | C |
| ATOM | 1371 | NZ | LYS A 217 | 36.670 | -6.029 | 16.251 | 1.00 | 87.08 | N |
| ATOM | 1372 | C | LYS A 217 | 40.878 | -1.391 | 18.373 | 1.00 | 41.56 | C |
| ATOM | 1373 | O | LYS A 217 | 41.597 | -0.561 | 17.830 | 1.00 | 41.47 | O |
| ATOM | 1374 | N | LYS A 218 | 41.244 | -2.048 | 19.470 | 1.00 | 38.38 | N |
| ATOM | 1375 | CA | LYS A 218 | 42.502 | -1.797 | 20.172 | 1.00 | 38.38 | C |
| ATOM | 1376 | CB | LYS A 218 | 42.228 | -1.523 | 21.648 | 1.00 | 41.12 | C |
| ATOM | 1377 | CG | LYS A 218 | 41.842 | -0.045 | 21.872 | 1.00 | 38.16 | C |
| ATOM | 1378 | CD | LYS A 218 | 40.664 | 0.068 | 22.782 | 1.00 | 43.94 | C |
| ATOM | 1379 | CE | LYS A 218 | 39.535 | 0.964 | 22.166 | 1.00 | 54.29 | C |
| ATOM | 1380 | NZ | LYS A 218 | 39.929 | 2.389 | 21.994 | 1.00 | 47.72 | N |
| ATOM | 1381 | C | LYS A 218 | 43.645 | -2.784 | 19.997 | 1.00 | 44.46 | C |
| ATOM | 1382 | O | LYS A 218 | 44.584 | -2.827 | 20.793 | 1.00 | 43.35 | O |
| ATOM | 1383 | N | THR A 219 | 43.597 | -3.525 | 18.903 | 1.00 | 42.96 | N |
| ATOM | 1384 | CA | THR A 219 | 44.625 | -4.512 | 18.578 | 1.00 | 43.49 | C |
| ATOM | 1385 | CB | THR A 219 | 44.026 | -5.564 | 17.633 | 1.00 | 56.56 | C |
| ATOM | 1386 | OG1 | THR A 219 | 43.240 | -4.888 | 16.637 | 1.00 | 58.78 | O |
| ATOM | 1387 | CG2 | THR A 219 | 43.099 | -6.533 | 18.429 | 1.00 | 54.61 | C |
| ATOM | 1388 | C | THR A 219 | 45.949 | -3.902 | 18.040 | 1.00 | 46.46 | C |
| ATOM | 1389 | O | THR A 219 | 45.979 | -2.804 | 17.466 | 1.00 | 45.84 | O |
| ATOM | 1390 | N | ILE A 220 | 47.057 | -4.593 | 18.277 | 1.00 | 42.31 | N |
| ATOM | 1391 | CA | ILE A 220 | 48.346 | -4.098 | 17.822 | 1.00 | 42.01 | C |
| ATOM | 1392 | CB | ILE A 220 | 49.421 | -4.386 | 18.854 | 1.00 | 45.11 | C |
| ATOM | 1393 | CG2 | ILE A 220 | 50.665 | -3.531 | 18.604 | 1.00 | 47.21 | C |
| ATOM | 1394 | CG1 | ILE A 220 | 48.889 | -4.052 | 20.246 | 1.00 | 45.58 | C |
| ATOM | 1395 | CD1 | ILE A 220 | 49.957 | -3.588 | 21.158 | 1.00 | 49.61 | C |
| ATOM | 1396 | C | ILE A 220 | 48.676 | -4.637 | 16.424 | 1.00 | 46.68 | C |
| ATOM | 1397 | O | ILE A 220 | 48.678 | -5.845 | 16.194 | 1.00 | 46.62 | O |
| ATOM | 1398 | N | CYS A 221 | 48.866 | -3.741 | 15.464 | 1.00 | 44.38 | N |
| ATOM | 1399 | CA | CYS A 221 | 49.210 | -4.163 | 14.111 | 1.00 | 43.42 | C |
| ATOM | 1400 | CB | CYS A 221 | 47.981 | -4.667 | 13.320 | 1.00 | 45.59 | C |
| ATOM | 1401 | SG | CYS A 221 | 46.646 | -3.461 | 12.969 | 1.00 | 50.77 | S |
| ATOM | 1402 | C | CYS A 221 | 49.932 | -3.043 | 13.389 | 1.00 | 42.87 | C |
| ATOM | 1403 | O | CYS A 221 | 49.979 | -1.930 | 13.889 | 1.00 | 42.97 | O |
| ATOM | 1404 | N | GLY A 222 | 50.499 | -3.354 | 12.222 | 1.00 | 37.36 | N |
| ATOM | 1405 | CA | GLY A 222 | 51.276 | -2.421 | 11.421 | 1.00 | 36.32 | C |
| ATOM | 1406 | C | GLY A 222 | 52.710 | -2.912 | 11.491 | 1.00 | 41.44 | C |
| ATOM | 1407 | O | GLY A 222 | 53.104 | -3.535 | 12.477 | 1.00 | 40.44 | O |
| ATOM | 1408 | N | THR A 223 | 53.517 | -2.657 | 10.468 | 1.00 | 38.32 | N |
| ATOM | 1409 | CA | THR A 223 | 54.885 | -3.084 | 10.598 | 1.00 | 37.84 | C |
| ATOM | 1410 | CB | THR A 223 | 55.613 | -3.280 | 9.259 | 1.00 | 42.33 | C |
| ATOM | 1411 | OG1 | THR A 223 | 56.823 | -2.524 | 9.214 | 1.00 | 44.33 | O |
| ATOM | 1412 | CG2 | THR A 223 | 54.715 | -2.974 | 8.118 | 1.00 | 30.94 | C |
| ATOM | 1413 | C | THR A 223 | 55.611 | -2.345 | 11.731 | 1.00 | 40.26 | C |
| ATOM | 1414 | O | THR A 223 | 55.465 | -1.140 | 11.866 | 1.00 | 37.39 | O |
| ATOM | 1415 | N | PRO A 224 | 56.297 | -3.096 | 12.627 | 1.00 | 39.09 | N |
| ATOM | 1416 | CD | PRO A 224 | 56.713 | -4.491 | 12.371 | 1.00 | 40.85 | C |

Figure 6-25

| | | Atom Type | Resid | # | X | Y | Z | OCC | B | |
|---|---|---|---|---|---|---|---|---|---|---|
| ATOM | 1417 | CA | PRO A | 224 | 56.913 | -2.581 | 13.860 | 1.00 | 39.68 | C |
| ATOM | 1418 | CB | PRO A | 224 | 57.724 | -3.781 | 14.407 | 1.00 | 41.63 | C |
| ATOM | 1419 | CG | PRO A | 224 | 57.135 | -4.975 | 13.731 | 1.00 | 44.88 | C |
| ATOM | 1420 | C | PRO A | 224 | 57.711 | -1.288 | 13.788 | 1.00 | 40.21 | C |
| ATOM | 1421 | O | PRO A | 224 | 57.458 | -0.389 | 14.575 | 1.00 | 37.87 | O |
| ATOM | 1422 | N | ASN A | 225 | 58.617 | -1.142 | 12.822 | 1.00 | 37.28 | N |
| ATOM | 1423 | CA | ASN A | 225 | 59.371 | 0.131 | 12.710 | 1.00 | 37.91 | C |
| ATOM | 1424 | CB | ASN A | 225 | 60.442 | 0.078 | 11.607 | 1.00 | 36.94 | C |
| ATOM | 1425 | CG | ASN A | 225 | 61.696 | -0.678 | 12.040 | 1.00 | 54.61 | C |
| ATOM | 1426 | OD1 | ASN A | 225 | 62.124 | -1.620 | 11.365 | 1.00 | 57.77 | O |
| ATOM | 1427 | ND2 | ASN A | 225 | 62.302 | -0.252 | 13.140 | 1.00 | 38.65 | N |
| ATOM | 1428 | C | ASN A | 225 | 58.553 | 1.399 | 12.487 | 1.00 | 40.94 | C |
| ATOM | 1429 | O | ASN A | 225 | 59.056 | 2.509 | 12.689 | 1.00 | 43.39 | O |
| ATOM | 1430 | N | TYR A | 226 | 57.368 | 1.251 | 11.916 | 1.00 | 34.69 | N |
| ATOM | 1431 | CA | TYR A | 226 | 56.527 | 2.387 | 11.583 | 1.00 | 30.80 | C |
| ATOM | 1432 | CB | TYR A | 226 | 56.053 | 2.293 | 10.137 | 1.00 | 31.00 | C |
| ATOM | 1433 | CG | TYR A | 226 | 57.167 | 2.235 | 9.099 | 1.00 | 30.11 | C |
| ATOM | 1434 | CD1 | TYR A | 226 | 57.821 | 1.035 | 8.803 | 1.00 | 30.56 | C |
| ATOM | 1435 | CE1 | TYR A | 226 | 58.844 | 0.990 | 7.806 | 1.00 | 31.76 | C |
| ATOM | 1436 | CD2 | TYR A | 226 | 57.589 | 3.390 | 8.449 | 1.00 | 31.19 | C |
| ATOM | 1437 | CE2 | TYR A | 226 | 58.599 | 3.341 | 7.477 | 1.00 | 32.29 | C |
| ATOM | 1438 | CZ | TYR A | 226 | 59.240 | 2.169 | 7.193 | 1.00 | 44.60 | C |
| ATOM | 1439 | OH | TYR A | 226 | 60.240 | 2.201 | 6.229 | 1.00 | 56.44 | O |
| ATOM | 1440 | C | TYR A | 226 | 55.295 | 2.592 | 12.488 | 1.00 | 37.51 | C |
| ATOM | 1441 | O | TYR A | 226 | 54.549 | 3.544 | 12.263 | 1.00 | 36.37 | O |
| ATOM | 1442 | N | VAL A | 227 | 55.051 | 1.676 | 13.428 | 1.00 | 34.37 | N |
| ATOM | 1443 | CA | VAL A | 227 | 53.876 | 1.715 | 14.342 | 1.00 | 35.46 | C |
| ATOM | 1444 | CB | VAL A | 227 | 53.733 | 0.366 | 15.175 | 1.00 | 40.62 | C |
| ATOM | 1445 | CG1 | VAL A | 227 | 52.287 | 0.128 | 15.618 | 1.00 | 39.67 | C |
| ATOM | 1446 | CG2 | VAL A | 227 | 54.271 | -0.845 | 14.410 | 1.00 | 41.27 | C |
| ATOM | 1447 | C | VAL A | 227 | 53.939 | 2.878 | 15.339 | 1.00 | 38.53 | C |
| ATOM | 1448 | O | VAL A | 227 | 54.932 | 3.052 | 16.029 | 1.00 | 38.98 | O |
| ATOM | 1449 | N | ALA A | 228 | 52.849 | 3.631 | 15.476 | 1.00 | 33.55 | N |
| ATOM | 1450 | CA | ALA A | 228 | 52.824 | 4.751 | 16.410 | 1.00 | 32.33 | C |
| ATOM | 1451 | CB | ALA A | 228 | 51.602 | 5.675 | 16.113 | 1.00 | 32.75 | C |
| ATOM | 1452 | C | ALA A | 228 | 52.778 | 4.257 | 17.864 | 1.00 | 35.79 | C |
| ATOM | 1453 | O | ALA A | 228 | 52.245 | 3.185 | 18.158 | 1.00 | 35.26 | O |
| ATOM | 1454 | N | PRO A | 229 | 53.217 | 5.101 | 18.803 | 1.00 | 32.59 | N |
| ATOM | 1455 | CD | PRO A | 229 | 53.850 | 6.398 | 18.499 | 1.00 | 33.92 | C |
| ATOM | 1456 | CA | PRO A | 229 | 53.219 | 4.796 | 20.240 | 1.00 | 33.43 | C |
| ATOM | 1457 | CB | PRO A | 229 | 53.617 | 6.147 | 20.896 | 1.00 | 34.83 | C |
| ATOM | 1458 | CG | PRO A | 229 | 54.283 | 6.917 | 19.867 | 1.00 | 38.20 | C |
| ATOM | 1459 | C | PRO A | 229 | 51.859 | 4.363 | 20.791 | 1.00 | 37.12 | C |
| ATOM | 1460 | O | PRO A | 229 | 51.802 | 3.387 | 21.567 | 1.00 | 36.78 | O |
| ATOM | 1461 | N | GLU A | 230 | 50.798 | 5.144 | 20.481 | 1.00 | 34.78 | N |
| ATOM | 1462 | CA | GLU A | 230 | 49.440 | 4.856 | 20.971 | 1.00 | 35.57 | C |
| ATOM | 1463 | CB | GLU A | 230 | 48.367 | 5.864 | 20.494 | 1.00 | 37.35 | C |
| ATOM | 1464 | CG | GLU A | 230 | 48.814 | 7.184 | 20.012 | 1.00 | 56.66 | C |
| ATOM | 1465 | CD | GLU A | 230 | 49.454 | 7.159 | 18.643 | 1.00 | 60.42 | C |
| ATOM | 1466 | OE1 | GLU A | 230 | 48.790 | 7.480 | 17.621 | 1.00 | 34.17 | O |
| ATOM | 1467 | OE2 | GLU A | 230 | 50.687 | 7.035 | 18.644 | 1.00 | 60.94 | O |
| ATOM | 1468 | C | GLU A | 230 | 48.967 | 3.459 | 20.559 | 1.00 | 37.87 | C |
| ATOM | 1469 | O | GLU A | 230 | 48.176 | 2.854 | 21.259 | 1.00 | 35.27 | O |
| ATOM | 1470 | N | VAL A | 231 | 49.391 | 2.975 | 19.388 | 1.00 | 35.18 | N |
| ATOM | 1471 | CA | VAL A | 231 | 48.969 | 1.653 | 18.983 | 1.00 | 34.16 | C |
| ATOM | 1472 | CB | VAL A | 231 | 49.048 | 1.387 | 17.443 | 1.00 | 37.56 | C |
| ATOM | 1473 | CG1 | VAL A | 231 | 49.999 | 2.269 | 16.786 | 1.00 | 38.42 | C |
| ATOM | 1474 | CG2 | VAL A | 231 | 49.356 | -0.072 | 17.137 | 1.00 | 36.44 | C |
| ATOM | 1475 | C | VAL A | 231 | 49.650 | 0.611 | 19.849 | 1.00 | 40.91 | C |

Figure 6-26

| | | Atom Type | Resid | # | X | Y | Z | OCC | B | |
|---|---|---|---|---|---|---|---|---|---|---|
| ATOM | 1476 | O | VAL A | 231 | 49.010 | -0.360 | 20.264 | 1.00 | 41.15 | O |
| ATOM | 1477 | N | LEU A | 232 | 50.914 | 0.860 | 20.195 | 1.00 | 37.03 | N |
| ATOM | 1478 | CA | LEU A | 232 | 51.662 | -0.028 | 21.077 | 1.00 | 35.12 | C |
| ATOM | 1479 | CB | LEU A | 232 | 53.108 | 0.417 | 21.208 | 1.00 | 34.82 | C |
| ATOM | 1480 | CG | LEU A | 232 | 53.907 | 0.293 | 19.926 | 1.00 | 39.50 | C |
| ATOM | 1481 | CD1 | LEU A | 232 | 55.350 | 0.797 | 20.207 | 1.00 | 40.25 | C |
| ATOM | 1482 | CD2 | LEU A | 232 | 53.846 | -1.140 | 19.428 | 1.00 | 35.83 | C |
| ATOM | 1483 | C | LEU A | 232 | 51.038 | 0.008 | 22.453 | 1.00 | 37.94 | C |
| ATOM | 1484 | O | LEU A | 232 | 51.053 | -0.980 | 23.173 | 1.00 | 36.11 | O |
| ATOM | 1485 | N | LEU A | 233 | 50.504 | 1.167 | 22.810 | 1.00 | 33.96 | N |
| ATOM | 1486 | CA | LEU A | 233 | 49.856 | 1.362 | 24.109 | 1.00 | 33.55 | C |
| ATOM | 1487 | CB | LEU A | 233 | 49.979 | 2.826 | 24.536 | 1.00 | 33.29 | C |
| ATOM | 1488 | CG | LEU A | 233 | 51.414 | 3.282 | 24.842 | 1.00 | 38.54 | C |
| ATOM | 1489 | CD1 | LEU A | 233 | 51.434 | 4.712 | 25.299 | 1.00 | 38.16 | C |
| ATOM | 1490 | CD2 | LEU A | 233 | 52.133 | 2.380 | 25.856 | 1.00 | 40.10 | C |
| ATOM | 1491 | C | LEU A | 233 | 48.396 | 0.956 | 24.064 | 1.00 | 40.13 | C |
| ATOM | 1492 | O | LEU A | 233 | 47.628 | 1.318 | 24.950 | 1.00 | 41.70 | O |
| ATOM | 1493 | N | ARG A | 234 | 48.023 | 0.243 | 22.994 | 1.00 | 36.95 | N |
| ATOM | 1494 | CA | ARG A | 234 | 46.678 | -0.312 | 22.794 | 1.00 | 35.39 | C |
| ATOM | 1495 | CB | ARG A | 234 | 46.419 | -1.458 | 23.779 | 1.00 | 37.49 | C |
| ATOM | 1496 | CG | ARG A | 234 | 47.459 | -2.611 | 23.649 | 1.00 | 42.82 | C |
| ATOM | 1497 | CD | ARG A | 234 | 47.408 | -3.595 | 24.823 | 1.00 | 54.43 | C |
| ATOM | 1498 | NE | ARG A | 234 | 48.458 | -4.628 | 24.795 | 1.00 | 51.23 | N |
| ATOM | 1499 | CZ | ARG A | 234 | 48.541 | -5.623 | 23.906 | 1.00 | 68.21 | C |
| ATOM | 1500 | NH1 | ARG A | 234 | 47.646 | -5.742 | 22.927 | 1.00 | 59.17 | N |
| ATOM | 1501 | NH2 | ARG A | 234 | 49.526 | -6.516 | 24.003 | 1.00 | 65.84 | N |
| ATOM | 1502 | C | ARG A | 234 | 45.558 | 0.711 | 22.811 | 1.00 | 39.01 | C |
| ATOM | 1503 | O | ARG A | 234 | 44.478 | 0.470 | 23.376 | 1.00 | 38.71 | O |
| ATOM | 1504 | N | GLN A | 235 | 45.798 | 1.860 | 22.178 | 1.00 | 35.56 | N |
| ATOM | 1505 | CA | GLN A | 235 | 44.761 | 2.881 | 22.060 | 1.00 | 33.29 | C |
| ATOM | 1506 | CB | GLN A | 235 | 45.319 | 4.282 | 22.296 | 1.00 | 32.91 | C |
| ATOM | 1507 | CG | GLN A | 235 | 45.936 | 4.468 | 23.672 | 1.00 | 39.64 | C |
| ATOM | 1508 | CD | GLN A | 235 | 44.918 | 4.288 | 24.791 | 1.00 | 55.24 | C |
| ATOM | 1509 | OE1 | GLN A | 235 | 44.034 | 5.125 | 24.982 | 1.00 | 51.92 | O |
| ATOM | 1510 | NE2 | GLN A | 235 | 44.986 | 3.152 | 25.474 | 1.00 | 55.56 | N |
| ATOM | 1511 | C | GLN A | 235 | 44.091 | 2.813 | 20.701 | 1.00 | 36.30 | C |
| ATOM | 1512 | O | GLN A | 235 | 43.227 | 3.628 | 20.390 | 1.00 | 36.90 | O |
| ATOM | 1513 | N | GLY A | 236 | 44.533 | 1.866 | 19.878 | 1.00 | 35.19 | N |
| ATOM | 1514 | CA | GLY A | 236 | 44.050 | 1.705 | 18.514 | 1.00 | 33.93 | C |
| ATOM | 1515 | C | GLY A | 236 | 44.661 | 2.746 | 17.588 | 1.00 | 34.57 | C |
| ATOM | 1516 | O | GLY A | 236 | 45.386 | 3.628 | 18.043 | 1.00 | 33.08 | O |
| ATOM | 1517 | N | HIS A | 237 | 44.362 | 2.642 | 16.283 | 1.00 | 29.92 | N |
| ATOM | 1518 | CA | HIS A | 237 | 44.869 | 3.565 | 15.246 | 1.00 | 27.74 | C |
| ATOM | 1519 | CB | HIS A | 237 | 45.098 | 2.840 | 13.863 | 1.00 | 26.85 | C |
| ATOM | 1520 | CG | HIS A | 237 | 46.311 | 1.964 | 13.794 | 1.00 | 28.56 | C |
| ATOM | 1521 | CD2 | HIS A | 237 | 47.462 | 2.086 | 13.087 | 1.00 | 28.81 | C |
| ATOM | 1522 | ND1 | HIS A | 237 | 46.349 | 0.702 | 14.362 | 1.00 | 31.12 | N |
| ATOM | 1523 | CE1 | HIS A | 237 | 47.495 | 0.113 | 14.062 | 1.00 | 29.06 | C |
| ATOM | 1524 | NE2 | HIS A | 237 | 48.205 | 0.946 | 13.313 | 1.00 | 28.97 | N |
| ATOM | 1525 | C | HIS A | 237 | 43.844 | 4.681 | 14.980 | 1.00 | 28.44 | C |
| ATOM | 1526 | O | HIS A | 237 | 42.654 | 4.418 | 14.761 | 1.00 | 28.79 | O |
| ATOM | 1527 | N | GLY A | 238 | 44.336 | 5.912 | 14.941 | 1.00 | 25.82 | N |
| ATOM | 1528 | CA | GLY A | 238 | 43.582 | 7.101 | 14.584 | 1.00 | 26.01 | C |
| ATOM | 1529 | C | GLY A | 238 | 44.352 | 7.650 | 13.398 | 1.00 | 29.46 | C |
| ATOM | 1530 | O | GLY A | 238 | 45.368 | 7.068 | 12.985 | 1.00 | 28.66 | O |
| ATOM | 1531 | N | PRO A | 239 | 43.839 | 8.729 | 12.778 | 1.00 | 26.54 | N |
| ATOM | 1532 | CD | PRO A | 239 | 42.697 | 9.549 | 13.241 | 1.00 | 28.38 | C |
| ATOM | 1533 | CA | PRO A | 239 | 44.482 | 9.310 | 11.607 | 1.00 | 25.87 | C |
| ATOM | 1534 | CB | PRO A | 239 | 43.532 | 10.447 | 11.220 | 1.00 | 27.51 | C |

Figure 6-27

| | | Atom Type | Resid | # | X | Y | Z | OCC | B | |
|---|---|---|---|---|---|---|---|---|---|---|
| ATOM | 1535 | CG | PRO A | 239 | 42.223 | 10.146 | 11.986 | 1.00 | 32.42 | C |
| ATOM | 1536 | C | PRO A | 239 | 45.893 | 9.821 | 11.947 | 1.00 | 30.54 | C |
| ATOM | 1537 | O | PRO A | 239 | 46.754 | 9.844 | 11.073 | 1.00 | 27.21 | O |
| ATOM | 1538 | N | GLU A | 240 | 46.113 | 10.214 | 13.209 | 1.00 | 26.66 | N |
| ATOM | 1539 | CA | GLU A | 240 | 47.439 | 10.641 | 13.667 | 1.00 | 29.56 | C |
| ATOM | 1540 | CB | GLU A | 240 | 47.398 | 11.506 | 14.960 | 1.00 | 32.03 | C |
| ATOM | 1541 | CG | GLU A | 240 | 46.655 | 10.976 | 16.135 | 1.00 | 49.83 | C |
| ATOM | 1542 | CD | GLU A | 240 | 45.171 | 10.767 | 15.885 | 1.00 | 51.80 | C |
| ATOM | 1543 | OE1 | GLU A | 240 | 44.379 | 11.718 | 16.045 | 1.00 | 42.70 | O |
| ATOM | 1544 | OE2 | GLU A | 240 | 44.791 | 9.597 | 15.723 | 1.00 | 37.79 | O |
| ATOM | 1545 | C | GLU A | 240 | 48.529 | 9.549 | 13.701 | 1.00 | 33.27 | C |
| ATOM | 1546 | O | GLU A | 240 | 49.726 | 9.855 | 13.677 | 1.00 | 30.17 | O |
| ATOM | 1547 | N | ALA A | 241 | 48.082 | 8.283 | 13.742 | 1.00 | 29.36 | N |
| ATOM | 1548 | CA | ALA A | 241 | 48.931 | 7.115 | 13.669 | 1.00 | 26.76 | C |
| ATOM | 1549 | CB | ALA A | 241 | 48.164 | 5.880 | 14.089 | 1.00 | 26.24 | C |
| ATOM | 1550 | C | ALA A | 241 | 49.462 | 6.951 | 12.227 | 1.00 | 30.36 | C |
| ATOM | 1551 | O | ALA A | 241 | 50.627 | 6.632 | 12.048 | 1.00 | 31.07 | O |
| ATOM | 1552 | N | ASP A | 242 | 48.633 | 7.212 | 11.222 | 1.00 | 26.65 | N |
| ATOM | 1553 | CA | ASP A | 242 | 49.092 | 7.184 | 9.825 | 1.00 | 27.56 | C |
| ATOM | 1554 | CB | ASP A | 242 | 47.932 | 7.442 | 8.831 | 1.00 | 28.47 | C |
| ATOM | 1555 | CG | ASP A | 242 | 47.093 | 6.167 | 8.478 | 1.00 | 28.36 | C |
| ATOM | 1556 | OD1 | ASP A | 242 | 47.494 | 5.039 | 8.821 | 1.00 | 25.82 | O |
| ATOM | 1557 | OD2 | ASP A | 242 | 46.016 | 6.316 | 7.836 | 1.00 | 28.72 | O |
| ATOM | 1558 | C | ASP A | 242 | 50.123 | 8.327 | 9.665 | 1.00 | 33.09 | C |
| ATOM | 1559 | O | ASP A | 242 | 51.086 | 8.187 | 8.929 | 1.00 | 29.63 | O |
| ATOM | 1560 | N | VAL A | 243 | 49.893 | 9.466 | 10.341 | 1.00 | 30.47 | N |
| ATOM | 1561 | CA | VAL A | 243 | 50.806 | 10.621 | 10.273 | 1.00 | 30.20 | C |
| ATOM | 1562 | CB | VAL A | 243 | 50.178 | 11.919 | 10.872 | 1.00 | 32.89 | C |
| ATOM | 1563 | CG1 | VAL A | 243 | 51.284 | 13.010 | 11.148 | 1.00 | 32.10 | C |
| ATOM | 1564 | CG2 | VAL A | 243 | 49.108 | 12.446 | 9.942 | 1.00 | 31.79 | C |
| ATOM | 1565 | C | VAL A | 243 | 52.191 | 10.300 | 10.862 | 1.00 | 30.39 | C |
| ATOM | 1566 | O | VAL A | 243 | 53.212 | 10.556 | 10.230 | 1.00 | 26.99 | O |
| ATOM | 1567 | N | TRP A | 244 | 52.188 | 9.666 | 12.034 | 1.00 | 30.07 | N |
| ATOM | 1568 | CA | TRP A | 244 | 53.393 | 9.171 | 12.679 | 1.00 | 29.86 | C |
| ATOM | 1569 | CB | TRP A | 244 | 53.020 | 8.398 | 13.962 | 1.00 | 28.15 | C |
| ATOM | 1570 | CG | TRP A | 244 | 54.130 | 7.628 | 14.521 | 1.00 | 29.32 | C |
| ATOM | 1571 | CD2 | TRP A | 244 | 54.988 | 7.994 | 15.652 | 1.00 | 30.11 | C |
| ATOM | 1572 | CE2 | TRP A | 244 | 55.973 | 6.991 | 15.762 | 1.00 | 32.48 | C |
| ATOM | 1573 | CE3 | TRP A | 244 | 55.052 | 9.108 | 16.511 | 1.00 | 31.72 | C |
| ATOM | 1574 | CD1 | TRP A | 244 | 54.621 | 6.443 | 14.045 | 1.00 | 31.11 | C |
| ATOM | 1575 | NE1 | TRP A | 244 | 55.690 | 6.035 | 14.817 | 1.00 | 29.00 | N |
| ATOM | 1576 | CZ2 | TRP A | 244 | 57.013 | 7.040 | 16.741 | 1.00 | 33.34 | C |
| ATOM | 1577 | CZ3 | TRP A | 244 | 56.009 | 9.101 | 17.570 | 1.00 | 33.34 | C |
| ATOM | 1578 | CH2 | TRP A | 244 | 56.995 | 8.093 | 17.646 | 1.00 | 33.75 | C |
| ATOM | 1579 | C | TRP A | 244 | 54.214 | 8.273 | 11.713 | 1.00 | 32.72 | C |
| ATOM | 1580 | O | TRP A | 244 | 55.423 | 8.484 | 11.527 | 1.00 | 31.80 | O |
| ATOM | 1581 | N | SER A | 245 | 53.551 | 7.311 | 11.070 | 1.00 | 28.90 | N |
| ATOM | 1582 | CA | SER A | 245 | 54.222 | 6.383 | 10.107 | 1.00 | 28.64 | C |
| ATOM | 1583 | CB | SER A | 245 | 53.216 | 5.376 | 9.519 | 1.00 | 30.07 | C |
| ATOM | 1584 | OG | SER A | 245 | 52.630 | 4.572 | 10.523 | 1.00 | 32.96 | O |
| ATOM | 1585 | C | SER A | 245 | 54.875 | 7.148 | 8.969 | 1.00 | 30.75 | C |
| ATOM | 1586 | O | SER A | 245 | 55.914 | 6.747 | 8.484 | 1.00 | 31.10 | O |
| ATOM | 1587 | N | LEU A | 246 | 54.214 | 8.206 | 8.506 | 1.00 | 27.12 | N |
| ATOM | 1588 | CA | LEU A | 246 | 54.767 | 9.104 | 7.489 | 1.00 | 27.68 | C |
| ATOM | 1589 | CB | LEU A | 246 | 53.717 | 10.141 | 7.111 | 1.00 | 28.43 | C |
| ATOM | 1590 | CG | LEU A | 246 | 52.645 | 9.576 | 6.170 | 1.00 | 34.88 | C |
| ATOM | 1591 | CD1 | LEU A | 246 | 52.034 | 10.624 | 5.270 | 1.00 | 34.25 | C |
| ATOM | 1592 | CD2 | LEU A | 246 | 53.243 | 8.445 | 5.340 | 1.00 | 41.70 | C |
| ATOM | 1593 | C | LEU A | 246 | 56.068 | 9.819 | 7.980 | 1.00 | 30.35 | C |

Figure 6-28

| | | Atom Type | Resid | # | X | Y | Z | OCC | B | |
|---|---|---|---|---|---|---|---|---|---|---|
| ATOM | 1594 | O | LEU A | 246 | 56.984 | 10.082 | 7.189 | 1.00 | 27.26 | O |
| ATOM | 1595 | N | GLY A | 247 | 56.131 | 10.133 | 9.273 | 1.00 | 30.08 | N |
| ATOM | 1596 | CA | GLY A | 247 | 57.309 | 10.743 | 9.886 | 1.00 | 30.81 | C |
| ATOM | 1597 | C | GLY A | 247 | 58.441 | 9.712 | 9.899 | 1.00 | 34.82 | C |
| ATOM | 1598 | O | GLY A | 247 | 59.611 | 10.035 | 9.702 | 1.00 | 35.55 | O |
| ATOM | 1599 | N | CYS A | 248 | 58.097 | 8.449 | 10.106 | 1.00 | 32.70 | N |
| ATOM | 1600 | CA | CYS A | 248 | 59.107 | 7.399 | 10.046 | 1.00 | 31.75 | C |
| ATOM | 1601 | CB | CYS A | 248 | 58.575 | 6.095 | 10.629 | 1.00 | 30.93 | C |
| ATOM | 1602 | SG | CYS A | 248 | 58.189 | 6.188 | 12.414 | 1.00 | 34.76 | S |
| ATOM | 1603 | C | CYS A | 248 | 59.547 | 7.202 | 8.581 | 1.00 | 32.54 | C |
| ATOM | 1604 | O | CYS A | 248 | 60.671 | 6.919 | 8.331 | 1.00 | 33.03 | O |
| ATOM | 1605 | N | VAL A | 249 | 58.641 | 7.314 | 7.623 | 1.00 | 28.61 | N |
| ATOM | 1606 | CA | VAL A | 249 | 58.981 | 7.140 | 6.196 | 1.00 | 28.09 | C |
| ATOM | 1607 | CB | VAL A | 249 | 57.698 | 7.319 | 5.328 | 1.00 | 28.56 | C |
| ATOM | 1608 | CG1 | VAL A | 249 | 58.030 | 7.621 | 3.856 | 1.00 | 27.87 | C |
| ATOM | 1609 | CG2 | VAL A | 249 | 56.727 | 6.180 | 5.514 | 1.00 | 26.68 | C |
| ATOM | 1610 | C | VAL A | 249 | 59.969 | 8.260 | 5.804 | 1.00 | 33.79 | C |
| ATOM | 1611 | O | VAL A | 249 | 60.959 | 8.046 | 5.056 | 1.00 | 32.08 | O |
| ATOM | 1612 | N | MET A | 250 | 59.606 | 9.479 | 6.201 | 1.00 | 30.39 | N |
| ATOM | 1613 | CA | MET A | 250 | 60.410 | 10.667 | 5.884 | 1.00 | 31.12 | C |
| ATOM | 1614 | CB | MET A | 250 | 59.766 | 11.948 | 6.408 | 1.00 | 32.99 | C |
| ATOM | 1615 | CG | MET A | 250 | 60.630 | 13.214 | 6.241 | 1.00 | 34.12 | C |
| ATOM | 1616 | SD | MET A | 250 | 59.825 | 14.712 | 6.927 | 1.00 | 36.13 | S |
| ATOM | 1617 | CE | MET A | 250 | 61.300 | 15.986 | 6.871 | 1.00 | 32.92 | C |
| ATOM | 1618 | C | MET A | 250 | 61.810 | 10.522 | 6.475 | 1.00 | 33.64 | C |
| ATOM | 1619 | O | MET A | 250 | 62.785 | 10.797 | 5.808 | 1.00 | 32.68 | O |
| ATOM | 1620 | N | TYR A | 251 | 61.890 | 10.146 | 7.742 | 1.00 | 32.32 | N |
| ATOM | 1621 | CA | TYR A | 251 | 63.171 | 9.933 | 8.376 | 1.00 | 33.43 | C |
| ATOM | 1622 | CB | TYR A | 251 | 62.963 | 9.612 | 9.850 | 1.00 | 34.32 | C |
| ATOM | 1623 | CG | TYR A | 251 | 64.240 | 9.406 | 10.646 | 1.00 | 37.12 | C |
| ATOM | 1624 | CD1 | TYR A | 251 | 64.574 | 10.261 | 11.709 | 1.00 | 38.50 | C |
| ATOM | 1625 | CE1 | TYR A | 251 | 65.708 | 10.036 | 12.490 | 1.00 | 38.61 | C |
| ATOM | 1626 | CD2 | TYR A | 251 | 65.041 | 8.287 | 10.426 | 1.00 | 38.86 | C |
| ATOM | 1627 | CE2 | TYR A | 251 | 66.195 | 8.059 | 11.195 | 1.00 | 40.55 | C |
| ATOM | 1628 | CZ | TYR A | 251 | 66.514 | 8.925 | 12.218 | 1.00 | 44.53 | C |
| ATOM | 1629 | OH | TYR A | 251 | 67.642 | 8.672 | 12.963 | 1.00 | 47.52 | O |
| ATOM | 1630 | C | TYR A | 251 | 64.003 | 8.813 | 7.705 | 1.00 | 40.04 | C |
| ATOM | 1631 | O | TYR A | 251 | 65.223 | 8.940 | 7.531 | 1.00 | 41.51 | O |
| ATOM | 1632 | N | THR A | 252 | 63.387 | 7.667 | 7.432 | 1.00 | 33.65 | N |
| ATOM | 1633 | CA | THR A | 252 | 64.148 | 6.606 | 6.788 | 1.00 | 34.72 | C |
| ATOM | 1634 | CB | THR A | 252 | 63.581 | 5.160 | 6.904 | 1.00 | 39.03 | C |
| ATOM | 1635 | OG1 | THR A | 252 | 63.500 | 4.531 | 5.628 | 1.00 | 47.19 | O |
| ATOM | 1636 | CG2 | THR A | 252 | 62.333 | 5.110 | 7.562 | 1.00 | 26.42 | C |
| ATOM | 1637 | C | THR A | 252 | 64.721 | 6.932 | 5.427 | 1.00 | 37.14 | C |
| ATOM | 1638 | O | THR A | 252 | 65.855 | 6.575 | 5.136 | 1.00 | 36.42 | O |
| ATOM | 1639 | N | LEU A | 253 | 63.951 | 7.635 | 4.617 | 1.00 | 34.12 | N |
| ATOM | 1640 | CA | LEU A | 253 | 64.391 | 8.070 | 3.288 | 1.00 | 32.99 | C |
| ATOM | 1641 | CB | LEU A | 253 | 63.223 | 8.750 | 2.554 | 1.00 | 31.02 | C |
| ATOM | 1642 | CG | LEU A | 253 | 62.130 | 7.826 | 1.990 | 1.00 | 32.52 | C |
| ATOM | 1643 | CD1 | LEU A | 253 | 61.040 | 8.635 | 1.234 | 1.00 | 30.86 | C |
| ATOM | 1644 | CD2 | LEU A | 253 | 62.787 | 6.836 | 1.028 | 1.00 | 35.34 | C |
| ATOM | 1645 | C | LEU A | 253 | 65.584 | 9.069 | 3.356 | 1.00 | 40.20 | C |
| ATOM | 1646 | O | LEU A | 253 | 66.471 | 9.073 | 2.500 | 1.00 | 38.70 | O |
| ATOM | 1647 | N | LEU A | 254 | 65.552 | 9.944 | 4.349 | 1.00 | 39.69 | N |
| ATOM | 1648 | CA | LEU A | 254 | 66.584 | 10.964 | 4.524 | 1.00 | 40.49 | C |
| ATOM | 1649 | CB | LEU A | 254 | 66.031 | 12.074 | 5.415 | 1.00 | 39.81 | C |
| ATOM | 1650 | CG | LEU A | 254 | 64.966 | 12.962 | 4.751 | 1.00 | 42.74 | C |
| ATOM | 1651 | CD1 | LEU A | 254 | 64.331 | 13.843 | 5.794 | 1.00 | 41.04 | C |
| ATOM | 1652 | CD2 | LEU A | 254 | 65.560 | 13.789 | 3.587 | 1.00 | 44.58 | C |

Figure 6-29

| | Atom Type | Resid | # | X | Y | Z | OCC | B | |
|---|---|---|---|---|---|---|---|---|---|
| ATOM | 1653 | C | LEU A | 254 | 67.873 | 10.403 | 5.140 | 1.00 | 45.34 | C |
| ATOM | 1654 | O | LEU A | 254 | 68.988 | 10.772 | 4.747 | 1.00 | 47.66 | O |
| ATOM | 1655 | N | CYS A | 255 | 67.702 | 9.539 | 6.129 | 1.00 | 40.05 | N |
| ATOM | 1656 | CA | CYS A | 255 | 68.807 | 8.981 | 6.875 | 1.00 | 39.81 | C |
| ATOM | 1657 | CB | CYS A | 255 | 68.468 | 8.962 | 8.352 | 1.00 | 39.46 | C |
| ATOM | 1658 | SG | CYS A | 255 | 67.744 | 10.511 | 8.931 | 1.00 | 43.21 | S |
| ATOM | 1659 | C | CYS A | 255 | 69.289 | 7.599 | 6.468 | 1.00 | 45.66 | C |
| ATOM | 1660 | O | CYS A | 255 | 70.359 | 7.194 | 6.910 | 1.00 | 45.52 | O |
| ATOM | 1661 | N | GLY A | 256 | 68.451 | 6.841 | 5.756 | 1.00 | 40.81 | N |
| ATOM | 1662 | CA | GLY A | 256 | 68.773 | 5.505 | 5.306 | 1.00 | 39.84 | C |
| ATOM | 1663 | C | GLY A | 256 | 68.301 | 4.369 | 6.198 | 1.00 | 42.15 | C |
| ATOM | 1664 | O | GLY A | 256 | 68.517 | 3.209 | 5.881 | 1.00 | 40.77 | O |
| ATOM | 1665 | N | SER A | 257 | 67.760 | 4.666 | 7.366 | 1.00 | 38.67 | N |
| ATOM | 1666 | CA | SER A | 257 | 67.296 | 3.571 | 8.217 | 1.00 | 38.99 | C |
| ATOM | 1667 | CB | SER A | 257 | 68.453 | 2.976 | 9.034 | 1.00 | 42.15 | C |
| ATOM | 1668 | OG | SER A | 257 | 68.601 | 3.640 | 10.283 | 1.00 | 58.37 | O |
| ATOM | 1669 | C | SER A | 257 | 66.111 | 4.040 | 9.084 | 1.00 | 45.42 | C |
| ATOM | 1670 | O | SER A | 257 | 66.000 | 5.219 | 9.388 | 1.00 | 45.67 | O |
| ATOM | 1671 | N | PRO A | 258 | 65.173 | 3.136 | 9.429 | 1.00 | 41.89 | N |
| ATOM | 1672 | CD | PRO A | 258 | 64.945 | 1.735 | 9.033 | 1.00 | 43.60 | C |
| ATOM | 1673 | CA | PRO A | 258 | 64.052 | 3.676 | 10.231 | 1.00 | 40.68 | C |
| ATOM | 1674 | CB | PRO A | 258 | 63.127 | 2.454 | 10.423 | 1.00 | 42.39 | C |
| ATOM | 1675 | CG | PRO A | 258 | 63.462 | 1.553 | 9.256 | 1.00 | 47.59 | C |
| ATOM | 1676 | C | PRO A | 258 | 64.508 | 4.247 | 11.570 | 1.00 | 40.97 | C |
| ATOM | 1677 | O | PRO A | 258 | 65.405 | 3.701 | 12.203 | 1.00 | 40.47 | O |
| ATOM | 1678 | N | PRO A | 259 | 63.867 | 5.342 | 12.035 | 1.00 | 37.75 | N |
| ATOM | 1679 | CD | PRO A | 259 | 62.675 | 5.961 | 11.408 | 1.00 | 37.17 | C |
| ATOM | 1680 | CA | PRO A | 259 | 64.263 | 6.044 | 13.265 | 1.00 | 37.15 | C |
| ATOM | 1681 | CB | PRO A | 259 | 63.192 | 7.133 | 13.438 | 1.00 | 38.38 | C |
| ATOM | 1682 | CG | PRO A | 259 | 62.045 | 6.702 | 12.550 | 1.00 | 42.39 | C |
| ATOM | 1683 | C | PRO A | 259 | 64.359 | 5.226 | 14.535 | 1.00 | 42.73 | C |
| ATOM | 1684 | O | PRO A | 259 | 65.145 | 5.587 | 15.432 | 1.00 | 42.32 | O |
| ATOM | 1685 | N | PHE A | 260 | 63.546 | 4.171 | 14.646 | 1.00 | 38.68 | N |
| ATOM | 1686 | CA | PHE A | 260 | 63.512 | 3.361 | 15.865 | 1.00 | 37.82 | C |
| ATOM | 1687 | CB | PHE A | 260 | 62.118 | 3.358 | 16.507 | 1.00 | 38.42 | C |
| ATOM | 1688 | CG | PHE A | 260 | 61.568 | 4.736 | 16.745 | 1.00 | 36.46 | C |
| ATOM | 1689 | CD1 | PHE A | 260 | 60.718 | 5.330 | 15.823 | 1.00 | 34.63 | C |
| ATOM | 1690 | CD2 | PHE A | 260 | 61.963 | 5.461 | 17.852 | 1.00 | 36.11 | C |
| ATOM | 1691 | CE1 | PHE A | 260 | 60.275 | 6.637 | 16.005 | 1.00 | 33.60 | C |
| ATOM | 1692 | CE2 | PHE A | 260 | 61.502 | 6.757 | 18.060 | 1.00 | 37.14 | C |
| ATOM | 1693 | CZ | PHE A | 260 | 60.626 | 7.323 | 17.141 | 1.00 | 35.64 | C |
| ATOM | 1694 | C | PHE A | 260 | 64.069 | 1.947 | 15.764 | 1.00 | 45.11 | C |
| ATOM | 1695 | O | PHE A | 260 | 64.002 | 1.168 | 16.734 | 1.00 | 42.55 | O |
| ATOM | 1696 | N | GLU A | 261 | 64.681 | 1.644 | 14.622 | 1.00 | 45.27 | N |
| ATOM | 1697 | CA | GLU A | 261 | 65.270 | 0.334 | 14.385 | 1.00 | 47.15 | C |
| ATOM | 1698 | CB | GLU A | 261 | 65.901 | 0.303 | 13.002 | 1.00 | 48.45 | C |
| ATOM | 1699 | CG | GLU A | 261 | 65.897 | -1.080 | 12.394 | 1.00 | 59.39 | C |
| ATOM | 1700 | CD | GLU A | 261 | 66.359 | -1.073 | 10.960 | 1.00 | 78.82 | C |
| ATOM | 1701 | OE1 | GLU A | 261 | 65.630 | -1.627 | 10.101 | 1.00 | 69.72 | O |
| ATOM | 1702 | OE2 | GLU A | 261 | 67.438 | -0.492 | 10.699 | 1.00 | 65.37 | O |
| ATOM | 1703 | C | GLU A | 261 | 66.321 | -0.037 | 15.438 | 1.00 | 55.36 | C |
| ATOM | 1704 | O | GLU A | 261 | 67.163 | 0.795 | 15.786 | 1.00 | 55.75 | O |
| ATOM | 1705 | N | THR A | 262 | 66.256 | -1.271 | 15.947 | 1.00 | 54.54 | N |
| ATOM | 1706 | CA | THR A | 262 | 67.209 | -1.763 | 16.958 | 1.00 | 55.98 | C |
| ATOM | 1707 | CB | THR A | 262 | 66.787 | -1.464 | 18.449 | 1.00 | 55.45 | C |
| ATOM | 1708 | OG1 | THR A | 262 | 65.873 | -2.461 | 18.920 | 1.00 | 54.29 | O |
| ATOM | 1709 | CG2 | THR A | 262 | 66.202 | -0.071 | 18.617 | 1.00 | 51.41 | C |
| ATOM | 1710 | C | THR A | 262 | 67.516 | -3.245 | 16.765 | 1.00 | 64.29 | C |
| ATOM | 1711 | O | THR A | 262 | 67.157 | -3.831 | 15.744 | 1.00 | 63.62 | O |

Figure 6-30

|  |  | Atom Type | Resid | # | X | Y | Z | OCC | B |  |
|---|---|---|---|---|---|---|---|---|---|---|
| ATOM | 1712 | N | ALA A | 263 | 68.184 | -3.833 | 17.757 | 1.00 | 65.36 | N |
| ATOM | 1713 | CA | ALA A | 263 | 68.530 | -5.261 | 17.753 | 1.00 | 66.93 | C |
| ATOM | 1714 | CB | ALA A | 263 | 69.059 | -5.687 | 19.133 | 1.00 | 67.92 | C |
| ATOM | 1715 | C | ALA A | 263 | 67.303 | -6.084 | 17.385 | 1.00 | 71.92 | C |
| ATOM | 1716 | O | ALA A | 263 | 67.298 | -6.811 | 16.390 | 1.00 | 72.14 | O |
| ATOM | 1717 | N | ASP A | 264 | 66.258 | -5.952 | 18.191 | 1.00 | 69.64 | N |
| ATOM | 1718 | CA | ASP A | 264 | 64.993 | -6.620 | 17.918 | 1.00 | 70.59 | C |
| ATOM | 1719 | CB | ASP A | 264 | 65.029 | -8.131 | 18.211 | 1.00 | 74.12 | C |
| ATOM | 1720 | CG | ASP A | 264 | 64.740 | -8.994 | 16.958 | 1.00 | 89.51 | C |
| ATOM | 1721 | OD1 | ASP A | 264 | 63.546 | -9.212 | 16.634 | 1.00 | 88.94 | O |
| ATOM | 1722 | OD2 | ASP A | 264 | 65.711 | -9.479 | 16.320 | 1.00 | 97.27 | O |
| ATOM | 1723 | C | ASP A | 264 | 63.772 | -5.925 | 18.529 | 1.00 | 70.87 | C |
| ATOM | 1724 | O | ASP A | 264 | 63.886 | -4.895 | 19.209 | 1.00 | 69.70 | O |
| ATOM | 1725 | N | LEU A | 265 | 62.609 | -6.489 | 18.223 | 1.00 | 64.17 | N |
| ATOM | 1726 | CA | LEU A | 265 | 61.324 | -5.951 | 18.603 | 1.00 | 62.29 | C |
| ATOM | 1727 | CB | LEU A | 265 | 60.224 | -6.995 | 18.422 | 1.00 | 62.52 | C |
| ATOM | 1728 | CG | LEU A | 265 | 59.069 | -6.630 | 17.488 | 1.00 | 67.55 | C |
| ATOM | 1729 | CD1 | LEU A | 265 | 57.735 | -7.114 | 18.045 | 1.00 | 67.20 | C |
| ATOM | 1730 | CD2 | LEU A | 265 | 59.035 | -5.128 | 17.226 | 1.00 | 70.90 | C |
| ATOM | 1731 | C | LEU A | 265 | 61.212 | -5.229 | 19.934 | 1.00 | 63.55 | C |
| ATOM | 1732 | O | LEU A | 265 | 60.998 | -4.014 | 19.963 | 1.00 | 61.69 | O |
| ATOM | 1733 | N | LYS A | 266 | 61.291 | -5.969 | 21.036 | 1.00 | 59.09 | N |
| ATOM | 1734 | CA | LYS A | 266 | 61.104 | -5.369 | 22.357 | 1.00 | 58.05 | C |
| ATOM | 1735 | CB | LYS A | 266 | 61.374 | -6.371 | 23.473 | 1.00 | 61.04 | C |
| ATOM | 1736 | CG | LYS A | 266 | 60.949 | -7.792 | 23.128 | 1.00 | 81.37 | C |
| ATOM | 1737 | CD | LYS A | 266 | 59.470 | -7.863 | 22.748 | 1.00 | 90.41 | C |
| ATOM | 1738 | CE | LYS A | 266 | 58.634 | -8.376 | 23.910 | 1.00 | 98.76 | C |
| ATOM | 1739 | NZ | LYS A | 266 | 59.482 | -8.691 | 25.097 | 1.00 | 103.54 | N |
| ATOM | 1740 | C | LYS A | 266 | 61.881 | -4.085 | 22.567 | 1.00 | 59.53 | C |
| ATOM | 1741 | O | LYS A | 266 | 61.373 | -3.139 | 23.161 | 1.00 | 60.34 | O |
| ATOM | 1742 | N | GLU A | 267 | 63.097 | -4.044 | 22.041 | 1.00 | 53.06 | N |
| ATOM | 1743 | CA | GLU A | 267 | 63.961 | -2.869 | 22.156 | 1.00 | 52.40 | C |
| ATOM | 1744 | CB | GLU A | 267 | 65.392 | -3.217 | 21.729 | 1.00 | 54.54 | C |
| ATOM | 1745 | CG | GLU A | 267 | 65.925 | -4.549 | 22.342 | 1.00 | 74.79 | C |
| ATOM | 1746 | CD | GLU A | 267 | 65.614 | -5.803 | 21.497 | 1.00 | 85.08 | C |
| ATOM | 1747 | OE1 | GLU A | 267 | 66.177 | -5.921 | 20.391 | 1.00 | 79.93 | O |
| ATOM | 1748 | OE2 | GLU A | 267 | 64.865 | -6.698 | 21.965 | 1.00 | 52.45 | O |
| ATOM | 1749 | C | GLU A | 267 | 63.423 | -1.634 | 21.404 | 1.00 | 52.46 | C |
| ATOM | 1750 | O | GLU A | 267 | 63.383 | -0.533 | 21.973 | 1.00 | 53.03 | O |
| ATOM | 1751 | N | THR A | 268 | 62.976 | -1.822 | 20.156 | 1.00 | 46.29 | N |
| ATOM | 1752 | CA | THR A | 268 | 62.392 | -0.727 | 19.361 | 1.00 | 45.61 | C |
| ATOM | 1753 | CB | THR A | 268 | 62.504 | -0.921 | 17.819 | 1.00 | 48.15 | C |
| ATOM | 1754 | OG1 | THR A | 268 | 61.245 | -0.677 | 17.166 | 1.00 | 49.27 | O |
| ATOM | 1755 | CG2 | THR A | 268 | 63.010 | -2.264 | 17.480 | 1.00 | 42.00 | C |
| ATOM | 1756 | C | THR A | 268 | 61.016 | -0.243 | 19.854 | 1.00 | 47.70 | C |
| ATOM | 1757 | O | THR A | 268 | 60.685 | 0.927 | 19.727 | 1.00 | 44.43 | O |
| ATOM | 1758 | N | TYR A | 269 | 60.267 | -1.135 | 20.495 | 1.00 | 46.97 | N |
| ATOM | 1759 | CA | TYR A | 269 | 58.979 | -0.780 | 21.073 | 1.00 | 47.45 | C |
| ATOM | 1760 | CB | TYR A | 269 | 58.199 | -2.041 | 21.465 | 1.00 | 49.68 | C |
| ATOM | 1761 | CG | TYR A | 269 | 57.507 | -2.705 | 20.302 | 1.00 | 51.95 | C |
| ATOM | 1762 | CD1 | TYR A | 269 | 57.344 | -2.043 | 19.088 | 1.00 | 54.41 | C |
| ATOM | 1763 | CE1 | TYR A | 269 | 56.704 | -2.649 | 18.009 | 1.00 | 54.07 | C |
| ATOM | 1764 | CD2 | TYR A | 269 | 57.031 | -3.994 | 20.407 | 1.00 | 53.59 | C |
| ATOM | 1765 | CE2 | TYR A | 269 | 56.386 | -4.612 | 19.340 | 1.00 | 54.60 | C |
| ATOM | 1766 | CZ | TYR A | 269 | 56.224 | -3.938 | 18.142 | 1.00 | 62.01 | C |
| ATOM | 1767 | OH | TYR A | 269 | 55.529 | -4.543 | 17.099 | 1.00 | 63.42 | O |
| ATOM | 1768 | C | TYR A | 269 | 59.219 | 0.134 | 22.265 | 1.00 | 49.51 | C |
| ATOM | 1769 | O | TYR A | 269 | 58.494 | 1.104 | 22.443 | 1.00 | 48.96 | O |
| ATOM | 1770 | N | ARG A | 270 | 60.284 | -0.125 | 23.032 | 1.00 | 44.41 | N |

Figure 6-31

|  | | Atom Type | Resid | # | X | Y | Z | OCC | B | |
|---|---|---|---|---|---|---|---|---|---|---|
| ATOM | 1771 | CA | ARG A | 270 | 60.673 | 0.750 | 24.151 | 1.00 | 43.05 | C |
| ATOM | 1772 | CB | ARG A | 270 | 61.963 | 0.240 | 24.809 | 1.00 | 45.17 | C |
| ATOM | 1773 | CG | ARG A | 270 | 61.778 | -0.512 | 26.138 | 1.00 | 59.79 | C |
| ATOM | 1774 | CD | ARG A | 270 | 63.030 | -1.354 | 26.488 | 1.00 | 68.12 | C |
| ATOM | 1775 | NE | ARG A | 270 | 62.702 | -2.762 | 26.725 | 1.00 | 78.99 | N |
| ATOM | 1776 | CZ | ARG A | 270 | 63.350 | -3.799 | 26.189 | 1.00 | 87.60 | C |
| ATOM | 1777 | NH1 | ARG A | 270 | 64.393 | -3.609 | 25.379 | 1.00 | 65.69 | N |
| ATOM | 1778 | NH2 | ARG A | 270 | 62.950 | -5.034 | 26.472 | 1.00 | 70.54 | N |
| ATOM | 1779 | C | ARG A | 270 | 60.959 | 2.148 | 23.606 | 1.00 | 43.38 | C |
| ATOM | 1780 | O | ARG A | 270 | 60.502 | 3.149 | 24.148 | 1.00 | 42.66 | O |
| ATOM | 1781 | N | CYS A | 271 | 61.731 | 2.183 | 22.527 | 1.00 | 38.65 | N |
| ATOM | 1782 | CA | CYS A | 271 | 62.151 | 3.396 | 21.838 | 1.00 | 38.66 | C |
| ATOM | 1783 | CB | CYS A | 271 | 63.206 | 3.039 | 20.780 | 1.00 | 39.20 | C |
| ATOM | 1784 | SG | CYS A | 271 | 64.850 | 2.630 | 21.479 | 1.00 | 44.25 | S |
| ATOM | 1785 | C | CYS A | 271 | 61.011 | 4.177 | 21.190 | 1.00 | 41.11 | C |
| ATOM | 1786 | O | CYS A | 271 | 61.068 | 5.403 | 21.077 | 1.00 | 39.88 | O |
| ATOM | 1787 | N | ILE A | 272 | 60.008 | 3.462 | 20.686 | 1.00 | 38.48 | N |
| ATOM | 1788 | CA | ILE A | 272 | 58.857 | 4.124 | 20.075 | 1.00 | 37.21 | C |
| ATOM | 1789 | CB | ILE A | 272 | 57.975 | 3.123 | 19.238 | 1.00 | 39.31 | C |
| ATOM | 1790 | CG2 | ILE A | 272 | 56.613 | 3.771 | 18.867 | 1.00 | 33.68 | C |
| ATOM | 1791 | CG1 | ILE A | 272 | 58.744 | 2.673 | 17.986 | 1.00 | 38.51 | C |
| ATOM | 1792 | CD1 | ILE A | 272 | 58.216 | 1.401 | 17.292 | 1.00 | 43.79 | C |
| ATOM | 1793 | C | ILE A | 272 | 58.082 | 4.799 | 21.200 | 1.00 | 37.30 | C |
| ATOM | 1794 | O | ILE A | 272 | 57.770 | 5.987 | 21.128 | 1.00 | 35.71 | O |
| ATOM | 1795 | N | LYS A | 273 | 57.808 | 4.049 | 22.258 | 1.00 | 35.25 | N |
| ATOM | 1796 | CA | LYS A | 273 | 57.060 | 4.593 | 23.398 | 1.00 | 38.32 | C |
| ATOM | 1797 | CB | LYS A | 273 | 56.780 | 3.523 | 24.454 | 1.00 | 39.75 | C |
| ATOM | 1798 | CG | LYS A | 273 | 55.696 | 2.536 | 24.044 | 1.00 | 49.70 | C |
| ATOM | 1799 | CD | LYS A | 273 | 55.785 | 1.235 | 24.841 | 1.00 | 53.59 | C |
| ATOM | 1800 | CE | LYS A | 273 | 54.483 | 0.443 | 24.718 | 1.00 | 55.48 | C |
| ATOM | 1801 | NZ | LYS A | 273 | 54.468 | -0.777 | 25.566 | 1.00 | 69.29 | N |
| ATOM | 1802 | C | LYS A | 273 | 57.663 | 5.806 | 24.073 | 1.00 | 46.20 | C |
| ATOM | 1803 | O | LYS A | 273 | 56.935 | 6.632 | 24.626 | 1.00 | 45.99 | O |
| ATOM | 1804 | N | GLN A | 274 | 58.993 | 5.869 | 24.109 | 1.00 | 44.72 | N |
| ATOM | 1805 | CA | GLN A | 274 | 59.674 | 6.988 | 24.756 | 1.00 | 44.50 | C |
| ATOM | 1806 | CB | GLN A | 274 | 60.857 | 6.498 | 25.609 | 1.00 | 46.08 | C |
| ATOM | 1807 | CG | GLN A | 274 | 60.425 | 5.764 | 26.899 | 1.00 | 56.46 | C |
| ATOM | 1808 | CD | GLN A | 274 | 61.536 | 4.908 | 27.510 | 1.00 | 82.78 | C |
| ATOM | 1809 | OE1 | GLN A | 274 | 61.711 | 3.736 | 27.154 | 1.00 | 78.23 | O |
| ATOM | 1810 | NE2 | GLN A | 274 | 62.276 | 5.489 | 28.450 | 1.00 | 75.10 | N |
| ATOM | 1811 | C | GLN A | 274 | 60.150 | 7.958 | 23.696 | 1.00 | 46.91 | C |
| ATOM | 1812 | O | GLN A | 274 | 60.844 | 8.921 | 24.003 | 1.00 | 46.60 | O |
| ATOM | 1813 | N | VAL A | 275 | 59.702 | 7.729 | 22.457 | 1.00 | 40.66 | N |
| ATOM | 1814 | CA | VAL A | 275 | 60.115 | 8.529 | 21.311 | 1.00 | 39.23 | C |
| ATOM | 1815 | CB | VAL A | 275 | 59.304 | 9.827 | 21.170 | 1.00 | 41.56 | C |
| ATOM | 1816 | CG1 | VAL A | 275 | 59.498 | 10.417 | 19.745 | 1.00 | 40.15 | C |
| ATOM | 1817 | CG2 | VAL A | 275 | 57.846 | 9.578 | 21.493 | 1.00 | 41.38 | C |
| ATOM | 1818 | C | VAL A | 275 | 61.621 | 8.807 | 21.397 | 1.00 | 44.72 | C |
| ATOM | 1819 | O | VAL A | 275 | 62.068 | 9.952 | 21.396 | 1.00 | 43.42 | O |
| ATOM | 1820 | N | HIS A | 276 | 62.395 | 7.738 | 21.501 | 1.00 | 41.59 | N |
| ATOM | 1821 | CA | HIS A | 276 | 63.830 | 7.870 | 21.605 | 1.00 | 41.67 | C |
| ATOM | 1822 | CB | HIS A | 276 | 64.351 | 6.951 | 22.713 | 1.00 | 43.59 | C |
| ATOM | 1823 | CG | HIS A | 276 | 65.814 | 7.098 | 22.968 | 1.00 | 48.97 | C |
| ATOM | 1824 | CD2 | HIS A | 276 | 66.824 | 6.198 | 22.911 | 1.00 | 51.64 | C |
| ATOM | 1825 | ND1 | HIS A | 276 | 66.397 | 8.311 | 23.266 | 1.00 | 52.24 | N |
| ATOM | 1826 | CE1 | HIS A | 276 | 67.701 | 8.157 | 23.374 | 1.00 | 51.55 | C |
| ATOM | 1827 | NE2 | HIS A | 276 | 67.987 | 6.876 | 23.188 | 1.00 | 51.74 | N |
| ATOM | 1828 | C | HIS A | 276 | 64.504 | 7.558 | 20.262 | 1.00 | 43.08 | C |
| ATOM | 1829 | O | HIS A | 276 | 64.447 | 6.434 | 19.767 | 1.00 | 42.27 | O |

Figure 6-32

| Atom Type | | Resid | # | X | Y | Z | OCC | B | |
|---|---|---|---|---|---|---|---|---|---|
| ATOM | 1830 | N | TYR A 277 | 65.110 | 8.569 | 19.657 | 1.00 | 39.36 | N |
| ATOM | 1831 | CA | TYR A 277 | 65.816 | 8.396 | 18.382 | 1.00 | 38.36 | C |
| ATOM | 1832 | CB | TYR A 277 | 64.819 | 8.296 | 17.204 | 1.00 | 39.30 | C |
| ATOM | 1833 | CG | TYR A 277 | 64.127 | 9.604 | 16.913 | 1.00 | 41.12 | C |
| ATOM | 1834 | CD1 | TYR A 277 | 64.501 | 10.387 | 15.827 | 1.00 | 42.53 | C |
| ATOM | 1835 | CE1 | TYR A 277 | 63.930 | 11.609 | 15.618 | 1.00 | 43.46 | C |
| ATOM | 1836 | CD2 | TYR A 277 | 63.114 | 10.071 | 17.739 | 1.00 | 43.21 | C |
| ATOM | 1837 | CE2 | TYR A 277 | 62.503 | 11.291 | 17.514 | 1.00 | 43.94 | C |
| ATOM | 1838 | CZ | TYR A 277 | 62.918 | 12.058 | 16.456 | 1.00 | 50.43 | C |
| ATOM | 1839 | OH | TYR A 277 | 62.324 | 13.287 | 16.247 | 1.00 | 49.63 | O |
| ATOM | 1840 | C | TYR A 277 | 66.702 | 9.621 | 18.221 | 1.00 | 42.34 | C |
| ATOM | 1841 | O | TYR A 277 | 66.627 | 10.548 | 19.030 | 1.00 | 43.01 | O |
| ATOM | 1842 | N | THR A 278 | 67.530 | 9.629 | 17.181 | 1.00 | 40.38 | N |
| ATOM | 1843 | CA | THR A 278 | 68.439 | 10.751 | 16.914 | 1.00 | 41.03 | C |
| ATOM | 1844 | CB | THR A 278 | 69.960 | 10.373 | 17.146 | 1.00 | 51.33 | C |
| ATOM | 1845 | OG1 | THR A 278 | 70.298 | 9.203 | 16.395 | 1.00 | 54.07 | O |
| ATOM | 1846 | CG2 | THR A 278 | 70.228 | 10.066 | 18.598 | 1.00 | 49.61 | C |
| ATOM | 1847 | C | THR A 278 | 68.215 | 11.364 | 15.532 | 1.00 | 43.89 | C |
| ATOM | 1848 | O | THR A 278 | 67.881 | 10.668 | 14.565 | 1.00 | 43.45 | O |
| ATOM | 1849 | N | LEU A 279 | 68.364 | 12.682 | 15.462 | 1.00 | 40.04 | N |
| ATOM | 1850 | CA | LEU A 279 | 68.252 | 13.394 | 14.212 | 1.00 | 40.02 | C |
| ATOM | 1851 | CB | LEU A 279 | 67.528 | 14.714 | 14.431 | 1.00 | 39.03 | C |
| ATOM | 1852 | CG | LEU A 279 | 66.016 | 14.469 | 14.557 | 1.00 | 41.73 | C |
| ATOM | 1853 | CD1 | LEU A 279 | 65.282 | 15.750 | 14.958 | 1.00 | 41.24 | C |
| ATOM | 1854 | CD2 | LEU A 279 | 65.525 | 13.988 | 13.223 | 1.00 | 37.69 | C |
| ATOM | 1855 | C | LEU A 279 | 69.662 | 13.649 | 13.712 | 1.00 | 46.76 | C |
| ATOM | 1856 | O | LEU A 279 | 70.459 | 14.238 | 14.443 | 1.00 | 46.82 | O |
| ATOM | 1857 | N | PRO A 280 | 70.009 | 13.152 | 12.493 | 1.00 | 44.25 | N |
| ATOM | 1858 | CD | PRO A 280 | 69.323 | 12.126 | 11.679 | 1.00 | 43.54 | C |
| ATOM | 1859 | CA | PRO A 280 | 71.381 | 13.393 | 11.997 | 1.00 | 43.29 | C |
| ATOM | 1860 | CB | PRO A 280 | 71.384 | 12.747 | 10.614 | 1.00 | 43.65 | C |
| ATOM | 1861 | CG | PRO A 280 | 70.436 | 11.607 | 10.775 | 1.00 | 47.46 | C |
| ATOM | 1862 | C | PRO A 280 | 71.598 | 14.874 | 11.851 | 1.00 | 46.27 | C |
| ATOM | 1863 | O | PRO A 280 | 70.699 | 15.610 | 11.431 | 1.00 | 43.55 | O |
| ATOM | 1864 | N | ALA A 281 | 72.801 | 15.302 | 12.214 | 1.00 | 42.94 | N |
| ATOM | 1865 | CA | ALA A 281 | 73.148 | 16.706 | 12.179 | 1.00 | 43.32 | C |
| ATOM | 1866 | CB | ALA A 281 | 74.502 | 16.930 | 12.861 | 1.00 | 44.86 | C |
| ATOM | 1867 | C | ALA A 281 | 73.135 | 17.307 | 10.796 | 1.00 | 44.14 | C |
| ATOM | 1868 | O | ALA A 281 | 72.960 | 18.510 | 10.665 | 1.00 | 46.39 | O |
| ATOM | 1869 | N | SER A 282 | 73.290 | 16.473 | 9.769 | 1.00 | 37.45 | N |
| ATOM | 1870 | CA | SER A 282 | 73.328 | 16.932 | 8.376 | 1.00 | 35.68 | C |
| ATOM | 1871 | CB | SER A 282 | 74.086 | 15.935 | 7.506 | 1.00 | 40.15 | C |
| ATOM | 1872 | OG | SER A 282 | 73.383 | 14.711 | 7.335 | 1.00 | 43.29 | O |
| ATOM | 1873 | C | SER A 282 | 71.988 | 17.247 | 7.686 | 1.00 | 38.41 | C |
| ATOM | 1874 | O | SER A 282 | 71.954 | 17.774 | 6.546 | 1.00 | 33.90 | O |
| ATOM | 1875 | N | LEU A 283 | 70.894 | 16.917 | 8.361 | 1.00 | 35.78 | N |
| ATOM | 1876 | CA | LEU A 283 | 69.568 | 17.173 | 7.810 | 1.00 | 36.49 | C |
| ATOM | 1877 | CB | LEU A 283 | 68.498 | 16.465 | 8.658 | 1.00 | 36.65 | C |
| ATOM | 1878 | CG | LEU A 283 | 68.401 | 14.944 | 8.635 | 1.00 | 42.32 | C |
| ATOM | 1879 | CD1 | LEU A 283 | 67.053 | 14.510 | 9.295 | 1.00 | 43.44 | C |
| ATOM | 1880 | CD2 | LEU A 283 | 68.482 | 14.453 | 7.200 | 1.00 | 45.90 | C |
| ATOM | 1881 | C | LEU A 283 | 69.330 | 18.672 | 7.849 | 1.00 | 39.03 | C |
| ATOM | 1882 | O | LEU A 283 | 69.749 | 19.339 | 8.789 | 1.00 | 35.27 | O |
| ATOM | 1883 | N | SER A 284 | 68.674 | 19.217 | 6.834 | 1.00 | 37.19 | N |
| ATOM | 1884 | CA | SER A 284 | 68.354 | 20.650 | 6.866 | 1.00 | 36.62 | C |
| ATOM | 1885 | CB | SER A 284 | 67.482 | 21.005 | 5.684 | 1.00 | 40.36 | C |
| ATOM | 1886 | OG | SER A 284 | 66.160 | 20.543 | 5.921 | 1.00 | 46.57 | O |
| ATOM | 1887 | C | SER A 284 | 67.581 | 21.001 | 8.141 | 1.00 | 42.21 | C |
| ATOM | 1888 | O | SER A 284 | 67.045 | 20.124 | 8.826 | 1.00 | 40.37 | O |

Figure 6-33

| | | Atom Type | Resid | # | X | Y | Z | OCC | B | |
|---|---|---|---|---|---|---|---|---|---|---|
| ATOM | 1889 | N | LEU A | 285 | 67.502 | 22.284 | 8.473 | 1.00 | 41.12 | N |
| ATOM | 1890 | CA | LEU A | 285 | 66.736 | 22.675 | 9.673 | 1.00 | 41.17 | C |
| ATOM | 1891 | CB | LEU A | 285 | 66.944 | 24.167 | 9.981 | 1.00 | 41.56 | C |
| ATOM | 1892 | CG | LEU A | 285 | 67.100 | 24.506 | 11.460 | 1.00 | 46.94 | C |
| ATOM | 1893 | CD1 | LEU A | 285 | 65.987 | 23.984 | 12.318 | 1.00 | 44.41 | C |
| ATOM | 1894 | CD2 | LEU A | 285 | 68.416 | 23.889 | 11.908 | 1.00 | 56.92 | C |
| ATOM | 1895 | C | LEU A | 285 | 65.207 | 22.416 | 9.502 | 1.00 | 40.03 | C |
| ATOM | 1896 | O | LEU A | 285 | 64.516 | 22.019 | 10.445 | 1.00 | 36.59 | O |
| ATOM | 1897 | N | PRO A | 286 | 64.660 | 22.758 | 8.327 | 1.00 | 38.32 | N |
| ATOM | 1898 | CD | PRO A | 286 | 65.323 | 23.545 | 7.264 | 1.00 | 38.70 | C |
| ATOM | 1899 | CA | PRO A | 286 | 63.213 | 22.556 | 8.082 | 1.00 | 39.48 | C |
| ATOM | 1900 | CB | PRO A | 286 | 63.013 | 23.072 | 6.643 | 1.00 | 41.14 | C |
| ATOM | 1901 | CG | PRO A | 286 | 64.199 | 24.026 | 6.395 | 1.00 | 43.49 | C |
| ATOM | 1902 | C | PRO A | 286 | 62.862 | 21.071 | 8.153 | 1.00 | 43.51 | C |
| ATOM | 1903 | O | PRO A | 286 | 61.758 | 20.711 | 8.557 | 1.00 | 42.85 | O |
| ATOM | 1904 | N | ALA A | 287 | 63.797 | 20.219 | 7.724 | 1.00 | 40.34 | N |
| ATOM | 1905 | CA | ALA A | 287 | 63.604 | 18.766 | 7.803 | 1.00 | 39.67 | C |
| ATOM | 1906 | CB | ALA A | 287 | 64.612 | 18.005 | 6.919 | 1.00 | 40.83 | C |
| ATOM | 1907 | C | ALA A | 287 | 63.640 | 18.291 | 9.252 | 1.00 | 42.27 | C |
| ATOM | 1908 | O | ALA A | 287 | 62.769 | 17.546 | 9.689 | 1.00 | 40.47 | O |
| ATOM | 1909 | N | ARG A | 288 | 64.603 | 18.773 | 10.034 | 1.00 | 37.04 | N |
| ATOM | 1910 | CA | ARG A | 288 | 64.660 | 18.392 | 11.435 | 1.00 | 36.13 | C |
| ATOM | 1911 | CB | ARG A | 288 | 66.009 | 18.804 | 12.059 | 1.00 | 32.52 | C |
| ATOM | 1912 | CG | ARG A | 288 | 67.173 | 17.852 | 11.706 | 1.00 | 43.99 | C |
| ATOM | 1913 | CD | ARG A | 288 | 68.300 | 17.883 | 12.781 | 1.00 | 51.13 | C |
| ATOM | 1914 | NE | ARG A | 288 | 68.722 | 19.253 | 13.058 | 1.00 | 51.10 | N |
| ATOM | 1915 | CZ | ARG A | 288 | 69.095 | 20.105 | 12.113 | 1.00 | 60.65 | C |
| ATOM | 1916 | NH1 | ARG A | 288 | 69.143 | 19.671 | 10.869 | 1.00 | 47.26 | N |
| ATOM | 1917 | NH2 | ARG A | 288 | 69.450 | 21.365 | 12.400 | 1.00 | 37.23 | N |
| ATOM | 1918 | C | ARG A | 288 | 63.464 | 18.913 | 12.260 | 1.00 | 41.65 | C |
| ATOM | 1919 | O | ARG A | 288 | 63.063 | 18.277 | 13.230 | 1.00 | 40.95 | O |
| ATOM | 1920 | N | GLN A | 289 | 62.904 | 20.067 | 11.880 | 1.00 | 40.12 | N |
| ATOM | 1921 | CA | GLN A | 289 | 61.739 | 20.625 | 12.585 | 1.00 | 38.97 | C |
| ATOM | 1922 | CB | GLN A | 289 | 61.516 | 22.097 | 12.221 | 1.00 | 40.56 | C |
| ATOM | 1923 | CG | GLN A | 289 | 62.749 | 22.976 | 12.342 | 1.00 | 46.59 | C |
| ATOM | 1924 | CD | GLN A | 289 | 62.542 | 24.396 | 11.867 | 1.00 | 54.51 | C |
| ATOM | 1925 | OE1 | GLN A | 289 | 62.795 | 25.336 | 12.617 | 1.00 | 56.05 | O |
| ATOM | 1926 | NE2 | GLN A | 289 | 62.185 | 24.567 | 10.591 | 1.00 | 40.88 | N |
| ATOM | 1927 | C | GLN A | 289 | 60.488 | 19.821 | 12.190 | 1.00 | 40.34 | C |
| ATOM | 1928 | O | GLN A | 289 | 59.650 | 19.521 | 13.028 | 1.00 | 38.71 | O |
| ATOM | 1929 | N | LEU A | 290 | 60.369 | 19.475 | 10.906 | 1.00 | 35.70 | N |
| ATOM | 1930 | CA | LEU A | 290 | 59.226 | 18.691 | 10.477 | 1.00 | 35.35 | C |
| ATOM | 1931 | CB | LEU A | 290 | 59.172 | 18.475 | 8.948 | 1.00 | 34.26 | C |
| ATOM | 1932 | CG | LEU A | 290 | 57.773 | 18.488 | 8.246 | 1.00 | 36.17 | C |
| ATOM | 1933 | CD1 | LEU A | 290 | 57.641 | 17.597 | 7.041 | 1.00 | 31.04 | C |
| ATOM | 1934 | CD2 | LEU A | 290 | 56.525 | 18.328 | 9.158 | 1.00 | 38.07 | C |
| ATOM | 1935 | C | LEU A | 290 | 59.197 | 17.385 | 11.238 | 1.00 | 38.85 | C |
| ATOM | 1936 | O | LEU A | 290 | 58.186 | 17.008 | 11.818 | 1.00 | 38.25 | O |
| ATOM | 1937 | N | LEU A | 291 | 60.306 | 16.674 | 11.219 | 1.00 | 35.71 | N |
| ATOM | 1938 | CA | LEU A | 291 | 60.360 | 15.392 | 11.906 | 1.00 | 35.40 | C |
| ATOM | 1939 | CB | LEU A | 291 | 61.725 | 14.692 | 11.688 | 1.00 | 35.23 | C |
| ATOM | 1940 | CG | LEU A | 291 | 61.995 | 14.111 | 10.275 | 1.00 | 38.32 | C |
| ATOM | 1941 | CD1 | LEU A | 291 | 63.508 | 13.906 | 10.011 | 1.00 | 37.12 | C |
| ATOM | 1942 | CD2 | LEU A | 291 | 61.221 | 12.807 | 10.078 | 1.00 | 39.83 | C |
| ATOM | 1943 | C | LEU A | 291 | 60.047 | 15.503 | 13.386 | 1.00 | 39.47 | C |
| ATOM | 1944 | O | LEU A | 291 | 59.389 | 14.602 | 13.961 | 1.00 | 35.81 | O |
| ATOM | 1945 | N | ALA A | 292 | 60.596 | 16.524 | 14.052 | 1.00 | 37.00 | N |
| ATOM | 1946 | CA | ALA A | 292 | 60.335 | 16.642 | 15.490 | 1.00 | 38.14 | C |
| ATOM | 1947 | CB | ALA A | 292 | 61.234 | 17.723 | 16.143 | 1.00 | 39.03 | C |

Figure 6-34

| | | Atom Type | Resid | # | X | Y | Z | OCC | B | |
|---|---|---|---|---|---|---|---|---|---|---|
| ATOM | 1948 | C | ALA A | 292 | 58.833 | 16.939 | 15.720 | 1.00 | 42.52 | C |
| ATOM | 1949 | O | ALA A | 292 | 58.225 | 16.403 | 16.670 | 1.00 | 41.85 | O |
| ATOM | 1950 | N | ALA A | 293 | 58.234 | 17.722 | 14.810 | 1.00 | 36.90 | N |
| ATOM | 1951 | CA | ALA A | 293 | 56.799 | 18.056 | 14.883 | 1.00 | 38.15 | C |
| ATOM | 1952 | CB | ALA A | 293 | 56.448 | 19.175 | 13.877 | 1.00 | 39.03 | C |
| ATOM | 1953 | C | ALA A | 293 | 55.868 | 16.837 | 14.709 | 1.00 | 40.26 | C |
| ATOM | 1954 | O | ALA A | 293 | 54.843 | 16.724 | 15.367 | 1.00 | 38.41 | O |
| ATOM | 1955 | N | ILE A | 294 | 56.282 | 15.891 | 13.867 | 1.00 | 37.11 | N |
| ATOM | 1956 | CA | ILE A | 294 | 55.537 | 14.655 | 13.627 | 1.00 | 34.49 | C |
| ATOM | 1957 | CB | ILE A | 294 | 55.874 | 14.090 | 12.239 | 1.00 | 36.10 | C |
| ATOM | 1958 | CG2 | ILE A | 294 | 55.157 | 12.743 | 11.984 | 1.00 | 34.27 | C |
| ATOM | 1959 | CG1 | ILE A | 294 | 55.549 | 15.131 | 11.180 | 1.00 | 35.58 | C |
| ATOM | 1960 | CD1 | ILE A | 294 | 56.054 | 14.764 | 9.796 | 1.00 | 40.74 | C |
| ATOM | 1961 | C | ILE A | 294 | 55.730 | 13.616 | 14.706 | 1.00 | 38.50 | C |
| ATOM | 1962 | O | ILE A | 294 | 54.777 | 13.066 | 15.249 | 1.00 | 39.19 | O |
| ATOM | 1963 | N | LEU A | 295 | 56.976 | 13.310 | 15.000 | 1.00 | 35.03 | N |
| ATOM | 1964 | CA | LEU A | 295 | 57.289 | 12.268 | 15.970 | 1.00 | 35.31 | C |
| ATOM | 1965 | CB | LEU A | 295 | 58.677 | 11.668 | 15.678 | 1.00 | 35.40 | C |
| ATOM | 1966 | CG | LEU A | 295 | 58.786 | 11.081 | 14.247 | 1.00 | 39.14 | C |
| ATOM | 1967 | CD1 | LEU A | 295 | 60.240 | 10.818 | 13.850 | 1.00 | 38.70 | C |
| ATOM | 1968 | CD2 | LEU A | 295 | 57.966 | 9.767 | 14.113 | 1.00 | 34.84 | C |
| ATOM | 1969 | C | LEU A | 295 | 57.105 | 12.681 | 17.446 | 1.00 | 41.10 | C |
| ATOM | 1970 | O | LEU A | 295 | 58.051 | 12.698 | 18.201 | 1.00 | 40.99 | O |
| ATOM | 1971 | N | ARG A | 296 | 55.853 | 12.898 | 17.851 | 1.00 | 39.57 | N |
| ATOM | 1972 | CA | ARG A | 296 | 55.475 | 13.255 | 19.231 | 1.00 | 40.09 | C |
| ATOM | 1973 | CB | ARG A | 296 | 54.552 | 14.504 | 19.228 | 1.00 | 39.55 | C |
| ATOM | 1974 | CG | ARG A | 296 | 55.006 | 15.634 | 18.328 | 1.00 | 52.50 | C |
| ATOM | 1975 | CD | ARG A | 296 | 55.870 | 16.653 | 19.075 | 1.00 | 51.48 | C |
| ATOM | 1976 | NE | ARG A | 296 | 55.101 | 17.472 | 20.001 | 1.00 | 57.21 | N |
| ATOM | 1977 | CZ | ARG A | 296 | 54.749 | 18.731 | 19.758 | 1.00 | 80.80 | C |
| ATOM | 1978 | NH1 | ARG A | 296 | 55.105 | 19.310 | 18.618 | 1.00 | 74.23 | N |
| ATOM | 1979 | NH2 | ARG A | 296 | 54.052 | 19.411 | 20.657 | 1.00 | 71.37 | N |
| ATOM | 1980 | C | ARG A | 296 | 54.706 | 12.093 | 19.839 | 1.00 | 42.81 | C |
| ATOM | 1981 | O | ARG A | 296 | 53.862 | 11.529 | 19.180 | 1.00 | 43.86 | O |
| ATOM | 1982 | N | ALA A | 297 | 54.977 | 11.758 | 21.099 | 1.00 | 36.93 | N |
| ATOM | 1983 | CA | ALA A | 297 | 54.298 | 10.656 | 21.783 | 1.00 | 35.74 | C |
| ATOM | 1984 | CB | ALA A | 297 | 54.782 | 10.548 | 23.243 | 1.00 | 35.24 | C |
| ATOM | 1985 | C | ALA A | 297 | 52.773 | 10.770 | 21.763 | 1.00 | 41.41 | C |
| ATOM | 1986 | O | ALA A | 297 | 52.057 | 9.771 | 21.616 | 1.00 | 42.30 | O |
| ATOM | 1987 | N | SER A | 298 | 52.276 | 11.972 | 22.010 | 1.00 | 38.48 | N |
| ATOM | 1988 | CA | SER A | 298 | 50.841 | 12.166 | 22.082 | 1.00 | 37.79 | C |
| ATOM | 1989 | CB | SER A | 298 | 50.431 | 13.085 | 23.252 | 1.00 | 39.57 | C |
| ATOM | 1990 | OG | SER A | 298 | 49.449 | 13.992 | 22.835 | 1.00 | 40.24 | O |
| ATOM | 1991 | C | SER A | 298 | 50.222 | 12.527 | 20.737 | 1.00 | 39.95 | C |
| ATOM | 1992 | O | SER A | 298 | 50.630 | 13.478 | 20.075 | 1.00 | 38.25 | O |
| ATOM | 1993 | N | PRO A | 299 | 49.284 | 11.681 | 20.271 | 1.00 | 37.25 | N |
| ATOM | 1994 | CD | PRO A | 299 | 48.645 | 10.675 | 21.136 | 1.00 | 37.43 | C |
| ATOM | 1995 | CA | PRO A | 299 | 48.635 | 11.798 | 18.948 | 1.00 | 37.27 | C |
| ATOM | 1996 | CB | PRO A | 299 | 47.452 | 10.802 | 19.026 | 1.00 | 38.71 | C |
| ATOM | 1997 | CG | PRO A | 299 | 47.786 | 9.878 | 20.161 | 1.00 | 42.21 | C |
| ATOM | 1998 | C | PRO A | 299 | 48.136 | 13.201 | 18.645 | 1.00 | 38.59 | C |
| ATOM | 1999 | O | PRO A | 299 | 48.324 | 13.700 | 17.526 | 1.00 | 36.93 | O |
| ATOM | 2000 | N | ARG A | 300 | 47.507 | 13.837 | 19.644 | 1.00 | 35.75 | N |
| ATOM | 2001 | CA | ARG A | 300 | 46.958 | 15.198 | 19.501 | 1.00 | 36.03 | C |
| ATOM | 2002 | CB | ARG A | 300 | 46.095 | 15.585 | 20.712 | 1.00 | 41.65 | C |
| ATOM | 2003 | CG | ARG A | 300 | 46.521 | 14.903 | 22.010 | 1.00 | 66.09 | C |
| ATOM | 2004 | CD | ARG A | 300 | 46.314 | 15.806 | 23.231 | 1.00 | 89.13 | C |
| ATOM | 2005 | NE | ARG A | 300 | 45.540 | 15.143 | 24.284 | 1.00 | 106.71 | N |
| ATOM | 2006 | CZ | ARG A | 300 | 45.839 | 15.180 | 25.581 | 1.00 | 127.54 | C |

Figure 6-35

| | | Atom Type | Resid | # | X | Y | Z | OCC | B | |
|---|---|---|---|---|---|---|---|---|---|---|
| ATOM | 2007 | NH1 | ARG A | 300 | 46.905 | 15.850 | 26.005 | 1.00 | 117.27 | N |
| ATOM | 2008 | NH2 | ARG A | 300 | 45.070 | 14.548 | 26.462 | 1.00 | 116.27 | N |
| ATOM | 2009 | C | ARG A | 300 | 47.952 | 16.334 | 19.217 | 1.00 | 41.27 | C |
| ATOM | 2010 | O | ARG A | 300 | 47.538 | 17.378 | 18.723 | 1.00 | 42.74 | O |
| ATOM | 2011 | N | ASP A | 301 | 49.236 | 16.160 | 19.543 | 1.00 | 37.28 | N |
| ATOM | 2012 | CA | ASP A | 301 | 50.238 | 17.202 | 19.295 | 1.00 | 37.50 | C |
| ATOM | 2013 | CB | ASP A | 301 | 51.402 | 17.091 | 20.290 | 1.00 | 40.82 | C |
| ATOM | 2014 | CG | ASP A | 301 | 51.001 | 17.499 | 21.695 | 1.00 | 48.63 | C |
| ATOM | 2015 | OD1 | ASP A | 301 | 51.620 | 17.007 | 22.662 | 1.00 | 51.25 | O |
| ATOM | 2016 | OD2 | ASP A | 301 | 49.996 | 18.222 | 21.815 | 1.00 | 48.53 | O |
| ATOM | 2017 | C | ASP A | 301 | 50.799 | 17.153 | 17.899 | 1.00 | 43.43 | C |
| ATOM | 2018 | O | ASP A | 301 | 51.493 | 18.083 | 17.457 | 1.00 | 43.98 | O |
| ATOM | 2019 | N | ARG A | 302 | 50.478 | 16.076 | 17.186 | 1.00 | 39.56 | N |
| ATOM | 2020 | CA | ARG A | 302 | 51.005 | 15.877 | 15.843 | 1.00 | 36.10 | C |
| ATOM | 2021 | CB | ARG A | 302 | 50.857 | 14.401 | 15.469 | 1.00 | 29.75 | C |
| ATOM | 2022 | CG | ARG A | 302 | 51.972 | 13.558 | 16.016 | 1.00 | 29.70 | C |
| ATOM | 2023 | CD | ARG A | 302 | 51.813 | 12.088 | 15.666 | 1.00 | 30.90 | C |
| ATOM | 2024 | NE | ARG A | 302 | 52.049 | 11.308 | 16.865 | 1.00 | 35.07 | N |
| ATOM | 2025 | CZ | ARG A | 302 | 51.444 | 10.168 | 17.173 | 1.00 | 39.93 | C |
| ATOM | 2026 | NH1 | ARG A | 302 | 50.630 | 9.584 | 16.310 | 1.00 | 31.19 | N |
| ATOM | 2027 | NH2 | ARG A | 302 | 51.685 | 9.610 | 18.347 | 1.00 | 38.67 | N |
| ATOM | 2028 | C | ARG A | 302 | 50.267 | 16.758 | 14.853 | 1.00 | 38.96 | C |
| ATOM | 2029 | O | ARG A | 302 | 49.044 | 16.924 | 14.933 | 1.00 | 39.02 | O |
| ATOM | 2030 | N | PRO A | 303 | 50.978 | 17.265 | 13.849 | 1.00 | 32.48 | N |
| ATOM | 2031 | CD | PRO A | 303 | 52.401 | 17.179 | 13.476 | 1.00 | 33.39 | C |
| ATOM | 2032 | CA | PRO A | 303 | 50.208 | 18.102 | 12.921 | 1.00 | 31.37 | C |
| ATOM | 2033 | CB | PRO A | 303 | 51.313 | 18.822 | 12.129 | 1.00 | 32.46 | C |
| ATOM | 2034 | CG | PRO A | 303 | 52.428 | 17.803 | 12.114 | 1.00 | 37.79 | C |
| ATOM | 2035 | C | PRO A | 303 | 49.278 | 17.309 | 11.972 | 1.00 | 36.24 | C |
| ATOM | 2036 | O | PRO A | 303 | 49.499 | 16.124 | 11.732 | 1.00 | 36.75 | O |
| ATOM | 2037 | N | SER A | 304 | 48.246 | 17.973 | 11.433 | 1.00 | 32.97 | N |
| ATOM | 2038 | CA | SER A | 304 | 47.335 | 17.365 | 10.455 | 1.00 | 33.64 | C |
| ATOM | 2039 | CB | SER A | 304 | 46.061 | 18.196 | 10.301 | 1.00 | 36.35 | C |
| ATOM | 2040 | OG | SER A | 304 | 46.334 | 19.380 | 9.589 | 1.00 | 41.00 | O |
| ATOM | 2041 | C | SER A | 304 | 48.032 | 17.299 | 9.097 | 1.00 | 36.05 | C |
| ATOM | 2042 | O | SER A | 304 | 49.083 | 17.915 | 8.906 | 1.00 | 32.94 | O |
| ATOM | 2043 | N | ILE A | 305 | 47.421 | 16.609 | 8.135 | 1.00 | 33.46 | N |
| ATOM | 2044 | CA | ILE A | 305 | 48.003 | 16.586 | 6.801 | 1.00 | 32.62 | C |
| ATOM | 2045 | CB | ILE A | 305 | 47.241 | 15.698 | 5.795 | 1.00 | 34.90 | C |
| ATOM | 2046 | CG2 | ILE A | 305 | 47.740 | 16.005 | 4.384 | 1.00 | 32.05 | C |
| ATOM | 2047 | CG1 | ILE A | 305 | 47.582 | 14.212 | 6.063 | 1.00 | 34.60 | C |
| ATOM | 2048 | CD1 | ILE A | 305 | 46.397 | 13.338 | 6.116 | 1.00 | 34.33 | C |
| ATOM | 2049 | C | ILE A | 305 | 48.268 | 17.987 | 6.268 | 1.00 | 37.91 | C |
| ATOM | 2050 | O | ILE A | 305 | 49.425 | 18.315 | 5.893 | 1.00 | 31.93 | O |
| ATOM | 2051 | N | ASP A | 306 | 47.196 | 18.804 | 6.275 | 1.00 | 38.04 | N |
| ATOM | 2052 | CA | ASP A | 306 | 47.209 | 20.202 | 5.822 | 1.00 | 38.94 | C |
| ATOM | 2053 | CB | ASP A | 306 | 45.855 | 20.898 | 6.063 | 1.00 | 42.41 | C |
| ATOM | 2054 | CG | ASP A | 306 | 44.746 | 20.397 | 5.132 | 1.00 | 60.62 | C |
| ATOM | 2055 | OD1 | ASP A | 306 | 45.064 | 19.870 | 4.042 | 1.00 | 60.90 | O |
| ATOM | 2056 | OD2 | ASP A | 306 | 43.551 | 20.596 | 5.473 | 1.00 | 68.79 | O |
| ATOM | 2057 | C | ASP A | 306 | 48.305 | 21.023 | 6.481 | 1.00 | 40.66 | C |
| ATOM | 2058 | O | ASP A | 306 | 48.960 | 21.825 | 5.817 | 1.00 | 37.37 | O |
| ATOM | 2059 | N | GLN A | 307 | 48.470 | 20.840 | 7.792 | 1.00 | 38.15 | N |
| ATOM | 2060 | CA | GLN A | 307 | 49.537 | 21.494 | 8.546 | 1.00 | 37.67 | C |
| ATOM | 2061 | CB | GLN A | 307 | 49.373 | 21.248 | 10.050 | 1.00 | 39.01 | C |
| ATOM | 2062 | CG | GLN A | 307 | 48.246 | 22.115 | 10.596 | 1.00 | 46.51 | C |
| ATOM | 2063 | CD | GLN A | 307 | 48.030 | 22.004 | 12.079 | 1.00 | 49.24 | C |
| ATOM | 2064 | OE1 | GLN A | 307 | 47.485 | 22.919 | 12.695 | 1.00 | 46.06 | O |
| ATOM | 2065 | NE2 | GLN A | 307 | 48.295 | 20.849 | 12.628 | 1.00 | 40.06 | N |

Figure 6-36

| | | Atom Type | Resid | # | X | Y | Z | OCC | B | |
|---|---|---|---|---|---|---|---|---|---|---|
| ATOM | 2066 | C | GLN A | 307 | 50.937 | 21.076 | 8.078 | 1.00 | 40.24 | C |
| ATOM | 2067 | O | GLN A | 307 | 51.823 | 21.926 | 7.897 | 1.00 | 38.12 | O |
| ATOM | 2068 | N | ILE A | 308 | 51.146 | 19.769 | 7.911 | 1.00 | 34.44 | N |
| ATOM | 2069 | CA | ILE A | 308 | 52.426 | 19.293 | 7.422 | 1.00 | 33.90 | C |
| ATOM | 2070 | CB | ILE A | 308 | 52.426 | 17.747 | 7.207 | 1.00 | 35.32 | C |
| ATOM | 2071 | CG2 | ILE A | 308 | 53.586 | 17.334 | 6.267 | 1.00 | 34.95 | C |
| ATOM | 2072 | CG1 | ILE A | 308 | 52.490 | 17.011 | 8.550 | 1.00 | 34.39 | C |
| ATOM | 2073 | CD1 | ILE A | 308 | 51.992 | 15.564 | 8.495 | 1.00 | 37.62 | C |
| ATOM | 2074 | C | ILE A | 308 | 52.770 | 20.008 | 6.108 | 1.00 | 38.18 | C |
| ATOM | 2075 | O | ILE A | 308 | 53.912 | 20.378 | 5.897 | 1.00 | 38.90 | O |
| ATOM | 2076 | N | LEU A | 309 | 51.804 | 20.108 | 5.196 | 1.00 | 36.04 | N |
| ATOM | 2077 | CA | LEU A | 309 | 52.053 | 20.713 | 3.893 | 1.00 | 36.54 | C |
| ATOM | 2078 | CB | LEU A | 309 | 50.915 | 20.437 | 2.937 | 1.00 | 36.32 | C |
| ATOM | 2079 | CG | LEU A | 309 | 50.850 | 18.996 | 2.440 | 1.00 | 40.57 | C |
| ATOM | 2080 | CD1 | LEU A | 309 | 49.485 | 18.730 | 1.798 | 1.00 | 39.74 | C |
| ATOM | 2081 | CD2 | LEU A | 309 | 51.981 | 18.799 | 1.466 | 1.00 | 42.98 | C |
| ATOM | 2082 | C | LEU A | 309 | 52.320 | 22.210 | 3.920 | 1.00 | 42.00 | C |
| ATOM | 2083 | O | LEU A | 309 | 52.777 | 22.778 | 2.925 | 1.00 | 40.31 | O |
| ATOM | 2084 | N | ARG A | 310 | 52.006 | 22.839 | 5.047 | 1.00 | 40.17 | N |
| ATOM | 2085 | CA | ARG A | 310 | 52.243 | 24.282 | 5.241 | 1.00 | 41.38 | C |
| ATOM | 2086 | CB | ARG A | 310 | 51.095 | 24.951 | 6.015 | 1.00 | 41.99 | C |
| ATOM | 2087 | CG | ARG A | 310 | 49.888 | 25.294 | 5.146 | 1.00 | 50.42 | C |
| ATOM | 2088 | CD | ARG A | 310 | 50.362 | 25.955 | 3.843 | 1.00 | 73.69 | C |
| ATOM | 2089 | NE | ARG A | 310 | 49.848 | 25.291 | 2.646 | 1.00 | 89.73 | N |
| ATOM | 2090 | CZ | ARG A | 310 | 50.389 | 25.394 | 1.437 | 1.00 | 102.88 | C |
| ATOM | 2091 | NH1 | ARG A | 310 | 51.480 | 26.126 | 1.254 | 1.00 | 92.26 | N |
| ATOM | 2092 | NH2 | ARG A | 310 | 49.837 | 24.757 | 0.413 | 1.00 | 87.46 | N |
| ATOM | 2093 | C | ARG A | 310 | 53.546 | 24.518 | 5.978 | 1.00 | 43.81 | C |
| ATOM | 2094 | O | ARG A | 310 | 53.863 | 25.644 | 6.346 | 1.00 | 45.77 | O |
| ATOM | 2095 | N | HIS A | 311 | 54.314 | 23.451 | 6.172 | 1.00 | 37.15 | N |
| ATOM | 2096 | CA | HIS A | 311 | 55.585 | 23.537 | 6.842 | 1.00 | 34.91 | C |
| ATOM | 2097 | CB | HIS A | 311 | 55.959 | 22.160 | 7.408 | 1.00 | 36.25 | C |
| ATOM | 2098 | CG | HIS A | 311 | 57.076 | 22.202 | 8.396 | 1.00 | 39.48 | C |
| ATOM | 2099 | CD2 | HIS A | 311 | 57.070 | 22.150 | 9.749 | 1.00 | 40.47 | C |
| ATOM | 2100 | ND1 | HIS A | 311 | 58.397 | 22.370 | 8.021 | 1.00 | 41.70 | N |
| ATOM | 2101 | CE1 | HIS A | 311 | 59.154 | 22.406 | 9.097 | 1.00 | 40.73 | C |
| ATOM | 2102 | NE2 | HIS A | 311 | 58.377 | 22.252 | 10.159 | 1.00 | 41.18 | N |
| ATOM | 2103 | C | HIS A | 311 | 56.666 | 24.064 | 5.913 | 1.00 | 39.80 | C |
| ATOM | 2104 | O | HIS A | 311 | 56.628 | 23.838 | 4.703 | 1.00 | 38.81 | O |
| ATOM | 2105 | N | ASP A | 312 | 57.651 | 24.757 | 6.493 | 1.00 | 40.25 | N |
| ATOM | 2106 | CA | ASP A | 312 | 58.796 | 25.285 | 5.735 | 1.00 | 40.67 | C |
| ATOM | 2107 | CB | ASP A | 312 | 59.831 | 25.908 | 6.695 | 1.00 | 41.87 | C |
| ATOM | 2108 | CG | ASP A | 312 | 59.390 | 27.288 | 7.234 | 1.00 | 53.00 | C |
| ATOM | 2109 | OD1 | ASP A | 312 | 60.154 | 27.888 | 8.017 | 1.00 | 54.60 | O |
| ATOM | 2110 | OD2 | ASP A | 312 | 58.288 | 27.774 | 6.890 | 1.00 | 54.85 | O |
| ATOM | 2111 | C | ASP A | 312 | 59.459 | 24.164 | 4.907 | 1.00 | 44.06 | C |
| ATOM | 2112 | O | ASP A | 312 | 60.022 | 24.425 | 3.839 | 1.00 | 41.62 | O |
| ATOM | 2113 | N | PHE A | 313 | 59.408 | 22.915 | 5.402 | 1.00 | 40.38 | N |
| ATOM | 2114 | CA | PHE A | 313 | 59.992 | 21.809 | 4.635 | 1.00 | 39.13 | C |
| ATOM | 2115 | CB | PHE A | 313 | 59.819 | 20.436 | 5.338 | 1.00 | 40.39 | C |
| ATOM | 2116 | CG | PHE A | 313 | 60.476 | 19.290 | 4.598 | 1.00 | 38.98 | C |
| ATOM | 2117 | CD1 | PHE A | 313 | 61.872 | 19.185 | 4.550 | 1.00 | 38.90 | C |
| ATOM | 2118 | CD2 | PHE A | 313 | 59.712 | 18.380 | 3.858 | 1.00 | 37.39 | C |
| ATOM | 2119 | CE1 | PHE A | 313 | 62.499 | 18.178 | 3.808 | 1.00 | 37.74 | C |
| ATOM | 2120 | CE2 | PHE A | 313 | 60.335 | 17.314 | 3.191 | 1.00 | 39.57 | C |
| ATOM | 2121 | CZ | PHE A | 313 | 61.736 | 17.250 | 3.137 | 1.00 | 37.08 | C |
| ATOM | 2122 | C | PHE A | 313 | 59.422 | 21.785 | 3.218 | 1.00 | 43.20 | C |
| ATOM | 2123 | O | PHE A | 313 | 60.151 | 21.556 | 2.233 | 1.00 | 44.12 | O |
| ATOM | 2124 | N | PHE A | 314 | 58.126 | 22.066 | 3.109 | 1.00 | 38.93 | N |

Figure 6-37

| | Atom Type | Resid | # | X | Y | Z | OCC | B | |
|---|---|---|---|---|---|---|---|---|---|
| ATOM | 2125 | CA | PHE A | 314 | 57.466 | 22.126 | 1.813 | 1.00 | 38.94 | C |
| ATOM | 2126 | CB | PHE A | 314 | 56.043 | 21.518 | 1.887 | 1.00 | 39.28 | C |
| ATOM | 2127 | CG | PHE A | 314 | 56.027 | 20.020 | 2.136 | 1.00 | 39.50 | C |
| ATOM | 2128 | CD1 | PHE A | 314 | 56.234 | 19.115 | 1.080 | 1.00 | 40.70 | C |
| ATOM | 2129 | CD2 | PHE A | 314 | 55.863 | 19.510 | 3.427 | 1.00 | 37.77 | C |
| ATOM | 2130 | CE1 | PHE A | 314 | 56.253 | 17.737 | 1.303 | 1.00 | 38.72 | C |
| ATOM | 2131 | CE2 | PHE A | 314 | 55.883 | 18.134 | 3.649 | 1.00 | 39.35 | C |
| ATOM | 2132 | CZ | PHE A | 314 | 56.064 | 17.250 | 2.568 | 1.00 | 36.68 | C |
| ATOM | 2133 | C | PHE A | 314 | 57.376 | 23.553 | 1.243 | 1.00 | 48.26 | C |
| ATOM | 2134 | O | PHE A | 314 | 57.633 | 23.779 | 0.063 | 1.00 | 46.74 | O |
| ATOM | 2135 | N | THR A | 315 | 56.942 | 24.497 | 2.070 | 1.00 | 48.79 | N |
| ATOM | 2136 | CA | THR A | 315 | 56.687 | 25.860 | 1.608 | 1.00 | 48.86 | C |
| ATOM | 2137 | CB | THR A | 315 | 55.858 | 26.650 | 2.621 | 1.00 | 51.36 | C |
| ATOM | 2138 | OG1 | THR A | 315 | 56.628 | 26.882 | 3.803 | 1.00 | 48.05 | O |
| ATOM | 2139 | CG2 | THR A | 315 | 54.596 | 25.872 | 2.985 | 1.00 | 45.51 | C |
| ATOM | 2140 | C | THR A | 315 | 57.883 | 26.636 | 1.093 | 1.00 | 54.67 | C |
| ATOM | 2141 | O | THR A | 315 | 57.787 | 27.423 | 0.144 | 1.00 | 53.32 | O |
| ATOM | 2142 | N | LYS A | 316 | 59.024 | 26.388 | 1.705 | 1.00 | 53.31 | N |
| ATOM | 2143 | CA | LYS A | 316 | 60.217 | 27.114 | 1.355 | 1.00 | 53.54 | C |
| ATOM | 2144 | CB | LYS A | 316 | 60.780 | 27.805 | 2.599 | 1.00 | 55.62 | C |
| ATOM | 2145 | CG | LYS A | 316 | 59.919 | 28.996 | 3.049 | 1.00 | 60.77 | C |
| ATOM | 2146 | CD | LYS A | 316 | 60.082 | 29.296 | 4.536 | 1.00 | 72.72 | C |
| ATOM | 2147 | CE | LYS A | 316 | 61.140 | 30.363 | 4.789 | 1.00 | 85.79 | C |
| ATOM | 2148 | NZ | LYS A | 316 | 62.301 | 29.851 | 5.576 | 1.00 | 91.84 | N |
| ATOM | 2149 | C | LYS A | 316 | 61.237 | 26.233 | 0.671 | 1.00 | 58.48 | C |
| ATOM | 2150 | O | LYS A | 316 | 62.264 | 26.707 | 0.253 | 1.00 | 58.63 | O |
| ATOM | 2151 | N | GLY A | 317 | 60.918 | 24.955 | 0.507 | 1.00 | 55.85 | N |
| ATOM | 2152 | CA | GLY A | 317 | 61.813 | 24.017 | -0.147 | 1.00 | 53.83 | C |
| ATOM | 2153 | C | GLY A | 317 | 61.495 | 23.752 | -1.610 | 1.00 | 52.56 | C |
| ATOM | 2154 | O | GLY A | 317 | 60.360 | 23.913 | -2.066 | 1.00 | 50.30 | O |
| ATOM | 2155 | N | TYR A | 318 | 62.523 | 23.310 | -2.328 | 1.00 | 47.79 | N |
| ATOM | 2156 | CA | TYR A | 318 | 62.454 | 22.993 | -3.751 | 1.00 | 47.36 | C |
| ATOM | 2157 | CB | TYR A | 318 | 63.843 | 23.163 | -4.367 | 1.00 | 48.32 | C |
| ATOM | 2158 | CG | TYR A | 318 | 63.881 | 22.624 | -5.767 | 1.00 | 51.18 | C |
| ATOM | 2159 | CD1 | TYR A | 318 | 63.112 | 23.206 | -6.750 | 1.00 | 52.60 | C |
| ATOM | 2160 | CE1 | TYR A | 318 | 63.104 | 22.706 | -8.023 | 1.00 | 56.48 | C |
| ATOM | 2161 | CD2 | TYR A | 318 | 64.593 | 21.462 | -6.082 | 1.00 | 51.86 | C |
| ATOM | 2162 | CE2 | TYR A | 318 | 64.562 | 20.937 | -7.357 | 1.00 | 52.40 | C |
| ATOM | 2163 | CZ | TYR A | 318 | 63.808 | 21.565 | -8.324 | 1.00 | 56.42 | C |
| ATOM | 2164 | OH | TYR A | 318 | 63.778 | 21.100 | -9.616 | 1.00 | 51.89 | O |
| ATOM | 2165 | C | TYR A | 318 | 61.940 | 21.577 | -4.130 | 1.00 | 49.42 | C |
| ATOM | 2166 | O | TYR A | 318 | 62.583 | 20.578 | -3.851 | 1.00 | 45.82 | O |
| ATOM | 2167 | N | THR A | 319 | 60.842 | 21.518 | -4.874 | 1.00 | 47.39 | N |
| ATOM | 2168 | CA | THR A | 319 | 60.289 | 20.255 | -5.329 | 1.00 | 46.38 | C |
| ATOM | 2169 | CB | THR A | 319 | 58.827 | 20.093 | -4.871 | 1.00 | 56.96 | C |
| ATOM | 2170 | OG1 | THR A | 319 | 58.694 | 20.493 | -3.496 | 1.00 | 57.39 | O |
| ATOM | 2171 | CG2 | THR A | 319 | 58.372 | 18.638 | -5.049 | 1.00 | 56.29 | C |
| ATOM | 2172 | C | THR A | 319 | 60.364 | 20.159 | -6.841 | 1.00 | 48.59 | C |
| ATOM | 2173 | O | THR A | 319 | 59.776 | 20.964 | -7.538 | 1.00 | 48.18 | O |
| ATOM | 2174 | N | PRO A | 320 | 61.056 | 19.142 | -7.372 | 1.00 | 45.36 | N |
| ATOM | 2175 | CD | PRO A | 320 | 62.093 | 18.274 | -6.783 | 1.00 | 46.38 | C |
| ATOM | 2176 | CA | PRO A | 320 | 61.041 | 19.107 | -8.846 | 1.00 | 45.49 | C |
| ATOM | 2177 | CB | PRO A | 320 | 62.082 | 18.037 | -9.212 | 1.00 | 46.66 | C |
| ATOM | 2178 | CG | PRO A | 320 | 62.531 | 17.417 | -7.925 | 1.00 | 50.75 | C |
| ATOM | 2179 | C | PRO A | 320 | 59.666 | 18.695 | -9.367 | 1.00 | 51.49 | C |
| ATOM | 2180 | O | PRO A | 320 | 58.851 | 18.146 | -8.621 | 1.00 | 51.83 | O |
| ATOM | 2181 | N | ASP A | 321 | 59.413 | 18.957 | -10.649 | 1.00 | 49.13 | N |
| ATOM | 2182 | CA | ASP A | 321 | 58.125 | 18.654 | -11.267 | 1.00 | 49.99 | C |
| ATOM | 2183 | CB | ASP A | 321 | 57.906 | 19.516 | -12.530 | 1.00 | 53.58 | C |

Figure 6-38

| | | Atom Type | Resid | # | X | Y | Z | OCC | B | |
|---|---|---|---|---|---|---|---|---|---|---|
| ATOM | 2184 | CG | ASP A | 321 | 57.536 | 20.978 | -12.202 | 1.00 | 72.84 | C |
| ATOM | 2185 | OD1 | ASP A | 321 | 57.760 | 21.869 | -13.055 | 1.00 | 72.98 | O |
| ATOM | 2186 | OD2 | ASP A | 321 | 57.052 | 21.239 | -11.076 | 1.00 | 83.93 | O |
| ATOM | 2187 | C | ASP A | 321 | 57.989 | 17.170 | -11.614 | 1.00 | 53.02 | C |
| ATOM | 2188 | O | ASP A | 321 | 56.878 | 16.635 | -11.641 | 1.00 | 51.03 | O |
| ATOM | 2189 | N | ARG A | 322 | 59.122 | 16.529 | -11.911 | 1.00 | 50.83 | N |
| ATOM | 2190 | CA | ARG A | 322 | 59.179 | 15.090 | -12.223 | 1.00 | 51.10 | C |
| ATOM | 2191 | CB | ARG A | 322 | 58.808 | 14.815 | -13.682 | 1.00 | 51.55 | C |
| ATOM | 2192 | CG | ARG A | 322 | 58.753 | 13.314 | -14.018 | 1.00 | 63.66 | C |
| ATOM | 2193 | CD | ARG A | 322 | 57.425 | 12.895 | -14.626 | 1.00 | 70.98 | C |
| ATOM | 2194 | NE | ARG A | 322 | 57.573 | 12.261 | -15.936 | 1.00 | 82.26 | N |
| ATOM | 2195 | CZ | ARG A | 322 | 56.673 | 12.349 | -16.915 | 1.00 | 97.32 | C |
| ATOM | 2196 | NH1 | ARG A | 322 | 55.563 | 13.050 | -16.728 | 1.00 | 90.17 | N |
| ATOM | 2197 | NH2 | ARG A | 322 | 56.878 | 11.744 | -18.082 | 1.00 | 72.56 | N |
| ATOM | 2198 | C | ARG A | 322 | 60.595 | 14.595 | -11.931 | 1.00 | 53.33 | C |
| ATOM | 2199 | O | ARG A | 322 | 61.558 | 15.325 | -12.170 | 1.00 | 52.36 | O |
| ATOM | 2200 | N | LEU A | 323 | 60.715 | 13.404 | -11.338 | 1.00 | 48.19 | N |
| ATOM | 2201 | CA | LEU A | 323 | 62.024 | 12.847 | -10.974 | 1.00 | 46.26 | C |
| ATOM | 2202 | CB | LEU A | 323 | 61.930 | 11.940 | -9.736 | 1.00 | 45.14 | C |
| ATOM | 2203 | CG | LEU A | 323 | 61.870 | 12.619 | -8.358 | 1.00 | 46.68 | C |
| ATOM | 2204 | CD1 | LEU A | 323 | 62.052 | 11.594 | -7.238 | 1.00 | 46.29 | C |
| ATOM | 2205 | CD2 | LEU A | 323 | 62.938 | 13.706 | -8.236 | 1.00 | 47.17 | C |
| ATOM | 2206 | C | LEU A | 323 | 62.543 | 12.052 | -12.157 | 1.00 | 51.25 | C |
| ATOM | 2207 | O | LEU A | 323 | 61.796 | 11.328 | -12.815 | 1.00 | 53.23 | O |
| ATOM | 2208 | N | PRO A | 324 | 63.826 | 12.199 | -12.471 | 1.00 | 47.76 | N |
| ATOM | 2209 | CD | PRO A | 324 | 65.061 | 12.663 | -11.812 | 1.00 | 48.90 | C |
| ATOM | 2210 | CA | PRO A | 324 | 64.114 | 11.367 | -13.638 | 1.00 | 48.43 | C |
| ATOM | 2211 | CB | PRO A | 324 | 65.490 | 11.875 | -14.076 | 1.00 | 49.73 | C |
| ATOM | 2212 | CG | PRO A | 324 | 66.150 | 12.258 | -12.781 | 1.00 | 53.63 | C |
| ATOM | 2213 | C | PRO A | 324 | 64.152 | 9.878 | -13.253 | 1.00 | 54.34 | C |
| ATOM | 2214 | O | PRO A | 324 | 64.147 | 9.520 | -12.077 | 1.00 | 55.45 | O |
| ATOM | 2215 | N | ILE A | 325 | 64.198 | 9.016 | -14.249 | 1.00 | 53.24 | N |
| ATOM | 2216 | CA | ILE A | 325 | 64.263 | 7.575 | -14.029 | 1.00 | 53.94 | C |
| ATOM | 2217 | CB | ILE A | 325 | 63.931 | 6.851 | -15.312 | 1.00 | 58.57 | C |
| ATOM | 2218 | CG2 | ILE A | 325 | 64.913 | 5.712 | -15.613 | 1.00 | 60.03 | C |
| ATOM | 2219 | CG1 | ILE A | 325 | 62.455 | 6.478 | -15.326 | 1.00 | 59.33 | C |
| ATOM | 2220 | CD1 | ILE A | 325 | 61.692 | 7.067 | -16.501 | 1.00 | 67.86 | C |
| ATOM | 2221 | C | ILE A | 325 | 65.541 | 7.053 | -13.325 | 1.00 | 56.90 | C |
| ATOM | 2222 | O | ILE A | 325 | 65.488 | 6.065 | -12.584 | 1.00 | 55.37 | O |
| ATOM | 2223 | N | SER A | 326 | 66.673 | 7.730 | -13.527 | 1.00 | 52.09 | N |
| ATOM | 2224 | CA | SER A | 326 | 67.942 | 7.344 | -12.889 | 1.00 | 50.08 | C |
| ATOM | 2225 | CB | SER A | 326 | 69.050 | 8.339 | -13.261 | 1.00 | 50.95 | C |
| ATOM | 2226 | OG | SER A | 326 | 68.781 | 9.649 | -12.751 | 1.00 | 52.85 | O |
| ATOM | 2227 | C | SER A | 326 | 67.818 | 7.297 | -11.366 | 1.00 | 53.12 | C |
| ATOM | 2228 | O | SER A | 326 | 68.486 | 6.491 | -10.691 | 1.00 | 51.51 | O |
| ATOM | 2229 | N | SER A | 327 | 67.020 | 8.227 | -10.839 | 1.00 | 49.59 | N |
| ATOM | 2230 | CA | SER A | 327 | 66.779 | 8.342 | -9.406 | 1.00 | 48.42 | C |
| ATOM | 2231 | CB | SER A | 327 | 65.799 | 9.493 | -9.088 | 1.00 | 52.37 | C |
| ATOM | 2232 | OG | SER A | 327 | 64.444 | 9.136 | -9.315 | 1.00 | 63.67 | O |
| ATOM | 2233 | C | SER A | 327 | 66.351 | 7.024 | -8.767 | 1.00 | 48.94 | C |
| ATOM | 2234 | O | SER A | 327 | 66.543 | 6.829 | -7.579 | 1.00 | 47.57 | O |
| ATOM | 2235 | N | CYS A | 328 | 65.798 | 6.117 | -9.567 | 1.00 | 46.66 | N |
| ATOM | 2236 | CA | CYS A | 328 | 65.384 | 4.792 | -9.093 | 1.00 | 47.35 | C |
| ATOM | 2237 | CB | CYS A | 328 | 64.634 | 4.054 | -10.197 | 1.00 | 48.18 | C |
| ATOM | 2238 | SG | CYS A | 328 | 62.959 | 4.571 | -10.526 | 1.00 | 53.07 | S |
| ATOM | 2239 | C | CYS A | 328 | 66.605 | 3.944 | -8.715 | 1.00 | 49.43 | C |
| ATOM | 2240 | O | CYS A | 328 | 66.582 | 3.152 | -7.770 | 1.00 | 46.18 | O |
| ATOM | 2241 | N | VAL A | 329 | 67.670 | 4.111 | -9.481 | 1.00 | 46.21 | N |
| ATOM | 2242 | CA | VAL A | 329 | 68.870 | 3.328 | -9.261 | 1.00 | 47.20 | C |

Figure 6-39

| | Atom Type | Resid | # | X | Y | Z | OCC | B | |
|---|---|---|---|---|---|---|---|---|---|
| ATOM | 2243 | CB | VAL A | 329 | 69.149 | 2.477 | -10.504 | 1.00 | 49.74 | C |
| ATOM | 2244 | CG1 | VAL A | 329 | 67.820 | 2.032 | -11.095 | 1.00 | 48.89 | C |
| ATOM | 2245 | CG2 | VAL A | 329 | 69.930 | 3.286 | -11.553 | 1.00 | 48.90 | C |
| ATOM | 2246 | C | VAL A | 329 | 70.119 | 4.048 | -8.699 | 1.00 | 54.64 | C |
| ATOM | 2247 | O | VAL A | 329 | 71.000 | 3.407 | -8.114 | 1.00 | 55.01 | O |
| ATOM | 2248 | N | THR A | 330 | 70.173 | 5.376 | -8.832 | 1.00 | 52.58 | N |
| ATOM | 2249 | CA | THR A | 330 | 71.356 | 6.147 | -8.419 | 1.00 | 51.81 | C |
| ATOM | 2250 | CB | THR A | 330 | 72.458 | 5.942 | -9.501 | 1.00 | 59.29 | C |
| ATOM | 2251 | OG1 | THR A | 330 | 73.707 | 6.489 | -9.049 | 1.00 | 61.77 | O |
| ATOM | 2252 | CG2 | THR A | 330 | 72.008 | 6.573 | -10.870 | 1.00 | 48.33 | C |
| ATOM | 2253 | C | THR A | 330 | 71.030 | 7.649 | -8.289 | 1.00 | 54.15 | C |
| ATOM | 2254 | O | THR A | 330 | 70.005 | 8.099 | -8.822 | 1.00 | 53.31 | O |
| ATOM | 2255 | N | VAL A | 331 | 71.895 | 8.426 | -7.622 | 1.00 | 50.31 | N |
| ATOM | 2256 | CA | VAL A | 331 | 71.633 | 9.880 | -7.483 | 1.00 | 50.14 | C |
| ATOM | 2257 | CB | VAL A | 331 | 72.736 | 10.679 | -6.712 | 1.00 | 53.82 | C |
| ATOM | 2258 | CG1 | VAL A | 331 | 73.251 | 9.906 | -5.526 | 1.00 | 53.89 | C |
| ATOM | 2259 | CG2 | VAL A | 331 | 73.878 | 11.088 | -7.639 | 1.00 | 53.29 | C |
| ATOM | 2260 | C | VAL A | 331 | 71.246 | 10.550 | -8.813 | 1.00 | 55.84 | C |
| ATOM | 2261 | O | VAL A | 331 | 71.929 | 10.398 | -9.832 | 1.00 | 54.44 | O |
| ATOM | 2262 | N | PRO A | 332 | 70.102 | 11.255 | -8.831 | 1.00 | 54.38 | N |
| ATOM | 2263 | CD | PRO A | 332 | 69.517 | 11.909 | -7.647 | 1.00 | 56.83 | C |
| ATOM | 2264 | CA | PRO A | 332 | 69.673 | 11.898 | -10.075 | 1.00 | 55.73 | C |
| ATOM | 2265 | CB | PRO A | 332 | 68.288 | 12.458 | -9.714 | 1.00 | 57.36 | C |
| ATOM | 2266 | CG | PRO A | 332 | 68.280 | 12.591 | -8.205 | 1.00 | 61.29 | C |
| ATOM | 2267 | C | PRO A | 332 | 70.625 | 13.033 | -10.494 | 1.00 | 65.60 | C |
| ATOM | 2268 | O | PRO A | 332 | 70.969 | 13.134 | -11.704 | 1.00 | 64.73 | O |
| ATOM | 2269 | OXT | PRO A | 332 | 71.080 | 13.789 | -9.602 | 1.00 | 70.34 | O |
| TER | 2270 | | PRO A | 332 | | | | | | |
| HETATM | 2271 | O5* | ADN B | 1 | 52.184 | -8.598 | -2.886 | 1.00 | 81.77 | O |
| HETATM | 2272 | C5* | ADN B | 1 | 52.877 | -7.427 | -2.366 | 1.00 | 79.84 | C |
| HETATM | 2273 | C4* | ADN B | 1 | 53.763 | -6.873 | -3.507 | 1.00 | 79.06 | C |
| HETATM | 2274 | O4* | ADN B | 1 | 52.884 | -6.427 | -4.535 | 1.00 | 78.34 | O |
| HETATM | 2275 | C3* | ADN B | 1 | 54.621 | -5.629 | -3.183 | 1.00 | 78.99 | C |
| HETATM | 2276 | O3* | ADN B | 1 | 55.957 | -6.094 | -3.104 | 1.00 | 79.59 | O |
| HETATM | 2277 | C2* | ADN B | 1 | 54.536 | -4.750 | -4.484 | 1.00 | 78.09 | C |
| HETATM | 2278 | O2* | ADN B | 1 | 55.821 | -4.481 | -5.132 | 1.00 | 77.74 | O |
| HETATM | 2279 | C1* | ADN B | 1 | 53.603 | -5.538 | -5.418 | 1.00 | 77.40 | C |
| HETATM | 2280 | N9 | ADN B | 1 | 52.552 | -4.744 | -6.077 | 1.00 | 75.63 | N |
| HETATM | 2281 | C8 | ADN B | 1 | 51.211 | -4.735 | -5.707 | 1.00 | 75.48 | C |
| HETATM | 2282 | N7 | ADN B | 1 | 50.547 | -3.957 | -6.517 | 1.00 | 75.10 | N |
| HETATM | 2283 | C5 | ADN B | 1 | 51.406 | -3.440 | -7.481 | 1.00 | 74.00 | C |
| HETATM | 2284 | C6 | ADN B | 1 | 51.266 | -2.585 | -8.605 | 1.00 | 73.91 | C |
| HETATM | 2285 | N6 | ADN B | 1 | 50.033 | -2.054 | -8.951 | 1.00 | 73.68 | N |
| HETATM | 2286 | N1 | ADN B | 1 | 52.356 | -2.333 | -9.342 | 1.00 | 73.50 | N |
| HETATM | 2287 | C2 | ADN B | 1 | 53.552 | -2.837 | -9.016 | 1.00 | 73.66 | C |
| HETATM | 2288 | N3 | ADN B | 1 | 53.738 | -3.646 | -7.993 | 1.00 | 74.03 | N |
| HETATM | 2289 | C4 | ADN B | 1 | 52.707 | -3.969 | -7.207 | 1.00 | 74.36 | C |
| HETATM | 2290 | O | HOH W | 1 | 57.867 | -3.281 | -23.855 | 1.00 | 58.42 | O |
| HETATM | 2291 | O | HOH W | 2 | 39.677 | 1.077 | -18.628 | 1.00 | 69.46 | O |
| HETATM | 2292 | O | HOH W | 3 | 66.207 | -2.383 | -5.489 | 1.00 | 39.58 | O |
| HETATM | 2293 | O | HOH W | 4 | 44.468 | 13.832 | 9.312 | 1.00 | 32.11 | O |
| HETATM | 2294 | O | HOH W | 5 | 40.779 | 20.260 | 4.927 | 1.00 | 60.65 | O |
| HETATM | 2295 | O | HOH W | 6 | 61.910 | 0.035 | 5.727 | 1.00 | 53.10 | O |
| HETATM | 2296 | O | HOH W | 7 | 47.976 | 14.216 | 12.741 | 1.00 | 43.01 | O |
| HETATM | 2297 | O | HOH W | 8 | 70.104 | 1.396 | 18.447 | 1.00 | 61.93 | O |
| HETATM | 2298 | O | HOH W | 9 | 68.161 | -5.254 | 12.617 | 1.00 | 88.77 | O |
| HETATM | 2299 | O | HOH W | 10 | 61.330 | 17.498 | 22.863 | 1.00 | 52.02 | O |
| HETATM | 2300 | O | HOH W | 11 | 48.304 | -23.905 | 5.378 | 1.00 | 84.92 | O |
| HETATM | 2301 | O | HOH W | 12 | 47.658 | -10.407 | 0.764 | 1.00 | 60.32 | O |

Figure 6-40

| | Atom Type | Resid | # | X | Y | Z | OCC | B | |
|---|---|---|---|---|---|---|---|---|---|
| HETATM | 2302 | O | HOH W | 13 | 29.520 | -2.331 | 7.429 | 1.00 | 58.14 | O |
| HETATM | 2303 | O | HOH W | 14 | 39.271 | 4.432 | -12.108 | 1.00 | 47.10 | O |
| HETATM | 2304 | O | HOH W | 15 | 65.246 | 0.554 | -8.078 | 1.00 | 36.35 | O |
| HETATM | 2305 | O | HOH W | 16 | 73.107 | -0.403 | -4.935 | 1.00 | 45.35 | O |
| HETATM | 2306 | O | HOH W | 17 | 69.640 | 17.120 | -0.124 | 1.00 | 45.94 | O |
| HETATM | 2307 | O | HOH W | 18 | 40.055 | -2.793 | 12.792 | 1.00 | 48.48 | O |
| HETATM | 2308 | O | HOH W | 19 | 43.258 | -5.831 | 12.371 | 1.00 | 39.67 | O |
| HETATM | 2309 | O | HOH W | 20 | 59.880 | -5.437 | 5.160 | 1.00 | 88.43 | O |
| HETATM | 2310 | O | HOH W | 21 | 52.066 | 6.649 | -19.910 | 1.00 | 59.61 | O |
| HETATM | 2311 | O | HOH W | 22 | 54.255 | 6.989 | 24.386 | 1.00 | 53.52 | O |
| HETATM | 2312 | O | HOH W | 23 | 43.069 | 12.253 | -8.257 | 1.00 | 37.42 | O |
| HETATM | 2313 | O | HOH W | 24 | 50.595 | 15.270 | -9.322 | 1.00 | 54.34 | O |
| HETATM | 2314 | O | HOH W | 25 | 35.214 | -5.489 | -8.950 | 1.00 | 55.29 | O |
| HETATM | 2315 | O | HOH W | 26 | 33.627 | -1.756 | -16.534 | 1.00 | 67.21 | O |
| HETATM | 2316 | O | HOH W | 27 | 55.202 | 14.409 | -14.979 | 1.00 | 63.62 | O |
| HETATM | 2317 | O | HOH W | 28 | 52.439 | -11.559 | 12.716 | 1.00 | 60.19 | O |
| HETATM | 2318 | O | HOH W | 29 | 72.568 | 10.946 | 1.217 | 1.00 | 33.81 | O |
| HETATM | 2319 | O | HOH W | 30 | 63.785 | -2.520 | 14.868 | 1.00 | 49.60 | O |
| HETATM | 2320 | O | HOH W | 31 | 42.719 | 16.975 | 17.356 | 1.00 | 60.23 | O |
| HETATM | 2321 | O | HOH W | 32 | 47.622 | 20.664 | 24.293 | 1.00 | 62.54 | O |
| HETATM | 2322 | O | HOH W | 33 | 58.566 | -4.238 | -14.445 | 1.00 | 50.86 | O |
| HETATM | 2323 | O | HOH W | 34 | 45.066 | 16.588 | -4.048 | 1.00 | 43.95 | O |
| HETATM | 2324 | O | HOH W | 35 | 42.751 | 16.781 | 10.467 | 1.00 | 47.37 | O |
| HETATM | 2325 | O | HOH W | 36 | 45.179 | 15.436 | 8.410 | 1.00 | 34.99 | O |
| HETATM | 2326 | O | HOH W | 37 | 59.716 | -3.447 | 11.462 | 1.00 | 45.88 | O |
| HETATM | 2327 | O | HOH W | 38 | 48.732 | -2.528 | 27.153 | 1.00 | 51.48 | O |
| HETATM | 2328 | O | HOH W | 39 | 64.570 | -11.753 | 13.721 | 1.00 | 65.37 | O |
| HETATM | 2329 | O | HOH W | 40 | 56.349 | -4.555 | 24.468 | 1.00 | 71.44 | O |
| HETATM | 2330 | O | HOH W | 41 | 62.620 | 26.848 | 8.665 | 1.00 | 64.13 | O |
| HETATM | 2331 | O | HOH W | 42 | 42.851 | 19.623 | 8.884 | 1.00 | 38.84 | O |
| HETATM | 2332 | O | HOH W | 43 | 48.126 | 22.691 | 3.548 | 1.00 | 43.29 | O |
| HETATM | 2333 | O | HOH W | 44 | 65.296 | -1.416 | -17.093 | 1.00 | 64.73 | O |
| HETATM | 2334 | O | HOH W | 45 | 49.753 | -4.574 | -24.364 | 1.00 | 53.20 | O |
| HETATM | 2335 | O | HOH W | 46 | 54.826 | -11.599 | -24.986 | 1.00 | 51.64 | O |
| HETATM | 2336 | O | HOH W | 47 | 50.879 | -16.773 | -5.195 | 1.00 | 52.86 | O |
| HETATM | 2337 | O | HOH W | 48 | 40.074 | 8.179 | -10.152 | 1.00 | 67.94 | O |
| HETATM | 2338 | O | HOH W | 49 | 49.325 | 4.600 | -13.958 | 1.00 | 48.46 | O |
| HETATM | 2339 | O | HOH W | 50 | 63.022 | 0.550 | -9.682 | 1.00 | 49.69 | O |
| HETATM | 2340 | O | HOH W | 51 | 71.575 | 9.454 | -2.376 | 1.00 | 39.59 | O |
| HETATM | 2341 | O | HOH W | 52 | 70.216 | 18.625 | 4.119 | 1.00 | 62.31 | O |
| HETATM | 2342 | O | HOH W | 53 | 48.983 | 17.221 | -4.852 | 1.00 | 60.20 | O |
| HETATM | 2343 | O | HOH W | 54 | 41.932 | -4.028 | 8.756 | 1.00 | 47.16 | O |
| HETATM | 2344 | O | HOH W | 55 | 71.539 | -3.231 | 12.635 | 1.00 | 52.35 | O |
| HETATM | 2345 | O | HOH W | 56 | 67.799 | 4.034 | 12.883 | 1.00 | 52.66 | O |
| HETATM | 2346 | O | HOH W | 57 | 66.224 | -0.856 | 23.997 | 1.00 | 56.73 | O |
| HETATM | 2347 | O | HOH W | 58 | 59.325 | -13.624 | 25.681 | 1.00 | 61.56 | O |
| HETATM | 2348 | O | HOH W | 59 | 63.964 | 8.689 | 25.797 | 1.00 | 54.82 | O |
| HETATM | 2349 | O | HOH W | 60 | 72.457 | 14.848 | 15.950 | 1.00 | 57.00 | O |
| HETATM | 2350 | O | HOH W | 61 | 51.365 | 20.650 | 24.113 | 1.00 | 63.71 | O |
| HETATM | 2351 | O | HOH W | 62 | 55.913 | 23.966 | 20.032 | 1.00 | 68.78 | O |
| HETATM | 2352 | O | HOH W | 63 | 53.533 | 21.582 | 21.567 | 1.00 | 51.55 | O |
| HETATM | 2353 | O | HOH W | 64 | 41.199 | 20.695 | 12.048 | 1.00 | 60.74 | O |
| HETATM | 2354 | O | HOH W | 65 | 59.542 | -2.803 | -17.636 | 1.00 | 59.27 | O |
| HETATM | 2355 | O | HOH W | 66 | 44.037 | -19.434 | -14.262 | 1.00 | 48.09 | O |
| HETATM | 2356 | O | HOH W | 67 | 41.106 | -5.476 | -20.544 | 1.00 | 43.09 | O |
| HETATM | 2357 | O | HOH W | 68 | 35.920 | -7.415 | 13.276 | 1.00 | 51.15 | O |
| HETATM | 2358 | O | HOH W | 69 | 47.780 | -5.206 | 1.306 | 1.00 | 45.21 | O |
| HETATM | 2359 | O | HOH W | 70 | 32.622 | -8.532 | 1.133 | 1.00 | 53.37 | O |
| HETATM | 2360 | O | HOH W | 71 | 31.954 | -12.911 | 0.608 | 1.00 | 82.79 | O |

Figure 6-41

| | Atom Type | Resid | # | X | Y | Z | OCC | B | |
|---|---|---|---|---|---|---|---|---|---|
| HETATM | 2361 | O | HOH W | 72 | 41.882 | 15.858 | -13.081 | 1.00 | 61.59 | O |
| HETATM | 2362 | O | HOH W | 73 | 35.640 | -7.729 | -9.834 | 1.00 | 39.15 | O |
| HETATM | 2363 | O | HOH W | 74 | 43.176 | -24.917 | -2.951 | 1.00 | 53.98 | O |
| HETATM | 2364 | O | HOH W | 75 | 66.576 | 16.333 | -7.093 | 1.00 | 36.90 | O |
| HETATM | 2365 | O | HOH W | 76 | 68.670 | 20.124 | -0.897 | 1.00 | 58.75 | O |
| HETATM | 2366 | O | HOH W | 77 | 64.088 | 8.021 | -6.247 | 1.00 | 44.39 | O |
| HETATM | 2367 | O | HOH W | 78 | 46.831 | -1.363 | 4.804 | 1.00 | 25.38 | O |
| HETATM | 2368 | O | HOH W | 79 | 50.594 | 1.137 | 11.814 | 1.00 | 37.07 | O |
| HETATM | 2369 | O | HOH W | 80 | 50.387 | 3.491 | 9.133 | 1.00 | 24.59 | O |
| HETATM | 2370 | O | HOH W | 81 | 37.229 | -1.547 | 8.953 | 1.00 | 38.92 | O |
| HETATM | 2371 | O | HOH W | 82 | 38.034 | -0.096 | 14.737 | 1.00 | 45.28 | O |
| HETATM | 2372 | O | HOH W | 83 | 39.839 | 4.045 | 14.010 | 1.00 | 34.66 | O |
| HETATM | 2373 | O | HOH W | 84 | 31.920 | -2.434 | 8.643 | 1.00 | 67.91 | O |
| HETATM | 2374 | O | HOH W | 85 | 30.705 | 5.707 | 17.830 | 1.00 | 55.41 | O |
| HETATM | 2375 | O | HOH W | 86 | 35.503 | 0.809 | 24.396 | 1.00 | 53.56 | O |
| HETATM | 2376 | O | HOH W | 87 | 44.680 | 7.685 | 20.966 | 1.00 | 37.84 | O |
| HETATM | 2377 | O | HOH W | 88 | 37.687 | 13.698 | 9.660 | 1.00 | 46.33 | O |
| HETATM | 2378 | O | HOH W | 89 | 47.202 | 15.498 | 15.439 | 1.00 | 41.55 | O |
| HETATM | 2379 | O | HOH W | 90 | 58.686 | 2.556 | 27.370 | 1.00 | 53.97 | O |
| HETATM | 2380 | O | HOH W | 91 | 48.982 | 14.398 | 27.507 | 1.00 | 56.13 | O |
| HETATM | 2381 | O | HOH W | 92 | 53.103 | 22.625 | 0.231 | 1.00 | 40.85 | O |
| HETATM | 2382 | O | HOH W | 93 | 51.481 | 19.530 | -2.095 | 1.00 | 61.96 | O |
| HETATM | 2383 | O | HOH W | 94 | 63.655 | 27.736 | 4.746 | 1.00 | 53.70 | O |
| HETATM | 2384 | O | HOH W | 95 | 67.990 | 17.742 | -8.886 | 1.00 | 66.25 | O |
| HETATM | 2385 | O | HOH W | 96 | 45.141 | -3.667 | -1.841 | 1.00 | 40.35 | O |
| HETATM | 2386 | O | HOH W | 97 | 38.391 | -10.920 | -16.773 | 1.00 | 42.29 | O |
| HETATM | 2387 | O | HOH W | 98 | 40.290 | 1.442 | -6.730 | 1.00 | 36.19 | O |
| HETATM | 2388 | O | HOH W | 99 | 42.610 | 5.059 | -7.551 | 1.00 | 29.15 | O |
| HETATM | 2389 | O | HOH W 100 | | 43.802 | 14.727 | -1.830 | 1.00 | 36.98 | O |
| HETATM | 2390 | O | HOH W 101 | | 41.171 | 14.653 | -1.946 | 1.00 | 48.14 | O |
| HETATM | 2391 | O | HOH W 102 | | 40.569 | 21.097 | 7.007 | 1.00 | 49.75 | O |
| HETATM | 2392 | O | HOH W 103 | | 28.776 | -7.209 | -8.338 | 1.00 | 57.64 | O |
| HETATM | 2393 | O | HOH W 104 | | 34.186 | -17.560 | -8.093 | 1.00 | 48.25 | O |
| HETATM | 2394 | O | HOH W 105 | | 36.086 | -12.454 | -3.417 | 1.00 | 78.46 | O |
| HETATM | 2395 | O | HOH W 106 | | 72.663 | 7.212 | -0.818 | 1.00 | 57.02 | O |
| HETATM | 2396 | O | HOH W 107 | | 65.940 | 20.510 | -0.424 | 1.00 | 48.52 | O |
| HETATM | 2397 | O | HOH W 108 | | 33.854 | 5.946 | 2.513 | 1.00 | 38.12 | O |
| HETATM | 2398 | O | HOH W 109 | | 53.175 | 0.432 | 11.139 | 1.00 | 51.72 | O |
| HETATM | 2399 | O | HOH W 110 | | 53.175 | 0.432 | 11.139 | 1.00 | 51.72 | O |
| HETATM | 2400 | O | HOH W 111 | | 50.949 | 3.753 | 13.166 | 1.00 | 31.04 | O |
| HETATM | 2401 | O | HOH W 112 | | 57.409 | 3.731 | 14.781 | 1.00 | 30.06 | O |
| HETATM | 2402 | O | HOH W 113 | | 53.810 | 0.175 | 8.462 | 1.00 | 35.18 | O |
| HETATM | 2403 | O | HOH W 114 | | 47.269 | -2.610 | -3.804 | 1.00 | 37.44 | O |
| HETATM | 2404 | O | HOH W 115 | | 42.016 | 9.763 | 17.149 | 1.00 | 34.50 | O |
| HETATM | 2405 | O | HOH W 116 | | 42.613 | 0.298 | 15.581 | 1.00 | 33.09 | O |
| HETATM | 2406 | O | HOH W 117 | | 44.802 | -1.129 | 15.896 | 1.00 | 38.61 | O |
| HETATM | 2407 | O | HOH W 118 | | 46.485 | -0.461 | 19.666 | 1.00 | 31.80 | O |
| HETATM | 2408 | O | HOH W 119 | | 61.785 | 2.910 | 13.086 | 1.00 | 36.51 | O |
| HETATM | 2409 | O | HOH W 120 | | 44.645 | 6.286 | 18.564 | 1.00 | 44.01 | O |
| HETATM | 2410 | O | HOH W 121 | | 71.708 | 14.460 | 5.336 | 1.00 | 35.13 | O |
| HETATM | 2411 | O | HOH W 122 | | 53.932 | 14.896 | 22.529 | 1.00 | 49.22 | O |
| HETATM | 2412 | O | HOH W 123 | | 53.870 | 19.113 | 16.618 | 1.00 | 36.39 | O |
| HETATM | 2413 | O | HOH W 124 | | 45.994 | 13.451 | 11.701 | 1.00 | 42.31 | O |
| HETATM | 2414 | O | HOH W 125 | | 44.341 | 20.860 | 10.169 | 1.00 | 39.26 | O |
| HETATM | 2415 | O | HOH W 126 | | 50.422 | -6.522 | 11.212 | 1.00 | 42.50 | O |
| HETATM | 2416 | O | HOH W 127 | | 60.950 | -15.169 | -5.587 | 1.00 | 65.77 | O |
| HETATM | 2417 | O | HOH W 128 | | 40.721 | -14.081 | -24.104 | 1.00 | 53.09 | O |
| HETATM | 2418 | O | HOH W 129 | | 47.290 | -0.832 | -15.672 | 1.00 | 53.10 | O |
| HETATM | 2419 | O | HOH W 130 | | 40.037 | -20.107 | 0.628 | 1.00 | 58.91 | O |

Figure 6-42

| | Atom Type | Resid | | # | X | Y | Z | OCC | B | |
|---|---|---|---|---|---|---|---|---|---|---|
| HETATM | 2420 | O | HOH | W 131 | 41.654 | 6.180 | -10.402 | 1.00 | 45.79 | O |
| HETATM | 2421 | O | HOH | W 132 | 45.833 | 5.742 | -9.706 | 1.00 | 36.29 | O |
| HETATM | 2422 | O | HOH | W 133 | 36.939 | -0.844 | -9.130 | 1.00 | 52.60 | O |
| HETATM | 2423 | O | HOH | W 134 | 53.695 | 1.664 | -14.461 | 1.00 | 39.89 | O |
| HETATM | 2424 | O | HOH | W 135 | 53.832 | 1.128 | -17.489 | 1.00 | 43.90 | O |
| HETATM | 2425 | O | HOH | W 136 | 55.989 | 0.295 | -18.338 | 1.00 | 50.75 | O |
| HETATM | 2426 | O | HOH | W 137 | 59.119 | -1.225 | 4.151 | 1.00 | 39.49 | O |
| HETATM | 2427 | O | HOH | W 138 | 69.969 | 19.057 | 1.554 | 1.00 | 57.75 | O |
| HETATM | 2428 | O | HOH | W 139 | 65.967 | 16.138 | -9.157 | 1.00 | 53.56 | O |
| HETATM | 2429 | O | HOH | W 140 | 49.893 | 17.139 | -1.982 | 1.00 | 45.70 | O |
| HETATM | 2430 | O | HOH | W 141 | 47.244 | 17.394 | -1.283 | 1.00 | 45.79 | O |
| HETATM | 2431 | O | HOH | W 142 | 42.286 | -6.413 | 8.040 | 1.00 | 52.02 | O |
| HETATM | 2432 | O | HOH | W 143 | 44.257 | -8.371 | 2.637 | 1.00 | 42.74 | O |
| HETATM | 2433 | O | HOH | W 144 | 39.035 | 1.438 | 13.028 | 1.00 | 48.47 | O |
| HETATM | 2434 | O | HOH | W 145 | 41.829 | 0.291 | 13.061 | 1.00 | 44.95 | O |
| HETATM | 2435 | O | HOH | W 146 | 46.219 | 7.489 | 16.590 | 1.00 | 30.43 | O |
| HETATM | 2436 | O | HOH | W 147 | 63.994 | -4.529 | 15.946 | 1.00 | 66.60 | O |
| HETATM | 2437 | O | HOH | W 148 | 57.238 | 13.621 | 22.486 | 1.00 | 41.38 | O |
| HETATM | 2438 | O | HOH | W 149 | 48.201 | 19.994 | 17.036 | 1.00 | 63.65 | O |
| HETATM | 2439 | O | HOH | W 150 | 45.403 | -23.040 | -2.977 | 1.00 | 46.15 | O |
| HETATM | 2440 | O | HOH | W 151 | 55.524 | 15.623 | -5.889 | 1.00 | 38.71 | O |
| HETATM | 2441 | O | HOH | W 152 | 50.907 | 15.987 | -5.926 | 1.00 | 54.16 | O |
| HETATM | 2442 | O | HOH | W 153 | 35.314 | 15.891 | 2.266 | 1.00 | 67.11 | O |
| HETATM | 2443 | O | HOH | W 154 | 63.268 | -4.283 | 13.497 | 1.00 | 60.99 | O |
| HETATM | 2444 | O | HOH | W 155 | 69.309 | 14.206 | 18.224 | 1.00 | 55.70 | O |
| HETATM | 2445 | O | HOH | W 156 | 59.528 | 20.974 | 15.084 | 1.00 | 48.32 | O |
| HETATM | 2446 | O | HOH | W 157 | 44.544 | 17.601 | 7.186 | 1.00 | 39.84 | O |
| HETATM | 2447 | O | HOH | W 158 | 55.868 | 27.829 | 5.789 | 1.00 | 46.91 | O |
| HETATM | 2448 | O | HOH | W 159 | 56.136 | 17.763 | -8.376 | 1.00 | 55.42 | O |
| HETATM | 2449 | O | HOH | W 160 | 72.420 | 1.436 | -6.862 | 1.00 | 55.31 | O |
| HETATM | 2450 | O | HOH | W 161 | 49.060 | -4.233 | -3.880 | 1.00 | 66.40 | O |
| HETATM | 2451 | O | HOH | W 162 | 42.064 | -6.275 | 5.694 | 1.00 | 50.76 | O |
| END | | | | | | | | | | |

CRYSTAL STRUCTURE OF POLO-LIKE KINASE 3 (PLK3) AND BINDING POCKETS THEREOF

TECHNICAL FIELD OF THE INVENTION

The present application claims the benefit under 35 U.S.C. §119 of U.S. Provisional patent application No. 60/813,427, filed Jun. 14, 2006, the entire contents of which are incorporated herein by reference.

The present invention relates to the design of crystallisable Polo-like Kinase 3 (PLK3) complexes and the X-ray analysis of crystalline molecules or molecular complexes of this protein. The present invention provides for the first time the crystal structure of PLK3 protein bound to adenosine. The present invention also provides crystalline molecules or molecular complexes that comprise binding pockets of PLK3 kinase (PLK3) and/or its structural homologues, the structure of these molecules or molecular complexes. The present invention further provides crystals of PLK3 complexed with adenosine and methods for producing these crystals. This invention also relates to crystallizable compositions from which the protein-ligand complexes may be obtained. The present invention also relates to a data storage medium encoded with the structural coordinates of molecules and molecular complexes that comprise the ATP-binding pockets of PLK3 or their structural homologues. The present invention also relates to a computer comprising such data storage material. The computer may generate a three-dimensional structure or graphical three-dimensional representation of such molecules or molecular complexes. This invention also relates to methods of using the structure coordinates to solve the structure of homologous proteins or protein complexes. This invention also relates to computational methods of using structure coordinates of the PLK3 complex(es) to screen for, identify and design compounds, including inhibitory compounds and antibodies, that interact with PLK3 or homologues thereof.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.*, 9:576-596 (1995); Knighton et al., *Science*, 253:407-414 (1991); Hiles et al., *Cell*, 70:419-429 (1992); Kunz et al., *Cell*, 73:585-596 (1993); Garcia-Bustos et al., *EMBO J.*, 13:2352-2361 (1994)).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Among medically important serine/threonine kinases is the family of polo-like kinases that have an important role in several stages of mitosis. This family includes the mammalian PLK1, PLK2 (serum-inducible kinase, Snk), PLK3 (fibroblast growth factor-inducible kinase, Fnk/proliferation-related kinase, Prk) and PLK4 (Sak). Polo-like kinase 1 (PLK1) has been suggested to promote mitotic entry by activating cyclin B/cdk1 by phosphorylating cyclin B itself, by phosphorylating the Cdk1-activating phosphatase Cdc25c and by phosphorylating the Cdk1-inhibiting kinases Myt1/Wee1 (Abrieu, A., et al. *Cell Sci* 111, 1751-1757 (1998); Jackman, M. et al *Nat Cell Biol.* 5, 143-148 (2003); Nakajima, H. et al. *J. Biol. Chem.* 278, 25277-25280 (2003); Qian, Y. W. et al. *Mol. Cell. Biol.* 18, 4262-4271 (1998); Toyoshima-Morimoto, F. et al. *Nature* 410, 215-220 (2001); Watanabe, N. et al. *Proc. Nat. Acad. Sci. USA* 101, 4419-4424 (2004)). Furthermore, PLK1 has been implicated in centrosome maturation and separation, with defects giving rise to monopolar spindles (Lane, H. A., et al. *J. Cell Biol.* 135, 1701-1713 (1996); Sunkel, C. E., et al. *J. Cell Sci.* 89, 25-38 (1988)). Studies on human cells and in vitro have indicated a role for PLK1 in activating the anaphase-promoting complex/cyclosome (APC/C) (Golan, A. et al *J. Biol. Chem.* 277, 15552-15557 (2002); Kotani, S. et al. *Mol. Cell* 1, 371-380 (1998). PLK1 is located mostly in the cytoplasm during interphase and translocates to the nucleus in early mitosis. PLK1 also has been shown to associate with centrosomes from G2 up to metaphase, to translocate to kinetochores at metaphase, and to locate at the midbody from anaphase to telophase (Golsteyn, R. M. et al. *J. Cell Biol.* 129, 1617-1628 (1995); Lee et al. *Mol. Cell Biol.* 15, 7143-7151 (1995)).

In contrast to PLK1, PLK2 and PLK3 appear to perform different functions, and PLK3 plays some functions that might directly antagonize PLK1 function (Smits et al. *Nat. Cell Biol.* 2 672-676 (2000); Xie et al. *J. Biol. Chem.* 276, 43305-43312 (2001). Small interfering RNA (siRNA)-mediated inhibition of PLK3 expression suggests that PLK3 is essential for superoxide-induced cell death, and deletion analysis of PLK3 showed that the N-terminal domain (amino-acids 1-26) is essential for induction of delayed onset of apoptosis (Li Z. et al. *J. Biol. Chem.* 280, 16843-16850 (2005)). Over-expression of PLK1 has been observed to cause oncogenic transformation in NIH 3T3 cells (Smith et al. *Biochem. Biophys. Res. Commun.* 234, 397-405 (1997), while overexpression of PLK3 induces apoptosis (Conn et al. *Cancer Res.* 60, 6826-6831 (2000).

Polo-like kinases are characterized by an N-terminal catalytic Ser/Thr kinase domain and a C-terminal non-catalytic region containing two tandem Polo-boxes (Sonnhammer et al. *Nucleic Acids Res.* 26, 320-322 (1998). The Polo-box domain is required for correct subcellular localization (Lee et al., *Proc. Natl. Acad. Sci. USA* 95, 9301-9306 (1998); Ma et al., *Mol. Cancer. Res.* 1, 376-384 (2003); May et al., *J. Cell Biol.* 156, 23-28 (2002); Reynolds & Ohkura *J. Cell Sci.*, 116, 1377-1387 (2003)), and the crystal structure of the polo-box domain in PLK1 has been determined (Elia et al. *Cell* 115, 83-95 (2003); Cheng et al., *EMBO J.* 22, 5757-5768 (2003)). The Polo-box domain recognizes a conserved phosphothreonine/serine motif in the substrate which binds along a positively-charged cleft located at the edge of the Polo-box interface. Mutations of key residues to disrupt the phosphodependent interactions abolishes cell-cycle dependent localization but does not affect its kinase activity (Lee et al., *Proc. Natl. Acad. Sci. USA* 95, 9301-9306 (1998), and suggests that substrate binding to the Polo-box domain is required for proper mitotic progression (Elia et al. *Cell* 115, 83-95 (2003)).

Because of their link to cellular proliferation, PLK family proteins have been associated with cancer development and progression. In fact, the over-expression of murine PLK1 in NIH3T3 cells has been observed to be transforming (Smith, M. R. et al. *Biochem. Biophys. Res. Commun.* 234, 397-405 (1997)). In addition, PLK1 has been seen to be over-expressed in a wide variety of primary tumor cell lines, including breast cancer (Wolf G. et al. *Pathol. Res. Pract.* 196, 753-759 (2000)), colorectal cancer (Takahashi T. et al. *Cancer Sci.* 94, 148-152 (2003)), non-small-cell lung cells (Wolf G. et al. *Oncogene* 14, 543-549 (1997)), head and neck squamous cell carcinomas (Knecht R. et al. *Cancer Res.* 59, 479-480 (1999)), ovarian carcinomas (Takai N. et al. *Cancer Lett.* 164, 41-49 (2001)), prostate (Weichert W. et al *Prostate* 60, 240-245 (2004)) and pancreatic cancer (Gray P. J. et al. *Mol. Cancer. Ther.* 3, 641-646 (2004)) and is positively correlated with aggressiveness and prognosis (Takai N., et al *Oncogene* 24, 287-291 (2005)).

Whilst the precise function of PLK2 is uncertain, the expression of PLK3 is negatively correlated with the development of certain cancers. PLK3 mRNA is either undetectable or markedly downregulated in lung carcinomas (Li B. et al. *J. Biol. Chem.* 271, 19402-19408 (1996)) head and neck squamous cell carcinomas (Dai W. et al. *Genes Chromosomes Cancer* 27, 332-336 (2000)) and in colon tumors (Dai W. et al. *Int. J. Oncol.* 20, 121-126 (2002)). In support of these observations, the expression of PLK3 in vitro reduces the rate of fibroblast cell proliferation (Dai W. et al. *Genes Chromosomes Cancer* 27, 332-336 (2000)) and the enforced expression of constructs expressing kinase-active PLK3 induces rapid cell cycle arrest and apoptosis (Conn C. W. et al. *Cancer Res.* 60, 6826-6831 (2000); Wang Q. et al. *Mol. Cell. Biol.* 22, 3450-3459 (2002)). PLK3 has been shown to be a stress response protein involved in DNA damage checkpoint (Bahassi E. M. et al. *Oncogene* 21, 6633-6640 (2002); Xie S. et al. *J. Biol. Chem.* 276, 43305-43312 (2001)). In this role, PLK3 only becomes phosphorylated following DNA damage or mitotic spindle disruption, whereupon its kinase activity is enhanced, otherwise, PLK3 is not phosphorylated during normal cell cycle progression. Consistent with this, possible substrates of PLK3 are thought to include both the tumor suppressors Chk2 and p53, which have both been shown to bind to PLK3 in vivo, and be phosphorylated by PLK3 in vitro.

The role of PLK3 in DNA damage checkpoint leads to the interest in designing PLK3 inhibitors that are effective as therapeutic agents. A challenge has been to find protein kinase inhibitors that act in a selective manner, targeting only PLK3. Since there are numerous protein kinases that are involved in a variety of cellular responses, non-selective inhibitors may lead to unwanted side effects. In this regard, the three-dimensional structure of the kinase would assist in the rational design of inhibitors. The determination of the amino acid residues in PLK3 binding pockets and the determination of the shape of those binding pockets would allow one to design selective inhibitors that bind favorably to this class of enzymes. The determination of the amino acid residues in PLK3 binding pockets and the determination of the shape of those binding pockets would also allow one to design inhibitors that can bind to PLK3.

For example, a general approach to designing inhibitors that are selective for an enzyme target is to determine how a putative inhibitor interacts with the three dimensional structure of the enzyme. For this reason it is useful to obtain the enzyme protein in crystal form and perform X-ray diffraction techniques to determine its three dimensional structure coordinates. If the enzyme is crystallized as a complex with a ligand, one can interactively elucidate the binding pocket, and determine both the shape of the enzyme binding pocket when bound to the ligand, as well as the amino acid residues that are capable of close contact with the ligand. By knowing the shape and amino acid residues in the binding pocket, one may design new ligands that will interact favorably with the enzyme. With such structural information, available computational methods may be used to predict how strong the ligand binding interaction will be. Such methods thus enable the design of inhibitors that bind strongly, as well as selectively to the target enzyme.

Despite the fact that the genes for PLK3 has been isolated and the amino acid sequence of PLK3 is known, no one has described X-ray crystal structural coordinate information of PLK3 protein. As discussed above, such information would be extremely useful in identifying and designing potential inhibitors of the PLK3 kinase or homologues thereof, which, in turn, could have therapeutic utility.

The structures of several serine/threonine kinases have been solved by X-ray diffraction and analyzed. Specifically, the crystal structures of P38 kinase (Wilson et al., *J. Biol. Chem.*, 271, pp. 27696-27700 (1996)) and MAPKAP Kinase 2 (U.S. Provisional application 60/337,513) have been studied in detail.

To date, no crystal structures of PLK3 kinase have been reported. Thus the crystal structure of unphosphorylated PLK3 kinase domain complexes with inhibitors are of great importance for defining the active conformation of PLK3 kinase. This information is essential for the rational design of selective and potent inhibitors of PLK3.

SUMMARY OF THE INVENTION

The present invention provides for the first time, crystallizable compositions, crystals, and the crystal structures of a PLK3—inhibitor complex. The PLK3 protein used in these studies corresponds to a single polypeptide chain, which encompasses the complete catalytic kinase domain, amino acids 48 to 332. Solving this crystal structure has allowed the applicants to determine the key structural features of PLK3, particularly the shape of its substrate and ATP-binding pockets.

Thus, in one aspect, the present invention provides molecules or molecular complexes comprising all or parts of these binding pockets, or homologues of these binding pockets that have similar three-dimensional shapes.

In another aspect, the present invention further provides crystals of PLK3 complexed with adenosine and methods for producing these crystals. In this embodiment, PLK3 is unphosphorylated.

In a further aspect, the present invention provides crystallizable compositions from which PLK3-ligand complexes may be obtained.

In another aspect, the present invention provides for a general strategy for the design of protein constructs for producing crystallisable kinase domains.

In another aspect, the invention provides a data storage medium that comprises the structure coordinates of molecules and molecular complexes that comprise all or part of the PLK3 binding pockets. Such storage medium encoded with these data when read and utilized by a computer programmed with appropriate software displays, on a computer screen or similar viewing device, a three-dimensional graphical representation of a molecule or molecular complex comprising such binding pockets or similarly shaped homologous binding pockets.

In yet another aspect, the invention provides computational methods of using structure coordinates of the PLK3 complex to screen for, identify and design compounds, including inhibitory compounds and antibodies that interact with PLK3, PLK1, PLK2 or other homologues thereof. In certain embodiments, the invention provides methods for designing, evaluating and identifying compounds, which bind to the aforementioned binding pockets. In certain embodiments, such compounds are potential inhibitors of PLK3, PLK1, PLK2 or their homologues.

BRIEF DESCRIPTION OF THE DRAWING

FIG. 1 (1-1 to 1-42) lists the atomic structure coordinates for the unphosphorylated PLK3—9-β-D-Ribofuranosyladenine ("adenosine") inhibitor complex (residues 52-327 of SEQ ID NO:1) as derived by X-ray diffraction from the crystal. The PLK3 in the crystal comprises amino acid residues 48-332 of SEQ ID NO:1.

The following abbreviations are used in FIG. 1 and FIG. 6:

"Atom type" refers to the identity of the element whose coordinates are measured. The first letter in the column defines the actual type of atom (i.e., C for carbon, N for nitrogen, O for oxygen, etc.).

"Resid" refers to the amino acid residue or molecule identity in the molecular model. The amino acid residues or molecule identity are designated A, B and W for PLK3, adenosine (ADN) or water (HOH), respectively.

"#" refers to the amino acid residue number.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Figure 2:
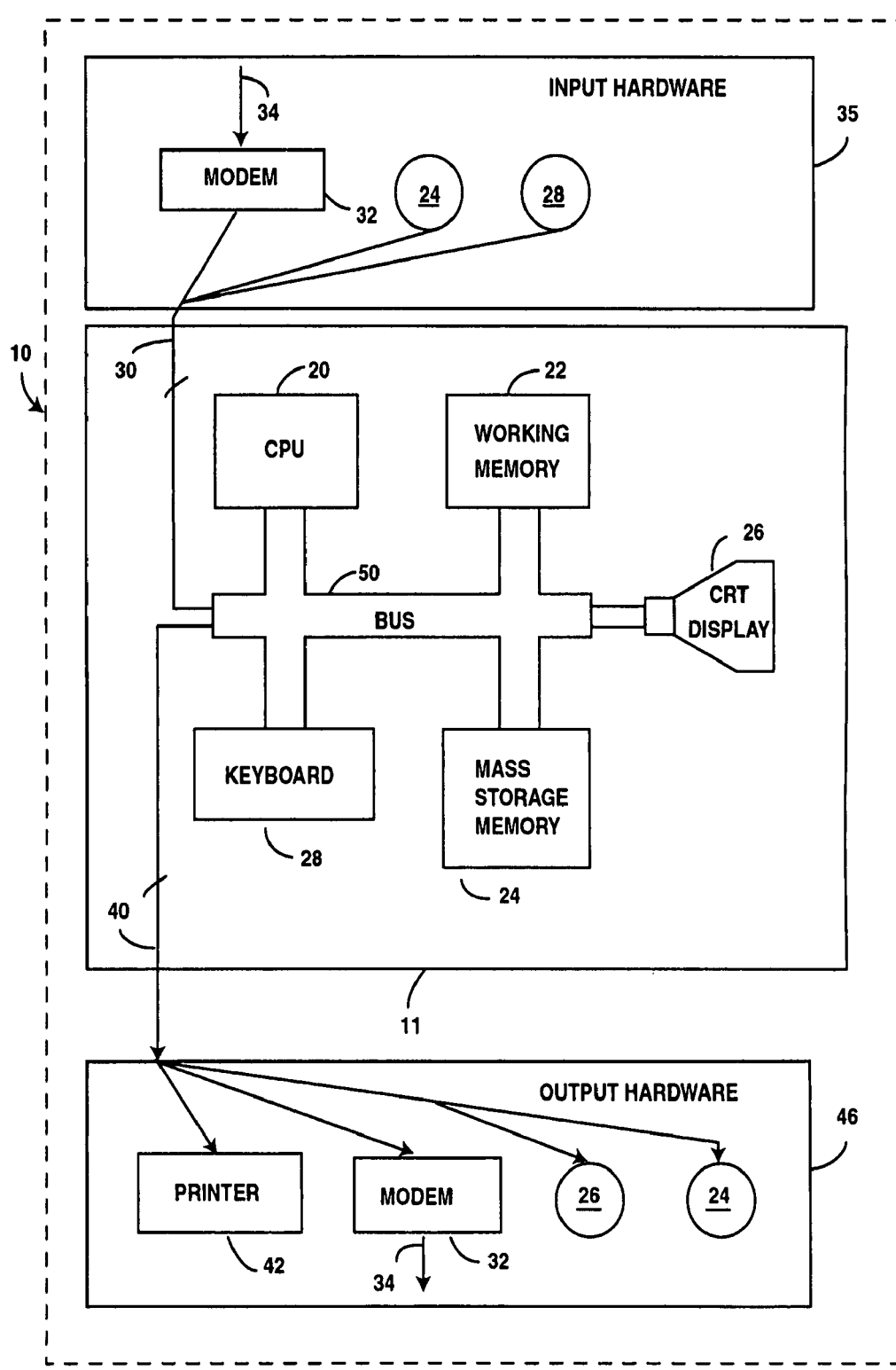
Figure 3:
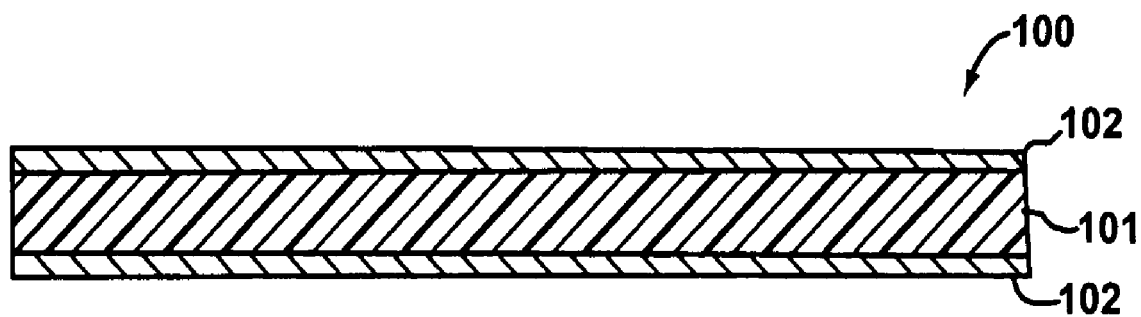
Figure 4:
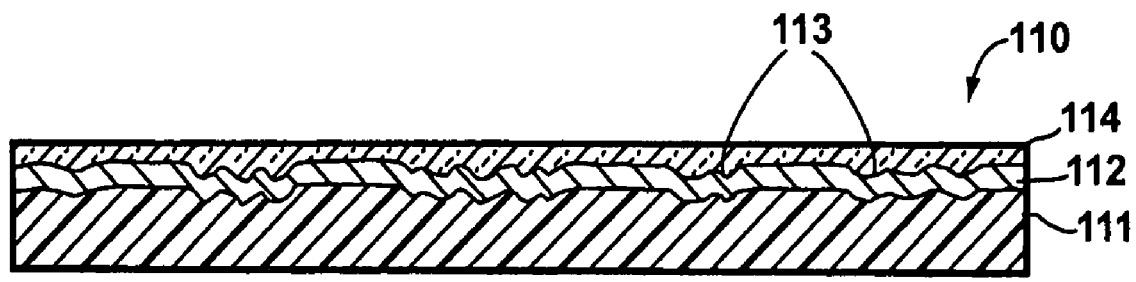

FIG. 2 shows a diagram of a system used to carry out the instructions encoded by the storage medium of FIGS. 3 and 4.

FIG. 3 shows a cross section of a magnetic storage medium.

FIG. 4 shows a cross section of an optically-readable data storage medium.

Figure 5:
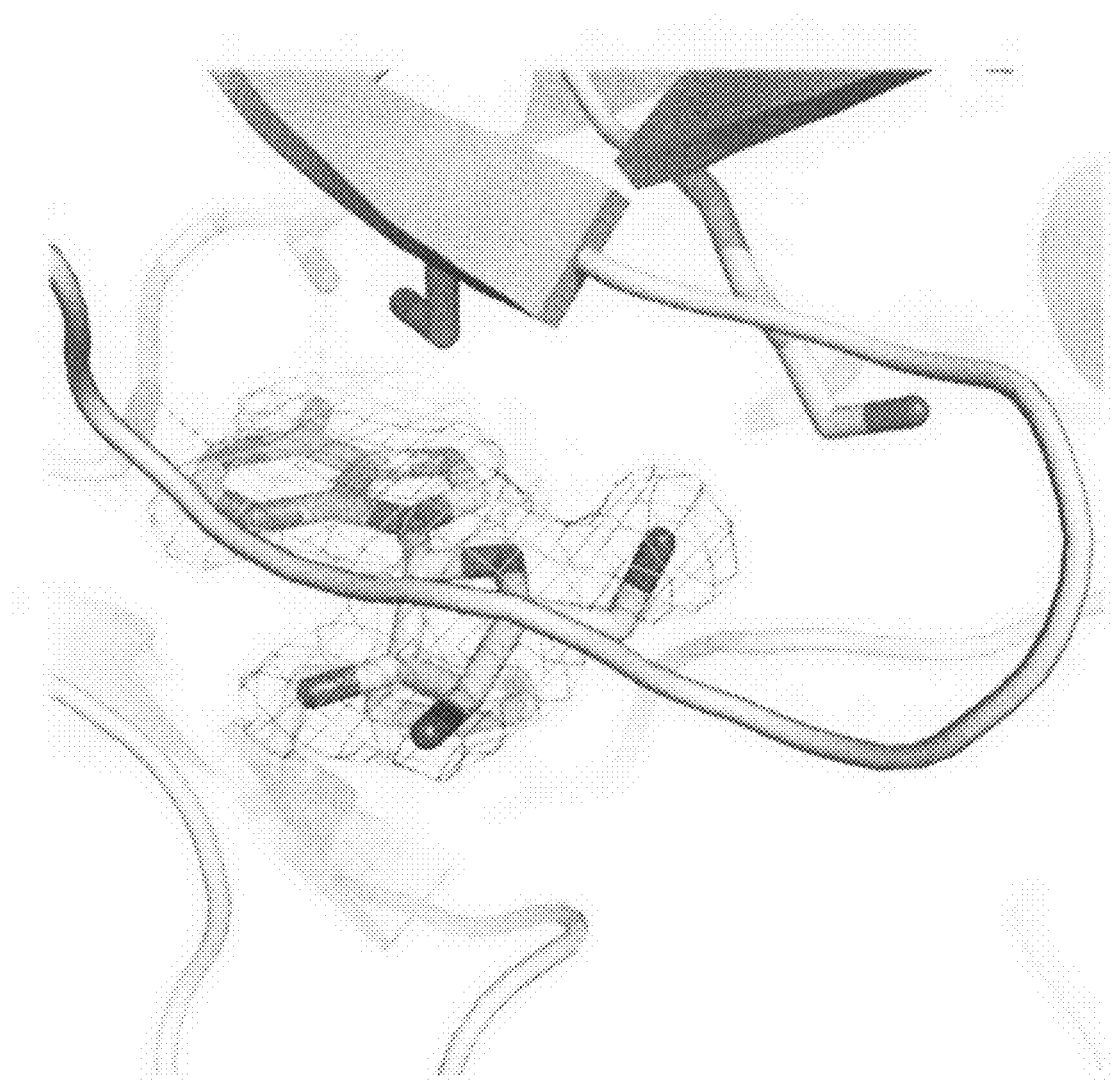

FIG. 5 shows adenosine bound in the active site of the catalytic kinase domain of PLK3—9-β-D-Ribofuranosyladenine ("adenosine") inhibitor complex.

FIG. 6 (6-1 to 6-42) lists the atomic structure coordinates after further refinement for the unphosphorylated PLK3—9-β-D-Ribofuranosyladenine ("adenosine") inhibitor complex (residues 52-332 of SEQ ID NO:1) as derived by X-ray diffraction from the crystal. The PLK3 in the crystal comprises amino acid residues 48-332 of SEQ ID NO:1.

DETAILED DESCRIPTION OF THE INVENTION

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | | | | | |
|---|---|---|---|---|---|
| A = | Ala = | Alanine | T = | Thr = | Threonine |
| V = | Val = | Valine | C = | Cys = | Cysteine |
| L = | Leu = | Leucine | Y = | Tyr = | Tyrosine |
| I = | Ile = | Isoleucine | N = | Asn = | Asparagine |
| P = | Pro = | Proline | Q = | Gln = | Glutamine |
| F = | Phe = | Phenylalanine | D = | Asp = | Aspartic Acid |
| W = | Trp = | Tryptophan | E = | Glu = | Glutamic Acid |
| M = | Met = | Methionine | K = | Lys = | Lysine |
| G = | Gly = | Glycine | R = | Arg = | Arginine |
| S = | Ser = | Serine | H = | His = | Histidine |

Additional definitions are set forth below.

The term "associating with" refers to a condition of proximity between a chemical entity or compound, or portions thereof, and a binding pocket or binding site on a protein. The association may be non-covalent—wherein hydrogen bonding or Van der Waals or electrostatic interactions energetically favor the juxtaposition—or it may be covalent.

The term "binding pocket", as used herein, refers to a region of a molecule or molecular complex, that, as a result of its shape and charge, favorably associates with another chemical entity or compound. The term "pocket" includes, but is not limited to, cleft, channel or site. PLK or PLK-like molecules may have binding pockets which include, but are not limited to, peptide or substrate binding, ATP-binding and antibody binding sites.

The term "chemical entity", as used herein, refers to chemical compounds, complexes of at least two chemical compounds, and fragments of such compounds or complexes. The chemical entity may be, for example, a ligand, a substrate, a nucleotide triphosphate, a nucleotide diphosphate, phosphate, a nucleotide, an agonist, antagonist, inhibitor, antibody, drug, peptide, protein or compound.

"Conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure,* 5, pp. 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "corresponding amino acid" or "residue that corresponds to" refers to a particular amino acid or analogue thereof in a PLK3 homologue that corresponds to an amino acid in the PLK3 structure. The corresponding amino acid may be an identical, mutated, chemically modified, conserved, conservatively substituted, functionally equivalent or homologous amino acid when compared to the PLK3 amino acid to which it corresponds.

Methods for identifying a corresponding amino acid are known in the art and are based upon sequence, structural alignment, its functional position or a combination thereof as compared to the PLK3 structure. For example, corresponding amino acids may be identified by superimposing the backbone atoms of the amino acids in PLK3 and the PLK3 homologue using well known software applications, such as QUANTA® [Molecular Simulations, Inc., San Diego, Calif.; now part of Accelrys, San Diego, Calif.]. The corresponding amino acids may also be identified using sequence alignment programs such as the "bestfit" program available from the Genetics Computer Group which uses the local homology algorithm described by Smith and Waterman in *Adv. Appl. Math.,* 2, 482 (1981), which is incorporated herein by reference.

The term "domain" refers to a portion of the PLK3 protein or homologue that can be separated according to its biological function, for example, catalysis. The domain is usually conserved in sequence or structure when compared to other kinases or related proteins. The domain can comprise a binding pocket, or a sequence or structural motif.

The term "sub-domain" refers to a portion of the domain as defined above in the PLK3 protein or homologue. The catalytic kinase domain (amino acid residues 48 to 332) of PLK3 is a bi-lobal structure consisting of an N-terminal, β-strand sub-domain (residues 48 to 139) and a C-terminal, α-helical sub-domain (residues 144 to 332).

The term "catalytic active site" refers to the area of the protein kinase to which nucleotide substrates bind. The catalytic active site of plk3 is at the interface between the N-terminal, β-strand sub-domain and the C-terminal, α-helical sub-domain.

The "PLK3 ATP-binding pocket" of a molecule or molecular complex is defined by the structure coordinates of a certain set of amino acid residues present in the PLK3 structure, as described below. In general, the ligand for the ATP-binding pocket is a nucleotide such as ATP. This binding pocket is in the catalytic active site of the kinase domain. In the protein kinase family, the ATP-binding pocket is generally located at the interface of the α-helical and β-strand sub-domains, and is bordered by the glycine rich loop and the hinge [See, Xie et al., *Structure,* 6, pp. 983-991 (1998), incorporated herein by reference].

The term "PLK3-like" refers to all or a portion of a molecule or molecular complex that has a commonality of shape to all or a portion of the PLK3 protein. In the PLK3-like ATP-binding pocket, the commonality of shape is defined by a root mean square deviation of the structure coordinates of the backbone atoms between the amino acids in the PLK3-like ATP-binding pocket and the amino acids in the PLK3 ATP-binding pocket (as set forth in FIG. 1 or FIG. 6). Compared to an amino acid in the PLK3 ATP-binding pocket, the corresponding amino acids in the PLK3-like ATP-binding pocket may or may not be identical.

The term "part of an PLK3 ATP-binding pocket" or "part of an PLK3-like ATP-binding pocket" refers to less than all of the amino acid residues that define the PLK3 or PLK3-like ATP-binding pocket. The structure coordinates of residues that constitute part of an PLK3 or PLK3-like ATP-binding pocket may be specific for defining the chemical environment of the binding pocket, or useful in designing fragments of an inhibitor that may interact with those residues. For example, the portion of residues may be key residues that play a role in ligand binding, or may be residues that are spatially related and define a three-dimensional compartment of the binding pocket. The residues may be contiguous or non-contiguous in primary sequence. In one embodiment, part of the PLK3 or PLK3-like ATP-binding pocket is at least two amino acid residues, preferably, E140 and C142. In another embodiment, the amino acids are selected from the group consisting of L68, H114, V123, L139, E140, C142, K145 and F192.

The term "PLK3 kinase domain" refers to the catalytic domain of PLK3. The kinase domain includes, for example, the catalytic active site, which comprises the catalytic residues, the activation loop or phosphorylation lip, the DFG motif, and the glycine-rich phosphate anchor or glycine-rich loop [See, Xie et al., Structure, 6, pp. 983-991 (1998); R. Giet and C. Prigent, J. Cell Sci., 112, pp. 3591-3601 (1999), incorporated herein by reference]. The kinase domain in the PLK3 protein comprises residues from about 48 to 332.

The term "part of a PLK3 kinase domain" or "part of a PLK3-like kinase domain" refers to a portion of the PLK3 or PLK3-like catalytic domain. The structure coordinates of residues that constitute part of a PLK3 or PLK3-like kinase domain may be specific for defining the chemical environment of the domain, or useful in designing fragments of an inhibitor that may interact with those residues. For example, the portion of residues may be key residues that play a role in ligand binding, or may be residues that are spatially related and define a three-dimensional compartment of the domain. The residues may be contiguous or non-contiguous in primary sequence. For example, part of a PLK3 kinase domain can be the active site, the glycine-rich loop, the activation loop, or the catalytic loop [see Xie et al., supra].

The term "homologue of PLK3" or "PLK3 homologue" refers to a molecule or molecular complex that is homologous to PLK3 by three-dimensional structure or sequence and retains the kinase activity of PLK3. Examples of homologues include but are not limited to the following: human PLK3 with mutations, conservative substitutions, additions, deletions or a combination thereof; PLK3 from a species other than human; a protein comprising an PLK3-like ATP-binding pocket, a kinase domain; another member of the protein kinase family, preferably the Polo-like kinase family or the CDK kinase family.

The term "part of a PLK3 protein" or "part of a PLK3 homologue" refers to a portion of the amino acid residues of a PLK3 protein or homologue. In one embodiment, part of a PLK3 protein or homologue defines the binding pockets, domains, sub-domains, and motifs of the protein or homologue. The structure coordinates of residues that constitute part of a PLK3 protein or homologue may be specific for defining the chemical environment of the protein, or useful in designing fragments of an inhibitor that may interact with those residues. The portion of residues may also be residues that are spatially related and define a three-dimensional compartment of a binding pocket, motif or domain. The residues may be contiguous or non-contiguous in primary sequence. For example, the portion of residues may be key residues that play a role in ligand or substrate binding, peptide binding, antibody binding, catalysis, structural stabilization or degradation.

The term "PLK3 protein complex" or "PLK3 homologue complex" refers to a molecular complex formed by associating the PLK3 protein or PLK3 homologue with a chemical entity, for example, a ligand, a substrate, nucleotide triphosphate, an agonist or antagonist, inhibitor, drug or compound. In one embodiment, the chemical entity is selected from the group consisting of an ATP, a nucleotide triphosphate and an inhibitor for the ATP-binding pocket. In another embodiment, the inhibitor is an ATP analog such as MgAMP-PNP (adenylyl imidodiphosphate) or adenosine.

The term "motif" refers to a portion of the PLK3 protein or homologue that defines a structural compartment or carries out a function in the protein, for example, catalysis, structural stabilization, or phosphorylation. The motif may be conserved in sequence, structure and function when compared to other kinases or related proteins. The motif can be contiguous in primary sequence or three-dimensional space. The motif can comprise α-helices and/or β-sheets. Examples of a motif include but are not limited to a binding pocket, active site, phosphorylation lip or activation loop, the glycine-rich phosphate anchor loop and the catalytic loop [See, Xie et al., *Structure*, 6, pp. 983-991 (1998); R. Giet and C. Prigent, *J. Cell Sci.*, 112, pp. 3591-3601 (1999)].

The term "root mean square deviation" or "RMSD" means the square root of the arithmetic mean of the squares of the deviations from the mean. It is a way to express the deviation or variation from a trend or object. For purposes of this invention, the "root mean square deviation" defines the variation in the backbone of a protein from the backbone of PLK3, a binding pocket, a motif, a domain, or portion thereof, as defined by the structure coordinates of PLK3 described herein.

The term "sufficiently homologous to PLK3" refers to a protein that has a sequence homology of at least 35% compared to PLK3 protein. In one embodiment, the sequence homology is at least 40%, at least 60%, at least 80%, at least 90% or at least 95%.

The term "soaked" refers to a process in which the crystal is transferred to a solution containing the compound of interest. In certain embodiments, the compound is diffused into the crystal.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex. It would be readily apparent to those skilled in the art that all or part of the structure coordinates of FIG. 1 or FIG. 6 may have a RMSD deviation of 0.1 Å because of standard error.

The term "about" when used in the context of RMSD values takes into consideration the standard error of the RMSD value, which is ±0.1 Å.

The term "crystallization solution" refers to a solution that promotes crystallization. The solution comprises at least one agent, and may include a buffer, one or more salts, a precipitating agent, one or more detergents, sugars or organic compounds, lanthanide ions, a poly-ionic compound and/or a stabilizer.

The term "generating a three-dimensional structure" or "generating a three-dimensional graphical representation" refers to converting the lists of structure coordinates into structural models in three-dimensional space. This can be achieved through commercially or publicly available software. The three-dimensional structure may be displayed as a graphical representation or used to perform computer modeling or fitting operations. In addition, the structure coordinates themselves may be used to perform computer modeling and fitting operations.

The term "homology model" refers to a structural model derived from known three-dimensional structure(s). Generation of the homology model, termed "homology modeling", can include sequence alignment, residue replacement, residue conformation adjustment through energy minimization, or a combination thereof The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for a PLK3 molecule or molecular complex or homologues thereof, calculating or minimizing energies for an association of a PLK3 molecule or molecular complex or homologues thereof to a chemical entity.

Crystallizable Compositions and Crystals of PLK3 Complexes

According to one embodiment, the invention provides a crystal or crystallizable composition comprising unphosphorylated PLK3 protein. In one embodiment, the PLK3 protein is human PLK3 protein or a catalytic domain thereof. In another embodiment, the invention provides a crystal or crystallizable composition comprising unphosphorylated PLK3 catalytic domain. In another embodiment, the invention provides a crystal or a crystallizable composition comprising unphosphorylated PLK3 protein, or catalytic domain thereof, and a substrate analogue, such as, but not limited, to adenosine. In one embodiment, the invention provides a crystal or a crystallizable composition comprising unphosphorylated PLK3 protein, or catalytic domain thereof, and adenosine. In one embodiment, the aforementioned crystallizable composition further comprises a precipitant, 900-1100 mM sodium dihydrogen phosphate/1100-900 mM potassium hydrogen phosphate (i.e., the concentration of sodium di-hydrogen phosphate plus the concentration of di-potassium hydrogen phosphate is 2M) and a buffer that maintains pH at between about 6.6 and 8.6. The composition may further comprise a reducing agent, such as dithiothreitol (DTT) at between about 1 to 10 mM. The unphosphorylated PLK3 protein or complex is preferably 85-100% pure prior to forming the composition.

According to another embodiment, the invention provides a crystal composition comprising PLK3 protein complex. In one embodiment, the crystal has a unit cell dimension of a=146 Å, b=59 Å, c=47 Å, α=γ=90°, β=95° and belongs to space group C2. It will be readily apparent to those skilled in the art that the unit cells of the crystal compositions may deviate ±1-2 Å from the above cell dimensions and the beta angle may vary ±1-2 degrees depending on the deviation in the unit cell calculations.

As used herein, the PLK3 protein in the crystal or crystallizable compositions can be a truncated protein with amino acids 48 to 332 of SEQ ID NO:1; and the truncated protein with conservative substitutions.

The PLK3 protein may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. Preferably, the protein is overexpressed from a baculovirus system.

The invention also relates to a method of making crystals of PLK3 complexes or PLK3 homologue complexes. Such methods comprise the steps of:
 a) producing a composition comprising a crystallization solution and PLK3 protein or homologue thereof complexed with a chemical entity; and
 b) subjecting said composition to devices or conditions which promote crystallization.

In one embodiment, the invention provides a crystal or a crystallizable composition comprising unphosphorylated PLK3 protein, or catalytic domain thereof, and a chemical entity. In one embodiment, the chemical entity is selected from the group consisting of an ATP analogue, nucleotide triphosphate, nucleotide diphosphate, phosphate, adenosine, or an active site inhibitor. In another embodiment, the chemical entity is selected from the group consisting of adenosine, ATP, an ATP analogue, AMP-PNP, a nucleotide triphosphate, a nucleotide diphosphate, phosphate and an active site inhibitor. In another embodiment, the chemical entity is an ATP analogue. In yet another embodiment, the crystallization solution is as described previously. In another embodiment, the composition is treated with micro-crystals of PLK3 or PLK3 complexes or homologues thereof. In another embodiment, the composition is treated with micro-crystals of PLK3 complexes or homologues thereof.

In certain embodiments, the invention provides a method of making PLK3 crystals, the method comprising steps of:
 a) producing and purifying PLK3 protein;
 b) producing a crystallizable composition; and
 c) subjecting said composition to devices which promote crystallization.

In one embodiment, the crystallizable composition of step b) is made according to the conditions discussed above.

Devices for promoting crystallization can include but are not limited to the hanging-drop, sitting-drop, dialysis or microtube batch devices. [U.S. Pat. Nos. 4,886,646, 5,096,676, 5,130,105, 5,221,410 and 5,400,741; Pav et al., *Proteins: Structure, Function, and Genetics*, 20, pp. 98-102 (1994), incorporated herein by reference]. The hanging-drop or sitting-drop methods produce crystals by vapor diffusion. The hanging-drop, sitting-drop, and some adaptations of the microbatch methods [D'Arcy et al., J. Cryst. Growth, 168, pp. 175-180 (1996) and Chayen, J. Appl. Cryst., 30, pp. 198-202 (1997)] produce crystals by vapor diffusion. The hanging drop and sitting drop containing the crystallizable composition is equilibrated in a reservoir containing a higher or lower concentration of the precipitant. As the drop approaches equilibrium with the reservoir, the saturation of protein in the solution leads to the formation of crystals.

Microseeding or seeding may be used to obtain larger, or better quality (i.e., crystals with higher resolution diffraction or single crystals) crystals from initial micro-crystals. Microseeding involves the use of crystalline particles to provide nucleation under controlled crystallization conditions. Microseeding is used to increase the size and quality of crystals. In this instance, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art following the teachings of the specification to vary the crystallization conditions disclosed herein to identify other crystallization conditions that would produce crystals of PLK3 homologue, PLK3 homologue complex, PLK3 protein or other PLK3 protein complexes. Such variations include, but are not limited to, adjusting pH, protein concentration and/or crystallization temperature, changing the identity or concentration of salt and/or precipitant used, using a different method of crystallization, or introducing additives such as detergents (e.g., TWEEN 20 (monolaurate), LDAO, Brij 30 (4 lauryl ether)), sugars (e.g., glucose, maltose), organic compounds (e.g., dioxane, dimethylformamide), lanthanide ions or polyionic compounds that aid in crystallization. High throughput crystallization assays may also be used to assist in finding or optimizing the crystallization conditions.

Binding Pockets of PLK3 Protein or Homologues thereof

As disclosed above, applicants have provided for the first time the three-dimensional X-ray crystal structures of a PLK3-inhibitor complex. The crystal structure of PLK3 presented here is the first reported for PLK3. The invention is useful for inhibitor design to study the role of PLK3 in cell signaling. Atomic or structure coordinates are presented in FIG. 1 and FIG. 6.

In order to use the structure coordinates generated for PLK3, their complexes, one of their binding pockets, or a PLK3-like binding pocket thereof, it is often at times necessary to convert the coordinates into a three-dimensional shape. This is achieved through the use of commercially available software that is capable of generating three-dimensional graphical representations (e.g., three-dimensional structures) of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The ATP and substrate binding pockets of this invention will be important for drug design.

In one embodiment, the ATP-binding pocket comprises amino acids L68, G69, K70, G71, G72, F73, A74, R75, C76, A89, K91, E110, H114, V123, L139, E140, L141, C142, S143, R144, K145, S146, H149, G189, N190, F192, D203 and F204 using the structure of the PLK3-adenosine complex according to FIG. 1 or FIG. 6. In resolving the crystal structures of the unphosphorylated PLK3-inhibitor complexes, applicants have determined that the above amino acids are within 5 Å ("5 Å sphere amino acids") of the inhibitor bound in the ATP-binding pockets. Using the program QUANTA® [Molecular Simulations, Inc., San Diego, Calif.; now part of Accelrys, San Diego, Calif.], O [T. A. Jones et al., *Acta Cryst. A*, 47, pp. 110-119 (1991)] and RIBBONS [Carson, *J. Appl. Cryst.*, 24, pp. 958-961 (1991)], applicant has identified this binding pocket. The programs allow one to display and output all residues within 5 Å from the inhibitor. One skilled in the art can then visual inspect and identify the binding pocket. Thus, a binding pocket defined by the structural coordinates of these amino acids, as set forth in FIG. 1 or FIG. 6 is considered a PLK3-ATP binding pocket of this invention.

In another embodiment, the ATP-binding pocket comprises amino acids R66, L67, L68, G69, K70, G71, G72, F73, A74, R75, C76, Y77, E78, Y88, A89, V90, K91, V92, I93, E110, H114, V123, R124, I137, L139, E140, L141, C142, S143, R144, K145, S146, L147, A148, H149, L188, G189, N190, F191, F192, I193, T194, E195, K200, V201, G202 and D203 using the structure of the PLK3—adenosine complex according to FIG. 1 or FIG. 6. In the crystal structures of the PLK3-inhibitor complexes, applicants have determined that the above amino acids are within 8 Å ("8 Å sphere amino acids") of the inhibitor bound in the ATP-binding pocket. Using the programs QUANTA®, O and RIBBONS, supra, applicants determined this binding pocket Thus, a binding pocket defined by the structural coordinates of these amino acids, as set forth in FIG. 1 or FIG. 6 is considered a PLK3-ATP binding pocket of this invention.

In another embodiment, the ATP-binding pocket comprises amino acids R66, L67, L68, G69, K70, G71, G72, F73, A74, R75, C76, Y77, E78, Y88, A89, V90, K91, V92, I93, Q103, K106, I107, E110, I111, H114, V123, R124, F125, I137, F138, L139, E140, L141, C142, S143, R144, K145, S146, L147, A148, H149, W151, K152, H183, D185, K187, L188, G189, N190, F191, F192, I193, T194, E195, K200, V201, G202, D203, F204, G205, L206, T223 and Y226 using the structure of the PLK3—adenosine complex according to FIG. 1 or FIG. 6. Using a multiple alignment program to compare each PLK3 structure and structures of other members of the protein kinase family [Gerstein et al., J. Mol. Biol., 251, pp. 161-175 (1995), incorporated herein by reference], applicants have identified the above amino acids as the ATP-binding pocket. First, a sequence alignment between members of the protein kinase family including Wee1 [Squire et al. Structure 13, 541-550 (2005); *PDB accession number* 1X8B], p38 [K. P. Wilson et al., J. Biol. Chem., 271, pp. 27696-27700 (1996); Z. Wang et al., Proc. Natl. Acad. Sci. U.S.A., 94, pp. 2327-32 (1997)], CDK2 [PDB Accession number 1B38], ITK [Brown et al., J. Biol. Chem. 279, pp. 18727 (2004); *PDB Accession number* 1SM2], MK2 [U.S. Provisional application 60/337,513] and PDK1 [Komander et al. Biochem J., 375, 255-261 (2003); PDB Accession code 1OKY] was performed. Then, a putative core was constructed by superimposing a series of corresponding structures in the protein kinase family. Then, residues of high spatial variation were discarded, and the core alignment was iteratively refined. The amino acids that make up the final core structure have low structural variance and have the same local and global conformation relative to the corresponding residues in the protein family. See Table 1 discussed in detail below.

In one embodiment, the ATP-binding pocket comprises the amino acids of L68, H114, V123, L139, E140, C142, K145 and F192 according to FIG. 1 or FIG. 6. It will be readily apparent to those of skill in the art that the numbering of amino acids in other homologues of PLK3 may be different than that set forth for PLK3. Corresponding amino acids in homologues of PLK3 are easily identified by visual inspection of the amino acid sequences or by using commercially available sequence homology, structural homology or structure superimposition software programs.

Those of skill in the art understand that a set of structure coordinates for a molecule or a molecular-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated because of mathematical manipulations of the PLK3 structure coordinates. For example, the structure coordinates set forth in FIG. 1 or FIG. 6 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that bound to the binding pocket of PLK3 would also be expected to bind to another binding pocket whose structure coordinates defined a shape that fell within the acceptable root mean square deviation.

Various computational analyses maybe necessary to determine whether a binding pocket, motif, domain or portion thereof of a molecule or molecular complex is sufficiently similar to the binding pocket, motif, domain or portion thereof of PLK3. Such analyses may be carried out in well known software applications, such as ProFit [A. C. R. Martin, SciTech Software, ProFit version 1.8, University College London, http://www.bioinf.org.uk/software], Swiss-Pdb Viewer [Guex et al., *Electrophoresis*, 18, pp. 2714-2723 (1997)], the Molecular Similarity application of QUANTA® [Molecular Simulations, Inc., San Diego, Calif.; now part of Accelrys, San Diego, Calif.] and as described in the accompanying User's Guide, which are incorporated herein by reference.

The above programs permit comparisons between different structures, different conformations of the same structure, and different parts of the same structure. The procedure used in QUANTA® [Molecular Simulations, Inc., San Diego, Calif.; now part of Accelrys, San Diego, Calif.] and Swiss-Pdb Viewer to compare structures is divided into four steps: 1) load the structures to be compared; 2) define the atom equivalences in these structures; 3) perform a fitting operation on the structures; and 4) analyze the results. The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within the above programs is defined by user input, for the purpose of this invention we will define equivalent atoms as protein backbone atoms (N, Cα, C and O) for PLK3 amino acids and corresponding amino acids in the structures being compared.

The corresponding amino acids may be identified by sequence alignment programs such as the "bestfit" program available from the Genetics Computer Group which uses the local homology algorithm described by Smith and Waterman in Advances in Applied Mathematics 2, 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids with the second protein [Hanks et al., *Science,* 241, 42 (1988); Hanks and Quinn, *Meth. Enzymol.,* 200, 38 (1991)]. The identification of equivalent residues can also be assisted by secondary structure alignment, for example, aligning the α-helices, β-sheets in the structure. The program Swiss-Pdb Viewer has its own best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program sets an RMSD cutoff for eliminating pairs of equivalent atoms that have high RMSD values. For programs that calculate an average of the individual RMSD values of the backbone atoms, an RMSD cutoff value can be used to exclude pairs of equivalent atoms with extreme individual RMSD values. In the program ProFit, the RMSD cutoff value can be specified by the user.

The RMSD values between other protein kinases the PLK3 protein complex (FIG. 1) and other kinases are illustrated in Table 1. The RMSD values were determined by the programs ProFit from initial rigid fitting results from QUANTA® [Molecular Simulations, Inc., San Diego, Calif.; now part of Accelrys, San Diego, Calif.]. The RMSD values provided in Table 1 are averages of individual RMSD values calculated for the backbone atoms in the kinase or ATP-binding pocket. The RMSD cutoff value in ProFit was specified as 3 Å.

TABLE 1

RMSD values for PLK3-adenosine complex

| Protein | RMSD value between ATP-binding pocket (8 Å sphere of amino acids) and corresponding amino acids in protein (Å) | RMSD value between ATP-binding pocket (5 Å sphere of amino acids) and corresponding amino acids in protein (Å) | RMSD value between PLK3-complex kinase domain and kinase domain in protein (Å) |
| --- | --- | --- | --- |
| Wee1[a] | 1.77 | 1.98 | 1.41 |
| P38[b] | 2.94 | 2.74 | 4.09 |
| PDK1[c] | 1.52 | 1.66 | 1.32 |
| ITK[d] | 2.41 | 2.45 | 2.14 |
| MKK2[e] | 5.73 | 6.68 | 6.68 |
| Cdk2[f] | 2.19 | 2.25 | 2.36 |

[a]Wee1: Squire et al. Structure 13, 541-550 (2005); PDB accession number 1X8B
[b]p38: Wilson et al., J. Biol. Chem., 271, pp. 27696-27700 (1996); Z. Wang et al., Proc. Natl. Acad. Sci. U.S.A., 94, pp. 2327-2332 (1997); PDB Accession number 1WFC
[c]phosphoinositide dependent protein kinase 1 (PDK1): Komander et al. Biochem J., 375, 255-261 (2003); PDB Accession code 1OKY
[d]Interleukin-2 Tyrosine Kinase: Brown et al., J. Biol. Chem. 279, pp. 18727 (2004); PDB Accession number 1SM2.
[e]Mitogen activated protein kinase activated protein (MAPKAP) kinase 2: U.S. application Ser. No. 10/497,767 which is a national stage entry of PCT/US02/39070 which claims priority to U.S. Provisional Application No. 60/337,513, filed Dec. 5, 2001.
[f]Human cyclin-dependent kinase 2 (cdk2): Brown et al. J. Biol. Chem. 274, 8746-8752 (1999)

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIG. 1 or FIG. 6 are encompassed by this invention.

Therefore, one embodiment of this invention provides a molecule or molecular complex comprising all or part of a PLK3 ATP-binding pocket defined by structure coordinates of PLK3 amino acids L68, G69, K70, G71, G72, F73, A74, R75, C76, A89, K91, E110, H114, V123, L139, E140, L141, C142, S143, R144, K145, S146, H149, G189, N190, F192, D203 and F204 according to FIG. 1 or FIG. 6; or a molecule or molecular complex comprising all or part of a PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å, or 1.0 Å; or a molecule or molecular complex comprising all or part of a PLK3-like ATP-binding pocket defined by structure coordinates of a set of corresponding amino acids, wherein the root mean square deviation of the backbone atoms between said set of corresponding amino acids and said PLK3 amino acids is not more than about 1.1 Å, 0.9 Å, 0.7 Å, or 0.5 Å and wherein at least one of said corresponding amino acids is not identical to the PLK3 amino acid to which it corresponds.

Another embodiment of this invention provides a molecule or molecular complex comprising all or part of an PLK3 ATP-binding pocket defined by structure coordinates of PLK3 amino acids R66, L67, L68, G69, K70, G71, G72, F73, A74, R75, C76, Y77, E78, Y88, A89, V90, K91, V92, I93, E110, H114, V123, R124, I137, L139, E140, L141, C142, S143, R144, K145, S146, L147, A148, H149, L188, G189, N190, F191, F192, I193, T194, E195, K200, V201, G202 and D203 according to FIG. 1 or FIG. 6; or a molecule or molecular complex comprising all or part of a PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å, or 1.0 Å; or a molecule or molecular complex comprising all or part of a PLK3-like ATP-binding pocket defined by structure coordinates of a set of corresponding amino acids, wherein the root mean square deviation of the backbone atoms between said set of corresponding amino acids and said PLK3 amino acids is not more than about 1.0 Å, 0.8 Å, or 0.6 Å, and wherein at least one of said corresponding amino acids is not identical to the PLK3 amino acid to which it corresponds.

Yet other embodiments of this invention provide a molecule or molecular complex comprising all or part of other PLK3 ATP-binding pockets defined in this invention and by the structure coordinates of PLK3 amino acids according to FIG. 1 or FIG. 6, wherein the root mean square deviation of the backbone atoms between said corresponding amino acids and said PLK3 amino acids is not more than about 3.0 Å, 2.5 Å, 2.0 Å, 1.5 Å, 1.0 Å, 0.8 Å, or 0.6 Å.

In one embodiment, the above molecules or molecular complexes are in crystalline form.

Computer Systems

According to another embodiment of this invention is provided a machine-readable data storage medium, comprising a data storage material encoded with machine-readable data, wherein said data comprises all or part of an PLK3 ATP-binding pocket defined by structure coordinates of PLK3 amino acids L68, G69, K70, G71, G72, F73, A74, R75, C76, A89, K91, E110, H114, V123, L139, E140, L141, C142, S143, R144, K145, S146, H149, G189, N190, F192, D203 and F204, according to FIG. 1 or FIG. 6; or a molecule or molecular complex comprising all or part of an PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å, or 1.0 Å; or a molecule or molecular complex comprising all or part of an PLK3-like ATP-binding pocket defined by structure coordinates of a set of corresponding amino acids, wherein the root mean square deviation of the backbone atoms between said set of corresponding amino acids and said PLK3 amino acids is not more than about 1.1, 0.9, 0.7 or 0.5 Å, and wherein at least one of said corresponding amino acids is not identical to the PLK3 amino acid to which it corresponds.

In other embodiments of this invention is provided a machine-readable data storage medium, comprising a data storage material encoded with machine-readable data, wherein said data comprises all or part of any molecule or molecular complex discussed in the above paragraphs.

In one embodiment of this invention is provided a computer comprising:

a machine-readable data storage medium, comprising a data storage material encoded with machine-readable data, wherein said data comprises all or part of a PLK3 ATP-binding pocket defined by structure coordinates of PLK3 amino acids L68, G69, K70, G71, G72, F73, A74, R75, C76, A89, K91, E110, H114, V123, L139, E140, L141, C142, S143, R144, K145, S146, H149, G189, N190, F192, D203 and F204, according to FIG. 1 or FIG. 6; or a molecule or molecular complex comprising all or part of a PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å, or 1.0 Å; or a molecule or molecular complex comprising all or part of a PLK3-like ATP-binding pocket defined by structure coordinates of a set of corresponding amino acids, wherein the root mean square deviation of the backbone atoms between said set of corresponding amino acids and said PLK3 amino acids is not more than about 0.5 Å, and wherein at least one of said corresponding amino acids is not identical to the PLK3 amino acid to which it corresponds.

In one embodiment, a computer according to this invention comprises a working memory for storing instructions for processing the machine-readable data, a central-processing unit coupled to the working memory and to said machine-readable data storage medium for processing said machine-readable data into the three-dimensional structure. In one embodiment, the computer further comprises a display for displaying the three-dimensional structure as a graphical representation. In another embodiment, the computer further comprises commercially available software program to display the graphical representation. Examples of software programs include but are not limited to QUANTA® [Molecular Simulations, Inc., San Diego, Calif.; now part of Accelrys, San Diego, Calif.], O [Jones et al., *Acta Cryst. A*, 47, pp. 110-119 (1991)] and RIBBONS [M. Carson, *J. Appl. Cryst.*, 24, pp. 958-961 (1991)], which are incorporated herein by reference.

In another embodiment, a computer according to this invention comprises executable code for:

(a) using structural coordinates according to FIG. 1 or FIG. 6 as a 3-dimensional model of a catalytic domain of Polo-like Kinase 3 (PLK3) protein;

(b) analyzing a binding site of the 3-dimensional model; and (c) screening in silico a library for small molecules that fit into said binding site. In another embodiment, the computer further comprises executable code for: (d) controlling a unit for assaying the small molecules determined in step (c) in a protein binding assay. Using structural coordinates may include displaying the coordinates graphically or manipulating the structure coordinates with computational programs.

This invention also provides a computer comprising:

a) a machine-readable data storage medium comprising a data storage material encoded with machine-readable data, wherein the data defines any one of the above binding pockets or protein of the molecule or molecular complex;

b) a working memory for storing instructions for processing said machine-readable data;

c) a central processing unit (CPU) coupled to the working memory and to the machine-readable data storage medium for processing said machine readable data as well as an instruction or set of instructions for generating three-dimensional structural information of said binding pocket or protein; and d) output hardware coupled to the CPU for outputting three-dimensional structural information of the binding pocket or protein, or information produced by using the three-dimensional structural information of said binding pocket or protein. The output hardware may include monitors, touchscreens, printers, facsimile machines, modems, disk drives, CD-ROMs, etc.

Three-dimensional data generation may be provided by an instruction or set of instructions such as a computer program or commands for generating a three-dimensional structure or graphical representation from structure coordinates, or by subtracting distances between atoms, calculating chemical energies for a PLK3 molecule or molecular complex or homologues thereof, or calculating or minimizing energies for an association of a PLK3 molecule or molecular complex or homologues thereof to a chemical entity. The graphical representation can be generated or displayed by commercially available software programs. Examples of software programs include but are not limited to QUANTA® [Molecular Simulations, Inc., San Diego, Calif.; now part of Accelrys, San Diego, Calif.], O [Jones et al., *Acta Crystallogr. A*47, pp. 110-119 (1991)] and RIBBONS [Carson, *J. Appl. Crystallogr.*, 24, pp. 9589-961 (1991)], Coot [Emsley, P. and Cowtan, K. *Acta Crystallogr. D*60, pp. 2126-2132 Part 12 Sp. Iss. 1 (December 2004)], and PyMol™ [DeLano, W. L. The PyMOL Molecular Graphics System (2002) DeLano Scientific™, Palo Alto, Calif., USA.], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

Information about said binding pocket or information produced by using said binding pocket can be outputted through display terminals, touchscreens, printers, modems, facsimile machines, CD-ROMs or disk drives. The information can be in graphical or alphanumeric form.

FIG. 2 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA® [Molecular Simulations, Inc., San Diego, Calif.; now part of Accelrys, San Diego, Calif.] as described herein. Output hardware might also include a printer 42, so that hard copy output may be produced, or a disk drive 24, to store system output for later use. Output hardware may also include a display terminal, a CD or DVD recorder, ZIP™ or JAZ™ drive, or other machine-readable data storage device.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 3 shows a cross section of a magnetic data storage medium 100 which can be encoded with a machine-readable data that can be carried out by a system such as system 10 of FIG. 2. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in a manner that may be conventional, machine readable data such as that described herein, for execution by a system such as system 10 of FIG. 2.

FIG. 4 shows a cross section of an optically-readable data storage medium 110 which also can be encoded with such a machine-readable data, or set of instructions, which can be carried out by a system such as system 10 of FIG. 2. Medium 110 can be a conventional compact disk read only memory (CD-ROM) or a rewritable medium such as a magneto-optical disk that is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

In one embodiment, the data defines the above-mentioned binding pockets by comprising the structure coordinates of said amino acid residues according to FIG. 1 or FIG. 6.

To use the structure coordinates generated for PLK3 or PLK3 homologue, one of its binding pockets, motifs, domains, or portion thereof, it is at times necessary to convert them into a three-dimensional shape or to generate three-dimensional structural information from them. This is achieved through the use of commercially or publicly available software that is capable of generating a three-dimensional structure of molecules or portions thereof from a set of structure coordinates. In one embodiment, the three-dimensional structure may be displayed as a graphical representation.

Therefore, according to another embodiment, this invention provides a machine-readable data storage medium comprising a data storage material encoded with machine readable data. In one embodiment, a machine programmed with instructions for using said data, is capable of generating a three-dimensional structure of any of the molecule or molecular complexes, or binding pockets thereof, that are described herein.

In certain embodiment, this invention also provides a computer for producing a three-dimensional structure of:

a) a molecule or molecular complex comprising all or part of a PLK ATP-binding pocket defined by structure coordinates of PLK3 amino acids C76, A89, V123, L139, E140, L141, C142, S146, F192 and G202, according to FIG. 1 or FIG. 6;

b) a molecule or molecular complex comprising all or part of a PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å or 1.0 Å; or 0.5 Å; and/or c) a molecule or molecular complex comprising all or part of a PLK3-like ATP-binding pocket defined by structure coordinates of a set of corresponding amino acids, wherein the root mean square deviation of the backbone atoms between said set of corresponding amino acids and said PLK3 amino acids is not more than about 0.6 Å, 0.5 Å or 0.4 Å, and wherein at least one of said corresponding amino acids is not identical to the PLK3 amino acid to which it corresponds, comprising:

i) a machine-readable data storage medium, comprising a data storage material encoded with machine-readable data, wherein said data comprises all or part of a PLK3 ATP-binding pocket defined by structure coordinates of PLK3 amino acids C76, A89, V123, L139, E140, L141, C142, S146, F192 and G202, according to FIG. 1 or FIG. 6; all or part of a PLK3-like ATP-binding pocket defined by structure coordinates of corresponding amino acids that are identical to said PLK3 amino acids, wherein the root mean square deviation of the backbone atoms between said corresponding amino acids and said PLK3 amino acids is not more than about 3.0 Å, 2.5 Å, 2.0 Å, 1.5 Å or 1.0 Å; or all or part of a PLK3-like ATP-binding pocket defined by structure coordinates of a set of corresponding amino acids, wherein the root mean square deviation of the backbone atoms between said set of corresponding amino acids and said PLK3 amino acids is not more than about 0.6 Å, 0.5 Å or 0.4 Å, and wherein at least one of said corresponding amino acids is not identical to the PLK3 amino acid to which it corresponds; and ii) instructions for processing said machine-readable data into said three-dimensional structure.

According to other embodiments, the computer is also for producing the three-dimensional structure of the aforementioned molecules and molecular complexes and comprises the corresponding machine-readable data storage mediums. In one embodiment, the three-dimensional structure is displayed as a graphical representation.

In one embodiment, the structure coordinates of said molecules or molecular complexes are produced by homology modeling of at least a portion of the structure coordinates of FIG. 1 or FIG. 6. Homology modeling can be used to generate structural models of PLK3 homologues or other homologous proteins based on the known structure of PLK3. This can be achieved by performing one or more of the following steps: performing sequence alignment between the amino acid sequence of an unknown molecule against the amino acid sequence of PLK3; identifying conserved and variable regions by sequence or structure; generating structure coordinates for structurally conserved residues of the unknown structure from those of PLK3; generating conformations for the structurally variable residues in the unknown structure; replacing the non-conserved residues of PLK3 with residues in the unknown structure; building side chain conformations; and refining and/or evaluating the unknown structure.

For example, since the protein sequence of the catalytic domains of PLK3 and homologues thereof can be aligned relative to each other, it is possible to construct models of the structures of PLK3 homologues, particularly in the regions of the active site, using the PLK3 structure. Software programs that are useful in homology modeling include XALIGN [Wishart, D. S. et al., *Comput. Appl. Biosci.,* 10, pp. 687-88 (1994)] and CLUSTAL W Alignment Tool [Higgins D. G. et al., *Methods Enzymol,* 266, pp. 383-402 (1996)]. See also, U.S. Pat. No. 5,884,230. These references are incorporated herein by reference.

To perform the sequence alignment, programs such as the "bestfit" program available from the Genetics Computer Group [Waterman in *Advances in Applied Mathematics* 2, 482 (1981), which is incorporated herein by reference] and CLUSTAL W Alignment Tool [Higgins D. G. et al., *Methods Enzymol,* 266, pp. 383-402 (1996), which is incorporated by reference] can be used. To model the amino acid side chains of homologous PLK3 proteins, the amino acid residues in PLK3 can be replaced, using a computer graphics program such as "O" [Jones et al, (1991) *Acta Crest. Sect. A* 47: 110-119], by those of the homologous protein, where they differ. The same orientation or a different orientation of the amino acid can be used. Insertions and deletions of amino acid residues may be necessary where gaps occur in the sequence alignment.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol.* 256: 701-719 (1996); Blundell et al., *Nature* 326: 347-352 (1987); Fetrow and Bryant, *Bio/Technology* 11:479-484 (1993); Greer, *Methods in Enzymology* 202: 239-252 (1991); and Johnson et al, *Crit. Rev. Biochem. Mol. Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three dimensional structure of the above molecules or molecular complexes (e.g., PLK3, homologues and portions thereof), or binding pockets thereof, can be stored in a machine-readable storage medium, which is capable of displaying three-dimensional structural information or a graphical three-dimensional representation of the structure.

Rational Drug Design

The PLK3 structure coordinates or the three-dimensional graphical representation generated from these coordinates may be used in conjunction with a computer for a variety of purposes, including drug discovery. In certain embodiments, the computer is programmed with software to translate those coordinates into the three-dimensional structure of PLK3.

For example, the structure encoded by the data may be computationally evaluated for its ability to associate with chemical entities. Chemical entities that associate with PLK3 may inhibit or activate PLK3 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention provides a method for designing, selecting and/or optimizing a chemical entity that binds to the molecule or molecular complex comprising the steps of:

(a) providing the structure coordinates of said molecule or molecular complex on a computer comprising the means for generating three-dimensional structural information from said structure coordinates; and (b) designing, selecting and/or optimizing said chemical entity by employing means for performing a fitting operation between said chemical entity and said three-dimensional structural information of said molecule or molecular complex.

Three-dimensional structural information in step (a) may be generated by instructions such as a computer program or commands that can generate a three-dimensional structure or graphical representation; subtract distances between atoms; calculate chemical energies for a PLK3 molecule, molecular complex or homologues thereof; or calculate or minimize energies of an association of PLK3 molecule, molecular complex or homologues thereof to a chemical entity. These types of computer programs are known in the art. The graphical representation can be generated or displayed by commercially available software programs. Examples of software programs include but are not limited to QUANTA® [Molecular Simulations, Inc., San Diego, Calif.; now part of Accelrys, San Diego, Calif.], O [Jones et al., *Acta Crystallogr. A*47, pp. 110-119 (1991)] and RIBBONS [Carson, *J. Appl. Crystallogr.,* 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

Another embodiment of the invention provides a method for evaluating the potential of a chemical entity to associate with the molecule or molecular complex as described previously.

This method comprises the steps of: a) employing computational means to perform a fitting operation between the chemical entity and the molecule or molecular complex described before; b) analyzing the results of said fitting operation to quantify the association between the chemical entity and the molecule or molecular complex; and, optionally, c) outputting said quantified association to a suitable output hardware, such as a CRT display terminal, a printer, a CD or DVD recorder, ZIP™ or JAZ™ drive, a disk drive, or other machine-readable data storage device, as described previously. The method may further comprise generating a three-dimensional structure, graphical representation thereof, or both, of the molecule or molecular complex prior to step a). In one embodiment, the method is for evaluating the ability of a chemical entity to associate with the binding pocket of a molecule or molecular complex.

In another embodiment, the method comprises the steps of:
a) constructing a computer model of a binding pocket of the molecule or molecular complex;
b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a PLK3 protein or homologue thereof;
c) employing computational means to perform a fitting program operation between computer models of said chemical entity to be evaluated and said binding pocket in order to provide an energy-minimized configuration of said chemical entity in the binding pocket; and
d) evaluating the results of said fitting operation to quantify the association between said chemical entity and the binding pocket model, thereby evaluating the ability of said chemical entity to associate with said binding pocket.

In another embodiment, the invention provides a method of using a computer for evaluating the ability of a chemical entity to associate with the molecule or molecular complex, wherein said computer comprises a machine-readable data storage medium comprising a data storage material encoded with said structure coordinates defining said binding pocket and means for generating a three-dimensional graphical representation of the binding pocket, and wherein said method comprises the steps of:
(a) positioning a first chemical entity within all or part of said binding pocket using a graphical three-dimensional representation of the structure of the chemical entity and the binding pocket;
(b) performing a fitting operation between said chemical entity and said binding pocket by employing computational means;
(c) analyzing the results of said fitting operation to quantitate the association between said chemical entity and all or part of the binding pocket; and
(d) outputting said quantitated association to a suitable output hardware.

The above method may further comprise the steps of:
(e) repeating steps (a) through (d) with a second chemical entity; and
(f) selecting at least one of said first or second chemical entity that associates with said all or part of said binding pocket based on said quantitated association of said first or second chemical entity.

Alternatively, the structure coordinates of the PLK binding pockets may be utilized in a method for identifying an agonist or antagonist of a molecule comprising a binding pocket of PLK. In certain embodiments, the method comprises steps of:
a) using a three-dimensional structure of the molecule or molecular complex to design, select or optimize a chemical entity;
b) contacting the chemical entity with the molecule or molecular complex;
c) monitoring the catalytic activity of the molecule or molecular complex; and
d) classifying the chemical entity as an agonist or antagonist based on the effect of the chemical entity on the catalytic activity of the molecule or molecular complex.

In one embodiment, step a) is performed using a graphical representation of the binding pocket or portion thereof of the molecule or molecular complex.

In one embodiment, the three-dimensional structure is displayed as a graphical representation.

In another embodiment, the method comprises the steps of:
a) constructing a computer model of a binding pocket of the molecule or molecular complex;
b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a PLK3 protein or homologue thereof;
c) employing computational means to perform a fitting program operation between computer models of said chemical entity to be evaluated and said binding pocket in order to provide an energy-minimized configuration of said chemical entity in the binding pocket; and
d) evaluating the results of said fitting operation to quantify the association between said chemical entity and the binding pocket model, thereby evaluating the ability of said chemical entity to associate with said binding pocket;
e) obtaining said chemical entity; and
f) contacting said chemical entity with said molecule or molecular complex to determine the ability of said compound to activate or inhibit said molecule. Obtaining said chemical entity includes synthesizing the chemical entity, obtaining a commercially available product, or isolating the chemical entity.

For the first time, the present invention permits the use of molecular design techniques to identify, select and design chemical entities, including inhibitory compounds, capable of binding to PLK3 or PLK3-like binding pockets, motifs and domains.

Applicants' elucidation of binding pockets on PLK3 provides the necessary information for designing new chemical entities and compounds that may interact with PLK3 or PLK3-like substrate or ATP-binding pockets, in whole or in part.

Assays to determine if a compound binds to PLK3 are well known in the art and are exemplified below.

The design of chemical entities that bind to or inhibit PLK3 binding pockets according to this invention generally involves consideration of two factors. First, the entity must be capable of physically and structurally associating with parts or all of the PLK3 binding pockets. Non-covalent molecular interactions important in this association include hydrogen bonding, van der Waals interactions, hydrophobic interactions and electrostatic interactions.

Second, the entity must be able to assume a conformation that allows it to associate with the PLK3 binding pockets directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the PLK3 or PLK3-like binding pockets.

The potential inhibitory or binding effect of a chemical entity on PLK3 binding pockets may be analyzed prior to its actual synthesis and testing by the use of computer modeling techniques. If the theoretical structure of the given entity suggests insufficient interaction and association between it and the PLK3 binding pockets, testing of the entity is obviated. However, if computer modeling indicates a strong interaction, the compound may then be synthesized and tested for its ability to bind to a PLK3 binding pocket. This may be achieved by testing the ability of the molecule to inhibit PLK3 using the assays described in Example 9. In this manner, synthesis of inoperative compounds may be avoided.

A potential inhibitor of a PLK3 binding pocket may be computationally evaluated by means of a series of steps in which chemical entities or fragments are screened and selected for their ability to associate with the PLK3 binding pockets.

One skilled in the art may use one of several methods to screen chemical entities or fragments for their ability to associate with a PLK3 binding pocket. This process may begin by visual inspection of, for example, a PLK3 binding pocket on the computer screen based on the PLK3 structure coordinates in FIG. 1 or FIG. 6 or other coordinates which define a similar shape generated from the machine-readable storage medium. Selected fragments or chemical entities may then be positioned in a variety of orientations, or docked, within that binding pocket as defined supra. Docking may be accomplished using software such as QUANTA® [Molecular Simulations, Inc., San Diego, Calif.; now part of Accelrys, San Diego, Calif.] and SYBYL® [Tripos Associates, St. Louis, Mo.], followed by energy minimization and molecular dynamics with standard molecular mechanics force fields, such as CHARMm® [Accelrys, San Diego, Calif.] and AMBER.

Specialized computer programs may also assist in the process of selecting fragments or chemical entities. These include:

1. GRID [P. J. Goodford, "A Computational Procedure for Determining Energetically Favorable Binding Sites on Biologically Important Macromolecules", *J. Med. Chem.*, 28, pp. 849-857 (1985)]. GRID is available from Oxford University, Oxford, UK.
2. MCSS [A. Miranker et al., "Functionality Maps of Binding Sites: A Multiple Copy Simultaneous Search Method." *Proteins: Structure, Function and Genetics*, 11, pp. 29-34 (1991)]. MCSS is available from Molecular Simulations, San Diego, Calif.
3. AUTODOCK [D. S. Goodsell et al., "Automated Docking of Substrates to Proteins by Simulated Annealing", *Proteins: Structure, Function, and Genetics*, 8, pp. 195-202 (1990)]. AUTODOCK is available from Scripps Research Institute, La Jolla, Calif.
4. DOCK [I. D. Kuntz et al., "A Geometric Approach to Macromolecule-Ligand Interactions", *J. Mol. Biol.*, 161, pp. 269-288 (1982)]. DOCK is available from University of California, San Francisco, Calif.
5. GLIDE [Schrödinger, Portland, Oreg. 97204, USA; Thomas A. Halgren, Robert B. Murphy, Richard A. Friesner, Hege S. Beard, Leah L. Frye, W. Thomas Pollard, and Jay L. Banks "Glide: A New Approach for Rapid, Accurate Docking and Scoring. 2. Enrichment Factors in Database Screening", *J. Med. Chem.* 47 (7), pp. 1750-1759 (2004)]

Once suitable chemical entities or fragments have been selected, they can be assembled into a single compound or complex of compounds. Assembly may be preceded by visual inspection of the relationship of the fragments to each other on the three-dimensional image displayed on a computer screen in relation to the structure coordinates of PLK3. This would be followed by manual model building using software such as QUANTA® and DISCOVERY STUDIO® [Molecular Simulations, Inc., San Diego, Calif.; now part of Accelrys, San Diego, Calif.], SYBYL® [Tripos Associates, St. Louis, Mo.] or MAESTRO [Schrödinger, Portland, Oreg. 97204, USA], or OPENEYE [Copyright © 1997-2006, OpenEye Scientific Software, SanteFe, N. Mex. 87508, USA].

Useful programs to aid one of skill in the art in building an inhibitor of a PLK3 binding pocket in a step-wise fashion, including one fragment or chemical entity at a time, include:

1. CAVEAT [P. A. Bartlett et al., "CAVEAT: A Program to Facilitate the Structure-Derived Design of Biologically Active Molecules", in Molecular Recognition in Chemical and Biological Problems", *Special Pub., Royal Chem. Soc.*, 78, pp. 182-196 (1989); G. Lauri and P. A. Bartlett, "CAVEAT: a Program to Facilitate the Design of Organic Molecules", *J. Comput. Aided Mol. Des.*, 8, pp. 51-66 (1994)]. CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", *J. Med. Chem.*, 35, pp. 2145-2154 (1992).
3. HOOK [M. B. Eisen et al., "HOOK: A Program for Finding Novel Molecular Architectures that Satisfy the Chemical and Steric Requirements of a Macromolecule Binding Site", Proteins: *Struct. Funct. Genet.*, 19, pp. 199-221 (1994)]. HOOK is available from Molecular Simulations, San Diego, Calif.

Instead of proceeding to build an inhibitor of a PLK3 binding pocket in a step-wise fashion one fragment or chemical entity at a time as described above, inhibitory or other PLK binding compounds may be designed as a whole or "de novo" using either an empty binding pocket or optionally including some portion(s) of a known inhibitor(s). There are many de novo ligand design methods including:

1. LUDI [H.-J. Bohm, "The Computer Program LUDI: A New Method for the De Novo Design of Enzyme Inhibitors", *J. Comp. Aid. Molec. Design*, 6, pp. 61-78 (1992)]. LUDI is available from Molecular Simulations Incorporated, San Diego, Calif.; now Accelrys, San Diego, Calif.
2. LEGEND [Y. Nishibata et al., *Tetrahedron*, 47, p. 8985 (1991)]. LEGEND is available from Molecular Simulations Incorporated, San Diego, Calif.; now Acclerys, San Diego, Calif.

3. LEAPFROG® [available from Tripos Associates, St. Louis, Mo.].
4. SPROUT [V. Gillet et al., "SPROUT: A Program for Structure Generation)", *J. Comput. Aided Mol. Design*, 7, pp. 127-153 (1993)]. SPROUT is available from the University of Leeds, UK.
5. NEWLEAD (V. Tschinke and N. C. Cohen, "The NEWLEAD Program: A New Method for the Design of Candidate Structures from Pharmacophoric Hypotheses", *J. Med. Chem.*, 36, 3863-3870 (1993)).

Other molecular modeling techniques may also be employed in accordance with this invention [see, e.g., N. C. Cohen et al., "Molecular Modeling Software and Methods for Medicinal Chemistry, *J. Med. Chem.*, 33, pp. 883-894 (1990); see also, M. A. Navia and M. A. Murcko, "The Use of Structural Information in Drug Design", *Current Opinions in Structural Biology*, 2, pp. 202-210 (1992); L. M. Balbes et al., "A Perspective of Modern Methods in Computer-Aided Drug Design", *Reviews in Computational Chemistry*, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology*, 4, pp. 777-781 (1994)].

Once a chemical entity has been designed or selected by the above methods, the efficiency with which that chemical entity may bind to a PLK3 binding pocket may be tested and optimized by computational evaluation. For example, an effective PLK3 binding pocket inhibitor must preferably demonstrate a relatively small difference in energy between its bound and free states (i.e., a small deformation energy of binding). Thus, the most efficient PLK3 binding pocket inhibitors should preferably be designed with a deformation energy of binding of not greater than about 10 kcal/mole, more preferably, not greater than 7 kcal/mole. PLK3 binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to a PLK3 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C [M. J. Frisch, Gaussian, Inc., Pittsburgh, Pa. ©1995]; AMBER, version 4.1 [P. A. Kollman, University of California at San Francisco, ©1995]; QUANTA®/CHARMm® [Accelrys, San Diego, Calif.]; Insight II®/Discovery Studio® [Accelrys, San Diego, Calif. ©2001, 2002]; DelPhi [Accelrys, San Diego, Calif. ©2001, 2002]; and AMSOL [Quantum Chemistry Program Exchange, Indiana University]. These programs may be implemented, for instance, using a Silicon Graphics® workstation such as an INDIGO2 with "IMPACT™" graphics. Other hardware systems and software packages will be known to those skilled in the art.

Another approach enabled by this invention, is the computational screening of small molecule databases for chemical entities or compounds that can bind in whole, or in part, to a PLK binding pocket. In this screening, the quality of fit of such entities to the binding pocket may be judged either by shape complementarity or by estimated interaction energy [E. C. Meng et al., *J. Comp. Chem.*, 13, pp. 505-524 (1992)].

Another particularly useful drug design technique enabled by this invention is iterative drug design. Iterative drug design is a method for optimizing associations between a protein and a compound by determining and evaluating the three-dimensional structures of successive sets of protein/compound complexes.

According to another embodiment, the invention provides compounds which associate with a PLK3 binding pocket produced or identified by the method set forth above.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex.

In one embodiment, this invention provides for a method of designing a compound which binds to a catalytic domain of a Polo-like Kinase 3 (PLK3) protein comprising a binding pocket, wherein said catalytic domain is characterized by:

(i) the atomic coordinates of amino acids 52-327 of SEQ ID NO:1 shown in FIG. 1 positioned within a rmsd of 1.2 Å or the atomic coordinates of amino acids 52-332 of SEQ ID NO:1 shown in FIG. 6 positioned within a rmsd of 1.2 Å;

(ii) the atomic coordinates of said binding pocket defined by amino acids L68, G69, K70, G71, G72, F73, A74, R75, C76, A89, K91, E110, H114, V123, L139, E140, L141, C142, S143, R144, K145, S146, H149, G189, N190, F192, D203 and F204 of FIG. 1 or FIG. 6 and which are within a rmsd of 1.2 Å;

(iii) the atomic coordinates of said binding pocket defined by amino acids R66, L67, L68, G69, K70, G71, G72, F73, A74, R75, C76, Y77, E78, Y88, A89, V90, K91, V92, I93, E110, H114, V123, R124, I137, L139, E140, L141, C142, S143, R144, K145, S146, L147, A148, H149, L188, G189, N190, F191, F192, I193, T194, E195, K200, V201, G202 and D203 of FIG. 1 or FIG. 6 and which are within a rmsd of 1.2 Å;

(iv) the atomic coordinates of said binding pocket defined by amino acids R66, L67, L68, G69, K70, G71, G72, F73, A74, R75, C76, Y77, E78, Y88, A89, V90, K91, V92, I93, Q103, K106, I107, E110, I111, H114, V123, R124, F125, I137, F138, L139, E140, L141, C142, S143, R144, K145, S146, L147, A148, H149, W151, K152, H183, D185, K187, L188, G189, N190, F191, F192, I193, T194, E195, K200, V201, G202, D203, F204, G205, L206, T223 and Y226 of FIG. 1 or FIG. 6 and which are within a rmsd of 1.0 Å; or (v) the atomic coordinates of said binding pocket defined by amino acids L68, H114, V123, L139, E140, C142, K145 and F192 of FIG. 1 or FIG. 6 and which are within a rmsd of 1.0 Å;

said method comprising the steps of:

(a) using the atomic coordinates of FIG. 1 or FIG. 6 to build a 3-D computer model of a compound interaction region of said protein comprising at least one of (i)-(v);

(b) assessing the stereochemical complementarity between a compound and said interaction region;

(c) optimizing said stereochemical complementarity in an iterative approach by observing changes in the protein or compound that affect the protein/compound associations; and (d) designing a compound which optimizes said protein/compound stereochemical complementarity.

In another embodiment, the invention provides for a method of identifying a potential inhibitor of a Polo-like Kinase 3 (PLK3) protein comprising a binding pocket, wherein said method comprising the steps of:

(a) using the structure coordinates of FIG. 1 or FIG. 6 to generate a three-dimensional model;

(b) identifying said binding pocket residues, and using said residues to generate a specific three-dimensional (3-D) target;

(c) employing said 3-D target of (b) to design or select said potential inhibitor;

(d) obtaining said potential inhibitor; and (e) contacting said potential inhibitor with said Polo-like Kinase 3 (PLK3) protein in vitro to determine the ability of said potential inhibitor to interact with said Polo-like Kinase 3 (PLK3) protein; whereby the ability to interact is an indication that said potential inhibitor of said Polo-like Kinase 3 (PLK3) protein is identified. Obtaining said potential inhibitor includes synthesizing the potential inhibitor, obtaining a commercially available product or isolating the potential inhibitor.

In another embodiment, this invention provides for a method of identifying a candidate inhibitor of a molecule or molecular complex comprising a binding pocket or domain selected from the group consisting of:

(i) a set of amino acid residues that are identical to human Polo-like Kinase 3 (PLK3) amino acid residues of said binding pocket according to FIG. 1 or FIG. 6, wherein the root mean square deviation of the backbone atoms between said set of amino acid residues and said human Polo-like Kinase 3 (PLK3) amino acid residues is not greater than about 1.0 Å; and (ii) a set of amino acid residues that are identical to human Polo-like Kinase 3 (PLK3) amino acid residues according to FIG. 1 or FIG. 6, wherein the root mean square deviation between said set of amino acid residues and said human Polo-like Kinase 3 (PLK3) amino acid residues is not more than about 1.0 Å;

comprising the steps of:

(a) using a three-dimensional structure of the binding pocket or domain to design, select or optimize a plurality of chemical entities;

(b) contacting each chemical entity with the molecule or the molecular complex;

(c) monitoring the inhibition to the catalytic activity of the molecule or molecular complex by each chemical entity; and (d) selecting a chemical entity based on the inhibitory effect of the chemical entity on the catalytic activity of the molecule or molecular In one embodiment, this invention provides for a method for identifying a candidate inhibitor that interacts with a binding site of a human Polo-Like Kinase 3 (PLK3) protein or a homologue thereof, comprising the steps of:

(a) obtaining a crystal comprising said human Polo-Like Kinase 3 (PLK3) protein, wherein the crystal is characterized with space group C2 and has unit cell parameters of a=146 Å, b=59 Å, c=47 Å; β=95°;

(b) obtaining the structure coordinates of amino acids of the crystal of step (a);

(c) generating a three-dimensional model of said human Polo-Like Kinase 3 (PLK3) protein or said homologue thereof using the structure coordinates of the amino acids generated in step (b), a root mean square deviation from backbone atoms of said amino acids of not more than ±1.0 Å;

(d) determining a binding site of said human Polo-Like Kinase 3 (PLK3) protein or said homologue thereof from said three-dimensional model; and (e) performing computer fitting analysis to design or identify the candidate inhibitor which interacts with said binding site.

(f) contacting the designed or identified candidate inhibitor with said human Polo-Like Kinase 3 (PLK3) protein or said homologue thereof in vitro in order to determine the effect of the inhibitor on human Polo-Like Kinase 3 (PLK3) protein activity.

In another embodiment, this invention provides the methods of identifying above, wherein the binding site of said human Polo-Like Kinase 3 (PLK3) protein or said homologue thereof determined in step (d) comprises the structure coordinates according to FIG. 1 or FIG. 6 of a set of amino acid residues that are identical to human Polo-Like Kinase 3 (PLK3) amino acid residues R66, L67, L68, G69, K70, G71, G72, F73, A74, R75, C76, Y77, E78, Y88, A89, V90, K91, V92, I93, Q103, K106, I107, E110, I111, H114, V123, R124, F125, I137, F138, L139, E140, L141, C142, S143, R144, K145, S146, L147, A148, H149, W151, K152, H183, D185, K187, L188, G189, N190, F191, F192, I193, T194, E195, K200, V201, G202, D203, F204, G205, L206, T223 and Y226, wherein the root mean square deviation from the backbone atoms of said amino acids is not more than ±1.0 Å.

In another embodiment, this invention provides the methods of identifying above, wherein the binding site of said human Polo-Like Kinase 3 (PLK3) protein or said homologue thereof determined in step (d) comprises the structure coordinates according to FIG. 1 or FIG. 6 of a set of amino acid residues that are identical to human Polo-Like Kinase 3 (PLK3) amino acid residues R66, L67, L68, G69, K70, G71, G72, F73, A74, R75, C76, Y77, E78, Y88, A89, V90, K91, V92, I93, E110, H114, V123, R124, I137, L139, E140, L141, C142, S143, R144, K145, S146, L147, A148, H149, L188, G189, N190, F191, F192, I193, T194, E195, K200, V201, G202 and D203, wherein the root mean square deviation from the backbone atoms of said amino acids is not more than ±1.2 Å.

In another embodiment, this invention provides the methods of identifying above, wherein the binding site of said human Polo-Like Kinase 3 (PLK3) protein or said homologue thereof determined in step (d) comprises the structure coordinates according to FIG. 1 or FIG. 6 of a set of amino acid residues that are identical to human Polo-Like Kinase 3 (PLK3) amino acid residues L68, G69, K70, G71, G72, F73, A74, R75, C76, A89, K91, E110, H114, V123, L139, E140, L141, C142, S143, R144, K145, S146, H149, G189, N190, F192, D203 and F204, wherein the root mean square deviation from the backbone atoms of said amino acids is not more than ±1.2 Å.

In another embodiment, this invention provides the methods of identifying above, wherein the binding site of said human Polo-Like Kinase 3 (PLK3) protein or said homologue thereof determined in step (d) comprises the structure coordinates according to FIG. 1 or FIG. 6 of a set of amino acid residues that are identical to human Polo-Like Kinase 3 (PLK3) amino acid residues L68, H114, V123, L139, E140, C142, K145 and F192, wherein the root mean square deviation from the backbone atoms of said amino acids is not more than ±1.0 Å.

One embodiment of this invention provides for a method of identifying compounds that bind Polo-like Kinase 3 (PLK3) protein comprising:
  (a) obtaining a 3-D molecular model of Polo-like Kinase 3 (PLK3) protein;
  (b) reducing said model to a 3-D molecular model of the binding pocket of Polo-like Kinase 3 (PLK3) protein;
  (c) using the model of (b) in a method of rational drug design to identify candidate compounds that can bind Polo-like Kinase 3 (PLK3) protein; and
  (d) assaying for Polo-like Kinase 3 (PLK3) protein activity in the presence of the binding candidate compounds identified in step (c);

to thereby identify compounds that bind Polo-like Kinase 3 (PLK3) protein. In this invention, the 3-D molecular model of Polo-like Kinase 3 (PLK3) protein is represented by the structure coordinates according to FIG. 1 or FIG. 6. In one embodiment, the 3-D molecular model of Polo-like Kinase 3 (PLK3) protein comprises the structure coordinates according to FIG. 1 or FIG. 6. In another embodiment, the 3-D molecular model comprises amino acid residues 48-332 of SEQ ID NO:1.

One embodiment of this invention provides for a method of identifying compounds that bind Polo-like Kinase 3 (PLK3) protein selectively comprising:
  (a) obtaining a 3-D molecular model of Polo-like Kinase 3 (PLK3) protein;
  (b) reducing said model to a 3-D molecular model of the binding pocket of Polo-like Kinase 3 (PLK3) protein;
  (c) using the model of (b) in a method of rational drug design to identify candidate compounds that can bind Polo-like Kinase 3 (PLK3) protein; and
  (d) assaying for Polo-like Kinase 1 (PLK1) protein activity, Polo-like Kinase 2 (PLK2) protein activity, Polo-like Kinase 3 (PLK3) protein activity and Polo-like Kinase 4 (PLK4) protein activity in the presence of the binding candidate compounds identified in step (c);

to thereby identify compounds that bind Polo-like Kinase 3 (PLK3) protein selectively. In this invention, the 3-D molecular model of Polo-like Kinase 3 (PLK3) protein is represented by the structure coordinates according to FIG. 1 or FIG. 6. In one embodiment, the 3-D molecular model of Polo-like Kinase 3 (PLK3) protein comprises the structure coordinates according to FIG. 1 or FIG. 6. In another embodiment, the 3-D molecular model comprises amino acid residues 48-332 of SEQ ID NO:1.

Another embodiment of this invention provides for a method of identifying compounds that bind Polo-like Kinase 3 (PLK3) protein comprising:
  (a) obtaining a 3-D molecular model of Polo-like Kinase 3 (PLK3) protein;
  (b) reducing said model to a 3-D molecular model of the binding pocket of Polo-like Kinase 3 (PLK3) protein;
  (c) comparing the model of (b) with a library of 3-D molecular models representing structures of candidate compounds to electronically screen said library;
  (d) identifying candidate compounds whose structures electronically fit in model of (b) as compounds that can bind Polo-like Kinase 3 (PLK3) protein; and
  (e) assaying for Polo-like Kinase 3 (PLK3) protein activity in the presence of the binding candidate compounds identified in step (d);

to thereby identify compounds that bind Polo-like Kinase 3 (PLK3) protein. In this invention, the 3-D molecular model of Polo-like Kinase 3 (PLK3) protein is represented by the structure coordinates according to FIG. 1 or FIG. 6. In one embodiment, the 3-D molecular model of Polo-like Kinase 3 (PLK3) protein comprises the structure coordinates according to FIG. 1 or FIG. 6. In another embodiment, the 3-D molecular model comprises amino acid residues 48-332 of SEQ ID NO:1.

Another embodiment of this invention provides for a method of identifying compounds that bind Polo-like Kinase 3 (PLK3) protein selectively comprising:
  (a) obtaining a 3-D molecular model of Polo-like Kinase 3 (PLK3) protein;
  (b) reducing said model to a 3-D molecular model of the binding pocket of Polo-like Kinase 3 (PLK3) protein;
  (c) comparing the model of (b) with a library of 3-D molecular models representing structures of candidate compounds to electronically screen said library;
  (d) identifying candidate compounds whose structures electronically fit in model of (b) as compounds that can bind Polo-like Kinase 3 (PLK3) protein; and
  (e) assaying for Polo-like Kinase 1 (PLK1) protein activity, Polo-like Kinase 2 (PLK2) protein activity, Polo-like Kinase 3 (PLK3) protein activity and Polo-like Kinase 4 (PLK4) protein activity in the presence of the binding candidate compounds identified in step (d);

to thereby identify compounds that bind Polo-like Kinase 3 (PLK3) protein selectively. In this invention, the 3-D molecular model of Polo-like Kinase 3 (PLK3) protein is represented by the structure coordinates according to FIG. 1 or FIG. 6. In one embodiment, the 3-D molecular model of Polo-like Kinase 3 (PLK3) protein comprises the structure coordinates according to FIG. 1 or FIG. 6. In another embodiment, the 3-D molecular model comprises amino acid residues 48-332 of SEQ ID NO:1.

Structure Determination of Other Molecules

The structure coordinates set forth in FIG. 1 or FIG. 6 can also be used to aid in obtaining structural information about another crystallized molecule or molecular complex. This may be achieved by any of a number of well-known techniques, including molecular replacement.

According to an alternate embodiment, the machine-readable data storage medium comprises a data storage material encoded with a first set of machine readable data which comprises the Fourier transform of at least a portion of the structure coordinates set forth in FIG. 1 or FIG. 6 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex, wherein said computer comprises:
  a) a machine-readable data storage medium comprising a data storage material encoded with machine-readable data, wherein said data comprises at least a portion of the structural coordinates of PLK3 according to FIG. 1 or FIG. 6 or homology model thereof;
  b) a machine-readable data storage medium comprising a data storage material encoded with machine-readable data, wherein said data comprises X-ray diffraction data obtained from said molecule or molecular complex; and
  c) instructions for performing a Fourier transform of the machine readable data of (a) and for processing said machine readable data of (b) into structure coordinates.

For example, the Fourier transform of at least a portion of the structure coordinates set forth in FIG. 1 or FIG. 6 or homology model thereof may be used to determine at least a portion of the structure coordinates of PLK3 homologues.

Therefore, in another embodiment this invention provides a method of utilizing molecular replacement to obtain structural information about a molecule or molecular complex whose structure is unknown comprising the steps of:
  a) crystallizing said molecule or molecular complex of unknown structure;
  b) generating an X-ray diffraction pattern from said crystallized molecule or molecular complex;
  c) applying at least a portion of the structure coordinates set forth in FIG. 1 or FIG. 6 or homology model thereof to the X-ray diffraction pattern to generate a three-dimensional electron density map of the molecule or molecular complex whose structure is unknown; and
  d) generating a structural model of the molecule or molecular complex from the three-dimensional electron density map.

In one embodiment, the method is performed using a computer. In another embodiment, the molecule is selected from the group consisting of PLK3 and PLK3 homologues. In another embodiment, the molecule is a PLK3 molecular complex or homologue thereof.

By using molecular replacement, all or part of the structure coordinates of the PLK3 as provided by this invention (and set forth in FIG. 1 or FIG. 6) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the PLK3 according to FIG. 1 or FIG. 6 or homology model thereof within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55-77 (1985); M. G. Rossmann, ed., "The Molecular Replacement Method", *Int. Sci. Rev. Ser., No.* 13, Gordon & Breach, New York (1972)].

The structure of any portion of any crystallized molecule or molecular complex that is sufficiently homologous to any portion of the PLK3 can be resolved by this method.

In a preferred embodiment, the method of molecular replacement is utilized to obtain structural information about a PLK3 homologue. The structure coordinates of PLK3 as provided by this invention are particularly useful in solving the structure of PLK3 complexes that are bound by ligands, substrates and inhibitors.

Furthermore, the structure coordinates of PLK3 as provided by this invention are useful in solving the structure of PLK3 proteins that have amino acid substitutions, additions and/or deletions (referred to collectively as "PLK3 mutants", as compared to naturally occurring PLK3). These PLK3 mutants may optionally be crystallized in co-complex with a chemical entity, such as a non-hydrolyzable ATP analog or a suicide substrate. The crystal structures of a series of such complexes may then be solved by molecular replacement and compared with that of wild-type PLK3. Potential sites for modification within the various binding pockets of the enzyme may thus be identified. This information provides an additional tool for determining the most efficient binding interactions, for example, increased hydrophobic interactions, between PLK3 and a chemical entity or compound.

The structure coordinates are also particularly useful in solving the structure of crystals of PLK3 or PLK3 homologues co-complexed with a variety of chemical entities. This approach enables the determination of the optimal sites for interaction between chemical entities, including candidate PLK3 inhibitors. For example, high resolution X-ray diffraction data collected from crystals exposed to different types of solvent allows the determination of where each type of solvent molecule resides. Small molecules that bind tightly to those sites can then be designed and synthesized and tested for their PLK3 inhibition activity.

All of the complexes referred to above may be studied using well-known X-ray diffraction techniques and may be refined versus 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)), CNS (Brunger et al., *Acta Crystallogr. D. Biol. Crystallogr.*, 54, pp. 905-921, (1998)) or CNX (Accelrys, ©2000, 2001). This information may thus be used to optimize known PLK inhibitors, and more importantly, to design new PLK inhibitors.

In order that this invention be more fully understood, the following examples are set forth. These examples are for the purpose of illustration only and are not to be construed as limiting the scope of the invention in any way.

EXAMPLE 1

Expression and Purification of PLK3 Constructs for Crystallography and Enzymology Human cDNA encoding the PLK3 kinase domain (amino acids 48-332) was obtained by PCR from cDNA library using the following gene specific oligonucleotides; 5'CAT ATG GAC CCC GGG CGC CTC ATC ACG G 3' (pBev10-TOPO Forward primer D48; SEQ ID NO:2) and 5'CTA TTG GGA CTG TCA CGC AGC TGC TG 3' (pBev10-TOPO Reverse Primer P332; SEQ ID NO:3). The PCR product was gel purified on a 0.8% agarose gel, excised from the gel and solubilized using the QIAGEN® QIAEX® II Gel Extraction Kit following the manufacturer's instructions. The PCR product was resuspended in TE pH8.0 buffer (30 ul). This fusion product was subcloned downstream of the polyhedrin promoter in the baculovirus donor vector, pBEV10TOPO, using the BamHI and EcoRI sites. The vector incorporated an N-terminal hexa-histidine purification tag and thrombin cleavage site.

The expression of PLK3 was carried out using standard procedures known in the art.

pBEV10TOPO is a Bac-to-Bac compatible pBEV10 vector TOPO® adapted by Invitrogen Corporation via Invitrogen's Custom TOPO® Cloning Adaptation Service. Recombinant virus was generated according to the manufacturer's recommendations. These initially transfected *Spodoptera frugiperda* (Sf9) cells were tested for the expression of PLK3 (D48-P332) protein by loading a crude extract of the transfected insect cells onto an SDS-PAGE (sodium dodecyl sulfate polyacrylamide gel electrophoresis) gel and immunoblot analysis using an anti-His (Sigma) antibody. Upon confirmation of the expression of the PLK3 (D48-P332) protein the virus was further amplified two times to obtain high titer stocks and used for optimisation of expression studies in Hi5 and Sf9 insect cells ($1.5 \times 10^6$ cells/ml) at 27° C. with shaking at 100 rpm, using defined volumes of virus. After infection, cells were harvested at regular intervals of 24, 48 and 72 hours and optimum expression was determined by SDS-PAGE gel and immunoblot analysis using an anti-His (Sigma) antibody. Large-scale cultivation/expression was conducted with Hi5 insect cells ($1.5 \times 10^6$ cells/ml) using a multiplicity of infection (M.O.I.) of between 2 and 5 of recombinant PLK3 (D48-P332) virus particles/cell, incubated at 27° C., 100 rpm and harvested 48 hours post-infection.

The PLK3 (D48-P332) cell pellets were resuspended into Lysis buffer (50 mM Hepes, pH 8.0, 300 mM NaCl, 5 mM β-mercaptoethanol, 10% Glycerol (v/v), 0.25% Tween, 5 mM Imidazole, 0.5 mM Sodium orthovanadate, 50 mM sodium fluoride, 10 mM β-glycerophosphate, Protease inhibitor Cocktail I (Roche Diagnostics GmbH, Germany) and Phosphatase Inhibitor) and disrupted by dounce homogenization, on ice. Resuspended cells were further mechanically disrupted using a MICROFLUIDIZER® (MICROFLUIDICS™, Newton, Mass.). The cell debris was removed by centrifugation (21,000 rpm, 15 min at 4° C.) and the supernatant incubated for 2.5 hours at 4° C. with pre-equilibrated Nickel-NTA metal affinity resin. The Ni-NTA resin was collected by centrifugation (1000 g, 4 min) and the non-specifically bound protein was removed by washing with 30× bead volume of Lysis buffer. The PLK3 (D48-P332) protein was eluted 3 times with Lysis buffer containing 200 mM Imidazole and a final elution was carried out using Lysis buffer containing 500 mM Imidazole. The N-terminal hexa-histidine tagged protein was then purified by size-exclusion on a Superdex 200(26/60) column (Amersham Biotech, Sweden) pre-equilibrated in Gel Filtration Buffer (50 mM Hepes, pH 8.0, 300 mM NaCl, 2 mM DTT and 10% Glycerol). The N-terminal hexa-histidine tag was removed by a 4° C. overnight incubation using 30 Units thrombin (Sigma) per mg of eluted protein and successful cleavage analysed by SDS-PAGE gel. The cleaved protein was then isolated by further purification using cation exchange chromatography. Protein post size exclusion was diluted with Buffer A (20 mM Hepes, pH 7.3, 10% Glycerol and 2 mM DTT) to reach a final salt concentration of 50 mM. Protein was then applied to a 10 ml MUSTANG™ S module (Pall Corporation) pre-equilibrated with Buffer A at a flow rate of 5 ml/min. Unbound protein was washed extensively with 10CV (column volumes) of Buffer. Bound protein was eluted using a salt gradient of 0-100% in 25 minutes at a flow rate of 3 ml/min. The resultant protein fractions were analysed by SDS-PAGE gel and fractions containing purified PLK3 (D48-P332) protein (amino acids 48-322 of SEQ ID NO:1) were pooled accordingly. The purified protein sample was dialysed against 25 mM Tris pH8.0 containing 200 mM NaCl, 10% glycerol and 2 mM DTT at 4° C. and concentrated to 10 mg/ml for crystallization. The crystallisable PLK3 (D48-P332) protein (amino acids 48-322 of SEQ ID NO:1) was found to elute between 49-54% NaCl.

```
                                                                    SEQ ID NO:1
  1 MEPAAGFLSP RPFQRAAAAP APPAGPGPPP SALRGPELEM LAGLPTSDPG RLITDPRSGR

61 TYLKGRLLGK GGFARCYEAT DTETGSAYAV KVIPQSRVAK PHQREKILNE IELHRDLQHR

121 HIVRFSHHFE DADNIYIFLE LCSRKSLAHI WKARHTLLEP EVRYYLRQIL SGLKYLHQRG

181 ILHRDLKLGN FFITENMELK VGDFGLAARL EPPEQRKKTI CGTPNYVAPE VLLRQGHGPE

241 ADVWSLGCVM YTLLCGSPPF ETADLKETYR CIKQVHYTLP ASLSLPARQL LAAILRASPR

301 DRPSIDQILR HDFFTKGYTP DRLPISSCVT VPDLTPPNPA RSLFAKVTKS LFGRKKKSKN

361 HAQERDEVSG LVSGLMRTSV GHQDARPEAP AASGPAPVSL VETAPEDSSP RGTLASSGDG

421 FEEGLTVATV VESALCALRN CIAFMPPAEQ NPAPLAQPEP LVWVSKWVDY SNKFGFGYQL

481 SSRRVAVLFN DGTHMALSAN RKTVHYNPTS TKHFSFSVGA VPRALQPQLG ILRYFASYME

541 QHLMKGGDLP SVEEVEVPAP PLLLQWVKTD QALLMLFSDG TVQVNFYGDH TKLILSGWEP

601 LLVTFVARNR SACTYLASHL RQLGCSPDLR QRLRYALRLL RDRSPA
```

EXAMPLE 2

Enzymatic Characterization of PLK3 Proteins

Activity of the PLK3 constructs was determined using a standard coupled enzyme system (Fox et al., *Protein Sci.,* 7, pp. 2249 (1998)). Reactions were carried out in a solution containing 100 mM HEPES (pH 7.5), 10 mM $MgCl_2$, 25 mM NaCl, 2 mM DTT and 3% DMSO. Final peptidic substrate (full length Myelin Basic Protein (MBP), Vertex Pharmaceuticals Inc., Cambridge, Mass.) concentration in the assay was 15 µM. Reactions were carried out at 30° C. in the presence of 500 nM PLK3 construct and a titration of ATP (Sigma Chemicals, St Louis, Mo.) at final assay concentrations spanning 0 to 500 µM. Final concentrations of the components of the coupled enzyme system were 2.5 mM phosphoenolpyruvate, 300 µM NADH, 60 µg/ml pyruvate kinase and 20 µg/ml lactate dehydrogenase. An assay stock buffer solution was prepared containing all of the reagents listed above with the exception of ATP and DMSO. The assay stock buffer solution (60 µl) was incubated in a 96 well plate with 2 µl DMSO. The reaction was initiated by the addition of 5 µl of ATP (final assay concentrations spanning 0 to 500 µM). Rates of reaction were obtained using a Molecular Devices Spectramax plate reader (Sunnyvale, Calif.) over 10 min at 30° C. The ATP Km and Vmax values were determined from the rate data as a function of ATP concentration using computerized nonlinear regression (PRISM® 4.0a, Graphpad Software, San Diego, Calif.).

EXAMPLE 3

Formation of PLK3-Inhibitor Complex for Crystallization

Crystals of PLK3-inhibitor complex crystals were formed by co-crystallizing the protein with adenosine. Adenosine was added to the PLK3 protein solution immediately after the final protein concentration step (Example 1) and immediately prior to setting up the crystallization drop. The PLK3-adenosine co-complex was prepared by incubating protein on ice with 3 mM adenosine for 30 minutes. Specifically, 5.72 µl protein stock solution and 1.2 µl of adenosine at a concentration of 50 mM was added to 14.28 µl of PLK3 at a concentration of 11.7 mg/ml and left on ice for 30 minutes prior to setting up the hanging drops.

EXAMPLE 4

Crystallization of the PLK3-Adenosine Complex

Crystallization of PLK3 was carried out using the hanging drop vapor diffusion technique. The PLK3 formed rod-like crystals over a reservoir containing 900-1100 mM sodium di-hydrogen phosphate/100-900 mM di-potassium hydrogen phosphate (i.e., the concentration of sodium di-hydrogen phosphate plus the concentration of di-potassium hydrogen phosphate is 2M), 100 mM MES pH6.6 and 10 mM DTT. The crystallization droplet contained 0.50 µl of 8 mg ml$^{-1}$ protein solution and 0.50 µl of reservoir solution. Crystals formed in approximately 72 hours.

The formed crystals were transferred to a reservoir solution containing 25% glycerol. After soaking the crystals in 25% glycerol for less than 2 minutes, the crystals were scooped up with a cryo-loop, frozen in liquid nitrogen and stored for data collection.

EXAMPLE 5

X-Ray Data Collection and Structure Determination

The PLK3—adenosine structure was solved by molecular replacement as describe below using X-ray diffraction data collected at SRS Daresbury, station 14.1. A summary of data collection is given in Table 2. The diffraction images were processed with the program MOSFLM [A. G. Leslie, *Acta Cryst. D,* 55, pp. 1696-1702 (1999)] and the data was scaled using SCALA [Collaborative Computational Project, N., *Acta Cryst. D,* 50, pp. 760-763 (1994)].

The data statistics, unit cell parameters and spacegroup of the PLK3—adenosine crystal structure is given in Table 2. The starting phases for the PLK3 complexes were obtained by molecular replacement using as a search model the coordinates of a PLK3 homology model based on Wee1 (Protein Data Bank (PDB) code 1X8B) in the program AMoRe [J. Navaza, *Acta. Cryst. A,* 50, pp. 157-163 (1994)]. The asymmetric unit contained a single PLK3 complex. Multiple rounds of rebuilding with QUANTA® [Molecular Simulations, Inc., San Diego, Calif.; now part of Accelrys Inc.] and initial refinement with CNX [Accelrys Inc., San Diego, Calif. ©2000] resulted in a model that included residues 52 to 327 of PLK3. The model after initial refinement had a crystallographic R-factor of 30.2% and R-free of 33.2% (see initial refinement in Table 3 for details for data 20-2.0 Å). Further refinement was performed with BUSTER-TNT (Global Phasing Ltd., Cambridge, UK) on data from 13-2.1 Å with I/σ(I) of 10.2/1.9, and Rmerge*(%) (overall/outer shell) of 5.0/40.9 and resulted in a final model that included residues 52 to 332 of PLK3. Information on the further refinement is also given in Table 3.

EXAMPLE 6

Overall Structure of PLK3

PLK3 has the typical bi-lobal catalytic kinase fold or structural domain [S. K. Hanks, et al., *Science,* 241, pp. 42-52 (1988); Hanks, S. K. and A. M. Quinn, *Meth. Enzymol.,* 200, pp. 38-62 (1991)] with a β-strand sub-domain (residues 52-137) at the N-terminal end and an α-helical sub-domain at the C-terminal end (residues 146-327). The ATP-binding pocket is at the interface of the α-helical and β-strand sub-domains, and is bordered by the glycine rich loop and the hinge.

Comparison with other kinases such as Itk, p38 and cdk3 revealed that the structure of PLK3 resembles closely the substrate-bound, activated, form of a kinase. The overall topology of the kinase domain is similar to other serine/threonine kinases, particularly Wee1 and PDK1, and distinct from tyrosine kinases such as Itk, MKK2 (Table 1).

EXAMPLE 7

The Use of PLK3 Coordinates for Inhibitor Design

The coordinates of FIG. 1 or FIG. 6 are used to design compounds, including inhibitory compounds, that associate with PLK3 or homologues of PLK3. This process may be aided by using a computer comprising a machine-readable data storage medium encoded with a set of machine-executable instructions, wherein the recorded instructions are capable of displaying a three-dimensional representation of the PLK3 or a portion thereof. The graphical representation is used according to the methods described herein to design compounds. Such compounds associate with the PLK3 at the ATP-binding pocket, substrate binding pocket or PLK3 binding pocket.

EXAMPLE 8

The Use of PLK3 Coordinates in the Design of PLK3-Specific Antibodies

The atomic coordinates in FIG. 1 or FIG. 6 also define, in great detail, the external solvent-accessible, hydrophilic, and mobile surface regions of the PLK3 catalytic kinase domain. Anti-peptide antibodies are known to react strongly against highly mobile regions but do not react with well-ordered regions of proteins. Mobility is therefore a major factor in the recognition of proteins by anti-peptide antibodies [J. A. Tainer et al., *Nature*, 312, pp. 127-134 (1984)]

One skilled in the art would therefore be able to use the X-ray crystallography data to determine possible antigenic sites in the PLK3 kinase domain. Possible antigenic sites are exposed, small and mobile regions on the kinase surface which have atomic B-factors of greater than 80 $Å^2$ in FIG. 1 or FIG. 6. This information can be used in conjunction with data from immunological studies to design and produce specific monoclonal or polyclonal antibodies.

This process may be aided by using a computer comprising a machine-readable data storage medium encoded with a set of machine-executable instructions, wherein the recorded instructions are capable of displaying a three-dimensional representation of the PLK3 or a portion thereof.

EXAMPLE 9

PLK3 Inhibition Assay

Compounds were screened for their ability to inhibit PLK3 using a radioactive-phosphate incorporation assay. Assays were carried out in a mixture of 25 mM HEPES (pH 7.5), 10 mM $MgCl_2$, and 1 mM DTT. Final substrate concentrations were 75 µM [γ-33P]ATP (60 mCi 33P ATP/mmol ATP, Amersham Pharmacia Biotech/Sigma Chemicals) and 110 µM peptide (SAM68 protein Δ332-443). Assays were carried out at 25° C. in the presence of 5 nM PLK3 (S38-A340). An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10µM with 2-fold serial dilutions) in duplicate (final DMSO concentration 5%). The plate was pre-incubated for 10 minutes at 25° C. and the reaction initiated by addition of 8 µL [γ-33P]ATP (final concentration 75 µM).

The reaction was stopped after 60 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad PRISM® version 3.0cx for Macintosh, GraphPad Software, San Diego Calif., USA).

EXAMPLE 10

Polo-Like Kinase 1 (PLK1) Inhibition Assay

Compounds were screened for their ability to inhibit PLK1 using a radioactive-phosphate incorporation assay. Assays were carried out in a mixture of 25 mM HEPES (pH 7.5), 10 mM MgCl2, and 1 mM DTT. Final substrate concentrations were 50 µM [γ-33P]ATP (136 mCi 33P ATP/mmol ATP, Amersham Pharmacia Biotech/Sigma Chemicals) and 10 µM peptide (SAM68 protein Δ332-443). Assays were carried out at 25° C. in the presence of 15 nM PLK1 (A20-K338). An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 50 µM).

The reaction was stopped after 60 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad PRISM® version 3.0cx for Macintosh, GraphPad Software, San Diego Calif., USA).

EXAMPLE 11

Polo-Like Kinase 1 (PLK1) Inhibition Assay

Compounds were screened for their ability to inhibit PLK1 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 150 µM [γ-33P]ATP (115 mCi 33P ATP/mmol ATP, Amersham Pharmacia Biotech/Sigma Chemicals) and 300 µM peptide (KKKISDELMDATFADQEAK) (SEQ ID NO:4. Assays were carried out at 25° C. in the presence of 4 nM PLK1. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 150 µM).

The reaction was stopped after 90 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad PRISM® version 3.0cx for Macintosh, GraphPad Software, San Diego Calif., USA).

EXAMPLE 12

Polo-Like Kinase 2 (PLK2) Inhibition Assay

Compounds were screened for their ability to inhibit PLK2 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 200 µM [γ-33P]ATP (57 mCi 33P ATP/mmol ATP, Amersham Pharmacia Biotech/Sigma Chemicals) and 300 µM peptide (KKKISDELMDATFADQEAK) (SEQ ID NO:4). Assays were carried out at 25° C. in the presence of 25 nM PLK2. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 200 µM).

The reaction was stopped after 90 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 4×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad PRISM® version 3.0cx for Macintosh, GraphPad Software, San Diego Calif., USA).

EXAMPLE 13

Polo-Like Kinase 4 (PLK4) Inhibition Assay

Compounds are screened for their ability to inhibit PLK4 using a radioactive-phosphate incorporation assay. Assays are carried out in a mixture of 8 mM MOPS (pH 7.5), 10 mM $MgCl_2$, 0.1% BSA and 2 mM DTT. Final substrate concentrations are 15 µM [γ-33P]ATP (227 mCi 33P ATP/mmol ATP, Amersham Pharmacia Biotech/Sigma Chemicals) and 300 µM peptide (KKKMDATFADQ) (SEQ ID NO:5). Assays are carried out at 25° C. in the presence of 25 nM PLK4. An assay stock buffer solution is prepared containing all of the reagents listed above, with the exception of ATP and the test compound of interest. 30 µL of the stock solution is placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate is pre-incubated for 10 minutes at 25° C. and the reaction initiated by addition of 8 µL [γ-33P]ATP (final concentration 15 µM).

The reaction is stopped after 180 minutes by the addition of 100 µL 0.14M phosphoric acid. A multiscreen phosphocellulose filter 96-well plate (Millipore, Cat no. MAPHN0B50) is pretreated with 100 µL 0.2M phosphoric acid prior to the addition of 125 µL of the stopped assay mixture. The plate is washed with 4×200 µL 0.2M phosphoric acid. After drying, 100 µL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad PRISM® version 3.0cx for Macintosh, GraphPad Software, San Diego Calif., USA).

TABLE 2

Summary of data collection for PLK3-adenosine complex
Space Group: C2
Unit Cell: a = 145.95 Å, b = 58.82 Å, c = 47.10 Å;
$\alpha = \gamma = 90°; \beta = 94.9°$

| Source | Daresbury SRS 14.1 |
|---|---|
| Wavelength (λ) | 1.488 |
| Resolution (Å) | 2.0 |
| No. of Reflections (measured/unique) | 143239/26685 |
| Completeness (%) (overall/outer shell) | 99.8/99.6 |
| I/σ(I) (overall/outer shell) | 10.5/2.1 |
| $R_{merge}$* (%) (overall/outer shell) | 4.6/43.9 |
| Molecules per asymmetric unit | 1 |

*$R_{merge} = 100 \times \Sigma_h \Sigma_j |<I(h)> - I(h)_j|/\Sigma_h \Sigma_j <I(h)>$ Structure Refinement

TABLE 3

Summary of refinements for PLK3-adenosine complex

| | Initial Refinement | Further Refinement |
|---|---|---|
| Resolution (Å) | 20-2.0 | 13-2.1 |
| No. of reflections | 19722 | 26547 |
| R factor (%) | 30.2 | 21.9 |
| Free R factor (%) | 33.2† | 26.9†† |
| RMSD values Bond lengths (Å)/angles (°) | 0.010/1.9 | 0.010/2.0 |

†The Free R factor was calculated with 2.0% of the data.
††The Free R factor was calculated with 5.0% of the data.

We claim:

1. A crystal comprising an unphosphorylated Polo-Like Kinase 3 (PLK3) catalytic kinase domain polypeptide in complex with adenosine, wherein said PLK3 catalytic kinase domain polypeptide consists of amino acids 48-332 of SEQ ID NO: 1, and wherein said crystal is in space group C2 and has unit cell dimensions of a=145.95 Å, b=58.82 Å, c=47.10 Å, α=γ=90° and β=94.9°.

2. A crystallizable composition comprising an unphosphorylated Polo-Like Kinase 3 (PLK3) catalytic kinase domain polypeptide in complex with adenosine, wherein said PLK3 catalytic kinase domain polypeptide consists of amino acids 48-332 of SEQ ID NO: 1, wherein the crystallizable composition forms crystals that are of X-ray diffraction quality.

* * * * *

SEQUENCE LISTING

<160> NUMBER OF SEQ ID NOS: 5

<210> SEQ ID NO 1
<211> LENGTH: 646
<212> TYPE: PRT
<213> ORGANISM: Homo sapiens

<400> SEQUENCE: 1

```
Met Glu Pro Ala Ala Gly Phe Leu Ser Pro Arg Pro Phe Gln Arg Ala
 1               5                  10                  15

Ala Ala Ala Pro Ala Pro Ala Gly Pro Gly Pro Pro Ser Ala
            20                  25                  30

Leu Arg Gly Pro Glu Leu Glu Met Leu Ala Gly Leu Pro Thr Ser Asp
            35                  40                  45

Pro Gly Arg Leu Ile Thr Asp Pro Arg Ser Gly Arg Thr Tyr Leu Lys
            50                  55                  60

Gly Arg Leu Leu Gly Lys Gly Gly Phe Ala Arg Cys Tyr Glu Ala Thr
 65                  70                  75                  80

Asp Thr Glu Thr Gly Ser Ala Tyr Ala Val Lys Val Ile Pro Gln Ser
                85                  90                  95

Arg Val Ala Lys Pro His Gln Arg Glu Lys Ile Leu Asn Glu Ile Glu
                100                 105                 110

Leu His Arg Asp Leu Gln His Arg His Ile Val Arg Phe Ser His His
            115                 120                 125

Phe Glu Asp Ala Asp Asn Ile Tyr Ile Phe Leu Glu Leu Cys Ser Arg
130                 135                 140

Lys Ser Leu Ala His Ile Trp Lys Ala Arg His Thr Leu Leu Glu Pro
145                 150                 155                 160

Glu Val Arg Tyr Tyr Leu Arg Gln Ile Leu Ser Gly Leu Lys Tyr Leu
                165                 170                 175

His Gln Arg Gly Ile Leu His Arg Asp Leu Lys Leu Gly Asn Phe Phe
            180                 185                 190

Ile Thr Glu Asn Met Glu Leu Lys Val Gly Asp Phe Gly Leu Ala Ala
            195                 200                 205

Arg Leu Glu Pro Pro Glu Gln Arg Lys Lys Thr Ile Cys Gly Thr Pro
210                 215                 220

Asn Tyr Val Ala Pro Glu Val Leu Arg Gln Gly His Gly Pro Glu
225                 230                 235                 240

Ala Asp Val Trp Ser Leu Gly Cys Val Met Tyr Thr Leu Leu Cys Gly
                245                 250                 255

Ser Pro Pro Phe Glu Thr Ala Asp Leu Lys Glu Thr Tyr Arg Cys Ile
            260                 265                 270

Lys Gln Val His Tyr Thr Leu Pro Ala Ser Leu Ser Leu Pro Ala Arg
            275                 280                 285

Gln Leu Leu Ala Ala Ile Leu Arg Ala Ser Pro Arg Asp Arg Pro Ser
        290                 295                 300

Ile Asp Gln Ile Leu Arg His Asp Phe Phe Thr Lys Gly Tyr Thr Pro
305                 310                 315                 320

Asp Arg Leu Pro Ile Ser Ser Cys Val Thr Val Pro Asp Leu Thr Pro
                325                 330                 335

Pro Asn Pro Ala Arg Ser Leu Phe Ala Lys Val Thr Lys Ser Leu Phe
            340                 345                 350

Gly Arg Lys Lys Lys Ser Lys Asn His Ala Gln Glu Arg Asp Glu Val
```

```
                355                 360                 365
Ser Gly Leu Val Ser Gly Leu Met Arg Thr Ser Val Gly His Gln Asp
    370                 375                 380

Ala Arg Pro Glu Ala Pro Ala Ala Ser Gly Pro Ala Pro Val Ser Leu
385                 390                 395                 400

Val Glu Thr Ala Pro Glu Asp Ser Ser Pro Arg Gly Thr Leu Ala Ser
                405                 410                 415

Ser Gly Asp Gly Phe Glu Gly Leu Thr Val Ala Thr Val Val Glu
                420                 425                 430

Ser Ala Leu Cys Ala Leu Arg Asn Cys Ile Ala Phe Met Pro Pro Ala
            435                 440                 445

Glu Gln Asn Pro Ala Pro Leu Ala Gln Pro Glu Pro Leu Val Trp Val
    450                 455                 460

Ser Lys Trp Val Asp Tyr Ser Asn Lys Phe Gly Phe Gly Tyr Gln Leu
465                 470                 475                 480

Ser Ser Arg Arg Val Ala Val Leu Phe Asn Asp Gly Thr His Met Ala
                485                 490                 495

Leu Ser Ala Asn Arg Lys Thr Val His Tyr Asn Pro Thr Ser Thr Lys
            500                 505                 510

His Phe Ser Phe Ser Val Gly Ala Val Pro Arg Ala Leu Gln Pro Gln
    515                 520                 525

Leu Gly Ile Leu Arg Tyr Phe Ala Ser Tyr Met Glu Gln His Leu Met
    530                 535                 540

Lys Gly Gly Asp Leu Pro Ser Val Glu Glu Val Glu Val Pro Ala Pro
545                 550                 555                 560

Pro Leu Leu Leu Gln Trp Val Lys Thr Asp Gln Ala Leu Leu Met Leu
                565                 570                 575

Phe Ser Asp Gly Thr Val Gln Val Asn Phe Tyr Gly Asp His Thr Lys
                580                 585                 590

Leu Ile Leu Ser Gly Trp Glu Pro Leu Leu Val Thr Phe Val Ala Arg
            595                 600                 605

Asn Arg Ser Ala Cys Thr Tyr Leu Ala Ser His Leu Arg Gln Leu Gly
    610                 615                 620

Cys Ser Pro Asp Leu Arg Gln Arg Leu Arg Tyr Ala Leu Arg Leu Leu
625                 630                 635                 640

Arg Asp Arg Ser Pro Ala
                645

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catatggacc ccgggcgcct catcacgg                                         28

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
ctattgggac tgtcacgcag ctgctg                                              26

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Lys Lys Ile Ser Asp Glu Leu Met Asp Ala Thr Phe Ala Asp Gln
 1               5                  10                  15

Glu Ala Lys

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Lys Met Asp Ala Thr Phe Ala Asp Gln
 1               5                  10
```